(12) United States Patent
Musunuru et al.

(10) Patent No.: US 10,208,319 B2
(45) Date of Patent: Feb. 19, 2019

(54) THERAPEUTIC USES OF GENOME EDITING WITH CRISPR/CAS SYSTEMS

(71) Applicants: President and Fellows of Harvard College, Cambridge, MA (US); The Children's Medical Center Corporation, Boston, MA (US)

(72) Inventors: Kiran Musunuru, Cambridge, MA (US); Chad A. Cowan, Boston, MA (US); Derrick J. Rossi, Roslindale, MA (US)

(73) Assignees: President and Fellows of Harvard College, Cambridge, MA (US); The Children's Medical Center Corporation, Boston, MA (US)

( * ) Notice: Subject to any disclaimer, the term of this patent is extended or adjusted under 35 U.S.C. 154(b) by 22 days.

(21) Appl. No.: 14/509,924

(22) Filed: Oct. 8, 2014

(65) Prior Publication Data

US 2015/0152436 A1    Jun. 4, 2015

Related U.S. Application Data

(63) Continuation-in-part of application No. PCT/US2014/046034, filed on Jul. 9, 2014.

(60) Provisional application No. 61/844,333, filed on Jul. 9, 2013, provisional application No. 61/869,369, filed on Aug. 23, 2013.

(51) Int. Cl.
| | |
|---|---|
| *C12N 15/90* | (2006.01) |
| *A61K 38/46* | (2006.01) |
| *C12N 9/22* | (2006.01) |
| *A61K 48/00* | (2006.01) |

(52) U.S. Cl.
CPC .......... *C12N 15/907* (2013.01); *A61K 38/465* (2013.01); *C12N 9/22* (2013.01); *A61K 48/00* (2013.01); *C12N 2800/80* (2013.01)

(58) Field of Classification Search
CPC .............................. C12N 15/63; C12N 15/907
See application file for complete search history.

(56) References Cited

U.S. PATENT DOCUMENTS

| | | |
|---|---|---|
| 8,013,143 B2 | 9/2011 | Mcswiggen et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 9,822,370 B2 | 11/2017 | Musunuru et al. |
| 2002/0106742 A1 | 8/2002 | Samson et al. |
| 2006/0024819 A1 | 2/2006 | Finney |
| 2008/0188000 A1 | 8/2008 | Reik et al. |
| 2010/0062003 A1 | 3/2010 | Murphy et al. |
| 2010/0076057 A1 | 3/2010 | Sontheimer et al. |
| 2010/0093617 A1 | 4/2010 | Barrangou et al. |
| 2010/0227805 A1 | 9/2010 | Karin et al. |
| 2011/0262406 A1 | 10/2011 | Del Campo et al. |
| 2011/0300538 A1 | 12/2011 | Barrangou et al. |
| 2012/0088676 A1 | 4/2012 | Weill et al. |
| 2012/0142062 A1 | 6/2012 | Doyon et al. |
| 2012/0192298 A1 | 7/2012 | Weinstein et al. |
| 2012/0225927 A1 | 9/2012 | Sah et al. |
| 2012/0251618 A1 | 10/2012 | Schrum et al. |
| 2013/0122591 A1 | 5/2013 | Cost et al. |
| 2013/0156849 A1 | 6/2013 | De Fougerolles |
| 2013/0288251 A1 | 10/2013 | Horvath et al. |
| 2013/0330778 A1 | 12/2013 | Zeiner et al. |
| 2014/0080216 A1 | 3/2014 | Cost et al. |
| 2014/0093913 A1 | 4/2014 | Cost et al. |
| 2014/0134143 A1 | 5/2014 | Baylink et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang et al. |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273230 A1 | 9/2014 | Chen et al. |
| 2014/0273231 A1 | 9/2014 | Zhang |
| 2014/0273232 A1 | 9/2014 | Zhang et al. |
| 2014/0273233 A1 | 9/2014 | Chen et al. |
| 2014/0273234 A1 | 9/2014 | Zhang et al. |
| 2014/0287938 A1 | 9/2014 | Zhang et al. |
| 2014/0295556 A1 | 10/2014 | Joung et al. |
| 2014/0295557 A1 | 10/2014 | Joung et al. |
| 2014/0301990 A1 | 10/2014 | Gregory et al. |
| 2014/0302563 A1 | 10/2014 | Doudna et al. |
| 2014/0310830 A1 | 10/2014 | Zhang et al. |
| 2014/0315985 A1 | 10/2014 | May et al. |

(Continued)

FOREIGN PATENT DOCUMENTS

| | | |
|---|---|---|
| WO | WO 2013/016446 | 1/2013 |
| WO | WO 2013/126794 A1 | 8/2013 |

(Continued)

OTHER PUBLICATIONS

Mali et al. (Science. Feb. 15, 2013; 339(6121): 823-826).*

(Continued)

*Primary Examiner* — Scott Long
(74) *Attorney, Agent, or Firm* — Lisa M. Warren, Esq.; Morse, Barnes-Brown & Pendleton, P.C.

(57) ABSTRACT

Disclosed herein are methods, compositions, and kits for high efficiency, site-specific genomic editing of cells for treating or preventing genetic blood disorders.

11 Claims, 186 Drawing Sheets
Specification includes a Sequence Listing.

(56) References Cited

U.S. PATENT DOCUMENTS

| | | | |
|---|---|---|---|
| 2014/0335620 | A1 | 11/2014 | Zhang et al. |
| 2014/0336133 | A1 | 11/2014 | Miller et al. |
| 2014/0342456 | A1 | 11/2014 | Mali et al. |
| 2014/0342457 | A1 | 11/2014 | Mali et al. |
| 2014/0342458 | A1 | 11/2014 | Mali et al. |
| 2014/0349405 | A1 | 11/2014 | Sontheimer et al. |
| 2014/0356956 | A1 | 12/2014 | Church et al. |
| 2014/0356958 | A1 | 12/2014 | Mali et al. |
| 2014/0356959 | A1 | 12/2014 | Church et al. |
| 2014/0357530 | A1 | 12/2014 | Zhang et al. |
| 2014/0377868 | A1 | 12/2014 | Joung et al. |
| 2015/0020223 | A1 | 1/2015 | Zhang et al. |
| 2015/0031132 | A1 | 1/2015 | Church et al. |
| 2015/0031133 | A1 | 1/2015 | Church et al. |
| 2015/0031134 | A1 | 1/2015 | Zhang et al. |
| 2015/0044191 | A1 | 2/2015 | Liu et al. |
| 2015/0044192 | A1 | 2/2015 | Liu et al. |
| 2015/0056705 | A1 | 2/2015 | Conway et al. |
| 2015/0071889 | A1 | 3/2015 | Musunuru et al. |
| 2015/0166969 | A1* | 6/2015 | Takeuchi ............ A61K 38/465 435/196 |
| 2015/0176013 | A1 | 6/2015 | Musunuru et al. |
| 2015/0344912 | A1 | 12/2015 | Kim et al. |
| 2016/0024524 | A1 | 1/2016 | Joung et al. |

FOREIGN PATENT DOCUMENTS

| | | |
|---|---|---|
| WO | WO 2014/065596 | 5/2014 |
| WO | WO 2014/093622 | 6/2014 |
| WO | WO 2014/150624 | 9/2014 |
| WO | WO 2014/151994 | 9/2014 |
| WO | WO 2014/153115 A2 | 9/2014 |
| WO | WO 2014/165825 | 10/2014 |
| WO | WO 2014/204726 A1 | 12/2014 |
| WO | WO 2015/006498 | 1/2015 |
| WO | WO 2016/057821 | 4/2016 |
| WO | WO 2016/057835 | 4/2016 |

OTHER PUBLICATIONS

Kariko et al. (Molecular Therapy. 2008; 16(11): 1833-1840).*
GenBank: AY136510.1, Kutlar, et al., "A new hemoglobin, beta chain variant 'Hb S-Wake' confirmed to be on the same chromosome with hemoglobin S mutation, detected in an African-American family," Retrieved from the internet on Dec. 23, 2015 < http://www.ncbi.nlm.nih.govInucleotide/23268448?report=genbanl<&log$=nuclalign&blast_rank=2&RID=7NNHZVRH014>.
Cho, et al., "Targeted genome engineering in human cells with the Cas9 RNA-guided endonuclease," Nature Biotechnology 31(3): 230-232 (2013).
Cong, et al., "Multiplex Genome Engineering Using CRISPR/Cas Systems," Science 339: 819-823 (2013).
Jinek, et al., "RNA-programmed genome editing in human cells," eLife Research Article pp. 1-9 (2013).
Jinek, et al., "A programmable Dual-RNA-Guided DNA Endonuclease in Adaptive Bacterial Immunity," Science 337: 816-821 (2012).
Mali, et al., "RNA-Guided Human Genome Engineering via Cas9," Science 339: 823-826 (2013).
Ran, et al., "Double Nicking by RNA-Guided CRISPR Cas9 for Enhanced Genome Editing Specificity," Cell 154: 1380-1389 (2013).
Holt, et al., "Human hematopoietic stem/progenitor cells modified by zinc-finger nucleases targeted to CCRG control HIV-1 in vivo," Nature biotechnology 28.8, 839-847 (2010).
Randau, "RNA processing in the minimal organism Nanoarchaeum equitans," Genome Biol 13.7 : 6 (2012).
Cho, et al., "Analysis of off-target effects of CRISPR/Cas-derived RNA-guided endonucleases and nickases," Genome Research (24): 132-141 (2014).
Cradick, et al., "CRISPR/Cas9 systems targeting B-globin and CCR5 genes have substantial off-target activity," Nucleic Acids Research, 1-9 (2013).
Hruscha, et al., "Efficient CRISPR/Cas9 genome editing with low off-target effects in zebrafish,"Development (140):4982-4987 (2013).
Lin, et al., "CRISPR/Cas9 systems have off-target activity with insertions or deletions between target DNA and guide RNA sequences," Nucleic Acids Research 1-13 (2014).
Talkowski, et al., "Next-Generation Sequencing Strategies Enable Routine Detection of Balanced Chromosome Rearrangements for Clinical Diagnostics and Genetic Research," The American Journal of Human Genetics (88): 469-481 (2011).
Cong,et al., "Multiplex genome engineering using CRISPR/Cas Systems," Science 21 339(6121): 819-823 (2013).
Gaj, et al., "ZFN, TALEN, and CRISPR/Cas-based methods for genome engineering," Trends in Biotechnology 31(7): 397-405 (2013).
GenBank~ M13792.1 Human adenosine deaminase (ADA) gene, complete cds [online] Oct. 4, 1995 [retrieved Oct. 25, 2014]. Available on the internet: <URL: http://www.ncbi.nlm.nih.gov/nuccore/M13792>. Especially p. 17 n\35125-35147 and nt 35090-35112.
International Search Report for International Application PCT/US2014/033082, dated Nov. 4, 2014.
International Search Report for International Application PCT/US2014/46034, dated Jan. 23, 2015.
Porteus, et al., "Gene targeting using zinc finger nucleases," Nature Biotechnology 23(8): 967-973 (2005).
Ramirez, et al., "Unexpected failure rates for modular assembly of engineered zinc fingers," Nature Methods 5(5): 374-375 (2008).
Geurts,et al., "Knockout Rats via Embryo Microinjection of Zinc-Finger Nucleases," Science 325:433 (2009).
Christian, et al., "Treating DNA Double-Strand Breaks with TAL Effector Nucleases," Genetics 757-761 (2010).
Li, et al., "In vivo genome editing restores haemostasis in a mouse model of haemophilia," Nature 475: 217-221 (2011).
High, et al., "DNA-cleaving enzymes trigger a repair process that can now be harnessed to correct mutations in the human genome in vitro. This represents another step towards gene-correction strategies for treating human disease," Nature 435 pp. 577 & 579 (2005).
Non-Final Office Action for U.S. Appl. No. 14/485,288, dated Mar. 26, 2015.
Ding, et al., "Enhanced Efficiency of Human Pluripotent Stem Cell Genome Editing through Replacing TALENs with CRISPRs," Cell Stem Cell 12: 393-394; plus supplemental materials (2013) (published online on Apr. 4, 2013).
Third Party Submission Under 37 CFR 1.290 for U.S. Appl. No. 14/485,288, made/submitted Jul. 14, 2015.
Third Party Observation for PCT Application PCT/US2014/033082, made/submitted Aug. 3, 2015.
Final Office Action for U.S. Appl. No. 14/485,288, dated Aug. 24, 2015.
GenBank: EF150856.1, Kutlar, et al., "*Homo sapiens* beta-globin (HBB) gene, HBB-Hb sickle-Monroe allele, exons 1, 2 and partial cds," Retrieved from the internet on Feb. 22, 2016.http://www.ncbi.nlm.nih.gov/nuccore/EF150856>.
Schwank, et al., "Functional Repair of CFTR by CRISPR/Cas9 in Intestinal Stem Cell Organoids of Cystic Fibrosis Patients," Cell Stem Cell 13: 653-658 (2013).
Wiginton, et al., "Complete Sequence and Structure of the Gene for Human Adenosine Deaminase," Biochemistry 25(25): 8234-8244. Abstract (1986).
Rieder, et al., *Homo sapiens* Interleukin 2 Receptor, Gamma (Severe Combined Immunodeficiency) (IL2RG) Gene, Complete cds: GENBANK: AY692262.1. Jul. 21, 2004 [Retrieved on Mar. 3, 2016]. Retrieved from the Internet: <URL: http://www.ncbi.nlm.nih.gov/nucleotide/50897 469>; pp. 1-4.
Tasher, et al., "The Genetic Basis of Severe Combined Immunodeficiency and its Variants," The Application of Clinical Genetics 5: 67-80 (2012).
Woodbine, et al., PRKDC Mutations in a SCID Patient with Profound Neurological Abnormalities. The Journal of Clinical Investigation 123(7): 2969-2980. (2013).
Kutlar, et al., A New Hemoglobin, Beta Chain Variant 'Hb S-Wake' Confirmed to be on the Same Chromosome with Hemoglobin S Mutation, Detected in an African-American Family: GENBANK: AY13651 0.1. Jul. 26, 2002 [Retrieved on Dec. 23, 2015]. Retrieved from the Internet: URL:http://www.ncbi.nlm.nih.gov/nucleotide/23268448.

(56) References Cited

OTHER PUBLICATIONS

Hendel, et al., "Quantifying Genome-Editing Outcomes at Endogenous Loci with SMRT Sequencing," Cell Reports 7: 293-305 (2014).
Lagresle-Peyrou, et al., "Human adenyiate kinase 2 deficiency causes a profound haematopoietic defect associated with sensorineural deafness," Nat Genet 41(1): 106-111 (2009).
Ding, et al., "A TALEN genome editing system to generate human stem cell-based disease models," Cell Stem Cell 12(2): 238-251 (2013).
Palu, et al.,"In pursuit of new developments for gene therapy of human diseases[1]," Journal of Biotechnology 68:1-13 (1999).
Luo, et al., "Synthetic DNA delivery systems," Nature Biotechnology 18: 33-37 (2000).
Pfeifer, et al., "Gene Therapy: Promises and Problems," Annu. Rev. Genomics Hum. Genet. 2: 177-211 (2001).
Johnson-Salbia, et al., "Gene Therapy: Optimising DNA Delivery to the Nucleus," Current Drug Targets 2: 371-399 (2001).
Shoji, et al., "Current Status of Delivery Systems to Improve Target Efficacy of Oligonucleotides," Current Pharmaceutical Design 10: 785-796 (2004).
Edelstein, et al., "Gene therapy clinical trials worldwide 1989-2004—an overview," The Journal of Gene Medicine 6: 597-302 (2004).
International Preliminary Report on Patentability for International Application PCT/US2014/46034, dated Jan. 21, 2016.
International Search Report for International Application PCT/US2015/054762, dated Mar. 11, 2016.
Non-Final Office Action for U.S. Appl. No. 14/509,787, dated Apr. 11, 2016.
Extended European Search Report from European Application 14822545.1, dated Oct. 24, 2016.
Smithies, et al., "Insertion of DNA Sequences Into the Human Chromosomal β-Globin Locus by Homologous Recombination," Nature, 317(19):230-234, (Sep. 1985).
Final Office Action for U.S. Appl. No. 14/509,787, dated Dec. 2, 2016.
Non-Final Office Action for U.S. Appl. No. 14/485,288, dated Sep. 6, 2016).
Chiba et al., "Genome Editing in Human Pluripotent Stem Cells Using Site-Specific Nucleases," Methods in Molecular Biology, 1239:267-280, (2015).
Cowan, "Human Cell-Based Models of Primary Adipocyte Disorders," National Institutes of Health Grant No. *1R01DK095384-01* (Funding Start Date Apr. 1, 2012), Abstract.
Cowan, "Integrating Lipid Genotypes and Phenotypes in IPS Derived Hepatocytes/Adipocytes," National Institutes of Health Grant No. *1U01HL107440-01* (Funding Start Date Jul. 5, 2011), Abstract.
Doudna et al., "The new frontier of genome engineering with CRISPR-Cas9," Science, 346(6213):1077, 1258096-1 through 1258096-9, (2014).
Gonzalez et al., "An iCRISPR Platform for Rapid, Multiplexable, and Inducible Genome Editing in Human Pluripotent Stem Cells," Cell Stem Cell, 15:215-226, (2014).
Hsu et al., "Development and Applications of CRISPR-Cas9 for Genome Engineering," Cell, 157:1262-1278, (2014).
Jun et al., "CRISPR/Cas: a novel way of RNA-guided genome editing," Hereditas, 35(11):1265-1273, (2013), English Abstract.
Khalili et al., "Genome editing strategies: potential tools for eradicating HIV-1/AIDS," J. Neurovirol, 21(3)310-321, (2015).
Late Breaking Abstracts: Presented at the American Society of Gene & Cell Therapy's 16th Annual Meeting, May 15-18, 2013, Salt Lake City, Utah (56 pages).
Li et al., "MAGeCK enables robust identification of essential genes from genome-scale CRISPR/Cas9 knockout screens," Genome Biology, 15:1-12, (2014).
Lin et al., "Enhanced homology-directed human genome engineering by controlled timing of CRISPR/Cas9 delivery," Elife, DOI: 10.7554:1-13, (2014).
Lloyd et al., "Beyond the antigen receptor: editing the genome of T-Cells for cancer adoptive cellular therapies," Frontiers in Immunology, 4(22):1-7, (2013).
Merkle et al., "Modeling Human Disease with Pluripotent Stem Cells: from Genome Association to Function," Cell Stem Cell, 12:656-668, (2013).
Musunuru, "Genetic and Functional Analysis of a Novel Locus Associated with LDL-C and MI," National Institutes of Health Grant No. *1K99HL098364-01*, (Funding Start Date May 3, 2010), Abstract.
Musunuru, "Stem Cell Models of Familial Combined Hypolipidemia," National Institutes of Health Grant No. *1R01HL118744-01* (Funding Start Date Feb. 1, 2013), Abstract.
Pelletier et al., "Mouse Genome Engineering via CRISPR-Cas9 for Study of Immune Function," Cell Press, 42:18-27, (2015).
Shalem et al., "Genome-Scale CRISPR-Cas9 Knockout Screening in Human Cells," Science, 343:84-87, (2014).
Wang et al., "Genetic Screens in Human Cells Using the CRISPR-Cas9 System," Science, 343:80-84, (2014).
Wang et al., "One-Step Generation of Mice Carrying Mutations in Multiple Genes by CRISPR/Cas-Mediated Genome Engineering," Cell, 153:910-918, (2013).
Wu et al., "Target specificity of the CRISPR-Cas9 system," Quantitative Biology, 2(2):59-70, 2014.
Xie et al., "Seamless gene correction of β-thalassemia mutations in patient-specific iPSCs using CRISPR/Cas9 and piggyBac," Genome Research, 24:1526-1533, (2014).
Zhang et al., "CRISPR/Cas9 for genome editing: progress, implications and challenges," HMG Advance Acess, Published Mar. 20, 2014 pp. 1-21.
International Search Report for International Application PCT/US2015/054747, dated Apr. 29, 2016.
Hwang, et al., "Efficient Genome Editing in Zebrafish Using a CRISPR-Cas System," Nature Biotechnology, 31(3):227-229, (Mar. 2013).
Jiang, et al., "RBA-Guided Editing of Bacterial Genomes Using CRISPR-Cas Systems," Nature Biotechnology, 31(3):233-239, (Mar. 2013).
Mandal, et al., "Reprogramming Human Fibroblasts to Pluripotency Using Modified mRNA," Nature Protocols, 8(3):568-582, (2013).
Ramalingam, et al., "A CRISPR Way to Engineer the Human Genome," Genome Biology, 14(107):1-4, (2013).
Shen, et al., "Generation of Gene-Modified Mice via Cas9/RNA-Mediated Gene Targeting," Cell Research, 23:720-723, (2013).
Wilen, et al., "Engineering HIV-Resistant Human CD4+ T Cells With CXCR4-Specific Zinc-Finger Nucleases," PLoS Pathogens, 7(4):1-15, (Apr. 2011).
Extended European Search Report from European Application 14779492.9, dated Dec. 20, 2016.
Cho, et al., "Targeted Genome Engineering in Human Cells with RNA-Guided Endonucleases," Supplementary Information, Nature Biotechnology, pp. 1-11, (2013).
Mandal, et al., "Efficient Ablation of Genes in Human Hematopoietic Stem and Effector Cells using CRISPR/Cas9," Cell Stem Cell, 15:643-652, (Nov. 6, 2014).
Tebas, et al., "Gene Editing of CCR5 in Autologous CD4 T Cells of Persons Infected with HIV,"The New England Journal of Medicine, 370(10):901-910, (Mar. 6, 2014).
Final Office Action for U.S. Appl. No. 14/485,288, dated Apr. 26, 2017.
Notice of Allowance for U.S. Appl. No. 14/485,288, dated Jul. 14, 2017).
Final Office Action for U.S. Appl. No. 14/509,787, dated May 24, 2018.

\* cited by examiner

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 20 | 43248474 | + | GCTTCTCTGAACCAACGAGCAGG | 1 | 2 | 17 | SEQ ID NO. 1 |
| (N20)NGG | 20 | 43248475 | + | CTTCTCTGAACCAACGAGCAGGG | 2 | 3 | 21 | SEQ ID NO. 2 |
| (N20)NGG | 20 | 43248463 | - | AGAGGTTCTGCCCTGCTCGTTGG | 1 | 2 | 19 | SEQ ID NO. 3 |
| (N20)NGG | 20 | 43248481 | - | TGGAGGAGTGGCGTCTTCAGAGG | 1 | 3 | 36 | SEQ ID NO. 4 |
| (N20)NGG | 20 | 43248951 | + | GCCTTTCCAGAACATCAATGCCG | 1 | 3 | 35 | SEQ ID NO. 5 |
| (N20)NGG | 20 | 43248986 | + | TCCTCCCAGAAGATGAAAAGAGG | 1 | 8 | 88 | SEQ ID NO. 6 |
| (N20)NGG | 20 | 43248987 | + | CCTCCCAGAAGATGAAAAGAGGG | 1 | 8 | 120 | SEQ ID NO. 7 |
| (N20)NGG | 20 | 43249018 | + | GACCTGCTCTATAAAGCCTATGG | 1 | 3 | 20 | SEQ ID NO. 8 |
| (N20)NGG | 20 | 43249019 | + | ACCTGCTCTATAAAGCCTATGGG | 1 | 5 | 24 | SEQ ID NO. 9 |
| (N20)NGG | 20 | 43249042 | + | ATGCCACCTTCAGCCTCTGCAGG | 2 | 6 | 74 | SEQ ID NO. 10 |
| (N20)NGG | 20 | 43249046 | + | CACCTTCAGCCTCTGCAGGTAGG | 1 | 5 | 86 | SEQ ID NO. 11 |
| (N20)NGG | 20 | 43249057 | + | TCTGCAGGTAGGTTCCTGTCTGG | 1 | 2 | 32 | SEQ ID NO. 12 |
| (N20)NGG | 20 | 43249058 | + | CTGCAGGTAGGTTCCTGTCTGGG | 3 | 10 | 82 | SEQ ID NO. 13 |
| (N20)NGG | 20 | 43249065 | + | TAGGTTCCTGTCTGGGCTTCTGG | 1 | 1 | 40 | SEQ ID NO. 14 |
| (N20)NGG | 20 | 43249066 | + | AGGTTCCTGTCTGGGCTTCTGGG | 1 | 5 | 66 | SEQ ID NO. 15 |
| (N20)NGG | 20 | 43248921 | - | ATGTTCTGGAAAGGCCAGAATGG | 1 | 2 | 78 | SEQ ID NO. 16 |
| (N20)NGG | 20 | 43248930 | - | GCCGCATTGATGTTCTGGAAAGG | 1 | 1 | 17 | SEQ ID NO. 17 |
| (N20)NGG | 20 | 43248935 | - | ATTTGGCCGCATTGATGTTCTGG | 1 | 1 | 9 | SEQ ID NO. 18 |
| (N20)NGG | 20 | 43248952 | - | TTCTGGGAGGAAACTAGATTTGG | 1 | 6 | 76 | SEQ ID NO. 19 |
| (N20)NGG | 20 | 43248965 | - | CCCTCTTTTCATCTTCTGGGAGG | 3 | 7 | 75 | SEQ ID NO. 20 |
| (N20)NGG | 20 | 43248968 | - | GCTCCCTCTTTTCATCTTCTGGG | 2 | 10 | 106 | SEQ ID NO. 21 |
| (N20)NGG | 20 | 43248969 | - | AGCTCCCTCTTTTCATCTTCTGG | 1 | 6 | 99 | SEQ ID NO. 22 |
| (N20)NGG | 20 | 43248998 | - | TCCCATAGGCTTTATAGAGCAGG | 1 | 2 | 13 | SEQ ID NO. 23 |
| (N20)NGG | 20 | 43249012 | - | GGCTGAAGGTGGCATCCCATAGG | 1 | 2 | 34 | SEQ ID NO. 24 |
| (N20)NGG | 20 | 43249023 | - | CTACCTGCAGAGGCTGAAGGTGG | 1 | 7 | 86 | SEQ ID NO. 25 |
| (N20)NGG | 20 | 43249026 | - | AACCTACCTGCAGAGGCTGAAGG | 1 | 4 | 42 | SEQ ID NO. 26 |
| (N20)NGG | 20 | 43249033 | - | AGACAGGAACCTACCTGCAGAGG | 2 | 9 | 79 | SEQ ID NO. 27 |
| (N20)NGG | 20 | 43249658 | + | TCTCCTCCTCCCTCTTCTGCAGG | 4 | 24 | 329 | SEQ ID NO. 28 |
| (N20)NGG | 20 | 43249674 | + | CTGCAGGCTCAAAAATGACCAGG | 1 | 5 | 39 | SEQ ID NO. 29 |
| (N20)NGG | 20 | 43249725 | + | GCTCATCTTCAAGTCCACCCTGG | 1 | 1 | 26 | SEQ ID NO. 30 |
| (N20)NGG | 20 | 43249751 | + | CTGATTACCAGATGACCAAACGG | 1 | 4 | 33 | SEQ ID NO. 31 |

FIG. 1

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 20 | 43249752 | + | TGATTACCAGATGACCAAACGGG | | 1 | 2 | 21 SEQ ID NO. 32 |
| (N20)NGG | 20 | 43249758 | + | CCAGATGACCAAACGGGACATGG | | 1 | 1 | 20 SEQ ID NO. 33 |
| (N20)NGG | 20 | 43249759 | + | CAGATGACCAAACGGGACATGGG | | 1 | 2 | 14 SEQ ID NO. 34 |
| (N20)NGG | 20 | 43249773 | + | GGACATGGGCTTTACTGAAGAGG | | 1 | 3 | 29 SEQ ID NO. 35 |
| (N20)NGG | 20 | 43249784 | + | TTACTGAAGAGGAGTTTAAAAGG | | 1 | 4 | 74 SEQ ID NO. 36 |
| (N20)NGG | 20 | 43249788 | + | TGAAGAGGAGTTTAAAAGGCTGG | | 1 | 6 | 79 SEQ ID NO. 37 |
| (N20)NGG | 20 | 43249795 | + | GAGTTTAAAAGGCTGGTGAGTGG | | 3 | 6 | 46 SEQ ID NO. 38 |
| (N20)NGG | 20 | 43249796 | + | AGTTTAAAAGGCTGGTGAGTGGG | | 1 | 6 | 48 SEQ ID NO. 39 |
| (N20)NGG | 20 | 43249811 | + | TGAGTGGGTGTGAGCCATACTGG | | 1 | 1 | 16 SEQ ID NO. 40 |
| (N20)NGG | 20 | 43249639 | - | GAGCCTGCAGAAGAGGAGGGAGG | | 4 | 21 | 222 SEQ ID NO. 41 |
| (N20)NGG | 20 | 43249642 | - | TTTGAGCCTGCAGAAGAGGAGGG | | 1 | 6 | 78 SEQ ID NO. 42 |
| (N20)NGG | 20 | 43249645 | - | ATTTTTGAGCCTGCAGAAGAGGG | | 1 | 10 | 102 SEQ ID NO. 43 |
| (N20)NGG | 20 | 43249646 | - | CATTTTTGAGCCTGCAGAAGAGG | | 1 | 8 | 72 SEQ ID NO. 44 |
| (N20)NGG | 20 | 43249670 | - | TGTTGAGCGAGTAGTTAGCCTGG | | 1 | 1 | 4 SEQ ID NO. 45 |
| (N20)NGG | 20 | 43249700 | - | GGGTGGACTTGAAGATGAGCGGG | | 1 | 4 | 28 SEQ ID NO. 46 |
| (N20)NGG | 20 | 43249701 | - | AGGGTGGACTTGAAGATGAGCCG | | 2 | 7 | 80 SEQ ID NO. 47 |
| (N20)NGG | 20 | 43249717 | - | CTGGTAATCAGTGTCCAGGGTGG | | 1 | 4 | 27 SEQ ID NO. 48 |
| (N20)NGG | 20 | 43249720 | - | CATCTGGTAATCAGTGTCCAGGG | | 1 | 2 | 30 SEQ ID NO. 49 |
| (N20)NGG | 20 | 43249721 | - | TCATCTGGTAATCAGTGTCCAGG | | 1 | 2 | 25 SEQ ID NO. 50 |
| (N20)NGG | 20 | 43249736 | - | CCATGTCCCGTTTGGTCATCTGG | | 1 | 1 | 8 SEQ ID NO. 51 |
| (N20)NGG | 20 | 43249744 | - | AGTAAACGCCCATGTCCCGTTTGG | | 1 | 1 | 6 SEQ ID NO. 52 |
| (N20)NGG | 20 | 43251239 | + | TGCTCTTCCAGATCTGCCCCTGG | | 2 | 5 | 61 SEQ ID NO. 53 |
| (N20)NGG | 20 | 43251256 | + | CCCTGGTCCAGCTACCTCACTGG | | 2 | 5 | 30 SEQ ID NO. 54 |
| (N20)NGG | 20 | 43251263 | + | CCAGCTACCTCACTGGTGCCTGG | | 1 | 5 | 42 SEQ ID NO. 55 |
| (N20)NGG | 20 | 43251270 | + | CCTCACTGGTGCCTGGAAGCCGG | | 1 | 8 | 72 SEQ ID NO. 56 |
| (N20)NGG | 20 | 43251276 | + | TGGTGCCTGGAAGCCGGACACGG | | 1 | 3 | 32 SEQ ID NO. 57 |
| (N20)NGG | 20 | 43251293 | + | ACACGGAGCATGCAGTCATTCGG | | 1 | 1 | 25 SEQ ID NO. 58 |
| (N20)NGG | 20 | 43251311 | + | TTCGGTGAGCTCTGTTCCCCTGG | | 1 | 2 | 25 SEQ ID NO. 59 |
| (N20)NGG | 20 | 43251312 | + | TCGGTGAGCTCTGTTCCCCTGGG | | 1 | 1 | 18 SEQ ID NO. 60 |
| (N20)NGG | 20 | 43251204 | - | TGGAAGACCAGGTGTGTGGCTGG | | 1 | 6 | 147 SEQ ID NO. 61 |
| (N20)NGG | 20 | 43251208 | - | GATCTGGAAGAGACAGGTGTGTGG | | 1 | 11 | 97 SEQ ID NO. 62 |

FIG. 1 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 20 | 43251215 | - | AGGGGCAGATCTGGAAGAGCAGG | | 1 | 8 | 82 SEQ ID NO. 63 |
| (N20)NGG | 20 | 43251224 | - | AGCTGGACCAGGGGCAGATCTGG | | 1 | 4 | 62 SEQ ID NO. 64 |
| (N20)NGG | 20 | 43251233 | - | CAGTGAGGTAGCTGGACCAGGGG | | 1 | 4 | 65 SEQ ID NO. 65 |
| (N20)NGG | 20 | 43251234 | - | CCAGTGAGGTAGCTGGACCAGGG | | 1 | 2 | 47 SEQ ID NO. 66 |
| (N20)NGG | 20 | 43251235 | - | ACCAGTGAGGTAGCTGGACCAGG | | 1 | 4 | 35 SEQ ID NO. 67 |
| (N20)NGG | 20 | 43251241 | - | CCAGGCACCAGTGAGGTAGCTGG | | 1 | 5 | 53 SEQ ID NO. 68 |
| (N20)NGG | 20 | 43251248 | - | CCGGCTTCCAGGCACCAGTGAGG | | 1 | 2 | 49 SEQ ID NO. 69 |
| (N20)NGG | 20 | 43251259 | - | ATGCTCCGTGTCCGGCTTCCAGG | | 1 | 1 | 10 SEQ ID NO. 70 |
| (N20)NGG | 20 | 43251267 | - | ATGACTGCATGCTCCGTGTCCGG | | 2 | 3 | 36 SEQ ID NO. 71 |
| (N20)NGG | 20 | 43251469 | + | GCTCTATTCTGCTTCTCTACAGG | | 1 | 4 | 34 SEQ ID NO. 72 |
| (N20)NGG | 20 | 43251475 | + | TTCTGCTTCTCTACAGGCTGTGG | | 1 | 11 | 100 SEQ ID NO. 73 |
| (N20)NGG | 20 | 43251495 | + | TGGACATACTCAAGACAGAGCGG | | 1 | 2 | 48 SEQ ID NO. 74 |
| (N20)NGG | 20 | 43251499 | + | CATACTCAAGACAGAGCGGCTGG | | 1 | 3 | 14 SEQ ID NO. 75 |
| (N20)NGG | 20 | 43251500 | + | ATACTCAAGACAGAGCGGCTGGG | | 1 | 1 | 16 SEQ ID NO. 76 |
| (N20)NGG | 20 | 43251506 | + | AAGACAGAGCGGCTGGGACACGG | | 1 | 9 | 81 SEQ ID NO. 77 |
| (N20)NGG | 20 | 43251520 | + | GGGACACGGCTACCACACCCTGG | | 1 | 1 | 15 SEQ ID NO. 78 |
| (N20)NGG | 20 | 43251529 | + | CTACCACACCCTGGAAGACCAGG | | 1 | 3 | 42 SEQ ID NO. 79 |
| (N20)NGG | 20 | 43251543 | + | AAGACCAGGCCCTTTATAACAGG | | 1 | 3 | 34 SEQ ID NO. 80 |
| (N20)NGG | 20 | 43251549 | + | AGGCCCTTTATAACAGGCTGCGG | | 1 | 2 | 25 SEQ ID NO. 81 |
| (N20)NGG | 20 | 43251553 | + | CCTTTATAACAGGCTGCGGCAGG | | 1 | 2 | 16 SEQ ID NO. 82 |
| (N20)NGG | 20 | 43251571 | + | GCAGGAAAACATGCACTTCGAGG | | 1 | 4 | 26 SEQ ID NO. 83 |
| (N20)NGG | 20 | 43251578 | + | AACATGCACTTCGAGGTAAGCGG | | 1 | 1 | 14 SEQ ID NO. 84 |
| (N20)NGG | 20 | 43251579 | + | ACATGCACTTCGAGGTAAGCGGG | | 1 | 1 | 10 SEQ ID NO. 85 |
| (N20)NGG | 20 | 43251584 | + | CACTTCGAGGTAAGCGGGCCAGG | | 1 | 1 | 7 SEQ ID NO. 86 |
| (N20)NGG | 20 | 43251585 | + | ACTTCGAGGTAAGCGGGCCAGGG | | 1 | 1 | 9 SEQ ID NO. 87 |
| (N20)NGG | 20 | 43251590 | + | GAGGTAAGCGGGCCAGGGAGTGG | | 2 | 6 | 85 SEQ ID NO. 88 |
| (N20)NGG | 20 | 43251591 | + | AGGTAAGCGGGCCAGGGAGTGGG | | 1 | 2 | 38 SEQ ID NO. 89 |
| (N20)NGG | 20 | 43251592 | + | GGTAAGCGGGCCAGGGAGTGGGG | | 1 | 3 | 47 SEQ ID NO. 90 |
| (N20)NGG | 20 | 43251595 | + | AAGCGGGCCAGGGAGTGGGGAGG | | 2 | 10 | 143 SEQ ID NO. 91 |
| (N20)NGG | 20 | 43251510 | - | GGGCCTGGTCTTCCAGGGTGTGG | | 1 | 5 | 82 SEQ ID NO. 92 |
| (N20)NGG | 20 | 43251515 | - | ATAAAGGGCCTGGTCTTCCAGGG | | 2 | 5 | 38 SEQ ID NO. 93 |

FIG. 1 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 20 | 43251516 | - | TATAAGGGCCTGGTCTTCCAGG | 1 | 3 | 20 | SEQ ID NO. 94 |
| (N20)NGG | 20 | 43251525 | - | GCAGCCTGTTATAAAGGGCCTGG | 1 | 4 | 23 | SEQ ID NO. 95 |
| (N20)NGG | 20 | 43251530 | - | CTGCCGCAGCCTGTTATAAAGG | 1 | 1 | 13 | SEQ ID NO. 96 |
| (N20)NGG | 20 | 43251531 | - | CCTGCCGCAGCCTGTTATAAAGG | 1 | 1 | 7 | SEQ ID NO. 97 |
| (N20)NGG | 20 | 43251647 | + | GACCTGGCTCTCCCCCTTCCAGG | 1 | 5 | 127 | SEQ ID NO. 98 |
| (N20)NGG | 20 | 43251650 | + | CTGGCTCTCCCCCTTCCAGGAGG | 1 | 4 | 116 | SEQ ID NO. 99 |
| (N20)NGG | 20 | 43251663 | + | TTCCAGGAGGCTGTGAAGAGCGG | 3 | 7 | 125 | SEQ ID NO. 100 |
| (N20)NGG | 20 | 43251687 | + | ATTCACCGTACTGTCCACGCCGG | 1 | 2 | 47 | SEQ ID NO. 101 |
| (N20)NGG | 20 | 43251688 | + | TTCACCGTACTGTCCACGCCGGG | 1 | 1 | 11 | SEQ ID NO. 102 |
| (N20)NGG | 20 | 43251689 | + | TCACCGTACTGTCCACGCCGGGG | 1 | 1 | 2 | SEQ ID NO. 103 |
| (N20)NGG | 20 | 43251692 | + | CCGTACTGTCCACGCCGGGGAGG | 1 | 1 | 3 | SEQ ID NO. 104 |
| (N20)NGG | 20 | 43251695 | + | TACTGTCCACGCCGGGGAGGTGG | 1 | 1 | 4 | SEQ ID NO. 105 |
| (N20)NGG | 20 | 43251696 | + | ACTGTCCACGCCGGGGAGGTGGG | 1 | 1 | 11 | SEQ ID NO. 106 |
| (N20)NGG | 20 | 43251701 | + | CCACGCCGGGGAGGTGGGCTCGG | 1 | 6 | 45 | SEQ ID NO. 107 |
| (N20)NGG | 20 | 43251719 | + | CTCGGCCGAAGTAGTAAAAGAGG | 1 | 2 | 6 | SEQ ID NO. 108 |
| (N20)NGG | 20 | 43251724 | + | CCGAAGTAGTAAAAGAGGTGAGG | 1 | 1 | 13 | SEQ ID NO. 109 |
| (N20)NGG | 20 | 43251725 | + | CGAAGTAGTAAAAGAGGTGAGGG | 1 | 2 | 51 | SEQ ID NO. 110 |
| (N20)NGG | 20 | 43251730 | + | TAGTAAAAGAGGTGAGGGCCTGG | 1 | 3 | 44 | SEQ ID NO. 111 |
| (N20)NGG | 20 | 43251731 | + | AGTAAAAGAGGTGAGGGCCTGGG | 1 | 2 | 55 | SEQ ID NO. 112 |
| (N20)NGG | 20 | 43251735 | + | AAAGAGGTGAGGGCCTGGGCTGG | 2 | 15 | 136 | SEQ ID NO. 113 |
| (N20)NGG | 20 | 43251741 | + | GTGAGGGCCTGGGCTGGCCATGG | 3 | 11 | 158 | SEQ ID NO. 114 |
| (N20)NGG | 20 | 43251742 | + | TGAGGGCCTGGGCTGGCCATGGG | 2 | 10 | 99 | SEQ ID NO. 115 |
| (N20)NGG | 20 | 43251743 | + | GAGGGCCTGGGCTGGCCATGGGG | 1 | 17 | 142 | SEQ ID NO. 116 |
| (N20)NGG | 20 | 43251627 | - | CTCCTGGAAGGGGAGAGCCAGG | 2 | 7 | 106 | SEQ ID NO. 117 |
| (N20)NGG | 20 | 43251636 | - | CTTCACAGCCTCCTGGAAGGGGG | 1 | 7 | 115 | SEQ ID NO. 118 |
| (N20)NGG | 20 | 43251637 | - | TCTTCACAGCCTCCTGGAAGGGG | 1 | 7 | 86 | SEQ ID NO. 119 |
| (N20)NGG | 20 | 43251638 | - | CTCTTCACAGCCTCCTGGAAGGG | 1 | 9 | 79 | SEQ ID NO. 120 |
| (N20)NGG | 20 | 43251639 | - | GCTCTTCACAGCCTCCTGGAAGG | 1 | 5 | 96 | SEQ ID NO. 121 |
| (N20)NGG | 20 | 43251643 | - | TGCCGCTCTTCACAGCCTCCTGG | 1 | 3 | 39 | SEQ ID NO. 122 |
| (N20)NGG | 20 | 43251670 | - | CCTCCCCGGCGTGGACAGTACGG | 1 | 1 | 6 | SEQ ID NO. 123 |
| (N20)NGG | 20 | 43251679 | - | CCGAGCCCACCTCCCCGGCGTGG | 1 | 5 | 37 | SEQ ID NO. 124 |

FIG. 1 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 20 | 43251684 | - | TTCGGCGAGCCGACCCCACTCCCGG | | 1 | 3 | 19 SEQ ID NO. 125 |
| (N20)NGG | 20 | 43251702 | - | CCTCACCTCTTTTACTACTTCGG | | 1 | 4 | 46 SEQ ID NO. 126 |
| (N20)NGG | 20 | 43252846 | + | TGGGCATCTCGCCCACAGACTGG | | 1 | 2 | 13 SEQ ID NO. 127 |
| (N20)NGG | 20 | 43252856 | + | GCCCACAGACTGGTCCCCAAGG | | 1 | 6 | 43 SEQ ID NO. 128 |
| (N20)NGG | 20 | 43252859 | + | CACAGACTGGTCCCCAAGGTGG | | 1 | 1 | 37 SEQ ID NO. 129 |
| (N20)NGG | 20 | 43252862 | + | AGACTGGTCCCCAAGGTGGTGG | | 1 | 2 | 36 SEQ ID NO. 130 |
| (N20)NGG | 20 | 43252895 | + | GAAGTACCAGCAGCAGACCGTGG | | 1 | 1 | 34 SEQ ID NO. 131 |
| (N20)NGG | 20 | 43252910 | + | GACCGTGGTAGCCATTGACCTGG | | 1 | 1 | 10 SEQ ID NO. 132 |
| (N20)NGG | 20 | 43252914 | + | GTGGTAGCCATTGACCTGCTGG | | 1 | 2 | 21 SEQ ID NO. 133 |
| (N20)NGG | 20 | 43252932 | + | GCTGGAGATGAGACCATCCCAGG | | 1 | 4 | 44 SEQ ID NO. 134 |
| (N20)NGG | 20 | 43252950 | + | CCAGGAAGCAGCCTCTTGCCTGG | | 2 | 11 | 127 SEQ ID NO. 135 |
| (N20)NGG | 20 | 43252961 | + | CCTCTTGCCTGGACATGTCCAGG | | 1 | 4 | 42 SEQ ID NO. 136 |
| (N20)NGG | 20 | 43252970 | + | TGGACATGTCCAGGCCTACCAGG | | 1 | 3 | 18 SEQ ID NO. 137 |
| (N20)NGG | 20 | 43252973 | + | ACATGTCCAGGCCTACCAGGTGG | | 1 | 6 | 45 SEQ ID NO. 138 |
| (N20)NGG | 20 | 43252974 | + | CATGTCCAGGCCTACCAGGTGGG | | 1 | 4 | 24 SEQ ID NO. 139 |
| (N20)NGG | 20 | 43252987 | + | ACCAGGTGGGTCCTGTGAGAAGG | | 1 | 6 | 35 SEQ ID NO. 140 |
| (N20)NGG | 20 | 43252992 | + | GTGGGTCCTGTGAGAAGGAATGG | | 1 | 14 | 148 SEQ ID NO. 141 |
| (N20)NGG | 20 | 43252818 | - | TGTGGGCGAGATGCCCACCCAGG | | 1 | 3 | 19 SEQ ID NO. 142 |
| (N20)NGG | 20 | 43252835 | - | ACCTTGGGGACCAGTCTGTGGG | | 1 | 2 | 23 SEQ ID NO. 143 |
| (N20)NGG | 20 | 43252835 | - | CACCTTGGGGACCAGTCTGTGG | | 1 | 3 | 29 SEQ ID NO. 144 |
| (N20)NGG | 20 | 43252848 | - | ACACAGCTCCACCACCTTGGGG | | 1 | 5 | 37 SEQ ID NO. 145 |
| (N20)NGG | 20 | 43252849 | - | TACACAGCTCCACCACCTTGGG | | 1 | 2 | 24 SEQ ID NO. 146 |
| (N20)NGG | 20 | 43252850 | - | TTACACAGCTCCACCACCTTGG | | 1 | 1 | 34 SEQ ID NO. 147 |
| (N20)NGG | 20 | 43252851 | - | CTTACACAGCTCCACCACCTTG | | 1 | 3 | 29 SEQ ID NO. 148 |
| (N20)NGG | 20 | 43252879 | - | TGGCTACCACCGTCTGCTCTGG | | 1 | 3 | 22 SEQ ID NO. 149 |
| (N20)NGG | 20 | 43252890 | - | AGCCAGGTCAATGGCTACCACGG | | 1 | 2 | 24 SEQ ID NO. 150 |
| (N20)NGG | 20 | 43252899 | - | CTCATCTCCAGCCAGGTCAATGG | | 1 | 7 | 131 SEQ ID NO. 151 |
| (N20)NGG | 20 | 43252906 | - | GGATGGTCTCATCTCCAGCCAGG | | 1 | 2 | 44 SEQ ID NO. 152 |
| (N20)NGG | 20 | 43252923 | - | CAAGAGGCTGCTTCCTGGGATGG | | 3 | 8 | 86 SEQ ID NO. 153 |
| (N20)NGG | 20 | 43252927 | - | CAGGCAAGAGGCTGCTTCCTGGG | | 2 | 7 | 85 SEQ ID NO. 154 |
| (N20)NGG | 20 | 43252928 | - | CCAGGCAAGAGGCTGCTTCCTGG | | 1 | 7 | 113 SEQ ID NO. 155 |

FIG. 1 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 20 | 43252939 | - | CCTGGACATGTCCAGGCAAGAGG | 1 | 2 | 50 | SEQ ID NO. 156 |
| (N20)NGG | 20 | 43252946 | - | TGGTAGGCCTGGACATGTCCAGG | 1 | 2 | 17 | SEQ ID NO. 157 |
| (N20)NGG | 20 | 43252957 | - | CAGGACCCACCTGGTAGGCCTGG | 1 | 3 | 33 | SEQ ID NO. 158 |
| (N20)NGG | 20 | 43252962 | - | TCTCACAGGACCCACCTGGTAGG | 1 | 2 | 28 | SEQ ID NO. 159 |
| (N20)NGG | 20 | 43252966 | - | TCCTTCTCACAGGACCCACCTGG | 1 | 6 | 55 | SEQ ID NO. 160 |
| (N20)NGG | 20 | 43254211 | + | CTACTCCTCTCCTCACACAGAGG | 1 | 5 | 119 | SEQ ID NO. 161 |
| (N20)NGG | 20 | 43254212 | + | TACTCCTCTCCTCACACAGAGGG | 1 | 10 | 105 | SEQ ID NO. 162 |
| (N20)NGG | 20 | 43254213 | + | ACTCCTCTCCTCACACAGAGGGG | 1 | 6 | 66 | SEQ ID NO. 163 |
| (N20)NGG | 20 | 43254231 | + | AGGGGACCTCACCCAGACGAGGG | 1 | 1 | 26 | SEQ ID NO. 164 |
| (N20)NGG | 20 | 43254234 | + | GGACCTCACCCAGACGAGGTGG | 1 | 1 | 21 | SEQ ID NO. 165 |
| (N20)NGG | 20 | 43254237 | + | CCTCACCCAGACGAGGTGGTGG | 1 | 2 | 40 | SEQ ID NO. 166 |
| (N20)NGG | 20 | 43254246 | + | AGACGAGGTGGTGGCCCTAGTGG | 1 | 2 | 24 | SEQ ID NO. 167 |
| (N20)NGG | 20 | 43254247 | + | GACGAGGTGGTGGCCCTAGTGTGG | 1 | 2 | 13 | SEQ ID NO. 168 |
| (N20)NGG | 20 | 43254252 | + | GGTGGTGGCCCTAGTGGGCCAGG | 1 | 2 | 48 | SEQ ID NO. 169 |
| (N20)NGG | 20 | 43254253 | + | GTGGTGGCCCTAGTGGGCCAGGG | 1 | 3 | 40 | SEQ ID NO. 170 |
| (N20)NGG | 20 | 43254261 | + | CCTAGTGGGCCAGGGCCTGCAGG | 1 | 4 | 43 | SEQ ID NO. 171 |
| (N20)NGG | 20 | 43254264 | + | AGTGGGCCAGGGCCTGCAGGAGG | 3 | 14 | 163 | SEQ ID NO. 172 |
| (N20)NGG | 20 | 43254265 | + | GTGGGCCAGGGCCTGCAGGAGGG | 1 | 14 | 225 | SEQ ID NO. 173 |
| (N20)NGG | 20 | 43254266 | + | TGGGCCAGGGCCTGCAGGAGGGG | 2 | 18 | 238 | SEQ ID NO. 174 |
| (N20)NGG | 20 | 43254267 | + | GGGCCAGGGCCTGCAGGAGGGGG | 2 | 32 | 318 | SEQ ID NO. 175 |
| (N20)NGG | 20 | 43254280 | + | CAGGAGGGGAGCGAGACTTCGG | 1 | 2 | 39 | SEQ ID NO. 176 |
| (N20)NGG | 20 | 43254281 | + | AGGAGGGGAGCGAGACTTCGGG | 1 | 2 | 35 | SEQ ID NO. 177 |
| (N20)NGG | 20 | 43254282 | + | GGAGGGGGAGCGAGACTTCGGGG | 1 | 1 | 29 | SEQ ID NO. 178 |
| (N20)NGG | 20 | 43254288 | + | GGAGCGAGACTTCGGGGTCAAGG | 1 | 2 | 20 | SEQ ID NO. 179 |
| (N20)NGG | 20 | 43254293 | + | GAGACTTCGGGGTCAAGGCCCGG | 1 | 2 | 18 | SEQ ID NO. 180 |
| (N20)NGG | 20 | 43254333 | - | GCGCCACCAGCCCAGTGAGTAGG | 1 | 1 | 15 | SEQ ID NO. 181 |
| (N20)NGG | 20 | 43254187 | - | TCTGTGTGAGGAGGAGGAGTAGG | 2 | 10 | 104 | SEQ ID NO. 182 |
| (N20)NGG | 20 | 43254188 | - | CCTGTGTGAGGAGGAGGAGTAGG | 2 | 11 | 148 | SEQ ID NO. 183 |
| (N20)NGG | 20 | 43254194 | - | GGTCCCCTCTGTGTGAGGAGAGG | 1 | 4 | 52 | SEQ ID NO. 184 |
| (N20)NGG | 20 | 43254199 | - | GGTGAGGTCCCCTCTGTGTGAGG | 1 | 3 | 51 | SEQ ID NO. 185 |
| (N20)NGG | 20 | 43254215 | - | CCACCACCTCGTCTGGGGTGAGG | 1 | 4 | 100 | SEQ ID NO. 186 |

FIG. 1 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 20 | 43254220 | - | TAGGGCCACCACCTCGTCTGGGG | 1 | 1 | 11 | SEQ ID NO. 187 |
| (N20)NGG | 20 | 43254221 | - | CTAGGGCCACCACCTCGTCTGGG | 1 | 2 | 16 | SEQ ID NO. 188 |
| (N20)NGG | 20 | 43254222 | - | ACTAGGGCCACCACCTCGTCTGG | 1 | 1 | 17 | SEQ ID NO. 189 |
| (N20)NGG | 20 | 43254238 | - | CTGCAGGGCCCTGGCCCACTAGGG | 1 | 7 | 54 | SEQ ID NO. 190 |
| (N20)NGG | 20 | 43254239 | - | CCTGCAGGGCCCTGGCCCACTAGG | 3 | 5 | 89 | SEQ ID NO. 191 |
| (N20)NGG | 20 | 43254248 | - | GCTCCCCTCCTGCAGGCCCTGG | 1 | 17 | 186 | SEQ ID NO. 192 |
| (N20)NGG | 20 | 43254254 | - | AGTCTCGCTCCCCTCCTGCAGG | 1 | 4 | 38 | SEQ ID NO. 193 |
| (N20)NGG | 20 | 43254289 | - | CATGCAGCACAGGATGGACCGGG | 1 | 3 | 34 | SEQ ID NO. 194 |
| (N20)NGG | 20 | 43254290 | - | GCATGCAGCACAGGATGGACCGG | 1 | 3 | 42 | SEQ ID NO. 195 |
| (N20)NGG | 20 | 43254295 | - | GTGCGCATGCAGCACAGGATGG | 1 | 3 | 62 | SEQ ID NO. 196 |
| (N20)NGG | 20 | 43254299 | - | GCTGGTGGCGCATGCAGCACAGG | 1 | 1 | 22 | SEQ ID NO. 197 |
| (N20)NGG | 20 | 43254314 | - | GATCCTACTCACTGGGCTGGTGG | 1 | 2 | 32 | SEQ ID NO. 198 |
| (N20)NGG | 20 | 43254317 | - | GGTGATCCTACTCACTGGGCTGG | 1 | 2 | 13 | SEQ ID NO. 199 |
| (N20)NGG | 20 | 43254321 | - | GGGCGGTGATCCTACTCACTGGG | 1 | 1 | 10 | SEQ ID NO. 200 |
| (N20)NGG | 20 | 43254322 | - | AGGGCGGTGATCCTACTCACTGG | 1 | 1 | 14 | SEQ ID NO. 201 |
| (N20)NGG | 20 | 43255096 | + | AACCCTTTCTTCCCTTCCCAGG | 1 | 11 | 148 | SEQ ID NO. 202 |
| (N20)NGG | 20 | 43255097 | + | ACCCCTTTCTTCCCTTCCCAGGG | 5 | 16 | 156 | SEQ ID NO. 203 |
| (N20)NGG | 20 | 43255098 | + | CCCCTTTCTTCCCTTCCCAGGGG | 1 | 18 | 215 | SEQ ID NO. 204 |
| (N20)NGG | 20 | 43255105 | + | CTTCCCTTCCCAGGGGCTGCCGG | 1 | 15 | 150 | SEQ ID NO. 205 |
| (N20)NGG | 20 | 43255106 | + | TTCCCTTCCCAGGGGCTGCCGGG | 2 | 11 | 144 | SEQ ID NO. 206 |
| (N20)NGG | 20 | 43255109 | + | CCTTCCCAGGGGCTGCCGGGAGG | 2 | 15 | 134 | SEQ ID NO. 207 |
| (N20)NGG | 20 | 43255120 | + | GCTGCCGGGAGGCTATCAAAAGG | 1 | 2 | 9 | SEQ ID NO. 208 |
| (N20)NGG | 20 | 43255148 | + | CTATGAGTTTGTAGAGATGAAGG | 1 | 2 | 59 | SEQ ID NO. 209 |
| (N20)NGG | 20 | 43255157 | + | TGTAGAGATGAAGGCCAAAGAGG | 1 | 7 | 68 | SEQ ID NO. 210 |
| (N20)NGG | 20 | 43255158 | + | GTAGAGATGAAGGCCAAAGAGGG | 1 | 10 | 86 | SEQ ID NO. 211 |
| (N20)NGG | 20 | 43255163 | + | GATGAAGGCCAAAGAGGGCGTGG | 1 | 1 | 33 | SEQ ID NO. 212 |
| (N20)NGG | 20 | 43255172 | + | CAAAGAGGGCGTGGTGTATGTGG | 1 | 3 | 17 | SEQ ID NO. 213 |
| (N20)NGG | 20 | 43255175 | + | AGAGGGCGTGGTGTATGTGGAGG | 1 | 3 | 39 | SEQ ID NO. 214 |
| (N20)NGG | 20 | 43255180 | + | GCGTGGTGTATGTGGAGGTGCGG | 1 | 3 | 88 | SEQ ID NO. 215 |
| (N20)NGG | 20 | 43255199 | + | GCGGTACAGTCCGCACCTGCTGG | 1 | 1 | 2 | SEQ ID NO. 216 |
| (N20)NGG | 20 | 43255214 | + | CCTGCTGGCCAACTCCAAAGTGG | 1 | 3 | 32 | SEQ ID NO. 217 |

FIG. 1 cont.

| site type | site chromosome | site start nucleotide | site strand | target site sequence with NGG | genome wide hits with 1 or less mismatches | genome wide hits with 2 or less mismatches | genome wide hits with 3 or less mismatches | |
|---|---|---|---|---|---|---|---|---|
| (N20)NGG | 20 | 43255228 | + | CCAAAGTGGAGCCAATCCCTGG | | 2 | 5 | 22 SEQ ID NO. 218 |
| (N20)NGG | 20 | 43255235 | + | GGAGCCAATCCCTGGAACCAGG | | 1 | 1 | 30 SEQ ID NO. 219 |
| (N20)NGG | 20 | 43255250 | + | GAACCAGGCTGAGTGAGTGATGG | | 1 | 4 | 65 SEQ ID NO. 220 |
| (N20)NGG | 20 | 43255251 | + | AACCAGGCTGAGTGAGTGATGGG | | 1 | 3 | 48 SEQ ID NO. 221 |
| (N20)NGG | 20 | 43255256 | + | GGCTGAGTGAGTGATGGGCCTGG | | 1 | 2 | 70 SEQ ID NO. 222 |
| (N20)NGG | 20 | 43255260 | + | GAGTGAGTGATGGGCCTGGAAGG | | 1 | 7 | 91 SEQ ID NO. 223 |
| (N20)NGG | 20 | 43255261 | + | AGTGAGTGATGGGCCTGGAAGGG | | 2 | 8 | 97 SEQ ID NO. 224 |
| (N20)NGG | 20 | 43255262 | + | GTGAGTGATGGGCCTGGAAGGGG | | 1 | 9 | 107 SEQ ID NO. 225 |
| (N20)NGG | 20 | 43255071 | - | GGGAAGGGAAGAAAGGGGTTGG | | 2 | 22 | 449 SEQ ID NO. 226 |
| (N20)NGG | 20 | 43255072 | - | TGGGAAGGGAAGAAAGGGGTTGG | | 3 | 32 | 451 SEQ ID NO. 227 |
| (N20)NGG | 20 | 43255076 | - | CCCCTGGGAAGGGAAGAAAGGGG | | 2 | 23 | 175 SEQ ID NO. 228 |
| (N20)NGG | 20 | 43255077 | - | GCCCCTGGGAAGGGAAGAAAAGG | | 2 | 13 | 169 SEQ ID NO. 229 |
| (N20)NGG | 20 | 43255078 | - | AGCCCCTGGGAAGGGAAGAAAGG | | 1 | 22 | 197 SEQ ID NO. 230 |
| (N20)NGG | 20 | 43255086 | - | CTCCCGGCAGCCCCTGGGAAGGG | | 2 | 7 | 127 SEQ ID NO. 231 |
| (N20)NGG | 20 | 43255087 | - | CCTCCCGGCAGCCCCTGGGAAGG | | 2 | 11 | 137 SEQ ID NO. 232 |
| (N20)NGG | 20 | 43255091 | - | ATAGCCTCCCGGCAGCCCCTGGG | | 1 | 2 | 20 SEQ ID NO. 233 |
| (N20)NGG | 20 | 43255092 | - | GATAGCCTCCCGGCAGCCCCTGG | | 1 | 1 | 15 SEQ ID NO. 234 |
| (N20)NGG | 20 | 43255102 | - | CGATCCTTTTGATAGCCTCCGG | | 1 | 1 | 11 SEQ ID NO. 235 |
| (N20)NGG | 20 | 43255125 | - | CTTCATCTCTACAAACTCATAGG | | 3 | 5 | 67 SEQ ID NO. 236 |
| (N20)NGG | 20 | 43255149 | - | CACATACACCACGCCCTCTTTGG | | 1 | 1 | 15 SEQ ID NO. 237 |
| (N20)NGG | 20 | 43255187 | - | TTGGAGTTGGCCAGCAGGTGCGG | | 1 | 5 | 56 SEQ ID NO. 238 |
| (N20)NGG | 20 | 43255192 | - | CCACTTTGGAGTTGGCCAGAGG | | 1 | 3 | 26 SEQ ID NO. 239 |
| (N20)NGG | 20 | 43255200 | - | GATTGGCTCCACTTTGGAGTTGG | | 1 | 5 | 22 SEQ ID NO. 240 |
| (N20)NGG | 20 | 43255206 | - | CCAGGGATTGGCTCCACTTTGG | | 1 | 2 | 18 SEQ ID NO. 241 |
| (N20)NGG | 20 | 43255217 | - | TCAGCCTGGTTCCAGGGGATTGG | | 1 | 4 | 79 SEQ ID NO. 242 |
| (N20)NGG | 20 | 43255222 | - | CTCACTCAGCCTGGTTCCAGGGG | | 1 | 5 | 69 SEQ ID NO. 243 |
| (N20)NGG | 20 | 43255223 | - | ACTCACTCAGCCTGGTTCCAGGG | | 1 | 7 | 79 SEQ ID NO. 244 |
| (N20)NGG | 20 | 43255224 | - | CACTCACTCAGCCTGGTTCCAGG | | 1 | 3 | 62 SEQ ID NO. 245 |
| (N20)NGG | 20 | 43255231 | - | GGCCATCACTCACTCAGCCTGG | | 1 | 2 | 39 SEQ ID NO. 246 |
| (N20)NGG | 20 | 43257687 | + | CCACTCACTGTTTTGTTTCCAGG | | 1 | 5 | 76 SEQ ID NO. 247 |
| (N20)NGG | 20 | 43257690 | + | CTCACTGTTTTGTTTCCAGGAGG | | 1 | 6 | 88 SEQ ID NO. 248 |

FIG. 1 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 20 | 43257695 | + | TGTTTGTTTCCAGGAGGAGAGG | 1 | 1 | 7 | 117 SEQ ID NO. 249 |
| (N20)NGG | 20 | 43257696 | + | GTTTTGTTTCCAGGACGAGAGGG | 1 | 1 | 11 | 95 SEQ ID NO. 250 |
| (N20)NGG | 20 | 43257724 | + | CCTCCCAGCTAACACAGCAGAGG | 1 | 1 | 5 | 52 SEQ ID NO. 251 |
| (N20)NGG | 20 | 43257725 | + | CTCCCAGCTAACACAGCAGAGGG | 1 | 1 | 5 | 66 SEQ ID NO. 252 |
| (N20)NGG | 20 | 43257726 | + | TCCCAGCTAACACAGCAGAGGGG | 1 | 1 | 7 | 53 SEQ ID NO. 253 |
| (N20)NGG | 20 | 43257743 | + | GAGGGCTGCTGAACGTCATTGG | 1 | 1 | 1 | 28 SEQ ID NO. 254 |
| (N20)NGG | 20 | 43257748 | + | GCTGCTGAACGTCATTGGCATG | 1 | 1 | 2 | 26 SEQ ID NO. 255 |
| (N20)NGG | 20 | 43257778 | + | GCTCACCCTTCCAGACTTCCTGG | 1 | 1 | 5 | 47 SEQ ID NO. 256 |
| (N20)NGG | 20 | 43257832 | + | GTGAGTTGCCCCCAACCCACAGG | 1 | 2 | 2 | 28 SEQ ID NO. 257 |
| (N20)NGG | 20 | 43257662 | - | GGAAACAAAACAGTGAGTGGTGG | 1 | 2 | 9 | 97 SEQ ID NO. 258 |
| (N20)NGG | 20 | 43257665 | - | CCTGAAACAAAACAGTGAGTGG | 1 | 2 | 5 | 106 SEQ ID NO. 259 |
| (N20)NGG | 20 | 43257683 | - | GAGGCGATCCCCTCTCCTCCTGG | 1 | 1 | 4 | 21 SEQ ID NO. 260 |
| (N20)NGG | 20 | 43257701 | - | CCTCTGCTGTGTTAGCTGGGAGG | 1 | 1 | 7 | 73 SEQ ID NO. 261 |
| (N20)NGG | 20 | 43257702 | - | CCTCTGCTGTGTTAGCTGGGAGG | 1 | 1 | 4 | 56 SEQ ID NO. 262 |
| (N20)NGG | 20 | 43257705 | - | GCCCCTCTGCTGTGTTAGCTGG | 1 | 1 | 3 | 34 SEQ ID NO. 263 |
| (N20)NGG | 20 | 43257706 | - | AGCCCCTCTGCTGTGTTAGCTGG | 1 | 1 | 4 | 32 SEQ ID NO. 264 |
| (N20)NGG | 20 | 43257754 | - | AGGAAGTCTGGAAGGGTGAGCGG | 1 | 1 | 8 | 158 SEQ ID NO. 265 |
| (N20)NGG | 20 | 43257761 | - | CTTGGCCAGGAAGTCTGGAAGG | 1 | 1 | 2 | 37 SEQ ID NO. 266 |
| (N20)NGG | 20 | 43257762 | - | ACTTGGCCAGGAAGTCTGGAAGG | 1 | 1 | 4 | 48 SEQ ID NO. 267 |
| (N20)NGG | 20 | 43257766 | - | TCAAACTTGGCCAGGAAGTCTGG | 1 | 1 | 4 | 39 SEQ ID NO. 268 |
| (N20)NGG | 20 | 43257774 | - | TGTAGTAGTCAAACTTGGCCAGG | 1 | 1 | 1 | 16 SEQ ID NO. 269 |
| (N20)NGG | 20 | 43257779 | - | AGGCATGTAGTAGTCAAACTTGG | 1 | 1 | 3 | 33 SEQ ID NO. 270 |
| (N20)NGG | 20 | 43257799 | + | GGGGCAACTCACGGATAGCAGG | 1 | 1 | 1 | 2 SEQ ID NO. 271 |
| (N20)NGG | 20 | 43264867 | + | TCTTCCCCTGCCCCCTTGCAGGTGG | 1 | 1 | 11 | 106 SEQ ID NO. 272 |
| (N20)NGG | 20 | 43264870 | + | TCCCCTGCCCCCTTGCAGGTGG | 1 | 1 | 5 | 90 SEQ ID NO. 273 |
| (N20)NGG | 20 | 43264892 | + | GAACTGCATGTCCACCTAGACG | 1 | 1 | 1 | 25 SEQ ID NO. 274 |
| (N20)NGG | 20 | 43264925 | + | CCTGAAACCATCTTATACTATGG | 1 | 1 | 5 | 49 SEQ ID NO. 275 |
| (N20)NGG | 20 | 43264929 | + | AAACCATCTTATACTATGGCAGG | 1 | 1 | 2 | 23 SEQ ID NO. 276 |
| (N20)NGG | 20 | 43264849 | - | TCCACCTGCAAGGGGCAGGGGG | 1 | 1 | 12 | 174 SEQ ID NO. 277 |
| (N20)NGG | 20 | 43264850 | - | TTCCACCTGCAAGGGGCAGGGG | 1 | 1 | 5 | 64 SEQ ID NO. 278 |
| (N20)NGG | 20 | 43264851 | - | GTTCCACCTGCAAGGGGCAGGG | 1 | 1 | 6 | 42 SEQ ID NO. 279 |

FIG. 1 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 20 | 43264852 | - | AGTTCCACCTGCAAGGGGCAGG | 1 | 1 | 41 | SEQ ID NO. 280 |
| (N20)NGG | 20 | 43264856 | - | ATGCAGTTCCACCTGCAAGGGG | 1 | 4 | 33 | SEQ ID NO. 281 |
| (N20)NGG | 20 | 43264857 | - | CATGCAGTTCCACCTGCAAGGG | 1 | 2 | 29 | SEQ ID NO. 282 |
| (N20)NGG | 20 | 43264858 | - | ACATGCAGTTCCACCTGCAAGG | 1 | 1 | 38 | SEQ ID NO. 283 |
| (N20)NGG | 20 | 43264859 | - | GACATGCAGTTCCACCTGCAAGG | 1 | 2 | 51 | SEQ ID NO. 284 |
| (N20)NGG | 20 | 43264881 | - | GCTTGATGGATCCGTCTAGGTGG | 1 | 2 | 5 | SEQ ID NO. 285 |
| (N20)NGG | 20 | 43264884 | - | CAGGCTTGATGGATCCGTCTAGG | 1 | 1 | 5 | SEQ ID NO. 286 |
| (N20)NGG | 20 | 43264895 | - | TAAGATGGTTTCAGGCTTGATGG | 1 | 1 | 26 | SEQ ID NO. 287 |
| (N20)NGG | 20 | 43264903 | - | CCATAGTATAAGATGGTTTCAGG | 1 | 1 | 23 | SEQ ID NO. 288 |
| (N20)NGG | 20 | 43264910 | - | TTACCTGCCATAGTATAAGATGG | 1 | 5 | 28 | SEQ ID NO. 289 |
| (N20)NGG | 20 | 43280218 | + | CGGGGCGCACAGAGGGCACCATGG | 1 | 1 | 14 | SEQ ID NO. 290 |
| (N20)NGG | 20 | 43280261 | + | AAGCCCAAAAGTGAGCGCGCGCGG | 1 | 1 | 7 | SEQ ID NO. 291 |
| (N20)NGG | 20 | 43280262 | + | AGCCCAAAAGTGAGCGCGCGCGGG | 1 | 1 | 4 | SEQ ID NO. 292 |
| (N20)NGG | 20 | 43280263 | + | GCCCAAAAGTGAGCGCGCGCGGGG | 1 | 1 | 8 | SEQ ID NO. 293 |
| (N20)NGG | 20 | 43280264 | + | CCCAAAAGTGAGCGCGCGCGGGGG | 1 | 1 | 11 | SEQ ID NO. 294 |
| (N20)NGG | 20 | 43280270 | + | GTGAGCGCGCGCGGGGCTCCGG | 1 | 3 | 41 | SEQ ID NO. 295 |
| (N20)NGG | 20 | 43280271 | + | TGAGCGCGCGCGGGGCTCCGG | 1 | 3 | 24 | SEQ ID NO. 296 |
| (N20)NGG | 20 | 43280272 | + | GAGCGCGCGCGGGGCTCCGGG | 1 | 3 | 44 | SEQ ID NO. 297 |
| (N20)NGG | 20 | 43280195 | - | CATGGTGCCCTGTGCGCCCGG | 1 | 2 | 15 | SEQ ID NO. 298 |
| (N20)NGG | 20 | 43280213 | - | GAAGGCGGGCGTCTGGGCCATGG | 1 | 2 | 26 | SEQ ID NO. 299 |
| (N20)NGG | 20 | 43280219 | - | CTTGTCGAAGGCGGGCGTCTGG | 1 | 1 | 6 | SEQ ID NO. 300 |
| (N20)NGG | 20 | 43280220 | - | GCTTGTCGAAGGCGGGCGTCGG | 1 | 1 | 9 | SEQ ID NO. 301 |
| (N20)NGG | 20 | 43280227 | - | ACTTTGGGCTTGTCGAAGGCGG | 1 | 2 | 17 | SEQ ID NO. 302 |
| (N20)NGG | 20 | 43280228 | - | CACTTTGGGCTTGTCGAAGGCGG | 1 | 2 | 18 | SEQ ID NO. 303 |
| (N20)NGG | 20 | 43280231 | - | GCTCACTTTGGGCTTGTCGAAGG | 1 | 1 | 21 | SEQ ID NO. 304 |
| (N20)NGG | 20 | 43280242 | - | CCCCGCGGCGCTCACTTTGG | 1 | 1 | 9 | SEQ ID NO. 305 |
| (N20)NGG | 20 | 43280243 | - | GCCCCGCGGCGCTCACTTTGG | 2 | 6 | 11 | SEQ ID NO. 306 |

FIG. 1 cont.

| site_type | site_chr omosome | site_start nucleotide | site_s trand | target site sequence with NGG | genome_wide hits_with_ 1_or_less_m ismatches | genome_wide hits_with_2 _or_less_mism atches | genome_wide hits_with_3 _or_less_mism atches | | |
|---|---|---|---|---|---|---|---|---|---|
| (N20)NGG | 1 | 33476443 | + | TATTTCAGCCTAGTATCAGAAGG | 1 | 2 | 38 | SEQ ID NO. | 307 |
| (N20)NGG | 1 | 33476448 | + | CAGCCTAGTATCAGAAGGCCAGG | 2 | 4 | 49 | SEQ ID NO. | 308 |
| (N20)NGG | 1 | 33476415 | - | GATACTAGGCTGAAATAGAGAGG | 1 | 2 | 28 | SEQ ID NO. | 309 |
| (N20)NGG | 1 | 33476429 | - | TCGCCTGGCCTTCTGATACTAGG | 2 | 3 | 20 | SEQ ID NO. | 310 |
| (N20)NGG | 1 | 33478814 | + | TCTTCCTGTTCTCAGATCACCGG | 4 | 452 | 2834 | SEQ ID NO. | 311 |
| (N20)NGG | 1 | 33478815 | + | CTTCCTGTTCTCAGATCACCGGG | 2 | 5 | 408 | SEQ ID NO. | 312 |
| (N20)NGG | 1 | 33478816 | + | TTCCTGTTCTCAGATCACCGGGG | 1 | 1 | 25 | SEQ ID NO. | 313 |
| (N20)NGG | 1 | 33478852 | + | TCGATCAGATGATAATGAAAAGG | 2 | 3 | 34 | SEQ ID NO. | 314 |
| (N20)NGG | 1 | 33478914 | + | CCCCACTCATAGAGTACTACAGG | 2 | 2 | 8 | SEQ ID NO. | 315 |
| (N20)NGG | 1 | 33478920 | + | TCATAGAGTACTACAGGAAACGG | 2 | 2 | 44 | SEQ ID NO. | 316 |
| (N20)NGG | 1 | 33478921 | + | CATAGAGTACTACAGGAAACGGG | 2 | 2 | 35 | SEQ ID NO. | 317 |
| (N20)NGG | 1 | 33478922 | + | ATAGAGTACTACAGGAAACGGGG | 2 | 2 | 26 | SEQ ID NO. | 318 |
| (N20)NGG | 1 | 33478923 | + | TAGAGTACTACAGGAAACGGGGG | 2 | 3 | 11 | SEQ ID NO. | 319 |
| (N20)NGG | 1 | 33479014 | + | CAAAGCCACATGTAAAGACTTGG | 1 | 6 | 64 | SEQ ID NO. | 320 |
| (N20)NGG | 1 | 33478796 | - | TTCCCGGTGATCTGAGAACAGG | 1 | 1 | 13 | SEQ ID NO. | 321 |
| (N20)NGG | 1 | 33478811 | - | TCGACGGATCAAGGGTTCCCCGG | 2 | 2 | 2 | SEQ ID NO. | 322 |
| (N20)NGG | 1 | 33478819 | - | TCATCTGATCGACGGATCAAGG | 2 | 2 | 4 | SEQ ID NO. | 323 |
| (N20)NGG | 1 | 33478820 | - | ATCATCTGATCGACGGATCAAGG | 2 | 3 | 9 | SEQ ID NO. | 324 |
| (N20)NGG | 1 | 33478827 | - | TTTTCATTATCATCTGATCGACGG | 2 | 3 | 41 | SEQ ID NO. | 325 |
| (N20)NGG | 1 | 33478853 | - | GGCTTGCAGCGGATTTTCAAGG | 1 | 3 | 16 | SEQ ID NO. | 326 |
| (N20)NGG | 1 | 33478863 | - | GAGTGTGGTAGGCTTGCAGGCGG | 2 | 4 | 44 | SEQ ID NO. | 327 |
| (N20)NGG | 1 | 33478866 | - | TTTGAGTGTGGTAGGCTTGCAGG | 2 | 2 | 17 | SEQ ID NO. | 328 |
| (N20)NGG | 1 | 33478874 | - | TGGGGTGGTTTGAGTGTGGTAGG | 2 | 6 | 77 | SEQ ID NO. | 329 |
| (N20)NGG | 1 | 33478878 | - | TGAGTGGGGTGGTTTGAGTGTGG | 2 | 5 | 86 | SEQ ID NO. | 330 |
| (N20)NGG | 1 | 33478889 | - | GTAGTACTCTATGAGTGGGGTGG | 2 | 2 | 15 | SEQ ID NO. | 331 |
| (N20)NGG | 1 | 33478892 | - | CTTGTAGTACTCTATGAGTGGGG | 2 | 2 | 16 | SEQ ID NO. | 332 |
| (N20)NGG | 1 | 33478893 | - | TCCTGTAGTACTCTATGAGTGG | 2 | 3 | 23 | SEQ ID NO. | 333 |
| (N20)NGG | 1 | 33478894 | - | TTCCTGTAGTACTCTATGAGTGG | 1 | 2 | 11 | SEQ ID NO. | 334 |
| (N20)NGG | 1 | 33478926 | - | GGGATGCATCGATGGCGGAGTGG | 2 | 2 | 43 | SEQ ID NO. | 335 |
| (N20)NGG | 1 | 33478931 | - | GGTCTGGGATGCATCGATGGCGG | 1 | 4 | 26 | SEQ ID NO. | 336 |
| (N20)NGG | 1 | 33478934 | - | GGGGGTCTGGGATGCATCGATGG | 2 | 2 | 3 | SEQ ID NO. | 337 |
| (N20)NGG | 1 | 33478946 | - | GAACACGACATCGGGGGTCTGG | 2 | 2 | 3 | SEQ ID NO. | 338 |
| (N20)NGG | 1 | 33478947 | - | CGAACACGACATCGGGGGTCTGG | 2 | 2 | 3 | SEQ ID NO. | 339 |
| (N20)NGG | 1 | 33478952 | - | GCTTGCGAACACGACATCGGGGG | 2 | 2 | 3 | SEQ ID NO. | 340 |
| (N20)NGG | 1 | 33478953 | - | TGCTTGCGAACACGACATCGGGG | 2 | 3 | 4 | SEQ ID NO. | 341 |
| (N20)NGG | 1 | 33478954 | - | ATGCTTGCGAACACGACATCGGG | 2 | 2 | 37 | SEQ ID NO. | 342 |
| (N20)NGG | 1 | 33478955 | - | GATGCTTGCGAACACGACATCGG | 2 | 2 | 5 | SEQ ID NO. | 343 |
| (N20)NGG | 1 | 33478977 | - | TGGCTTTGGAAGGCTGCTAGG | 3 | 9 | 93 | SEQ ID NO. | 344 |

FIG. 2

| site_type | site_chromosome | site_start_nucleotide | site_strand | target site sequence with NGG | genome_wide_hits_with_1_or_less_mismatches | genome_wide_hits_with_2_or_less_mismatches | genome_wide_hits_with_3_or_less_mismatches | | |
|---|---|---|---|---|---|---|---|---|---|
| (N20)NGG | 1 | 33478985 | - | TTTACATGTGGCTTTGAGAAGG | 2 | | 4 | 94 | SEQ ID NO. 345 |
| (N20)NGG | 1 | 33478991 | - | CAAGTCTTTACATGTGGCTTTGG | 2 | | 3 | 39 | SEQ ID NO. 346 |
| (N20)NGG | 1 | 33478997 | - | CATAACCAAGTCTTTACATGTGG | 1 | | 1 | 29 | SEQ ID NO. 347 |
| (N20)NGG | 1 | 33480122 | + | ATATTCATTTGTGTCTTTCAGG | 1 | | 3 | 129 | SEQ ID NO. 348 |
| (N20)NGG | 1 | 33480142 | + | AGGCTGATTCACCCCAAGAGTGG | 1 | | 1 | 23 | SEQ ID NO. 349 |
| (N20)NGG | 1 | 33480159 | + | GAGTGGCCGTTCCTACCACGAGG | 2 | | 2 | 6 | SEQ ID NO. 350 |
| (N20)NGG | 1 | 33480209 | + | AAGATGACGTATGTAAACTCAGG | 1 | | 1 | 11 | SEQ ID NO. 351 |
| (N20)NGG | 1 | 33480131 | - | GGTAGGAACGGCCACTCTTGGGG | 2 | | 2 | 15 | SEQ ID NO. 352 |
| (N20)NGG | 1 | 33480132 | - | TGGTAGGAACGGCCACTCTTGGG | 2 | | 2 | 13 | SEQ ID NO. 353 |
| (N20)NGG | 1 | 33480133 | - | GTGGTAGGAACGGCCACTCTTGG | 2 | | 2 | 62 | SEQ ID NO. 354 |
| (N20)NGG | 1 | 33480143 | - | TGAACTCCTGCGTGGTAGGAACGG | 2 | | 3 | 20 | SEQ ID NO. 355 |
| (N20)NGG | 1 | 33480148 | - | AGGGTTGAACTCCTCGTGGTAGG | 2 | | 2 | 10 | SEQ ID NO. 356 |
| (N20)NGG | 1 | 33480152 | - | TTGGAGGGTTGAACTCCTCGTGG | 2 | | 2 | 11 | SEQ ID NO. 357 |
| (N20)NGG | 1 | 33480167 | - | CTTTCATGGGCTCTTTTGGAGGG | 2 | | 6 | 59 | SEQ ID NO. 358 |
| (N20)NGG | 1 | 33480168 | - | TCTTTCATGGGCTCTTTTGGAGG | 2 | | 4 | 62 | SEQ ID NO. 359 |
| (N20)NGG | 1 | 33480171 | - | TCATCTTTCATGGGCTCTTTTGG | 2 | | 4 | 61 | SEQ ID NO. 360 |
| (N20)NGG | 1 | 33480180 | - | TTACATACGTCATCTTTCATGGG | 1 | | 1 | 28 | SEQ ID NO. 361 |
| (N20)NGG | 1 | 33480181 | - | TTTACATACGTCATCTTTCATGG | 1 | | 3 | 43 | SEQ ID NO. 362 |
| (N20)NGG | 1 | 33486982 | + | TTTCAGCTCGATGACCTCATGG | 1 | | 2 | 15 | SEQ ID NO. 363 |
| (N20)NGG | 1 | 33486990 | + | TCGATGACCTCATGGAGAAGAGG | 3 | | 4 | 27 | SEQ ID NO. 364 |
| (N20)NGG | 1 | 33487058 | + | CTGCTGATCCGAAGAATCACAGG | 2 | | 3 | 23 | SEQ ID NO. 365 |
| (N20)NGG | 1 | 33487062 | + | TGATCCGAAGAATCACAGGAAGG | 2 | | 2 | 27 | SEQ ID NO. 366 |
| (N20)NGG | 1 | 33487079 | + | GGAAGGTATTTGTCCCTTGAAGG | 1 | | 2 | 30 | SEQ ID NO. 367 |
| (N20)NGG | 1 | 33486949 | - | TCGAGCTGTAAAAGAATGTGTGG | 1 | | 1 | 22 | SEQ ID NO. 368 |
| (N20)NGG | 1 | 33486975 | - | TCTCTTTTCCTCTTCTCCATGAGG | 4 | | 20 | 282 | SEQ ID NO. 369 |
| (N20)NGG | 1 | 33487026 | - | TTCGGATCAGCAGAGAGTCTGGG | 2 | | 4 | 14 | SEQ ID NO. 370 |
| (N20)NGG | 1 | 33487027 | - | CTTCGGATCAGCAGAGAGTCTGG | 2 | | 3 | 16 | SEQ ID NO. 371 |
| (N20)NGG | 1 | 33487044 | - | AATACCTTCCTGTAACTTCCAGG | 1 | | 5 | 70 | SEQ ID NO. 372 |
| (N20)NGG | 1 | 33487193 | + | CTATTTTGTTCCTAACTTCCAGG | 1 | | 2 | 84 | SEQ ID NO. 373 |
| (N20)NGG | 1 | 33487208 | + | CTTCCAGGTGAGTGATGAAATGG | 1 | | 6 | 75 | SEQ ID NO. 374 |
| (N20)NGG | 1 | 33487214 | + | GGTGAGTGATGAAATGGTAGTGG | 3 | | 5 | 43 | SEQ ID NO. 375 |
| (N20)NGG | 1 | 33487235 | + | GGAGCTCATTGAAGAAGAATTTGG | 3 | | 4 | 77 | SEQ ID NO. 376 |
| (N20)NGG | 1 | 33487257 | + | GAGACCCCCTTGTGCAAAAATGG | 2 | | 4 | 39 | SEQ ID NO. 377 |
| (N20)NGG | 1 | 33487268 | + | GTGCAAAAATGGTTTTCTTCTGG | 3 | | 7 | 58 | SEQ ID NO. 378 |
| (N20)NGG | 1 | 33487272 | + | AAAAATGGTTTTCTTCTGGATGG | 3 | | 8 | 176 | SEQ ID NO. 379 |
| (N20)NGG | 1 | 33487282 | + | TTCTTCTGGATGGCTTCCCTCGG | 3 | | 18 | 115 | SEQ ID NO. 380 |
| (N20)NGG | 1 | 33487291 | + | ATGGCTTCCCTCGGACTGTGAGG | 3 | | 4 | 29 | SEQ ID NO. 381 |
| (N20)NGG | 1 | 33487295 | + | CTTCCCTCGGACTGTGAGGCAGG | 3 | | 5 | 27 | SEQ ID NO. 382 |

FIG. 2 cont.

| site type | site_chr onosome | site_start_ nucleotide | site_s trand | target site sequence with NGG | genome_wide_ hits_with_ 1_or_less_m ismatches | genome_wide_ hits_with_2_ or_less_mism atches | genome_wide_ hits_with_3_ or_less_mism atches | | |
|---|---|---|---|---|---|---|---|---|---|
| (N20)NGG | 1 | 33487304 | + | GACTGTGAGGCAGGCAGAAATGG | 3 | 3 | 13 | 146 | SEQ ID NO. 383 |
| (N20)NGG | 1 | 33487307 | + | TGTGAGGCAGGCAGAAATGGTGG | | 1 | 19 | 158 | SEQ ID NO. 384 |
| (N20)NGG | 1 | 33487308 | + | GTGAGGCAGGCAGAAATGGTGGG | | 1 | 6 | 94 | SEQ ID NO. 385 |
| (N20)NGG | 1 | 33487181 | - | TCATCACTCACCTGGAAGTTAGG | 1 | 1 | 3 | 50 | SEQ ID NO. 386 |
| (N20)NGG | 1 | 33487189 | - | CTACCATTTCATCACTCACCTGG | | 4 | 5 | 32 | SEQ ID NO. 387 |
| (N20)NGG | 1 | 33487239 | - | AAAACCATTTTGCACAAGGGGG | | 3 | 5 | 70 | SEQ ID NO. 388 |
| (N20)NGG | 1 | 33487240 | - | GAAACCATTTTGCACAAGGGG | | 3 | 5 | 73 | SEQ ID NO. 389 |
| (N20)NGG | 1 | 33487241 | - | AGAAAACCATTTTGCACAAGGG | 3 | 3 | 12 | 122 | SEQ ID NO. 390 |
| (N20)NGG | 1 | 33487242 | - | AAGAAAACCATTTTGCACAAGG | | 3 | 6 | 134 | SEQ ID NO. 391 |
| (N20)NGG | 1 | 33487276 | - | CTGCCTGCCTCACAGTCCGAGG | | 3 | 14 | 388 | SEQ ID NO. 392 |
| (N20)NGG | 1 | 33487277 | - | TCTGCCTGCCTCACAGTCCAGG | | 3 | 8 | 84 | SEQ ID NO. 393 |
| (N20)NGG | 1 | 33490042 | + | GTTTTTGTCTTCCTCTCTGTAGG | | 1 | 18 | 183 | SEQ ID NO. 394 |
| (N20)NGG | 1 | 33490054 | + | CTCTCTGTAGGCACCCAGATTGG | | 1 | 2 | 25 | SEQ ID NO. 395 |
| (N20)NGG | 1 | 33490088 | + | TGTGTCTGCCATTTAGCTACTGG | | 2 | 6 | 41 | SEQ ID NO. 396 |
| (N20)NGG | 1 | 33490089 | + | GTGTCTGCCATTTAGCTACTGGG | | 2 | 7 | 36 | SEQ ID NO. 397 |
| (N20)NGG | 1 | 33490090 | + | TGTCTGCCATTTAGCTACTGGGG | | 3 | 4 | 44 | SEQ ID NO. 398 |
| (N20)NGG | 1 | 33490101 | + | TAGCTACTGGGGACATGCTGAGG | | 2 | 3 | 37 | SEQ ID NO. 399 |
| (N20)NGG | 1 | 33490102 | + | AGCTACTGGGGACATGCTGAGGG | | 2 | 4 | 51 | SEQ ID NO. 400 |
| (N20)NGG | 1 | 33490108 | + | TGGGGACATGCTGAGGGCCATGG | | 3 | 8 | 96 | SEQ ID NO. 401 |
| (N20)NGG | 1 | 33490111 | + | GGACATGCTGAGGGCCATGGTGG | | 3 | 6 | 74 | SEQ ID NO. 402 |
| (N20)NGG | 1 | 33490118 | + | CTGAGGGCCATGGTGCCTTCTGG | | 4 | 12 | 93 | SEQ ID NO. 403 |
| (N20)NGG | 1 | 33490130 | + | GTGGCTTCTGGCTCAGAGCTAGG | | 4 | 8 | 79 | SEQ ID NO. 404 |
| (N20)NGG | 1 | 33490144 | + | AGAGCTAGGAAAAAAGCTGAAGG | | 2 | 6 | 111 | SEQ ID NO. 405 |
| (N20)NGG | 1 | 33490153 | + | AAAAAAGCTGAAGGCAACTATGG | | 1 | 5 | 175 | SEQ ID NO. 406 |
| (N20)NGG | 1 | 33490160 | + | CTGAAGGCAACTATGATGCTGG | | 1 | 3 | 27 | SEQ ID NO. 407 |
| (N20)NGG | 1 | 33490161 | + | TGAAGGCAACTATGATGCTGGG | | 3 | 4 | 32 | SEQ ID NO. 408 |
| (N20)NGG | 1 | 33490168 | + | AACTATGGATGCTGGGAAACTGG | | 3 | 8 | 44 | SEQ ID NO. 409 |
| (N20)NGG | 1 | 33490172 | + | ATGGATGCTGGGAAACTGGTAGG | | 3 | 4 | 72 | SEQ ID NO. 410 |
| (N20)NGG | 1 | 33490177 | + | TGCTGGGAAACTGGTAGGTTTGG | | 2 | 1 | 41 | SEQ ID NO. 411 |
| (N20)NGG | 1 | 33490180 | + | TGGGAAACTGGTAGGTTTGGTGG | | 4 | 3 | 43 | SEQ ID NO. 412 |
| (N20)NGG | 1 | 33490031 | - | CAATCTGGTGCCTACAGAGAGG | | 1 | 1 | 22 | SEQ ID NO. 413 |
| (N20)NGG | 1 | 33490045 | - | CAGAAGTTTTCAGCCAATCTGG | | 3 | 4 | 65 | SEQ ID NO. 414 |
| (N20)NGG | 1 | 33490046 | - | ACAGAAGTTTTCAGCCAATCTG | | 3 | 8 | 40 | SEQ ID NO. 415 |
| (N20)NGG | 1 | 33490074 | - | GCATGTCCCAGTAGCTAAATGG | | 2 | 4 | 24 | SEQ ID NO. 416 |
| (N20)NGG | 1 | 33490103 | - | CTCTGAGCCAGAAGCCACCATGG | | 5 | 13 | 113 | SEQ ID NO. 417 |
| (N20)NGG | 1 | 33502333 | + | GTGCAGTGAGAGACTTCGGCGG | | 2 | 4 | 28 | SEQ ID NO. 418 |
| (N20)NGG | 1 | 33502339 | + | GTGAGAGACTTCGGCGGACATGG | | 2 | 3 | 8 | SEQ ID NO. 419 |
| (N20)NGG | 1 | 33502357 | + | CATGCTCCCAGCGTGCCAGCGG | | 3 | 6 | 37 | SEQ ID NO. 420 |

FIG. 2 cont.

| site_type | site_chr omosome | site_start nucleotide | site_s trand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 1 | 33502379 | + | GCAGAACCCGAGTATCCTAAAGG | 3 | 3 | 19 | SEQ ID NO. 421 |
| (N20)NGG | 1 | 33502386 | + | CCGAGTATCCTAAAGGCATCCGG |  | 4 | 9 | SEQ ID NO. 422 |
| (N20)NGG | 1 | 33502387 | + | CGAGTATCCTAAAGGCATCCGGG | 2 | 2 | 10 | SEQ ID NO. 423 |
| (N20)NGG | 1 | 33502399 | + | AGGCATCCGGGCCGTGCTGCTGG | 2 | 2 | 13 | SEQ ID NO. 424 |
| (N20)NGG | 1 | 33502400 | + | GGCATCCGGGCCGTGCTGCTGGG | 2 | 2 | 12 | SEQ ID NO. 425 |
| (N20)NGG | 1 | 33502401 | + | GCATCCGGGCCGTGCTGCTGGGG | 2 | 3 | 22 | SEQ ID NO. 426 |
| (N20)NGG | 1 | 33502409 | + | GCCGTGCTGCTGGGGCCTCCCGG | 3 | 5 | 80 | SEQ ID NO. 427 |
| (N20)NGG | 1 | 33502410 | + | CCGTGCTGCTGGGGCCTCCCGGG | 3 | 14 | 165 | SEQ ID NO. 428 |
| (N20)NGG | 1 | 33502411 | + | CGTGCTGCTGGGGCCTCCCGGGG | 2 | 3 | 50 | SEQ ID NO. 429 |
| (N20)NGG | 1 | 33502415 | + | CTGCTGGGGCCTCCCGGGGCCGG | 3 | 27 | 142 | SEQ ID NO. 430 |
| (N20)NGG | 1 | 33502421 | + | GGGCCTCCCGGGGCCGGTAAAGG | 3 | 5 | 22 | SEQ ID NO. 431 |
| (N20)NGG | 1 | 33502422 | + | GGCCTCCCGGGGCCGGTAAAGGG | 1 | 3 | 15 | SEQ ID NO. 432 |
| (N20)NGG | 1 | 33502429 | + | CGGGGCCGGTAAAGGGACCCAGG | 1 | 3 | 11 | SEQ ID NO. 433 |
| (N20)NGG | 1 | 33502436 | + | GGTAAAGGGACCCAGGTGAGCGG | 1 | 3 | 55 | SEQ ID NO. 434 |
| (N20)NGG | 1 | 33502440 | + | AAGGGACCCAGGTGAGCGCAGG | 1 | 1 | 29 | SEQ ID NO. 435 |
| (N20)NGG | 1 | 33502445 | + | ACCCAGGTGAGCGCAGGACTGG | 1 | 3 | 43 | SEQ ID NO. 436 |
| (N20)NGG | 1 | 33502446 | + | CCCAGGTGAGCGGCAGGACTGGG | 1 | 7 | 55 | SEQ ID NO. 437 |
| (N20)NGG | 1 | 33502451 | + | GTGAGCGGCAGGACTGGGCTTGG | 1 | 5 | 101 | SEQ ID NO. 438 |
| (N20)NGG | 1 | 33502342 | - | GGTTCTGCCGCTGGCACGCTGGG | 3 | 3 | 16 | SEQ ID NO. 439 |
| (N20)NGG | 1 | 33502343 | - | GGGTTCTGCCGCTGGCACGCTGG | 3 | 3 | 14 | SEQ ID NO. 440 |
| (N20)NGG | 1 | 33502351 | - | GGATACTCGGGTTCTGCCGCTGG | 3 | 3 | 9 | SEQ ID NO. 441 |
| (N20)NGG | 1 | 33502363 | - | CGGATGCCTTTAGGATACTCGGG | 2 | 2 | 11 | SEQ ID NO. 442 |
| (N20)NGG | 1 | 33502364 | - | CCGGATGCCTTTAGGATACTCGG | 2 | 3 | 12 | SEQ ID NO. 443 |
| (N20)NGG | 1 | 33502372 | - | AGCACGGCCCGGATGCCTTTAGG | 2 | 2 | 17 | SEQ ID NO. 444 |
| (N20)NGG | 1 | 33502383 | - | GAGGCCCCAGCAGCACGGCCCGG | 3 | 7 | 90 | SEQ ID NO. 445 |
| (N20)NGG | 1 | 33502388 | - | CCCGGAGGCCCCAGCAGCACGG | 3 | 9 | 114 | SEQ ID NO. 446 |
| (N20)NGG | 1 | 33502402 | - | GTCCCTTTACCGGCCCCGGGAGG | 1 | 3 | 13 | SEQ ID NO. 447 |
| (N20)NGG | 1 | 33502405 | - | TGGGTCCCTTTACCGGCCCCGGG | 1 | 6 | 19 | SEQ ID NO. 448 |
| (N20)NGG | 1 | 33502406 | - | CTGGGTCCCTTTACCGGCCCCGG | 2 | 4 | 16 | SEQ ID NO. 449 |
| (N20)NGG | 1 | 33502412 | - | GCTCACCTGGGTCCCTTTACCGG | 1 | 2 | 24 | SEQ ID NO. 450 |
| (N20)NGG | 1 | 33502424 | - | CCCAGTCCTGCCGCTCACCTGGG | 2 | 7 | 62 | SEQ ID NO. 451 |
| (N20)NGG | 1 | 33502425 | - | GCCCAGTCCTGCCGCTCACCTGG |  | 1 | 46 | SEQ ID NO. 452 |

FIG. 2 cont.

| site_type | site_chr omosome | site_start_ nucleotide | site_s trand | target_site_sequence_wit h_NGG | genome_wide_ hits_with_1_ or_less_mism atches | genome_wide_ hits_with_2_ or_less_mism atches | genome_wide_ hits_with_3_ or_less_mism atches | |
|---|---|---|---|---|---|---|---|---|
| (N20)NGG | 11 | 118209916 | + | GATGCTCAGTACAGCCACCTTGG | 1 | 1 | 32 | SEQ ID NO. 453 |
| (N20)NGG | 11 | 118209919 | + | GCTCAGTACAGCCACCTTGGAGG | 1 | 4 | 47 | SEQ ID NO. 454 |
| (N20)NGG | 11 | 118209926 | + | ACAGCCACCTTGGAGGAAACTGG | 1 | 3 | 56 | SEQ ID NO. 455 |
| (N20)NGG | 11 | 118209927 | + | CAGCCACCTTGGAGGAAACTGGG | 1 | 6 | 70 | SEQ ID NO. 456 |
| (N20)NGG | 11 | 118209932 | + | ACCTTGGAGGAAACTGGGCTCGG | 1 | 7 | 61 | SEQ ID NO. 457 |
| (N20)NGG | 11 | 118209953 | + | GGAACAGTGAACCTGAGACTGG | 1 | 1 | 31 | SEQ ID NO. 458 |
| (N20)NGG | 11 | 118209956 | + | ACAAGTGAACCTGAGACTGGTGG | 1 | 1 | 29 | SEQ ID NO. 459 |
| (N20)NGG | 11 | 118209852 | - | TAAGAGAGGAGAAGAGAAAACG | 6 | 116 | 1279 | SEQ ID NO. 460 |
| (N20)NGG | 11 | 118209866 | - | GATCTCCGAGGGGCTAAGAGAGG | 1 | 2 | 45 | SEQ ID NO. 461 |
| (N20)NGG | 11 | 118209876 | - | GCATCATCTCGATCTCCGAGGGG | 1 | 1 | 9 | SEQ ID NO. 462 |
| (N20)NGG | 11 | 118209877 | - | AGCATCATCTCGATCTCCGAGGG | 1 | 1 | 5 | SEQ ID NO. 463 |
| (N20)NGG | 11 | 118209878 | - | GAGCATCATCTCGATCTCGAGG | 1 | 1 | 4 | SEQ ID NO. 464 |
| (N20)NGG | 11 | 118209881 | - | ACTGAGCATCATCTCGATCTCGG | 1 | 2 | 10 | SEQ ID NO. 465 |
| (N20)NGG | 11 | 118209908 | - | GAGCCCAGTTTCCTCCAAGGTGG | 1 | 4 | 48 | SEQ ID NO. 466 |
| (N20)NGG | 11 | 118209911 | - | TCCGAGCCCAGTTTCCTCCAAGG | 1 | 3 | 44 | SEQ ID NO. 467 |
| (N20)NGG | 11 | 118209943 | - | TTCTAGAAGCCACCAGTCTCAGG | 1 | 6 | 53 | SEQ ID NO. 468 |
| (N20)NGG | 11 | 118210190 | + | CCGACACACAAGCTCTGTTGAGG | 1 | 1 | 13 | SEQ ID NO. 469 |
| (N20)NGG | 11 | 118210200 | + | AGCTCTGTTGAGGAATGACCAGG | 1 | 3 | 27 | SEQ ID NO. 470 |
| (N20)NGG | 11 | 118210209 | + | GAGGAATGACCAGGTCTATCAGG | 1 | 1 | 23 | SEQ ID NO. 471 |
| (N20)NGG | 11 | 118210221 | + | GGTCTATCAGGTGAGCGTTGAGG | 1 | 1 | 10 | SEQ ID NO. 472 |
| (N20)NGG | 11 | 118210222 | + | GTCTATCAGGTGAGCGTTGAGGG | 1 | 1 | 15 | SEQ ID NO. 473 |
| (N20)NGG | 11 | 118210223 | + | TCTATCAGGTGAGCGTTGAGGGG | 1 | 2 | 18 | SEQ ID NO. 474 |
| (N20)NGG | 11 | 118210227 | + | TCAGGTGAGCGTTGAGGGGAAGG | 1 | 8 | 42 | SEQ ID NO. 475 |
| (N20)NGG | 11 | 118210230 | + | GGTGAGCGTTGAGGGGAAGGAGG | 1 | 4 | 95 | SEQ ID NO. 476 |
| (N20)NGG | 11 | 118210168 | - | CCTCAACAGCTCACCTGATAGACCTGG | 1 | 4 | 26 | SEQ ID NO. 477 |
| (N20)NGG | 11 | 118210196 | - | CAACGCTCACCTGATAGACCTGG | 1 | 3 | 11 | SEQ ID NO. 478 |
| (N20)NGG | 11 | 118210506 | + | CACAGTGTGCCAGAGCTGTGTGG | 1 | 12 | 110 | SEQ ID NO. 479 |
| (N20)NGG | 11 | 118210512 | + | GTGCCAGAGCTGTGTGGAGCTGG | 1 | 6 | 58 | SEQ ID NO. 480 |
| (N20)NGG | 11 | 118210527 | + | GGAGCTGGATCCAGCCACCGTGG | 1 | 3 | 32 | SEQ ID NO. 481 |
| (N20)NGG | 11 | 118210531 | + | CTGGATCCAGCCACCGTGGCTGG | 1 | 2 | 43 | SEQ ID NO. 482 |
| (N20)NGG | 11 | 118210575 | + | TGCCACTCTGCTCCTTGCTTTGG | 2 | 5 | 71 | SEQ ID NO. 483 |
| (N20)NGG | 11 | 118210576 | + | GCCACTCTGCTCCTTGCTTTGGG | 1 | 3 | 60 | SEQ ID NO. 484 |
| (N20)NGG | 11 | 118210594 | + | TTGGGAGTCTTTCTGCTTTGCTGG | 1 | 2 | 44 | SEQ ID NO. 485 |

FIG. 3

| site_type | site_chr omosome | site_start nucleotide | site_s trand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 11 | 118210606 | + | TGCTTTGCTGGACATGAGACTGG | 1 | 2 | 47 | SEQ ID NO. 486 |
| (N20)NGG | 11 | 118210610 | + | TTGCTGGACATGAGACTGGAAGG | 1 | 5 | 66 | SEQ ID NO. 487 |
| (N20)NGG | 11 | 118210618 | + | CATGAGACTGGAAGGCTGTCTGG | 1 | 2 | 38 | SEQ ID NO. 488 |
| (N20)NGG | 11 | 118210619 | + | ATGAGACTGGAAGGCTGTCTGGG | 1 | 4 | 51 | SEQ ID NO. 489 |
| (N20)NGG | 11 | 118210620 | + | TGAGACTGGAAGGCTGTCTGGGG | 1 | 4 | 76 | SEQ ID NO. 490 |
| (N20)NGG | 11 | 118210621 | + | GAGACTGGAAGGCTGTCTGGGGG | 1 | 7 | 78 | SEQ ID NO. 491 |
| (N20)NGG | 11 | 118210628 | + | GAAGGCTGTCTGGGGTTAGTGG | 1 | 4 | 51 | SEQ ID NO. 492 |
| (N20)NGG | 11 | 118210465 | - | TGTGGGGAAGGGAGGAGAGAGAG | 9 | 73 | 815 | SEQ ID NO. 493 |
| (N20)NGG | 11 | 118210472 | - | GGCACACTGTGGGGGAAGGGAGG | 1 | 7 | 129 | SEQ ID NO. 494 |
| (N20)NGG | 11 | 118210475 | - | CTGGCACACTGTGGGGGAAGG | 1 | 4 | 46 | SEQ ID NO. 495 |
| (N20)NGG | 11 | 118210476 | - | CTCTGGCACACTGTGGGGGAAGG | 1 | 1 | 51 | SEQ ID NO. 496 |
| (N20)NGG | 11 | 118210480 | - | ACAGCTCTGGCACACTGTGGGG | 1 | 7 | 59 | SEQ ID NO. 497 |
| (N20)NGG | 11 | 118210481 | - | CACAGCTCTGGCACACTGTGGG | 1 | 4 | 70 | SEQ ID NO. 498 |
| (N20)NGG | 11 | 118210482 | - | ACACAGCTCTGGCACACTGTGG | 2 | 6 | 59 | SEQ ID NO. 499 |
| (N20)NGG | 11 | 118210483 | - | CACACAGCTCTGGCACACTGTGG | 2 | 9 | 112 | SEQ ID NO. 500 |
| (N20)NGG | 11 | 118210493 | - | GATCCAGCTCCACACAGCTCTGG | 1 | 4 | 45 | SEQ ID NO. 501 |
| (N20)NGG | 11 | 118210515 | - | ATGATGCCAGCCACGGTGGCTGG | 1 | 2 | 54 | SEQ ID NO. 502 |
| (N20)NGG | 11 | 118210519 | - | GACAATGATGCCAGCCACGGTGG | 1 | 5 | 65 | SEQ ID NO. 503 |
| (N20)NGG | 11 | 118210522 | - | AGTGACAATGATGCCAGCCACGG | 1 | 3 | 47 | SEQ ID NO. 504 |
| (N20)NGG | 11 | 118210555 | - | TCCCAAAGCAAGGAGCAGAGTGG | 1 | 8 | 105 | SEQ ID NO. 505 |
| (N20)NGG | 11 | 118210565 | - | AGCAGAAGACTCCCAAAGCAAGG | 1 | 7 | 54 | SEQ ID NO. 506 |
| (N20)NGG | 11 | 118211115 | + | CCCCTTCAAGATACCTATAGAGG | 1 | 2 | 22 | SEQ ID NO. 507 |
| (N20)NGG | 11 | 118211124 | + | GATACCTATAGAGGAACTTGAGG | 1 | 1 | 15 | SEQ ID NO. 508 |
| (N20)NGG | 11 | 118211162 | + | ATTGCAATACCAGCATCACATGG | 1 | 4 | 44 | SEQ ID NO. 509 |
| (N20)NGG | 11 | 118211163 | + | TTGCAATACCAGCATCACATGGG | 1 | 1 | 32 | SEQ ID NO. 510 |
| (N20)NGG | 11 | 118211169 | + | TACCAGCATCACATGGGTAGAGG | 1 | 4 | 70 | SEQ ID NO. 511 |
| (N20)NGG | 11 | 118211170 | + | ACCAGCATCACATGGGTAGAGGG | 1 | 2 | 37 | SEQ ID NO. 512 |
| (N20)NGG | 11 | 118211175 | + | CATCACATGGGTAGAGGGAACGG | 1 | 4 | 69 | SEQ ID NO. 513 |
| (N20)NGG | 11 | 118211178 | + | CACATGGGTAGAGGGAACGGTGG | 1 | 2 | 38 | SEQ ID NO. 514 |
| (N20)NGG | 11 | 118211179 | + | ACATGGGTAGAGGGAACGGTGGG | 1 | 3 | 29 | SEQ ID NO. 515 |
| (N20)NGG | 11 | 118211208 | + | GCTCTCAGACATTACAAGACTGG | 1 | 4 | 31 | SEQ ID NO. 516 |
| (N20)NGG | 11 | 118211214 | + | AGACATTACAAGACTGGACCTGG | 1 | 1 | 27 | SEQ ID NO. 517 |
| (N20)NGG | 11 | 118211215 | + | GACATTACAAGACTGGACCTGGG | 1 | 1 | 18 | SEQ ID NO. 518 |

FIG. 3 cont.

| site type | site chr omosome | site start nucleotide | site strand | target_site_sequence_with NGG | genome_wide_hits_with_1_mism or_less mism atches | genome_wide_hits_with_2_mism or_less mism atches | genome_wide_hits_with_3_mism or_less mism atches | |
|---|---|---|---|---|---|---|---|---|
| (N20)NGG | 11 | 118211229 | + | GGACCTGGGAAAACGCATCCTGG | 1 | 1 | 17 | SEQ ID NO. 519 |
| (N20)NGG | 11 | 118211239 | + | AAACGCATCCTGACCCACGAGG | 1 | 1 | 5 | SEQ ID NO. 520 |
| (N20)NGG | 11 | 118211249 | + | TGGACCCACGAGGAATATATAGG | 1 | 2 | 13 | SEQ ID NO. 521 |
| (N20)NGG | 11 | 118211257 | + | CGAGGAATATATAGGTGTAATGG | 1 | 1 | 22 | SEQ ID NO. 522 |
| (N20)NGG | 11 | 118211258 | + | GAGGAATATATAGGTGTAATGGG | 1 | 1 | 51 | SEQ ID NO. 523 |
| (N20)NGG | 11 | 118211274 | + | TAATGGGACAGATATATACAAGG | 1 | 9 | 142 | SEQ ID NO. 524 |
| (N20)NGG | 11 | 118211331 | + | TACGTGCTTCCTGAACCCTTTGG | 1 | 2 | 14 | SEQ ID NO. 525 |
| (N20)NGG | 11 | 118211332 | + | ACGTGCTTCCTGAACCCTTTGGG | 1 | 1 | 17 | SEQ ID NO. 526 |
| (N20)NGG | 11 | 118211080 | - | CTTGAAGGGGCTCACTAAAGGGG | 1 | 1 | 20 | SEQ ID NO. 527 |
| (N20)NGG | 11 | 118211081 | - | TCTTGAAGGGGCTCACTAAAGG | 1 | 2 | 23 | SEQ ID NO. 528 |
| (N20)NGG | 11 | 118211082 | - | ATCTTGAAGGGGCTCACTAAAGG | 1 | 2 | 15 | SEQ ID NO. 529 |
| (N20)NGG | 11 | 118211093 | - | CCTCTATAGGTATCTTGAAGGGG | 1 | 1 | 18 | SEQ ID NO. 530 |
| (N20)NGG | 11 | 118211094 | - | TCCTCTATAGGTATCTTGAAGGG | 1 | 3 | 21 | SEQ ID NO. 531 |
| (N20)NGG | 11 | 118211095 | - | TTCCTCTATAGGTATCTTGAAGG | 1 | 1 | 33 | SEQ ID NO. 532 |
| (N20)NGG | 11 | 118211106 | - | CTGTCCTCAAGTTCCTCTATAGG | 1 | 3 | 35 | SEQ ID NO. 533 |
| (N20)NGG | 11 | 118211149 | - | TCCCTCTACCCATGTGATGCTGG | 1 | 1 | 54 | SEQ ID NO. 534 |
| (N20)NGG | 11 | 118211210 | - | GGTCCAGGATGCGTTTTCCCAGG | 1 | 3 | 19 | SEQ ID NO. 535 |
| (N20)NGG | 11 | 118211225 | - | TATATATTCCTCGTGGGTCCAGG | 1 | 1 | 11 | SEQ ID NO. 536 |
| (N20)NGG | 11 | 118211231 | - | TACACCTATATATTCCTCGTGGG | 1 | 1 | 9 | SEQ ID NO. 537 |
| (N20)NGG | 11 | 118211232 | - | TTACACCTATATATTCCTCGTGG | 1 | 2 | 34 | SEQ ID NO. 538 |
| (N20)NGG | 11 | 118211287 | - | ACTTCGATAATGAACTTGCACGG | 2 | 1 | 14 | SEQ ID NO. 539 |
| (N20)NGG | 11 | 118213264 | + | TCTACTGGATGAGTTCCGCTGGG | 1 | 1 | 9 | SEQ ID NO. 540 |
| (N20)NGG | 11 | 118213270 | + | GGATGAGTTCCGCTGGGAGATGG | 1 | 3 | 31 | SEQ ID NO. 541 |
| (N20)NGG | 11 | 118213292 | + | GAACATAGCACGTTTCTCTCTGG | 1 | 1 | 17 | SEQ ID NO. 542 |
| (N20)NGG | 11 | 118213297 | + | TAGCACGTTTCTCTCTGGCCTGG | 1 | 4 | 39 | SEQ ID NO. 543 |
| (N20)NGG | 11 | 118213303 | + | GTTTCTCTCTGGCCTGGTACTGG | 1 | 2 | 19 | SEQ ID NO. 544 |
| (N20)NGG | 11 | 118213322 | + | CTGACTACCCTTCTCTCGCAAGG | 2 | 5 | 27 | SEQ ID NO. 545 |
| (N20)NGG | 11 | 118213327 | + | TACCCTTCTCTCGCAAGGTAAGG | 1 | 2 | 12 | SEQ ID NO. 546 |
| (N20)NGG | 11 | 118213337 | + | TCGCAAGGTAAGGCTACTCCAGG | 1 | 1 | 4 | SEQ ID NO. 547 |
| (N20)NGG | 11 | 118213340 | + | CAAGGTAAGGCTACTCCAGGTGG | 1 | 2 | 30 | SEQ ID NO. 548 |
| (N20)NGG | 11 | 118213341 | + | AAGGTAAGGCTACTCCAGGTGGG | 1 | 2 | 29 | SEQ ID NO. 549 |
| (N20)NGG | 11 | 118213344 | + | GTAAGGCTACTCCAGGTGGGTGG | 1 | 3 | 26 | SEQ ID NO. 550 |
| (N20)NGG | 11 | 118213345 | + | TAAGGCTACTCCAGGTGGGTGGG | 1 | 2 | 24 | SEQ ID NO. 551 |

FIG. 3 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 11 | 118213346 | + | AAGGCTACTCCAGGTGGGTCGGG | 1 | 2 | 27 | SEQ ID NO. 552 |
| (N20)NGG | 11 | 118213257 | - | TGCTATGTTCCATCTCCCAGCGG | 1 | 4 | 57 | SEQ ID NO. 553 |
| (N20)NGG | 11 | 118213293 | - | AGAGAAGGGTAGCCAGTACCAGG | 1 | 4 | 38 | SEQ ID NO. 554 |
| (N20)NGG | 11 | 118213307 | - | AGCCTTACCTTGCGAGAAGGG | 1 | 1 | 14 | SEQ ID NO. 555 |
| (N20)NGG | 11 | 118213308 | - | TAGCCTTACCTTGCGAGAGAAGG | 1 | 1 | 9 | SEQ ID NO. 556 |

FIG. 3 cont.

| site_type | site_chr omosome | site_start_ nucleotide | site_s trand | target_site_sequence_wi th_NGG | genome_wide_ hits_with_1_ or_less_mism atches | genome_wide_ hits_with_2_ or_less_mism atches | genome_wide_ hits_with_3_ or_less_mism atches | |
|---|---|---|---|---|---|---|---|---|
| (N20)NGG | 10 | 14950408 | + | CTGTTTTGTTTGTCCACAGAGG | 3 | 7 | 100 | SEQ ID NO. 557 |
| (N20)NGG | 10 | 14950411 | + | TTTTGTTTGTCCCACAGAGAGG | 1 | 8 | 95 | SEQ ID NO. 558 |
| (N20)NGG | 10 | 14950455 | + | ATCCTCTGCCAATACCTTTAAGG | 1 | 4 | 37 | SEQ ID NO. 559 |
| (N20)NGG | 10 | 14950474 | + | AAGGCACAAAGTTCCATACCCGG | 1 | 1 | 31 | SEQ ID NO. 560 |
| (N20)NGG | 10 | 14950492 | + | CCCGAAACTTTTCACCCTGAGG | 1 | 2 | 12 | SEQ ID NO. 561 |
| (N20)NGG | 10 | 14950550 | + | GAAAACTGAGACAAACCCCAGG | 1 | 6 | 60 | SEQ ID NO. 562 |
| (N20)NGG | 10 | 14950640 | + | AGTGAAAGTGAAGAAGAAGTAGG | 1 | 14 | 197 | SEQ ID NO. 563 |
| (N20)NGG | 10 | 14950661 | + | GGAATCCCAGCTTCACTGCAAGG | 1 | 3 | 67 | SEQ ID NO. 564 |
| (N20)NGG | 10 | 14950669 | + | AGCTTCACTGCAAGGAGATCTGG | 1 | 2 | 28 | SEQ ID NO. 565 |
| (N20)NGG | 10 | 14950670 | + | GCTTCACTGCAAGGAGATCTGGG | 1 | 4 | 40 | SEQ ID NO. 566 |
| (N20)NGG | 10 | 14950693 | + | CTCTGTACTTCACCTGCAAAAGG | 1 | 3 | 51 | SEQ ID NO. 567 |
| (N20)NGG | 10 | 14950700 | + | CTTCACCTGCAAAAGGCTGATGG | 1 | 2 | 53 | SEQ ID NO. 568 |
| (N20)NGG | 10 | 14950701 | + | TTCACCTGCAAAAGGCTGATGGG | 1 | 4 | 44 | SEQ ID NO. 569 |
| (N20)NGG | 10 | 14950702 | + | TCACCTGCAAAAGGCTGATGGGG | 1 | 5 | 52 | SEQ ID NO. 570 |
| (N20)NGG | 10 | 14950716 | + | CTGATGGGGATGTACCCCAGTGG | 1 | 2 | 23 | SEQ ID NO. 571 |
| (N20)NGG | 10 | 14950717 | + | TGATGGGGATGTACCCCAGTGGG | 1 | 1 | 21 | SEQ ID NO. 572 |
| (N20)NGG | 10 | 14950762 | + | TGAAATCACAGATGAGAGTTTGG | 2 | 4 | 66 | SEQ ID NO. 573 |
| (N20)NGG | 10 | 14950786 | + | AAACTTCCCTTCCTCCACAGTGG | 1 | 4 | 85 | SEQ ID NO. 574 |
| (N20)NGG | 10 | 14950790 | + | TTCCCTTCCTCCACAGTGGCAGG | 1 | 7 | 90 | SEQ ID NO. 575 |
| (N20)NGG | 10 | 14950791 | + | TCCCCTTCCTCCACAGTGGCAGGG | 1 | 6 | 83 | SEQ ID NO. 576 |
| (N20)NGG | 10 | 14950792 | + | CCCTTCCTCCACAGTGGCAGGGG | 1 | 8 | 112 | SEQ ID NO. 577 |
| (N20)NGG | 10 | 14950793 | + | CCTTCCTCCACAGTGGCAGGGGG | 3 | 8 | 98 | SEQ ID NO. 578 |
| (N20)NGG | 10 | 14950829 | + | AAGCTTTTCAGTGACTCTGATGG | 1 | 3 | 63 | SEQ ID NO. 579 |
| (N20)NGG | 10 | 14950889 | + | TCAACACACATAACAGAACAAGG | 1 | 4 | 82 | SEQ ID NO. 580 |
| (N20)NGG | 10 | 14950898 | + | ATAACAGAACAAGGAAGTCAAGG | 1 | 10 | 104 | SEQ ID NO. 581 |
| (N20)NGG | 10 | 14950902 | + | CAGAACAAGGAAGTCAAGGCTGG | 1 | 6 | 74 | SEQ ID NO. 582 |
| (N20)NGG | 10 | 14950903 | + | AGAACAAGGAAGTCAAGGCTGGG | 1 | 14 | 244 | SEQ ID NO. 583 |
| (N20)NGG | 10 | 14950952 | + | TCTTCCAAGAGAGAAACAGTGG | 1 | 7 | 125 | SEQ ID NO. 584 |
| (N20)NGG | 10 | 14950953 | + | CTTTCCAAGAGAGAAACAGTGGG | 1 | 5 | 98 | SEQ ID NO. 585 |
| (N20)NGG | 10 | 14950954 | + | TTCCCAAGAGAGAAACAGTGGGG | 1 | 6 | 70 | SEQ ID NO. 586 |
| (N20)NGG | 10 | 14950969 | + | CAGTGGGGATATTCCTCTCCTTGG | 1 | 1 | 30 | SEQ ID NO. 587 |
| (N20)NGG | 10 | 14951023 | + | GAATATTCCTGCCTCTCATGG | 1 | 4 | 39 | SEQ ID NO. 588 |
| (N20)NGG | 10 | 14951047 | + | ACAAAATGTAATTTGCCCAAAGG | 2 | 12 | 88 | SEQ ID NO. 589 |

FIG. 4

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | SEQ ID NO. |
|---|---|---|---|---|---|---|---|---|
| (N20)NGG | 10 | 14951105 | + | GTGACAATAGTTCCTAGTACTGG | | 1 | 19 | SEQ ID NO. 590 |
| (N20)NGG | 10 | 14951146 | + | CAGTGAGACACATATACCCGAGG | | 2 | 8 | SEQ ID NO. 591 |
| (N20)NGG | 10 | 14951272 | + | ACAATATTTATATGAGAAGCTGG | | 5 | 70 | SEQ ID NO. 592 |
| (N20)NGG | 10 | 14951279 | + | TTATATGAGAAGCTGGCAACTGG | | 3 | 39 | SEQ ID NO. 593 |
| (N20)NGG | 10 | 14950385 | - | CTCTGTGGGACAAACAAAACAGG | | 5 | 76 | SEQ ID NO. 594 |
| (N20)NGG | 10 | 14950399 | - | TAGTCATCTTCCTCCTCTGTGGG | | 6 | 82 | SEQ ID NO. 595 |
| (N20)NGG | 10 | 14950400 | - | ATAGTCATCTTCCTCCTCTGTGG | | 5 | 77 | SEQ ID NO. 596 |
| (N20)NGG | 10 | 14950435 | - | TGCCCTAAAGGTATTGGCAGAGG | | 3 | 28 | SEQ ID NO. 597 |
| (N20)NGG | 10 | 14950441 | - | ACTTTGTGCCTTAAAGGTATTGG | | 2 | 37 | SEQ ID NO. 598 |
| (N20)NGG | 10 | 14950447 | - | TATGGAACTTTGTGCCTTAAAGG | | 3 | 49 | SEQ ID NO. 599 |
| (N20)NGG | 10 | 14950465 | - | GGGTGAAAAGTTTCCGGGTATGG | 1 | 1 | 17 | SEQ ID NO. 600 |
| (N20)NGG | 10 | 14950470 | - | CCTCAGGGTGAAAAGTTTCCGGG | | 6 | 69 | SEQ ID NO. 601 |
| (N20)NGG | 10 | 14950471 | - | ACCTCAGGGTGAAAAGTTTCCGG | 4 | 6 | 46 | SEQ ID NO. 602 |
| (N20)NGG | 10 | 14950485 | - | CAGTCATTGAAAATACCTCAGGG | | 2 | 52 | SEQ ID NO. 603 |
| (N20)NGG | 10 | 14950486 | - | GCAGTCATTGAAAATACCTCAGG | | 2 | 29 | SEQ ID NO. 604 |
| (N20)NGG | 10 | 14950525 | - | GGGGTTTGTCTCAGTTTTTCAGG | 1 | 4 | 48 | SEQ ID NO. 605 |
| (N20)NGG | 10 | 14950544 | - | CTCTGCTCTGCAGCATCCTGGGG | 2 | 17 | 132 | SEQ ID NO. 606 |
| (N20)NGG | 10 | 14950545 | - | ACTCTGCTCTGCAGCATCCTGGG | 3 | 10 | 93 | SEQ ID NO. 607 |
| (N20)NGG | 10 | 14950546 | - | CACTCTGCTCTGCAGCATCCTGG | 1 | 9 | 79 | SEQ ID NO. 608 |
| (N20)NGG | 10 | 14950613 | - | TTCTTCTTCACTTTCACTGTTGG | 1 | 10 | 150 | SEQ ID NO. 609 |
| (N20)NGG | 10 | 14950644 | - | GATCTCCTTGCAGTGAAGCTGGG | 1 | 2 | 33 | SEQ ID NO. 610 |
| (N20)NGG | 10 | 14950645 | - | AGATCTCCTTGCAGTGAAGCTGG | 1 | 4 | 45 | SEQ ID NO. 611 |
| (N20)NGG | 10 | 14950683 | - | CATCCCCATCAGCCTTTTGCAGG | 1 | 6 | 57 | SEQ ID NO. 612 |
| (N20)NGG | 10 | 14950708 | - | TTAAAGAATACTTCCCACTGGGG | 1 | 6 | 67 | SEQ ID NO. 613 |
| (N20)NGG | 10 | 14950709 | - | TTTAAAGAATACTTCCCACTGGG | 1 | 4 | 89 | SEQ ID NO. 614 |
| (N20)NGG | 10 | 14950710 | - | TTTTAAAGAATACTTCCCACTGG | 2 | 9 | 108 | SEQ ID NO. 615 |
| (N20)NGG | 10 | 14950770 | - | CCCCTGCCACTGTGGAGGAAGGG | 1 | 5 | 68 | SEQ ID NO. 616 |
| (N20)NGG | 10 | 14950771 | - | CCCCCTGCCACTGTGGAGGAAGG | 1 | 4 | 70 | SEQ ID NO. 617 |
| (N20)NGG | 10 | 14950775 | - | AGATCCCCCTGCCACTGTGGAGG | 1 | 3 | 43 | SEQ ID NO. 618 |
| (N20)NGG | 10 | 14950778 | - | CTGAGATCCCCCTGCCACTGTGG | 1 | 3 | 67 | SEQ ID NO. 619 |
| (N20)NGG | 10 | 14950804 | - | TCAGAGTCACTGAAAAGCTTTGG | 1 | 6 | 66 | SEQ ID NO. 620 |
| (N20)NGG | 10 | 14950847 | - | TGACTGGGAAGAATTCTGGGAGG | 1 | 4 | 86 | SEQ ID NO. 621 |
| (N20)NGG | 10 | 14950850 | - | TGTTGACTGGGAAGAATTCTGGG | 1 | 6 | 74 | SEQ ID NO. 622 |

FIG. 4 cont.

| site type | site chromosome | site_start_nucleotide | site strand | target_site_sequence_with NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 10 | 14950851 | - | GTGTTGACTGGAAGAATTCTGG | 1 | 4 | 57 | SEQ ID NO. 623 |
| (N20)NGG | 10 | 14950862 | - | TTCTGTTATGTGTTGACTGGG | 1 | 7 | 48 | SEQ ID NO. 624 |
| (N20)NGG | 10 | 14950863 | - | GTTCTGTTATGTGTTGACTGG | 1 | 2 | 37 | SEQ ID NO. 625 |
| (N20)NGG | 10 | 14950908 | - | ATAACAAAACAGTATCAGATTGG | 1 | 7 | 120 | SEQ ID NO. 626 |
| (N20)NGG | 10 | 14950934 | - | ATCCCCACTGTTTCTCTCTTGG | 1 | 4 | 83 | SEQ ID NO. 627 |
| (N20)NGG | 10 | 14950935 | - | TATCCCCACTGTTTCTCTCTTGG | 1 | 4 | 66 | SEQ ID NO. 628 |
| (N20)NGG | 10 | 14950964 | - | TCTGTAGTCAGCTTTGTCAAGG | 1 | 2 | 46 | SEQ ID NO. 629 |
| (N20)NGG | 10 | 14950987 | - | GGAATATTCTCTTTGATTGTTGG | 1 | 1 | 64 | SEQ ID NO. 630 |
| (N20)NGG | 10 | 14951008 | - | TTTTGTTCCATGAGAGAGGCAGG | 1 | 3 | 41 | SEQ ID NO. 631 |
| (N20)NGG | 10 | 14951012 | - | TACATTTGTTCCATGAGAGAGG | 1 | 3 | 70 | SEQ ID NO. 632 |
| (N20)NGG | 10 | 14951040 | - | AATCAGAGTAAGTATCCTTTGGG | 1 | 5 | 70 | SEQ ID NO. 633 |
| (N20)NGG | 10 | 14951041 | - | AAATCAGAGTAAGTATCCTTTGG | 1 | 4 | 59 | SEQ ID NO. 634 |
| (N20)NGG | 10 | 14951095 | - | GTAGTTGGTTCTCCAGTACTAGG | 1 | 2 | 33 | SEQ ID NO. 635 |
| (N20)NGG | 10 | 14951110 | - | GTCCTCACTGCTTAGAGTAGTTGG | 1 | 1 | 19 | SEQ ID NO. 636 |
| (N20)NGG | 10 | 14951140 | - | TTTAGCAAACTTTTTCCTCGG | 1 | 10 | 106 | SEQ ID NO. 637 |
| (N20)NGG | 10 | 14951141 | - | ATTTAGCAAACTTTTTTCCTCGG | 2 | 9 | 151 | SEQ ID NO. 638 |
| (N20)NGG | 10 | 14951183 | - | TTCAAAATCAGAAGAGCTCTGGG | 1 | 4 | 77 | SEQ ID NO. 639 |
| (N20)NGG | 10 | 14951184 | - | CTTCAAAATCAGAAGAGCTCTGG | 1 | 3 | 62 | SEQ ID NO. 640 |
| (N20)NGG | 10 | 14951209 | - | AACTCAGCTTCTGGAGTTGAGGG | 1 | 9 | 165 | SEQ ID NO. 641 |
| (N20)NGG | 10 | 14951210 | - | TAACTCAGCTTCTGGAGTTGAGG | 1 | 3 | 77 | SEQ ID NO. 642 |
| (N20)NGG | 10 | 14951218 | - | CGTTTAGGTAACTCAGCTTCGG | 1 | 2 | 12 | SEQ ID NO. 643 |
| (N20)NGG | 10 | 14951233 | - | TATTGTAAATGCTCTCGTTTAGG | 1 | 3 | 37 | SEQ ID NO. 644 |
| (N20)NGG | 10 | 14951324 | - | TTGAAACGCTTTGAATTCTTAGG | 2 | 6 | 54 | SEQ ID NO. 645 |
| (N20)NGG | 10 | 14961754 | + | TCAGCTTAAAGCTTTATGCCGG | 1 | 4 | 22 | SEQ ID NO. 646 |
| (N20)NGG | 10 | 14961770 | + | ATGCCGGTCTTCCAAAGTACGG | 1 | 2 | 11 | SEQ ID NO. 647 |
| (N20)NGG | 10 | 14961791 | + | GGAGCCAAAGTATAAACCACTGG | 1 | 2 | 33 | SEQ ID NO. 648 |
| (N20)NGG | 10 | 14961792 | + | GAGCCAAAGTATAAACCACTGGG | 1 | 3 | 43 | SEQ ID NO. 649 |
| (N20)NGG | 10 | 14961831 | + | AGAACAGTTCACCGAGACTCAGG | 1 | 1 | 17 | SEQ ID NO. 650 |
| (N20)NGG | 10 | 14961843 | + | CGAGACTCAGGTAAGAAAAATGG | 1 | 3 | 71 | SEQ ID NO. 651 |
| (N20)NGG | 10 | 14961849 | + | TCAGTAAGAAAAATGGTCCTGG | 1 | 3 | 48 | SEQ ID NO. 652 |
| (N20)NGG | 10 | 14961850 | + | CAGGTAAGAAAAATGGTCCTGGG | 1 | 7 | 69 | SEQ ID NO. 653 |
| (N20)NGG | 10 | 14961743 | - | CTTTGGGAAGACCGGCATAAAGG | 1 | 2 | 8 | SEQ ID NO. 654 |
| (N20)NGG | 10 | 14961751 | - | GCTCCGTACTTTGGGAAGACCGG | 1 | 4 | 91 | SEQ ID NO. 655 |

FIG. 4 cont.

| site type | site chr omosome | site start nucleotide | site s trand | target_site_sequence_wi th NGG | genome_wide_ hits_with_1 or_less_mism atches | genome_wide_ hits_with_2 or_less_mism atches | genome_wide_ hits_with_3 or_less_mism atches | | |
|---|---|---|---|---|---|---|---|---|---|
| (N20)NGG | 10 | 14961759 | - | ATACTTTGGCTCCGTACTTTGGG | 1 | 3 | 20 | SEQ ID NO. | 656 |
| (N20)NGG | 10 | 14961760 | - | TATACTTTGGCTCCGTACTTTGG | 1 | 1 | 8 | SEQ ID NO. | 657 |
| (N20)NGG | 10 | 14961773 | - | TTTCCCAGTGGTTTATACTTTGG | 1 | 4 | 78 | SEQ ID NO. | 658 |
| (N20)NGG | 10 | 14961785 | - | GCTCTCTTCAGTTTTCCCAGTGG | 1 | 9 | 90 | SEQ ID NO. | 659 |
| (N20)NGG | 10 | 14961820 | - | CATTTTTCTTACCTGAGTCTCGG | 2 | 10 | 114 | SEQ ID NO. | 660 |
| (N20)NGG | 10 | 14965040 | + | TATCCAAATGTCATTCCAGTTGG | 1 | 3 | 53 | SEQ ID NO. | 661 |
| (N20)NGG | 10 | 14965051 | + | CATTCCAGTTGGCACAACTATGG | 1 | 2 | 25 | SEQ ID NO. | 662 |
| (N20)NGG | 10 | 14965082 | + | GTCGAAATGTGAGTAGTCACTGG | 1 | 1 | 9 | SEQ ID NO. | 663 |
| (N20)NGG | 10 | 14965088 | + | ATGTGAGTAGTCACTGGTTGTGG | 1 | 4 | 27 | SEQ ID NO. | 664 |
| (N20)NGG | 10 | 14965089 | + | TGTGAGTAGTCACTGGTTGTGGG | 2 | 2 | 28 | SEQ ID NO. | 665 |
| (N20)NGG | 10 | 14964956 | - | CTAGAAAAAGGAAAATCACATGG | 3 | 15 | 312 | SEQ ID NO. | 666 |
| (N20)NGG | 10 | 14964968 | - | GAAATCTTTAATCTAGAAAAAGG | 2 | 19 | 176 | SEQ ID NO. | 667 |
| (N20)NGG | 10 | 14964999 | - | GATATGCGTTCACAGGACAGAGG | 1 | 2 | 12 | SEQ ID NO. | 668 |
| (N20)NGG | 10 | 14965006 | - | ACATTTGGATATGCGTTCACAGG | 1 | 1 | 13 | SEQ ID NO. | 669 |
| (N20)NGG | 10 | 14965021 | - | GTGCCAACTGGAATGACATTTGG | 1 | 1 | 33 | SEQ ID NO. | 670 |
| (N20)NGG | 10 | 14965033 | - | TTATCCATAGTTGTGCCAACTGG | 1 | 2 | 22 | SEQ ID NO. | 671 |
| (N20)NGG | 10 | 14968841 | + | TTGTGTTTTCACTTCCCTTTAGG | 2 | 12 | 229 | SEQ ID NO. | 672 |
| (N20)NGG | 10 | 14968846 | + | TTTTTCACTTCCCTTTAGGACTGG | 1 | 2 | 54 | SEQ ID NO. | 673 |
| (N20)NGG | 10 | 14968896 | + | TTTTCACTCCTCCTACAGTCAGG | 1 | 1 | 51 | SEQ ID NO. | 674 |
| (N20)NGG | 10 | 14968903 | + | TCCTCCTACAGTGAGGTAAGAGG | 2 | 2 | 27 | SEQ ID NO. | 675 |
| (N20)NGG | 10 | 14968833 | - | GAACTCTCTCCAGTCCTAAAGGG | 1 | 4 | 27 | SEQ ID NO. | 676 |
| (N20)NGG | 10 | 14968834 | - | TGAACTCTCTCCAGTCCTAAAGG | 1 | 1 | 28 | SEQ ID NO. | 677 |
| (N20)NGG | 10 | 14968882 | - | TCCTCTTACCTCACTGTAGGAGG | 2 | 2 | 44 | SEQ ID NO. | 678 |
| (N20)NGG | 10 | 14968885 | - | GGATCCTCTTACCTCACTGTAGG | 1 | 5 | 33 | SEQ ID NO. | 679 |
| (N20)NGG | 10 | 14970014 | + | CTATGCTTTTTATCTTTTTTAGG | 1 | 55 | 838 | SEQ ID NO. | 680 |
| (N20)NGG | 10 | 14970020 | + | TTTTTATCTTTTTTAGGCAGAGG | 2 | 43 | 1301 | SEQ ID NO. | 681 |
| (N20)NGG | 10 | 14970034 | + | AGGCAGAGAGGAATATTTTCAGTGG | 2 | 9 | 115 | SEQ ID NO. | 682 |
| (N20)NGG | 10 | 14970051 | + | CAGTGGAGCAAATTACCCTGTGG | 1 | 3 | 35 | SEQ ID NO. | 683 |
| (N20)NGG | 10 | 14970112 | + | GCATTAAGCATCCACCATGTGG | 1 | 2 | 21 | SEQ ID NO. | 684 |
| (N20)NGG | 10 | 14970117 | + | AAGCCATCCACCATGTGGTTTGG | 1 | 4 | 38 | SEQ ID NO. | 685 |
| (N20)NGG | 10 | 14970124 | + | CCACCATGTGGTTTGGAGAAAGG | 1 | 7 | 49 | SEQ ID NO. | 686 |
| (N20)NGG | 10 | 14970151 | + | GAAAAACAAATGTAATTGTGAGG | 2 | 11 | 216 | SEQ ID NO. | 687 |
| (N20)NGG | 10 | 14970171 | + | AGGTAAGAGAGCAATATCATAGG | 1 | 1 | 33 | SEQ ID NO. | 688 |

FIG. 4 cont.

| site type | site chr omosome | site start nucleotide | site s trand | target site sequence with NGG | genome wide hits with 1 or less mism atches | genome wide hits with 2 or less mism atches | genome wide hits with 3 or less mism atches | |
|---|---|---|---|---|---|---|---|---|
| (N20)NGG | 10 | 14970044 | - | TTTCTGGAAGTAATTCCACAGGG | 2 | 8 | 107 | SEQ ID NO. 689 |
| (N20)NGG | 10 | 14970045 | - | ATTTCTGGAAGTAATTCCACAGG | 2 | 5 | 67 | SEQ ID NO. 690 |
| (N20)NGG | 10 | 14970060 | - | GTGGAGTGGAATTCTATTTCTGG | 1 | 1 | 38 | SEQ ID NO. 691 |
| (N20)NGG | 10 | 14970074 | - | TTAATGCTGATTATGTGGAGTGG | 1 | 1 | 60 | SEQ ID NO. 692 |
| (N20)NGG | 10 | 14970079 | - | ATGGCTTAATGCTGATTATGTGG | 1 | 8 | 65 | SEQ ID NO. 693 |
| (N20)NGG | 10 | 14970098 | - | TCTCCAAACCACATGGTGGATGG | 1 | 4 | 51 | SEQ ID NO. 694 |
| (N20)NGG | 10 | 14970102 | - | CCTTTCTCCAAACCACATGGTGG | 1 | 9 | 53 | SEQ ID NO. 695 |
| (N20)NGG | 10 | 14970105 | - | GCTCCTTTCTCCAAACCACATGG | 2 | 10 | 84 | SEQ ID NO. 696 |
| (N20)NGG | 10 | 14974852 | + | ATGTATGTATTATTTGCCTTAGG | 1 | 7 | 147 | SEQ ID NO. 697 |
| (N20)NGG | 10 | 14974881 | + | TGAATAAGCTAGACATGTTTAGG | 2 | 4 | 58 | SEQ ID NO. 698 |
| (N20)NGG | 10 | 14974944 | + | ACACTCAGATCCATGCATGCCGG | 2 | 5 | 43 | SEQ ID NO. 699 |
| (N20)NGG | 10 | 14974954 | + | CCATGCATGCCGGCATCCCAAGG | 1 | 2 | 34 | SEQ ID NO. 700 |
| (N20)NGG | 10 | 14974846 | - | AGCTTATTCACATGAACCTAAGG | 1 | 5 | 45 | SEQ ID NO. 701 |
| (N20)NGG | 10 | 14974888 | - | GTGAGATGATGAAGGATCTCAGG | 2 | 4 | 58 | SEQ ID NO. 702 |
| (N20)NGG | 10 | 14974896 | - | GGTCTGTTGTGAGATGATGAAGG | 2 | 6 | 47 | SEQ ID NO. 703 |
| (N20)NGG | 10 | 14974917 | - | ATGCATGGATCTGAGTGTTGCGG | 2 | 6 | 47 | SEQ ID NO. 704 |
| (N20)NGG | 10 | 14974932 | - | CCTTGGGATGCCGGCATGCCGG | 1 | 1 | 23 | SEQ ID NO. 705 |
| (N20)NGG | 10 | 14974941 | - | GCACACGTACCTTGGGATGCCGG | 1 | 1 | 7 | SEQ ID NO. 706 |
| (N20)NGG | 10 | 14974948 | - | ATCACTTGCACACGTACCTTGGG | 1 | 1 | 10 | SEQ ID NO. 707 |
| (N20)NGG | 10 | 14974949 | - | AATCACTTGCACACGTACCTTGG | 2 | 1 | 22 | SEQ ID NO. 708 |
| (N20)NGG | 10 | 14976378 | + | GTCTCTTTAAAATCCTGTCTAGG | 2 | 6 | 86 | SEQ ID NO. 709 |
| (N20)NGG | 10 | 14976381 | + | TCTTTAAAATCCTGTCTAGGAGG | 2 | 6 | 64 | SEQ ID NO. 710 |
| (N20)NGG | 10 | 14976394 | + | GTCTAGGAGGAGTGTTTAAGTGG | 2 | 2 | 30 | SEQ ID NO. 711 |
| (N20)NGG | 10 | 14976408 | + | TTTAAGTGGAGTCTTAGAGCTGG | 2 | 2 | 35 | SEQ ID NO. 712 |
| (N20)NGG | 10 | 14976419 | + | TCTTAGAGCTGGTCCGAAGCTGG | 1 | 3 | 9 | SEQ ID NO. 713 |
| (N20)NGG | 10 | 14976428 | + | TGGTCCGAAGCTGGATCACTCGG | 1 | 2 | 8 | SEQ ID NO. 714 |
| (N20)NGG | 10 | 14976449 | + | GGAGCCCGTACCATGTTGTGTGG | 1 | 2 | 13 | SEQ ID NO. 715 |
| (N20)NGG | 10 | 14976465 | + | TGTGTGGCTGAACTGCAAAGCGG | 2 | 5 | 52 | SEQ ID NO. 716 |
| (N20)NGG | 10 | 14976472 | + | CTGAACTGCAAAGCGGCTTATGG | 3 | 3 | 31 | SEQ ID NO. 717 |
| (N20)NGG | 10 | 14976511 | + | ACCAACCTTAGTGAAGAATTAGG | 3 | 4 | 32 | SEQ ID NO. 718 |
| (N20)NGG | 10 | 14976519 | + | TAGTGAAGAATTAGGAGTCCAGG | 2 | 5 | 35 | SEQ ID NO. 719 |
| (N20)NGG | 10 | 14976524 | + | AAGAATTAGGAGTCCAGGTATGG | 2 | 6 | 86 | SEQ ID NO. 720 |
| (N20)NGG | 10 | 14976369 | - | CTTAAACACTCCTCCTAGACAGG | 2 | 4 | 25 | SEQ ID NO. 721 |

FIG. 4 cont.

| site_type | site_chr omosome | site_start_ nucleotide | site_s trand | target_site_sequence_wi th_NGG | genome_wide_ hits_with_1 or_less_mism atches | genome_wide_ hits_with_2 or_less_mism atches | genome_wide_ hits_with_3 or_less_mism atches | | |
|---|---|---|---|---|---|---|---|---|---|
| (N20)NGG | 10 | 14976410 | - | GGCTCCAGTGATCCAGCTTCGG | 1 | 3 | 22 | SEQ ID NO. | 722 |
| (N20)NGG | 10 | 14976431 | - | TCAGCCACACAACATGGTACGGG | 2 | 8 | 158 | SEQ ID NO. | 723 |
| (N20)NGG | 10 | 14976432 | - | TTCAGCCACACAACATGGTACGG | 2 | 4 | 30 | SEQ ID NO. | 724 |
| (N20)NGG | 10 | 14976437 | - | TGCAGTTCAGCCACACAACATGG | 2 | 3 | 60 | SEQ ID NO. | 725 |
| (N20)NGG | 10 | 14976490 | - | TCCTAATTCTTCACTAAGGTTGG | 2 | 6 | 37 | SEQ ID NO. | 726 |
| (N20)NGG | 10 | 14976494 | - | GGACTCCTAATTCTTCACTAAGG | 2 | 2 | 18 | SEQ ID NO. | 727 |
| (N20)NGG | 10 | 14976515 | - | GAATGAACAGTCACCATACCTGG | 2 | 6 | 26 | SEQ ID NO. | 728 |
| (N20)NGG | 10 | 14976729 | + | AGACATCCAAAGTGTATATTTGG | 2 | 6 | 50 | SEQ ID NO. | 729 |
| (N20)NGG | 10 | 14976773 | + | GATTTTACCAAATTCCAAGTCGG | 4 | 8 | 74 | SEQ ID NO. | 730 |
| (N20)NGG | 10 | 14976774 | + | ATTTTACCAAATTCCAAGTCGGG | 2 | 5 | 52 | SEQ ID NO. | 731 |
| (N20)NGG | 10 | 14976787 | + | CCAAGTCGGGTAAGTCTGCCTGG | 2 | 2 | 14 | SEQ ID NO. | 732 |
| (N20)NGG | 10 | 14976790 | + | AGTCGGGTAAGTCTGCCTGGAGG | 2 | 4 | 29 | SEQ ID NO. | 733 |
| (N20)NGG | 10 | 14976796 | + | GTAAGTCTGCCTGGAGGAACAGG | 2 | 5 | 41 | SEQ ID NO. | 734 |
| (N20)NGG | 10 | 14976797 | + | TAAGTCTGCCTGGAGGAACAGGG | 2 | 3 | 53 | SEQ ID NO. | 735 |
| (N20)NGG | 10 | 14976713 | + | TAGTATCCAAATATACACTTTGG | 2 | 8 | 49 | SEQ ID NO. | 736 |
| (N20)NGG | 10 | 14976747 | - | CTTGGAATTTGGTAAAATCTTGG | 3 | 13 | 87 | SEQ ID NO. | 737 |
| (N20)NGG | 10 | 14976758 | - | GACTTACCCGACTTGGAATTTGG | 2 | 2 | 15 | SEQ ID NO. | 738 |
| (N20)NGG | 10 | 14976765 | - | CCAGGCAGACTTACCCGACTTGG | 2 | 2 | 16 | SEQ ID NO. | 739 |
| (N20)NGG | 10 | 14977461 | + | CTGGGATATATTTCTTTTTTCAGG | 2 | 7 | 140 | SEQ ID NO. | 740 |
| (N20)NGG | 10 | 14977474 | + | CTTTTTCAGGTTTTTATTTCAGG | 3 | 21 | 378 | SEQ ID NO. | 741 |
| (N20)NGG | 10 | 14977475 | + | TTTTTTCAGGTTTTTATTTCAGGG | 5 | 53 | 552 | SEQ ID NO. | 742 |
| (N20)NGG | 10 | 14977484 | + | TTTTTATTTCAGGCAATAATGG | 2 | 11 | 217 | SEQ ID NO. | 743 |
| (N20)NGG | 10 | 14977502 | + | AATGGAACTGTCCTGTACACAGG | 1 | 6 | 36 | SEQ ID NO. | 744 |
| (N20)NGG | 10 | 14977516 | + | GTACACAGGAGACTTCAGATTGG | 2 | 3 | 44 | SEQ ID NO. | 745 |
| (N20)NGG | 10 | 14977523 | + | GGAGACTTCAGATTGGCGCAAGG | 1 | 3 | 15 | SEQ ID NO. | 746 |
| (N20)NGG | 10 | 14977540 | + | GCAAGGAGAAGCTGCTAGAATGG | 3 | 7 | 73 | SEQ ID NO. | 747 |
| (N20)NGG | 10 | 14977556 | + | AGAATGGAGCTTCTGCACTCCGG | 2 | 5 | 95 | SEQ ID NO. | 748 |
| (N20)NGG | 10 | 14977557 | + | GAATGGAGCTTCTGCACTCCGGG | 2 | 2 | 36 | SEQ ID NO. | 749 |
| (N20)NGG | 10 | 14977558 | + | AATGGAGCTTCTGCACTCCGGGG | 2 | 2 | 17 | SEQ ID NO. | 750 |
| (N20)NGG | 10 | 14977559 | + | ATGGAGCTTCTGCACTCCGGGGG | 2 | 3 | 20 | SEQ ID NO. | 751 |
| (N20)NGG | 10 | 14977563 | + | AGCTTCTGCACTCCGGGGGCAGG | 2 | 4 | 36 | SEQ ID NO. | 752 |
| (N20)NGG | 10 | 14977569 | + | TGCACTCCGGGGGCAGGTACTGG | 2 | 5 | 19 | SEQ ID NO. | 753 |
| (N20)NGG | 10 | 14977570 | + | GCACTCCGGGGGCAGGTACTGGG | 2 | 2 | 11 | SEQ ID NO. | 754 |

FIG. 4 cont.

| site_type | site_chr omosome | site_start_ nucleotide | site_s trand | target_site_sequence with NGG | genome_wide_ hits_with_1_ or_less_mism atches | genome_wide_ hits_with_2_ or_less_mism atches | genome_wide_ hits_with_3_ or_less_mism atches | |
|---|---|---|---|---|---|---|---|---|
| (N20)NGG | 10 | 14977581 | + | GCAGGTACTGGGCCTCGTATAGG | | 2 | 3 | 14 SEQ ID NO. 755 |
| (N20)NGG | 10 | 14977491 | - | ATCTGAAGTCTCCTGTGTACAGG | | 2 | 4 | 39 SEQ ID NO. 756 |
| (N20)NGG | 10 | 14977553 | - | CGAGGCCCAGTACCTGCCCCCGG | | 2 | 4 | 57 SEQ ID NO. 757 |
| (N20)NGG | 10 | 14978539 | + | TTCTTTATTTTCTTTTTAGAAGG | | 15 | 1012 | 20720 SEQ ID NO. 758 |
| (N20)NGG | 10 | 14978570 | + | GTTGTGACTCTCTTACCAGCTGG | | 1 | 2 | 25 SEQ ID NO. 759 |
| (N20)NGG | 10 | 14978581 | + | CTTACCAGCTGGTCACTGTCCGG | | 1 | 2 | 23 SEQ ID NO. 760 |
| (N20)NGG | 10 | 14978582 | + | TTACCAGCTGGTCACTGTCCGGG | | 1 | 3 | 29 SEQ ID NO. 761 |
| (N20)NGG | 10 | 14978597 | + | TGTCCGGGATCAGTTATGTAAGG | | 1 | 1 | 4 SEQ ID NO. 762 |
| (N20)NGG | 10 | 14978598 | + | GTCCGGGATCAGTTATGTAAGGG | | 1 | 1 | 6 SEQ ID NO. 763 |
| (N20)NGG | 10 | 14978599 | + | CCGGGATCAGTTATGTAAGGGG | | 1 | 1 | 9 SEQ ID NO. 764 |
| (N20)NGG | 10 | 14978600 | + | CCGGGATCAGTTATGTAAGGGGG | | 1 | 1 | 7 SEQ ID NO. 765 |
| (N20)NGG | 10 | 14978563 | - | GATCCCGGACAGTGACCAGCTGG | | 1 | 1 | 11 SEQ ID NO. 766 |
| (N20)NGG | 10 | 14978578 | - | CCCCCTTACATAACTGATCCCGG | | 1 | 1 | 5 SEQ ID NO. 767 |
| (N20)NGG | 10 | 14981850 | + | TCCTACCCAGATATCTTTAGTGG | | 2 | 4 | 28 SEQ ID NO. 768 |
| (N20)NGG | 10 | 14981863 | + | TCTTTAGTGGATGAAGCATCAGG | | 2 | 2 | 30 SEQ ID NO. 769 |
| (N20)NGG | 10 | 14981868 | + | AGTGGATGAAGCATCAGGAGAGG | | 2 | 7 | 68 SEQ ID NO. 770 |
| (N20)NGG | 10 | 14981829 | - | TCCACTAAAGATATCTGGGTAGG | | 2 | 4 | 31 SEQ ID NO. 771 |
| (N20)NGG | 10 | 14981833 | - | TTCATCCACTAAAGATATCTGGG | | 2 | 4 | 48 SEQ ID NO. 772 |
| (N20)NGG | 10 | 14981834 | - | CTTCATCCACTAAAGATATCTGG | | 2 | 2 | 29 SEQ ID NO. 773 |
| (N20)NGG | 10 | 14987110 | + | CTTTTTTTCCTTTCAGCTGAAGG | | 1 | 8 | 175 SEQ ID NO. 774 |
| (N20)NGG | 10 | 14987140 | + | ATACTGTTCACCTGTGACTAAGG | | 1 | 1 | 23 SEQ ID NO. 775 |
| (N20)NGG | 10 | 14987175 | + | CGAGCCCGAAATACAGATTTTGG | | 1 | 1 | 14 SEQ ID NO. 776 |
| (N20)NGG | 10 | 14987095 | - | AGATAAACCTTCAAGCTGAAAGG | | 1 | 5 | 44 SEQ ID NO. 777 |
| (N20)NGG | 10 | 14987128 | - | AACAACAACTCCTTAGTCACAGG | | 1 | 1 | 17 SEQ ID NO. 778 |
| (N20)NGG | 10 | 14987157 | - | TCTTCCAAAATCTGTATTTCGGG | | 1 | 16 | 173 SEQ ID NO. 779 |
| (N20)NGG | 10 | 14987158 | - | TTCTTCCAAAATCTGTATTTCGG | | 4 | 19 | 226 SEQ ID NO. 780 |
| (N20)NGG | 10 | 14991046 | + | TTGTTTTTAGATCACATGAAAGG | | 1 | 6 | 109 SEQ ID NO. 781 |
| (N20)NGG | 10 | 14991074 | + | GAGCCCTACCTTGAAAAGAAGG | | 1 | 6 | 40 SEQ ID NO. 782 |
| (N20)NGG | 10 | 14991078 | + | CCCTACCTTGAAAAGAAGGTTGG | | 1 | 2 | 29 SEQ ID NO. 783 |
| (N20)NGG | 10 | 14991086 | + | TGAAAAGAAGGTTGGAGTGCAGG | | 1 | 3 | 60 SEQ ID NO. 784 |
| (N20)NGG | 10 | 14991055 | - | CAACCTTCTTTTCAAGGTAGGGG | | 1 | 2 | 64 SEQ ID NO. 785 |
| (N20)NGG | 10 | 14991056 | - | CCAACCTTCTTTTCAAGGTAGG | | 1 | 3 | 43 SEQ ID NO. 786 |
| (N20)NGG | 10 | 14991057 | - | TCCAACCTTCTTTTCAAGGTAGG | | 2 | 6 | 53 SEQ ID NO. 787 |

FIG. 4 cont.

| site_type | site_chr omosome | site_start_ nucleotide | site_s trand | target_site_sequence_wi th_NGG | genome_wide_ hits_with_1_ or_less_mism atches | genome_wide_ hits_with_2_ or_less_mism atches | genome_wide_ hits_with_3_ or_less_mism atches | |
|---|---|---|---|---|---|---|---|---|
| (N20)NGG | 10 | 14991061 | - | GCACTCCAACCTTCTTTTCAAGG | 2 | 2 | 45 | SEQ ID NO. 788 |
| (N20)NGG | 10 | 14995915 | + | CGGGCTATGAGTTCTTTCGAGG | 1 | 1 | 2 | SEQ ID NO. 789 |
| (N20)NGG | 10 | 14995916 | + | GGGCTATGAGTTCTTTCGAGGG | 1 | 1 | 4 | SEQ ID NO. 790 |
| (N20)NGG | 10 | 14995917 | + | GCGCTATGAGTTCTTTCGAGGGG | 1 | 1 | 8 | SEQ ID NO. 791 |
| (N20)NGG | 10 | 14995924 | + | GAGTTCTTTCGAGGGCAGATGG | 1 | 2 | 33 | SEQ ID NO. 792 |
| (N20)NGG | 10 | 14995962 | + | TCTCCATAGACCGCTTCGATAGG | 1 | 1 | 5 | SEQ ID NO. 793 |
| (N20)NGG | 10 | 14995963 | + | CTCCATAGACCGCTTCGATAGG | 1 | 1 | 1 | SEQ ID NO. 794 |
| (N20)NGG | 10 | 14995974 | + | GCTTCGATAGGGAGAACCTGAGG | 1 | 1 | 9 | SEQ ID NO. 795 |
| (N20)NGG | 10 | 14995975 | + | CTTCGATAGGGAGAACCTGAGG | 1 | 1 | 9 | SEQ ID NO. 796 |
| (N20)NGG | 10 | 14996009 | + | TTTCGTCCCACTGCCACAAAGG | 1 | 6 | 52 | SEQ ID NO. 797 |
| (N20)NGG | 10 | 14996018 | + | CACTGCCACAAAGGTGAGTGAGG | 1 | 4 | 42 | SEQ ID NO. 798 |
| (N20)NGG | 10 | 14996019 | + | ACTGCCACAAAGGTGAGTGAGG | 1 | 5 | 56 | SEQ ID NO. 799 |
| (N20)NGG | 10 | 14995875 | - | CGCCGCCGATCCCAGAGTCCGG | 1 | 1 | 13 | SEQ ID NO. 800 |
| (N20)NGG | 10 | 14995876 | - | GCGCCGCCGATCCCAGAGTCGG | 1 | 1 | 10 | SEQ ID NO. 801 |
| (N20)NGG | 10 | 14995925 | - | TATGGAGATAGTTGGATATCGG | 1 | 1 | 25 | SEQ ID NO. 802 |
| (N20)NGG | 10 | 14995933 | - | AAGCGGTCTATGGAGATAGTTGG | 1 | 1 | 10 | SEQ ID NO. 803 |
| (N20)NGG | 10 | 14995943 | - | CTCCCTATCGAAGCGGTCTATGG | 1 | 2 | 2 | SEQ ID NO. 804 |
| (N20)NGG | 10 | 14995950 | - | TCAGGTTCTCCCTATCGAAGCGG | 1 | 1 | 10 | SEQ ID NO. 805 |
| (N20)NGG | 10 | 14995968 | - | GGAAGTAGGCGCGGGCCCTCAGG | 1 | 2 | 18 | SEQ ID NO. 806 |
| (N20)NGG | 10 | 14995976 | - | GTGGGACAGGAAGTAGGCGCGG | 1 | 5 | 51 | SEQ ID NO. 807 |
| (N20)NGG | 10 | 14995977 | - | AGTGGGACAGGAAGTAGGCGCGG | 1 | 4 | 48 | SEQ ID NO. 808 |
| (N20)NGG | 10 | 14995982 | - | GTGGCAGTGGACAGGAAGTAGG | 1 | 5 | 123 | SEQ ID NO. 809 |
| (N20)NGG | 10 | 14995989 | - | CACCTTTGTGGCAGTGGACAGG | 1 | 4 | 35 | SEQ ID NO. 810 |
| (N20)NGG | 10 | 14995994 | - | TCACTCACCTTTGTGGCAGTGG | 1 | 4 | 43 | SEQ ID NO. 811 |
| (N20)NGG | 10 | 14995995 | - | CTCACTCACCTTTGTGGCAGTGG | 1 | 6 | 55 | SEQ ID NO. 812 |
| (N20)NGG | 10 | 14996001 | - | GCAGCCCTCACTCACCTTTGTGG | 1 | 6 | 73 | SEQ ID NO. 813 |

FIG. 4 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 11 | 5246833 | + | TATCTTCCTCCCACAGCTCCTGG | 1 | 6 | 114 | SEQ ID NO. 814 |
| (N20)NGG | 11 | 5246834 | + | ATCTTCCTCCCACAGCTCCTGGG | 2 | 14 | 155 | SEQ ID NO. 815 |
| (N20)NGG | 11 | 5246845 | + | ACAGCTCCTGGGCAACGTGCTGG | 1 | 6 | 44 | SEQ ID NO. 816 |
| (N20)NGG | 11 | 5246857 | + | CAACGTGCTGGTCTGTGTCTGG | 1 | 5 | 25 | SEQ ID NO. 817 |
| (N20)NGG | 11 | 5246870 | + | TGTGTGCTGGCCCATCACTTTGG | 1 | 2 | 47 | SEQ ID NO. 818 |
| (N20)NGG | 11 | 5246896 | + | AGAATTCACCCCACCAGTGCAGG | | 3 | 31 | SEQ ID NO. 819 |
| (N20)NGG | 11 | 5246914 | + | GCAGGCTGCCTATCAGAAAGTGG | 1 | 5 | 34 | SEQ ID NO. 820 |
| (N20)NGG | 11 | 5246917 | + | GGCTGCCTATCAGAAAGTGGTGG | 2 | 5 | 50 | SEQ ID NO. 821 |
| (N20)NGG | 11 | 5246921 | + | GCCTATCAGAAAGTGGTGCTGG | 2 | 7 | 86 | SEQ ID NO. 822 |
| (N20)NGG | 11 | 5246926 | + | TCAGAAAGTGGTGGCTGGTGTGG | 3 | 6 | 74 | SEQ ID NO. 823 |
| (N20)NGG | 11 | 5246938 | + | GGCTGGTGTGCTAATGCCCTGG | 2 | 5 | 34 | SEQ ID NO. 824 |
| (N20)NGG | 11 | 5246806 | - | AGCTGTGGGAGGAAGATAAGAGG | 1 | 9 | 146 | SEQ ID NO. 825 |
| (N20)NGG | 11 | 5246817 | - | CGTTGCCCAGGAGCTGTGGGAGG | 1 | 4 | 62 | SEQ ID NO. 826 |
| (N20)NGG | 11 | 5246820 | - | GCACGTTGCCCAGGAGCTGTGG | 1 | 3 | 39 | SEQ ID NO. 827 |
| (N20)NGG | 11 | 5246821 | - | AGCACGTTGCCCAGGAGCTGTGG | 1 | 3 | 57 | SEQ ID NO. 828 |
| (N20)NGG | 11 | 5246829 | - | CACAGACCAGCACGTTGCCCAGG | 1 | 3 | 26 | SEQ ID NO. 829 |
| (N20)NGG | 11 | 5246858 | - | GAATTCTTTGCCAAAGTGATGG | 1 | 6 | 77 | SEQ ID NO. 830 |
| (N20)NGG | 11 | 5246859 | - | TGAATTCTTTGCCAAAGTGATGG | 1 | 6 | 102 | SEQ ID NO. 831 |
| (N20)NGG | 11 | 5246882 | - | ATAGGCAGCCTGCACTGGTCGGG | 1 | 2 | 25 | SEQ ID NO. 832 |
| (N20)NGG | 11 | 5246883 | - | GATAGGCAGCCTGCACTGGTCGG | 1 | 2 | 30 | SEQ ID NO. 833 |
| (N20)NGG | 11 | 5246884 | - | TGATAGGCAGCCTGCACTGGTGG | 1 | 3 | 28 | SEQ ID NO. 834 |
| (N20)NGG | 11 | 5246887 | - | TTCTGATAGGCAGCCTGCACTGG | 1 | 3 | 35 | SEQ ID NO. 835 |
| (N20)NGG | 11 | 5246900 | - | ACCAGCACCACCACTTTCTGATAGG | 2 | 4 | 59 | SEQ ID NO. 836 |
| (N20)NGG | 11 | 5246993 | - | TTAGTGATACTTGTGGGCCAGG | 1 | 3 | 27 | SEQ ID NO. 837 |
| (N20)NGG | 11 | 5246934 | - | CTTAGTGATACTTGTGGGCCAGG | 1 | 1 | 22 | SEQ ID NO. 838 |
| (N20)NGG | 11 | 5246939 | - | GCGAGCTTAGTGATACTTGTGGG | 1 | 1 | 1 | SEQ ID NO. 839 |
| (N20)NGG | 11 | 5246940 | - | AGCGAGCTTAGTGATACTTGTGG | 1 | 1 | 8 | SEQ ID NO. 840 |
| (N20)NGG | 11 | 5247806 | + | TGGTCTATTTTCCACCCTTAGG | 2 | 6 | 54 | SEQ ID NO. 841 |
| (N20)NGG | 11 | 5247813 | + | TTTTCCCACCCTTAGGCTGCTGG | 1 | 2 | 40 | SEQ ID NO. 842 |
| (N20)NGG | 11 | 5247816 | + | TCCCACCCTTAGGCTGCTGGTGG | 1 | 7 | 50 | SEQ ID NO. 843 |
| (N20)NGG | 11 | 5247827 | + | GGCTGCTGGTCTACCCTTGG | 1 | 1 | 34 | SEQ ID NO. 844 |
| (N20)NGG | 11 | 5247836 | + | TGGTCTACCCTTGGACCCAGAGG | 2 | 6 | 27 | SEQ ID NO. 845 |
| (N20)NGG | 11 | 5247853 | + | CAGAGGTTCTTTGAGTCCTTTGG | 2 | 2 | 55 | SEQ ID NO. 846 |

FIG. 5

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 11 | 5247854 | + | AGAGGTTCTTTGAGTCCTTTGGG |  | 3 | 5 | 87 SEQ ID NO. 847 |
| (N20)NGG | 11 | 5247855 | + | GAGGTTCTTTGAGTCCTTTGGGG |  | 2 | 8 | 65 SEQ ID NO. 848 |
| (N20)NGG | 11 | 5247882 | + | GTCCACTCCTGATGCTGTTATGG |  | 2 | 6 | 50 SEQ ID NO. 849 |
| (N20)NGG | 11 | 5247883 | + | TCCACTCCTGATGCTGTTATGGG |  | 2 | 4 | 33 SEQ ID NO. 850 |
| (N20)NGG | 11 | 5247894 | + | TGCTGTTATGGCAACCCTAAGG |  | 2 | 4 | 23 SEQ ID NO. 851 |
| (N20)NGG | 11 | 5247900 | + | TATGGCAACCCTAAGGTGAAGG |  | 2 | 3 | 23 SEQ ID NO. 852 |
| (N20)NGG | 11 | 5247907 | + | AACCCTAAGGTGAAGGCTCATGG |  | 2 | 4 | 31 SEQ ID NO. 853 |
| (N20)NGG | 11 | 5247922 | + | GCTCATGGCAAGAAAGTGCTCGG |  | 2 | 6 | 45 SEQ ID NO. 854 |
| (N20)NGG | 11 | 5247937 | + | GTGCTCGGTGCCTTTAGTGATGG |  | 2 | 4 | 20 SEQ ID NO. 855 |
| (N20)NGG | 11 | 5247942 | + | CGGTGCCTTTAGTGATGGCCTGG |  | 2 | 3 | 23 SEQ ID NO. 856 |
| (N20)NGG | 11 | 5247951 | + | TAGTGATGGCCTGGCTCACCTGG |  | 2 | 5 | 29 SEQ ID NO. 857 |
| (N20)NGG | 11 | 5247963 | + | GGCTCACCTGGACAACCTCAAGG |  | 2 | 2 | 29 SEQ ID NO. 858 |
| (N20)NGG | 11 | 5247964 | + | GCTCACCTGGACAACCTCAAGGG |  | 2 | 3 | 40 SEQ ID NO. 859 |
| (N20)NGG | 11 | 5248011 | + | GCACTGTGACAAGCTGCACGTGG |  | 6 | 7 | 23 SEQ ID NO. 860 |
| (N20)NGG | 11 | 5248028 | + | ACGTGGATCCTGAGAACTTCAGG |  | 5 | 6 | 18 SEQ ID NO. 861 |
| (N20)NGG | 11 | 5248029 | + | CGTGGATCCTGAGAACTTCAGGG |  | 5 | 6 | 21 SEQ ID NO. 862 |
| (N20)NGG | 11 | 5248040 | + | AGAACTTCAGGGTGAGTCTATGG |  | 1 | 15 | 83 SEQ ID NO. 863 |
| (N20)NGG | 11 | 5248041 | + | GAACTTCAGGGTGAGTCTATGGG |  | 1 | 5 | 32 SEQ ID NO. 864 |
| (N20)NGG | 11 | 5247795 | − | ACCACCAGCAGCCTAAGGGTGGG |  | 1 | 1 | 26 SEQ ID NO. 865 |
| (N20)NGG | 11 | 5247796 | − | GACCACCAGCAGCCTAAGGGTGG |  | 1 | 4 | 36 SEQ ID NO. 866 |
| (N20)NGG | 11 | 5247799 | − | GTAGACCACCAGCAGCCTAAGG |  | 1 | 2 | 24 SEQ ID NO. 867 |
| (N20)NGG | 11 | 5247800 | − | GGTAGACCACCAGCAGCCTAAGG |  | 1 | 2 | 20 SEQ ID NO. 868 |
| (N20)NGG | 11 | 5247821 | − | CAAAGAACCTCTGGGTCCAAGG |  | 4 | 8 | 41 SEQ ID NO. 869 |
| (N20)NGG | 11 | 5247822 | − | TCAAAGAACCTCTGGGTCCAAGG |  | 5 | 11 | 32 SEQ ID NO. 870 |
| (N20)NGG | 11 | 5247829 | − | AAAGGACTCAAAGAACCTCTGG |  | 2 | 7 | 59 SEQ ID NO. 871 |
| (N20)NGG | 11 | 5247830 | − | CAAAGGACTCAAAGAACCTCTGG |  | 2 | 6 | 61 SEQ ID NO. 872 |
| (N20)NGG | 11 | 5247847 | − | AGGAGTGGACAGATCCCCAAAGG |  | 2 | 3 | 38 SEQ ID NO. 873 |
| (N20)NGG | 11 | 5247862 | − | GCCCATAACAGCATCAGGAGTGG |  | 2 | 2 | 42 SEQ ID NO. 874 |
| (N20)NGG | 11 | 5247857 | − | GGGTTGCCCATAACAGCATCAGG |  | 2 | 2 | 11 SEQ ID NO. 875 |
| (N20)NGG | 11 | 5247887 | − | TGCCATGAGCCTTCACCTTAGG |  | 2 | 2 | 32 SEQ ID NO. 876 |
| (N20)NGG | 11 | 5247888 | − | TTGCCATGAGCCTTCACCTTAGG |  | 2 | 4 | 35 SEQ ID NO. 877 |
| (N20)NGG | 11 | 5247925 | − | GTGAGCCAGGCCATCACTAAAGG |  | 2 | 2 | 23 SEQ ID NO. 878 |
| (N20)NGG | 11 | 5247938 | − | TGAGGTTGTCCAGGTGAGCCAGG |  | 2 | 7 | 55 SEQ ID NO. 879 |

FIG. 5 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 11 | 5247947 | - | AGGTGCCCTTGAGGTTGTCCAGG | 2 | 3 | 19 | SEQ ID NO. 880 |
| (N20)NGG | 11 | 5247956 | - | GTGTGGCAAAGTGCCCTTGAGG | 1 | 2 | 36 | SEQ ID NO. 881 |
| (N20)NGG | 11 | 5247967 | - | CAGCTCACTCAGTGTGGCAAAGG | 1 | 4 | 40 | SEQ ID NO. 882 |
| (N20)NGG | 11 | 5247973 | - | ACAGTGCAGCTCACTCAGTGTGG | 2 | 8 | 46 | SEQ ID NO. 883 |
| (N20)NGG | 11 | 5248014 | - | AGACTCACCCTGAAGTTCTCAGG | 2 | 7 | 74 | SEQ ID NO. 884 |
| (N20)NGG | 11 | 5248162 | + | GCAACCTCAAACAGACACCATGG | 2 | 3 | 35 | SEQ ID NO. 885 |
| (N20)NGG | 11 | 5248180 | + | CATGGTGCATCTGACTCCTGAGG | 2 | 6 | 43 | SEQ ID NO. 886 |
| (N20)NGG | 11 | 5248206 | + | AGTCTGCCGTTACTGCCCTGTGG | 1 | 3 | 20 | SEQ ID NO. 887 |
| (N20)NGG | 11 | 5248207 | + | GTCTGCCGTTACTGCCCTGTGGG | 1 | 2 | 12 | SEQ ID NO. 888 |
| (N20)NGG | 11 | 5248208 | + | TCTGCCGTTACTGCCCTGTGGGG | 1 | 3 | 32 | SEQ ID NO. 889 |
| (N20)NGG | 11 | 5248213 | + | CGTTACTGCCCTGTGGGCAAGG | 1 | 2 | 18 | SEQ ID NO. 890 |
| (N20)NGG | 11 | 5248222 | + | CCTGTGGGCAAGGTGAACGTGG | 4 | 5 | 33 | SEQ ID NO. 891 |
| (N20)NGG | 11 | 5248232 | + | AAGGTGAACGTGGATGAAGTTGG | 1 | 3 | 34 | SEQ ID NO. 892 |
| (N20)NGG | 11 | 5248235 | + | GTGAACGTGGATGAAGTTGGTGG | 2 | 9 | 139 | SEQ ID NO. 893 |
| (N20)NGG | 11 | 5248240 | + | CGTGGATGAAGTTGGTGGTGAGG | 2 | 4 | 30 | SEQ ID NO. 894 |
| (N20)NGG | 11 | 5248246 | + | TGAAGTTGGTGGTGAGGCCCTGG | 2 | 5 | 49 | SEQ ID NO. 895 |
| (N20)NGG | 11 | 5248247 | + | GAAGTTGGTGGTGAGGCCCTGGG | 2 | 5 | 46 | SEQ ID NO. 896 |
| (N20)NGG | 11 | 5248251 | + | TTGGTGGTGAGGCCCTGGGCAGG | 2 | 13 | 109 | SEQ ID NO. 897 |
| (N20)NGG | 11 | 5248255 | + | TGGTGAGGCCCTGGGCAGGTTGG | 3 | 14 | 130 | SEQ ID NO. 898 |
| (N20)NGG | 11 | 5248263 | + | CCCTGGGCAGGTTGGTATCAAGG | 2 | 2 | 38 | SEQ ID NO. 899 |
| (N20)NGG | 11 | 5248275 | + | TGGTATCAAGGTTACAAGACAGG | 1 | 5 | 45 | SEQ ID NO. 900 |
| (N20)NGG | 11 | 5248144 | - | TGCACCATGGTGTCTGTTTGAGG | 2 | 5 | 45 | SEQ ID NO. 901 |
| (N20)NGG | 11 | 5248157 | - | CTCAGGAGTCAGATGCACCATGG | 2 | 7 | 85 | SEQ ID NO. 902 |
| (N20)NGG | 11 | 5248174 | - | GTAACGGCAGACTTCTCCTCAGG | 1 | 1 | 11 | SEQ ID NO. 903 |
| (N20)NGG | 11 | 5248190 | - | CTTGCCCACAGGGCAGTAACGG | 1 | 2 | 48 | SEQ ID NO. 904 |
| (N20)NGG | 11 | 5248199 | - | CACGTTCACCTTGCCCACAGGG | 2 | 4 | 22 | SEQ ID NO. 905 |
| (N20)NGG | 11 | 5248200 | - | CCAAGTTCACCTTGCCCACAGG | 4 | 5 | 26 | SEQ ID NO. 906 |
| (N20)NGG | 11 | 5248241 | - | CCTTGATACCAACCTGCCCAGG | 2 | 2 | 16 | SEQ ID NO. 907 |
| (N20)NGG | 11 | 5248242 | - | ACCTTGATACCAACCTGCCCAGG | 2 | 2 | 20 | SEQ ID NO. 908 |

FIG. 5 cont.

| site_type | site_chromosome | site_start_nucleotide | site_strand | target_site_sequence with NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | X | 70327585 | + | ACCTGGACATATCTGTCTTTAGG | 1 | 4 | 62 | SEQ ID NO. 909 |
| (N20)NGG | X | 70327590 | + | GACATATCTGTCTTTAGGCCTGG | 1 | 2 | 39 | SEQ ID NO. 910 |
| (N20)NGG | X | 70327595 | + | ATCTGTCTTTAGGCCTGGAGTGG | 1 | 2 | 52 | SEQ ID NO. 911 |
| (N20)NGG | X | 70327606 | + | GGCCTGGAGTGGTGTGTCTAAGG | 1 | 4 | 54 | SEQ ID NO. 912 |
| (N20)NGG | X | 70327607 | + | GCCTGGAGTGGTGTGTCTAAGGG | 1 | 2 | 45 | SEQ ID NO. 913 |
| (N20)NGG | X | 70327612 | + | GAGTGGTGTGTCTAAGGGACTGG | 1 | 1 | 32 | SEQ ID NO. 914 |
| (N20)NGG | X | 70327676 | + | GTCAGTGAGATTCCCCCAAAAGG | 1 | 2 | 30 | SEQ ID NO. 915 |
| (N20)NGG | X | 70327679 | + | AGTGAGATTCCCCCAAAAGGAGG | 1 | 4 | 51 | SEQ ID NO. 916 |
| (N20)NGG | X | 70327680 | + | GTGAGATTCCCCCAAAAGGAGGG | 1 | 2 | 59 | SEQ ID NO. 917 |
| (N20)NGG | X | 70327681 | + | TGAGATTCCCCCAAAAGGAGGGG | 1 | 3 | 53 | SEQ ID NO. 918 |
| (N20)NGG | X | 70327688 | + | CCCCCAAAAGGAGGGGCCCTTGG | 1 | 3 | 28 | SEQ ID NO. 919 |
| (N20)NGG | X | 70327689 | + | CCCCAAAAGGAGGGGCCCTTTGG | 1 | 1 | 33 | SEQ ID NO. 920 |
| (N20)NGG | X | 70327690 | + | CCCAAAAGGAGGGGCCCTTTGGG | 1 | 3 | 33 | SEQ ID NO. 921 |
| (N20)NGG | X | 70327693 | + | AAAAGGAGGGGCCCTTTGGGAGG | 1 | 3 | 95 | SEQ ID NO. 922 |
| (N20)NGG | X | 70327694 | + | AAAGGAGGGGCCCTTTGGGAGGG | 1 | 10 | 110 | SEQ ID NO. 923 |
| (N20)NGG | X | 70327695 | + | AAGGAGGGGCCCTTTGGGAGGGG | 2 | 8 | 140 | SEQ ID NO. 924 |
| (N20)NGG | X | 70327700 | + | GGGGCCCTTTGGGAGGGGCCTGG | 1 | 30 | 212 | SEQ ID NO. 925 |
| (N20)NGG | X | 70327701 | + | GGGCCCTTTGGGAGGGGCCTGGG | 1 | 16 | 187 | SEQ ID NO. 926 |
| (N20)NGG | X | 70327702 | + | GGCCCTTTGGGAGGGGCCTGGGG | 4 | 30 | 206 | SEQ ID NO. 927 |
| (N20)NGG | X | 70327734 | + | GCAACCAGCATAGCCCCTACTGG | 1 | 3 | 14 | SEQ ID NO. 928 |
| (N20)NGG | X | 70327735 | + | CAACCAGCATAGCCCCTACTGGG | 1 | 1 | 13 | SEQ ID NO. 929 |
| (N20)NGG | X | 70327564 | – | GCCTAAAGACAGATATGTCCAGG | 1 | 3 | 24 | SEQ ID NO. 930 |
| (N20)NGG | X | 70327586 | – | TCCCTTAGACACCACTCCAGG | 1 | 2 | 26 | SEQ ID NO. 931 |
| (N20)NGG | X | 70327627 | – | CAGAGTCGTTCACTGTAGTCTGG | 1 | 2 | 69 | SEQ ID NO. 932 |
| (N20)NGG | X | 70327650 | – | TTGGGGAATCTCACTGACGAGG | 1 | 2 | 16 | SEQ ID NO. 933 |
| (N20)NGG | X | 70327666 | – | CCAAGGCCCCTCCTTTTTGGGGG | 1 | 4 | 39 | SEQ ID NO. 934 |
| (N20)NGG | X | 70327667 | – | CCCAAGGCCCCTCCTTTTTGGGG | 1 | 4 | 51 | SEQ ID NO. 935 |
| (N20)NGG | X | 70327668 | – | CCCCAAGGCCCCTCCTTTTTGGG | 1 | 4 | 44 | SEQ ID NO. 936 |
| (N20)NGG | X | 70327669 | – | TCCCCAAGGCCCCTCCTTTTTGG | 2 | 2 | 53 | SEQ ID NO. 937 |
| (N20)NGG | X | 70327682 | – | GGCCCCAGGCCCCTCCCCAAGGG | 5 | 10 | 147 | SEQ ID NO. 938 |
| (N20)NGG | X | 70327683 | – | AGGCCCCAGGCCCCTCCCCAAGG | 1 | 22 | 285 | SEQ ID NO. 939 |
| (N20)NGG | X | 70327696 | – | TGGTTGCATGGGAGGCCCCAGG | 1 | 1 | 74 | SEQ ID NO. 940 |
| (N20)NGG | X | 70327703 | – | GCTATGCTGGTTGCATGGGAGG | 1 | 3 | 22 | SEQ ID NO. 941 |
| (N20)NGG | X | 70327706 | – | GGGGCTATGCTGGTTGCATGGGG | 1 | 1 | 26 | SEQ ID NO. 942 |

FIG. 6

| site_type | site_chromosome | site_start_nucleotide | site_strand | target_site_sequence_with NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | X | 70327707 | - | AGGGGCTATGCTGGTTGCATGGG | 1 | 3 | 29 | SEQ ID NO. 943 |
| (N20)NGG | X | 70327708 | - | TAGGGGCTATGCTGGTTGCATGG | 1 | 3 | 28 | SEQ ID NO. 944 |
| (N20)NGG | X | 70327716 | - | GGGCCCAGTAGGGGCTATGCTGG | 1 | 1 | 20 | SEQ ID NO. 945 |
| (N20)NGG | X | 70327725 | - | AACATGGGGGGGCCCAGTAGGGG | 1 | 1 | 23 | SEQ ID NO. 946 |
| (N20)NGG | X | 70327726 | - | TAACATGGGGGGGCCCAGTAGGG | 1 | 1 | 6 | SEQ ID NO. 947 |
| (N20)NGG | X | 70327727 | - | GTAACATGGGGGGGCCCAGTAGG | 1 | 1 | 15 | SEQ ID NO. 948 |
| (N20)NGG | X | 70327736 | - | CTTTAGGGTGTAACATGGGGGGG | 1 | 1 | 19 | SEQ ID NO. 949 |
| (N20)NGG | X | 70327737 | - | GCTTTAGGGTGTAACATGGGGGG | 1 | 2 | 17 | SEQ ID NO. 950 |
| (N20)NGG | X | 70327738 | - | GGCTTTAGGGTGTAACATGGGGG | 1 | 1 | 16 | SEQ ID NO. 951 |
| (N20)NGG | X | 70327739 | - | AGGCTTTAGGGTGTAACATGGGG | 1 | 2 | 23 | SEQ ID NO. 952 |
| (N20)NGG | X | 70327740 | - | CAGGCTTTAGGGTGTAACATGGG | 1 | 1 | 17 | SEQ ID NO. 953 |
| (N20)NGG | X | 70327741 | - | TCAGGCTTTAGGGTGTAACATGG | 1 | 2 | 24 | SEQ ID NO. 954 |
| (N20)NGG | X | 70327751 | - | GGTTCAGGTTTCAGGCTTTAGGG | 1 | 2 | 50 | SEQ ID NO. 955 |
| (N20)NGG | X | 70327752 | - | GGGATTGGGGTTCAGGTTTCAGG | 1 | 7 | 64 | SEQ ID NO. 956 |
| (N20)NGG | X | 70327759 | - | AGGATTGGGGTTCAGGTTTCAGG | 1 | 3 | 35 | SEQ ID NO. 957 |
| (N20)NGG | X | 70327766 | - | CTGTCAGAGAGATTGGGGTTCAGG | 1 | 6 | 51 | SEQ ID NO. 958 |
| (N20)NGG | X | 70327772 | - | GTTCTTCTGTCAGAGGATTGGGG | 1 | 3 | 46 | SEQ ID NO. 959 |
| (N20)NGG | X | 70327773 | - | GGTTCTTCTGTCAGAGGATTGGG | 1 | 4 | 33 | SEQ ID NO. 960 |
| (N20)NGG | X | 70328126 | + | CTCCCTCTTTCTCCCCTGTCAGG | 1 | 15 | 220 | SEQ ID NO. 961 |
| (N20)NGG | X | 70328163 | + | TCCACCCTGAAGAACCTAGAGG | 1 | 2 | 23 | SEQ ID NO. 962 |
| (N20)NGG | X | 70328185 | + | GATCTTGTTACTGAATACCACGG | 1 | 3 | 34 | SEQ ID NO. 963 |
| (N20)NGG | X | 70328186 | + | ATCTTGTTACTGAATACCACGGG | 1 | 2 | 24 | SEQ ID NO. 964 |
| (N20)NGG | X | 70328196 | + | TGAATACCACGGGAACTTTTCGG | 1 | 2 | 17 | SEQ ID NO. 965 |
| (N20)NGG | X | 70328106 | - | GTCCTGACAGGGGAGAAAGAGGG | 1 | 6 | 137 | SEQ ID NO. 966 |
| (N20)NGG | X | 70328107 | - | CGTCCTGACAGGGGAGAAAGAGG | 1 | 5 | 48 | SEQ ID NO. 967 |
| (N20)NGG | X | 70328116 | - | TCGGGGCATCGTCCTGACAGGGG | 1 | 1 | 8 | SEQ ID NO. 968 |
| (N20)NGG | X | 70328117 | - | TTCGGGGCATCGTCCTGACAGGG | 1 | 1 | 7 | SEQ ID NO. 969 |
| (N20)NGG | X | 70328118 | - | ATTCGGGGCATCGTCCTGACAGG | 1 | 1 | 2 | SEQ ID NO. 970 |
| (N20)NGG | X | 70328133 | - | TTCTTCAGGGTGGGAATTCGGGG | 1 | 1 | 33 | SEQ ID NO. 971 |
| (N20)NGG | X | 70328134 | - | GTTCTTCAGGGTGGGAATTCGGG | 2 | 3 | 62 | SEQ ID NO. 972 |
| (N20)NGG | X | 70328135 | - | GGTTCTTCAGGGTGGGAATTCGG | 1 | 6 | 42 | SEQ ID NO. 973 |
| (N20)NGG | X | 70328142 | - | TCCTCTAGGTTCTTCAGGGTGGG | 1 | 2 | 39 | SEQ ID NO. 974 |
| (N20)NGG | X | 70328143 | - | ATCCTCTAGGTTCTTCAGGGTGG | 1 | 2 | 36 | SEQ ID NO. 975 |
| (N20)NGG | X | 70328146 | - | AAGATCCTCTAGGTTCTTCAGGG | 1 | 2 | 48 | SEQ ID NO. 976 |

FIG. 6 cont.

| site type | site chromosome | site start nucleotide | site strand | target site sequence with NGG | genome wide hits with 1 or less mismatches | genome wide hits with 2 or less mismatches | genome wide hits with 3 or less mismatches | | |
|---|---|---|---|---|---|---|---|---|---|
| (N20)NGG | X | 70328147 | - | CAAGATCCTCTAGGTTCTTCAGG | 1 | 2 | 54 | SEQ ID NO. | 977 |
| (N20)NGG | X | 70328156 | - | ATTCAGTAACAAGATCCTCTAGG | 1 | 4 | 33 | SEQ ID NO. | 978 |
| (N20)NGG | X | 70328180 | - | TTCTCACCGAAAAGTTCCCGTGG | 1 | 1 | 9 | SEQ ID NO. | 979 |
| (N20)NGG | X | 70328471 | + | GAATCCTTTCCTGTTTGCATTGG | 1 | 4 | 54 | SEQ ID NO. | 980 |
| (N20)NGG | X | 70328480 | + | CCTGTTTGCATTGGAAGCCGTGG | 2 | 3 | 18 | SEQ ID NO. | 981 |
| (N20)NGG | X | 70328493 | + | GAAGCCGTGGTTATCTCTGTTGG | 1 | 1 | 16 | SEQ ID NO. | 982 |
| (N20)NGG | X | 70328501 | + | GGTTATCTCTGTTGGCTCCATGG | 1 | 1 | 36 | SEQ ID NO. | 983 |
| (N20)NGG | X | 70328502 | + | GTTATCTCTGTTGGCTCCATGGG | 1 | 5 | 55 | SEQ ID NO. | 984 |
| (N20)NGG | X | 70328536 | + | GCCTTCTCTGTGTATTTCTGG | 1 | 2 | 83 | SEQ ID NO. | 985 |
| (N20)NGG | X | 70328540 | + | TCTCTGTGTATTTCTGGCTGG | 2 | 9 | 112 | SEQ ID NO. | 986 |
| (N20)NGG | X | 70328545 | + | GTGTATTTCTGGCTGGAACGG | 1 | 5 | 78 | SEQ ID NO. | 987 |
| (N20)NGG | X | 70328555 | + | CTGGCTGGAACGGTGAGATTTGG | 1 | 3 | 14 | SEQ ID NO. | 988 |
| (N20)NGG | X | 70328453 | - | GCTTCCAATGCAAACAGGAAAGG | 1 | 1 | 54 | SEQ ID NO. | 989 |
| (N20)NGG | X | 70328458 | - | CCACGGCTTCCAATGCAAACAGG | 2 | 3 | 18 | SEQ ID NO. | 990 |
| (N20)NGG | X | 70328475 | - | GGAGCCAACAGAGATAACCACGG | 1 | 3 | 43 | SEQ ID NO. | 991 |
| (N20)NGG | X | 70328496 | - | AAGGCTGATAATCAATCCCATGG | 1 | 2 | 29 | SEQ ID NO. | 992 |
| (N20)NGG | X | 70328515 | - | GCCAGAAATACACACAGAGAAGG | 1 | 16 | 277 | SEQ ID NO. | 993 |
| (N20)NGG | X | 70329077 | + | CCTCATCCTCTTTCTCCTCAAGG | 2 | 27 | 343 | SEQ ID NO. | 994 |
| (N20)NGG | X | 70329089 | + | TCTCCTCAAGGAACAATCAGTGG | 1 | 1 | 33 | SEQ ID NO. | 995 |
| (N20)NGG | X | 70329122 | + | TAAGTTCTCCTTGCCTAGTGTGG | 1 | 2 | 29 | SEQ ID NO. | 996 |
| (N20)NGG | X | 70329126 | + | TTTCCTTGCCTAGTGTGGATGG | 1 | 4 | 66 | SEQ ID NO. | 997 |
| (N20)NGG | X | 70329127 | + | TCTCCTTGCCTAGTGTGGATGGG | 1 | 4 | 32 | SEQ ID NO. | 998 |
| (N20)NGG | X | 70329154 | + | AACGCTACACGTTTCGTGTTCGG | 1 | 1 | 2 | SEQ ID NO. | 999 |
| (N20)NGG | X | 70329177 | + | AGCCGCTTAACCACCTCTGTGG | 1 | 1 | 10 | SEQ ID NO. | 1000 |
| (N20)NGG | X | 70329193 | + | TCTGTGGAAGTGCTCAGCATTGG | 2 | 5 | 51 | SEQ ID NO. | 1001 |
| (N20)NGG | X | 70329202 | + | GTGCTCAGCATTGGAGTGAATGG | 1 | 2 | 36 | SEQ ID NO. | 1002 |
| (N20)NGG | X | 70329220 | + | AATGGAGCCACCCAATCCACTGG | 2 | 2 | 23 | SEQ ID NO. | 1003 |
| (N20)NGG | X | 70329221 | + | ATGGAGCCACCCAATCCACTGGG | 1 | 1 | 24 | SEQ ID NO. | 1004 |
| (N20)NGG | X | 70329222 | + | TGGAGCCACCCAATCCACTGGGG | 1 | 1 | 46 | SEQ ID NO. | 1005 |
| (N20)NGG | X | 70329223 | + | GGAGCCACCCAATCCACTGGGGG | 1 | 1 | 36 | SEQ ID NO. | 1006 |
| (N20)NGG | X | 70329240 | + | TGGGGAGCAATACTTCAAAAGG | 1 | 1 | 29 | SEQ ID NO. | 1007 |
| (N20)NGG | X | 70329248 | + | CAATACTTCAAAAGGTAAAATGG | 2 | 7 | 167 | SEQ ID NO. | 1008 |
| (N20)NGG | X | 70329249 | + | AATACTTCAAAAGGTAAAATGGG | 2 | 11 | 213 | SEQ ID NO. | 1009 |
| (N20)NGG | X | 70329054 | - | CTTGAGGAGAAAGAGGATGAGGG | 2 | 10 | 183 | SEQ ID NO. | 1010 |

FIG. 6 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | X | 70329055 | - | CCTTGAGGAGAAAGAGGATGAGG | 1 | 16 | 187 | SEQ ID NO. 1011 |
| (N20)NGG | X | 70329061 | - | ATTGTTCCTTGAGGAGAAAGAGG | 1 | 5 | 77 | SEQ ID NO. 1012 |
| (N20)NGG | X | 70329070 | - | AATCCACTGATTGTTCCTTGAGG | 1 | 3 | 31 | SEQ ID NO. 1013 |
| (N20)NGG | X | 70329108 | - | CTGCCCATCCACACTAGGCAAGG | 1 | 6 | 51 | SEQ ID NO. 1014 |
| (N20)NGG | X | 70329113 | - | CGTTTCTGCCCATCCACACTAGG | 1 | 1 | 18 | SEQ ID NO. 1015 |
| (N20)NGG | X | 70329157 | - | TTCCACAGAGTGGGTTAAAGCGG | 1 | 1 | 39 | SEQ ID NO. 1016 |
| (N20)NGG | X | 70329166 | - | GCTGAGCACTTCCACAGAGTGG | 1 | 3 | 36 | SEQ ID NO. 1017 |
| (N20)NGG | X | 70329167 | - | TGCTGAGCACTTCCACAGAGTGG | 2 | 8 | 90 | SEQ ID NO. 1018 |
| (N20)NGG | X | 70329205 | - | TGCTCCCCAGTGGATTGGGTGG | 1 | 4 | 50 | SEQ ID NO. 1019 |
| (N20)NGG | X | 70329208 | - | TATTGCTCCCCAGTGGATTGGG | 1 | 3 | 20 | SEQ ID NO. 1020 |
| (N20)NGG | X | 70329209 | - | GTATTGCTCCCCAGTGGATTGG | 1 | 2 | 18 | SEQ ID NO. 1021 |
| (N20)NGG | X | 70329214 | - | TTGAAGTATTGCTCCCCAGTGG | 1 | 1 | 18 | SEQ ID NO. 1022 |
| (N20)NGG | X | 70330015 | + | ACATATCTCCAGTGATCCCCTGG | 1 | 3 | 31 | SEQ ID NO. 1023 |
| (N20)NGG | X | 70330016 | + | CATATCTCCAGTGATCCCCTGGG | 1 | 1 | 31 | SEQ ID NO. 1024 |
| (N20)NGG | X | 70330072 | + | AATCCCAGTAGAACTGAACTGG | 1 | 4 | 32 | SEQ ID NO. 1025 |
| (N20)NGG | X | 70330100 | + | CAGATTCTTGAACCACTGTTTGG | 1 | 4 | 44 | SEQ ID NO. 1026 |
| (N20)NGG | X | 70330109 | + | GAACCACTGTTTGGAGCACTTGG | 1 | 3 | 36 | SEQ ID NO. 1027 |
| (N20)NGG | X | 70330120 | + | TGGAGCACTTGGTGCAGTACCGG | 1 | 3 | 23 | SEQ ID NO. 1028 |
| (N20)NGG | X | 70330129 | + | TGGTGCAGTACCGGACTGACTGG | 1 | 2 | 8 | SEQ ID NO. 1029 |
| (N20)NGG | X | 70330130 | + | GGTGCAGTACCGGACTGACTGGG | 1 | 1 | 1 | SEQ ID NO. 1030 |
| (N20)NGG | X | 70330141 | + | GGACTGACTGGGACCACAGCTGG | 1 | 4 | 50 | SEQ ID NO. 1031 |
| (N20)NGG | X | 70330157 | + | CAGCTGGACTGTGAGTGACTAGG | 1 | 2 | 57 | SEQ ID NO. 1032 |
| (N20)NGG | X | 70330158 | + | AGCTGGACTGTGAGTGACTAGGG | 1 | 2 | 35 | SEQ ID NO. 1033 |
| (N20)NGG | X | 70329981 | - | TGGAGATATGTGTGCATATGTGG | 1 | 11 | 182 | SEQ ID NO. 1034 |
| (N20)NGG | X | 70330001 | - | TCTGGAGCCCAGGGATCACTGG | 1 | 2 | 61 | SEQ ID NO. 1035 |
| (N20)NGG | X | 70330009 | - | TTAGCTTCTCTGGAGCCCAGGGG | 1 | 8 | 215 | SEQ ID NO. 1036 |
| (N20)NGG | X | 70330010 | - | GTTAGGTTCTCTGGAGCCCAGG | 1 | 4 | 40 | SEQ ID NO. 1037 |
| (N20)NGG | X | 70330011 | - | TGTTAGGTTCTCTGGAGCCCAGG | 1 | 4 | 112 | SEQ ID NO. 1038 |
| (N20)NGG | X | 70330019 | - | TTGTGAAGTGTTAGGTTCTCTGG | 1 | 1 | 31 | SEQ ID NO. 1039 |
| (N20)NGG | X | 70330027 | - | CACTCAGTTTGTGAAGTGTTAGG | 1 | 3 | 36 | SEQ ID NO. 1040 |
| (N20)NGG | X | 70330053 | - | GTTCCAGTTCAGTTCTAGCTGGG | 1 | 2 | 29 | SEQ ID NO. 1041 |
| (N20)NGG | X | 70330054 | - | TGTTCCAGTTCAGTTCTAGCTGG | 1 | 2 | 21 | SEQ ID NO. 1042 |
| (N20)NGG | X | 70330090 | - | GCACCAAGTGCTCCAAACAGTGG | 1 | 2 | 25 | SEQ ID NO. 1043 |
| (N20)NGG | X | 70330117 | - | AGCTGTGGTCCCAGTCAGTCCGG | 1 | 16 | 472 | SEQ ID NO. 1044 |

FIG. 6 cont.

| site type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | X | 70330132 | - | AGTCACTCACAGTCCAGCTGTGG | 1 | 5 | 52 | SEQ ID NO. 1045 |
| (N20)NGG | X | 70330353 | + | CCTTCCAACCTTTCTCCTCTAGG | 1 | 8 | 135 | SEQ ID NO. 1046 |
| (N20)NGG | X | 70330366 | + | CTCCTCTAGGTACAAGAACTCGG | 1 | 1 | 26 | SEQ ID NO. 1047 |
| (N20)NGG | X | 70330424 | + | TTCTCTGAAGAAATCACTTCTGG | 2 | 8 | 90 | SEQ ID NO. 1048 |
| (N20)NGG | X | 70330444 | + | TGGCTGTCAGTTGCAAAAAAAGG | 1 | 2 | 57 | SEQ ID NO. 1049 |
| (N20)NGG | X | 70330483 | + | AACATTTGTTGTTCAGCTCCAGG | 1 | 4 | 43 | SEQ ID NO. 1050 |
| (N20)NGG | X | 70330491 | + | TTGTTCAGCTCCAGGACCCACGG | 1 | 4 | 38 | SEQ ID NO. 1051 |
| (N20)NGG | X | 70330492 | + | TGTTCAGCTCCAGGACCCACGGG | 1 | 2 | 39 | SEQ ID NO. 1052 |
| (N20)NGG | X | 70330500 | + | TCCAGGACCCACGGGAACCCAGG | 1 | 6 | 53 | SEQ ID NO. 1053 |
| (N20)NGG | X | 70330507 | + | CCCACGGGAACCCAGGAGACAGG | 1 | 1 | 42 | SEQ ID NO. 1054 |
| (N20)NGG | X | 70330537 | + | GATGCTAAAACTGCAGAATCTGG | 2 | 7 | 55 | SEQ ID NO. 1055 |
| (N20)NGG | X | 70330538 | + | ATGCTAAAACTGCAGAATCTGGG | 3 | 20 | 217 | SEQ ID NO. 1056 |
| (N20)NGG | X | 70330546 | + | ACTGCAGAATCTGGGTAATTTGG | 1 | 2 | 48 | SEQ ID NO. 1057 |
| (N20)NGG | X | 70330555 | + | TCTGGGTAATTTGGAAAGAAAGG | 9 | 482 | 8109 | SEQ ID NO. 1058 |
| (N20)NGG | X | 70330556 | + | CTGGGTAATTTGGAAAGAAAGGG | 126 | 2902 | 13176 | SEQ ID NO. 1059 |
| (N20)NGG | X | 70330331 | - | CCTACAGGAGAAAGGTTCGAAGG | 1 | 5 | 75 | SEQ ID NO. 1060 |
| (N20)NGG | X | 70330335 | - | TGTACCTAGAGGAGAAAGGTTGG | 1 | 4 | 52 | SEQ ID NO. 1061 |
| (N20)NGG | X | 70330339 | - | TTCTTGTACCTAGAGGAGAAAGG | 1 | 2 | 43 | SEQ ID NO. 1062 |
| (N20)NGG | X | 70330346 | - | ATCCGAGTTCTTGTACCTAGAGG | 1 | 1 | 7 | SEQ ID NO. 1063 |
| (N20)NGG | X | 70330380 | - | ATAGATAGTGGCTGCACTTCTGG | 1 | 2 | 21 | SEQ ID NO. 1064 |
| (N20)NGG | X | 70330392 | - | TTTCTTCAGAGAATAGATAGTGG | 1 | 6 | 86 | SEQ ID NO. 1065 |
| (N20)NGG | X | 70330449 | - | CAACAAATGTTTGGTAGAGGTGG | 1 | 4 | 64 | SEQ ID NO. 1066 |
| (N20)NGG | X | 70330452 | - | GAACAACAAATGTTTGGTAGAGG | 1 | 5 | 45 | SEQ ID NO. 1067 |
| (N20)NGG | X | 70330458 | - | GGAGCTGAACAACAAATGTTTGG | 1 | 1 | 48 | SEQ ID NO. 1068 |
| (N20)NGG | X | 70330479 | - | TCCTGGGTTCCCGTGGGTCCTGG | 1 | 2 | 68 | SEQ ID NO. 1069 |
| (N20)NGG | X | 70330485 | - | CCTGTCTCCTGGGTTCCCGTGGG | 1 | 2 | 111 | SEQ ID NO. 1070 |
| (N20)NGG | X | 70330486 | - | GCCTGTCTCCTGGGTTCCCGTGG | 1 | 6 | 77 | SEQ ID NO. 1071 |
| (N20)NGG | X | 70330495 | - | ATCTGTGTGGCCTGTCTCTCTGG | 1 | 7 | 72 | SEQ ID NO. 1072 |
| (N20)NGG | X | 70330496 | - | CATCTGTGTGGCCTGTCTCCTGG | 1 | 5 | 62 | SEQ ID NO. 1073 |
| (N20)NGG | X | 70330508 | - | CTGCAGTTTTAGCATCTGTGTGG | 1 | 10 | 89 | SEQ ID NO. 1074 |
| (N20)NGG | X | 70330808 | + | TTCCACTCTGCCCCTCCCAGAGG | 3 | 7 | 115 | SEQ ID NO. 1075 |
| (N20)NGG | X | 70330852 | + | TCGAGTACATGAATTGCACTTGG | 1 | 1 | 9 | SEQ ID NO. 1076 |
| (N20)NGG | X | 70330900 | + | CCAACCTCACTCTGCATTATTGG | 1 | 6 | 42 | SEQ ID NO. 1077 |
| (N20)NGG | X | 70330910 | + | TCTGCATTATTGGTATGAGAAGG | 1 | 4 | 36 | SEQ ID NO. 1078 |

FIG. 6 cont.

| site type | site chromosome | site start nucleotide | site strand | target site sequence with NGG | genome wide hits with 1 or less mismatches | genome wide hits with 2 or less mismatches | genome wide hits with 3 or less mismatches | |
|---|---|---|---|---|---|---|---|---|
| (N20)NGG | X | 70330911 | + | CTGCATTATTGGTATCAGAAGGG | | 1 | 2 | 42 SEQ ID NO. 1079 |
| (N20)NGG | X | 70330917 | + | TATTGGTATGAGAAGGGACGAGG | | 1 | 2 | 23 SEQ ID NO. 1080 |
| (N20)NGG | X | 70330918 | + | ATTGGTATGAGAAGGGACGAGGG | | 1 | 1 | 23 SEQ ID NO. 1081 |
| (N20)NGG | X | 70330919 | + | TTGGTATGAGAAGGGACGAGGGG | | 1 | 3 | 25 SEQ ID NO. 1082 |
| (N20)NGG | X | 70330920 | + | TGGTATGAGAAGGGACGAGGGGG | | 2 | 6 | 57 SEQ ID NO. 1083 |
| (N20)NGG | X | 70330923 | + | TATGAGAAGGGACGAGGGGGAGG | | 1 | 6 | 62 SEQ ID NO. 1084 |
| (N20)NGG | X | 70330924 | + | ATGAGAAGGGACGAGGGGGAGGG | | 1 | 5 | 168 SEQ ID NO. 1085 |
| (N20)NGG | X | 70330723 | - | CTAGATTGGGGAGAAAATGAAGG | | 1 | 8 | 128 SEQ ID NO. 1086 |
| (N20)NGG | X | 70330735 | - | TCAGGAAGAAATCTAGATTGGGG | | 1 | 8 | 83 SEQ ID NO. 1087 |
| (N20)NGG | X | 70330736 | - | GTCAGGAAGAAATCTAGATTGGG | | 1 | 3 | 68 SEQ ID NO. 1088 |
| (N20)NGG | X | 70330737 | - | GGTCAGGAAGAAATCTAGATTGG | | 1 | 3 | 50 SEQ ID NO. 1089 |
| (N20)NGG | X | 70330753 | - | AGTCAGTGGGCATAGTGGTCAGG | | 1 | 2 | 42 SEQ ID NO. 1090 |
| (N20)NGG | X | 70330758 | - | GAGGGAGTCAGTGGGCATAGTGG | | 1 | 4 | 82 SEQ ID NO. 1091 |
| (N20)NGG | X | 70330766 | - | GAAACACTGAGGGAGTCAGTGGG | | 1 | 2 | 68 SEQ ID NO. 1092 |
| (N20)NGG | X | 70330767 | - | GAAACACTGAGGGAGTCAGTGG | | 1 | 6 | 81 SEQ ID NO. 1093 |
| (N20)NGG | X | 70330776 | - | GGGCAGAGTGGAAACACTGAGGG | | 2 | 6 | 93 SEQ ID NO. 1094 |
| (N20)NGG | X | 70330777 | - | GGGGCAGAGTGGAAACACTGAGG | | 2 | 8 | 95 SEQ ID NO. 1095 |
| (N20)NGG | X | 70330788 | - | AACCTCTGGGGCGGCAGAGTGG | | 1 | 6 | 132 SEQ ID NO. 1096 |
| (N20)NGG | X | 70330796 | - | AAACACTGAACCTCTGGGAGGG | | 1 | 3 | 46 SEQ ID NO. 1097 |
| (N20)NGG | X | 70330797 | - | AAAACACTGAACCTCTGGGAGGG | | 1 | 4 | 63 SEQ ID NO. 1098 |
| (N20)NGG | X | 70330798 | - | CAAAACACTGAACCTCTGGGAGG | | 1 | 8 | 69 SEQ ID NO. 1099 |
| (N20)NGG | X | 70330801 | - | ACACAAAACACTGAACCTCTGGG | | 1 | 11 | 102 SEQ ID NO. 1100 |
| (N20)NGG | X | 70330802 | - | AACACAAAACACTGAACCTCTGG | | 1 | 4 | 92 SEQ ID NO. 1101 |
| (N20)NGG | X | 70330868 | - | AGAGTGAGGTTGGTAGGCTGGGG | | 1 | 6 | 61 SEQ ID NO. 1102 |
| (N20)NGG | X | 70330869 | - | CAGAGTGAGGTTGGTAGGCTGGG | | 2 | 2 | 33 SEQ ID NO. 1103 |
| (N20)NGG | X | 70330870 | - | GCAGAGTGAGGTTGGTAGGCTGG | | 1 | 5 | 37 SEQ ID NO. 1104 |
| (N20)NGG | X | 70330874 | - | TAATGCAGAGTGAGGTTGGTAGG | | 1 | 1 | 32 SEQ ID NO. 1105 |
| (N20)NGG | X | 70330878 | - | CCAATAATGCAGAGTGAGGTTGG | | 1 | 5 | 31 SEQ ID NO. 1106 |
| (N20)NGG | X | 70330882 | - | CATACCAATAATGCAGAGTGAGG | | 1 | 3 | 28 SEQ ID NO. 1107 |
| (N20)NGG | X | 70331331 | + | ATTTCTGCAGCTGCCCCTGCTGG | | 1 | 8 | 110 SEQ ID NO. 1108 |
| (N20)NGG | X | 70331332 | + | TTTCCTGCAGCTGCCCCTGCTGG | | 2 | 21 | 144 SEQ ID NO. 1109 |
| (N20)NGG | X | 70331337 | + | GCAGCTGCCCCTGCTGGGAGTGG | | 1 | 15 | 206 SEQ ID NO. 1110 |
| (N20)NGG | X | 70331338 | + | CAGCTGCCCCTGCTGGGAGTGGG | | 2 | 13 | 196 SEQ ID NO. 1111 |
| (N20)NGG | X | 70331339 | + | AGCTGCCCCTGCTGGGAGTGGGG | | 1 | 8 | 162 SEQ ID NO. 1112 |

FIG. 6 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | | |
|---|---|---|---|---|---|---|---|---|---|
| (N20)NGG | X | 70331368 | + | ACGACAATTCTGACGCCCAATGG | | 1 | 3 | SEQ ID NO. | 1113 |
| (N20)NGG | X | 70331369 | + | CGACAATTCTGACGCCCAATGGG | 1 | 1 | 5 | SEQ ID NO. | 1114 |
| (N20)NGG | X | 70331389 | + | GGGAATGAAGACACCACAGCTGG | 1 | 5 | 59 | SEQ ID NO. | 1115 |
| (N20)NGG | X | 70331392 | + | AATGAAGACACCACAGCTGGTGG | 3 | 9 | 74 | SEQ ID NO. | 1116 |
| (N20)NGG | X | 70331393 | + | ATGAAGACACCACAGCTGGTGGG | 1 | 7 | 54 | SEQ ID NO. | 1117 |
| (N20)NGG | X | 70331401 | + | ACCACAGCTGGTGGGAAATCTGG | 1 | 2 | 34 | SEQ ID NO. | 1118 |
| (N20)NGG | X | 70331402 | + | CCACAGCTGGTGGGAAATCTGGG | 1 | 6 | 105 | SEQ ID NO. | 1119 |
| (N20)NGG | X | 70331407 | + | GCTGGTGGGAAATCTGGGACTGG | 2 | 8 | 64 | SEQ ID NO. | 1120 |
| (N20)NGG | X | 70331410 | + | GGTGGGAAATCTGGGACTGGAGG | 1 | 4 | 96 | SEQ ID NO. | 1121 |
| (N20)NGG | X | 70331411 | + | GTGGGAAATCTGGGACTGGAGGG | 2 | 7 | 66 | SEQ ID NO. | 1122 |
| (N20)NGG | X | 70331412 | + | TGGGAAATCTGGGACTGGAGGGG | 1 | 8 | 95 | SEQ ID NO. | 1123 |
| (N20)NGG | X | 70331413 | + | GGGAAATCTGGGACTGGAGGGGG | 1 | 4 | 101 | SEQ ID NO. | 1124 |
| (N20)NGG | X | 70331250 | - | GCGCTTGCTCTTCTTCATTCCCTGG | 1 | 2 | 21 | SEQ ID NO. | 1125 |
| (N20)NGG | X | 70331251 | - | GGCGCTTGCTCTTCTTCATTCCCTGG | 1 | 1 | 23 | SEQ ID NO. | 1126 |
| (N20)NGG | X | 70331272 | - | TGGTAATGATGGCTTCAACATGG | 2 | 4 | 44 | SEQ ID NO. | 1127 |
| (N20)NGG | X | 70331283 | - | AGGGATGTGAATGGTAATGATGG | 1 | 5 | 65 | SEQ ID NO. | 1128 |
| (N20)NGG | X | 70331292 | - | AGGAATAAGAGGGATGTGAATGG | 1 | 11 | 130 | SEQ ID NO. | 1129 |
| (N20)NGG | X | 70331302 | - | GGGCAGCTGCAGGAATAAGAGGG | 1 | 4 | 71 | SEQ ID NO. | 1130 |
| (N20)NGG | X | 70331303 | - | GGGGCAGCTGCAGGAATAAGAGG | 1 | 4 | 82 | SEQ ID NO. | 1131 |
| (N20)NGG | X | 70331312 | - | CTCCCAGCAGGGGCAGCTGCAGG | 3 | 44 | 380 | SEQ ID NO. | 1132 |
| (N20)NGG | X | 70331322 | - | TTCAGCCCCACTCCCAGCAGGGG | 1 | 12 | 114 | SEQ ID NO. | 1133 |
| (N20)NGG | X | 70331323 | - | GTTCAGCCCCACTCCCAGCAGGG | 2 | 8 | 74 | SEQ ID NO. | 1134 |
| (N20)NGG | X | 70331324 | - | TGTTCAGCCCCACTCCCAGCAGG | 1 | 4 | 89 | SEQ ID NO. | 1135 |
| (N20)NGG | X | 70331361 | - | GTGGTGTCTTCATTCCCATTGGG | 1 | 8 | 113 | SEQ ID NO. | 1136 |
| (N20)NGG | X | 70331362 | - | TGTGGTGTCTTCATTCCCATTGG | 4 | 45 | 242 | SEQ ID NO. | 1137 |
| (N20)NGG | X | 70331380 | - | CCCAGATTTCCCACCAGCTGTGG | 1 | 7 | 101 | SEQ ID NO. | 1138 |

FIG. 6 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 5 | 35857092 | + | TCTCTCAGAATGACAATTCTAGG | 1 | 5 | 65 | SEQ ID NO. 1139 |
| (N20)NGG | 5 | 35857104 | + | ACAATTCTAGGTACAACTTTTGG | 1 | 1 | 53 | SEQ ID NO. 1140 |
| (N20)NGG | 5 | 35857109 | + | TCTAGGTACAACTTTTGGCATGG | 1 | 2 | 25 | SEQ ID NO. 1141 |
| (N20)NGG | 5 | 35857137 | + | TCTTTACTTCAAGTCGTTTCTGG | 1 | 3 | 24 | SEQ ID NO. 1142 |
| (N20)NGG | 5 | 35857146 | + | CAAGTCGTTTCTGGAGAAAGTGG | 1 | 3 | 41 | SEQ ID NO. 1143 |
| (N20)NGG | 5 | 35857161 | + | GAAAGTGGCTATGCTCAAAATGG | 1 | 3 | 49 | SEQ ID NO. 1144 |
| (N20)NGG | 5 | 35860953 | + | CTGCATGTTTGTTCCTCCCCAG | 1 | 5 | 138 | SEQ ID NO. 1145 |
| (N20)NGG | 5 | 35860961 | + | TTGTTCCTCCCCAGGAGACTTGG | 1 | 7 | 43 | SEQ ID NO. 1146 |
| (N20)NGG | 5 | 35860976 | + | AGACTTGGAAGATGCAGAACTGG | 1 | 4 | 89 | SEQ ID NO. 1147 |
| (N20)NGG | 5 | 35861009 | + | ATTCTCATGCTATAGCCAGTTGG | 1 | 3 | 24 | SEQ ID NO. 1148 |
| (N20)NGG | 5 | 35861019 | + | TATAGCCAGTTGGAAGTGAATGG | 1 | 1 | 44 | SEQ ID NO. 1149 |
| (N20)NGG | 5 | 35861051 | + | CTCACTGACCTGTGCTTTTGAGG | 1 | 4 | 45 | SEQ ID NO. 1150 |
| (N20)NGG | 5 | 35861078 | + | AGATGTCAACATCACCAATCTGG | 1 | 3 | 27 | SEQ ID NO. 1151 |
| (N20)NGG | 5 | 35861092 | + | CCAATCTGGAATTTGAAATATGG | 1 | 2 | 84 | SEQ ID NO. 1152 |
| (N20)NGG | 5 | 35861097 | + | CTGGAATTTGAAATATGGTGAGG | 1 | 6 | 67 | SEQ ID NO. 1153 |
| (N20)NGG | 5 | 35861098 | + | TGGAATTTGAAATATGGTGAGGG | 1 | 3 | 109 | SEQ ID NO. 1154 |
| (N20)NGG | 5 | 35861102 | + | ATTTGAAATATGGTGAGGGATGG | 1 | 4 | 107 | SEQ ID NO. 1155 |
| (N20)NGG | 5 | 35861105 | + | TGAAATATGGTGAGGGATGGTGG | 1 | 6 | 79 | SEQ ID NO. 1156 |
| (N20)NGG | 5 | 35861114 | - | GTGAGGGATGGTGGTTTTTAATGG | 1 | 2 | 47 | SEQ ID NO. 1157 |
| (N20)NGG | 5 | 35860944 | - | ATCTTCCAAGTCTCCTGGGGAGG | 2 | 3 | 42 | SEQ ID NO. 1158 |
| (N20)NGG | 5 | 35860947 | - | TGCATCTTCCAAGTCTCCTGGGG | 1 | 7 | 71 | SEQ ID NO. 1159 |
| (N20)NGG | 5 | 35860948 | - | CTGCATCTTCCAAGTCTCCTGGG | 1 | 6 | 70 | SEQ ID NO. 1160 |
| (N20)NGG | 5 | 35860949 | - | TCTGCATCTTCCAAGTCTCCTGG | 1 | 5 | 86 | SEQ ID NO. 1161 |
| (N20)NGG | 5 | 35861002 | - | GCGATCCATTCACTTCCAACTGG | 1 | 8 | 82 | SEQ ID NO. 1162 |
| (N20)NGG | 5 | 35861037 | - | ATCTGGGTCCTCAAAAGCACAGG | 1 | 4 | 34 | SEQ ID NO. 1163 |
| (N20)NGG | 5 | 35861053 | - | GATTGGTGATGTTGACATCTGGG | 1 | 2 | 36 | SEQ ID NO. 1164 |
| (N20)NGG | 5 | 35861054 | - | AGATTGGTGATGTTGACATCTGG | 1 | 3 | 28 | SEQ ID NO. 1165 |
| (N20)NGG | 5 | 35861070 | - | CCATATTCAAATTCCAGATTGG | 1 | 4 | 91 | SEQ ID NO. 1166 |
| (N20)NGG | 5 | 35867409 | + | TCCCCTTTTTATTCCTACAGTGG | 1 | 3 | 68 | SEQ ID NO. 1167 |
| (N20)NGG | 5 | 35867410 | + | CCCCTTTTTATTCCTACAGTGGG | 1 | 5 | 52 | SEQ ID NO. 1168 |
| (N20)NGG | 5 | 35867411 | + | CCCTTTTTATTCCTACAGTGGGG | 1 | 9 | 56 | SEQ ID NO. 1169 |
| (N20)NGG | 5 | 35867420 | + | TTCCTACAGTGGGGCCCTCGTGG | 1 | 1 | 11 | SEQ ID NO. 1170 |
| (N20)NGG | 5 | 35867423 | + | CTACAGTGGGGCCCTCGTGGAGG | 1 | 3 | 22 | SEQ ID NO. 1171 |
| (N20)NGG | 5 | 35867443 | + | AGGTAAAGTGCCTGAATTTCAGG | 1 | 3 | 47 | SEQ ID NO. 1172 |

FIG. 7

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 5 | 35867493 | + | ACAAAGAAATTCTTACTGATTGG | 1 | 4 | 81 | SEQ ID NO. 1173 |
| (N20)NGG | 5 | 35867516 | + | AAAGAGCAATATATGTGTGAAGG | 2 | 9 | 100 | SEQ ID NO. 1174 |
| (N20)NGG | 5 | 35867520 | + | AGCAATATATGTGTGAAGGTTGG | 2 | 2 | 37 | SEQ ID NO. 1175 |
| (N20)NGG | 5 | 35867565 | + | AAAATAGACCTAACCACTATAGG | 1 | 3 | 38 | SEQ ID NO. 1176 |
| (N20)NGG | 5 | 35867388 | - | CCCACTGTAGGAATAAAAAGGGG | 1 | 2 | 57 | SEQ ID NO. 1177 |
| (N20)NGG | 5 | 35867389 | - | CCCCACTGTAGGAATAAAAAGGG | 1 | 5 | 66 | SEQ ID NO. 1178 |
| (N20)NGG | 5 | 35867390 | - | GCCCCACTGTAGGAATAAAAAGG | 1 | 5 | 43 | SEQ ID NO. 1179 |
| (N20)NGG | 5 | 35867400 | - | CTCCACGAGGGCCCCACTGTAGG | 1 | 1 | 30 | SEQ ID NO. 1180 |
| (N20)NGG | 5 | 35867412 | - | CAGGCACTTTACCTCCACGAGGG | 1 | 1 | 17 | SEQ ID NO. 1181 |
| (N20)NGG | 5 | 35867413 | - | TCAGGCACTTTACCTCCACGAGG | 1 | 2 | 20 | SEQ ID NO. 1182 |
| (N20)NGG | 5 | 35867431 | - | CTTGTAGTTTCCTGAAATTCAGG | 1 | 1 | 70 | SEQ ID NO. 1183 |
| (N20)NGG | 5 | 35867535 | - | GGTTAGGTCTATTTTTTCGAGG | 1 | 1 | 35 | SEQ ID NO. 1184 |
| (N20)NGG | 5 | 35867551 | - | ACTTCTTACCTATAGTGGTTAGG | 1 | 1 | 33 | SEQ ID NO. 1185 |
| (N20)NGG | 5 | 35867556 | - | ATACAACTTCTTACCTATAGTGG | 2 | 3 | 57 | SEQ ID NO. 1186 |
| (N20)NGG | 5 | 35871168 | + | TTCTTTTCCAGTTAAACCTGAGG | 1 | 6 | 90 | SEQ ID NO. 1187 |
| (N20)NGG | 5 | 35871197 | + | TTGACCTGAGTGTCGTCTATCGG | 1 | 3 | 13 | SEQ ID NO. 1188 |
| (N20)NGG | 5 | 35871198 | + | TGACCTGAGTGTCGTCTATCGGG | 1 | 4 | 13 | SEQ ID NO. 1189 |
| (N20)NGG | 5 | 35871202 | + | CTGAGTGTCGTCTATCGGAAGG | 1 | 1 | 3 | SEQ ID NO. 1190 |
| (N20)NGG | 5 | 35871219 | + | GGAAGGAGCCAATGACTTTGTGG | 1 | 3 | 70 | SEQ ID NO. 1191 |
| (N20)NGG | 5 | 35871291 | + | GCACGATGTAGCTTACCGCCAGG | 1 | 1 | 1 | SEQ ID NO. 1192 |
| (N20)NGG | 5 | 35871297 | + | TGTAGCTTACCGCCAGGAAAAGG | 1 | 2 | 11 | SEQ ID NO. 1193 |
| (N20)NGG | 5 | 35871311 | + | AGGAAAAGGATGAAAACAAATGG | 2 | 48 | 722 | SEQ ID NO. 1194 |
| (N20)NGG | 5 | 35871315 | + | AAAGGATGAAAACAAATGACGG | 3 | 70 | 1031 | SEQ ID NO. 1195 |
| (N20)NGG | 5 | 35871153 | - | AAAGGAGCCTCCAGGTTTAACTGG | 1 | 3 | 24 | SEQ ID NO. 1196 |
| (N20)NGG | 5 | 35871162 | - | CTCAGGTCAAAAGGAGCCTCAGG | 1 | 2 | 45 | SEQ ID NO. 1197 |
| (N20)NGG | 5 | 35871171 | - | TAGACGACACTCAGGTCAAAAGG | 1 | 3 | 13 | SEQ ID NO. 1198 |
| (N20)NGG | 5 | 35871179 | - | CTTCCCGATAGACGACACTCAGG | 2 | 10 | 217 | SEQ ID NO. 1199 |
| (N20)NGG | 5 | 35871205 | - | AAATGTCACCACAAAGTCATTGG | 1 | 5 | 2 | SEQ ID NO. 1200 |
| (N20)NGG | 5 | 35871284 | - | TGTTTTCATCCTTTTCCTGGCGG | 1 | 3 | 80 | SEQ ID NO. 1201 |
| (N20)NGG | 5 | 35871287 | - | ATTTGTTTTCATCCTTTTCCTGG | 1 | 10 | 151 | SEQ ID NO. 1202 |
| (N20)NGG | 5 | 35873635 | + | CCTGCAGAGAAAGCTCCAACCGG | 1 | 10 | 217 | SEQ ID NO. 1203 |
| (N20)NGG | 5 | 35873687 | + | ATCCCTGATCACTATTTTAAAGG | 1 | 5 | 50 | SEQ ID NO. 1204 |
| (N20)NGG | 5 | 35873694 | + | ATCACTATTTTAAAGGCTTCTGG | 2 | 3 | 48 | SEQ ID NO. 1205 |
| (N20)NGG | 5 | 35873703 | + | TTAAAGGCTTCTGGAGTGAATGG | 1 | 6 | 109 | SEQ ID NO. 1206 |

FIG. 7 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 5 | 35873750 | + | CCAGAGATCAATAATAGCTCAGG | 1 | 3 | 26 | SEQ ID NO. 1207 |
| (N20)NGG | 5 | 35873755 | + | GATCAATAATAGCTCAGGTAAGG | 1 | 2 | 20 | SEQ ID NO. 1208 |
| (N20)NGG | 5 | 35873760 | + | ATAATAGCTCAGGTAAGGAATGG | 1 | 9 | 58 | SEQ ID NO. 1209 |
| (N20)NGG | 5 | 35873763 | + | ATAGCTCAGGTAAGGAATGGTGG | 1 | 2 | 47 | SEQ ID NO. 1210 |
| (N20)NGG | 5 | 35873594 | - | CAGGAGTGTCAGCTTTGTGCTGG | 1 | 8 | 52 | SEQ ID NO. 1211 |
| (N20)NGG | 5 | 35873613 | - | CCGGTTGGAGCTTTCTCTGCAGG | 1 | 1 | 17 | SEQ ID NO. 1212 |
| (N20)NGG | 5 | 35873628 | - | TCTCATACATTGCTGCCGGTTGG | 1 | 5 | 57 | SEQ ID NO. 1213 |
| (N20)NGG | 5 | 35873632 | - | TTAATCTCATACATTGCTGCCGG | 1 | 9 | 114 | SEQ ID NO. 1214 |
| (N20)NGG | 5 | 35873663 | - | TTTAAAATAGTGATCAGGGATGG | 2 | 9 | 131 | SEQ ID NO. 1215 |
| (N20)NGG | 5 | 35873667 | - | AGCCTTTAAAATAGTGATCAGGG | 1 | 11 | 135 | SEQ ID NO. 1216 |
| (N20)NGG | 5 | 35873668 | - | AAGCCTTTAAAATAGTGATCAGG | 1 | 6 | 66 | SEQ ID NO. 1217 |
| (N20)NGG | 5 | 35873707 | - | GGAGTTCTGAAGTAATAACTTGG | 1 | 4 | 31 | SEQ ID NO. 1218 |
| (N20)NGG | 5 | 35873728 | - | CCTGAGCTATTATTGATCTCTGG | 1 | 1 | 25 | SEQ ID NO. 1219 |
| (N20)NGG | 5 | 35874550 | + | ACAATCTATTCTTGCTTTCCAGG | 1 | 10 | 59 | SEQ ID NO. 1220 |
| (N20)NGG | 5 | 35874551 | + | CAATCTATTCTTGCTTTCCAGGG | 1 | 8 | 70 | SEQ ID NO. 1221 |
| (N20)NGG | 5 | 35874552 | + | AATCTATTCTTGCTTTCCAGGGG | 2 | 7 | 77 | SEQ ID NO. 1222 |
| (N20)NGG | 5 | 35874558 | + | TTCTTGCTTTCCAGGGAGAGATGG | 1 | 11 | 89 | SEQ ID NO. 1223 |
| (N20)NGG | 5 | 35874612 | + | TTTTTTCTCTGCGCTCTGTTGG | 1 | 9 | 192 | SEQ ID NO. 1224 |
| (N20)NGG | 5 | 35874621 | + | TGTCGCTCTGTTGGTCATCTTGG | 1 | 1 | 26 | SEQ ID NO. 1225 |
| (N20)NGG | 5 | 35874635 | + | TCATCTTGGCCTGTGTGTTATGG | 1 | 4 | 46 | SEQ ID NO. 1226 |
| (N20)NGG | 5 | 35874644 | + | CCTGTGTTATGGAAAAAAAGG | 1 | 7 | 98 | SEQ ID NO. 1227 |
| (N20)NGG | 5 | 35874526 | - | TGGAAAGCAAGAATAGATTGTGG | 2 | 5 | 129 | SEQ ID NO. 1228 |
| (N20)NGG | 5 | 35874546 | - | AAGATAGGATCCATCTCCCCTGG | 1 | 3 | 27 | SEQ ID NO. 1229 |
| (N20)NGG | 5 | 35874561 | - | ATGCTGATGGTTAGTAAGATAGG | 1 | 2 | 30 | SEQ ID NO. 1230 |
| (N20)NGG | 5 | 35874574 | - | GAAAAAACTCAAAATGCTGATGG | 1 | 14 | 200 | SEQ ID NO. 1231 |
| (N20)NGG | 5 | 35874622 | - | CCTTTTTTCCATAACACACAGG | 1 | 1 | 75 | SEQ ID NO. 1232 |
| (N20)NGG | 5 | 35875613 | + | TATCAATGTTCTCTGATTTCAGG | 1 | 12 | 84 | SEQ ID NO. 1233 |
| (N20)NGG | 5 | 35875631 | + | TCAGGATTAAGCCTATCGTATGG | 1 | 1 | 5 | SEQ ID NO. 1234 |
| (N20)NGG | 5 | 35875662 | + | CCCCGATCATAAGAAGACTTCGG | 1 | 1 | 6 | SEQ ID NO. 1235 |
| (N20)NGG | 5 | 35875702 | + | CCAAGAAAGTGAGTGTTTTTGG | 1 | 17 | 122 | SEQ ID NO. 1236 |
| (N20)NGG | 5 | 35875620 | - | GGGAGACTGGCCATACGATAGG | 1 | 1 | 6 | SEQ ID NO. 1237 |
| (N20)NGG | 5 | 35875632 | - | TTCTTATGATCGGGAGGACTGG | 1 | 2 | 26 | SEQ ID NO. 1238 |
| (N20)NGG | 5 | 35875633 | - | CTTCTTATGATCGGGAGACTGG | 1 | 1 | 11 | SEQ ID NO. 1239 |
| (N20)NGG | 5 | 35875640 | - | CCAGAGTCTTCTTATGATCGGGG | 1 | 1 | 12 | SEQ ID NO. 1240 |

FIG. 7 cont.

| site_type | site_chr omosome | site_start_ nucleotide | site_st rand | target_site_sequence_with_NGG | genome_wide_ hits_with_1 or_less_mism atches | genome_wide_ hits_with_2 or_less_mism atches | genome_wide_h its_with_3_or _less_mismatc hes | | |
|---|---|---|---|---|---|---|---|---|---|
| (N20)NGG | 5 | 35875641 | - | TCCAGAGTCTCTTATGATCGGG | 1 | 2 | 27 | SEQ ID NO. | 1241 |
| (N20)NGG | 5 | 35875642 | - | TTCCAGAGTCTCTTATGATCGG | 1 | 5 | 82 | SEQ ID NO. | 1242 |
| (N20)NGG | 5 | 35875680 | - | CCAAAAACACTCACTTTTCTTGG | 1 | 5 | 106 | SEQ ID NO. | 1243 |
| (N20)NGG | 5 | 35876120 | + | TTTCAATCCTGAAAGTTTCCTGG | 1 | 7 | 96 | SEQ ID NO. | 1244 |
| (N20)NGG | 5 | 35876137 | + | TCCTGGACTGCCAGATTCATAGG | 1 | 1 | 37 | SEQ ID NO. | 1245 |
| (N20)NGG | 5 | 35876138 | + | CCTGGACTGCCAGATTCATAGGG | 1 | 2 | 39 | SEQ ID NO. | 1246 |
| (N20)NGG | 5 | 35876141 | + | GGACTGCCAGATTCATAGGGTGG | 1 | 1 | 22 | SEQ ID NO. | 1247 |
| (N20)NGG | 5 | 35876168 | + | CATTCAAGCTAGAGATGAAGTGG | 1 | 2 | 50 | SEQ ID NO. | 1248 |
| (N20)NGG | 5 | 35876172 | + | CAAGCTAGAGATGAAGTGAAGG | 2 | 4 | 66 | SEQ ID NO. | 1249 |
| (N20)NGG | 5 | 35876224 | + | TAGAAGAATCTGAGAAGCAGAGG | 3 | 17 | 163 | SEQ ID NO. | 1250 |
| (N20)NGG | 5 | 35876229 | + | GAATCTGAGAAGCAGAGGCTTGG | 1 | 12 | 241 | SEQ ID NO. | 1251 |
| (N20)NGG | 5 | 35876232 | + | TCTGAGAAGCAGAGGCTTGGAGG | 2 | 9 | 193 | SEQ ID NO. | 1252 |
| (N20)NGG | 5 | 35876233 | + | CTGAGAAGCAGAGGCTTGGAGGG | 1 | 17 | 261 | SEQ ID NO. | 1253 |
| (N20)NGG | 5 | 35876234 | + | TGAGAAGCAGAGGCTTGGAGGGG | 5 | 27 | | SEQ ID NO. | 1254 |
| (N20)NGG | 5 | 35876264 | + | GAGCCCAACTCCCCATCTGACG | 1 | 6 | 53 | SEQ ID NO. | 1255 |
| (N20)NGG | 5 | 35876292 | + | GTCATCACTCCAGAAAGCTTTGG | 1 | 2 | 35 | SEQ ID NO. | 1256 |
| (N20)NGG | 5 | 35876318 | + | AGATTCATCCCTCACATGCCTGG | 1 | 1 | 43 | SEQ ID NO. | 1257 |
| (N20)NGG | 5 | 35876322 | + | TCATCCCTCACATGCCTGGCTGG | 1 | 4 | 69 | SEQ ID NO. | 1258 |
| (N20)NGG | 5 | 35876323 | + | CATCCCTCACATGCCTGGCTGGG | 1 | 5 | 91 | SEQ ID NO. | 1259 |
| (N20)NGG | 5 | 35876365 | + | CCCCTATTCTCTCTCTTCCAGG | 3 | 15 | 178 | SEQ ID NO. | 1260 |
| (N20)NGG | 5 | 35876380 | + | CTTCCAGGTCCCTAGACTGCAGG | 1 | 3 | 69 | SEQ ID NO. | 1261 |
| (N20)NGG | 5 | 35876381 | + | TTCCAGGTCCCTAGACTGCAGGG | 1 | 8 | 143 | SEQ ID NO. | 1262 |
| (N20)NGG | 5 | 35876388 | + | TCCCTAGACTGCAGGGAGAGTGG | 1 | 3 | 75 | SEQ ID NO. | 1263 |
| (N20)NGG | 5 | 35876397 | + | TGCAGGGAGAGTGCCAAGAATGG | 2 | 13 | 157 | SEQ ID NO. | 1264 |
| (N20)NGG | 5 | 35876398 | + | GCAGGGAGAGTGCCAAGAATGGG | 2 | 7 | 94 | SEQ ID NO. | 1265 |
| (N20)NGG | 5 | 35876414 | + | GAATGGGCCTCATGTGTACCAGG | 1 | 2 | 18 | SEQ ID NO. | 1266 |
| (N20)NGG | 5 | 35876433 | + | CAGGACCTCCTGCTTAGCCTTGG | 2 | 37 | 129 | SEQ ID NO. | 1267 |
| (N20)NGG | 5 | 35876434 | + | AGGACCTCCTGCTTAGCCTTGGG | 2 | 4 | 43 | SEQ ID NO. | 1268 |
| (N20)NGG | 5 | 35876478 | + | CCTCCATTTTCTCTCCAATCTGG | 1 | 7 | 95 | SEQ ID NO. | 1269 |
| (N20)NGG | 5 | 35876507 | + | GACATTGAACCCAGTTGCTCAGG | 1 | 6 | 37 | SEQ ID NO. | 1270 |
| (N20)NGG | 5 | 35876508 | + | ACATTGAACCCAGTTGCTCAGGG | 1 | 4 | 49 | SEQ ID NO. | 1271 |
| (N20)NGG | 5 | 35876531 | + | TCAGCCCATTCTTACTTCCCTGG | 1 | 5 | 54 | SEQ ID NO. | 1272 |
| (N20)NGG | 5 | 35876532 | + | CAGCCCATTCTTACTTCCCTGGG | 1 | 2 | 59 | SEQ ID NO. | 1273 |
| (N20)NGG | 5 | 35876061 | - | CTGCACAGAAAAAGGAGAAAGG | 2 | 26 | 307 | SEQ ID NO. | 1274 |

FIG. 7 cont.

| site_type | site_chr omosome | site_start_ nucleotide | site_st rand | target_site_sequence_wit h_NGG | genome_wide_ hits_with_1_ or_less_mism atches | genome_wide_ hits_with_2_ or_less_mism atches | genome_wide_h its_with_3_or _less_mismatc hes | | |
|---|---|---|---|---|---|---|---|---|---|
| (N20)NGG | 5 | 35876062 | - | TCTGCACAGAAAAGGAGAAAGG | 2 | 15 | 207 | SEQ ID NO. | 1275 |
| (N20)NGG | 5 | 35876069 | - | TTTAAATTCTGCACAGAAAAGG | 2 | 22 | 385 | SEQ ID NO. | 1276 |
| (N20)NGG | 5 | 35876105 | - | TGGCAGTCCAGGAAACTTTCAGG | 1 | 3 | 25 | SEQ ID NO. | 1277 |
| (N20)NGG | 5 | 35876116 | - | CCCTATGAATCTGGCAGTCCAGG | 1 | 2 | 39 | SEQ ID NO. | 1278 |
| (N20)NGG | 5 | 35876125 | - | TGTCATCCACCCTATGAATCTGG | 1 | 2 | 8 | SEQ ID NO. | 1279 |
| (N20)NGG | 5 | 35876192 | - | TCAGATTCTTCTAGTTGCTGAGG | 1 | 4 | 66 | SEQ ID NO. | 1280 |
| (N20)NGG | 5 | 35876245 | - | CATCCTCAGATGGGCAGTTGGG | 1 | 2 | 52 | SEQ ID NO. | 1281 |
| (N20)NGG | 5 | 35876246 | - | ACATCCTCAGATGGGCAGTTGG | 1 | 2 | 33 | SEQ ID NO. | 1282 |
| (N20)NGG | 5 | 35876247 | - | TACATCCTCAGATGGGCAGTTGG | 1 | 2 | 36 | SEQ ID NO. | 1283 |
| (N20)NGG | 5 | 35876254 | - | TGATGACTACATCCTCAGATGGG | 1 | 3 | 25 | SEQ ID NO. | 1284 |
| (N20)NGG | 5 | 35876255 | - | GTGATGACTACATCCTCAGATGG | 2 | 3 | 23 | SEQ ID NO. | 1285 |
| (N20)NGG | 5 | 35876279 | - | GAATCTCTTCCAAAGCTTTCTGG | 2 | 9 | 69 | SEQ ID NO. | 1286 |
| (N20)NGG | 5 | 35876304 | - | ATTCCCAGCCAGGCATGTGAGG | 1 | 6 | 54 | SEQ ID NO. | 1287 |
| (N20)NGG | 5 | 35876305 | - | CATTCCCAGCCAGGCATGTGAGG | 1 | 9 | 61 | SEQ ID NO. | 1288 |
| (N20)NGG | 5 | 35876314 | - | ATGCACTGACATTCCCAGCCAGG | 1 | 4 | 42 | SEQ ID NO. | 1289 |
| (N20)NGG | 5 | 35876343 | - | CCTGGAAGAGGAGAATAGGGG | 2 | 10 | 144 | SEQ ID NO. | 1290 |
| (N20)NGG | 5 | 35876344 | - | ACCTGGAAGAGGAGAGAATAGG | 1 | 7 | 142 | SEQ ID NO. | 1291 |
| (N20)NGG | 5 | 35876345 | - | GACCTGGAAGAGGAGAGAATAGG | 1 | 7 | 150 | SEQ ID NO. | 1292 |
| (N20)NGG | 5 | 35876355 | - | GCAGTCTAGGGACCTGGAAGAGG | 1 | 5 | 109 | SEQ ID NO. | 1293 |
| (N20)NGG | 5 | 35876361 | - | CTCCCTGCAGTCTAGGGACCTGG | 1 | 2 | 69 | SEQ ID NO. | 1294 |
| (N20)NGG | 5 | 35876367 | - | GCCACTCTCCCTGCAGTCTAGG | 1 | 2 | 38 | SEQ ID NO. | 1295 |
| (N20)NGG | 5 | 35876368 | - | TGCCACTCTCCCTGCAGTCTAGG | 1 | 4 | 71 | SEQ ID NO. | 1296 |
| (N20)NGG | 5 | 35876399 | - | AGGAGGTCCTGGTACACATGAGG | 1 | 2 | 43 | SEQ ID NO. | 1297 |
| (N20)NGG | 5 | 35876410 | - | CAAGGCTAAGCAGGAGGTCCTGG | 1 | 2 | 28 | SEQ ID NO. | 1298 |
| (N20)NGG | 5 | 35876416 | - | TAGTCCCAAGGCTAAGCAGGAGG | 1 | 3 | 35 | SEQ ID NO. | 1299 |
| (N20)NGG | 5 | 35876419 | - | TTGTAGTCCCAAGGCTAAGCAGG | 1 | 1 | 21 | SEQ ID NO. | 1300 |
| (N20)NGG | 5 | 35876428 | - | GCGTGCTGTTTGTAGTCCCAAGG | 1 | 1 | 9 | SEQ ID NO. | 1301 |
| (N20)NGG | 5 | 35876453 | - | GATTGGAGAGAAAATGCAGGGGG | 1 | 19 | 192 | SEQ ID NO. | 1302 |
| (N20)NGG | 5 | 35876454 | - | AGATTGGAGAGAAAATGGAGGGG | 2 | 24 | 394 | SEQ ID NO. | 1303 |
| (N20)NGG | 5 | 35876455 | - | CAGATTGGAGAGAAAATGGAGGG | 4 | 13 | 191 | SEQ ID NO. | 1304 |
| (N20)NGG | 5 | 35876456 | - | CCAGATTGGAGAGAAAATGGAGG | 1 | 6 | 115 | SEQ ID NO. | 1305 |
| (N20)NGG | 5 | 35876459 | - | ATTCCAGATTGGAGAGAAAATGG | 2 | 11 | 145 | SEQ ID NO. | 1306 |
| (N20)NGG | 5 | 35876470 | - | TCAATGTCAGGATTCCAGATTGG | 1 | 4 | 39 | SEQ ID NO. | 1307 |
| (N20)NGG | 5 | 35876482 | - | GAGCAACTGGGTTCAATGTCAGG | 1 | 3 | 20 | SEQ ID NO. | 1308 |

FIG. 7 cont.

| site type | site_chr omosome | site_start nucleotide | site_st rand | target_site_sequence_with_NGG | genome_wide_ hits_with_1_ or_less_mism atches | genome_wide_ hits_with_2_ or_less_mism atches | genome_wide_h its_with_3_or _less_mismatc hes | |
|---|---|---|---|---|---|---|---|---|
| (N20)NGG | 5 | 35876494 | - | TGGGCTGACCCTGAGCAACTGGG | 1 | | 4 | 36 SEQ ID NO. 1309 |
| (N20)NGG | 5 | 35876495 | - | ATGGGCTGACCCTGAGCAACTCGG | 1 | | 3 | 39 SEQ ID NO. 1310 |
| (N20)NGG | 5 | 35876513 | - | GATCCCAGGGAAGTAAGAATGGG | 1 | | 7 | 81 SEQ ID NO. 1311 |
| (N20)NGG | 5 | 35876514 | - | TGATCCCAGGGAAGTAAGAATGG | 1 | | 18 | 211 SEQ ID NO. 1312 |
| (N20)NGG | 5 | 35876526 | - | TTCTTCTTGATTTGATCCCAGGG | 1 | | 2 | 82 SEQ ID NO. 1313 |
| (N20)NGG | 5 | 35876527 | - | CTTCTTCTTGATTTGATCCCAGG | 1 | | 7 | 173 SEQ ID NO. 1314 |
| (N20)NGG | 5 | 35876559 | - | GTTTTGGTAGAAGCTGGACATGG | 1 | | 5 | 131 SEQ ID NO. 1315 |
| (N20)NGG | 5 | 35876565 | - | TCACTGGTTTTGGTAGAAGCTGG | 1 | | 5 | 53 SEQ ID NO. 1316 |
| (N20)NGG | 5 | 35876575 | - | TTCTTACACTTCACTGGTTTTGG | 1 | | 7 | 62 SEQ ID NO. 1317 |
| (N20)NGG | 5 | 35876581 | - | CTGGGTTTCTTACACTTCACTGG | 1 | | 1 | 37 SEQ ID NO. 1318 |

FIG. 7 cont.

| site_type | site_chr omosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 19 | 17937551 | + | TTATCTGTCCCCGCCCCTCAGG | 1 | 2 | 35 | SEQ ID NO. 1319 |
| (N20)NGG | 19 | 17937577 | + | ACAGCTCATGAAGCTGTGCTGG | 1 | 3 | 13 | SEQ ID NO. 1320 |
| (N20)NGG | 19 | 17937578 | + | CAGCTCATGAAGCTGTGCTGGG | 1 | 3 | 18 | SEQ ID NO. 1321 |
| (N20)NGG | 19 | 17937593 | + | GTGCTGGGCCCCTAGCCCACAGG | 1 | 5 | 61 | SEQ ID NO. 1322 |
| (N20)NGG | 19 | 17937598 | + | GGGCCCCTAGCCCACAGGACCGG | 1 | 4 | 83 | SEQ ID NO. 1323 |
| (N20)NGG | 19 | 17937617 | + | CCGGCCATCATTCAGCGCCCTGG | 1 | 1 | 7 | SEQ ID NO. 1324 |
| (N20)NGG | 19 | 17937618 | + | CGGCCATCATTCAGCGCCCTGGG | 1 | 2 | 3 | SEQ ID NO. 1325 |
| (N20)NGG | 19 | 17937629 | + | CAGCGCCCTGGGCCCCCAGCTGG | 1 | 9 | 113 | SEQ ID NO. 1326 |
| (N20)NGG | 19 | 17937640 | + | GCCCCAGCTGGACATGCTGTGG | 1 | 3 | 74 | SEQ ID NO. 1327 |
| (N20)NGG | 19 | 17937645 | + | CAGCTGGACATGCTGTGAGCGG | 1 | 8 | 69 | SEQ ID NO. 1328 |
| (N20)NGG | 19 | 17937652 | + | ACATGCTGTGAGCGGAAGCCGG | 1 | 1 | 25 | SEQ ID NO. 1329 |
| (N20)NGG | 19 | 17937653 | + | CATGCTGTGAGCGGAAGCCGGG | 1 | 5 | 28 | SEQ ID NO. 1330 |
| (N20)NGG | 19 | 17937654 | + | ATGCTGTGAGCGGAAGCCGGGG | 1 | 2 | 18 | SEQ ID NO. 1331 |
| (N20)NGG | 19 | 17937655 | + | TGCTGTGGAGCGGAAGCCGGGGG | 1 | 1 | 21 | SEQ ID NO. 1332 |
| (N20)NGG | 19 | 17937689 | + | TGCCTTCACTGCTCACCCAGAGG | 1 | 2 | 60 | SEQ ID NO. 1333 |
| (N20)NGG | 19 | 17937690 | + | GCCTTCACTGCTCACCCAGAGGG | 1 | 7 | 51 | SEQ ID NO. 1334 |
| (N20)NGG | 19 | 17937739 | + | AGCTCCTGCCCGACAGACCTCTGG | 1 | 6 | 64 | SEQ ID NO. 1335 |
| (N20)NGG | 19 | 17937526 | - | GAGGGGCGGGGACAGATAATGG | 1 | 8 | 99 | SEQ ID NO. 1336 |
| (N20)NGG | 19 | 17937537 | - | CTCGTGAACCTGAGGGGCGGGG | 1 | 63 | 1843 | SEQ ID NO. 1337 |
| (N20)NGG | 19 | 17937538 | - | GCTCGTGAACCTGAGGGGCGGG | 1 | 5 | 100 | SEQ ID NO. 1338 |
| (N20)NGG | 19 | 17937539 | - | AGCTCGTGAACCTGAGGGGCGG | 1 | 3 | 36 | SEQ ID NO. 1339 |
| (N20)NGG | 19 | 17937540 | - | GAGCTCGTGAACCTGAGGGGGCGG | 1 | 1 | 22 | SEQ ID NO. 1340 |
| (N20)NGG | 19 | 17937543 | - | CATGAGCTCGTGAACCTGAGGGG | 1 | 1 | 9 | SEQ ID NO. 1341 |
| (N20)NGG | 19 | 17937544 | - | TCATGAGCTCGTGAACCTGAGG | 1 | 1 | 13 | SEQ ID NO. 1342 |
| (N20)NGG | 19 | 17937545 | - | TTCATGAGCTCGTGAACCTGAGG | 1 | 3 | 19 | SEQ ID NO. 1343 |
| (N20)NGG | 19 | 17937579 | - | TGGCCGTCCTGTGGGCTAGGGG | 1 | 5 | 18 | SEQ ID NO. 1344 |
| (N20)NGG | 19 | 17937580 | - | ATGGCCGTCCTGTGGGCTAGG | 1 | 1 | 14 | SEQ ID NO. 1345 |
| (N20)NGG | 19 | 17937581 | - | GATGGCCGGTCCTGTGGGCTAGG | 1 | 1 | 22 | SEQ ID NO. 1346 |
| (N20)NGG | 19 | 17937586 | - | TGAATGATGGCCGGTCCTGTGG | 1 | 7 | 93 | SEQ ID NO. 1347 |
| (N20)NGG | 19 | 17937587 | - | CTGAATGATGGCCGGTCCTGTGG | 1 | 2 | 16 | SEQ ID NO. 1348 |
| (N20)NGG | 19 | 17937595 | - | CCAGGGCGCTGAATCATGGCCGG | 1 | 1 | 12 | SEQ ID NO. 1349 |
| (N20)NGG | 19 | 17937599 | - | GGGCCCAGGGCGCTGAATGATGG | 1 | 3 | 33 | SEQ ID NO. 1350 |
| (N20)NGG | 19 | 17937612 | - | CATGTCCAGCTGGGGGCCCAGGG | 1 | 7 | 59 | SEQ ID NO. 1351 |

FIG. 8

| site type | site_chr omosome | site_start_ nucleotide | site_s trand | target_site_sequence_with_NGG | genome_wide_ hits_with_1_ or_less_mism atches | genome_wide_ hits_with_ 2_or_less_m ismatches | genome_wide_ hits_with_3_ or_less_mism atches | |
|---|---|---|---|---|---|---|---|---|
| (N20)NGG | 19 | 17937613 | - | GCATGTCCAGCTGGGGGCCAGG | | 1 | 6 | 70 SEQ ID NO. 1352 |
| (N20)NGG | 19 | 17937619 | - | TCCACAGCATGTCCAGCTGGGG | | 1 | 5 | 67 SEQ ID NO. 1353 |
| (N20)NGG | 19 | 17937620 | - | CTCCACAGCATGTCCAGCTGGG | | 1 | 2 | 71 SEQ ID NO. 1354 |
| (N20)NGG | 19 | 17937621 | - | GCTCCACAGCATGTCCAGCTGG | | 1 | 3 | 37 SEQ ID NO. 1355 |
| (N20)NGG | 19 | 17937622 | - | CGCTCCACAGCATGTCCAGCTGG | | 1 | 2 | 28 SEQ ID NO. 1356 |
| (N20)NGG | 19 | 17937649 | - | AGGCATGAGTCTCACACCCCGG | | 1 | 5 | 38 SEQ ID NO. 1357 |
| (N20)NGG | 19 | 17937669 | - | GCCCTCTGGGTGAGCAGTGAAGG | | 1 | 4 | 62 SEQ ID NO. 1358 |
| (N20)NGG | 19 | 17937682 | - | GGGAGTGGTGTGTTTGCCCTCTGG | | 1 | 2 | 42 SEQ ID NO. 1359 |
| (N20)NGG | 19 | 17937683 | - | AGGGAGTGGTGTTTGCCCTCTGG | | 1 | 4 | 49 SEQ ID NO. 1360 |
| (N20)NGG | 19 | 17937697 | - | GCTATGAAAAGACAGGGAGTGG | | 1 | 6 | 89 SEQ ID NO. 1361 |
| (N20)NGG | 19 | 17937702 | - | CAGGAGCTATGAAAAGGACAGG | | 2 | 6 | 79 SEQ ID NO. 1362 |
| (N20)NGG | 19 | 17937703 | - | GCAGGAGCTATGAAAAGGACAGG | | 1 | 4 | 47 SEQ ID NO. 1363 |
| (N20)NGG | 19 | 17937708 | - | TGCGGGCAGGAGCTATGAAAAGG | | 1 | 4 | 28 SEQ ID NO. 1364 |
| (N20)NGG | 19 | 17937721 | - | TAATCCAGAGGTCTGCGGGCAGG | | 1 | 1 | 21 SEQ ID NO. 1365 |
| (N20)NGG | 19 | 17940916 | + | ATGCGCTCCCTCCTTGGCTCCAGG | | 1 | 6 | 33 SEQ ID NO. 1366 |
| (N20)NGG | 19 | 17940927 | + | CTTGGCTCCAGGAGTTCCTGCGG | | 1 | 9 | 84 SEQ ID NO. 1367 |
| (N20)NGG | 19 | 17940934 | + | CCAGGAGTTCCTGCGGATGATGG | | 1 | 3 | 27 SEQ ID NO. 1368 |
| (N20)NGG | 19 | 17940935 | + | CAGGAGTTCCTGCGGATGATGGG | | 1 | 1 | 17 SEQ ID NO. 1369 |
| (N20)NGG | 19 | 17940945 | + | TGCGGATGATGGGGATGTGAGCGG | | 1 | 2 | 38 SEQ ID NO. 1370 |
| (N20)NGG | 19 | 17940946 | + | GCGGATGATGGGATGTGAGCGGG | | 1 | 1 | 19 SEQ ID NO. 1371 |
| (N20)NGG | 19 | 17940973 | + | CCCCGCCCTCTGCCGCCTCTTGG | | 1 | 8 | 80 SEQ ID NO. 1372 |
| (N20)NGG | 19 | 17940982 | + | CTGCCGCCTCTTGGAACTGCTGG | | 1 | 3 | 29 SEQ ID NO. 1373 |
| (N20)NGG | 19 | 17940985 | + | CCGCCTCTTGGAACTGCTGGAGG | | 2 | 5 | 31 SEQ ID NO. 1374 |
| (N20)NGG | 19 | 17940988 | + | CCTCTTGGAACTGCTGGAGGAGG | | 1 | 6 | 63 SEQ ID NO. 1375 |
| (N20)NGG | 19 | 17940989 | + | CTCTTGGAACTGCTGGAGGAGGG | | 1 | 3 | 67 SEQ ID NO. 1376 |
| (N20)NGG | 19 | 17940996 | + | AACTGCTGGAGGAGGGCCAGAGG | | 2 | 8 | 91 SEQ ID NO. 1377 |
| (N20)NGG | 19 | 17941003 | + | GGAGGAGGGCCAGAGGCTGCCGG | | 2 | 24 | 274 SEQ ID NO. 1378 |
| (N20)NGG | 19 | 17941027 | + | GCCTCCTGCCTGCCCCTGCTGAGG | | 5 | 32 | 242 SEQ ID NO. 1379 |
| (N20)NGG | 19 | 17941040 | + | CCTGCTGAGGTGAGCGCCGCAGG | | 1 | 1 | 26 SEQ ID NO. 1380 |
| (N20)NGG | 19 | 17941041 | + | CTGCTGAGGTGAGCGCCGCAGGG | | 1 | 2 | 17 SEQ ID NO. 1381 |
| (N20)NGG | 19 | 17940901 | - | AGGAACTCCTGGAGCCAAGGAGG | | 1 | 4 | 96 SEQ ID NO. 1382 |
| (N20)NGG | 19 | 17940904 | - | CGCAGGAACTCCTGGAGCCAAGG | | 1 | 5 | 67 SEQ ID NO. 1383 |
| (N20)NGG | 19 | 17940912 | - | CCATCATCCGCAGAACTCCTGG | | 1 | 1 | 21 SEQ ID NO. 1384 |

FIG. 8 cont.

| site_type | site_chr omosome | site_start_ nucleotide | site_s trand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 19 | 17940921 | - | GCTCACATCCCATCATCCGCAGG | | 1 | 1 | 10 SEQ ID NO. 1385 |
| (N20)NGG | 19 | 17940951 | - | CCAAGAGGCGGCAGAGGGCGGG | | 1 | 4 | 58 SEQ ID NO. 1386 |
| (N20)NGG | 19 | 17940952 | - | TCCAAGAGGCGGCAGAGGGCGG | | 1 | 2 | 46 SEQ ID NO. 1387 |
| (N20)NGG | 19 | 17940953 | - | TTCCAAGAGGCGGCAGACCCCG | | 2 | 3 | 53 SEQ ID NO. 1388 |
| (N20)NGG | 19 | 17940956 | - | CAGTTCCAAGAGGCGGCAGAGGG | | 1 | 3 | 33 SEQ ID NO. 1389 |
| (N20)NGG | 19 | 17940957 | - | GCAGTTCCAAGAGGCGGCAGAGG | | 1 | 2 | 34 SEQ ID NO. 1390 |
| (N20)NGG | 19 | 17940963 | - | CCTCCAGCAGTTCCAAGAGCGG | | 1 | 6 | 49 SEQ ID NO. 1391 |
| (N20)NGG | 19 | 17940966 | - | CCTCTCCAGCAGTTCCAAGAGG | | 1 | 6 | 64 SEQ ID NO. 1392 |
| (N20)NGG | 19 | 17940990 | - | CAGGAGGCGCCGGCAGCCTCTGG | | 1 | 4 | 60 SEQ ID NO. 1393 |
| (N20)NGG | 19 | 17941000 | - | GCAGGGCAGGCAGGAGGCGCCGG | | 2 | 28 | 284 SEQ ID NO. 1394 |
| (N20)NGG | 19 | 17941006 | - | ACCTCAGCAGGGCAGGCAGGAGG | | 2 | 9 | 170 SEQ ID NO. 1395 |
| (N20)NGG | 19 | 17941009 | - | CTCACCTCAGCAGGGCAGGCAGG | | 1 | 7 | 82 SEQ ID NO. 1396 |
| (N20)NGG | 19 | 17941013 | - | GGGCTCACCTCAGCAGGGCCAGG | | 1 | 2 | 30 SEQ ID NO. 1397 |
| (N20)NGG | 19 | 17941017 | - | CTGCGGCGCTCACCTCAGCAGGG | | 1 | 3 | 15 SEQ ID NO. 1398 |
| (N20)NGG | 19 | 17941018 | - | CCTGCGGCGCTCACCTCAGCAGG | | 1 | 1 | 25 SEQ ID NO. 1399 |
| (N20)NGG | 19 | 17941311 | + | CAAGACCTTGTCCCCTCTCCAGG | | 2 | 4 | 63 SEQ ID NO. 1400 |
| (N20)NGG | 19 | 17941333 | + | GTATGCCCCGAATCCCCTCTCGG | | 1 | 1 | 11 SEQ ID NO. 1401 |
| (N20)NGG | 19 | 17941365 | + | TCTCTGCCAGTCAGACTCTGG | | 1 | 2 | 9 SEQ ID NO. 1402 |
| (N20)NGG | 19 | 17941373 | + | CAGTCAGACGTCTGGAGCTTCGG | | 1 | 5 | 39 SEQ ID NO. 1403 |
| (N20)NGG | 19 | 17941374 | + | AGTCAGACGTCTGGAGCTTCGGG | | 1 | 1 | 15 SEQ ID NO. 1404 |
| (N20)NGG | 19 | 17941375 | + | GTCAGACGTCTGGAGCTTCGGGG | | 1 | 1 | 7 SEQ ID NO. 1405 |
| (N20)NGG | 19 | 17941426 | + | CGACAAAAGCTGCAGCCCCTCGG | | 1 | 2 | 34 SEQ ID NO. 1406 |
| (N20)NGG | 19 | 17941437 | + | GCAGCCCCTCGGCCGTGAGTCGG | | 1 | 2 | 31 SEQ ID NO. 1407 |
| (N20)NGG | 19 | 17941294 | - | GCATACCTGGAGAGGGACAAGG | | 1 | 3 | 70 SEQ ID NO. 1408 |
| (N20)NGG | 19 | 17941300 | - | TCGGGGCATACCTGGAGAGGGG | | 1 | 2 | 25 SEQ ID NO. 1409 |
| (N20)NGG | 19 | 17941301 | - | TTCGGGGCATACCTGGAGAGGG | | 1 | 2 | 24 SEQ ID NO. 1410 |
| (N20)NGG | 19 | 17941302 | - | ATTCGGGGCATACCTGGAGAGG | | 1 | 1 | 11 SEQ ID NO. 1411 |
| (N20)NGG | 19 | 17941307 | - | GAGGGATTCGGGGCATACCTGG | | 1 | 2 | 14 SEQ ID NO. 1412 |
| (N20)NGG | 19 | 17941316 | - | GTTGTCCGAGAGGGATTCGGGG | | 1 | 1 | 3 SEQ ID NO. 1413 |
| (N20)NGG | 19 | 17941317 | - | TGTTGTCCGAGAGGGATTCGGG | | 1 | 1 | 4 SEQ ID NO. 1414 |
| (N20)NGG | 19 | 17941318 | - | ATGTTGTCCGAGAGGGATTCGG | | 1 | 1 | 7 SEQ ID NO. 1415 |
| (N20)NGG | 19 | 17941319 | - | GATGTTGTCCGAGAGGGATTCGG | | 1 | 1 | 13 SEQ ID NO. 1416 |
| (N20)NGG | 19 | 17941325 | - | AGAGAAGATGTTGTCCGAGAGG | | 1 | 2 | 32 SEQ ID NO. 1417 |

FIG. 8 cont.

| site type | site chromosome | site start nucleotide | site strand | target_site_sequence_with_NGG | genome_wide_hits_with_1_or_less_mismatches | genome_wide_hits_with_2_or_less_mismatches | genome_wide_hits_with_3_or_less_mismatches | SEQ ID NO. |
|---|---|---|---|---|---|---|---|---|
| (N20)NGG | 19 | 17941326 | - | GAGAGAAGATGTTGTCCGAGAGG | | 1 | 4 | 26 SEQ ID NO. 1418 |
| (N20)NGG | 19 | 17941350 | - | CGAAGCTCCAGACGTCTGACTGG | | 1 | 1 | 4 SEQ ID NO. 1419 |
| (N20)NGG | 19 | 17941380 | - | AGTAGGTGAAGAGCTCGTACAGG | | 1 | 2 | 6 SEQ ID NO. 1420 |
| (N20)NGG | 19 | 17941397 | - | GCTGCAGCTTTTGTCGCAGTAGG | | 1 | 1 | 17 SEQ ID NO. 1421 |
| (N20)NGG | 19 | 17941419 | - | GAAGCCGACTCACGGCCGAGGGG | | 1 | 1 | 3 SEQ ID NO. 1422 |
| (N20)NGG | 19 | 17941420 | - | GGAAGCCGACTCACGGCCGAGG | | 1 | 1 | 3 SEQ ID NO. 1423 |
| (N20)NGG | 19 | 17941421 | - | GGGAAGCCGACTCACGGCCGAGG | | 1 | 1 | 4 SEQ ID NO. 1424 |
| (N20)NGG | 19 | 17941427 | - | GGCTTCTGGGAAGCCGACTCACGG | | 1 | 4 | 34 SEQ ID NO. 1425 |
| (N20)NGG | 19 | 17942036 | + | CGCTCACACCGCCCGCCCGCAGG | | 2 | 5 | 26 SEQ ID NO. 1426 |
| (N20)NGG | 19 | 17942037 | + | GCTCACACCGCCCGCCCGCAGGG | | 1 | 5 | 22 SEQ ID NO. 1427 |
| (N20)NGG | 19 | 17942042 | + | CACCGCCCGCCCGCAGGGCATGG | | 1 | 2 | 35 SEQ ID NO. 1428 |
| (N20)NGG | 19 | 17942051 | + | CCCGCAGGGCATGGAGTACCTGG | | 1 | 3 | 21 SEQ ID NO. 1429 |
| (N20)NGG | 19 | 17942052 | + | CCGCAGGGCATGGAGTACCTGGG | | 1 | 4 | 24 SEQ ID NO. 1430 |
| (N20)NGG | 19 | 17942081 | + | CCGCTGCGTGCACCGCGACCTGG | | 1 | 1 | 11 SEQ ID NO. 1431 |
| (N20)NGG | 19 | 17942102 | + | GGCCGCCGAAACATCCTCGTGG | | 1 | 1 | 6 SEQ ID NO. 1432 |
| (N20)NGG | 19 | 17942111 | + | AAACATCCTCGTGGAGAGCGAGG | | 1 | 1 | 5 SEQ ID NO. 1433 |
| (N20)NGG | 19 | 17942136 | + | CACGTCAAGATCGCTGACTTCGG | | 2 | 6 | 15 SEQ ID NO. 1434 |
| (N20)NGG | 19 | 17942177 | + | GCTTGACAAAGACTACTACGTGG | | 1 | 1 | 9 SEQ ID NO. 1435 |
| (N20)NGG | 19 | 17942190 | + | TACTACGTGGTCCGGAGCCAGG | | 1 | 1 | 3 SEQ ID NO. 1436 |
| (N20)NGG | 19 | 17942209 | + | CAGGCCAGAGCCCCATTTTCTGG | | 1 | 7 | 63 SEQ ID NO. 1437 |
| (N20)NGG | 19 | 17942212 | + | GCCAGAGCCCCATTTTTCTGGTGG | | 1 | 4 | 52 SEQ ID NO. 1438 |
| (N20)NGG | 19 | 17942213 | + | CCAGAGCCCCATTTTTCTGGTGGG | | 1 | 5 | 52 SEQ ID NO. 1439 |
| (N20)NGG | 19 | 17942214 | + | CAGAGCCCCATTTTTCTGGTGGGG | | 1 | 3 | 56 SEQ ID NO. 1440 |
| (N20)NGG | 19 | 17942228 | + | CTGGTGGGGAACCCGCGCCTAGG | | 1 | 1 | 19 SEQ ID NO. 1441 |
| (N20)NGG | 19 | 17942022 | - | CTCCATGCCCTGCCGGGGGGCGG | | 1 | 2 | 37 SEQ ID NO. 1442 |
| (N20)NGG | 19 | 17942025 | - | GTACTCCATGCCCTGCCGGGGGG | | 1 | 1 | 17 SEQ ID NO. 1443 |
| (N20)NGG | 19 | 17942026 | - | GGTACTCCATGCCCTGCCGGGGG | | 1 | 2 | 17 SEQ ID NO. 1444 |
| (N20)NGG | 19 | 17942029 | - | CCAGGTACTCCATGCCCTGCGG | | 1 | 3 | 54 SEQ ID NO. 1445 |
| (N20)NGG | 19 | 17942030 | - | CCCAGGTACTCCATGCCCTGCGG | | 1 | 3 | 70 SEQ ID NO. 1446 |
| (N20)NGG | 19 | 17942047 | - | GCACCAGCGGGCGGGAGCCCAGG | | 1 | 3 | 42 SEQ ID NO. 1447 |
| (N20)NGG | 19 | 17942055 | - | GTCGCGGTGCACGCAGCGGGGG | | 1 | 1 | 6 SEQ ID NO. 1448 |
| (N20)NGG | 19 | 17942056 | - | GGTCGCGGTGCACCGCAGCGGCGG | | 1 | 1 | 8 SEQ ID NO. 1449 |
| (N20)NGG | 19 | 17942059 | - | CCAGGTCGCGGTGCACGCAGCGG | | 1 | 1 | 15 SEQ ID NO. 1450 |

FIG. 8 cont.

| site type | site chr omosome | site start nucleotide | site strand | target site sequence with NGG | genome wide hits with 1 or less mismatches | genome wide hits with 2 or less mismatches | genome wide hits with 3 or less mismatches | |
|---|---|---|---|---|---|---|---|---|
| (N20)NGG | 19 | 17942071 | - | TGTTTCGGGCGGCCAGGTCGCGG | 2 | 2 | 10 | SEQ ID NO. 1451 |
| (N20)NGG | 19 | 17942077 | - | CGAGGATGTTTCGGGCGGCCAGG | | 6 | 13 | SEQ ID NO. 1452 |
| (N20)NGG | 19 | 17942082 | - | CTCCACGAGGATGTTTCGGGCGG | 1 | 2 | 14 | SEQ ID NO. 1453 |
| (N20)NGG | 19 | 17942085 | - | GCTCTCCACGAGGATGTTTCGGG | 1 | 1 | 17 | SEQ ID NO. 1454 |
| (N20)NGG | 19 | 17942086 | - | CGCTCTCCACGAGGATGTTTCGG | 1 | 1 | 7 | SEQ ID NO. 1455 |
| (N20)NGG | 19 | 17942095 | - | CGTGTGCCTGCTCTCCACGAGG | 1 | 1 | 13 | SEQ ID NO. 1456 |
| (N20)NGG | 19 | 17942137 | - | CAAGCGGCAGCAGCTTAGCTAGG | 1 | 1 | 32 | SEQ ID NO. 1457 |
| (N20)NGG | 19 | 17942153 | - | ACGTAGTAGTCTTTGTCAAGCGG | | 1 | 12 | SEQ ID NO. 1458 |
| (N20)NGG | 19 | 17942179 | - | TGGGGCTTCTGCCTGGCTCGCGG | 2 | 5 | 79 | SEQ ID NO. 1459 |
| (N20)NGG | 19 | 17942186 | - | CAGAAAATGGGGCTCTGGCCTGG | 1 | 7 | 80 | SEQ ID NO. 1460 |
| (N20)NGG | 19 | 17942191 | - | CCCACCAGAAAATGGGGCTCTGG | 1 | 5 | 46 | SEQ ID NO. 1461 |
| (N20)NGG | 19 | 17942197 | - | GGGTTCCCACCAGAAAATGGGG | 1 | 2 | 32 | SEQ ID NO. 1462 |
| (N20)NGG | 19 | 17942198 | - | CGGGTTCCCACCAGAAAATGGG | 1 | 3 | 19 | SEQ ID NO. 1463 |
| (N20)NGG | 19 | 17942199 | - | GCGGGTTCCCACCAGAAAATGG | 1 | 1 | 17 | SEQ ID NO. 1464 |
| (N20)NGG | 19 | 17942482 | + | TGACAGATCTGCCTTCTCCAGG | 1 | 4 | 66 | SEQ ID NO. 1465 |
| (N20)NGG | 19 | 17942498 | + | CTCCAGGCCGCCAGAGCCTGCGG | 1 | 12 | 92 | SEQ ID NO. 1466 |
| (N20)NGG | 19 | 17942502 | + | AGGCCGCCAGAGCCTGCGGCTGG | 2 | 3 | 29 | SEQ ID NO. 1467 |
| (N20)NGG | 19 | 17942508 | + | CCAGAGCCTGCGGCTGGTCATGG | 1 | 4 | 75 | SEQ ID NO. 1468 |
| (N20)NGG | 19 | 17942524 | + | GTCATGGAGTACCTGCCCAGCGG | 1 | 4 | 41 | SEQ ID NO. 1469 |
| (N20)NGG | 19 | 17942549 | + | GCTGCGCGACTTCCTGCAGCGG | 1 | 1 | 12 | SEQ ID NO. 1470 |
| (N20)NGG | 19 | 17942607 | + | CTATTCCTCGCAGATCTGCAAGG | 1 | 2 | 14 | SEQ ID NO. 1471 |
| (N20)NGG | 19 | 17942614 | + | TCGCAGATCTGCAAGGTGCGAGG | 1 | 3 | 14 | SEQ ID NO. 1472 |
| (N20)NGG | 19 | 17942615 | + | CGCAGATCTGCAAGGTGCGAGGG | 1 | 3 | 9 | SEQ ID NO. 1473 |
| (N20)NGG | 19 | 17942616 | + | GCAGATCTGCAAGGTGCGAGGGG | 1 | 3 | 25 | SEQ ID NO. 1474 |
| (N20)NGG | 19 | 17942617 | + | CAGATCTGCAAGGTGCGAGGGGG | 1 | 2 | 28 | SEQ ID NO. 1475 |
| (N20)NGG | 19 | 17942625 | + | CAAGGTGCGAGGGGGCGCCCGG | 1 | 1 | 25 | SEQ ID NO. 1476 |
| (N20)NGG | 19 | 17942626 | + | AAGGTGCGAGGGGGCGCCCCGGG | 1 | 2 | 16 | SEQ ID NO. 1477 |
| (N20)NGG | 19 | 17942468 | - | TCTGGGCCTTGCAGAAGGCAGG | 1 | 20 | 75 | SEQ ID NO. 1478 |
| (N20)NGG | 19 | 17942472 | - | AGGCTCTGGCCTTGCAGAAGG | 1 | 10 | 74 | SEQ ID NO. 1479 |
| (N20)NGG | 19 | 17942478 | - | AGCCCAGGCTCTGGCCTTGCGG | 1 | 3 | 36 | SEQ ID NO. 1480 |
| (N20)NGG | 19 | 17942483 | - | TGACCAGCCGCCAGGCTCTGGCGG | 1 | 5 | 49 | SEQ ID NO. 1481 |
| (N20)NGG | 19 | 17942486 | - | CCATGACCAGCCCGCAGGCTCTGG | 1 | 1 | 29 | SEQ ID NO. 1482 |
| (N20)NGG | 19 | 17942492 | - | GGTACTCCATGACCAGCCGCAGG | 1 | 1 | 10 | SEQ ID NO. 1483 |

FIG. 8 cont.

| site type | site chromosome | site start nucleotide | site strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 19 | 17942513 | - | CGCGCAAGCAGCCGCTGGGCAGG | 1 | 1 | 8 | SEQ ID NO. 1484 |
| (N20)NGG | 19 | 17942517 | - | AAGTCGCGCAAGCAGCCGCTGGG | 1 | 1 | 3 | SEQ ID NO. 1485 |
| (N20)NGG | 19 | 17942518 | - | GAAGTCGCGCAAGCAGCCGCTGG | 1 | 1 | 1 | SEQ ID NO. 1486 |
| (N20)NGG | 19 | 17942540 | - | GGCGCGGCGGGTGCCCGCTGCAGG | 1 | 2 | 38 | SEQ ID NO. 1487 |
| (N20)NGG | 19 | 17942552 | - | GGCTGGCATCGAGGCGCGCGCGG | 1 | 4 | 15 | SEQ ID NO. 1488 |
| (N20)NGG | 19 | 17942561 | - | GAAGGAGGCGGCTGGCATCGAGG | 1 | 2 | 28 | SEQ ID NO. 1489 |
| (N20)NGG | 19 | 17942569 | - | GGAATAGAGAAGGAGGCGGCTGG | 1 | 5 | 66 | SEQ ID NO. 1490 |
| (N20)NGG | 19 | 17942573 | - | GCCGAGGAATAGAGAAGGAGGCGG | 1 | 9 | 243 | SEQ ID NO. 1491 |
| (N20)NGG | 19 | 17942576 | - | TCTGCGAGGAATAGAGAAGGAGG | 1 | 4 | 45 | SEQ ID NO. 1492 |
| (N20)NGG | 19 | 17942579 | - | AGATCTGCGAGGAATAGAGAAGG | 1 | 6 | 38 | SEQ ID NO. 1493 |
| (N20)NGG | 19 | 17942590 | - | TCGCACCTTGCAGATCTGCGAGG | 1 | 1 | 11 | SEQ ID NO. 1494 |
| (N20)NGG | 19 | 17943327 | + | CATCAGTCCCGCTATCCCCCAGG | 1 | 1 | 10 | SEQ ID NO. 1495 |
| (N20)NGG | 19 | 17943328 | + | ATCAGTCCCGCTATCCCCCAGGG | 1 | 1 | 14 | SEQ ID NO. 1496 |
| (N20)NGG | 19 | 17943337 | + | GCTATCCCCCAGGGCAACTTTGG | 1 | 1 | 20 | SEQ ID NO. 1497 |
| (N20)NGG | 19 | 17943345 | + | CCAGGCAACTTTGGCAGCGTGG | 1 | 2 | 17 | SEQ ID NO. 1498 |
| (N20)NGG | 19 | 17943370 | + | CTGTGCCGCTATGACCCGCTAGG | 1 | 1 | 6 | SEQ ID NO. 1499 |
| (N20)NGG | 19 | 17943382 | + | GACCCGCTAGGCGACAATACAGG | 1 | 1 | 3 | SEQ ID NO. 1500 |
| (N20)NGG | 19 | 17943390 | + | AGGCGACAATACAGTGCCCTGG | 1 | 2 | 10 | SEQ ID NO. 1501 |
| (N20)NGG | 19 | 17943393 | + | CGACAATACAGGTGCCCTGGTGG | 1 | 2 | 12 | SEQ ID NO. 1502 |
| (N20)NGG | 19 | 17943418 | + | GTGAAACAGCTGCACCACAGCGG | 2 | 3 | 70 | SEQ ID NO. 1503 |
| (N20)NGG | 19 | 17943419 | + | TGAAACAGCTGCACCACAGCGGG | 2 | 4 | 97 | SEQ ID NO. 1504 |
| (N20)NGG | 19 | 17943434 | - | ACAGCGGGCCAGACCAGCAGAGG | 1 | 1 | 33 | SEQ ID NO. 1505 |
| (N20)NGG | 19 | 17943435 | - | CAGCGGGCCAGACCAGCAGAGGG | 1 | 3 | 30 | SEQ ID NO. 1506 |
| (N20)NGG | 19 | 17943446 | + | ACCAGCAGAGGGACTTTCAGCGG | 1 | 5 | 71 | SEQ ID NO. 1507 |
| (N20)NGG | 19 | 17943447 | + | CCAGCAGAGGGACTTTCAGCGGG | 1 | 5 | 65 | SEQ ID NO. 1508 |
| (N20)NGG | 19 | 17943499 | + | GATTTCATTGTCAAGTATCGTGG | 1 | 2 | 15 | SEQ ID NO. 1509 |
| (N20)NGG | 19 | 17943511 | + | AAGTATCGTGGTGTCAGCTATGG | 1 | 1 | 20 | SEQ ID NO. 1510 |
| (N20)NGG | 19 | 17943516 | + | TCGTGTGTCAGCTATGGCCCGG | 1 | 3 | 19 | SEQ ID NO. 1511 |
| (N20)NGG | 19 | 17943517 | + | CGTGGTGTCAGCTATGGCCCGGG | 2 | 11 | 26 | SEQ ID NO. 1512 |
| (N20)NGG | 19 | 17943532 | + | GGCCCGGTGAGCCAGCTCCCGG | 1 | 2 | 50 | SEQ ID NO. 1513 |
| (N20)NGG | 19 | 17943312 | - | AAGTTGCCCTGGGGATAGCGGG | 1 | 1 | 16 | SEQ ID NO. 1514 |
| (N20)NGG | 19 | 17943313 | - | AAAGTTGCCCTGGGGATAGCGG | 1 | 3 | 37 | SEQ ID NO. 1515 |
| (N20)NGG | 19 | 17943320 | - | CGCTGCCAAAGTTGCCCTGGGGG | 1 | 1 | 18 | SEQ ID NO. 1516 |

FIG. 8 cont.

| site_type | site_chr omosome | site_start_ nucleotide | site_s trand | target_site_sequence_with_NGG | genome_wide_hits_with_1_or_less_mism atches | genome_wide_hits_with_2_or_less_mism atches | genome_wide_hits_with_3_or_less_mism atches | |
|---|---|---|---|---|---|---|---|---|
| (N20)NGG | 19 | 17943321 | - | ACGCTGCCAAAGTTGCCCTGGGG | 1 | 2 | 22 | SEQ ID NO. 1517 |
| (N20)NGG | 19 | 17943322 | - | CCAGCTGCCAAAGTTGCCCTGGG | 1 | 1 | 13 | SEQ ID NO. 1518 |
| (N20)NGG | 19 | 17943323 | - | CCACGCTGCCAAAGTTGCCCTGG | 1 | 2 | 18 | SEQ ID NO. 1519 |
| (N20)NGG | 19 | 17943353 | - | TGTCGCCTAGCGGGTCATAGCGG | 1 | 1 | 4 | SEQ ID NO. 1520 |
| (N20)NGG | 19 | 17943362 | - | CACCTGTATTGTCGCCTAGCGGG | 1 | 1 | 5 | SEQ ID NO. 1521 |
| (N20)NGG | 19 | 17943363 | - | GCACCTGTATTGTCGCCTAGCGG | 1 | 1 | 5 | SEQ ID NO. 1522 |
| (N20)NGG | 19 | 17943385 | - | CAGCTGTTTCACGGCCACCAGGG | 1 | 3 | 21 | SEQ ID NO. 1523 |
| (N20)NGG | 19 | 17943386 | - | GCAGCTGTTTCACGGCCACCAGG | 1 | 3 | 17 | SEQ ID NO. 1524 |
| (N20)NGG | 19 | 17943394 | - | GCTGTGCTGCAGCTGTTTCACGG | 2 | 3 | 57 | SEQ ID NO. 1525 |
| (N20)NGG | 19 | 17943420 | - | TGAAAGTCCCTCTGCTGGTCTGG | 1 | 4 | 42 | SEQ ID NO. 1526 |
| (N20)NGG | 19 | 17943425 | - | CCCGCTGAAAGTCCCTCTGCTGG | 1 | 2 | 15 | SEQ ID NO. 1527 |
| (N20)NGG | 19 | 17943458 | - | AATCACTGTGCAGTGCTTTGAGG | 1 | 1 | 73 | SEQ ID NO. 1528 |
| (N20)NGG | 19 | 17943512 | - | ATCCGGGAGCTGGCTCACCCGGG | 1 | 2 | 19 | SEQ ID NO. 1529 |
| (N20)NGG | 19 | 17943513 | - | CATCCGGGAGCTGGCTCACCCGG | 1 | 3 | 24 | SEQ ID NO. 1530 |
| (N20)NGG | 19 | 17943628 | + | CTCCTCTCAGACCCACACCTGG | 3 | 14 | 136 | SEQ ID NO. 1531 |
| (N20)NGG | 19 | 17943636 | + | GACCCCACACCTGGTGCCCTGG | 2 | 7 | 51 | SEQ ID NO. 1532 |
| (N20)NGG | 19 | 17943649 | + | GGTGCCCTGGCACCTCGTGATGG | 1 | 1 | 17 | SEQ ID NO. 1533 |
| (N20)NGG | 19 | 17943650 | + | GTGCCCTGGCACCTCGTGATGGG | 1 | 2 | 9 | SEQ ID NO. 1534 |
| (N20)NGG | 19 | 17943656 | + | TGGCACCTCGTGATGGCTGTGG | 1 | 1 | 27 | SEQ ID NO. 1535 |
| (N20)NGG | 19 | 17943661 | + | CCTCGTGATGGCGTGTGGAATGG | 2 | 4 | 24 | SEQ ID NO. 1536 |
| (N20)NGG | 19 | 17943702 | + | CCAAGACCCCACGATCTTCGAGG | 1 | 1 | 5 | SEQ ID NO. 1537 |
| (N20)NGG | 19 | 17943732 | + | CCTCAAGTACATCTCACAGCTGG | 1 | 3 | 38 | SEQ ID NO. 1538 |
| (N20)NGG | 19 | 17943733 | + | CTCAAGTACATCTCACAGCTGGG | 1 | 3 | 43 | SEQ ID NO. 1539 |
| (N20)NGG | 19 | 17943738 | + | GTACATCTCACAGCTGGGCAAGG | 1 | 2 | 51 | SEQ ID NO. 1540 |
| (N20)NGG | 19 | 17943743 | + | TCTCACAGCTGGGCAAGGTAAGG | 1 | 5 | 66 | SEQ ID NO. 1541 |
| (N20)NGG | 19 | 17943746 | + | CACAGCTGGGCAAGGTAAGGTGG | 2 | 7 | 85 | SEQ ID NO. 1542 |
| (N20)NGG | 19 | 17943747 | + | ACAGCTGGGCAAGGTAAGGTGGG | 1 | 2 | 45 | SEQ ID NO. 1543 |
| (N20)NGG | 19 | 17943751 | + | CTGGGCAAGGTAAGGTGGGCAGG | 1 | 4 | 67 | SEQ ID NO. 1544 |
| (N20)NGG | 19 | 17943752 | + | TGGGCAAGGTAAGGTGGGCAGGG | 1 | 5 | 107 | SEQ ID NO. 1545 |
| (N20)NGG | 19 | 17943757 | + | AAGGTAAGGTGGGCAGGGCCAGG | 2 | 9 | 141 | SEQ ID NO. 1546 |
| (N20)NGG | 19 | 17943758 | + | AGGTAAGGTGGGCAGGGCCAGGG | 3 | 15 | 128 | SEQ ID NO. 1547 |
| (N20)NGG | 19 | 17943761 | + | TAAGGTGGGCAGGGCCAGGGTGG | 1 | 11 | 220 | SEQ ID NO. 1548 |
| (N20)NGG | 19 | 17943762 | + | AAGGTGGGCAGGGCCAGGGTGGG | 2 | 25 | 282 | SEQ ID NO. 1549 |

FIG. 8 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | | |
|---|---|---|---|---|---|---|---|---|---|
| (N20)NGG | 19 | 17943574 | - | TGGGGTGGGGCATGGGCAGTGG | | 6 | 54 | 656 | SEQ ID NO. 1550 |
| (N20)NGG | 19 | 17943580 | - | ATAGTCTGGGTGGGGGCATGG | | 1 | 5 | 88 | SEQ ID NO. 1551 |
| (N20)NGG | 19 | 17943581 | - | CATAGTCTGGGTGGGGCATGG | | 1 | 10 | 133 | SEQ ID NO. 1552 |
| (N20)NGG | 19 | 17943586 | - | GAGCTCATAGTCTGGGTGGGG | | 3 | 10 | 112 | SEQ ID NO. 1553 |
| (N20)NGG | 19 | 17943587 | - | GGAGCTCATAGTCTGGGGTGG | | 2 | 12 | 80 | SEQ ID NO. 1554 |
| (N20)NGG | 19 | 17943588 | - | AGGAGCTCATAGTCTGGGGTGG | | 1 | 13 | 121 | SEQ ID NO. 1555 |
| (N20)NGG | 19 | 17943589 | - | GAGGAGCTCATAGTCTGGGGTG | | 1 | 14 | 149 | SEQ ID NO. 1556 |
| (N20)NGG | 19 | 17943592 | - | TGAGAGGAGCTCATAGTCTGG | | 1 | 3 | 54 | SEQ ID NO. 1557 |
| (N20)NGG | 19 | 17943593 | - | CTGAGAGGAGCTCATAGTCTGG | | 1 | 4 | 51 | SEQ ID NO. 1558 |
| (N20)NGG | 19 | 17943594 | - | TCTGAGAGGAGCTCATAGTCTG | | 1 | 5 | 48 | SEQ ID NO. 1559 |
| (N20)NGG | 19 | 17943608 | - | CACCAGGTGTGGGTCTTGAGAGG | | 1 | 6 | 70 | SEQ ID NO. 1560 |
| (N20)NGG | 19 | 17943617 | - | GTGCCAGGGCACCAGGTGTGGG | | 4 | 14 | 64 | SEQ ID NO. 1561 |
| (N20)NGG | 19 | 17943618 | - | GGTGCCAGGGCACCAGGTGTGG | | 3 | 11 | 64 | SEQ ID NO. 1562 |
| (N20)NGG | 19 | 17943619 | - | AGGTGCCAGGGCACCAGGTGTG | | 2 | 6 | 82 | SEQ ID NO. 1563 |
| (N20)NGG | 19 | 17943624 | - | TCACGAGGTGCCAGGGCACCAGG | | 1 | 1 | 23 | SEQ ID NO. 1564 |
| (N20)NGG | 19 | 17943631 | - | CAGCCCATCACGAGGTGCCAGG | | 1 | 2 | 21 | SEQ ID NO. 1565 |
| (N20)NGG | 19 | 17943632 | - | ACAGCCCATCACGAGGTGCCAG | | 1 | 3 | 11 | SEQ ID NO. 1566 |
| (N20)NGG | 19 | 17943639 | - | CCATTCCACAGCCCATCACGAGG | | 2 | 3 | 24 | SEQ ID NO. 1567 |
| (N20)NGG | 19 | 17943664 | - | GTCTTGGCAGCATAGAGCTGG | | 1 | 3 | 36 | SEQ ID NO. 1568 |
| (N20)NGG | 19 | 17943665 | - | GGTCTTGGCAGCATAGAGCTG | | 2 | 5 | 53 | SEQ ID NO. 1569 |
| (N20)NGG | 19 | 17943676 | - | GAAGATCGTGGGTCTTGGCAGG | | 1 | 2 | 24 | SEQ ID NO. 1570 |
| (N20)NGG | 19 | 17943680 | - | CCTCGAAGATCGTGGGTCTTGG | | 1 | 1 | 7 | SEQ ID NO. 1571 |
| (N20)NGG | 19 | 17943686 | - | GTCTCTCCTCGAAGATCGTGGG | | 1 | 2 | 5 | SEQ ID NO. 1572 |
| (N20)NGG | 19 | 17943687 | - | TGTCTCTCCTCGAAGATCGTGG | | 1 | 1 | 6 | SEQ ID NO. 1573 |
| (N20)NGG | 19 | 17943688 | - | GTGTCTCTCCTCGAAGATCGTGG | | 1 | 2 | 7 | SEQ ID NO. 1574 |
| (N20)NGG | 19 | 17943710 | - | CCAGCTGTGAGATGTACTTGAGG | | 1 | 2 | 37 | SEQ ID NO. 1575 |
| (N20)NGG | 19 | 17945397 | + | TCAGAAACTCCAATTTTATGAGG | | 1 | 7 | 86 | SEQ ID NO. 1576 |
| (N20)NGG | 19 | 17945402 | + | AACTCCAATTTTATGAGGACCGG | | 1 | 3 | 40 | SEQ ID NO. 1577 |
| (N20)NGG | 19 | 17945415 | + | TGAGGACCGGCAGCAGTGCCGG | | 1 | 6 | 66 | SEQ ID NO. 1578 |
| (N20)NGG | 19 | 17945426 | + | AGCAGTGCCGGCCCCCAAGTGG | | 1 | 1 | 43 | SEQ ID NO. 1579 |
| (N20)NGG | 19 | 17945436 | + | GGCCCCAAGTGACAGAGCTGG | | 1 | 4 | 67 | SEQ ID NO. 1580 |
| (N20)NGG | 19 | 17945460 | + | CCTGCTGATTCAACAGTGCATGG | | 1 | 3 | 37 | SEQ ID NO. 1581 |
| (N20)NGG | 19 | 17945472 | + | ACAGTGCATGGCCTATGAGCCGG | | 1 | 2 | 32 | SEQ ID NO. 1582 |

FIG. 8 cont.

| site_type | site_chr omosome | site_start_ nucleotide | site_s trand | target_site_sequence_wit h_NGG | genome_wide_ hits_with_1_ or_less_mism atches | genome_wide_ hits_with_ 2_or_less_m ismatches | genome_wide_ hits_with_3_ or_less_mism atches | |
|---|---|---|---|---|---|---|---|---|
| (N20)NGG | 19 | 17945480 | + | TGGCCTATGAGCCGGTCCAGAGG | | 1 | 2 | 15 SEQ ID NO. 1583 |
| (N20)NGG | 19 | 17945530 | + | CTCAATAGCCTCATCTCTTCAGG | | 1 | 2 | 45 SEQ ID NO. 1584 |
| (N20)NGG | 19 | 17945540 | + | TCATCTCTTCAGGTGCCCGCTGG | | 1 | 2 | 16 SEQ ID NO. 1585 |
| (N20)NGG | 19 | 17945541 | + | CATCTCTTCAGTGCCCGCTGG | | 2 | 2 | 25 SEQ ID NO. 1586 |
| (N20)NGG | 19 | 17945545 | + | TCTTCAGGTGCCCGCTGGGACGG | | 2 | 2 | 27 SEQ ID NO. 1587 |
| (N20)NGG | 19 | 17945546 | + | CTTCAGGTGCCCGCTGGGACGGG | | 1 | 3 | 24 SEQ ID NO. 1588 |
| (N20)NGG | 19 | 17945550 | + | AGGTGCCCGCTGGGACGGGTTCG | | 1 | 2 | 12 SEQ ID NO. 1589 |
| (N20)NGG | 19 | 17945551 | + | GGTGCCCGCTGGGACGGGTTGGG | | 1 | 2 | 18 SEQ ID NO. 1590 |
| (N20)NGG | 19 | 17945554 | + | GCCCGCTGGGACGGGTTGGGTGG | | 1 | 1 | 22 SEQ ID NO. 1591 |
| (N20)NGG | 19 | 17945356 | - | CTGAGGGTGAGAGGAGCAGTCGG | | 1 | 6 | 131 SEQ ID NO. 1592 |
| (N20)NGG | 19 | 17945365 | - | TTGGAGTTTCTGAGGGTGAGAGG | | 1 | 10 | 100 SEQ ID NO. 1593 |
| (N20)NGG | 19 | 17945372 | - | CATAAAATTGGAGTTTCTGAGGG | | 1 | 8 | 117 SEQ ID NO. 1594 |
| (N20)NGG | 19 | 17945373 | - | TCATAAAATTGGAGTTTCTGAGG | | 1 | 10 | 88 SEQ ID NO. 1595 |
| (N20)NGG | 19 | 17945384 | - | GCTGCCGGTCCTCATAAAATTGG | | 1 | 2 | 12 SEQ ID NO. 1596 |
| (N20)NGG | 19 | 17945399 | - | TGGGGGCCGGCAGCTGCTGCCGG | | 1 | 8 | 83 SEQ ID NO. 1597 |
| (N20)NGG | 19 | 17945412 | - | AGCTCTGTCCACTTGGGGGCCGG | | 1 | 4 | 66 SEQ ID NO. 1598 |
| (N20)NGG | 19 | 17945416 | - | GGCCAGCTCTGTCCACTTGGGGG | | 1 | 11 | 71 SEQ ID NO. 1599 |
| (N20)NGG | 19 | 17945417 | - | GGGCCAGCTCTGTCCACTTGGGG | | 1 | 5 | 58 SEQ ID NO. 1600 |
| (N20)NGG | 19 | 17945418 | - | AGGGCCAGCTCTGTCCACTTGGG | | 1 | 7 | 74 SEQ ID NO. 1601 |
| (N20)NGG | 19 | 17945419 | - | CAGGGCCAGCTCTGTCCACTTGG | | 2 | 7 | 118 SEQ ID NO. 1602 |
| (N20)NGG | 19 | 17945437 | - | CATGCACTGTTGAATCAGCAGGG | | 1 | 3 | 32 SEQ ID NO. 1603 |
| (N20)NGG | 19 | 17945438 | - | CCATGCACTGTTGAATCAGCAGG | | 2 | 2 | 27 SEQ ID NO. 1604 |
| (N20)NGG | 19 | 17945461 | - | GGGCCTCTGGACCGGCTCATAGG | | 1 | 2 | 19 SEQ ID NO. 1605 |
| (N20)NGG | 19 | 17945469 | - | CGGAAGGAGGGCCTCTGGACCGG | | 1 | 2 | 23 SEQ ID NO. 1606 |
| (N20)NGG | 19 | 17945474 | - | CCGCTCGGAAGGAGGGCCTCTGG | | 1 | 2 | 12 SEQ ID NO. 1607 |
| (N20)NGG | 19 | 17945481 | - | CGAATGACGGCTCGGAAGGAGGG | | 1 | 1 | 4 SEQ ID NO. 1608 |
| (N20)NGG | 19 | 17945482 | - | ACGAATGACGGCTCGGAAGGAGG | | 1 | 1 | 4 SEQ ID NO. 1609 |
| (N20)NGG | 19 | 17945485 | - | GTCACGAATGACGGCTCGGAAGG | | 1 | 1 | 1 SEQ ID NO. 1610 |
| (N20)NGG | 19 | 17945489 | - | TGAGGTCACGAATGACGGCTCGG | | 1 | 1 | 9 SEQ ID NO. 1611 |
| (N20)NGG | 19 | 17945494 | - | GCTATTGAGGTCACGAATGACGG | | 1 | 1 | 15 SEQ ID NO. 1612 |
| (N20)NGG | 19 | 17945507 | - | CTGAAGAGATGAGGCTATTGAGG | | 1 | 3 | 54 SEQ ID NO. 1613 |
| (N20)NGG | 19 | 17945516 | - | AGCGGGCACCTGAAGAGATGAGG | | 1 | 3 | 26 SEQ ID NO. 1614 |
| (N20)NGG | 19 | 17945673 | + | TTCCCTCAGTGCTCACCGACAGG | | 1 | 1 | 25 SEQ ID NO. 1615 |

FIG. 8 cont.

| site_type | site_chr omosome | site_start_ nucleotide | site_s trand | target_site_sequence_with_NGG | genome_wide_ hits_with_1_ or_less_mism atches | genome_wide_ hits_with_ 2_or_less_m ismatches | genome_wide_ hits_with_3_ or_less_mism atches | |
|---|---|---|---|---|---|---|---|---|
| (N20)NGG | 19 | 17945682 | + | TGCTCACCGACAGGATCCCCTGG | 1 | 2 | 14 | SEQ ID NO. 1616 |
| (N20)NGG | 19 | 17945683 | + | GCTCACCGACAGGATCCCCTGGG | 1 | 2 | 12 | SEQ ID NO. 1617 |
| (N20)NGG | 19 | 17945686 | + | CACCGACAGGATCCCCTGGGTGG | 1 | 2 | 16 | SEQ ID NO. 1618 |
| (N20)NGG | 19 | 17945703 | + | GGGTGGCCCCGAGTGTCTCCGG | 1 | 1 | 13 | SEQ ID NO. 1619 |
| (N20)NGG | 19 | 17945704 | + | GGTGGCCCCGAGTGTCTCCGGG | 1 | 2 | 27 | SEQ ID NO. 1620 |
| (N20)NGG | 19 | 17945707 | + | GGCCCCGAGTGTCTCCGGGAGG | 1 | 2 | 24 | SEQ ID NO. 1621 |
| (N20)NGG | 19 | 17945725 | + | GGAGGCGCAGACACTTAGCTTGG | 1 | 1 | 9 | SEQ ID NO. 1622 |
| (N20)NGG | 19 | 17945739 | + | TTAGCTTGGAAGCTGACAAGTGG | 1 | 2 | 29 | SEQ ID NO. 1623 |
| (N20)NGG | 19 | 17945740 | + | TAGCTTGGAAGCTGACAAGTGGG | 1 | 5 | 33 | SEQ ID NO. 1624 |
| (N20)NGG | 19 | 17945741 | + | AGCTTGGAAGCTGACAAGTGGGG | 1 | 3 | 47 | SEQ ID NO. 1625 |
| (N20)NGG | 19 | 17945747 | + | GAAGCTGACAAGTGGGGCTTCGG | 1 | 2 | 38 | SEQ ID NO. 1626 |
| (N20)NGG | 19 | 17945755 | + | CAAGTGGGGCTTCGCGCCACGG | 1 | 1 | 8 | SEQ ID NO. 1627 |
| (N20)NGG | 19 | 17945760 | + | GGGGCTTCGCGCCACGGTCTGG | 1 | 1 | 9 | SEQ ID NO. 1628 |
| (N20)NGG | 19 | 17945761 | + | GGGCTTCGCGCCACGGTCTGGG | 1 | 1 | 8 | SEQ ID NO. 1629 |
| (N20)NGG | 19 | 17945774 | + | ACGGTCTGGGAAGTGTTTAGTGG | 1 | 1 | 16 | SEQ ID NO. 1630 |
| (N20)NGG | 19 | 17945800 | + | CACCATGCCCATCAGTGCCCTGG | 1 | 8 | 63 | SEQ ID NO. 1631 |
| (N20)NGG | 19 | 17945812 | + | CAGTGCCCTGGATCCTGCTAAGG | 1 | 4 | 51 | SEQ ID NO. 1632 |
| (N20)NGG | 19 | 17945830 | + | TAAGGTCAGAGCCCCTCACCCGG | 1 | 2 | 38 | SEQ ID NO. 1633 |
| (N20)NGG | 19 | 17945836 | + | CAGAGCCCCTCACCCGGCATCGG | 1 | 3 | 43 | SEQ ID NO. 1634 |
| (N20)NGG | 19 | 17945635 | - | CAGGGAATGAAAGTGGGATCAGG | 1 | 7 | 74 | SEQ ID NO. 1635 |
| (N20)NGG | 19 | 17945641 | - | AGCACTGAGGGAATGAAAGTGGG | 1 | 8 | 86 | SEQ ID NO. 1636 |
| (N20)NGG | 19 | 17945642 | - | GAGCACTGAGGGAATGAAAGTGG | 1 | 8 | 106 | SEQ ID NO. 1637 |
| (N20)NGG | 19 | 17945653 | - | ATCCTGTCGGTGAGCACTGAGG | 1 | 1 | 16 | SEQ ID NO. 1638 |
| (N20)NGG | 19 | 17945654 | - | GATCCTGTCGGTGAGCACTGAGG | 1 | 2 | 15 | SEQ ID NO. 1639 |
| (N20)NGG | 19 | 17945666 | - | GGCCACCCAGGGGATCCTGTCGG | 1 | 2 | 36 | SEQ ID NO. 1640 |
| (N20)NGG | 19 | 17945676 | - | GACACTGGGGGCCACCCAGGGG | 1 | 2 | 18 | SEQ ID NO. 1641 |
| (N20)NGG | 19 | 17945677 | - | AGACACTGGGGGCCACCCAGG | 1 | 1 | 25 | SEQ ID NO. 1642 |
| (N20)NGG | 19 | 17945678 | - | GAGACACTGGGGGCCACCAGG | 1 | 1 | 16 | SEQ ID NO. 1643 |
| (N20)NGG | 19 | 17945687 | - | CGCCTCCCGAGACACTCGGGG | 1 | 2 | 11 | SEQ ID NO. 1644 |
| (N20)NGG | 19 | 17945688 | - | GCGCCTCCCGAGACACTCGGGG | 1 | 2 | 13 | SEQ ID NO. 1645 |
| (N20)NGG | 19 | 17945689 | - | TGCGCCTCCCGAGACACTCGG | 1 | 1 | 14 | SEQ ID NO. 1646 |
| (N20)NGG | 19 | 17945690 | - | CTGCGCCTCCCGAGACACTCGG | 1 | 2 | 32 | SEQ ID NO. 1647 |
| (N20)NGG | 19 | 17945700 | - | AGCTAAGTGTCTGCGCCTCCCGG | 1 | 1 | 11 | SEQ ID NO. 1648 |

FIG. 8 cont.

| site_type | site_chromosome | site_start_nucleotide | site_strand | target_site_sequence with h NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 19 | 17945750 | - | ACTAAACACTTCCAGACCGTGG | 1 | | 2 | 14 SEQ ID NO. 1649 |
| (N20)NGG | 19 | 17945780 | - | ATCCAGGGCACTGATGGGCATGG | 1 | | 5 | 64 SEQ ID NO. 1650 |
| (N20)NGG | 19 | 17945785 | - | GCAGGATCCAGGGCACTGATGGG | 2 | | 7 | 75 SEQ ID NO. 1651 |
| (N20)NGG | 19 | 17945786 | - | AGCAGGATCCAGGGCACTGATGG | 1 | | 10 | 73 SEQ ID NO. 1652 |
| (N20)NGG | 19 | 17945795 | - | TCTGACCTTAGCAGGATCCAGGG | | 1 | | 26 SEQ ID NO. 1653 |
| (N20)NGG | 19 | 17945796 | - | CTCTGACCTTAGCAGGATCCAGG | 1 | | 2 | 25 SEQ ID NO. 1654 |
| (N20)NGG | 19 | 17945803 | - | TGAGGGGCTCTGACCTTAGCAGG | | | 3 | 36 SEQ ID NO. 1655 |
| (N20)NGG | 19 | 17945891 | + | TTCCTGTGTCTGGCCCCCTTAGG | 1 | | 6 | 38 SEQ ID NO. 1656 |
| (N20)NGG | 19 | 17945894 | + | CTGTGTCTGGCCCCCTTAGGAGG | 1 | | 2 | 37 SEQ ID NO. 1657 |
| (N20)NGG | 19 | 17945901 | + | TGGCCCCCTTAGGAGGACAAAGG | 1 | | 1 | 26 SEQ ID NO. 1658 |
| (N20)NGG | 19 | 17945913 | + | GAGGACAAAGGCTCTGCCCCATGG | 1 | | 1 | 82 SEQ ID NO. 1659 |
| (N20)NGG | 19 | 17945929 | + | CCCATGCAATGTCTCTGCCCGG | 1 | | 4 | 46 SEQ ID NO. 1660 |
| (N20)NGG | 19 | 17945933 | + | TGGCAATGTCTCTGCCCGGAAGG | 1 | | 3 | 31 SEQ ID NO. 1661 |
| (N20)NGG | 19 | 17945942 | + | CTCTGCCCGGAAGGTGCTCCTGG | 3 | | 3 | 60 SEQ ID NO. 1662 |
| (N20)NGG | 19 | 17945947 | + | CCCGGAAGGTGCTCCTGGCTCGG | 1 | | 4 | 52 SEQ ID NO. 1663 |
| (N20)NGG | 19 | 17945948 | + | CCGGAAGGTGCTCCTGGCTCGGG | 1 | | 3 | 33 SEQ ID NO. 1664 |
| (N20)NGG | 19 | 17945951 | + | GAAGGTGCTCCTGGCTCGGGAGG | 1 | | 2 | 38 SEQ ID NO. 1665 |
| (N20)NGG | 19 | 17945952 | + | AAGGTGCTCCTGGCTCGGGAGGG | 1 | | 2 | 32 SEQ ID NO. 1666 |
| (N20)NGG | 19 | 17945953 | + | AGGTGCTCCTGGCTCGGGAGGGG | 1 | | 2 | 58 SEQ ID NO. 1667 |
| (N20)NGG | 19 | 17945954 | + | GGTGCTCCTGGCTCGGGAGGGGG | 1 | | 4 | 61 SEQ ID NO. 1668 |
| (N20)NGG | 19 | 17945961 | + | CTGGCTCGGGAGGGGGCTGATGG | 1 | | 6 | 71 SEQ ID NO. 1669 |
| (N20)NGG | 19 | 17945962 | + | TGGCTCGGGAGGGGGCTGATGGG | 3 | | 2 | 41 SEQ ID NO. 1670 |
| (N20)NGG | 19 | 17945994 | + | TTCATCAAGCTGAGTGACCCTGG | 1 | | 5 | 37 SEQ ID NO. 1671 |
| (N20)NGG | 19 | 17945995 | + | TCATCAAGCTGAGTGACCCTGGG | 1 | | 4 | 59 SEQ ID NO. 1672 |
| (N20)NGG | 19 | 17945996 | + | CATCAAGCTGAGTGACCCTGGGG | 1 | | 8 | 61 SEQ ID NO. 1673 |
| (N20)NGG | 19 | 17946020 | + | CAGCCCGCTGTGTTAAGCCTGG | 1 | | 1 | 11 SEQ ID NO. 1674 |
| (N20)NGG | 19 | 17946035 | + | AAGCCTGGAGAGTAAGTTCCTGG | 1 | | 2 | 32 SEQ ID NO. 1675 |
| (N20)NGG | 19 | 17946038 | + | CCTGGAGAGTAAGTTCCTGGAGG | 2 | | 9 | 56 SEQ ID NO. 1676 |
| (N20)NGG | 19 | 17946041 | + | GGAGAGTAAGTTCCTGGAGGTGG | 1 | | 7 | 79 SEQ ID NO. 1677 |
| (N20)NGG | 19 | 17946044 | + | GAGTAAGTTCCTGGAGGTGGAGG | 3 | | 4 | 90 SEQ ID NO. 1678 |
| (N20)NGG | 19 | 17946047 | + | TAAGTTCCTGGAGGTGGAGGAGG | 1 | | 9 | 103 SEQ ID NO. 1679 |
| (N20)NGG | 19 | 17946048 | + | AAGTTCCTGGAGGTGGAGGAGGG | 2 | | 10 | 150 SEQ ID NO. 1680 |
| (N20)NGG | 19 | 17945871 | - | CTCCTAAGGGGCCAGACACAGG | 1 | | 1 | 23 SEQ ID NO. 1681 |

FIG. 8 cont.

| site_type | site_chr omosome | site_start_ nucleotide | site_s trand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 19 | 17945882 | - | AGGCCTTGTCTCCTAAGGGG | | 1 | 5 | 27 SEQ ID NO. 1682 |
| (N20)NGG | 19 | 17945883 | - | CAGGCCTTTGTCTCCTAAGGGG | | 1 | 4 | 42 SEQ ID NO. 1683 |
| (N20)NGG | 19 | 17945884 | - | GCAGGCCTTTGTCCTCCTAAGG | | 1 | 3 | 34 SEQ ID NO. 1684 |
| (N20)NGG | 19 | 17945885 | - | GGCAGGCCTTTGTCCTCCTAAGG | | 1 | 1 | 35 SEQ ID NO. 1685 |
| (N20)NGG | 19 | 17945902 | - | CAGAGACATTGCCATGGGCAGG | | 1 | 2 | 74 SEQ ID NO. 1686 |
| (N20)NGG | 19 | 17945906 | - | CGGGCAGAGACATTGCCATGGG | | 1 | 1 | 22 SEQ ID NO. 1687 |
| (N20)NGG | 19 | 17945907 | - | CCGGGCAGAGACATTGCCATGG | | 1 | 1 | 13 SEQ ID NO. 1688 |
| (N20)NGG | 19 | 17945908 | - | TCCGGGCAGAGACATTGCCATGG | | 2 | 3 | 22 SEQ ID NO. 1689 |
| (N20)NGG | 19 | 17945925 | - | CCGAGCCAGGAGCACCTTCCGG | | 2 | 3 | 29 SEQ ID NO. 1690 |
| (N20)NGG | 19 | 17945926 | - | CCCGAGCCAGGAGCACCTTCGG | | 1 | 3 | 26 SEQ ID NO. 1691 |
| (N20)NGG | 19 | 17945938 | - | CATCAGCCCCCTCCCGAGCCAGG | | 1 | 5 | 56 SEQ ID NO. 1692 |
| (N20)NGG | 19 | 17945965 | - | CACTCAGCTTGATGAAGGGCGG | | 1 | 4 | 36 SEQ ID NO. 1693 |
| (N20)NGG | 19 | 17945966 | - | TCACTCAGCTTGATGAAGGGCGG | | 1 | 3 | 36 SEQ ID NO. 1694 |
| (N20)NGG | 19 | 17945969 | - | GGGTCACTCAGCTTGATGAAGG | | 3 | 3 | 19 SEQ ID NO. 1695 |
| (N20)NGG | 19 | 17945970 | - | AGGGTCACTCAGCTTGATGAAGG | | 2 | 4 | 44 SEQ ID NO. 1696 |
| (N20)NGG | 19 | 17945989 | - | ACACAGCGGGGCTGACCCCAGG | | 1 | 2 | 31 SEQ ID NO. 1697 |
| (N20)NGG | 19 | 17945990 | - | AACACAGCGGGGCTGACCCCAGG | | 1 | 2 | 18 SEQ ID NO. 1698 |
| (N20)NGG | 19 | 17946001 | - | TCTCCAGGCTTAACACAGCGGGG | | 1 | 1 | 24 SEQ ID NO. 1699 |
| (N20)NGG | 19 | 17946002 | - | CTCTCCAGGCTTAACACAGCGGG | | 1 | 3 | 26 SEQ ID NO. 1700 |
| (N20)NGG | 19 | 17946003 | - | ACTCTCCAGGCTTAACACAGCGG | | 1 | 3 | 46 SEQ ID NO. 1701 |
| (N20)NGG | 19 | 17946016 | - | CCTCCAGGAACTTACTCTCCAGG | | 2 | 7 | 64 SEQ ID NO. 1702 |
| (N20)NGG | 19 | 17946732 | + | GCCTCTCCCTGCTGCCAACCAGG | | 1 | 8 | 88 SEQ ID NO. 1703 |
| (N20)NGG | 19 | 17946740 | + | CTGCTGCCAACCAGGCACCATGG | | 1 | 8 | 71 SEQ ID NO. 1704 |
| (N20)NGG | 19 | 17946746 | + | CCAACCAGGCACCATGGTGCAGG | | 1 | 5 | 43 SEQ ID NO. 1705 |
| (N20)NGG | 19 | 17946761 | + | GGTGCAGGAATTTGTACACCTGG | | 1 | 2 | 22 SEQ ID NO. 1706 |
| (N20)NGG | 19 | 17946762 | + | GTGCAGGAATTTGTACACCTGGG | | 1 | 1 | 28 SEQ ID NO. 1707 |
| (N20)NGG | 19 | 17946763 | + | TGCAGGAATTTGTACACCTGGGG | | 1 | 2 | 33 SEQ ID NO. 1708 |
| (N20)NGG | 19 | 17946764 | + | GCAGGAATTTGTACACCTGGGGG | | 1 | 2 | 26 SEQ ID NO. 1709 |
| (N20)NGG | 19 | 17946792 | + | GACATGTATCTGCGAAAACGTGG | | 1 | 1 | 8 SEQ ID NO. 1710 |
| (N20)NGG | 19 | 17946800 | + | TCTGCGAAAACGTGGCCACCTGG | | 1 | 1 | 9 SEQ ID NO. 1711 |
| (N20)NGG | 19 | 17946814 | + | GCCACCTGGTGCCAGCCAGCTGG | | 1 | 7 | 83 SEQ ID NO. 1712 |
| (N20)NGG | 19 | 17946824 | + | GCCAGCTGGAAGCTGCAGG | | 2 | 7 | 88 SEQ ID NO. 1713 |
| (N20)NGG | 19 | 17946827 | + | AGCCACCTGGAAGCTGCAGGTGG | | 1 | 9 | 117 SEQ ID NO. 1714 |

FIG. 8 cont.

| site type | site chromosome | site start nucleotide | site strand | target_site_sequence_with_NGG | genome_wide_hits_with_1_or_less_mismatches | genome_wide_hits_with_2_or_less_mismatches | genome_wide_hits_with_3_or_less_mismatches | | |
|---|---|---|---|---|---|---|---|---|---|
| (N20)NGG | 19 | 17946839 | + | GCTGCAGGTGGTCAAACAGCTGG | 1 | 6 | 63 | SEQ ID NO. | 1715 |
| (N20)NGG | 19 | 17946860 | + | GGCCTACGCCCTCAACTATCTGG | 1 | 1 | 4 | SEQ ID NO. | 1716 |
| (N20)NGG | 19 | 17946707 | - | GGTTGGCAGCAGGAGAGGCGGG | 1 | 17 | 229 | SEQ ID NO. | 1717 |
| (N20)NGG | 19 | 17946708 | - | TGGTTGGCAGCAGGAGAGGCGG | 1 | 27 | 393 | SEQ ID NO. | 1718 |
| (N20)NGG | 19 | 17946711 | - | GCCTGGTTGGCAGCAGGAGAGG | 1 | 14 | 135 | SEQ ID NO. | 1719 |
| (N20)NGG | 19 | 17946716 | - | ATGGTGCCTGGTTGGCAGCAGG | 1 | 2 | 48 | SEQ ID NO. | 1720 |
| (N20)NGG | 19 | 17946717 | - | CATGGTGCCTGGTTGGCAGCAG | 1 | 5 | 66 | SEQ ID NO. | 1721 |
| (N20)NGG | 19 | 17946724 | - | CCTGCACCATGGTGCCTGGTTGG | 1 | 5 | 83 | SEQ ID NO. | 1722 |
| (N20)NGG | 19 | 17946728 | - | AATTCCTGCACCATGTGCCTGG | 1 | 2 | 26 | SEQ ID NO. | 1723 |
| (N20)NGG | 19 | 17946735 | - | GTGTACAAATTCCTGCACCATGG | 1 | 1 | 32 | SEQ ID NO. | 1724 |
| (N20)NGG | 19 | 17946757 | - | GATACATGTCTATGGCCCCCAGG | 1 | 3 | 18 | SEQ ID NO. | 1725 |
| (N20)NGG | 19 | 17946765 | - | TTTTCGCAGATACATGTCTATGG | 1 | 2 | 18 | SEQ ID NO. | 1726 |
| (N20)NGG | 19 | 17946793 | - | TCCAGCTGGCTGCGCACCAGTGG | 1 | 5 | 80 | SEQ ID NO. | 1727 |
| (N20)NGG | 19 | 17946796 | - | GCTTCCAGCTGGCTGCCACCAGG | 1 | 5 | 88 | SEQ ID NO. | 1728 |
| (N20)NGG | 19 | 17946803 | - | ACCTGCAGCTTCCAGCTGGCTGG | 1 | 3 | 63 | SEQ ID NO. | 1729 |
| (N20)NGG | 19 | 17946807 | - | GACCACCTGCAGCTTCCAGCTGG | 1 | 4 | 56 | SEQ ID NO. | 1730 |
| (N20)NGG | 19 | 17946840 | - | CACCAGATAGTTGAGGGCGTAGG | 1 | 1 | 12 | SEQ ID NO. | 1731 |
| (N20)NGG | 19 | 17946846 | - | AGCACTCACCAGATAGTTGAGGG | 1 | 3 | 35 | SEQ ID NO. | 1732 |
| (N20)NGG | 19 | 17946847 | - | GAGCACTCACCAGATAGTTGAGG | 1 | 1 | 26 | SEQ ID NO. | 1733 |
| (N20)NGG | 19 | 17947946 | + | CCACCTTCCCCAGTCATTCCTGG | 1 | 9 | 117 | SEQ ID NO. | 1734 |
| (N20)NGG | 19 | 17947981 | + | TGATGAGCCAAGTGTCGTACCGG | 1 | 1 | 12 | SEQ ID NO. | 1735 |
| (N20)NGG | 19 | 17948001 | + | CGGCATCTCGTCGTCCACGG | 1 | 2 | 13 | SEQ ID NO. | 1736 |
| (N20)NGG | 19 | 17948012 | + | GCTGCTCCACGGCGTGTGCATGG | 1 | 1 | 20 | SEQ ID NO. | 1737 |
| (N20)NGG | 19 | 17948016 | + | CTCCACGGCGTGTGCATGGCTGG | 1 | 2 | 12 | SEQ ID NO. | 1738 |
| (N20)NGG | 19 | 17947918 | - | ATGACTGGGGAAGGTGGGAAGGG | 2 | 9 | 149 | SEQ ID NO. | 1739 |
| (N20)NGG | 19 | 17947919 | - | AATGACTGGGGAAGGTGGGAAGG | 1 | 9 | 154 | SEQ ID NO. | 1740 |
| (N20)NGG | 19 | 17947923 | - | CAGGAATGACTGGGGAAGGTGGG | 1 | 11 | 118 | SEQ ID NO. | 1741 |
| (N20)NGG | 19 | 17947924 | - | CCAGGAATGACTGGGGAAGGTGG | 2 | 12 | 157 | SEQ ID NO. | 1742 |
| (N20)NGG | 19 | 17947927 | - | CTTCCAGGAATGACTGGGGAAGG | 2 | 7 | 86 | SEQ ID NO. | 1743 |
| (N20)NGG | 19 | 17947931 | - | GCTGCTTCCAGGAATGACTGGGG | 1 | 10 | 75 | SEQ ID NO. | 1744 |
| (N20)NGG | 19 | 17947932 | - | CGCTGCTTCCAGGAATGACTGGG | 1 | 2 | 27 | SEQ ID NO. | 1745 |
| (N20)NGG | 19 | 17947933 | - | TCGCTGCTTCCAGGAATGACTGG | 1 | 3 | 24 | SEQ ID NO. | 1746 |
| (N20)NGG | 19 | 17947942 | - | TCATCAAGCTCGCTGCTTCCAGG | 1 | 4 | 23 | SEQ ID NO. | 1747 |

FIG. 8 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 19 | 17947966 | - | CGAGATGCCGGTACGACACTTGG | | 1 | 3 | SEQ ID NO. 1748 |
| (N20)NGG | 19 | 17947978 | - | CGTGGAGCAGCACGAGATGCCGG | 1 | 2 | 16 | SEQ ID NO. 1749 |
| (N20)NGG | 19 | 17947996 | - | CTCCAGCCATGCACACGCCGTGG | 1 | 3 | 26 | SEQ ID NO. 1750 |
| (N20)NGG | 19 | 17948752 | + | CACCATTCAGCATGAGAACCTGG | 1 | 2 | 23 | SEQ ID NO. 1751 |
| (N20)NGG | 19 | 17948753 | + | ACCATTCAGCATGAGAACCTGGG | 1 | 2 | 30 | SEQ ID NO. 1752 |
| (N20)NGG | 19 | 17948759 | + | CAGCATGAGAACCTGGGCCATGG | 1 | 4 | 58 | SEQ ID NO. 1753 |
| (N20)NGG | 19 | 17948760 | + | AGCATGAGAACCTGGGCCATGGG | 1 | 3 | 36 | SEQ ID NO. 1754 |
| (N20)NGG | 19 | 17948781 | + | GGTCCTTCACCAAGATTTACCGG | 1 | 2 | 23 | SEQ ID NO. 1755 |
| (N20)NGG | 19 | 17948782 | + | GTCCTTCACCAAGATTTACCGGG | 1 | 2 | 32 | SEQ ID NO. 1756 |
| (N20)NGG | 19 | 17948783 | + | TCCTTCACCAAGATTTACCGGGG | 1 | 1 | 16 | SEQ ID NO. 1757 |
| (N20)NGG | 19 | 17948797 | + | TTACCGGGCTGTCGCCATGAGG | 1 | 1 | 5 | SEQ ID NO. 1758 |
| (N20)NGG | 19 | 17948800 | + | CCGGGCTGTCGCCATGAGGTGG | 1 | 3 | 21 | SEQ ID NO. 1759 |
| (N20)NGG | 19 | 17948803 | + | GGGCTGTCGCCATGAGGTGGTGG | 1 | 3 | 38 | SEQ ID NO. 1760 |
| (N20)NGG | 19 | 17948807 | + | TGTCGCCATGAGGTGGTGGATGG | 1 | 1 | 19 | SEQ ID NO. 1761 |
| (N20)NGG | 19 | 17948808 | + | GTCGCCATGAGGTGGTGGATGGG | 1 | 1 | 13 | SEQ ID NO. 1762 |
| (N20)NGG | 19 | 17948809 | + | TCGCCATGAGGTGGTGGATGGGG | 1 | 2 | 25 | SEQ ID NO. 1763 |
| (N20)NGG | 19 | 17948812 | + | CCATGAGGTGGTGGATGGGGAGG | 2 | 14 | 159 | SEQ ID NO. 1764 |
| (N20)NGG | 19 | 17948827 | + | TGGGGAGGCCCGAAAGACAGAGG | 1 | 3 | 36 | SEQ ID NO. 1765 |
| (N20)NGG | 19 | 17948839 | + | AAAGACAGAGGTGCTGCTGAAGG | 1 | 5 | 101 | SEQ ID NO. 1766 |
| (N20)NGG | 19 | 17948845 | + | AGAGGTGCTGCTGAAGTCATGG | 1 | 7 | 105 | SEQ ID NO. 1767 |
| (N20)NGG | 19 | 17948869 | + | TGCAAGCACAAGAACTGCATGG | 1 | 3 | 52 | SEQ ID NO. 1768 |
| (N20)NGG | 19 | 17948872 | + | CAAGCACAAGAACTGCATGGAGG | 1 | 26 | 858 | SEQ ID NO. 1769 |
| (N20)NGG | 19 | 17948886 | + | GCATGAGGTGAGAGCAATGTGG | 1 | 3 | 66 | SEQ ID NO. 1770 |
| (N20)NGG | 19 | 17948725 | - | TTCTCATGCTGAATGGTGAGGGG | 2 | 4 | 48 | SEQ ID NO. 1771 |
| (N20)NGG | 19 | 17948726 | - | GTTCTCATGCTGAATGGTGAGG | 1 | 8 | 52 | SEQ ID NO. 1772 |
| (N20)NGG | 19 | 17948727 | - | GGTTCTCATGCTGAATGGTGAGG | 1 | 5 | 36 | SEQ ID NO. 1773 |
| (N20)NGG | 19 | 17948732 | - | GCCCAGTTTCTCATGCTGAATGG | 1 | 1 | 35 | SEQ ID NO. 1774 |
| (N20)NGG | 19 | 17948748 | - | TGGTGAAGGACCCATGGCCCAGG | 1 | 1 | 41 | SEQ ID NO. 1775 |
| (N20)NGG | 19 | 17948754 | - | AAATCTTGGTGAAGGACCCATGG | 1 | 5 | 45 | SEQ ID NO. 1776 |
| (N20)NGG | 19 | 17948762 | - | GCCCCGGTAAATCTTGGTGAAGG | 1 | 1 | 8 | SEQ ID NO. 1777 |
| (N20)NGG | 19 | 17948768 | - | GCGACAGCCCGGTAAATCTTGG | 1 | 1 | 6 | SEQ ID NO. 1778 |
| (N20)NGG | 19 | 17948778 | - | CCACCTCATGGCGACAGCCCGG | 1 | 2 | 31 | SEQ ID NO. 1779 |
| (N20)NGG | 19 | 17948790 | - | CCTCCCCATCCACCACCTCATGG | 5 | 17 | 178 | SEQ ID NO. 1780 |

FIG. 8 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 19 | 17948813 | - | CAGCAGCACCTCTGTCTTTCGGG | 1 | 6 | 85 | SEQ ID NO. 1781 |
| (N20)NGG | 19 | 17948814 | - | TCAGCAGCACCTCTGTCTTTCGG |  | 5 | 70 | SEQ ID NO. 1782 |
| (N20)NGG | 19 | 17948849 | - | CTCCATGCAGTTCTTGTGCTTGG | 1 | 12 | 406 | SEQ ID NO. 1783 |
| (N20)NGG | 19 | 17949091 | + | AGAAAAGTCCAACCTGATCGTGG | 1 | 1 | 20 | SEQ ID NO. 1784 |
| (N20)NGG | 19 | 17949101 | + | AACCTGATCGTGGTCCAGAGAGG | 1 | 1 | 6 | SEQ ID NO. 1785 |
| (N20)NGG | 19 | 17949127 | + | CAGCCCACCCACATCATCCTTGG | 1 | 8 | 83 | SEQ ID NO. 1786 |
| (N20)NGG | 19 | 17949193 | + | CAAGATCCCTGCTGACAGCCTGG | 1 | 2 | 54 | SEQ ID NO. 1787 |
| (N20)NGG | 19 | 17949198 | + | TCCCTGCTGACAGCCTGGAGTGG | 1 | 8 | 92 | SEQ ID NO. 1788 |
| (N20)NGG | 19 | 17949199 | + | CCCTGCTGACAGCCTGGAGTGGG | 1 | 8 | 92 | SEQ ID NO. 1789 |
| (N20)NGG | 19 | 17949206 | + | GACAGCCTGGAGTGGGTAAGAGG | 1 | 4 | 56 | SEQ ID NO. 1790 |
| (N20)NGG | 19 | 17949212 | + | CTGGAGTGGGTAAGAGGCCCTGG | 1 | 3 | 58 | SEQ ID NO. 1791 |
| (N20)NGG | 19 | 17949213 | + | TGGAGTGGGTAAGAGGCCCTGGG | 2 | 4 | 45 | SEQ ID NO. 1792 |
| (N20)NGG | 19 | 17949221 | + | GTAAGAGGCCCTGGAAATGAGG | 1 | 8 | 122 | SEQ ID NO. 1793 |
| (N20)NGG | 19 | 17949051 | - | TTTTCTATGGGGAGAGGATGAGG | 1 | 12 | 105 | SEQ ID NO. 1794 |
| (N20)NGG | 19 | 17949052 | - | TTTTTCTATGGGGAGAGGATGGG | 2 | 9 | 112 | SEQ ID NO. 1795 |
| (N20)NGG | 19 | 17949058 | - | TTGGACTTTTCTATGGGGAGAGG | 1 | 4 | 44 | SEQ ID NO. 1796 |
| (N20)NGG | 19 | 17949063 | - | TCAGGTTGGACTTTTCTATGGGG | 1 | 3 | 31 | SEQ ID NO. 1797 |
| (N20)NGG | 19 | 17949064 | - | ATCAGGTTGGACTTTTCTATGGG | 2 | 2 | 30 | SEQ ID NO. 1798 |
| (N20)NGG | 19 | 17949065 | - | GATCAGGTTGGACTTTTCTATGG | 1 | 5 | 40 | SEQ ID NO. 1799 |
| (N20)NGG | 19 | 17949077 | - | TCTCTGGACCACGATCAGGTTGG | 1 | 1 | 8 | SEQ ID NO. 1800 |
| (N20)NGG | 19 | 17949081 | - | GACCTCTGGACCACGATCAGG | 1 | 1 | 5 | SEQ ID NO. 1801 |
| (N20)NGG | 19 | 17949093 | - | TGGGTGGGCTGTGACCTCTCTGG | 1 | 5 | 54 | SEQ ID NO. 1802 |
| (N20)NGG | 19 | 17949108 | - | GAACCAAGGATGATGTGGGTGGG | 1 | 3 | 40 | SEQ ID NO. 1803 |
| (N20)NGG | 19 | 17949109 | - | TGAACCAAGGATGATGTGGGTGG | 1 | 2 | 45 | SEQ ID NO. 1804 |
| (N20)NGG | 19 | 17949112 | - | GGCTGAACCAAGGATGATGTCGG | 1 | 2 | 27 | SEQ ID NO. 1805 |
| (N20)NGG | 19 | 17949113 | - | GGGCTGAACCAAGGATGATGTGG | 1 | 2 | 43 | SEQ ID NO. 1806 |
| (N20)NGG | 19 | 17949122 | - | TTGGATTGGGGCTGAACCAAGG | 1 | 1 | 34 | SEQ ID NO. 1807 |
| (N20)NGG | 19 | 17949133 | - | CTCAGCTGGTATTGGGATTGGG | 1 | 2 | 33 | SEQ ID NO. 1808 |
| (N20)NGG | 19 | 17949134 | - | ACTCAGCTGGTATTGGGATTGG | 1 | 2 | 30 | SEQ ID NO. 1809 |
| (N20)NGG | 19 | 17949135 | - | GACTCAGCTGGTATTGGGATTGG | 1 | 3 | 19 | SEQ ID NO. 1810 |
| (N20)NGG | 19 | 17949140 | - | CATCTGACTCAGCTGGTATTGGG | 1 | 2 | 29 | SEQ ID NO. 1811 |
| (N20)NGG | 19 | 17949141 | - | TCATCTGACTCAGCTGGTATTGG | 1 | 1 | 25 | SEQ ID NO. 1812 |
| (N20)NGG | 19 | 17949147 | - | GAAATGTCATCTGACTCAGCTGG | 1 | 4 | 172 | SEQ ID NO. 1813 |

FIG. 8 cont.

| site type | site_chr omosome | site_start_ nucleotide | site_s trand | target_site_sequence_wit h_NGG | genome_wide_ hits_with_1 or_less_mism atches | genome_wide_ hits_with_ 2_or_less_m ismatches | genome_wide_ hits_with_3 or_less_mism atches | | |
|---|---|---|---|---|---|---|---|---|---|
| (N20)NGG | 19 | 17949177 | - | CCCACTCCAGGCTGTCAGCAGGG | | 1 | 9 | 108 | SEQ ID NO. 1814 |
| (N20)NGG | 19 | 17949178 | - | ACCCACTCCAGGCTGTCAGCAGG | | 1 | 9 | 61 | SEQ ID NO. 1815 |
| (N20)NGG | 19 | 17949189 | - | CAGGGCCTCTTACCACTCCAGG | | 1 | 4 | 54 | SEQ ID NO. 1816 |
| (N20)NGG | 19 | 17950295 | + | TCTTCTTTGCAGAACCCCCTTGG | | 1 | 4 | 45 | SEQ ID NO. 1817 |
| (N20)NGG | 19 | 17950309 | + | CCCCTTGGTCCTGATTATAAGG | | 1 | 2 | 19 | SEQ ID NO. 1818 |
| (N20)NGG | 19 | 17950310 | + | CCCCTTGGTCCTGATTATAAGGG | | 1 | 3 | 38 | SEQ ID NO. 1819 |
| (N20)NGG | 19 | 17950323 | + | ATTATAAGGGCTGCCTCATCCGG | | 1 | 4 | 23 | SEQ ID NO. 1820 |
| (N20)NGG | 19 | 17950337 | + | CTCATCCGGCGCAGCCCCACAGG | | 1 | 1 | 15 | SEQ ID NO. 1821 |
| (N20)NGG | 19 | 17950351 | + | CCCCACAGGAACCTTCCTTCTGG | | 1 | 8 | 59 | SEQ ID NO. 1822 |
| (N20)NGG | 19 | 17950355 | + | ACAGGAACCTTCCTTCTGGTTGG | | 1 | 3 | 37 | SEQ ID NO. 1823 |
| (N20)NGG | 19 | 17950393 | + | CAGCAGTCTTCGAGAGCTCCTGG | | 1 | 5 | 27 | SEQ ID NO. 1824 |
| (N20)NGG | 19 | 17950404 | + | GAGAGCTCCTGGCAACCTGCTGG | | 2 | 7 | 66 | SEQ ID NO. 1825 |
| (N20)NGG | 19 | 17950405 | + | AGAGCTCCTGGCAACCTGCTGGG | | 1 | 2 | 41 | SEQ ID NO. 1826 |
| (N20)NGG | 19 | 17950409 | + | CTCCTGGCAACCTGCTGGGATGG | | 1 | 4 | 58 | SEQ ID NO. 1827 |
| (N20)NGG | 19 | 17950410 | + | TCCTGGCAACCTGCTGGGATGGG | | 1 | 1 | 49 | SEQ ID NO. 1828 |
| (N20)NGG | 19 | 17950411 | + | CCTGGCAACCTGCTGGGATGGGG | | 1 | 3 | 57 | SEQ ID NO. 1829 |
| (N20)NGG | 19 | 17950412 | + | CTGGCAACCTGCTGGGATGGGGG | | 1 | 4 | 56 | SEQ ID NO. 1830 |
| (N20)NGG | 19 | 17950413 | + | TGGCAACCTGCTGGGATGGGGGG | | 1 | 3 | 58 | SEQ ID NO. 1831 |
| (N20)NGG | 19 | 17950427 | + | GATGGGGGGCTGCACGTAGATGG | | 1 | 5 | 18 | SEQ ID NO. 1832 |
| (N20)NGG | 19 | 17950428 | + | ATGGGGGGCTGCACGTAGATGGG | | 1 | 1 | 6 | SEQ ID NO. 1833 |
| (N20)NGG | 19 | 17950429 | + | TGGGGGGCTGCACGTAGATGGGG | | 1 | 1 | 24 | SEQ ID NO. 1834 |
| (N20)NGG | 19 | 17950432 | + | GGGGCTGCACGTAGATGGGGTGG | | 1 | 6 | 41 | SEQ ID NO. 1835 |
| (N20)NGG | 19 | 17950472 | + | TGCTGTATCCCAGACCCAAAGG | | 1 | 9 | 97 | SEQ ID NO. 1836 |
| (N20)NGG | 19 | 17950492 | + | AGGTGAGCCCCTTCCTCCCCTGG | | 2 | 6 | 93 | SEQ ID NO. 1837 |
| (N20)NGG | 19 | 17950269 | - | CCCTGGGGTTCTGCAAAGAAGAGTGG | | 1 | 4 | 75 | SEQ ID NO. 1838 |
| (N20)NGG | 19 | 17950287 | - | CCTTATAATCAGGACCAAGGGGG | | 1 | 3 | 56 | SEQ ID NO. 1839 |
| (N20)NGG | 19 | 17950288 | - | CCCTTATAATCAGGACCAAGGG | | 1 | 3 | 28 | SEQ ID NO. 1840 |
| (N20)NGG | 19 | 17950289 | - | GCCCTTATAATCAGGACCAAGG | | 1 | 1 | 34 | SEQ ID NO. 1841 |
| (N20)NGG | 19 | 17950290 | - | AGCCCTTATAATCAGGACCAAG | | 1 | 2 | 18 | SEQ ID NO. 1842 |
| (N20)NGG | 19 | 17950297 | - | ATGAGGCAGCCCTTATAATCAGG | | 1 | 2 | 19 | SEQ ID NO. 1843 |
| (N20)NGG | 19 | 17950314 | - | CTGTGGGGCTGCGCCGGATGAGG | | 1 | 4 | 27 | SEQ ID NO. 1844 |
| (N20)NGG | 19 | 17950320 | - | AGGTTCCTGTGGGGCTGCGCCGG | | 1 | 5 | 44 | SEQ ID NO. 1845 |
| (N20)NGG | 19 | 17950329 | - | CCAGAAGGAAGTTCCTGTGGGG | | 1 | 3 | 70 | SEQ ID NO. 1846 |

FIG. 8 cont.

| site type | site chromosome | site start nucleotide | site strand | target site sequence with NGG | genome wide hits with 1 or less mismatches | genome wide hits with 2 or less mismatches | genome wide hits with 3 or less mismatches | | |
|---|---|---|---|---|---|---|---|---|---|
| (N20)NGG | 19 | 17950330 | - | ACCAGAAGGAAGGTTCCTGTGG | 1 | 3 | 50 | SEQ ID NO. | 1847 |
| (N20)NGG | 19 | 17950331 | - | AACCAGAAGGAAGGTTCCTGTGG | 1 | 5 | 83 | SEQ ID NO. | 1848 |
| (N20)NGG | 19 | 17950340 | - | GCTGAGGCCAACCAGAAGGAAGG | 1 | 2 | 60 | SEQ ID NO. | 1849 |
| (N20)NGG | 19 | 17950344 | - | GTCGGCTGAGGCCAACCAGAAGG | 1 | 1 | 16 | SEQ ID NO. | 1850 |
| (N20)NGG | 19 | 17950356 | - | GACTGCTGTGGGGTCGGCTGAGG | 1 | 11 | 462 | SEQ ID NO. | 1851 |
| (N20)NGG | 19 | 17950362 | - | CTGAAGACTGCTGTGGGGTCGG | 1 | 2 | 25 | SEQ ID NO. | 1852 |
| (N20)NGG | 19 | 17950366 | - | AGCTCTCGAAGACTGCTGTGGGG | 1 | 3 | 21 | SEQ ID NO. | 1853 |
| (N20)NGG | 19 | 17950367 | - | GAGCTCTCGAAGACTGCTGTGGG | 1 | 2 | 26 | SEQ ID NO. | 1854 |
| (N20)NGG | 19 | 17950368 | - | GGAGCTCTCGAAGACTGCTGTGG | 1 | 3 | 31 | SEQ ID NO. | 1855 |
| (N20)NGG | 19 | 17950389 | - | CCCCATCCAGCAGGTTGCCAGG | 1 | 2 | 68 | SEQ ID NO. | 1856 |
| (N20)NGG | 19 | 17950397 | - | GTGCAGCCCCCATCCAGCAGG | 2 | 6 | 62 | SEQ ID NO. | 1857 |
| (N20)NGG | 19 | 17950439 | - | GGGGATACAGCAGGAAGTGAGG | 3 | 16 | 147 | SEQ ID NO. | 1858 |
| (N20)NGG | 19 | 17950440 | - | TGGGGATACAGCAGGAAGTGAGG | 2 | 22 | 135 | SEQ ID NO. | 1859 |
| (N20)NGG | 19 | 17950448 | - | TTTGGGTCTGGGGATACAGCAGG | 1 | 1 | 76 | SEQ ID NO. | 1860 |
| (N20)NGG | 19 | 17950458 | - | GGGGCTCACCTTTGGGTCTGGG | 1 | 3 | 51 | SEQ ID NO. | 1861 |
| (N20)NGG | 19 | 17950459 | - | AGGGGCTCACCTTTGGGTCTGG | 1 | 3 | 37 | SEQ ID NO. | 1862 |
| (N20)NGG | 19 | 17950460 | - | AAGGGGCTCACCTTTGGGTCTG | 1 | 3 | 14 | SEQ ID NO. | 1863 |
| (N20)NGG | 19 | 17950465 | - | GGAGGAAGGGGCTCACCTTTGG | 1 | 8 | 53 | SEQ ID NO. | 1864 |
| (N20)NGG | 19 | 17950466 | - | GGGAGGAAGGGGCTCACCTTTG | 1 | 5 | 64 | SEQ ID NO. | 1865 |
| (N20)NGG | 19 | 17951042 | + | TCTCACCTTCCCCACAGTCTGG | 1 | 5 | 72 | SEQ ID NO. | 1866 |
| (N20)NGG | 19 | 17951070 | + | GCCATCAACAAGCTCAAGACTGG | 1 | 3 | 33 | SEQ ID NO. | 1867 |
| (N20)NGG | 19 | 17951071 | + | CCATCAACAAGCTCAAGACTGGG | 1 | 5 | 52 | SEQ ID NO. | 1868 |
| (N20)NGG | 19 | 17951072 | + | CATCAACAAGCTCAAGACTGGGG | 1 | 4 | 42 | SEQ ID NO. | 1869 |
| (N20)NGG | 19 | 17951073 | + | ATCAACAAGCTCAAGACTGGGGG | 1 | 3 | 35 | SEQ ID NO. | 1870 |
| (N20)NGG | 19 | 17951085 | + | AAGACTGGGGCTCACGTCCTGG | 1 | 1 | 19 | SEQ ID NO. | 1871 |
| (N20)NGG | 19 | 17951114 | + | TGTTCTCCGCCGCAGCCCCCAGG | 1 | 4 | 26 | SEQ ID NO. | 1872 |
| (N20)NGG | 19 | 17951150 | + | CCTCCTCACTGTCTGTGTCCAGG | 1 | 8 | 102 | SEQ ID NO. | 1873 |
| (N20)NGG | 19 | 17951154 | + | CTCACTGTCTGTGTCCAGGTCGG | 3 | 8 | 76 | SEQ ID NO. | 1874 |
| (N20)NGG | 19 | 17951166 | + | GTCCAGGTCGGTCTACTGCTAGG | 1 | 2 | 10 | SEQ ID NO. | 1875 |
| (N20)NGG | 19 | 17951167 | + | TCCAGGTCGGTCTACTGCTAGG | 1 | 2 | 13 | SEQ ID NO. | 1876 |
| (N20)NGG | 19 | 17951170 | + | AGGTCGGTCTACTGCTAGGGTGG | 1 | 1 | 6 | SEQ ID NO. | 1877 |
| (N20)NGG | 19 | 17951171 | + | GGTCGGTCTACTGCTAGGGTGGG | 1 | 1 | 3 | SEQ ID NO. | 1878 |
| (N20)NGG | 19 | 17951017 | - | GACTGTGGGGAAGGTGAGAGGG | 1 | 8 | 176 | SEQ ID NO. | 1879 |

FIG. 8 cont.

| site_type | site_chr omosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 19 | 17951018 | - | AGACTGTGGGGAAGGTGAGAGG | 1 | 12 | 195 | SEQ ID NO. 1880 |
| (N20)NGG | 19 | 17951025 | - | AAAGTCCAGACTGTGGGGAAGG | 2 | 5 | 65 | SEQ ID NO. 1881 |
| (N20)NGG | 19 | 17951029 | - | TGGCAAAGTCCAGACTGTGGGG | 1 | 7 | 80 | SEQ ID NO. 1882 |
| (N20)NGG | 19 | 17951030 | - | ATGGCAAAGTCCAGACTGTGGG | 1 | 3 | 54 | SEQ ID NO. 1883 |
| (N20)NGG | 19 | 17951031 | - | GATGGCAAAGTCCAGACTGTGG | 1 | 6 | 52 | SEQ ID NO. 1884 |
| (N20)NGG | 19 | 17951032 | - | TGATGGCAAAGTCCAGACTGTGG | 1 | 11 | 64 | SEQ ID NO. 1885 |
| (N20)NGG | 19 | 17951049 | - | CCCAGTCTTGAGCTTGTTGATGG | 1 | 2 | 30 | SEQ ID NO. 1886 |
| (N20)NGG | 19 | 17951081 | - | CGGCCGAGAACATAGGAGCCAGG | 1 | 1 | 6 | SEQ ID NO. 1887 |
| (N20)NGG | 19 | 17951088 | - | GGGGCTGCGCGCGAGAACATAGG | 1 | 1 | 15 | SEQ ID NO. 1888 |
| (N20)NGG | 19 | 17951098 | - | CAAAGTCCTGGGGGCTGCGGCGG | 1 | 8 | 72 | SEQ ID NO. 1889 |
| (N20)NGG | 19 | 17951101 | - | TGTCAAAGTCCTGGGGCTGCGG | 1 | 10 | 141 | SEQ ID NO. 1890 |
| (N20)NGG | 19 | 17951107 | - | GGAAGTCGTCAAAGTCCTGGGG | 1 | 9 | 85 | SEQ ID NO. 1891 |
| (N20)NGG | 19 | 17951108 | - | AGGAAGTCGTCAAAGTCCTGGG | 1 | 5 | 81 | SEQ ID NO. 1892 |
| (N20)NGG | 19 | 17951109 | - | GAGGAAGTCGTCAAAGTCCTGG | 1 | 2 | 57 | SEQ ID NO. 1893 |
| (N20)NGG | 19 | 17951110 | - | GGAGGAAGTCGTCAAAGTCCTG | 1 | 1 | 49 | SEQ ID NO. 1894 |
| (N20)NGG | 19 | 17951128 | - | CCTGGACACAGACAGTGAGGAGG | 1 | 6 | 106 | SEQ ID NO. 1895 |
| (N20)NGG | 19 | 17951131 | - | CGACCTGGACACAGACCGACCTGG | 1 | 3 | 26 | SEQ ID NO. 1896 |
| (N20)NGG | 19 | 17951146 | - | ACCCTAGCAGTAGACCGACCTGG | 1 | 1 | 6 | SEQ ID NO. 1897 |
| (N20)NGG | 19 | 17952197 | + | CTCTGACGCTTGTCCCTGCAGG | 1 | 1 | 10 | SEQ ID NO. 1898 |
| (N20)NGG | 19 | 17952200 | + | TGACGCTTGTCCCTGCAGGAGG | 1 | 1 | 6 | SEQ ID NO. 1899 |
| (N20)NGG | 19 | 17952213 | + | TCCAGGAGGCCGAGTTCCCAGG | 1 | 1 | 16 | SEQ ID NO. 1900 |
| (N20)NGG | 19 | 17952214 | + | CCGAGGAGGCCGAGTTCCCAGG | 1 | 4 | 28 | SEQ ID NO. 1901 |
| (N20)NGG | 19 | 17952224 | + | CGAGTTCCCAGGGCTGCCCAGG | 1 | 2 | 39 | SEQ ID NO. 1902 |
| (N20)NGG | 19 | 17952239 | + | GCCCGAGGCTCTGTCGTTCGTGG | 1 | 1 | 6 | SEQ ID NO. 1903 |
| (N20)NGG | 19 | 17952248 | + | TCTGTCGTTCGTGGCGCTCGTGG | 1 | 1 | 4 | SEQ ID NO. 1904 |
| (N20)NGG | 19 | 17952252 | + | TCGTTCGTGGCGCTCGTGGACGG | 1 | 1 | 6 | SEQ ID NO. 1905 |
| (N20)NGG | 19 | 17952262 | + | CGCTCGTGGACGGCTACTTCCGG | 1 | 1 | 2 | SEQ ID NO. 1906 |
| (N20)NGG | 19 | 17952272 | + | CGGCTACTTCCGGCTGACCACGG | 1 | 1 | 14 | SEQ ID NO. 1907 |
| (N20)NGG | 19 | 17952296 | + | CTCCCAGACACTTCTTCTGCAAGG | 1 | 6 | 100 | SEQ ID NO. 1908 |
| (N20)NGG | 19 | 17952299 | + | CCAGCACTTCTTCTGCAAGGAGG | 1 | 4 | 54 | SEQ ID NO. 1909 |
| (N20)NGG | 19 | 17952302 | + | GCACTTCTTCTGCAAGGAGGTGG | 1 | 4 | 43 | SEQ ID NO. 1910 |
| (N20)NGG | 19 | 17952313 | + | GCAAGGAGGTGGCACCGCCGAGG | 1 | 1 | 19 | SEQ ID NO. 1911 |
| (N20)NGG | 19 | 17952320 | + | GGTGGCACCGCCGAGGCTGCTGG | 1 | 4 | 29 | SEQ ID NO. 1912 |

FIG. 8 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | SEQ ID NO. |
|---|---|---|---|---|---|---|---|---|
| (N20)NGG | 19 | 17952323 | + | GGCACCGCCGAGGCTGCTGGAGG | | 1 | 2 | 49 SEQ ID NO. 1913 |
| (N20)NGG | 19 | 17952329 | + | GCCGAGGCTGCTGGAGGAAGTGG | | 3 | 15 | 162 SEQ ID NO. 1914 |
| (N20)NGG | 19 | 17952345 | + | GAAGTGGCCGAGCAGTGCCACGG | | 1 | 1 | 29 SEQ ID NO. 1915 |
| (N20)NGG | 19 | 17952360 | + | TGCCACGGCCCCATCACGTAAGG | | 1 | 2 | 10 SEQ ID NO. 1916 |
| (N20)NGG | 19 | 17952379 | + | AAGGACCTGTCCCCATTCCCGG | | 1 | 1 | 32 SEQ ID NO. 1917 |
| (N20)NGG | 19 | 17952188 | - | GGGAACTCGGCCTCCTGCGAGGG | | 1 | 1 | 8 SEQ ID NO. 1918 |
| (N20)NGG | 19 | 17952189 | - | TGGGAACTCGGCCTCCTGCGAGG | | 1 | 2 | 22 SEQ ID NO. 1919 |
| (N20)NGG | 19 | 17952201 | - | CTCGGGCAGCCCTGGAACTCGG | | 1 | 3 | 54 SEQ ID NO. 1920 |
| (N20)NGG | 19 | 17952208 | - | ACAGAGCCTCGGGCAGCCCTGGG | | 1 | 8 | 75 SEQ ID NO. 1921 |
| (N20)NGG | 19 | 17952209 | - | GACAGAGCCTCGGGCAGCCCTGG | | 2 | 7 | 70 SEQ ID NO. 1922 |
| (N20)NGG | 19 | 17952218 | - | GCCACGAACGACAGAGCCTCGGG | | 1 | 1 | 21 SEQ ID NO. 1923 |
| (N20)NGG | 19 | 17952219 | - | CGCCACGAACGACAGAGCCTCGG | | 1 | 1 | 9 SEQ ID NO. 1924 |
| (N20)NGG | 19 | 17952259 | - | GCTGGGAGTTCCGTGGTCAGCCGG | | 1 | 2 | 33 SEQ ID NO. 1925 |
| (N20)NGG | 19 | 17952267 | - | GAAGAAGTGCTGGAGAGTCCGTGG | | 1 | 1 | 41 SEQ ID NO. 1926 |
| (N20)NGG | 19 | 17952276 | - | CTCCTTGCAGAAGAAGTGCTGG | | 1 | 5 | 51 SEQ ID NO. 1927 |
| (N20)NGG | 19 | 17952277 | - | CCTCCTTGCAGAAGAAGTGCTGG | | 1 | 3 | 46 SEQ ID NO. 1928 |
| (N20)NGG | 19 | 17952305 | - | ACTTCCTCCAGCAGCCTCGGCGG | | 1 | 4 | 58 SEQ ID NO. 1929 |
| (N20)NGG | 19 | 17952308 | - | GCCACTTCCTCCAGCAGCCTCGG | | 1 | 12 | 123 SEQ ID NO. 1930 |
| (N20)NGG | 19 | 17952330 | - | GATGGGGCCGTGGCACTGCTCGG | | 1 | 2 | 21 SEQ ID NO. 1931 |
| (N20)NGG | 19 | 17952340 | - | GTCCTTACGTGATGGGGCCGTGG | | 1 | 1 | 7 SEQ ID NO. 1932 |
| (N20)NGG | 19 | 17952346 | - | GGACAGGTCCTTACGTGATGGGG | | 1 | 1 | 9 SEQ ID NO. 1933 |
| (N20)NGG | 19 | 17952347 | - | GGGACAGGTCCTTACGTGATGGG | | 1 | 1 | 13 SEQ ID NO. 1934 |
| (N20)NGG | 19 | 17952348 | - | GGGGACAGGTCCTTACGTGATGG | | 1 | 2 | 13 SEQ ID NO. 1935 |
| (N20)NGG | 19 | 17952448 | + | CGGTACTCCCCCTCCTTCCCAGG | | 1 | 3 | 41 SEQ ID NO. 1936 |
| (N20)NGG | 19 | 17952502 | + | CGTAGACATTAGCATCAAGCAGG | | 1 | 1 | 9 SEQ ID NO. 1937 |
| (N20)NGG | 19 | 17952515 | + | ATCAAGCAGGCCCCGCGCGTTGG | | 1 | 2 | 4 SEQ ID NO. 1938 |
| (N20)NGG | 19 | 17952520 | + | GCAGGCCCCGCGCGTTGGCCCGG | | 1 | 2 | 16 SEQ ID NO. 1939 |
| (N20)NGG | 19 | 17952524 | + | GCCCCGCGCGTTGGCCCGGCCGG | | 1 | 2 | 15 SEQ ID NO. 1940 |
| (N20)NGG | 19 | 17952538 | + | CCCGGCCGGAGAGCACCGCCTGG | | 1 | 2 | 30 SEQ ID NO. 1941 |
| (N20)NGG | 19 | 17952552 | + | ACCGCCTGGTCACTGTTACCAGG | | 1 | 1 | 4 SEQ ID NO. 1942 |
| (N20)NGG | 19 | 17952574 | + | GACAGACAACCAGATTTTAGTGG | | 1 | 3 | 47 SEQ ID NO. 1943 |
| (N20)NGG | 19 | 17952575 | + | ACAGACAACCAGATTTTAGTGGG | | 1 | 3 | 37 SEQ ID NO. 1944 |
| (N20)NGG | 19 | 17952581 | + | AACCAGATTTTAGTGGGTGCAGG | | 2 | 3 | 31 SEQ ID NO. 1945 |

FIG. 8 cont.

| site_type | site_chr omosome | site_start_ nucleotide | site_s trand | target_site_sequence_with_NGG | genome_wide_ hits_with_1 or_less_mism atches | genome_wide_ hits_with_2_or_less_m ismatches | genome_wide_ hits_with_3 or_less_mism atches | |
|---|---|---|---|---|---|---|---|---|
| (N20)NGG | 19 | 17952433 | - | TGGAGGACCTGGGAAGGAGGGGG | | 1 | 22 | 279 SEQ ID NO. 1946 |
| (N20)NGG | 19 | 17952434 | - | CTGGAGGACCTGGGAAGGAGGGG | | 2 | 15 | 206 SEQ ID NO. 1947 |
| (N20)NGG | 19 | 17952435 | - | GCTGGAGGACCTGGGAAGGAGGG | | 1 | 7 | 167 SEQ ID NO. 1948 |
| (N20)NGG | 19 | 17952436 | - | GGCTGGAGGACCTGGGAAGGAGG | | 1 | 14 | 219 SEQ ID NO. 1949 |
| (N20)NGG | 19 | 17952439 | - | AAGGGCTGGAGGACCTGGGAAGG | | 2 | 11 | 124 SEQ ID NO. 1950 |
| (N20)NGG | 19 | 17952443 | - | GCAGAAGGGCTGGAGGACCTGGG | | 1 | 6 | 100 SEQ ID NO. 1951 |
| (N20)NGG | 19 | 17952444 | - | CGCAGAAGGGCTGGAGGACCTGG | | 1 | 7 | 57 SEQ ID NO. 1952 |
| (N20)NGG | 19 | 17952450 | - | GAAAGTCGCAGAAGGGCTGGAGG | | 1 | 2 | 35 SEQ ID NO. 1953 |
| (N20)NGG | 19 | 17952453 | - | CTGGAAAGTCGCAGAAGGGCTGG | | 1 | 1 | 26 SEQ ID NO. 1954 |
| (N20)NGG | 19 | 17952457 | - | ATTTCTGAAAGTCGCAGAAGGG | | 1 | 3 | 44 SEQ ID NO. 1955 |
| (N20)NGG | 19 | 17952458 | - | GATTTCTGAAAGTCGCAGAAGG | | 1 | 2 | 37 SEQ ID NO. 1956 |
| (N20)NGG | 19 | 17952472 | - | ATGCTAATGTCTACGATTTCTGG | | 1 | 1 | 16 SEQ ID NO. 1957 |
| (N20)NGG | 19 | 17952503 | - | TCCGGCCGGGCCAACGCGCGGG | | 1 | 1 | 9 SEQ ID NO. 1958 |
| (N20)NGG | 19 | 17952504 | - | CTCCGGCCGGGCCAACGCGCGG | | 1 | 1 | 13 SEQ ID NO. 1959 |
| (N20)NGG | 19 | 17952505 | - | TCTCCGGCCGGGCCAACGCGCG | | 1 | 1 | 11 SEQ ID NO. 1960 |
| (N20)NGG | 19 | 17952516 | - | CCAGGCGGTGCTCTCCGGCCGGG | | 1 | 2 | 34 SEQ ID NO. 1961 |
| (N20)NGG | 19 | 17952517 | - | ACCAGGCGGTGCTCTCCGGCCGG | | 1 | 1 | 16 SEQ ID NO. 1962 |
| (N20)NGG | 19 | 17952521 | - | AGTGACACAGGCGGTGCTCTCCGG | | 1 | 2 | 20 SEQ ID NO. 1963 |
| (N20)NGG | 19 | 17952531 | - | TCCTGGTAACAGTGACACCAGCGG | | 1 | 3 | 35 SEQ ID NO. 1964 |
| (N20)NGG | 19 | 17952534 | - | CTGTCCTGTAACAGTGACCAGG | | 1 | 1 | 37 SEQ ID NO. 1965 |
| (N20)NGG | 19 | 17952548 | - | TAAAATCTGTTGTCTGTCCTGG | | 1 | 3 | 37 SEQ ID NO. 1966 |
| (N20)NGG | 19 | 17952561 | - | ATCCTGCACCCACTAAAATCTGG | | 1 | 3 | 30 SEQ ID NO. 1967 |
| (N20)NGG | 19 | 17953131 | + | CTCCAACCCCTGCAGCTACAAGG | | 1 | 5 | 78 SEQ ID NO. 1968 |
| (N20)NGG | 19 | 17953167 | + | AAGCCTGCGCGACCTGATCCAGG | | 1 | 1 | 7 SEQ ID NO. 1969 |
| (N20)NGG | 19 | 17953168 | + | AGCCTGCGCGACCTGATCCAGG | | 1 | 3 | 22 SEQ ID NO. 1970 |
| (N20)NGG | 19 | 17953187 | + | AGGGCCTGGAGCTTCGTGACGCGG | | 1 | 1 | 11 SEQ ID NO. 1971 |
| (N20)NGG | 19 | 17953190 | + | GCCTGAGCTTCGTGACGCGGAGG | | 1 | 1 | 3 SEQ ID NO. 1972 |
| (N20)NGG | 19 | 17953199 | + | TCGTGACGCGGAGGCGTATTCGG | | 1 | 1 | 1 SEQ ID NO. 1973 |
| (N20)NGG | 19 | 17953202 | + | TGACGGGAGGCGTATTCGAGG | | 1 | 1 | 3 SEQ ID NO. 1974 |
| (N20)NGG | 19 | 17953206 | + | GCGGAGGCGTATTCGGAGGACGG | | 1 | 1 | 7 SEQ ID NO. 1975 |
| (N20)NGG | 19 | 17953230 | + | GCGCAGAGCCCTGCCGCCGTGG | | 1 | 2 | 32 SEQ ID NO. 1976 |
| (N20)NGG | 19 | 17953242 | + | GCGCCGCGTGCCGCCTGCCAGG | | 1 | 3 | 27 SEQ ID NO. 1977 |
| (N20)NGG | 19 | 17953250 | + | TGGCCGCCTGCCAGGCAGACCGG | | 3 | 3 | 29 SEQ ID NO. 1978 |

FIG. 8 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 19 | 17953263 | + | GGCAGACCGGCACTCGCTCATGG | 1 | 1 | 9 | SEQ ID NO. 1979 |
| (N20)NGG | 19 | 17953278 | + | GCTCATGGCCAAGTACATCATGG |   | 2 | 4 | 39 SEQ ID NO. 1980 |
| (N20)NGG | 19 | 17953284 | + | GGCCAAGTACATCATGGACCTGG |   | 1 | 1 | 13 SEQ ID NO. 1981 |
| (N20)NGG | 19 | 17953289 | + | AGTACATCATGGACCTGGAGCGG |   | 1 | 1 | 34 SEQ ID NO. 1982 |
| (N20)NGG | 19 | 17953293 | + | CATCATGGACCTGGAGCGGCTGG |   | 1 | 5 | 22 SEQ ID NO. 1983 |
| (N20)NGG | 19 | 17953303 | + | CTGGAGCGGCTGGATCCAGCCGG |   | 1 | 3 | 46 SEQ ID NO. 1984 |
| (N20)NGG | 19 | 17953304 | + | TGGAGCGGCTGGATCCAGCCGGG |   | 2 | 4 | 44 SEQ ID NO. 1985 |
| (N20)NGG | 19 | 17953305 | + | GGAGCGGCTGGATCCAGCCGGGG |   | 1 | 6 | 33 SEQ ID NO. 1986 |
| (N20)NGG | 19 | 17953326 | + | GGCCCGCCGAGACCTTCCACGTGG |   | 1 | 1 | 8 SEQ ID NO. 1987 |
| (N20)NGG | 19 | 17953327 | + | GCCCGCCGAGACCTTCCACGTGGG |   | 1 | 1 | 5 SEQ ID NO. 1988 |
| (N20)NGG | 19 | 17953336 | + | ACCTTCCACGTGGGCCTCCCTGG |   | 2 | 11 | 234 SEQ ID NO. 1989 |
| (N20)NGG | 19 | 17953337 | + | CCTTCCACGTGGGCCTCCCCTGGG |   | 2 | 30 | 1326 SEQ ID NO. 1990 |
| (N20)NGG | 19 | 17953338 | + | CTTCCACGTGGGCCTCCCTGGGG |   | 1 | 2 | 74 SEQ ID NO. 1991 |
| (N20)NGG | 19 | 17953345 | + | GTGGGCCTCCCTGGGGCCCTTGG |   | 1 | 6 | 132 SEQ ID NO. 1992 |
| (N20)NGG | 19 | 17953348 | + | GGCCTCCCTGGGGCCCTTGGTGG |   | 1 | 7 | 129 SEQ ID NO. 1993 |
| (N20)NGG | 19 | 17953357 | + | GGGGCCCTTGGTGGCCACGACGG |   | 1 | 2 | 33 SEQ ID NO. 1994 |
| (N20)NGG | 19 | 17953358 | + | CCTTGTGGTGGCCACGACGGGCTGG |   | 1 | 5 | 23 SEQ ID NO. 1995 |
| (N20)NGG | 19 | 17953362 | + | CTTGGTGGCCACGACGGGCTGG |   | 1 | 3 | 26 SEQ ID NO. 1996 |
| (N20)NGG | 19 | 17953363 | + | TTGGTGGCCACGACGGGCTGGGG |   | 1 | 1 | 11 SEQ ID NO. 1997 |
| (N20)NGG | 19 | 17953364 | + | TGGTGGCCACGACGGGCTGGGGG |   | 1 | 3 | 26 SEQ ID NO. 1998 |
| (N20)NGG | 19 | 17953377 | + | CGGGCTGGGGCTGCTCCGCGTGG |   | 1 | 5 | 51 SEQ ID NO. 1999 |
| (N20)NGG | 19 | 17953381 | + | CTGGGGCTGCTCCGCGTGGCTGG |   | 1 | 3 | 49 SEQ ID NO. 2000 |
| (N20)NGG | 19 | 17953387 | + | CTGCTCCGCGTGGCTGGTGACGG |   | 1 | 1 | 35 SEQ ID NO. 2001 |
| (N20)NGG | 19 | 17953390 | + | CTCCGCGTGGCTGGTGACGGCGG |   | 1 | 1 | 15 SEQ ID NO. 2002 |
| (N20)NGG | 19 | 17953400 | + | CTGGTGACGGCGGCATCGCCTGG |   | 2 | 2 | 5 SEQ ID NO. 2003 |
| (N20)NGG | 19 | 17953407 | + | CGGCGGCATCGCCTGACCCAGG |   | 1 | 1 | 13 SEQ ID NO. 2004 |
| (N20)NGG | 19 | 17953408 | + | GGCGGCATCGCCTGACCCAGGG |   | 1 | 1 | 17 SEQ ID NO. 2005 |
| (N20)NGG | 19 | 17953416 | + | CGCCTGACCCAGGGAGAACAGG |   | 1 | 3 | 29 SEQ ID NO. 2006 |
| (N20)NGG | 19 | 17953419 | + | CTGACCCAGGGAGAACAGGAGAG |   | 2 | 13 | 137 SEQ ID NO. 2007 |
| (N20)NGG | 19 | 17953424 | + | CCAGGGAGAACAGGAGAGGTGAGG |   | 1 | 7 | 157 SEQ ID NO. 2008 |
| (N20)NGG | 19 | 17953425 | + | CCAGGGAGAACAGGAGAGGTGAGGG |   | 2 | 9 | 149 SEQ ID NO. 2009 |
| (N20)NGG | 19 | 17953428 | + | GGGAGAACAGGAGAGGTGAGGGCGG |   | 3 | 33 | 396 SEQ ID NO. 2010 |
| (N20)NGG | 19 | 17953441 | + | GTGAGGGCGGACTCCCCGCTGG |   | 1 | 2 | 12 SEQ ID NO. 2011 |

FIG. 8 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | | |
|---|---|---|---|---|---|---|---|---|---|
| (N20)NGG | 19 | 17953442 | + | TGAGGGCGGACTCCCCGCTGGG | 1 | 1 | 9 | SEQ ID NO. | 2012 |
| (N20)NGG | 19 | 17953102 | - | GCTGCAGGGGTTGGAGGGGAGG | 2 | 23 | 266 | SEQ ID NO. | 2013 |
| (N20)NGG | 19 | 17953103 | - | AGCTGCAGGGGTTGGAGGGGAG | 1 | 19 | 260 | SEQ ID NO. | 2014 |
| (N20)NGG | 19 | 17953106 | - | TGTAGCTGCAGGGGTTGGAGGG | 1 | 7 | 99 | SEQ ID NO. | 2015 |
| (N20)NGG | 19 | 17953107 | - | TTGTAGCTGCAGGGGTTGGAGG | 1 | 2 | 61 | SEQ ID NO. | 2016 |
| (N20)NGG | 19 | 17953108 | - | CTTGTAGCTGCAGGGGTTGGAG | 1 | 6 | 56 | SEQ ID NO. | 2017 |
| (N20)NGG | 19 | 17953111 | - | GGCCTTGTAGCTGCAGGGGTTGG | 1 | 4 | 54 | SEQ ID NO. | 2018 |
| (N20)NGG | 19 | 17953115 | - | GGCAGGCCTTGTAGCTGCAGGGG | 1 | 5 | 51 | SEQ ID NO. | 2019 |
| (N20)NGG | 19 | 17953116 | - | AGGCAGGCCTTGTAGCTGCAGGG | 1 | 3 | 43 | SEQ ID NO. | 2020 |
| (N20)NGG | 19 | 17953117 | - | TAGGCAGGCCTTGTAGCTGCAGG | 1 | 2 | 32 | SEQ ID NO. | 2021 |
| (N20)NGG | 19 | 17953132 | - | GCGCAGGCTTGGGGTAGGCAGG | 1 | 4 | 37 | SEQ ID NO. | 2022 |
| (N20)NGG | 19 | 17953136 | - | GGTCGCGCAGGCTTGGGGTAGG | 1 | 2 | 28 | SEQ ID NO. | 2023 |
| (N20)NGG | 19 | 17953140 | - | ATCAGTCGCGCAGGCTTGGGG | 1 | 1 | 5 | SEQ ID NO. | 2024 |
| (N20)NGG | 19 | 17953141 | - | GATCAGTCGCGCAGGCTTGGG | 1 | 1 | 10 | SEQ ID NO. | 2025 |
| (N20)NGG | 19 | 17953142 | - | GGATCAGTCGCGCAGGCTTGG | 1 | 1 | 11 | SEQ ID NO. | 2026 |
| (N20)NGG | 19 | 17953143 | - | TGGATCAGTCGCGCAGGCTTGG | 1 | 1 | 4 | SEQ ID NO. | 2027 |
| (N20)NGG | 19 | 17953148 | - | GGCCCTTGGATCAGTCGCGCAGG | 1 | 3 | 8 | SEQ ID NO. | 2028 |
| (N20)NGG | 19 | 17953157 | - | CGAAGCTCAGGCCCTTGGATCAGG | 1 | 3 | 34 | SEQ ID NO. | 2029 |
| (N20)NGG | 19 | 17953163 | - | GCGTCACGAAGCTCAGGCCCTGG | 1 | 1 | 13 | SEQ ID NO. | 2030 |
| (N20)NGG | 19 | 17953169 | - | GCCTCCGTCACGAAGCTCAGG | 1 | 1 | 25 | SEQ ID NO. | 2031 |
| (N20)NGG | 19 | 17953216 | - | GCAGGCGGCCACGCCGCGCAGG | 1 | 3 | 21 | SEQ ID NO. | 2032 |
| (N20)NGG | 19 | 17953217 | - | GCAGGCGGCCACGCCGCGCAGG | 1 | 3 | 35 | SEQ ID NO. | 2033 |
| (N20)NGG | 19 | 17953223 | - | CTGCCTGGCAGGCGGCCACGCGG | 2 | 8 | 56 | SEQ ID NO. | 2034 |
| (N20)NGG | 19 | 17953231 | - | GTGCCGGTCGTGCCTGGCAGGCGG | 1 | 2 | 37 | SEQ ID NO. | 2035 |
| (N20)NGG | 19 | 17953234 | - | CGAGTGCCGGTCTGCCTGGCAGG | 1 | 2 | 14 | SEQ ID NO. | 2036 |
| (N20)NGG | 19 | 17953238 | - | TGAGCGAGTGCCGGTCTGCCTGG | 1 | 1 | 9 | SEQ ID NO. | 2037 |
| (N20)NGG | 19 | 17953247 | - | ACTTGGCCATGAGCGAGTGCCGG | 1 | 2 | 8 | SEQ ID NO. | 2038 |
| (N20)NGG | 19 | 17953264 | - | CTCCAGTCCATGATGTACTTGG | 1 | 4 | 29 | SEQ ID NO. | 2039 |
| (N20)NGG | 19 | 17953280 | - | CGGCTGATCCAGCCGCTCCAGG | 2 | 5 | 33 | SEQ ID NO. | 2040 |
| (N20)NGG | 19 | 17953296 | - | AAGGTCTCGGCGGCCCCGGCTGG | 1 | 2 | 12 | SEQ ID NO. | 2041 |
| (N20)NGG | 19 | 17953300 | - | GTGGAAGTCTCGGCGGCCCCGG | 1 | 2 | 11 | SEQ ID NO. | 2042 |
| (N20)NGG | 19 | 17953306 | - | GCCCACGTGGAAGGTCTCGGCGG | 1 | 2 | 12 | SEQ ID NO. | 2043 |
| (N20)NGG | 19 | 17953309 | - | GAGGCCCACGTGGAAGGTCTCGG | 1 | 2 | 30 | SEQ ID NO. | 2044 |

FIG. 8 cont.

| site type | site_chr omosome | site_start_ nucleotide | site_s trand | target_site_sequence_with_NGG | genome_wide_ hits_with_1_ or_less_mism atches | genome_wide_ hits_with_ 2_or_less_m ismatches | genome_wide_ hits_with_3_ or_less_mism atches | |
|---|---|---|---|---|---|---|---|---|
| (N20)NGG | 19 | 17953315 | - | CCCAGGGAGGCCCACGTGAAGG | | 1 | 4 | 102 SEQ ID NO. 2045 |
| (N20)NGG | 19 | 17953319 | - | GGGCCCAGGGAGGCCCACGTGG | | 2 | 8 | 88 SEQ ID NO. 2046 |
| (N20)NGG | 19 | 17953328 | - | GGCCACCAAGGGCCCAGGGAGG | | 1 | 8 | 112 SEQ ID NO. 2047 |
| (N20)NGG | 19 | 17953331 | - | CGTGGCCACCAAGGGCCCAGGG | | 1 | 6 | 45 SEQ ID NO. 2048 |
| (N20)NGG | 19 | 17953332 | - | TCGTGGCCACCAAGGGCCCAGG | | 1 | 3 | 42 SEQ ID NO. 2049 |
| (N20)NGG | 19 | 17953339 | - | CAGCCCGTCGTGGCCACCAAGG | | 1 | 1 | 46 SEQ ID NO. 2050 |
| (N20)NGG | 19 | 17953340 | - | CCAGCCCGTCGTGGCCACCAAG | | 1 | 4 | 59 SEQ ID NO. 2051 |
| (N20)NGG | 19 | 17953349 | - | GGAGCAGCCCCAGCCCGTCGTG | | 1 | 6 | 49 SEQ ID NO. 2052 |
| (N20)NGG | 19 | 17953370 | - | TGCCCCGTCACCAGCCACGCGG | | 1 | 1 | 14 SEQ ID NO. 2053 |
| (N20)NGG | 19 | 17953396 | - | CTCCTGTTCTCCCTGGGTCCAGG | | 2 | 9 | 115 SEQ ID NO. 2054 |
| (N20)NGG | 19 | 17953402 | - | CCTCACCTCCTGTTCTCCCTGGG | | 1 | 7 | 141 SEQ ID NO. 2055 |
| (N20)NGG | 19 | 17953403 | - | CCCTCACCTCCTGTTCTCCCTGG | | 1 | 9 | 145 SEQ ID NO. 2056 |
| (N20)NGG | 19 | 17953850 | + | CCCCAGCACCGCAGTGACCTGG | | 1 | 5 | 53 SEQ ID NO. 2057 |
| (N20)NGG | 19 | 17953857 | + | CACCGCAGTGACCTGCTGAGTGG | | 1 | 2 | 32 SEQ ID NO. 2058 |
| (N20)NGG | 19 | 17953858 | + | ACCGCAGTGACCTGGTGAGTGGG | | 1 | 2 | 15 SEQ ID NO. 2059 |
| (N20)NGG | 19 | 17953871 | + | GGTGAGTGGGGCCTCCCCGTGG | | 1 | 4 | 34 SEQ ID NO. 2060 |
| (N20)NGG | 19 | 17953872 | + | GTGAGTGGGGCCTCCCCGTGGG | | 1 | 1 | 10 SEQ ID NO. 2061 |
| (N20)NGG | 19 | 17953886 | + | CCCCGTGGGCCTCAGTCTCAAGG | | 1 | 6 | 39 SEQ ID NO. 2062 |
| (N20)NGG | 19 | 17953892 | + | GGGCCTCAGTCTCAAGGAGCAGG | | 1 | 2 | 44 SEQ ID NO. 2063 |
| (N20)NGG | 19 | 17953893 | + | GGCCTCAGTCTCAAGGAGCAGGG | | 1 | 2 | 36 SEQ ID NO. 2064 |
| (N20)NGG | 19 | 17953910 | + | GCAGGGTGAGTGTCTCAGCCTGG | | 1 | 6 | 70 SEQ ID NO. 2065 |
| (N20)NGG | 19 | 17953919 | + | GTGTCTCAGCCTGGCCGTGTTGG | | 1 | 4 | 32 SEQ ID NO. 2066 |
| (N20)NGG | 19 | 17953925 | + | CAGCCTGGCCGTGTTGGACCTGG | | 1 | 10 | 30 SEQ ID NO. 2067 |
| (N20)NGG | 19 | 17953930 | + | TGGCCGTGTTGGACCTGGCCCGG | | 1 | 1 | 15 SEQ ID NO. 2068 |
| (N20)NGG | 19 | 17953934 | + | CGTGTTGGACCTGGCCCGGATGG | | 1 | 2 | 8 SEQ ID NO. 2069 |
| (N20)NGG | 19 | 17953946 | + | GGCCCGGATGGCCGGAGAGCAGG | | 1 | 1 | 10 SEQ ID NO. 2070 |
| (N20)NGG | 19 | 17953954 | + | TGGCGCCAGAGCAGGCCCAGCCGG | | 1 | 4 | 34 SEQ ID NO. 2071 |
| (N20)NGG | 19 | 17953958 | + | GCGAGAGCAGGCCCAGCGCCGG | | 1 | 3 | 47 SEQ ID NO. 2072 |
| (N20)NGG | 19 | 17953959 | + | CGAGAGCAGGCCCAGCGGCCGGG | | 1 | 9 | 45 SEQ ID NO. 2073 |
| (N20)NGG | 19 | 17953981 | + | GAGAGCTGCTGAAGACTGTCAGG | | 1 | 3 | 36 SEQ ID NO. 2074 |
| (N20)NGG | 19 | 17953995 | + | ACTGTCAGGTGAGAGCCACCAGG | | 2 | 5 | 65 SEQ ID NO. 2075 |
| (N20)NGG | 19 | 17954001 | + | AGGTGAGAGCCACCAGGCTGTGG | | 3 | 27 | 432 SEQ ID NO. 2076 |
| (N20)NGG | 19 | 17954002 | + | GGTGAGAGCCACCAGGCTGTGGG | | 1 | 5 | 69 SEQ ID NO. 2077 |

FIG. 8 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 19 | 17954003 | + | GTGAGAGCCACCAGGCTGTGGGG | 1 | 8 | 71 | SEQ ID NO. 2078 |
| (N20)NGG | 19 | 17953816 | - | GGTGCTGGGGGCCGCCACAGGG | | 2 | 29 | SEQ ID NO. 2079 |
| (N20)NGG | 19 | 17953817 | - | CGGTGCTGGGGGCCGCCACAGG | | 1 | 23 | SEQ ID NO. 2080 |
| (N20)NGG | 19 | 17953827 | - | CAGGTCACTGCGGTGCTGGGGG | 1 | 4 | 41 | SEQ ID NO. 2081 |
| (N20)NGG | 19 | 17953828 | - | CCAGGTCACTGCGGTGCTGGGG | 1 | 4 | 52 | SEQ ID NO. 2082 |
| (N20)NGG | 19 | 17953829 | - | ACCAGGTCACTGCGGTGCTGGG | 1 | 4 | 24 | SEQ ID NO. 2083 |
| (N20)NGG | 19 | 17953830 | - | CACCAGGTCACTGCGGTGCTGG | 1 | 1 | 29 | SEQ ID NO. 2084 |
| (N20)NGG | 19 | 17953831 | - | TCACCAGGTCACTGCGGTGCTG | 1 | 1 | 17 | SEQ ID NO. 2085 |
| (N20)NGG | 19 | 17953837 | - | GCCCACTCACCAGGTCACTGCG | 1 | 5 | 45 | SEQ ID NO. 2086 |
| (N20)NGG | 19 | 17953846 | - | CGGGGAGGCGCCCACTCACCAG | 1 | 3 | 35 | SEQ ID NO. 2087 |
| (N20)NGG | 19 | 17953861 | - | TGAGACTGAGGCCCACGGGGAG | 1 | 5 | 104 | SEQ ID NO. 2088 |
| (N20)NGG | 19 | 17953864 | - | CCTTGAGACTGAGGCCCACGGG | 1 | 4 | 29 | SEQ ID NO. 2089 |
| (N20)NGG | 19 | 17953865 | - | TCCTTGAGACTGAGGCCCACGG | 2 | 2 | 41 | SEQ ID NO. 2090 |
| (N20)NGG | 19 | 17953866 | - | CTCCTTGAGACTGAGGCCCACG | 2 | 8 | 69 | SEQ ID NO. 2091 |
| (N20)NGG | 19 | 17953873 | - | CACCCTGCTCCTTGAGACTGAGG | 1 | 2 | 40 | SEQ ID NO. 2092 |
| (N20)NGG | 19 | 17953906 | - | GGGCCAGGTCCAACACGGCCAGG | 1 | 2 | 24 | SEQ ID NO. 2093 |
| (N20)NGG | 19 | 17953911 | - | CATCCGGGCCAGGTCCAACACGG | 1 | 2 | 19 | SEQ ID NO. 2094 |
| (N20)NGG | 19 | 17953921 | - | GCTCTCGCGCCATCCGGGCCAGG | 1 | 1 | 6 | SEQ ID NO. 2095 |
| (N20)NGG | 19 | 17953926 | - | GGCCTGCTCTCGCGCCATCCGG | 1 | 2 | 16 | SEQ ID NO. 2096 |
| (N20)NGG | 19 | 17953927 | - | GGGCCTGCTCTCGCGCCATCCG | 1 | 2 | 12 | SEQ ID NO. 2097 |
| (N20)NGG | 19 | 17953947 | - | CAGCAGCTCTCCGGCCGCTGGG | 1 | 1 | 38 | SEQ ID NO. 2098 |
| (N20)NGG | 19 | 17953948 | - | TCAGCAGCTCTCCGGCCGCTGG | 1 | 1 | 25 | SEQ ID NO. 2099 |
| (N20)NGG | 19 | 17953955 | - | ACAGTCTTCAGCAGCTCTCCGG | 1 | 4 | 45 | SEQ ID NO. 2100 |
| (N20)NGG | 19 | 17954206 | + | ACAGCTTTTACTTCCCCAATTGG | 1 | 5 | 52 | SEQ ID NO. 2101 |
| (N20)NGG | 19 | 17954211 | + | TTTTACTTCCCCAATTGGTTTGG | 1 | 3 | 55 | SEQ ID NO. 2102 |
| (N20)NGG | 19 | 17954212 | + | TTTACTTCCCCAATTGGTTTGGG | 1 | 2 | 32 | SEQ ID NO. 2103 |
| (N20)NGG | 19 | 17954216 | + | CTTCCCCAATTGGTTTGGCTGG | 1 | 1 | 14 | SEQ ID NO. 2104 |
| (N20)NGG | 19 | 17954235 | + | CTTGAGAAGTGCCACCGCTTCGG | 1 | 2 | 13 | SEQ ID NO. 2105 |
| (N20)NGG | 19 | 17954236 | + | TGGAGAAGTGCCACCGCTTCGG | 1 | 2 | 14 | SEQ ID NO. 2106 |
| (N20)NGG | 19 | 17954246 | + | CCACCGCTTCGGGCTACGCAAGG | 1 | 1 | 2 | SEQ ID NO. 2107 |
| (N20)NGG | 19 | 17954252 | + | CTTCGGGCTACGCAAGGATTTGG | 1 | 2 | 4 | SEQ ID NO. 2108 |
| (N20)NGG | 19 | 17954282 | + | TATCCTTGACCTGCCAGTCCTGG | 1 | 2 | 28 | SEQ ID NO. 2109 |
| (N20)NGG | 19 | 17954300 | + | CCTGGAGCACCTCTTTGCCCAGG | 1 | 7 | 57 | SEQ ID NO. 2110 |

FIG. 8 cont.

| site type | site chr omosome | site start nucleotide | site strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 19 | 17954303 | + | GGAGCACCTCTTTGCCCAGGTGG |   |   | 4 | 46 SEQ ID NO. 2111 |
| (N20)NGG | 19 | 17954304 | + | GAGCACCTCTTTGCCCAGGTGGG | 1 |   | 6 | 43 SEQ ID NO. 2112 |
| (N20)NGG | 19 | 17954305 | + | AGCACCTCTTTGCCCAGGTGGGG | 1 |   | 7 | 64 SEQ ID NO. 2113 |
| (N20)NGG | 19 | 17954315 | + | TGCCCAGGTGGGGTTCTGCCTGG | 3 |   | 4 | 64 SEQ ID NO. 2114 |
| (N20)NGG | 19 | 17954316 | + | GCCCAGGTGGGGTTCTGCCTGGG | 2 |   | 4 | 58 SEQ ID NO. 2115 |
| (N20)NGG | 19 | 17954317 | + | CCCAGGTGGGGTTCTGCCTGGGG | 2 |   | 7 | 75 SEQ ID NO. 2116 |
| (N20)NGG | 19 | 17954163 | - | GTGAGGAGAGGAGAGAACCCTGG | 1 |   | 6 | 147 SEQ ID NO. 2117 |
| (N20)NGG | 19 | 17954175 | - | GAAGTAAAAGCTGTGAGGAGAGG | 1 |   | 7 | 74 SEQ ID NO. 2118 |
| (N20)NGG | 19 | 17954180 | - | TTGGGGAAGTAAAAGCTGTGAGG | 1 |   | 6 | 70 SEQ ID NO. 2119 |
| (N20)NGG | 19 | 17954197 | - | TCTCCAGCCCAAACCAATTGGGG | 1 |   | 1 | 40 SEQ ID NO. 2120 |
| (N20)NGG | 19 | 17954198 | - | TTCTCCAGCCCAAACCAATTGGG | 1 |   | 3 | 53 SEQ ID NO. 2121 |
| (N20)NGG | 19 | 17954199 | - | CTTCTCCAGCCCAAACCAATTGG | 1 |   | 3 | 46 SEQ ID NO. 2122 |
| (N20)NGG | 19 | 17954224 | - | CCTTGCGTAGCCCGAAGCGGTGG | 1 |   | 1 | 5 SEQ ID NO. 2123 |
| (N20)NGG | 19 | 17954227 | - | AATCCTTGCGTAGCCCGAAGCGG | 1 |   | 1 | 3 SEQ ID NO. 2124 |
| (N20)NGG | 19 | 17954253 | - | TGGCAGGTCAAGGATAGCACTGG | 1 |   | 1 | 40 SEQ ID NO. 2125 |
| (N20)NGG | 19 | 17954263 | - | GCTCCAGGACTGGCAGGTCAAGG | 1 |   | 3 | 62 SEQ ID NO. 2126 |
| (N20)NGG | 19 | 17954269 | - | AGAGGTGCTCCAGGACTGGCAGG | 1 |   | 4 | 60 SEQ ID NO. 2127 |
| (N20)NGG | 19 | 17954273 | - | GCAAAGAGGTGCTCCAGGACTGG | 1 |   | 2 | 34 SEQ ID NO. 2128 |
| (N20)NGG | 19 | 17954278 | - | CCTGGGCAAAGAGGTGCTCCAGG | 1 |   | 3 | 54 SEQ ID NO. 2129 |
| (N20)NGG | 19 | 17954287 | - | AGAACCCACCTGGGCAAAGAGAG | 2 |   | 2 | 46 SEQ ID NO. 2130 |
| (N20)NGG | 19 | 17954295 | - | CCCCAGGCAGAACCCCACCTGGG | 2 |   | 6 | 89 SEQ ID NO. 2131 |
| (N20)NGG | 19 | 17954296 | - | ACCCCAGGCAGAACCCCACCTGG | 1 |   | 4 | 61 SEQ ID NO. 2132 |
| (N20)NGG | 19 | 17954585 | + | CTGATGGGACCATCCCCTGTAGG | 1 |   | 2 | 22 SEQ ID NO. 2133 |
| (N20)NGG | 19 | 17954620 | + | GTACCACTCCCTCTTTGCTCTGG | 1 |   | 2 | 24 SEQ ID NO. 2134 |
| (N20)NGG | 19 | 17954626 | + | CTCCCTCTTTTGCTCTGGCCACGG | 1 |   | 2 | 126 SEQ ID NO. 2135 |
| (N20)NGG | 19 | 17954629 | + | CCTCTTTTGCTCTGGCCACGGAGG | 1 |   | 1 | 45 SEQ ID NO. 2136 |
| (N20)NGG | 19 | 17954643 | + | CCACGGAGGACCTGTCCTGCTGG | 1 |   | 1 | 24 SEQ ID NO. 2137 |
| (N20)NGG | 19 | 17954671 | + | CCCGAGCCACATCTTCTCCGTGG | 1 |   | 3 | 17 SEQ ID NO. 2138 |
| (N20)NGG | 19 | 17954674 | + | GAGCCACATCTTCTCCGTGGAGG | 1 |   | 2 | 23 SEQ ID NO. 2139 |
| (N20)NGG | 19 | 17954703 | + | GCACCCAAGTCCTGCTGTACAGG | 1 |   | 4 | 22 SEQ ID NO. 2140 |
| (N20)NGG | 19 | 17954709 | + | AAGTCCTGCTGTACAGGATTCGG | 1 |   | 1 | 32 SEQ ID NO. 2141 |
| (N20)NGG | 19 | 17954713 | + | CCTGCTGTACAGGATTCGGTAGG | 1 |   | 1 | 8 SEQ ID NO. 2142 |
| (N20)NGG | 19 | 17954572 | - | GGCAGGATGCCTACAGGGGATGG | 1 |   | 3 | 71 SEQ ID NO. 2143 |

FIG. 8 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 19 | 17954576 | - | CACAGGCAGGATGCCTACAGGGG | 1 | 8 | 69 | SEQ ID NO. 2144 |
| (N20)NGG | 19 | 17954577 | - | ACACAGGCAGGATGCCTACAGGG | 1 | 5 | 54 | SEQ ID NO. 2145 |
| (N20)NGG | 19 | 17954578 | - | TACACAGGCAGGATGCCTACAGG | 1 | 2 | 20 | SEQ ID NO. 2146 |
| (N20)NGG | 19 | 17954589 | - | AGAGGGAGTGGTACACAGGCAGG | 1 | 5 | 64 | SEQ ID NO. 2147 |
| (N20)NGG | 19 | 17954593 | - | GCAAAGAGGGAGTGGTACACAGG | 1 | 3 | 32 | SEQ ID NO. 2148 |
| (N20)NGG | 19 | 17954601 | - | TGGCCAGAGCAAAGAGGGAGTGG | 2 | 15 | 482 | SEQ ID NO. 2149 |
| (N20)NGG | 19 | 17954606 | - | CTCCGTGGCCAGAGCAAAGAGGG | 1 | 2 | 39 | SEQ ID NO. 2150 |
| (N20)NGG | 19 | 17954607 | - | CCTCCGTGGCCAGAGCAAAGAGG | 1 | 7 | 41 | SEQ ID NO. 2151 |
| (N20)NGG | 19 | 17954621 | - | CCAGCAGGACAGGTCTCCGTGG | 1 | 1 | 32 | SEQ ID NO. 2152 |
| (N20)NGG | 19 | 17954631 | - | TCGGGGGAACCAGCAGGACAGG | 1 | 1 | 20 | SEQ ID NO. 2153 |
| (N20)NGG | 19 | 17954636 | - | GTGGCTCGGGGGAACCAGCAGG | 1 | 2 | 25 | SEQ ID NO. 2154 |
| (N20)NGG | 19 | 17954646 | - | CGGAGAAGATGTGCTCGGGGGG | 1 | 1 | 21 | SEQ ID NO. 2155 |
| (N20)NGG | 19 | 17954647 | - | ACGGAGAAGATGTGCTCGGGGG | 1 | 2 | 17 | SEQ ID NO. 2156 |
| (N20)NGG | 19 | 17954648 | - | CACGGAGAAGATGTGGCTCGGG | 1 | 2 | 12 | SEQ ID NO. 2157 |
| (N20)NGG | 19 | 17954649 | - | CCACGGAGAAGATGTGGCTCGG | 1 | 4 | 25 | SEQ ID NO. 2158 |
| (N20)NGG | 19 | 17954650 | - | TCCACGGAGAAGATGTGGCTCG | 1 | 3 | 31 | SEQ ID NO. 2159 |
| (N20)NGG | 19 | 17954655 | - | CATCCTCCACGGAGAAGATGTGG | 1 | 3 | 32 | SEQ ID NO. 2160 |
| (N20)NGG | 19 | 17954666 | - | TTGGGTGCTGGCATCCTCCACGG | 1 | 3 | 53 | SEQ ID NO. 2161 |
| (N20)NGG | 19 | 17954678 | - | GTACAGCAGGACTTGGGTGCTGG | 1 | 3 | 38 | SEQ ID NO. 2162 |
| (N20)NGG | 19 | 17954684 | - | AATCCTGTACAGCAGGACTTGGG | 1 | 2 | 38 | SEQ ID NO. 2163 |
| (N20)NGG | 19 | 17954685 | - | GAATCCTGTACAGCAGGACTTGG | 1 | 2 | 25 | SEQ ID NO. 2164 |
| (N20)NGG | 19 | 17954691 | - | CCTACCGAATCCTGTACAGCAGG | 1 | 1 | 2 | SEQ ID NO. 2165 |
| (N20)NGG | 19 | 17955045 | + | CCCCAGGCAAGTTGCACTCATGG | 1 | 4 | 47 | SEQ ID NO. 2166 |
| (N20)NGG | 19 | 17955105 | + | TTCATGCAGCCTCTTTGTCCACGG | 1 | 2 | 48 | SEQ ID NO. 2167 |
| (N20)NGG | 19 | 17955108 | + | ATGCAGCCTCTTTGTCCACGGAGG | 1 | 2 | 13 | SEQ ID NO. 2168 |
| (N20)NGG | 19 | 17955112 | + | AGCCTCTTGTCCACGGAGGCTGG | 1 | 1 | 19 | SEQ ID NO. 2169 |
| (N20)NGG | 19 | 17955140 | + | TGCATGTGCTGCTGCCCGCTCGG | 1 | 2 | 22 | SEQ ID NO. 2170 |
| (N20)NGG | 19 | 17955141 | + | GCATGTGCTGCTGCCCGCTCGGG | 1 | 3 | 27 | SEQ ID NO. 2171 |
| (N20)NGG | 19 | 17955142 | + | CATGTGCTGCTGCCCGCTCGGGG | 1 | 2 | 7 | SEQ ID NO. 2172 |
| (N20)NGG | 19 | 17955148 | + | CTGCTGCCCGCTCGGGGCCCGG | 1 | 4 | 52 | SEQ ID NO. 2173 |
| (N20)NGG | 19 | 17955149 | + | TGCTGCCCGCTCGGGGCCCGGG | 1 | 1 | 51 | SEQ ID NO. 2174 |
| (N20)NGG | 19 | 17955178 | + | CAGGCCTATCTTTCTCCTTTGG | 1 | 2 | 27 | SEQ ID NO. 2175 |
| (N20)NGG | 19 | 17955179 | + | AGCGCCTATCTTTCTCCTTTGGG | 1 | 2 | 23 | SEQ ID NO. 2176 |

FIG. 8 cont.

| site type | site chromosome | site start nucleotide | site strand | target site sequence with NGG | genome wide hits with 1 or less mismatches | genome wide hits with 2 or less mismatches | genome wide hits with 3 or less mismatches | |
|---|---|---|---|---|---|---|---|---|
| (N20)NGG | 19 | 17955180 | + | GCGCCTATCTTTCTCCTTTGGGG | 1 | 1 | 20 | SEQ ID NO. 2177 |
| (N20)NGG | 19 | 17955189 | + | TTTCTCCTTTGGGACCACTTGG | 1 | 3 | 51 | SEQ ID NO. 2178 |
| (N20)NGG | 19 | 17955195 | + | CTTTGGGACCACTTGGCTGAGG | 1 | 4 | 72 | SEQ ID NO. 2179 |
| (N20)NGG | 19 | 17955210 | + | GGCTGAGGACCTGTGCGTGCAGG | 1 | 4 | 33 | SEQ ID NO. 2180 |
| (N20)NGG | 19 | 17955219 | + | CCTGTGCGTGCAGGCTGCCAAGG | 1 | 4 | 40 | SEQ ID NO. 2181 |
| (N20)NGG | 19 | 17955226 | + | GTGCAGGCTGCCAAGGCCAGCGG | 1 | 10 | 130 | SEQ ID NO. 2182 |
| (N20)NGG | 19 | 17955244 | + | AGCGGTGAGTGCATCCCTAGTGG | 2 | 2 | 6 | SEQ ID NO. 2183 |
| (N20)NGG | 19 | 17955249 | + | TGAGTGCATCCCTAGTGGATCGG | 1 | 2 | 31 | SEQ ID NO. 2184 |
| (N20)NGG | 19 | 17955250 | + | GAGTGCATCCCTAGTGGATCGGG | 1 | 1 | 10 | SEQ ID NO. 2185 |
| (N20)NGG | 19 | 17955023 | - | CCATGAGTGCAACTTGCCTGGGG | 1 | 12 | 546 | SEQ ID NO. 2186 |
| (N20)NGG | 19 | 17955024 | - | GCCATGAGTGCAACTTGCCTGGG | 1 | 9 | 338 | SEQ ID NO. 2187 |
| (N20)NGG | 19 | 17955025 | - | TGCCATGAGTGCAACTTGCCTGG | 1 | 3 | 34 | SEQ ID NO. 2188 |
| (N20)NGG | 19 | 17955048 | - | AGGGGCTCTCTTCACTTGGAGG | 1 | 1 | 17 | SEQ ID NO. 2189 |
| (N20)NGG | 19 | 17955051 | - | ATCAGGGCGTCTCTTCACTTGG | 1 | 1 | 12 | SEQ ID NO. 2190 |
| (N20)NGG | 19 | 17955066 | - | CATGAACCTGAGGGATCAGGGG | 1 | 2 | 19 | SEQ ID NO. 2191 |
| (N20)NGG | 19 | 17955067 | - | GCATGAACCTGAGGGATCAGGG | 1 | 1 | 23 | SEQ ID NO. 2192 |
| (N20)NGG | 19 | 17955068 | - | TGCATGAACCTGAGGGATCAGG | 1 | 1 | 21 | SEQ ID NO. 2193 |
| (N20)NGG | 19 | 17955074 | - | AGAGGCTGCATGAACGCTCAGG | 1 | 2 | 24 | SEQ ID NO. 2194 |
| (N20)NGG | 19 | 17955075 | - | AAGAGGCTGCATGAACGCTCAG | 1 | 2 | 34 | SEQ ID NO. 2195 |
| (N20)NGG | 19 | 17955092 | - | CACCAGCTCCGTGCAAGAGG | 1 | 3 | 27 | SEQ ID NO. 2196 |
| (N20)NGG | 19 | 17955100 | - | ATGCAGGCACCAGCCTCCGTGG | 1 | 3 | 36 | SEQ ID NO. 2197 |
| (N20)NGG | 19 | 17955115 | - | AGCGGGCAGCAGCACATGCAGG | 2 | 4 | 58 | SEQ ID NO. 2198 |
| (N20)NGG | 19 | 17955116 | - | GAGCGGGCAGCAGCACATGCAG | 1 | 3 | 47 | SEQ ID NO. 2199 |
| (N20)NGG | 19 | 17955132 | - | GGGGGCCCGGGCCCCGAGCGGG | 1 | 13 | 120 | SEQ ID NO. 2200 |
| (N20)NGG | 19 | 17955133 | - | GGGGGCCCGGGCCCCGAGCGG | 1 | 8 | 125 | SEQ ID NO. 2201 |
| (N20)NGG | 19 | 17955143 | - | ATAGGCGCTGGGGGCCCGGGG | 1 | 2 | 13 | SEQ ID NO. 2202 |
| (N20)NGG | 19 | 17955144 | - | GATAGGCGCTGGGGGCCCGGG | 1 | 2 | 33 | SEQ ID NO. 2203 |
| (N20)NGG | 19 | 17955145 | - | AGATAGGCGCTGGGGGCCCGG | 1 | 1 | 26 | SEQ ID NO. 2204 |
| (N20)NGG | 19 | 17955150 | - | AGAAAGATAGGCGCTGGGGGG | 1 | 1 | 45 | SEQ ID NO. 2205 |
| (N20)NGG | 19 | 17955151 | - | GGAGAAAGATAGGCGCTGGGGG | 1 | 9 | 159 | SEQ ID NO. 2206 |
| (N20)NGG | 19 | 17955152 | - | AGGAGAAAGATAGGCGCTGGGG | 1 | 3 | 129 | SEQ ID NO. 2207 |
| (N20)NGG | 19 | 17955153 | - | AAGGAGAAAGATAGGCGCTGGG | 1 | 5 | 50 | SEQ ID NO. 2208 |
| (N20)NGG | 19 | 17955154 | - | AAAGGAGAAAGATAGGCGCTGG | 1 | 5 | 45 | SEQ ID NO. 2209 |

FIG. 8 cont.

| site_type | site_chr omosome | site_start_ nucleotide | site_s trand | target_site_sequence_with_NGG | genome_wide_ hits_with_1_ or_less_mism atches | genome_wide_ hits_with_ 2_or_less_m ismatches | genome_wide_ hits_with_3_ or_less_mism atches | |
|---|---|---|---|---|---|---|---|---|
| (N20)NGG | 19 | 17955155 | - | CAAAGGAGAAAGATAGGCGCTGG | 1 | 2 | 48 | SEQ ID NO. 2210 |
| (N20)NGG | 19 | 17955161 | - | GGTCCCAAAGGAGAAAGATAGG | 1 | 7 | 46 | SEQ ID NO. 2211 |
| (N20)NGG | 19 | 17955172 | - | CTCAGCCAAGTGGTCCCAAAGG | 1 | 5 | 40 | SEQ ID NO. 2212 |
| (N20)NGG | 19 | 17955182 | - | CGCACAGGTCCTCAGCCAAGTGG | 1 | 3 | 20 | SEQ ID NO. 2213 |
| (N20)NGG | 19 | 17955197 | - | CCTTGGCAGCCTGCACGCACAGG | 1 | 5 | 30 | SEQ ID NO. 2214 |
| (N20)NGG | 19 | 17955214 | - | GATGCACTCACCGCTGGCCTTGG | 1 | 1 | 22 | SEQ ID NO. 2215 |
| (N20)NGG | 19 | 17955220 | - | ACTAGGGATGCACTCACCGCTGG | 1 | 2 | 4 | SEQ ID NO. 2216 |

FIG. 8 cont.

| site_type | site_chromosome | site_start_nucleotide | site_strand | target_site_sequence with NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 13 | 108860971 | + | GAACGAATACAGAGAAAAGTAAAGG | 1 | 4 | 132 | SEQ ID NO. 2217 |
| (N20)NGG | 13 | 108860999 | + | CAGAAAAAATCAGACACTTCAGG | 2 | 4 | 102 | SEQ ID NO. 2218 |
| (N20)NGG | 13 | 108861000 | + | AGAAAAAATCAGACACTTCAGGG | 1 | 7 | 193 | SEQ ID NO. 2219 |
| (N20)NGG | 13 | 108861017 | + | TCAGGGAATTTTTAGATTCTTGG | 1 | 4 | 97 | SEQ ID NO. 2220 |
| (N20)NGG | 13 | 108861120 | + | TCAGCTAGAAAGAGAGAGAATGG | 1 | 24 | 320 | SEQ ID NO. 2221 |
| (N20)NGG | 13 | 108861127 | + | GAAAGAGAGAGAATGGCCTATGG | 1 | 9 | 187 | SEQ ID NO. 2222 |
| (N20)NGG | 13 | 108861187 | + | TTGCTTAATTTACCTAGAGATGG | 1 | 3 | 71 | SEQ ID NO. 2223 |
| (N20)NGG | 13 | 108861229 | + | TTAAACTACAGAACACCCACTGG | 1 | 2 | 40 | SEQ ID NO. 2224 |
| (N20)NGG | 13 | 108861238 | + | AGAACACCCACTGGAACTCATGG | 1 | 5 | 43 | SEQ ID NO. 2225 |
| (N20)NGG | 13 | 108861247 | + | ACTGGAACTCATGGAGATGCTGG | 1 | 3 | 54 | SEQ ID NO. 2226 |
| (N20)NGG | 13 | 108861301 | + | AAGCCAAGATGTTTACAGAAAGG | 1 | 8 | 83 | SEQ ID NO. 2227 |
| (N20)NGG | 13 | 108861434 | + | GTTCAGCACTTGAGCAAAAGTGG | 2 | 4 | 30 | SEQ ID NO. 2228 |
| (N20)NGG | 13 | 108861443 | + | TTGAGCAAAAGTGGCTTATACGG | 1 | 1 | 42 | SEQ ID NO. 2229 |
| (N20)NGG | 13 | 108861456 | + | GCTTATACGGATGATCATAAAGG | 1 | 2 | 11 | SEQ ID NO. 2230 |
| (N20)NGG | 13 | 108861469 | + | ATCATAAAGGATTTAAAGCTTGG | 1 | 7 | 76 | SEQ ID NO. 2231 |
| (N20)NGG | 13 | 108861543 | + | GCATAATGTCACTACAGATCTGG | 1 | 2 | 17 | SEQ ID NO. 2232 |
| (N20)NGG | 13 | 108861557 | + | CAGATCTGGAAAAAGTCTGTAGG | 1 | 5 | 67 | SEQ ID NO. 2233 |
| (N20)NGG | 13 | 108861580 | + | CAACTGCATGATCCTTCTGTAGG | 1 | 3 | 22 | SEQ ID NO. 2234 |
| (N20)NGG | 13 | 108861663 | + | AGATATTGAGCACATTGAGAAGG | 1 | 3 | 47 | SEQ ID NO. 2235 |
| (N20)NGG | 13 | 108861706 | + | TACATAGAAACCAAGCTAGATGG | 1 | 3 | 65 | SEQ ID NO. 2236 |
| (N20)NGG | 13 | 108861733 | + | CGTATGCAAATGCACAAAGATGG | 1 | 6 | 63 | SEQ ID NO. 2237 |
| (N20)NGG | 13 | 108861763 | + | TATAAATACTTCTCTCGAAATGG | 1 | 3 | 55 | SEQ ID NO. 2238 |
| (N20)NGG | 13 | 108861787 | + | TATAACTACACTGATCAGTTTGG | 1 | 3 | 28 | SEQ ID NO. 2239 |
| (N20)NGG | 13 | 108861805 | + | TTTGGTGCTTCTCCTACTCGAAGG | 1 | 3 | 41 | SEQ ID NO. 2240 |
| (N20)NGG | 13 | 108861868 | + | ATACAAATCTGTATTCTTGATGG | 1 | 4 | 80 | SEQ ID NO. 2241 |
| (N20)NGG | 13 | 108861879 | + | TATTCTTGATGGTGAGATGATGG | 1 | 5 | 52 | SEQ ID NO. 2242 |
| (N20)NGG | 13 | 108861915 | + | TACACAAACTTTCATGCAAAAGG | 1 | 6 | 92 | SEQ ID NO. 2243 |
| (N20)NGG | 13 | 108861916 | + | ACACAAACTTTCATGCAAAAGGG | 1 | 9 | 109 | SEQ ID NO. 2244 |
| (N20)NGG | 13 | 108861942 | + | TAAGTTTGATATTAAAAGAATGG | 1 | 13 | 223 | SEQ ID NO. 2245 |
| (N20)NGG | 13 | 108861948 | + | TGATATTAAAAGAATGTAGAGG | 1 | 7 | 109 | SEQ ID NO. 2246 |
| (N20)NGG | 13 | 108861993 | + | TTGTGTTTTTGATGTATTGATGG | 1 | 8 | 188 | SEQ ID NO. 2247 |
| (N20)NGG | 13 | 108862012 | + | ATGGTTAATAATAAAAAGCTAGG | 1 | 10 | 140 | SEQ ID NO. 2248 |
| (N20)NGG | 13 | 108862013 | + | TGGTTAATAATAAAAAGCTAGGG | 1 | 5 | 129 | SEQ ID NO. 2249 |
| (N20)NGG | 13 | 108862034 | + | GGCATGAGACTCTGAGAAAGAGG | 2 | 6 | 82 | SEQ ID NO. 2250 |

FIG. 9

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 13 | 108862072 | + | AGTATTTTACACCAATTCCAGG |   | 2 | 2 | 72 SEQ ID NO. 2251 |
| (N20)NGG | 13 | 108862161 | + | AGCAATAGATAAAGAGAAGAGAG |   | 1 | 13 | 203 SEQ ID NO. 2252 |
| (N20)NGG | 13 | 108862162 | + | GCAATAGATAAAGAGAAGAGGG |   | 2 | 13 | 232 SEQ ID NO. 2253 |
| (N20)NGG | 13 | 108862170 | + | TAAAAGAGAAGAGGGAATTATGG |   | 1 | 13 | 241 SEQ ID NO. 2254 |
| (N20)NGG | 13 | 108862210 | + | ATCTACAAGCCAGACAAAAGAGAG |   | 2 | 10 | 219 SEQ ID NO. 2255 |
| (N20)NGG | 13 | 108862216 | + | AAGCCACACAAAAGAGGTGAAGG |   | 2 | 13 | 147 SEQ ID NO. 2256 |
| (N20)NGG | 13 | 108862217 | + | AGCCAGACAAAAGAGGTGAAGGG |   | 1 | 7 | 94 SEQ ID NO. 2257 |
| (N20)NGG | 13 | 108862220 | + | CAGACAAAAGAGGTGAACGGTGG |   | 1 | 5 | 107 SEQ ID NO. 2258 |
| (N20)NGG | 13 | 108862249 | + | ATTAAACCAGAGTATGTCAGTGG |   | 1 | 4 | 25 SEQ ID NO. 2259 |
| (N20)NGG | 13 | 108862257 | + | AGAGTATGTCAGTGGACTAATGG |   | 1 | 3 | 40 SEQ ID NO. 2260 |
| (N20)NGG | 13 | 108862266 | + | CAGTGGACTAATGGATGAATTGG |   | 2 | 6 | 92 SEQ ID NO. 2261 |
| (N20)NGG | 13 | 108862282 | + | GAATTGGACATTTTAATTGTTGG |   | 1 | 8 | 108 SEQ ID NO. 2262 |
| (N20)NGG | 13 | 108862285 | + | TTGGACATTTTAATTGTTGGAGG |   | 1 | 5 | 89 SEQ ID NO. 2263 |
| (N20)NGG | 13 | 108862292 | + | TTTTAATTGTTGGAGGATATTGG |   | 1 | 3 | 107 SEQ ID NO. 2264 |
| (N20)NGG | 13 | 108862293 | + | TTTAATTGTTGGAGGATATTGGG |   | 1 | 7 | 118 SEQ ID NO. 2265 |
| (N20)NGG | 13 | 108862294 | + | TTAATTGTTGGAGGATATTGGGG |   | 1 | 4 | 60 SEQ ID NO. 2266 |
| (N20)NGG | 13 | 108862300 | + | GTTGGAGGATATTGGGGTAAAGG |   | 1 | 4 | 35 SEQ ID NO. 2267 |
| (N20)NGG | 13 | 108862307 | + | GATATTGGGGTAAAGGATCACGG |   | 1 | 2 | 25 SEQ ID NO. 2268 |
| (N20)NGG | 13 | 108862308 | + | ATATTGGGGTAAAGGATCACGGG |   | 1 | 3 | 23 SEQ ID NO. 2269 |
| (N20)NGG | 13 | 108862309 | + | TATTGGGGTAAAGGATCACGGGG |   | 1 | 2 | 16 SEQ ID NO. 2270 |
| (N20)NGG | 13 | 108862312 | + | TGGGGTAAAGGATCACGGGGTGG |   | 1 | 2 | 18 SEQ ID NO. 2271 |
| (N20)NGG | 13 | 108862360 | + | GTAGCAGAAGCCCCTCCTCCTGG |   | 1 | 2 | 35 SEQ ID NO. 2272 |
| (N20)NGG | 13 | 108862399 | + | TTTCATACTCTCTCTCGTGTTGG |   | 1 | 2 | 23 SEQ ID NO. 2273 |
| (N20)NGG | 13 | 108862400 | + | TTCATACTCTCTCTCGTGTTGGG |   | 1 | 1 | 30 SEQ ID NO. 2274 |
| (N20)NGG | 13 | 108862405 | + | ACTCTCTCTCGTGTTGGGTCTGG |   | 1 | 1 | 13 SEQ ID NO. 2275 |
| (N20)NGG | 13 | 108862434 | + | CATGAAAGAACTGTATGATCTGG |   | 1 | 2 | 41 SEQ ID NO. 2276 |
| (N20)NGG | 13 | 108862435 | + | ATGAAAGAACTGTATGATCTGG |   | 1 | 4 | 76 SEQ ID NO. 2277 |
| (N20)NGG | 13 | 108862446 | + | GTATGATCTGGGTTTGAAATTGG |   | 1 | 2 | 51 SEQ ID NO. 2278 |
| (N20)NGG | 13 | 108862457 | + | GTTTGAAATTGGCCAAGTATTGG |   | 1 | 5 | 44 SEQ ID NO. 2279 |
| (N20)NGG | 13 | 108862501 | + | CCACCAAGCAGCATTTTATGTGG |   | 1 | 3 | 44 SEQ ID NO. 2280 |
| (N20)NGG | 13 | 108862597 | + | CCCAGTGATATGTATAAAACTGG |   | 1 | 4 | 34 SEQ ID NO. 2281 |
| (N20)NGG | 13 | 108862644 | + | TGAAAAGATAAGAGATGACAAGG |   | 1 | 10 | 202 SEQ ID NO. 2282 |
| (N20)NGG | 13 | 108862649 | + | AGATAAGAGATGACAAGGAGTGG |   | 2 | 11 | 152 SEQ ID NO. 2283 |
| (N20)NGG | 13 | 108862668 | + | GTGGCATGAGTGCATGACCCTGG |   | 1 | 1 | 50 SEQ ID NO. 2284 |

FIG. 9 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | | |
|---|---|---|---|---|---|---|---|---|---|
| (N20)NGG | 13 | 108862688 | + | TGGACGACCTAGAACAACTTAGG | | 2 | 8 | SEQ ID NO. | 2285 |
| (N20)NGG | 13 | 108862689 | + | GGACGACCTAGAACAACTTAGGG | | 2 | 6 | SEQ ID NO. | 2286 |
| (N20)NGG | 13 | 108862690 | + | GACGACCTAGAACAACTTAGGGG | | 1 | 12 | SEQ ID NO. | 2287 |
| (N20)NGG | 13 | 108862691 | + | ACGACCTAGAACAACTTAGGGGG | | 1 | 14 | SEQ ID NO. | 2288 |
| (N20)NGG | 13 | 108862695 | + | CCTAGAACAACTTAGGGGGAAGG | | 1 | 21 | SEQ ID NO. | 2289 |
| (N20)NGG | 13 | 108862702 | + | CAACTTAGGGGGAAGGCATCTGG | | 4 | 59 | SEQ ID NO. | 2290 |
| (N20)NGG | 13 | 108862732 | + | GCATCTAAACACCTTTATATAGG | 1 | 4 | 38 | SEQ ID NO. | 2291 |
| (N20)NGG | 13 | 108862735 | + | TCTAAACACCTTTATATAGGTGG | 1 | 2 | 40 | SEQ ID NO. | 2292 |
| (N20)NGG | 13 | 108862763 | + | ATGAACCACAAGAAAAAAAGCGG | 1 | 8 | 286 | SEQ ID NO. | 2293 |
| (N20)NGG | 13 | 108862795 | + | CCAAAGATGAAGAAAAGTTATTGG | 1 | 10 | 120 | SEQ ID NO. | 2294 |
| (N20)NGG | 13 | 108862885 | + | GTAGAGTTTTGTGTTATGAGTGG | 1 | 2 | 38 | SEQ ID NO. | 2295 |
| (N20)NGG | 13 | 108862914 | + | TAGCCAGCCAAAGCCTGACCTGG | 1 | 2 | 19 | SEQ ID NO. | 2296 |
| (N20)NGG | 13 | 108862936 | + | GAGAACAGAATTGCAGAATTTGG | 1 | 8 | 110 | SEQ ID NO. | 2297 |
| (N20)NGG | 13 | 108862939 | + | AACAGAATTGCAGAATTTGGTGG | 1 | 6 | 106 | SEQ ID NO. | 2298 |
| (N20)NGG | 13 | 108862960 | + | GGTTATATAGTACAAAATCCAGG | 1 | 2 | 21 | SEQ ID NO. | 2299 |
| (N20)NGG | 13 | 108862987 | + | GACACGTACTGTGTAATTGCAGG | 1 | 1 | 13 | SEQ ID NO. | 2300 |
| (N20)NGG | 13 | 108862988 | + | ACACGTACTGTGTAATTGCAGGG | 1 | 2 | 19 | SEQ ID NO. | 2301 |
| (N20)NGG | 13 | 108863054 | + | ATGATGTTGTCAAGCCTGCATGG | 1 | 5 | 38 | SEQ ID NO. | 2302 |
| (N20)NGG | 13 | 108863093 | + | AGAACAAAAGCTTTGTACCATGG | 1 | 3 | 40 | SEQ ID NO. | 2303 |
| (N20)NGG | 13 | 108863164 | + | GCCCGTGAATATGATTGCTATGG | 1 | 2 | 7 | SEQ ID NO. | 2304 |
| (N20)NGG | 13 | 108863205 | + | TACAGACTTGAACCAACTGAAGG | 1 | 1 | 38 | SEQ ID NO. | 2305 |
| (N20)NGG | 13 | 108863218 | + | CAACTGAAGGAAGTATTCTCAGG | 1 | 2 | 41 | SEQ ID NO. | 2306 |
| (N20)NGG | 13 | 108863256 | + | CGAGCAGACTCCTGAAGAAATGG | 1 | 2 | 37 | SEQ ID NO. | 2307 |
| (N20)NGG | 13 | 108863285 | + | TGATTGCTGATTTAGAATATCGG | 1 | 4 | 88 | SEQ ID NO. | 2308 |
| (N20)NGG | 13 | 108863294 | + | ATTTAGAATATCGGTATTCCTGG | 1 | 1 | 18 | SEQ ID NO. | 2309 |
| (N20)NGG | 13 | 108863295 | + | TTTAGAATATCGGTATTCCTGGG | 1 | 2 | 27 | SEQ ID NO. | 2310 |
| (N20)NGG | 13 | 108863340 | + | TCGACGCCACACCGTTTATTTGG | 1 | 1 | 2 | SEQ ID NO. | 2311 |
| (N20)NGG | 13 | 108863382 | + | TGACCTGAGTACCAAAAATGAGG | 1 | 3 | 33 | SEQ ID NO. | 2312 |
| (N20)NGG | 13 | 108863383 | + | GACCTGAGTACCAAAAATGAGGG | 1 | 2 | 32 | SEQ ID NO. | 2313 |
| (N20)NGG | 13 | 108863384 | + | ACCTGAGTACCAAAAATGAGGGG | 1 | 5 | 34 | SEQ ID NO. | 2314 |
| (N20)NGG | 13 | 108863390 | + | GTACCAAAAATGAGGGGACAAGG | 2 | 2 | 41 | SEQ ID NO. | 2315 |
| (N20)NGG | 13 | 108863409 | + | AAGGTTAGCTATTAAAGCCTTGG | 1 | 4 | 27 | SEQ ID NO. | 2316 |
| (N20)NGG | 13 | 108863417 | + | CTATTAAAGCCTTCGAGCTTCGG | 1 | 2 | 31 | SEQ ID NO. | 2317 |
| (N20)NGG | 13 | 108863425 | + | GCCTTGGAGCTTCGGTTTCATGG | 1 | 3 | 18 | SEQ ID NO. | 2318 |

FIG. 9 cont.

| site type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 13 | 108863454 | + | AGTAGTTTCTTCTTGTTTAGCTGAGG | 1 | 5 | 47 | SEQ ID NO. 2319 |
| (N20)NGG | 13 | 108863455 | + | GTAGTTTCTTCTTGTTTAGCTGAGGG | 1 | 4 | 51 | SEQ ID NO. 2320 |
| (N20)NGG | 13 | 108863476 | + | GGAGTGTCTCATGTAATAATAATTGG | 1 | 2 | 29 | SEQ ID NO. 2321 |
| (N20)NGG | 13 | 108863477 | + | GAGTGTCTCATGTAATAATAATTGGG | 1 | 7 | 48 | SEQ ID NO. 2322 |
| (N20)NGG | 13 | 108863478 | + | AGTGTCTCATGTAATAATAATTGGGG | 1 | 6 | 62 | SEQ ID NO. 2323 |
| (N20)NGG | 13 | 108863558 | + | TTAAAATCCTAAAAGAAAGTTGG | 2 | 22 | 272 | SEQ ID NO. 2324 |
| (N20)NGG | 13 | 108863559 | + | TAAAATCCTAAAAGAAAGTTTGG | 2 | 14 | 269 | SEQ ID NO. 2325 |
| (N20)NGG | 13 | 108860887 | - | AACAGTTTGTGAAGTTTGTGAGG | 1 | 6 | 80 | SEQ ID NO. 2326 |
| (N20)NGG | 13 | 108860922 | - | GTTGAACACAAATCTGCAAAAGG | 1 | 6 | 72 | SEQ ID NO. 2327 |
| (N20)NGG | 13 | 108861047 | - | AAGAGTCTGTGACATCTTTGTGG | 1 | 5 | 70 | SEQ ID NO. 2328 |
| (N20)NGG | 13 | 108861075 | - | GGAAGAATTAGTCTCATTGCTGG | 1 | 2 | 28 | SEQ ID NO. 2329 |
| (N20)NGG | 13 | 108861096 | - | ATTCTCTCTCTTTCTTAGCTGAGG | 1 | 10 | 144 | SEQ ID NO. 2330 |
| (N20)NGG | 13 | 108861121 | - | CATAGTTTCTTTAATTCCATAGG | 1 | 15 | 131 | SEQ ID NO. 2331 |
| (N20)NGG | 13 | 108861177 | - | AGGGCATCTTTTCCATCTCTAGG | 1 | 4 | 72 | SEQ ID NO. 2332 |
| (N20)NGG | 13 | 108861196 | - | TCTGTAGTTTAAAAGTTTGACGG | 1 | 14 | 139 | SEQ ID NO. 2333 |
| (N20)NGG | 13 | 108861197 | - | TTCTGTAGTTTAAAAGTTTCAGG | 1 | 12 | 235 | SEQ ID NO. 2334 |
| (N20)NGG | 13 | 108861222 | - | GCATCTCCATGAGTTCCAGTGG | 1 | 1 | 33 | SEQ ID NO. 2335 |
| (N20)NGG | 13 | 108861223 | - | AGCATCTCCATGAGTTCCAGTGG | 1 | 4 | 57 | SEQ ID NO. 2336 |
| (N20)NGG | 13 | 108861282 | - | CTTCCTTTCTGTAAACATCTTGG | 2 | 9 | 100 | SEQ ID NO. 2337 |
| (N20)NGG | 13 | 108861310 | - | AAGTCGTTTACTTGCTGTATGG | 1 | 1 | 14 | SEQ ID NO. 2338 |
| (N20)NGG | 13 | 108861329 | - | TGCTGGCAATTGAGTCTAAAAGG | 1 | 2 | 27 | SEQ ID NO. 2339 |
| (N20)NGG | 13 | 108861346 | - | TCTTTTAGCAGAATTATTGCTGG | 1 | 5 | 61 | SEQ ID NO. 2340 |
| (N20)NGG | 13 | 108861374 | - | GAAGAAGGCTCTTTTTTATTAGG | 1 | 4 | 98 | SEQ ID NO. 2341 |
| (N20)NGG | 13 | 108861389 | - | TCTGAGTTATAAGTTGAAGAAGG | 1 | 2 | 58 | SEQ ID NO. 2342 |
| (N20)NGG | 13 | 108861570 | - | ATATCACTGAGTCCTACAGAAGG | 2 | 4 | 39 | SEQ ID NO. 2343 |
| (N20)NGG | 13 | 108861621 | - | TCTCAATAGCAGCTAGCATTGG | 2 | 1 | 31 | SEQ ID NO. 2344 |
| (N20)NGG | 13 | 108861694 | - | CATAGCTTCACCATCTAGCTTGG | 1 | 1 | 15 | SEQ ID NO. 2345 |
| (N20)NGG | 13 | 108861795 | - | GGGGTAAGAGAACCTTCAGTAGG | 1 | 1 | 18 | SEQ ID NO. 2346 |
| (N20)NGG | 13 | 108861814 | - | GAATGCATTATGAATGAATGGGG | 2 | 21 | 230 | SEQ ID NO. 2347 |
| (N20)NGG | 13 | 108861815 | - | TGAATGCATTATGAATGAATGGG | 2 | 32 | 329 | SEQ ID NO. 2348 |
| (N20)NGG | 13 | 108861816 | - | TTGAATGCATTATGAATGAATGG | 1 | 10 | 174 | SEQ ID NO. 2349 |
| (N20)NGG | 13 | 108861880 | - | AGTTTGTGTATTAGGATTATAGG | 1 | 3 | 41 | SEQ ID NO. 2350 |
| (N20)NGG | 13 | 108861888 | - | TGCATGAAAGTTTCTGTATTAGG | 1 | 5 | 76 | SEQ ID NO. 2351 |
| (N20)NGG | 13 | 108862062 | - | ATTTCTATTCTACCTGGAATTGG | 1 | 5 | 154 | SEQ ID NO. 2352 |

FIG. 9 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 13 | 108862068 | - | TGCACTATTTCTATTCTACCTGG | 1 | 4 | 37 | SEQ ID NO. 2353 |
| (N20)NGG | 13 | 108862179 | - | TCTGGCTTGTAGAATGGATAGAGG | 1 | 5 | 35 | SEQ ID NO. 2354 |
| (N20)NGG | 13 | 108862186 | - | TCTTTTGTCTGGCTTGTAGATGG | 1 | 4 | 81 | SEQ ID NO. 2355 |
| (N20)NGG | 13 | 108862197 | - | CACCCTTCACCTCTTTTGTCTGG | 1 | 8 | 33 | SEQ ID NO. 2356 |
| (N20)NGG | 13 | 108862233 | - | ATTAGTCCACTGACATACTCTGG | 1 | 2 | 24 | SEQ ID NO. 2357 |
| (N20)NGG | 13 | 108862350 | - | GATGGCTTCTCACCAGGAGGGG | 1 | 9 | 121 | SEQ ID NO. 2358 |
| (N20)NGG | 13 | 108862351 | - | AGATGGCTTCTCACCAGGAGGG | 1 | 4 | 53 | SEQ ID NO. 2359 |
| (N20)NGG | 13 | 108862352 | - | CAGATGGCTTCTCACCAGGAGG | 2 | 8 | 60 | SEQ ID NO. 2360 |
| (N20)NGG | 13 | 108862353 | - | ACAGATGGCTTCTCACCAGGAGG | 2 | 5 | 74 | SEQ ID NO. 2361 |
| (N20)NGG | 13 | 108862356 | - | AACACAGATGGCTTCTCACCAGG | 1 | 5 | 49 | SEQ ID NO. 2362 |
| (N20)NGG | 13 | 108862368 | - | GAGAGAGTATGAAACACAGATGG | 1 | 15 | 279 | SEQ ID NO. 2363 |
| (N20)NGG | 13 | 108862411 | - | CAGATCATACAGTTCTTTCATGG | 1 | 5 | 51 | SEQ ID NO. 2364 |
| (N20)NGG | 13 | 108862447 | - | ATGAAAAGGCTTTCTCCAATACTTGG | 1 | 1 | 36 | SEQ ID NO. 2365 |
| (N20)NGG | 13 | 108862461 | - | GGTGAGCTTTTCTATGAAAAGG | 1 | 4 | 45 | SEQ ID NO. 2366 |
| (N20)NGG | 13 | 108862479 | - | CCACATAAAATCTGCTTGTGTGG | 1 | 2 | 44 | SEQ ID NO. 2367 |
| (N20)NGG | 13 | 108862482 | - | GTTCCACATAAAATGCTGCTTGG | 1 | 2 | 44 | SEQ ID NO. 2368 |
| (N20)NGG | 13 | 108862512 | - | CAAGGTTCAATGTATACTTCTGG | 1 | 2 | 24 | SEQ ID NO. 2369 |
| (N20)NGG | 13 | 108862530 | - | TGAACAATGACAGAATTACAAGG | 1 | 8 | 103 | SEQ ID NO. 2370 |
| (N20)NGG | 13 | 108862575 | - | CCAGTTTTATACATATCACTGGG | 1 | 3 | 54 | SEQ ID NO. 2371 |
| (N20)NGG | 13 | 108862576 | - | GCCAGTTTTATACATATCACTGG | 1 | 2 | 26 | SEQ ID NO. 2372 |
| (N20)NGG | 13 | 108862603 | - | TTCAATTCGTGAAAACGCAAGG | 1 | 2 | 13 | SEQ ID NO. 2373 |
| (N20)NGG | 13 | 108862614 | - | TCTCTTATCTTTTCAATTCGTGG | 1 | 3 | 54 | SEQ ID NO. 2374 |
| (N20)NGG | 13 | 108862663 | - | AAGTTGTTCTAGGTCGTCAGGG | 1 | 2 | 9 | SEQ ID NO. 2375 |
| (N20)NGG | 13 | 108862664 | - | TAAGTTGTTCTAGGTCGTCCAGG | 1 | 1 | 8 | SEQ ID NO. 2376 |
| (N20)NGG | 13 | 108862673 | - | CCTTCCCCCTAAGTTGTTCTAGG | 1 | 4 | 40 | SEQ ID NO. 2377 |
| (N20)NGG | 13 | 108862721 | - | CATCATCACCACCTATATAAAGG | 1 | 6 | 43 | SEQ ID NO. 2378 |
| (N20)NGG | 13 | 108862746 | - | GCTTTTCCGCTTTTTTTTCTTGTGG | 1 | 4 | 72 | SEQ ID NO. 2379 |
| (N20)NGG | 13 | 108862771 | - | AATAACTTTCTTCTTCATCTTTGGGG | 3 | 14 | 170 | SEQ ID NO. 2380 |
| (N20)NGG | 13 | 108862772 | - | CAATAACTTTCTTCTTCATCTTTGG | 1 | 13 | 151 | SEQ ID NO. 2381 |
| (N20)NGG | 13 | 108862773 | - | CCAATAACTTTCTTCTTCATCTTGG | 1 | 5 | 82 | SEQ ID NO. 2382 |
| (N20)NGG | 13 | 108862818 | - | TTGTTAACGTTAGTAAGGTTAGG | 1 | 2 | 14 | SEQ ID NO. 2383 |
| (N20)NGG | 13 | 108862823 | - | AAATTTTGTTAACGTTAGTAAGG | 1 | 3 | 83 | SEQ ID NO. 2384 |
| (N20)NGG | 13 | 108862895 | - | TCTCCAGGTCAGGCTTTGGCTGG | 1 | 2 | 36 | SEQ ID NO. 2385 |
| (N20)NGG | 13 | 108862899 | - | CTGTTCTCCAGGTCAGGCTTTGG | 1 | 4 | 47 | SEQ ID NO. 2386 |

FIG. 9 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 13 | 108862905 | - | GCAATTCTGTTCTCCAGGTCAGG | 1 | 4 | 30 | SEQ ID NO. 2387 |
| (N20)NGG | 13 | 108862910 | - | ATTCTGCAATTCTGTTCTCCAGG | 1 | 4 | 92 | SEQ ID NO. 2388 |
| (N20)NGG | 13 | 108862956 | - | ACACAGTACGTCTGGGCCTGG | 1 | 3 | 21 | SEQ ID NO. 2389 |
| (N20)NGG | 13 | 108862961 | - | CAATTACACAGTACGTGTCTGGG | 1 | 2 | 21 | SEQ ID NO. 2390 |
| (N20)NGG | 13 | 108862962 | - | GCAATTACACAGTACGTGTCTGG | 1 | 2 | 12 | SEQ ID NO. 2391 |
| (N20)NGG | 13 | 108863046 | - | AAACATTCTAAAAGCCATGCAGG | 2 | 3 | 51 | SEQ ID NO. 2392 |
| (N20)NGG | 13 | 108863074 | - | CTGCCATGGTACAAAGCTTTTGG | 1 | 5 | 31 | SEQ ID NO. 2393 |
| (N20)NGG | 13 | 108863088 | - | ATCATAAAGCGAGGCTGCCATGG | 1 | 2 | 14 | SEQ ID NO. 2394 |
| (N20)NGG | 13 | 108863097 | - | CACATATGAATCATAAAGCGAGG | 1 | 1 | 22 | SEQ ID NO. 2395 |
| (N20)NGG | 13 | 108863120 | - | CAAAATGTTCTTTGGTTGATGGG | 1 | 2 | 84 | SEQ ID NO. 2396 |
| (N20)NGG | 13 | 108863121 | - | GCAAAATGTTCTTTGGTTGATGG | 1 | 8 | 77 | SEQ ID NO. 2397 |
| (N20)NGG | 13 | 108863128 | - | TTCACGGGCAAAATGTTCTTTGG | 1 | 5 | 19 | SEQ ID NO. 2398 |
| (N20)NGG | 13 | 108863143 | - | ACCATAGCAATCATATTCACGGG | 1 | 2 | 26 | SEQ ID NO. 2399 |
| (N20)NGG | 13 | 108863144 | - | CACCATAGCAATCATATTCACGG | 1 | 1 | 44 | SEQ ID NO. 2400 |
| (N20)NGG | 13 | 108863195 | - | CTGAGAATACTTCCTTCAGTTGG | 1 | 4 | 48 | SEQ ID NO. 2401 |
| (N20)NGG | 13 | 108863244 | - | ATCAGAGAAGCCATTTCTTCAGG | 1 | 2 | 79 | SEQ ID NO. 2402 |
| (N20)NGG | 13 | 108863290 | - | ACTGAGAGGAGAGCAATCCCAGG | 1 | 3 | 43 | SEQ ID NO. 2403 |
| (N20)NGG | 13 | 108863304 | - | TGGCGTCGAAACATACTGAGAGG | 1 | 2 | 3 | SEQ ID NO. 2404 |
| (N20)NGG | 13 | 108863324 | - | ACGAGTCCAAATAAACGGTGTGG | 1 | 1 | 4 | SEQ ID NO. 2405 |
| (N20)NGG | 13 | 108863329 | - | AGCATACGAGTCCAAATAAACGG | 1 | 1 | 16 | SEQ ID NO. 2406 |
| (N20)NGG | 13 | 108863363 | - | TCCCCTCATTTTTGGTACTCAGG | 1 | 3 | 46 | SEQ ID NO. 2407 |
| (N20)NGG | 13 | 108863371 | - | TAACCTTGTCCCCTCATTTTTGG | 1 | 2 | 42 | SEQ ID NO. 2408 |
| (N20)NGG | 13 | 108863404 | - | TCCATGAAACCGAAGCTCCAAGG | 1 | 3 | 21 | SEQ ID NO. 2409 |
| (N20)NGG | 13 | 108863543 | - | CAGTTACCCAACTTTCTTTTAGG | 1 | 3 | 56 | SEQ ID NO. 2410 |

FIG. 9 cont.

| site_type | site_chr omosome | site_start_ nucleotide | site_s trand | target_site_sequence_with_NGG | genome_wide_hits_with_1_or_less_mism atches | genome_wide_hits_with_2_or_less_mism atches | genome_wide_hits_with_3_or_less_mism atches | | |
|---|---|---|---|---|---|---|---|---|---|
| (N20)NGG | 2 | 219941102 | + | ACTTGGGTTCCCTTTTTTCTAGG | 1 | 3 | 85 | SEQ ID NO. | 2411 |
| (N20)NGG | 2 | 219941103 | + | CTTGGGTTCCCTTTTTTTCTAGGG | 1 | 4 | 98 | SEQ ID NO. | 2412 |
| (N20)NGG | 2 | 219941112 | + | CCTTTTTTCTAGGGTACTTCAGG | 1 | 5 | 42 | SEQ ID NO. | 2413 |
| (N20)NGG | 2 | 219941141 | + | GCAGAGACCTCAGCTGTCAAAGG | 2 | 7 | 49 | SEQ ID NO. | 2414 |
| (N20)NGG | 2 | 219941149 | + | CTCAGCTGTCAAAGGTCAAGAGG | 1 | 5 | 67 | SEQ ID NO. | 2415 |
| (N20)NGG | 2 | 219941161 | + | AGGTCAAGAGGAAGAAGCCAAGG | 1 | 12 | 171 | SEQ ID NO. | 2416 |
| (N20)NGG | 2 | 219941162 | + | GGTCAAGAGGAAGAAGCCAAGGG | 1 | 9 | 103 | SEQ ID NO. | 2417 |
| (N20)NGG | 2 | 219941163 | + | GTCAAGAGGAAGAAGCCAAGGGG | 1 | 6 | 120 | SEQ ID NO. | 2418 |
| (N20)NGG | 2 | 219941186 | + | TCTCTTCAGTTAATCTGTTGTGG | 1 | 2 | 51 | SEQ ID NO. | 2419 |
| (N20)NGG | 2 | 219941201 | + | TGTTGTGGCCTCAGCTGCTGAGG | 2 | 5 | 75 | SEQ ID NO. | 2420 |
| (N20)NGG | 2 | 219941089 | - | CTGAAGTACCCTAGAAAAAAAGG | 2 | 2 | 53 | SEQ ID NO. | 2421 |
| (N20)NGG | 2 | 219941090 | - | CCTGAAGTACCCTAGAAAAAAAG | 1 | 5 | 44 | SEQ ID NO. | 2422 |
| (N20)NGG | 2 | 219941113 | - | ACAGCTGAGGTCTCTGCAGAGG | 1 | 13 | 200 | SEQ ID NO. | 2423 |
| (N20)NGG | 2 | 219941114 | - | GACAGCTGAGGTCTCTGCAGAGG | 3 | 7 | 90 | SEQ ID NO. | 2424 |
| (N20)NGG | 2 | 219941126 | - | CTCTTGACCTTTGACAGCTGAGG | 2 | 5 | 47 | SEQ ID NO. | 2425 |
| (N20)NGG | 2 | 219941156 | - | GATTAACTGAAGAGACCCCTTGG | 1 | 1 | 16 | SEQ ID NO. | 2426 |
| (N20)NGG | 2 | 219941967 | - | CTCTTGATCTTTCTGATTTCAGG | 1 | 5 | 119 | SEQ ID NO. | 2427 |
| (N20)NGG | 2 | 219942003 | + | TCAAACAGTGCTTCCCTGCAAGG | 1 | 3 | 57 | SEQ ID NO. | 2428 |
| (N20)NGG | 2 | 219942041 | + | TGTAAACCAGCCAGAACAACTGG | 1 | 4 | 61 | SEQ ID NO. | 2429 |
| (N20)NGG | 2 | 219942086 | + | AGCACCTGAGAAAGAGTCCACGG | 1 | 2 | 66 | SEQ ID NO. | 2430 |
| (N20)NGG | 2 | 219942108 | + | GTGAGTCATGAGCAGCTTCCTGG | 1 | 1 | 30 | SEQ ID NO. | 2431 |
| (N20)NGG | 2 | 219941972 | - | GAAGCACTGTTGAGGTATGAGG | 1 | 3 | 40 | SEQ ID NO. | 2432 |
| (N20)NGG | 2 | 219941979 | - | TTGCAGGGAAGCACTGTTTGAGG | 1 | 2 | 54 | SEQ ID NO. | 2433 |
| (N20)NGG | 2 | 219941994 | - | TTGGCTATCGATTCCTTGCAGG | 1 | 2 | 7 | SEQ ID NO. | 2434 |
| (N20)NGG | 2 | 219941995 | - | ATTGGCTATCGATTCCTTGCAGG | 1 | 1 | 30 | SEQ ID NO. | 2435 |
| (N20)NGG | 2 | 219942013 | - | GTTCTGGCTGGTTTACACATTGG | 1 | 3 | 38 | SEQ ID NO. | 2436 |
| (N20)NGG | 2 | 219942025 | - | AGGAGACCAGTTGTTCTGGCTGG | 1 | 1 | 31 | SEQ ID NO. | 2437 |
| (N20)NGG | 2 | 219942029 | - | GCTGAGGAGACCAGTTGTTCTGG | 1 | 1 | 23 | SEQ ID NO. | 2438 |
| (N20)NGG | 2 | 219942045 | - | TGCTGAGGGGTTGGGGCTGAGG | 1 | 12 | 181 | SEQ ID NO. | 2439 |
| (N20)NGG | 2 | 219942051 | - | CTCAGGTGCTGAGAGGGTTGGGG | 1 | 7 | 79 | SEQ ID NO. | 2440 |
| (N20)NGG | 2 | 219942052 | - | TCTCAGGTGCTGAGAGGGTTGG | 1 | 2 | 73 | SEQ ID NO. | 2441 |
| (N20)NGG | 2 | 219942053 | - | TTCTCAGGTGCTGAGAGGGTTGG | 1 | 6 | 74 | SEQ ID NO. | 2442 |
| (N20)NGG | 2 | 219942057 | - | CTCTTTCTCAGGTGCTGAGAGGG | 1 | 3 | 80 | SEQ ID NO. | 2443 |
| (N20)NGG | 2 | 219942058 | - | ACTCTTTCTCAGGTGCTGAGAGG | 1 | 2 | 58 | SEQ ID NO. | 2444 |

FIG. 10

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 2 | 219942068 | - | CTCACCGTGGACTCTTTCTCAGG | 1 | 2 | 39 | SEQ ID NO. 2445 |
| (N20)NGG | 2 | 219942081 | - | AAGCTGCTCATGACTCACCGTGG | 1 | 1 | 9 | SEQ ID NO. 2446 |
| (N20)NGG | 2 | 219942822 | + | TCTCTTACAGAAACTGCCAGAGG | 1 | 5 | 60 | SEQ ID NO. 2447 |
| (N20)NGG | 2 | 219942835 | + | CTGCCAGAGGCATGCAGCATTGG | 1 | 2 | 42 | SEQ ID NO. 2448 |
| (N20)NGG | 2 | 219942841 | + | GAGGCATGCAGCATTGGTGATGG | 1 | 6 | 90 | SEQ ID NO. 2449 |
| (N20)NGG | 2 | 219942867 | + | GCCCTTTGTCATGAATCTGCAGG | 1 | 2 | 33 | SEQ ID NO. 2450 |
| (N20)NGG | 2 | 219942879 | + | GAATCTGCAGGATCTGTATATGG | 1 | 5 | 31 | SEQ ID NO. 2451 |
| (N20)NGG | 2 | 219942897 | + | TATGGCAGTCACCACACAAGAGG | 1 | 3 | 28 | SEQ ID NO. 2452 |
| (N20)NGG | 2 | 219942906 | + | CACCACACAAGAGGTCCAAGTGG | 1 | 2 | 32 | SEQ ID NO. 2453 |
| (N20)NGG | 2 | 219942907 | + | ACCACACAAGAGGTCCAAGTGGG | 1 | 2 | 30 | SEQ ID NO. 2454 |
| (N20)NGG | 2 | 219942922 | + | CAAGTGGGACAGAAGCATCAAGG | 1 | 3 | 52 | SEQ ID NO. 2455 |
| (N20)NGG | 2 | 219942928 | + | GGACAAGAGCATCAAGGCGCTGG | 1 | 2 | 24 | SEQ ID NO. 2456 |
| (N20)NGG | 2 | 219942943 | + | GGCGCTGGTGAGCCCTCCAGAGG | 1 | 1 | 30 | SEQ ID NO. 2457 |
| (N20)NGG | 2 | 219942950 | + | GTGAGCCCTCCAGAGGTACCCGG | 1 | 1 | 23 | SEQ ID NO. 2458 |
| (N20)NGG | 2 | 219942796 | - | TGGCAGTTTCTGTAAGAGAGAGG | 1 | 3 | 78 | SEQ ID NO. 2459 |
| (N20)NGG | 2 | 219942816 | - | TCACCAATGCTGCATGCCTCTGG | 1 | 2 | 32 | SEQ ID NO. 2460 |
| (N20)NGG | 2 | 219942846 | - | TCCTGCAGATTCATGACAAAGGG | 1 | 2 | 47 | SEQ ID NO. 2461 |
| (N20)NGG | 2 | 219942847 | - | ATCCTGCAGATTCATGACAAAGG | 1 | 2 | 32 | SEQ ID NO. 2462 |
| (N20)NGG | 2 | 219942886 | - | TCCCACTTGGACCTCTTGTGTGG | 1 | 2 | 60 | SEQ ID NO. 2463 |
| (N20)NGG | 2 | 219942899 | - | CTTGATGCTTCTGTCCCACTTGG | 1 | 3 | 31 | SEQ ID NO. 2464 |
| (N20)NGG | 2 | 220011442 | + | ATTTGAAGAAAATTCCTTCTTGG | 1 | 15 | 228 | SEQ ID NO. 2465 |
| (N20)NGG | 2 | 220011460 | + | CTTGGAACAATTTATGATAGAGG | 1 | 5 | 45 | SEQ ID NO. 2466 |
| (N20)NGG | 2 | 220011465 | + | AACAATTTATGATAGAGGTAAGG | 1 | 2 | 83 | SEQ ID NO. 2467 |
| (N20)NGG | 2 | 220011387 | - | TCAATCGATCTGTAATAAGAAGG | 1 | 1 | 25 | SEQ ID NO. 2468 |
| (N20)NGG | 2 | 220011418 | - | AAGAAGGAATTTTCTTCAAAATGG | 1 | 16 | 274 | SEQ ID NO. 2469 |
| (N20)NGG | 2 | 220011434 | - | TATCATAAATTGTTCCAAGAAGG | 1 | 5 | 55 | SEQ ID NO. 2470 |
| (N20)NGG | 2 | 220012378 | + | ATTGATATATCTCTTCCCTCAAGG | 1 | 1 | 67 | SEQ ID NO. 2471 |
| (N20)NGG | 2 | 220012408 | + | ACATTTGATTCGTCCTCTGATGG | 1 | 2 | 14 | SEQ ID NO. 2472 |
| (N20)NGG | 2 | 220012409 | + | CATTTGATTCGTCCTCTGATGGG | 1 | 3 | 17 | SEQ ID NO. 2473 |
| (N20)NGG | 2 | 220012420 | + | TCCTCTGATGGGCATGAGTCTGG | 1 | 1 | 44 | SEQ ID NO. 2474 |
| (N20)NGG | 2 | 220012440 | + | TGGCATTACAGTGCCAAGTGAGG | 1 | 4 | 37 | SEQ ID NO. 2475 |
| (N20)NGG | 2 | 220012441 | + | GGCATTACAGTGCCAAGTGAGGG | 1 | 1 | 26 | SEQ ID NO. 2476 |
| (N20)NGG | 2 | 220012492 | + | CCTAGAGATCCAAGACTACCAGG | 1 | 1 | 12 | SEQ ID NO. 2477 |
| (N20)NGG | 2 | 220012499 | + | ATCCAAGACTACCAGGAGAGTGG | 1 | 4 | 42 | SEQ ID NO. 2478 |

FIG. 10 cont.

| site_type | site_chr omosome | site_start_ nucleotide | site_s trand | target_site_sequence_wit h_NGG | genome_wide_ hits_with_1_ or_less_mism atches | genome_wide_ hits_with_2_ or_less_mism atches | genome_wide_ hits_with_3_ or_less_mism atches | |
|---|---|---|---|---|---|---|---|---|
| (N20)NGG | 2 | 220012500 | + | TCCAAGACTACCAGGAGAGTGGG | | 1 | 6 | 44 SEQ ID NO. 2479 |
| (N20)NGG | 2 | 220012501 | + | CCAAGACTACCAGGAGAGTGGGG | | 2 | 4 | 44 SEQ ID NO. 2480 |
| (N20)NGG | 2 | 220012517 | + | AGTGGGCTACGCTGATTCGAGG | | 1 | 1 | 5 SEQ ID NO. 2481 |
| (N20)NGG | 2 | 220012524 | + | CTACGCTGATTCGAGTAAGAGG | | 1 | 1 | 5 SEQ ID NO. 2482 |
| (N20)NGG | 2 | 220012534 | + | TCGAGGTAAGAGGACATTCTTGG | | 1 | 2 | 55 SEQ ID NO. 2483 |
| (N20)NGG | 2 | 220012537 | + | AGGTAAGAGGACATTCTTGGAGG | | 1 | 3 | 66 SEQ ID NO. 2484 |
| (N20)NGG | 2 | 220012369 | - | AAATGTTGGGAGACCTTTGAGG | | 1 | 5 | 66 SEQ ID NO. 2485 |
| (N20)NGG | 2 | 220012370 | - | CAAATGTTGGGAGACCTTTGAGG | | 1 | 2 | 43 SEQ ID NO. 2486 |
| (N20)NGG | 2 | 220012382 | - | CAGAGGACGAATCAAATGTTGGG | | 1 | 3 | 22 SEQ ID NO. 2487 |
| (N20)NGG | 2 | 220012383 | - | TCAGAGGACGAATCAAATGTTGG | | 1 | 2 | 23 SEQ ID NO. 2488 |
| (N20)NGG | 2 | 220012399 | - | GCCAGACTCATGCCCATCAGAGG | | 1 | 3 | 33 SEQ ID NO. 2489 |
| (N20)NGG | 2 | 220012431 | - | ACGTTGCTAGCTCCCTCACTTGG | | 1 | 2 | 16 SEQ ID NO. 2490 |
| (N20)NGG | 2 | 220012470 | - | CCTGGTAGTCTTGGATCTCTAGG | | 1 | 1 | 25 SEQ ID NO. 2491 |
| (N20)NGG | 2 | 220012479 | - | CCCCACTTCCTCGGTAGTCTTGG | | 1 | 5 | 37 SEQ ID NO. 2492 |
| (N20)NGG | 2 | 220012488 | - | TCAGCGTAGCCCCACTTCCTCGG | | 1 | 3 | 63 SEQ ID NO. 2493 |
| (N20)NGG | 2 | 220022193 | + | TGTACCACTGCTCTCTCTTTAGG | | 1 | 6 | 57 SEQ ID NO. 2494 |
| (N20)NGG | 2 | 220022207 | + | CTCTTTAGGAGCTGAACAAGCGG | | 1 | 4 | 43 SEQ ID NO. 2495 |
| (N20)NGG | 2 | 220022244 | + | TGCAGCTTTCCTCGTCATTTGG | | 1 | 5 | 67 SEQ ID NO. 2496 |
| (N20)NGG | 2 | 220022271 | + | TCTCCTTCGCCCATTGTTGAAGG | | 3 | 13 | 95 SEQ ID NO. 2497 |
| (N20)NGG | 2 | 220022316 | + | TACCTTCCTGTGATTGTGTGG | | 4 | 70 | 594 SEQ ID NO. 2498 |
| (N20)NGG | 2 | 220022336 | + | TGGCAGATGCACTGATTCTACGG | | 1 | 3 | 32 SEQ ID NO. 2499 |
| (N20)NGG | 2 | 220022337 | + | GGCAGATGCACTGATTCTACGGG | | 1 | 2 | 19 SEQ ID NO. 2500 |
| (N20)NGG | 2 | 220022356 | + | CGGGTGCGAAGTGAGCTCTCGG | | 1 | 2 | 6 SEQ ID NO. 2501 |
| (N20)NGG | 2 | 220022372 | + | TCTCTGGCCTCCCCTTCTATTGG | | 1 | 6 | 82 SEQ ID NO. 2502 |
| (N20)NGG | 2 | 220022406 | + | CATGCTAGCTAGTCCTTCCCTGG | | 1 | 2 | 15 SEQ ID NO. 2503 |
| (N20)NGG | 2 | 220022426 | + | TGGTAAGTGTAATTCGAATGTGG | | 1 | 2 | 12 SEQ ID NO. 2504 |
| (N20)NGG | 2 | 220022427 | + | GGTAAGTGTAATTCGAATGTGGG | | 1 | 3 | 19 SEQ ID NO. 2505 |
| (N20)NGG | 2 | 220022428 | + | GTAAGTGTAATTCGAATGTGGGG | | 2 | 2 | 19 SEQ ID NO. 2506 |
| (N20)NGG | 2 | 220022175 | - | AGCTCCTAAAGAGAGAGCAGTGG | | 2 | 4 | 69 SEQ ID NO. 2507 |
| (N20)NGG | 2 | 220022217 | - | TGACAGAGGAAAGCTGCAGAGG | | 2 | 11 | 120 SEQ ID NO. 2508 |
| (N20)NGG | 2 | 220022220 | - | AAATGACAGAGGAAAGCTGCAGG | | 4 | 9 | 110 SEQ ID NO. 2509 |
| (N20)NGG | 2 | 220022231 | - | GGAGATTATCCAAATGACAGAGG | | 1 | 4 | 45 SEQ ID NO. 2510 |
| (N20)NGG | 2 | 220022252 | - | CGTCCTTCAACAATGGGCGAAGG | | 1 | 1 | 4 SEQ ID NO. 2511 |
| (N20)NGG | 2 | 220022258 | - | GAGCAGCGTCCTTCAACAATGGG | | 1 | 1 | 13 SEQ ID NO. 2512 |

FIG. 10 cont.

| site_type | site_chr omosome | site_start_ nucleotide | site_s trand | target_site_sequence_with_NGG | genome_wide_ hits_with_1_ or_less_mism atches | genome_wide_ hits_with_2_ or_less_mism atches | genome_wide_ hits_with_3_ or_less_mism atches | |
|---|---|---|---|---|---|---|---|---|
| (N20)NGG | 2 | 220022259 | - | TGAGCAGCGTCCTTCAACAATGG | 1 | 2 | 9 | SEQ ID NO. 2513 |
| (N20)NGG | 2 | 220022282 | - | AGGAGAAGGTAGCTTCGCTAGGG | 1 | 1 | 10 | SEQ ID NO. 2514 |
| (N20)NGG | 2 | 220022283 | - | CAGGAGAAGGTAGCTTCGCTAGG | 1 | 2 | 18 | SEQ ID NO. 2515 |
| (N20)NGG | 2 | 220022296 | - | TGCCACACAATCACAGAGAAGG | 1 | 6 | 119 | SEQ ID NO. 2516 |
| (N20)NGG | 2 | 220022302 | - | TGCATCTGCCACACAATCACAGG | 1 | 3 | 26 | SEQ ID NO. 2517 |
| (N20)NGG | 2 | 220022357 | - | GGAAAATTCCAATAGAAGGGGAGG | 1 | 3 | 48 | SEQ ID NO. 2518 |
| (N20)NGG | 2 | 220022360 | - | AGTGGAAATTCCAATAGAAGGGG | 2 | 4 | 68 | SEQ ID NO. 2519 |
| (N20)NGG | 2 | 220022361 | - | CAGTGGAAATTCCAATAGAAGGG | 1 | 4 | 79 | SEQ ID NO. 2520 |
| (N20)NGG | 2 | 220022362 | - | GCAGTGGAAATTCCAATAGAAGG | 1 | 3 | 33 | SEQ ID NO. 2521 |
| (N20)NGG | 2 | 220022378 | - | AAGGACTAGCTAGCATGCAGTGG | 1 | 1 | 20 | SEQ ID NO. 2522 |
| (N20)NGG | 2 | 220022397 | - | CGAATTACACTTACCAGGGAAGG | 1 | 1 | 14 | SEQ ID NO. 2523 |
| (N20)NGG | 2 | 220022401 | - | CATTCGAATTACACTTACCAGGG | 1 | 2 | 21 | SEQ ID NO. 2524 |
| (N20)NGG | 2 | 220022402 | - | ACATTCGAATTACACTTACCAGG | 1 | 3 | 14 | SEQ ID NO. 2525 |
| (N20)NGG | 2 | 220022910 | + | AATGAGACTTTTTGCAGATGG | 1 | 5 | 99 | SEQ ID NO. 2526 |
| (N20)NGG | 2 | 220022919 | + | TTTTTGCAGATGGAAGAACTGG | 1 | 7 | 146 | SEQ ID NO. 2527 |
| (N20)NGG | 2 | 220022926 | + | CAGATGAAGAACTGGAGCAAGG | 2 | 19 | 216 | SEQ ID NO. 2528 |
| (N20)NGG | 2 | 220022945 | + | AAGGCCTGTTGATGCAGCCATGG | 1 | 5 | 40 | SEQ ID NO. 2529 |
| (N20)NGG | 2 | 220022946 | + | AGGCCTGTTGATGCAGCCATGGG | 1 | 1 | 29 | SEQ ID NO. 2530 |
| (N20)NGG | 2 | 220022951 | + | TGTTGATGCAGCCATGGGCGTGG | 1 | 2 | 17 | SEQ ID NO. 2531 |
| (N20)NGG | 2 | 220022979 | + | GCTTGCAGAGAACTCCCTCTTGG | 1 | 3 | 30 | SEQ ID NO. 2532 |
| (N20)NGG | 2 | 220022985 | + | AGAGAACTCCCTCTTGGCCAAGG | 1 | 10 | 95 | SEQ ID NO. 2533 |
| (N20)NGG | 2 | 220023003 | + | CAAGGTTTTTATCACCAAGCAGG | 1 | 1 | 20 | SEQ ID NO. 2534 |
| (N20)NGG | 2 | 220023004 | + | AAGGTTTTTATCACCAAGCAGGG | 1 | 3 | 55 | SEQ ID NO. 2535 |
| (N20)NGG | 2 | 220023018 | + | CAAGCAGGGCTATGCCTTGTTGG | 1 | 1 | 25 | SEQ ID NO. 2536 |
| (N20)NGG | 2 | 220023036 | + | GTTGGTTTCAGATCTTCAACAGG | 1 | 1 | 28 | SEQ ID NO. 2537 |
| (N20)NGG | 2 | 220023041 | + | TTTCAGATCTTCAACAGGTGTGG | 1 | 2 | 31 | SEQ ID NO. 2538 |
| (N20)NGG | 2 | 220023051 | + | TCAACAGGTGTGCATGAACAGG | 1 | 2 | 38 | SEQ ID NO. 2539 |
| (N20)NGG | 2 | 220023054 | + | ACAGGTGTGCATGAACACAGGTGG | 1 | 3 | 58 | SEQ ID NO. 2540 |
| (N20)NGG | 2 | 220023066 | + | TGAACAGGTGGACACTAGTGTGG | 1 | 1 | 19 | SEQ ID NO. 2541 |
| (N20)NGG | 2 | 220023084 | + | TGTGGTCAGCCAGCCAGCCAAGG | 1 | 4 | 39 | SEQ ID NO. 2542 |
| (N20)NGG | 2 | 220023095 | + | AGCGAGCCAAGGTAAGTATGAGG | 1 | 1 | 14 | SEQ ID NO. 2543 |
| (N20)NGG | 2 | 220022927 | - | ACGCCCATGGCTGCATCAACAGG | 1 | 1 | 14 | SEQ ID NO. 2544 |
| (N20)NGG | 2 | 220022940 | - | GCAAGCTGTAGCCACGCCCATGG | 1 | 1 | 17 | SEQ ID NO. 2545 |
| (N20)NGG | 2 | 220022971 | - | GATAAAAACCTTGGCCAAGAGGG | 1 | 2 | 40 | SEQ ID NO. 2546 |

FIG. 10 cont.

| site_type | site_chr omosome | site_start_ nucleotide | site_s trand | target_site_sequence_with NGG | genome_wide_ hits_with_1_ or_less_mism atches | genome_wide_ hits_with_2_ or_less_mism atches | genome_wide_ hits_with_3_ or_less_mism atches | |
|---|---|---|---|---|---|---|---|---|
| (N20)NGG | 2 | 220022972 | - | TGATAAAAACCTTGGCCAAGAGG | 1 | 2 | 40 | SEQ ID NO. 2547 |
| (N20)NGG | 2 | 220022980 | - | CTGCTTGGTGATAAAAACCTTGG | 1 | 1 | 33 | SEQ ID NO. 2548 |
| (N20)NGG | 2 | 220022995 | - | CAACAAGGCATAGCCCTGCTTGG | 1 | 2 | 27 | SEQ ID NO. 2549 |
| (N20)NGG | 2 | 220023010 | - | TTGAAGATCTGAAACCAACAAGG | 1 | 3 | 66 | SEQ ID NO. 2550 |
| (N20)NGG | 2 | 220023071 | - | TCATACTTACCTTGGCTCGCTGG | 1 | 1 | 6 | SEQ ID NO. 2551 |
| (N20)NGG | 2 | 220023079 | - | ACTTCTCCTCATACTTACCTTGG | 1 | 2 | 35 | SEQ ID NO. 2552 |

FIG. 10 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | | |
|---|---|---|---|---|---|---|---|---|---|
| (N20)NGG | 14 | 20937686 | + | AGAAGGCGTCTGCGAGACCATGG | 1 | 1 | 13 | SEQ ID NO. | 2553 |
| (N20)NGG | 14 | 20937693 | + | GTCTGCGAGACCATGGAGAACGG | 1 | 2 | 21 | SEQ ID NO. | 2554 |
| (N20)NGG | 14 | 20937694 | + | TCTGCGAGACCATGGAGAACGGG | 1 | 2 | 25 | SEQ ID NO. | 2555 |
| (N20)NGG | 14 | 20937699 | + | GAGACCATGGAGAACGGGTGAGG | 1 | 3 | 40 | SEQ ID NO. | 2556 |
| (N20)NGG | 14 | 20937702 | + | ACCATGGAGAACGGGTGAGGAGG | 1 | 3 | 41 | SEQ ID NO. | 2557 |
| (N20)NGG | 14 | 20937703 | + | CCATGGAGAACGGGTGAGGAGGG | 1 | 2 | 47 | SEQ ID NO. | 2558 |
| (N20)NGG | 14 | 20937710 | + | GAACGGGTGAGGAGGGCACCAGG | 1 | 4 | 36 | SEQ ID NO. | 2559 |
| (N20)NGG | 14 | 20937718 | + | GAGGAGGGCACCAGGCCCGCAGG | 1 | 5 | 57 | SEQ ID NO. | 2560 |
| (N20)NGG | 14 | 20937681 | - | CCCTCCTCACCCGTTCTCCATGG | 1 | 4 | 50 | SEQ ID NO. | 2561 |
| (N20)NGG | 14 | 20940502 | + | ATTATAAGAACACTGCAGAATGG | 2 | 12 | 138 | SEQ ID NO. | 2562 |
| (N20)NGG | 14 | 20940549 | + | CCTCAAGTTGCAATAATCTGTGG | 1 | 1 | 37 | SEQ ID NO. | 2563 |
| (N20)NGG | 14 | 20940555 | + | GTTGCAATAATCTGTGGTTCTGG | 1 | 5 | 26 | SEQ ID NO. | 2564 |
| (N20)NGG | 14 | 20940561 | + | ATAATCTGTGGTTCTGGATTAGG | 1 | 2 | 54 | SEQ ID NO. | 2565 |
| (N20)NGG | 14 | 20940564 | + | ATCTGTGGTTCTGGATTAGGAGG | 1 | 5 | 39 | SEQ ID NO. | 2566 |
| (N20)NGG | 14 | 20940587 | + | TCTGACTGATAAATTAACTCAGG | 2 | 3 | 41 | SEQ ID NO. | 2567 |
| (N20)NGG | 14 | 20940606 | + | CAGGCCCAGATCTTTGACTACGG | 1 | 2 | 42 | SEQ ID NO. | 2568 |
| (N20)NGG | 14 | 20940636 | + | CCCAACTTTCCCGAAGTACAGG | 1 | 1 | 17 | SEQ ID NO. | 2569 |
| (N20)NGG | 14 | 20940642 | + | TTTCCCCGAAGTACAGTACTGG | 1 | 2 | 31 | SEQ ID NO. | 2570 |
| (N20)NGG | 14 | 20940647 | + | CCGAAGTACAGGTACTGGCAAGG | 1 | 2 | 14 | SEQ ID NO. | 2571 |
| (N20)NGG | 14 | 20940648 | + | CGAAGTACAGGTACTGGCAAGGG | 1 | 1 | 15 | SEQ ID NO. | 2572 |
| (N20)NGG | 14 | 20940655 | + | CAGGTACTGGCAAGGGAAAGTGG | 1 | 2 | 87 | SEQ ID NO. | 2573 |
| (N20)NGG | 14 | 20940656 | + | AGGTACTGGCAAGGGAAAGTGGG | 1 | 4 | 61 | SEQ ID NO. | 2574 |
| (N20)NGG | 14 | 20940657 | + | GGTACTGGCAAGGGAAAGTGGG | 1 | 5 | 69 | SEQ ID NO. | 2575 |
| (N20)NGG | 14 | 20940443 | - | CTGGGGGAGAGAAAAATATCAAGG | 1 | 10 | 154 | SEQ ID NO. | 2576 |
| (N20)NGG | 14 | 20940459 | - | ATCTTTCATAGGTGTATCTGGGGG | 1 | 1 | 33 | SEQ ID NO. | 2577 |
| (N20)NGG | 14 | 20940460 | - | AATCTTCATAGGTGTATCTGGGG | 1 | 2 | 39 | SEQ ID NO. | 2578 |
| (N20)NGG | 14 | 20940461 | - | TAATCTTCATAGGTGTATCTGGG | 1 | 6 | 47 | SEQ ID NO. | 2579 |
| (N20)NGG | 14 | 20940462 | - | ATAATCTTCATAGGTGTATCTGG | 1 | 3 | 36 | SEQ ID NO. | 2580 |
| (N20)NGG | 14 | 20940471 | - | AGTGTTCTTATAATCTTCATAGG | 1 | 1 | 75 | SEQ ID NO. | 2581 |
| (N20)NGG | 14 | 20940523 | - | AGATTATTGCAACTTGAGGTCGG | 1 | 7 | 57 | SEQ ID NO. | 2582 |
| (N20)NGG | 14 | 20940527 | - | CCACAGATTATTGCAACTTGAGG | 1 | 7 | 61 | SEQ ID NO. | 2583 |
| (N20)NGG | 14 | 20940588 | - | TTTCACCGTAGTCAAAGATCTGG | 1 | 1 | 11 | SEQ ID NO. | 2584 |
| (N20)NGG | 14 | 20940589 | - | TTTCACCGTAGTCAAAGATCTGG | 1 | 1 | 20 | SEQ ID NO. | 2585 |
| (N20)NGG | 14 | 20940613 | - | CTGTACTTCGGGGAAAGTTGGGG | 1 | 1 | 14 | SEQ ID NO. | 2586 |

FIG. 11

| site_type | site_chr omosome | site_start_ nucleotide | site_s trand | target_site_sequence_with_ NGG | genome_wide_ hits_with_1 or_less_mism atches | genome_wide_ hits_with_2 or less_mismatc hes | genome_wide_h its_with_3 or_less_mism atches | |
|---|---|---|---|---|---|---|---|---|
| (N20)NGG | 14 | 20940614 | - | CCTGTACTTCGGGAAAGTTGGG | | 1 | 1 | 12 SEQ ID NO. 2587 |
| (N20)NGG | 14 | 20940615 | - | ACCTGTACTTCGGGGAAAGTTGG | | 1 | 1 | 10 SEQ ID NO. 2588 |
| (N20)NGG | 14 | 20940623 | - | TTGCCAGTACCTGTACTTCGGGG | | 1 | 2 | 13 SEQ ID NO. 2589 |
| (N20)NGG | 14 | 20940624 | - | CTTGCCAGTACCTGTACTTCGGG | | 1 | 2 | 22 SEQ ID NO. 2590 |
| (N20)NGG | 14 | 20940625 | - | CCTTGCCAGTACCTGTACTTCCG | | 1 | 4 | 33 SEQ ID NO. 2591 |
| (N20)NGG | 14 | 20942636 | + | TCTGTTTTGTATACAGTGCCAGG | | 1 | 3 | 59 SEQ ID NO. 2592 |
| (N20)NGG | 14 | 20942645 | + | TATACAGTGCCAGTCATGCTCG | | 1 | 1 | 17 SEQ ID NO. 2593 |
| (N20)NGG | 14 | 20942653 | + | GCCAGTCATGCTGGCCGACTGG | | 1 | 1 | 7 SEQ ID NO. 2594 |
| (N20)NGG | 14 | 20942660 | + | CATGCTGGCCGACTGGTGTTTGG | | 1 | 2 | 16 SEQ ID NO. 2595 |
| (N20)NGG | 14 | 20942661 | + | ATGCTGCCGACTGGTGTTTTGGG | | 1 | 3 | 16 SEQ ID NO. 2596 |
| (N20)NGG | 14 | 20942672 | + | CTGGTGTTTGGGTTCCTGAATGG | | 2 | 4 | 41 SEQ ID NO. 2597 |
| (N20)NGG | 14 | 20942676 | + | TGTTTGGGTTCCTGAATGGCAGG | | 1 | 9 | 44 SEQ ID NO. 2598 |
| (N20)NGG | 14 | 20942677 | + | GTTTGGGTTCCTGAATGGCAGGG | | 2 | 2 | 43 SEQ ID NO. 2599 |
| (N20)NGG | 14 | 20942695 | + | CAGGGCCTGTCCTGTGATGATGCAGG | | 1 | 2 | 66 SEQ ID NO. 2600 |
| (N20)NGG | 14 | 20942696 | + | AGGGCCTGTCCTGTGATGATGCAGGG | | 1 | 3 | 46 SEQ ID NO. 2601 |
| (N20)NGG | 14 | 20942700 | + | CCTGTGTGATGATGCAGGGCAGG | | 1 | 3 | 43 SEQ ID NO. 2602 |
| (N20)NGG | 14 | 20942717 | + | GGCAGGTTCCACATGTATGAAGG | | 1 | 1 | 23 SEQ ID NO. 2603 |
| (N20)NGG | 14 | 20942718 | + | GCAGGTTCCACATGTATGAAGGG | | 1 | 2 | 38 SEQ ID NO. 2604 |
| (N20)NGG | 14 | 20942730 | + | TGTATGAAGGGTACCCACTCTGG | | 1 | 1 | 14 SEQ ID NO. 2605 |
| (N20)NGG | 14 | 20942734 | + | TGAAGGGTACCCACTCTGGAAGG | | 1 | 2 | 24 SEQ ID NO. 2606 |
| (N20)NGG | 14 | 20942745 | + | CACTCTGGAAGGTAAGTCAGAGG | | 2 | 7 | 158 SEQ ID NO. 2607 |
| (N20)NGG | 14 | 20942746 | + | ACTCTGGAAGGTAAGTCAGAGGG | | 1 | 8 | 112 SEQ ID NO. 2608 |
| (N20)NGG | 14 | 20942751 | + | GGAAGGTAAGTCAGAGGGATAGG | | 1 | 4 | 63 SEQ ID NO. 2609 |
| (N20)NGG | 14 | 20942756 | + | GTAAGTCAGAGGGATAGGTCCGG | | 2 | 2 | 29 SEQ ID NO. 2610 |
| (N20)NGG | 14 | 20942632 | - | ACCAGTCGGCCAGCATGACCTGG | | 1 | 1 | 8 SEQ ID NO. 2611 |
| (N20)NGG | 14 | 20942646 | - | ACCAGAACCCAAAACACCAGTCGG | | 2 | 2 | 31 SEQ ID NO. 2612 |
| (N20)NGG | 14 | 20942664 | - | TCACACAGGCCCTGCCATTCAGG | | 1 | 4 | 46 SEQ ID NO. 2613 |
| (N20)NGG | 14 | 20942678 | - | CCTGCCCTGCATCATCACACAGG | | 1 | 5 | 47 SEQ ID NO. 2614 |
| (N20)NGG | 14 | 20942703 | - | GTGGCTACCCTTCATACATGTGG | | 1 | 1 | 12 SEQ ID NO. 2615 |
| (N20)NGG | 14 | 20942721 | - | TCTGACTTACCTTCCAGAGTGG | | 1 | 5 | 48 SEQ ID NO. 2616 |
| (N20)NGG | 14 | 20942722 | - | CTCTGACTTACCTTCCAGAGTGG | | 1 | 6 | 92 SEQ ID NO. 2617 |
| (N20)NGG | 14 | 20942931 | + | TTTTCGGATTGTTTGCTTCGAAGG | | 2 | 2 | 17 SEQ ID NO. 2618 |
| (N20)NGG | 14 | 20942948 | + | CGAAGGTGACATTCCCAGTGAGG | | 1 | 1 | 23 SEQ ID NO. 2619 |
| (N20)NGG | 14 | 20942949 | + | GAAGGTGACATTCCCAGTGAGGG | | 1 | 6 | 55 SEQ ID NO. 2620 |

FIG. 11 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 14 | 20942964 | + | AGTGAGGGTTTTCCACCTTCTGG | 3 | | 7 | 40 SEQ ID NO. 2621 |
| (N20)NGG | 14 | 20942965 | + | GTGAGGGTTTTCCACCTTCTGGG | 1 | | 3 | 32 SEQ ID NO. 2622 |
| (N20)NGG | 14 | 20942970 | + | GGTTTTCCACCTTCTGGGTGTGG | 2 | | 3 | 33 SEQ ID NO. 2623 |
| (N20)NGG | 14 | 20942979 | + | CCTTCTGGGTGTGGACACCCTGG | 1 | | 8 | 59 SEQ ID NO. 2624 |
| (N20)NGG | 14 | 20942998 | + | CTGGTAGTCACCAATGCAGCAGG | 1 | | 1 | 21 SEQ ID NO. 2625 |
| (N20)NGG | 14 | 20943001 | + | GTAGTCACCAATGCAGCAGGAGG | 1 | | 1 | 22 SEQ ID NO. 2626 |
| (N20)NGG | 14 | 20943002 | + | TAGTCACCAATGCAGCAGGAGGG | 1 | | 1 | 35 SEQ ID NO. 2627 |
| (N20)NGG | 14 | 20943021 | + | AGGGCTGAACCCAAGTTTGAGG | 1 | | 6 | 51 SEQ ID NO. 2628 |
| (N20)NGG | 14 | 20943025 | + | CTGAACCCAAGTTTGAGGTTGG | 1 | | 7 | 48 SEQ ID NO. 2629 |
| (N20)NGG | 14 | 20943064 | + | CGTGACCATATCAACCTACCTGG | 1 | | 1 | 11 SEQ ID NO. 2630 |
| (N20)NGG | 14 | 20943073 | + | ATCAACCTACCTGGTTTCAGTGG | 1 | | 4 | 25 SEQ ID NO. 2631 |
| (N20)NGG | 14 | 20943091 | + | AGTGGTCAGAACCCTCTCAGAGG | 1 | | 2 | 29 SEQ ID NO. 2632 |
| (N20)NGG | 14 | 20943092 | + | GTGGTCAGAACCCTCTCAGAGGG | 1 | | 2 | 48 SEQ ID NO. 2633 |
| (N20)NGG | 14 | 20943107 | + | TCAGAGGGCCAATGATGAAAGG | 1 | | 3 | 26 SEQ ID NO. 2634 |
| (N20)NGG | 14 | 20942939 | - | GAAGGTGGAAAACCCTCACTGG | 3 | | 6 | 47 SEQ ID NO. 2635 |
| (N20)NGG | 14 | 20942940 | - | AGAAGGTGGAAAACCCTCACTGG | 1 | | 3 | 41 SEQ ID NO. 2636 |
| (N20)NGG | 14 | 20942954 | - | GGGGTGTCCACACCCAGAAGGTGG | 1 | | 3 | 75 SEQ ID NO. 2637 |
| (N20)NGG | 14 | 20942957 | - | CCAGGGTGTCCACACCCAGAAGG | 2 | | 4 | 66 SEQ ID NO. 2638 |
| (N20)NGG | 14 | 20942974 | - | TGCTTGCATTGGTGACTACCAGG | 1 | | 4 | 24 SEQ ID NO. 2639 |
| (N20)NGG | 14 | 20942975 | - | CTGCTGCATTGGTGACTACCAGG | 1 | | 3 | 23 SEQ ID NO. 2640 |
| (N20)NGG | 14 | 20942986 | - | GTTCAGCCCCTCCTGCTGCATTGG | 1 | | 6 | 37 SEQ ID NO. 2641 |
| (N20)NGG | 14 | 20943008 | - | TATCTCCAACCTCAAACTTGGG | 1 | | 2 | 45 SEQ ID NO. 2642 |
| (N20)NGG | 14 | 20943009 | - | ATATCTCCAACCTCAAACTTGGG | 1 | | 2 | 35 SEQ ID NO. 2643 |
| (N20)NGG | 14 | 20943010 | - | GATATCTCCAACCTCAAACTTGG | 1 | | 1 | 33 SEQ ID NO. 2644 |
| (N20)NGG | 14 | 20943041 | - | CAGGTAGGTTGATATGGTCACGG | 1 | | 3 | 24 SEQ ID NO. 2645 |
| (N20)NGG | 14 | 20943047 | - | TGAAACCAGGTAGGTTGATATGG | 1 | | 3 | 25 SEQ ID NO. 2646 |
| (N20)NGG | 14 | 20943056 | - | TCTGACCAAACCAGGTAGG | 1 | | 6 | 45 SEQ ID NO. 2647 |
| (N20)NGG | 14 | 20943060 | - | GGGTTCTGACCACTGAAACCAGG | 1 | | 2 | 20 SEQ ID NO. 2648 |
| (N20)NGG | 14 | 20943080 | - | CATCATTGGGCCCTCTGAGAGGG | 1 | | 2 | 20 SEQ ID NO. 2649 |
| (N20)NGG | 14 | 20943081 | - | TCATCATTGGGCCCTCTGAGAGG | 1 | | 1 | 27 SEQ ID NO. 2650 |
| (N20)NGG | 14 | 20943093 | - | CATACATACCTTTCATCATTGG | 1 | | 3 | 50 SEQ ID NO. 2651 |
| (N20)NGG | 14 | 20943094 | - | ACATACATACCTTTCATCATTGG | 1 | | 4 | 52 SEQ ID NO. 2652 |
| (N20)NGG | 14 | 20943220 | + | GATAATTCAACCTGTGTCCTAGG | 1 | | 2 | 32 SEQ ID NO. 2653 |
| (N20)NGG | 14 | 20943225 | + | TTCAACCTGTGTCCTAGGTTTGG | 1 | | 3 | 40 SEQ ID NO. 2654 |

| site type | site_chr omosome | site_start_ nucleotide | site_s trand | target_site_sequence_with_ NGG | genome_wide_ hits_with_1_ or_less_mism atches | genome_wide_ hits_with_2_or_ less_mismatc hes | genome_wide_h its_with_3_ or_less_mism atches | | |
|---|---|---|---|---|---|---|---|---|---|
| (N20)NGG | 14 | 20943262 | + | CCATGTCTGATGCCTACGACCGG | 1 | | 2 | 10 | SEQ ID NO. 2655 |
| (N20)NGG | 14 | 20943271 | + | ATGCCTACGACCGGACTATGAGG | 1 | | 1 | 3 | SEQ ID NO. 2656 |
| (N20)NGG | 14 | 20943277 | + | ACGACCGGACTATGAGGCAGAGG | 1 | | 1 | 9 | SEQ ID NO. 2657 |
| (N20)NGG | 14 | 20943278 | + | CGACCGGACTATGAGGCAGAGGG | 1 | | 1 | 9 | SEQ ID NO. 2658 |
| (N20)NGG | 14 | 20943292 | + | GGCAGAGGGCTCTCAGTACCTGG | 1 | | 4 | 36 | SEQ ID NO. 2659 |
| (N20)NGG | 14 | 20943302 | + | TCTCAGTACCTGGAAACAAATGG | 1 | | 5 | 70 | SEQ ID NO. 2660 |
| (N20)NGG | 14 | 20943303 | + | CTCAGTACCTGGAAACAAATGGG | 1 | | 2 | 54 | SEQ ID NO. 2661 |
| (N20)NGG | 14 | 20943304 | + | TCAGTACCTGGAAACAAATGGGG | 1 | | 5 | 60 | SEQ ID NO. 2662 |
| (N20)NGG | 14 | 20943305 | + | CAGTACCTGGAAACAAATGGGGG | 1 | | 8 | 49 | SEQ ID NO. 2663 |
| (N20)NGG | 14 | 20943323 | + | GGGGGAGCAACGTGAGCTACAGG | 1 | | 1 | 5 | SEQ ID NO. 2664 |
| (N20)NGG | 14 | 20943327 | + | GGAGCAACGTGAGCTACAGGAAGG | 1 | | 3 | 20 | SEQ ID NO. 2665 |
| (N20)NGG | 14 | 20943341 | + | ACAGGAAGGCACCTATGTGATGG | 2 | | 5 | 29 | SEQ ID NO. 2666 |
| (N20)NGG | 14 | 20943344 | + | GGAAGGCACCTATGTGATGGTGG | 1 | | 4 | 41 | SEQ ID NO. 2667 |
| (N20)NGG | 14 | 20943348 | + | GGCACCTATGTGATGGTCGCAGG | 1 | | 1 | 26 | SEQ ID NO. 2668 |
| (N20)NGG | 14 | 20943368 | + | AGGCCCCAGCTTTGAGACTGTGG | 1 | | 7 | 96 | SEQ ID NO. 2669 |
| (N20)NGG | 14 | 20943395 | + | ATGTCGTGTCTGCAGAAGCTGTG | 1 | | 7 | 37 | SEQ ID NO. 2670 |
| (N20)NGG | 14 | 20943396 | + | TGTCGTGTCTGCAGAAGCTGTTGG | 1 | | 2 | 25 | SEQ ID NO. 2671 |
| (N20)NGG | 14 | 20943411 | + | AAGCTGGGAGCAGACGCTGTTGG | 1 | | 4 | 38 | SEQ ID NO. 2672 |
| (N20)NGG | 14 | 20943419 | + | AGCAGACGCTGTTGGTGAGAAGG | 1 | | 2 | 35 | SEQ ID NO. 2673 |
| (N20)NGG | 14 | 20943420 | + | GCAGACGCTGTTGGTGAGAAGGG | 1 | | 3 | 37 | SEQ ID NO. 2674 |
| (N20)NGG | 14 | 20943421 | + | CAGACGCTGTTGGTGAGAAGGGG | 1 | | 2 | 39 | SEQ ID NO. 2675 |
| (N20)NGG | 14 | 20943428 | + | TGTTGGTGAGAAGGGGAATTTGG | 1 | | 2 | 109 | SEQ ID NO. 2676 |
| (N20)NGG | 14 | 20943432 | + | GGTGAGAAGGGGAATTTGGCTGG | 1 | | 9 | 57 | SEQ ID NO. 2677 |
| (N20)NGG | 14 | 20943208 | - | GATCTCCAAACCTAGGACACAGG | 1 | | 5 | 22 | SEQ ID NO. 2678 |
| (N20)NGG | 14 | 20943215 | - | GGGAAACGATCTCCAAACCTAGG | 1 | | 1 | 10 | SEQ ID NO. 2679 |
| (N20)NGG | 14 | 20943235 | - | CGTAGGCATCAGACATGGCAGG | 1 | | 1 | 17 | SEQ ID NO. 2680 |
| (N20)NGG | 14 | 20943236 | - | TCGTAGGCATCAGACATGGCAGG | 1 | | 2 | 17 | SEQ ID NO. 2681 |
| (N20)NGG | 14 | 20943240 | - | CCGGTCGTAGGCATCAGACATGG | 1 | | 1 | 4 | SEQ ID NO. 2682 |
| (N20)NGG | 14 | 20943252 | - | CTGCCTCATAGTCCGGTCGTAGG | 1 | | 1 | 6 | SEQ ID NO. 2683 |
| (N20)NGG | 14 | 20943259 | - | GAGCCTCTGCCTCATAGTCCGG | 1 | | 3 | 26 | SEQ ID NO. 2684 |
| (N20)NGG | 14 | 20943288 | - | TTGCTCCCCATTTGTTTCCAGG | 1 | | 5 | 49 | SEQ ID NO. 2685 |
| (N20)NGG | 14 | 20943330 | - | GGGGCCTGCCACCATCACATAGG | 1 | | 2 | 43 | SEQ ID NO. 2686 |
| (N20)NGG | 14 | 20943349 | - | CTGCCACAGTCTCAAAGCTGGGG | 1 | | 3 | 74 | SEQ ID NO. 2687 |
| (N20)NGG | 14 | 20943350 | - | TCTGCCACAGTCTCAAAGCTGGG | 1 | | 4 | 55 | SEQ ID NO. 2688 |

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 14 | 20943351 | - | TTCTGCCACAGTCTCAAAGCTGG | 1 | | 7 | 50 SEQ ID NO. 2689 |
| (N20)NGG | 14 | 20944542 | + | TTTCCATCTTTCTCACTATCAGG | 1 | | 13 | 112 SEQ ID NO. 2690 |
| (N20)NGG | 14 | 20944576 | + | TACCAGAAGTTATCGTTGCACGG | 1 | | 3 | 9 SEQ ID NO. 2691 |
| (N20)NGG | 14 | 20944584 | + | GTTATCGTTGCACGGCACTGTGG | 1 | | 1 | 10 SEQ ID NO. 2692 |
| (N20)NGG | 14 | 20944599 | + | CACTGTGGACTTCGAGTCTTTGG | 1 | | 2 | 23 SEQ ID NO. 2693 |
| (N20)NGG | 14 | 20944622 | + | CTTCTCACTCATCACTAACAAGG | 2 | | 3 | 48 SEQ ID NO. 2694 |
| (N20)NGG | 14 | 20944631 | + | CATCACTAACAAGGTCATCATGG | 2 | | 6 | 50 SEQ ID NO. 2695 |
| (N20)NGG | 14 | 20944646 | + | CATCATGGATTATGAAAAGCCTGG | 3 | | 10 | 43 SEQ ID NO. 2696 |
| (N20)NGG | 14 | 20944652 | + | GGATTATGAAAGCCTGGAGAAGG | 2 | | 4 | 62 SEQ ID NO. 2697 |
| (N20)NGG | 14 | 20944680 | + | CATGAAGAAGTCTTAGCAGCTGG | 2 | | 5 | 31 SEQ ID NO. 2698 |
| (N20)NGG | 14 | 20944703 | + | CAAACAAGCTGCACAGAAATTGG | 2 | | 5 | 57 SEQ ID NO. 2699 |
| (N20)NGG | 14 | 20944727 | + | ACAGTTTGTCTCCATTCTTATGG | 2 | | 5 | 60 SEQ ID NO. 2700 |
| (N20)NGG | 14 | 20944769 | + | CAAAGCCAGTTGACCTGCCTTGG | 1 | | 3 | 39 SEQ ID NO. 2701 |
| (N20)NGG | 14 | 20944779 | + | TGACCTGCCTTGGAGTCGTCTGG | 1 | | 1 | 14 SEQ ID NO. 2702 |
| (N20)NGG | 14 | 20944523 | - | ATGCCTGATAGTGAGAAAGATGG | 1 | | 5 | 60 SEQ ID NO. 2703 |
| (N20)NGG | 14 | 20944556 | - | TGCCGTGCAACGATAACTTCTGG | 1 | | 1 | 6 SEQ ID NO. 2704 |
| (N20)NGG | 14 | 20944642 | - | CTTCATGGTTGGCCTTCTCCAGG | 1 | | 1 | 32 SEQ ID NO. 2705 |
| (N20)NGG | 14 | 20944653 | - | TGCTAAGACTTCTTCATGGTTGG | 2 | | 4 | 30 SEQ ID NO. 2706 |
| (N20)NGG | 14 | 20944657 | - | CAGCTGCTAAGACTTCTTCATGG | 1 | | 5 | 56 SEQ ID NO. 2707 |
| (N20)NGG | 14 | 20944716 | - | TGGAATGCTGGCCATAAGAATGG | 1 | | 4 | 47 SEQ ID NO. 2708 |
| (N20)NGG | 14 | 20944728 | - | TTTGTCAGGAGTGGAATGCTGG | 1 | | 4 | 51 SEQ ID NO. 2709 |
| (N20)NGG | 14 | 20944736 | - | CAACTGGCTTTGTCAGGAGTGG | 1 | | 2 | 44 SEQ ID NO. 2710 |
| (N20)NGG | 14 | 20944741 | - | CAGGTCAACTGGCTTTGTCAGGG | 1 | | 4 | 36 SEQ ID NO. 2711 |
| (N20)NGG | 14 | 20944742 | - | GCAGGTCAACTGGCTTTGTCAG | 1 | | 1 | 22 SEQ ID NO. 2712 |
| (N20)NGG | 14 | 20944752 | - | CGACTCCAAGGCAGGTCAACTGG | 1 | | 1 | 13 SEQ ID NO. 2713 |
| (N20)NGG | 14 | 20944760 | - | ATGCCAGACGACTCCAAGGCAGG | 1 | | 1 | 10 SEQ ID NO. 2714 |

FIG. 11 cont.

| site type | site_chromosome | site_start_nucleotide | site_strand | target_site_sequence_with NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 8 | 48686749 | + | TTCCAGTGATGAGTACTCCTGG | | 1 | 3 | 23 SEQ ID NO. 2715 |
| (N20)NGG | 8 | 48686750 | + | TCCAGTGATGAGTACTCCTGGG | | 1 | 2 | 19 SEQ ID NO. 2716 |
| (N20)NGG | 8 | 48686761 | + | GCTACTCCTGGGTCATGAGAAGG | | 1 | 1 | 24 SEQ ID NO. 2717 |
| (N20)NGG | 8 | 48686785 | + | CCCTGCCTTCAGAGACTATGTGG | | 1 | 6 | 64 SEQ ID NO. 2718 |
| (N20)NGG | 8 | 48686791 | + | CTTCAGAGACTATGTGCTGTGG | | 1 | 3 | 39 SEQ ID NO. 2719 |
| (N20)NGG | 8 | 48686798 | + | GACTATGTGCTGTGGCACGAGG | | 1 | 2 | 27 SEQ ID NO. 2720 |
| (N20)NGG | 8 | 48686840 | + | CGTGCCCAAGAACCAGAGAGTGG | | 2 | 5 | 35 SEQ ID NO. 2721 |
| (N20)NGG | 8 | 48686841 | + | GTGCCCAAGAACCAGAGAGTGGG | | 2 | 4 | 44 SEQ ID NO. 2722 |
| (N20)NGG | 8 | 48686875 | + | GACTCAAGTGAAGTGCCTGATGG | | 1 | 2 | 29 SEQ ID NO. 2723 |
| (N20)NGG | 8 | 48686881 | + | AGTGAAGTGCCTGATGGACCAGG | | 1 | 3 | 51 SEQ ID NO. 2724 |
| (N20)NGG | 8 | 48686903 | + | GCAACAGACCCCAACATCCTTGG | | 1 | 7 | 44 SEQ ID NO. 2725 |
| (N20)NGG | 8 | 48686913 | + | CCAACATCCTTGGCAGAACCTGG | | 1 | 2 | 46 SEQ ID NO. 2726 |
| (N20)NGG | 8 | 48686914 | + | CAACATCCTTGGCAGAACCTGGG | | 1 | 4 | 41 SEQ ID NO. 2727 |
| (N20)NGG | 8 | 48686918 | + | ATCCTTGGCAGAACCTGGGAAGG | | 1 | 3 | 53 SEQ ID NO. 2728 |
| (N20)NGG | 8 | 48686922 | + | TTGGCAGAACCTGGGAAGGATGG | | 1 | 12 | 201 SEQ ID NO. 2729 |
| (N20)NGG | 8 | 48686923 | + | TGGCAGAACCTGGGAAGGATGGG | | 1 | 4 | 78 SEQ ID NO. 2730 |
| (N20)NGG | 8 | 48686931 | + | CCTGGGAAGGATGGGAGCCCTGG | | 2 | 13 | 133 SEQ ID NO. 2731 |
| (N20)NGG | 8 | 48686939 | + | GGATGGGAGCCCTGGATGTGAGG | | 1 | 9 | 87 SEQ ID NO. 2732 |
| (N20)NGG | 8 | 48686946 | + | AGCCCTGGATGTGAGGTCTGTGG | | 2 | 12 | 178 SEQ ID NO. 2733 |
| (N20)NGG | 8 | 48686947 | + | GCCCTGGATGTGAGGTCTGTGGG | | 1 | 5 | 45 SEQ ID NO. 2734 |
| (N20)NGG | 8 | 48686729 | - | ACCCAGGAGTAGCTCATCACTGG | | 1 | 1 | 23 SEQ ID NO. 2735 |
| (N20)NGG | 8 | 48686745 | - | CAGGGGCCTTCTCATGACCCAGG | | 1 | 5 | 41 SEQ ID NO. 2736 |
| (N20)NGG | 8 | 48686762 | - | CACATAGTCTCTGAAGGCAGGGG | | 1 | 1 | 97 SEQ ID NO. 2737 |
| (N20)NGG | 8 | 48686763 | - | CCACATAGTCTCTGAAGGCAGG | | 2 | 5 | 40 SEQ ID NO. 2738 |
| (N20)NGG | 8 | 48686764 | - | GCCACATAGTCTCTGAAGGCAG | | 1 | 2 | 28 SEQ ID NO. 2739 |
| (N20)NGG | 8 | 48686768 | - | CACAGCCACATAGTCTCTGAAGG | | 1 | 4 | 39 SEQ ID NO. 2740 |
| (N20)NGG | 8 | 48686822 | - | AAGCCCACTCTCTGGTTCTTGG | | 1 | 6 | 53 SEQ ID NO. 2741 |
| (N20)NGG | 8 | 48686823 | - | AAAGCCCACTCTCTGGTTCTTGG | | 2 | 6 | 91 SEQ ID NO. 2742 |
| (N20)NGG | 8 | 48686830 | - | TCTTCTGAAAGCCCACTCTCTGG | | 1 | 3 | 57 SEQ ID NO. 2743 |
| (N20)NGG | 8 | 48686868 | - | GGTCGTTGCCTGGTCATCAGG | | 1 | 1 | 14 SEQ ID NO. 2744 |
| (N20)NGG | 8 | 48686877 | - | GGATGTTGGGGTCGTTGCCTGG | | 1 | 1 | 28 SEQ ID NO. 2745 |
| (N20)NGG | 8 | 48686889 | - | AGGTTCTGCCAAGGATGTTGGGG | | 1 | 1 | 42 SEQ ID NO. 2746 |
| (N20)NGG | 8 | 48686890 | - | CAGGTTCTGCCAAGGATGTTGG | | 1 | 2 | 79 SEQ ID NO. 2747 |

FIG. 12

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 8 | 48686891 | - | CCAGTTCTGCCAAGGATGTTGG | 2 | 8 | 62 | SEQ ID NO. 2748 |
| (N20)NGG | 8 | 48686898 | - | ATCCTTCCCAGTTCTGCCAAGG | 1 | 4 | 65 | SEQ ID NO. 2749 |
| (N20)NGG | 8 | 48686909 | - | CCAGGGCTCCCATCCTTCCCAGG | 2 | 11 | 112 | SEQ ID NO. 2750 |
| (N20)NGG | 8 | 48686926 | - | TCCCACAGACCTCACATCCAGG | 2 | 4 | 162 | SEQ ID NO. 2751 |
| (N20)NGG | 8 | 48686927 | - | CTCCACAGACCTCACATCCAGG | 1 | 11 | 200 | SEQ ID NO. 2752 |
| (N20)NGG | 8 | 48689432 | + | GAACAGAAAATGCTGAAAAAAGG | 1 | 14 | 354 | SEQ ID NO. 2753 |
| (N20)NGG | 8 | 48689435 | + | CAGAAAATGCTGAAAAAAGGAGG | 1 | 15 | 204 | SEQ ID NO. 2754 |
| (N20)NGG | 8 | 48689436 | + | AGAAAATGCTGAAAAAAGGAGGG | 3 | 26 | 403 | SEQ ID NO. 2755 |
| (N20)NGG | 8 | 48689442 | + | TGCTGAAAAAAGGAGGGTCATGG | 1 | 4 | 67 | SEQ ID NO. 2756 |
| (N20)NGG | 8 | 48689475 | + | TAAATGTTGCTGAAAAAAATTGG | 3 | 49 | 626 | SEQ ID NO. 2757 |
| (N20)NGG | 8 | 48689519 | + | TACGCTAAGAGAAAGTTAGCAGG | 1 | 2 | 14 | SEQ ID NO. 2758 |
| (N20)NGG | 8 | 48689544 | + | CCAATCCAGCAGTCATTACTTGG | 1 | 4 | 28 | SEQ ID NO. 2759 |
| (N20)NGG | 8 | 48689562 | + | CTTGGTAAGATTTTCTGTCGGTGG | 1 | 5 | 95 | SEQ ID NO. 2760 |
| (N20)NGG | 8 | 48689478 | - | CGTAACATATTTTCTGTCGGGGG | 1 | 1 | 7 | SEQ ID NO. 2761 |
| (N20)NGG | 8 | 48689479 | - | GCGTAACATATTTTCTGTCGGG | 1 | 3 | 16 | SEQ ID NO. 2762 |
| (N20)NGG | 8 | 48689480 | - | AGCGTAACATATTTTCTGTCGG | 2 | 12 | 185 | SEQ ID NO. 2763 |
| (N20)NGG | 8 | 48689481 | - | TAGCGTAACATATTTTCTGTCG | 1 | 2 | 40 | SEQ ID NO. 2764 |
| (N20)NGG | 8 | 48689522 | - | CCAAGTAATGACTGCTGATTGG | 1 | 3 | 25 | SEQ ID NO. 2765 |
| (N20)NGG | 8 | 48689527 | - | TCTTACCAAGTAATGACTGCTGG | 1 | 3 | 21 | SEQ ID NO. 2766 |
| (N20)NGG | 8 | 48690278 | + | TCCCTGAGTTGATGCCTTTTCGG | 2 | 5 | 57 | SEQ ID NO. 2767 |
| (N20)NGG | 8 | 48690324 | + | GATGTTACCAATGAAAGAAACGG | 2 | 10 | 154 | SEQ ID NO. 2768 |
| (N20)NGG | 8 | 48690325 | + | ATGTTACCAATGAAAGAAACGGG | 3 | 19 | 266 | SEQ ID NO. 2769 |
| (N20)NGG | 8 | 48690345 | + | GGGCCTTATGTACAGCATCATGG | 1 | 4 | 31 | SEQ ID NO. 2770 |
| (N20)NGG | 8 | 48690359 | + | GCATCATGGTACACGCACTCCGG | 1 | 1 | 8 | SEQ ID NO. 2771 |
| (N20)NGG | 8 | 48690360 | + | CATCATGGTACACGCACTCCGGG | 1 | 1 | 8 | SEQ ID NO. 2772 |
| (N20)NGG | 8 | 48690379 | + | CGGGCCTTCCGCTCAGACCCTGG | 1 | 1 | 22 | SEQ ID NO. 2773 |
| (N20)NGG | 8 | 48690399 | + | TGGCCTGCTCACCAACACCATGG | 1 | 2 | 38 | SEQ ID NO. 2774 |
| (N20)NGG | 8 | 48690414 | + | CACCATGGATGTGTTTGTCAAGG | 1 | 3 | 47 | SEQ ID NO. 2775 |
| (N20)NGG | 8 | 48690431 | + | TCAAGGAGCCCTCCTTTGATTGG | 1 | 3 | 47 | SEQ ID NO. 2776 |
| (N20)NGG | 8 | 48690439 | - | CCCTCCTTTGATTGGAAAGTAGG | 1 | 6 | 31 | SEQ ID NO. 2777 |
| (N20)NGG | 8 | 48690224 | - | ACTAAACAAGAAAAAAGGCAAGG | 1 | 20 | 401 | SEQ ID NO. 2778 |
| (N20)NGG | 8 | 48690229 | - | CAGAAACTAAACAAGAAAAAAGG | 2 | 47 | 851 | SEQ ID NO. 2779 |
| (N20)NGG | 8 | 48690252 | - | AAAGGCATCAACTCAGGGACTGG | 1 | 3 | 36 | SEQ ID NO. 2780 |

FIG. 12 cont.

| site_type | site_chromosome | site_start_nucleotide | site_strand | target_site_sequence_with NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 8 | 48690257 | - | GCCGAAAAGGCATCAACTCAGGG | 1 | 1 | 12 | SEQ ID NO. 2781 |
| (N20)NGG | 8 | 48690258 | - | AGCCGAAAAGGCATCAACTCAGG | 1 | 2 | 15 | SEQ ID NO. 2782 |
| (N20)NGG | 8 | 48690270 | - | AACTGGCCAGTTAGCCGAAAAGG | 1 | 1 | 3 | SEQ ID NO. 2783 |
| (N20)NGG | 8 | 48690287 | - | GTAACATCAGATTGATAAACTGG | 1 | 7 | 35 | SEQ ID NO. 2784 |
| (N20)NGG | 8 | 48690309 | - | ATAAGGCCCGTTTCTTTCATTGG | 1 | 2 | 23 | SEQ ID NO. 2785 |
| (N20)NGG | 8 | 48690326 | - | GTACCATGATGCTGTACATAAGG | 1 | 2 | 25 | SEQ ID NO. 2786 |
| (N20)NGG | 8 | 48690356 | - | CAGGGTCTGAGCGGAAGGCCCGG | 1 | 3 | 35 | SEQ ID NO. 2787 |
| (N20)NGG | 8 | 48690361 | - | CAGGCCAGGTCTGAGCGGAAGG | 1 | 4 | 60 | SEQ ID NO. 2788 |
| (N20)NGG | 8 | 48690365 | - | TGAGCAGGCCAGGGTCTGAGCGG | 1 | 14 | 94 | SEQ ID NO. 2789 |
| (N20)NGG | 8 | 48690374 | - | TGGTGTTGGTGAGCAGGCCAGGG | 1 | 4 | 52 | SEQ ID NO. 2790 |
| (N20)NGG | 8 | 48690375 | - | ATGGTGTTGGTGAGCAGGCCAGG | 1 | 3 | 64 | SEQ ID NO. 2791 |
| (N20)NGG | 8 | 48690380 | - | CATCCATGGTGTTGGTGAGCAGG | 1 | 1 | 22 | SEQ ID NO. 2792 |
| (N20)NGG | 8 | 48690388 | - | GACAAACACATCCATGGTGTTGG | 1 | 2 | 42 | SEQ ID NO. 2793 |
| (N20)NGG | 8 | 48690394 | - | CTCCTTGACAAACACATCCATGG | 2 | 3 | 53 | SEQ ID NO. 2794 |
| (N20)NGG | 8 | 48690417 | - | CCTACTTTCCAATCAAAGGAGGG | 1 | 1 | 35 | SEQ ID NO. 2795 |
| (N20)NGG | 8 | 48690418 | - | ACCTACTTTCCAATCAAAGGAGG | 1 | 2 | 33 | SEQ ID NO. 2796 |
| (N20)NGG | 8 | 48690421 | - | AAAACTACTTTCCAATCAAAGG | 2 | 4 | 68 | SEQ ID NO. 2797 |
| (N20)NGG | 8 | 48691019 | + | CACAGCTGTGTCTCTTTTTGTAGG | 1 | 5 | 67 | SEQ ID NO. 2798 |
| (N20)NGG | 8 | 48691022 | + | AGCTGTGTCTCTTTTGTAGGCGG | 1 | 5 | 50 | SEQ ID NO. 2799 |
| (N20)NGG | 8 | 48691023 | + | GCTGTGTCTCTTTTGTAGGCGGG | 1 | 3 | 42 | SEQ ID NO. 2800 |
| (N20)NGG | 8 | 48691034 | + | TTTGTAGGCGGGCCTTCGTGAGG | 1 | 1 | 9 | SEQ ID NO. 2801 |
| (N20)NGG | 8 | 48691053 | + | GAGGATGAGTACAAGCCCTGAGG | 1 | 2 | 34 | SEQ ID NO. 2802 |
| (N20)NGG | 8 | 48691062 | + | TACAAGCCCTGAGGCTTTCCTGG | 2 | 5 | 39 | SEQ ID NO. 2803 |
| (N20)NGG | 8 | 48691115 | + | CTCTGATATGCATCAGCCACTGG | 1 | 1 | 28 | SEQ ID NO. 2804 |
| (N20)NGG | 8 | 48691123 | + | TGCATCAGCCACTGGATCCTCGG | 1 | 2 | 37 | SEQ ID NO. 2805 |
| (N20)NGG | 8 | 48691124 | + | GCATCAGCCACTGGATCCTCGGG | 1 | 2 | 36 | SEQ ID NO. 2806 |
| (N20)NGG | 8 | 48691129 | + | AGCCACTGGATCCTCGGGATTGG | 1 | 1 | 11 | SEQ ID NO. 2807 |
| (N20)NGG | 8 | 48691155 | + | CAGACATCTGAACAACTTTATGG | 2 | 3 | 37 | SEQ ID NO. 2808 |
| (N20)NGG | 8 | 48691158 | + | ACATCTGAACAACTTTATGTGG | 1 | 3 | 54 | SEQ ID NO. 2809 |
| (N20)NGG | 8 | 48691164 | + | GAACAACTTTATGGTGGCCATGG | 1 | 4 | 30 | SEQ ID NO. 2810 |
| (N20)NGG | 8 | 48691171 | + | TTTATGGTGGCCATGGAGACTGG | 1 | 5 | 49 | SEQ ID NO. 2811 |
| (N20)NGG | 8 | 48691174 | + | ATGGTGGCCATGGAGACTGCGG | 1 | 10 | 88 | SEQ ID NO. 2812 |
| (N20)NGG | 8 | 48691183 | + | ATGGAGACTGGCGGCGTGATCGG | | 2 | 7 | SEQ ID NO. 2813 |

FIG. 12 cont.

| site_type | site_chr omosome | site_start_ nucleotide | site_s trand | target_site_sequence_wi th NGG | genome_wide_ hits_with_1 or_less_mism atches | genome_wide_ hits_with_ 2_or_less_m ismatches | genome_wide_ hits_with_3 or_less_mism atches | |
|---|---|---|---|---|---|---|---|---|
| (N20)NGG | 8 | 48691184 | + | TGGAGACTGGCGCGTGATCGGG | | 1 | 16 | SEQ ID NO. 2814 |
| (N20)NGG | 8 | 48691195 | + | GGCGTGATCGGGATCGACTTTGG | | 1 | 3 | SEQ ID NO. 2815 |
| (N20)NGG | 8 | 48691196 | + | GCGTGATCGGGATCGACTTTGGG | | 1 | 1 | SEQ ID NO. 2816 |
| (N20)NGG | 8 | 48691207 | + | ATCGACTTTGGGCATGCGTTTGG | | 1 | 5 | SEQ ID NO. 2817 |
| (N20)NGG | 8 | 48691221 | + | TGCGTTTGGATCCGCTACACAGG | | 1 | 3 | SEQ ID NO. 2818 |
| (N20)NGG | 8 | 48690994 | - | ACAAAAGAGACACAGCTGTGCGG | | 1 | 106 | SEQ ID NO. 2819 |
| (N20)NGG | 8 | 48691024 | - | GCTTGTACTCATCCTCACGAAGG | | 7 | 8 | SEQ ID NO. 2820 |
| (N20)NGG | 8 | 48691046 | - | GGAGCGCCAGGAAAGCCTCAGGG | | 2 | 39 | SEQ ID NO. 2821 |
| (N20)NGG | 8 | 48691047 | - | CGGAGCGCCAGGAAAGCCTCAGG | | 3 | 24 | SEQ ID NO. 2822 |
| (N20)NGG | 8 | 48691058 | - | CGAAGTGGGAGCGAGCGCCAGG | | 1 | 15 | SEQ ID NO. 2823 |
| (N20)NGG | 8 | 48691067 | - | GAGAGCTGGCGAAGTGGGAGCGG | | 2 | 91 | SEQ ID NO. 2824 |
| (N20)NGG | 8 | 48691072 | - | AGCGTGAGAGCTGGCGAAGTGGG | | 6 | 12 | SEQ ID NO. 2825 |
| (N20)NGG | 8 | 48691073 | - | GAGCGTGAGAGCTGGCGAAGTGG | | 1 | 26 | SEQ ID NO. 2826 |
| (N20)NGG | 8 | 48691081 | - | GCATATCAGAGCGTGAGAGCTGG | | 1 | 27 | SEQ ID NO. 2827 |
| (N20)NGG | 8 | 48691109 | - | CTCCAATCCGAGGATCCAGTGG | | 2 | 23 | SEQ ID NO. 2828 |
| (N20)NGG | 8 | 48691118 | - | GATGTCTGTCTCCAATCCCGAGG | | 2 | 21 | SEQ ID NO. 2829 |
| (N20)NGG | 8 | 48691159 | - | GATCACGCCGCCAGTCTCCATGG | | 2 | 5 | SEQ ID NO. 2830 |
| (N20)NGG | 8 | 48691210 | - | CAGCAAGTGCACCTGTGTAGCGG | | 1 | 24 | SEQ ID NO. 2831 |
| (N20)NGG | 8 | 48691288 | + | TGTTTCTATTATTAAATCATAGG | | 1 | 240 | SEQ ID NO. 2832 |
| (N20)NGG | 8 | 48691289 | + | GTTTCTATTATTATTAAATCATAGGG | 2 | 4 | 146 | SEQ ID NO. 2833 |
| (N20)NGG | 8 | 48691290 | + | TTTCTATTATTATTAAATCATAGGGG | | 10 | 202 | SEQ ID NO. 2834 |
| (N20)NGG | 8 | 48691343 | - | ACTTACTTTAAGAGATCAGCAGG | | 11 | 45 | SEQ ID NO. 2835 |
| (N20)NGG | 8 | 48691573 | + | TCTCACTCATTAGTGATCCCAGG | | 2 | 28 | SEQ ID NO. 2836 |
| (N20)NGG | 8 | 48691574 | + | CTCACTCATTAGTGATCCCAGGG | | 3 | 36 | SEQ ID NO. 2837 |
| (N20)NGG | 8 | 48691600 | + | CGCCGTGTGAATATAAAGATTGG | | 2 | 5 | SEQ ID NO. 2838 |
| (N20)NGG | 8 | 48691617 | + | GATTGGCTGACAAAAATGTCAGG | 3 | 9 | 59 | SEQ ID NO. 2839 |
| (N20)NGG | 8 | 48691632 | + | ATGTCAGGAAAACATGATGTTGG | 2 | 6 | 92 | SEQ ID NO. 2840 |
| (N20)NGG | 8 | 48691663 | + | ATGTAATGTATAAGTAAGTTTGG | | 1 | 39 | SEQ ID NO. 2841 |
| (N20)NGG | 8 | 48691544 | - | TCACTAATGAGTGAGAAAAGGGG | | 10 | 154 | SEQ ID NO. 2842 |
| (N20)NGG | 8 | 48691545 | - | ATCACTAATGAGTGAGAAAAGGG | | 5 | 139 | SEQ ID NO. 2843 |
| (N20)NGG | 8 | 48691546 | - | GATCACTAATGAGTGAGAAAAGG | | 5 | 66 | SEQ ID NO. 2844 |
| (N20)NGG | 8 | 48691568 | - | TATTCACACGGCGGTGCCCTGGG | | 1 | 7 | SEQ ID NO. 2845 |
| (N20)NGG | 8 | 48691569 | - | ATATTCACACGGCGGTGCCCTGG | | 1 | 4 | SEQ ID NO. 2846 |

FIG. 12 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 8 | 48691577 | - | CAATCTTTATATTCACACGGCGG | 1 | 2 | 18 | SEQ ID NO. 2847 |
| (N20)NGG | 8 | 48691580 | - | AGCCAATCTTTATATTCACACGG | 1 | 2 | 65 | SEQ ID NO. 2848 |
| (N20)NGG | 8 | 48694722 | + | AACCTTTTATTCTCCCTTTCAGG | 1 | 4 | 95 | SEQ ID NO. 2849 |
| (N20)NGG | 8 | 48694727 | + | TTTATTCTCCCTTTCAGGTTAGG | 1 | 4 | 118 | SEQ ID NO. 2850 |
| (N20)NGG | 8 | 48694740 | + | TCAGGTTAGGATTAATTGAGTGG | 1 | 4 | 46 | SEQ ID NO. 2851 |
| (N20)NGG | 8 | 48694765 | + | TGAAATACTGTTACCTTGAAGG | 1 | 10 | 83 | SEQ ID NO. 2852 |
| (N20)NGG | 8 | 48694795 | + | TTTGAACACCATGTCCAAGAGG | 2 | 3 | 38 | SEQ ID NO. 2853 |
| (N20)NGG | 8 | 48694801 | + | CACCATGTCCAAGAGGAGAAGG | 1 | 7 | 62 | SEQ ID NO. 2854 |
| (N20)NGG | 8 | 48694804 | + | CATGTCCAAGAGGAGAAGGCGG | 1 | 7 | 94 | SEQ ID NO. 2855 |
| (N20)NGG | 8 | 48694815 | + | AGGAGAAGGCGGCTTACCTGAGG | 1 | 2 | 39 | SEQ ID NO. 2856 |
| (N20)NGG | 8 | 48694820 | + | AAGGCGGCTTACCTGAGGTAAGG | 1 | 10 | 658 | SEQ ID NO. 2857 |
| (N20)NGG | 8 | 48694821 | + | AGGCGGCTTACCTGAGGTAAGGG | 1 | 10 | 637 | SEQ ID NO. 2858 |
| (N20)NGG | 8 | 48694824 | + | CGGCTTACCTGAGGTAAGGCGG | 1 | 2 | 21 | SEQ ID NO. 2859 |
| (N20)NGG | 8 | 48694702 | - | AACCTGAAAGGCAGAGAATAAAGG | 1 | 4 | 134 | SEQ ID NO. 2860 |
| (N20)NGG | 8 | 48694713 | - | CAATTAATCCTAACCTGAAAGG | 1 | 3 | 48 | SEQ ID NO. 2861 |
| (N20)NGG | 8 | 48694714 | - | TCAATTAATCCTAACCTGAAAGG | 1 | 2 | 41 | SEQ ID NO. 2862 |
| (N20)NGG | 8 | 48694757 | - | GTTCAAAAGAGAGGTCCTTCAAGG | 1 | 3 | 31 | SEQ ID NO. 2863 |
| (N20)NGG | 8 | 48694767 | - | GGGACATGGTGTTCAAAAGAAGG | 1 | 3 | 53 | SEQ ID NO. 2864 |
| (N20)NGG | 8 | 48694781 | - | CGCCTTCTCCTCTTGGGACATGG | 1 | 4 | 36 | SEQ ID NO. 2865 |
| (N20)NGG | 8 | 48694787 | - | GTAAGCGCCTTCTCCTCTTGGG | 1 | 1 | 16 | SEQ ID NO. 2866 |
| (N20)NGG | 8 | 48694788 | - | GGTAAGCGCCTTCTCCTCTTGG | 1 | 2 | 18 | SEQ ID NO. 2867 |
| (N20)NGG | 8 | 48694809 | - | CGTGTGGCCGCCCTTACCTCAGG | 1 | 3 | 10 | SEQ ID NO. 2868 |
| (N20)NGG | 8 | 48694938 | + | GATGACATTCTGATTTTTGAAGG | 1 | 5 | 91 | SEQ ID NO. 2869 |
| (N20)NGG | 8 | 48694950 | + | ATTTTTGAAGGTGACAGTCATGG | 1 | 3 | 71 | SEQ ID NO. 2870 |
| (N20)NGG | 8 | 48694964 | + | CAGTCATGGCGTCTCTGCGAAGG | 1 | 1 | 7 | SEQ ID NO. 2871 |
| (N20)NGG | 8 | 48694987 | + | CCCAAGCGCATCATCATCCGTGG | 1 | 2 | 2 | SEQ ID NO. 2872 |
| (N20)NGG | 8 | 48695000 | + | TCATCCGTGGCCATGACGAGAGG | 1 | 1 | 9 | SEQ ID NO. 2873 |
| (N20)NGG | 8 | 48695001 | + | CATCCGTGGCCATGACGAGAGGG | 1 | 3 | 12 | SEQ ID NO. 2874 |
| (N20)NGG | 8 | 48695016 | + | CGAGAGGGAACACCCTTTCCTGG | 1 | 3 | 16 | SEQ ID NO. 2875 |
| (N20)NGG | 8 | 48695022 | + | GGAACACCCTTTCCTGGTGAAGG | 1 | 7 | 82 | SEQ ID NO. 2876 |
| (N20)NGG | 8 | 48695023 | + | GAACACCCTTTCCTGGTGAAGGG | 1 | 5 | 53 | SEQ ID NO. 2877 |
| (N20)NGG | 8 | 48695026 | + | CACCCTTTCCTGGTGAAGGGTGG | 1 | 5 | 84 | SEQ ID NO. 2878 |
| (N20)NGG | 8 | 48695031 | + | TTTCCTGGTGAAGGGTGGCGAGG | 1 | 1 | 38 | SEQ ID NO. 2879 |

FIG. 12 cont.

| site type | site chr omosome | site start nucleotide | site strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 8 | 48695039 | + | TGAAGGGTGCGAGGACCTGCGG | | | 3 | 40 SEQ ID NO. 2880 |
| (N20)NGG | 8 | 48695043 | + | GGGTGGCGAGGACCTGCGGCAGG | 1 | | 1 | 38 SEQ ID NO. 2881 |
| (N20)NGG | 8 | 48695055 | + | CCTGCGGCAGGACCAGCGCGTGG | 1 | | 6 | 32 SEQ ID NO. 2882 |
| (N20)NGG | 8 | 48695070 | + | GCGCGTGGAGCAGCTCTTCCAGG | 1 | | 3 | 24 SEQ ID NO. 2883 |
| (N20)NGG | 8 | 48695080 | + | CAGCTCTTCCAGGTCATGAATGG | 1 | | 6 | 56 SEQ ID NO. 2884 |
| (N20)NGG | 8 | 48695081 | + | AGCTCTTCCAGGTCATGAATGGG | 1 | | 2 | 50 SEQ ID NO. 2885 |
| (N20)NGG | 8 | 48695088 | + | CCAGGTCATGAATGGGATCCTGG | 1 | | 3 | 32 SEQ ID NO. 2886 |
| (N20)NGG | 8 | 48695114 | + | AAGACTCCGCCTGCAGCCAGAGG | 1 | | 3 | 37 SEQ ID NO. 2887 |
| (N20)NGG | 8 | 48695115 | + | AGACTCCGCCTGCAGCCAGAGGG | 1 | | 2 | 26 SEQ ID NO. 2888 |
| (N20)NGG | 8 | 48695129 | + | GCCAGAGGGCCCTGCAGCTGAGG | 1 | | 16 | 148 SEQ ID NO. 2889 |
| (N20)NGG | 8 | 48695159 | + | GCGTTGTGCCATGACCTTCCAGG | 1 | | 1 | 10 SEQ ID NO. 2890 |
| (N20)NGG | 8 | 48695170 | + | ATGACCTTCCAGGTAACTGCCAGG | 2 | | 5 | 28 SEQ ID NO. 2891 |
| (N20)NGG | 8 | 48694965 | - | CCACGGATGATGATGCGCTTGG | 1 | | 1 | 4 SEQ ID NO. 2892 |
| (N20)NGG | 8 | 48694966 | - | GCCACGGATGATGATGCGCTTGG | 1 | | 1 | 10 SEQ ID NO. 2893 |
| (N20)NGG | 8 | 48694982 | - | GTTCCCTCTCTCATGGCCACGG | 1 | | 1 | 9 SEQ ID NO. 2894 |
| (N20)NGG | 8 | 48694988 | - | AAGGGTGTTCCCTCTCGTCATGG | 1 | | 1 | 15 SEQ ID NO. 2895 |
| (N20)NGG | 8 | 48695006 | - | CGCCACCCTTCACCAGGAAAGG | 1 | | 2 | 36 SEQ ID NO. 2896 |
| (N20)NGG | 8 | 48695007 | - | TCGCCACCCTTCACCAGGAAAGG | 1 | | 2 | 25 SEQ ID NO. 2897 |
| (N20)NGG | 8 | 48695012 | - | GGTCCTCGCCACCCTTCACCAGG | 1 | | 1 | 37 SEQ ID NO. 2898 |
| (N20)NGG | 8 | 48695033 | - | CCAGCGCTGGTCCTCGCCGCAGG | 1 | | 4 | 24 SEQ ID NO. 2899 |
| (N20)NGG | 8 | 48695045 | - | GGAAGAGCTGCTCCACGCCTGG | 1 | | 2 | 23 SEQ ID NO. 2900 |
| (N20)NGG | 8 | 48695066 | - | CAGGATCCCATTCATGACCTGG | 1 | | 4 | 44 SEQ ID NO. 2901 |
| (N20)NGG | 8 | 48695084 | - | TGCAGGCGGAGTCTTGGGCAGG | 1 | | 2 | 36 SEQ ID NO. 2902 |
| (N20)NGG | 8 | 48695089 | - | CTGGCTGCAGGCGGAGTCTTGG | 1 | | 4 | 34 SEQ ID NO. 2903 |
| (N20)NGG | 8 | 48695090 | - | TCTGGCTGCAGGCGGAGTCTTGG | 2 | | 2 | 41 SEQ ID NO. 2904 |
| (N20)NGG | 8 | 48695098 | - | CAGGGCCCCTGGCTGCAGGCGG | 1 | | 11 | 187 SEQ ID NO. 2905 |
| (N20)NGG | 8 | 48695101 | - | CTGCAGGGCCCCTGGCTGCAGG | 2 | | 18 | 161 SEQ ID NO. 2906 |
| (N20)NGG | 8 | 48695108 | - | TCCTCAGCTGCAGGGCCCCTGG | 1 | | 12 | 121 SEQ ID NO. 2907 |
| (N20)NGG | 8 | 48695116 | - | GCTATAGGTCCTCAGCTGCAGG | 1 | | 2 | 18 SEQ ID NO. 2908 |
| (N20)NGG | 8 | 48695117 | - | CGCTATAGGTCCTCAGCTGCAGG | 1 | | 1 | 14 SEQ ID NO. 2909 |
| (N20)NGG | 8 | 48695131 | - | GGTCATGGGCACAACGCTATAGG | 1 | | 1 | 9 SEQ ID NO. 2910 |
| (N20)NGG | 8 | 48695145 | - | GGCAGTTACCTGGAGGTCATGG | 1 | | 5 | 55 SEQ ID NO. 2911 |
| (N20)NGG | 8 | 48695146 | - | TGGCAGTTACCTGGAGGTCATGG | 1 | | 6 | 46 SEQ ID NO. 2912 |

FIG. 12 cont.

| site_type | site_chromosome | site_start_nucleotide | site_strand | target_site_sequence with NGG | genome_wide hits with 1 or less mismatches | genome_wide hits with 2 or less mismatches | genome_wide hits with 3 or less mismatches | |
|---|---|---|---|---|---|---|---|---|
| (N20)NGG | 8 | 48695152 | - | GCAGCCTGGCAGTTACCTGGAGG | 1 | 7 | 62 | SEQ ID NO. 2913 |
| (N20)NGG | 8 | 48695155 | - | GGAGCAGCCTGGCAGTTACCTGG | 1 | 4 | 45 | SEQ ID NO. 2914 |
| (N20)NGG | 8 | 48696302 | + | GCAAGGTTCTGGTTTGTTTTAGG | 1 | 2 | 59 | SEQ ID NO. 2915 |
| (N20)NGG | 8 | 48696314 | + | TTTGTTTTAGGTCAGTATGACGG | 1 | 7 | 84 | SEQ ID NO. 2916 |
| (N20)NGG | 8 | 48696318 | + | TTTTAGGTCAGTATGACGGTAGG | 1 | 1 | 8 | SEQ ID NO. 2917 |
| (N20)NGG | 8 | 48696319 | + | TTTAGGTCAGTATGACGGTAGGG | 1 | 3 | 11 | SEQ ID NO. 2918 |
| (N20)NGG | 8 | 48696320 | + | TTAGGTCAGTATGACGGTAGGGG | 1 | 1 | 8 | SEQ ID NO. 2919 |
| (N20)NGG | 8 | 48696356 | + | GAGTACCACGTGCGAATCGCCGG | 1 | 1 | 2 | SEQ ID NO. 2920 |
| (N20)NGG | 8 | 48696357 | + | AGTACCACGTGCGAATCGCCGGG | 1 | 1 | 3 | SEQ ID NO. 2921 |
| (N20)NGG | 8 | 48696369 | + | GAATCGCCGGGTTTGATGAGCGG | 1 | 1 | 4 | SEQ ID NO. 2922 |
| (N20)NGG | 8 | 48696370 | + | AATCGCCGGGTTTGATGAGCGGG | 1 | 1 | 3 | SEQ ID NO. 2923 |
| (N20)NGG | 8 | 48696374 | + | GCCGGGTTTGATGAGCGGGTAGG | 1 | 1 | 8 | SEQ ID NO. 2924 |
| (N20)NGG | 8 | 48696381 | + | TTGATGAGCGGGTAGGTGTGAGG | 1 | 3 | 46 | SEQ ID NO. 2925 |
| (N20)NGG | 8 | 48696382 | + | TGATGAGCGGGTAGGTGTGAGGG | 1 | 1 | 20 | SEQ ID NO. 2926 |
| (N20)NGG | 8 | 48696325 | - | CGCACGTGGTACTCTGGCAATGG | 1 | 1 | 10 | SEQ ID NO. 2927 |
| (N20)NGG | 8 | 48696331 | - | GCGATTCGCACGTGGTACTCTGG | 1 | 1 | 5 | SEQ ID NO. 2928 |
| (N20)NGG | 8 | 48696339 | - | CAAACCCGGCGATTCGCACGTGG | 1 | 1 | 1 | SEQ ID NO. 2929 |
| (N20)NGG | 8 | 48696353 | - | ACCTACCCGCTCATCAAACCCGG | 1 | 1 | 6 | SEQ ID NO. 2930 |
| (N20)NGG | 8 | 48697680 | + | TCTTACTAATTTCAGACTTTTGG | 1 | 7 | 117 | SEQ ID NO. 2931 |
| (N20)NGG | 8 | 48697704 | + | AAAGAATTTGATAAACATTTTGG | 2 | 20 | 413 | SEQ ID NO. 2932 |
| (N20)NGG | 8 | 48697705 | + | AAGAATTTGATAAACATTTTGGG | 1 | 26 | 397 | SEQ ID NO. 2933 |
| (N20)NGG | 8 | 48697710 | + | TTTGATAAACATTTTGGGAAAGG | 1 | 14 | 188 | SEQ ID NO. 2934 |
| (N20)NGG | 8 | 48697713 | + | GATAAACATTTTGGGAAAGGAGG | 1 | 11 | 192 | SEQ ID NO. 2935 |
| (N20)NGG | 8 | 48697803 | + | AACAAAGACTCAAAGCCCCCTGG | 1 | 5 | 32 | SEQ ID NO. 2936 |
| (N20)NGG | 8 | 48697804 | + | ACAAAGACTCAAAGCCCCCTGGG | 1 | 3 | 28 | SEQ ID NO. 2937 |
| (N20)NGG | 8 | 48697828 | + | ATCTGAAAGAATGTTCACCCTGG | 1 | 2 | 43 | SEQ ID NO. 2938 |
| (N20)NGG | 8 | 48697847 | + | CTGGATGAGCGACTTCAAAGTGG | 1 | 2 | 18 | SEQ ID NO. 2939 |
| (N20)NGG | 8 | 48697868 | + | GGAGTTCCTGAGAAATGAGCTGG | 1 | 5 | 56 | SEQ ID NO. 2940 |
| (N20)NGG | 8 | 48697878 | + | AGAAATGAGCTGGAGATTCCCGG | 1 | 3 | 62 | SEQ ID NO. 2941 |
| (N20)NGG | 8 | 48697894 | + | TTCCCGGTGAGTTAACCTCCAGG | 1 | 2 | 12 | SEQ ID NO. 2942 |
| (N20)NGG | 8 | 48697895 | + | TCCCGGTGAGTTAACCTCCAGGG | 1 | 1 | 6 | SEQ ID NO. 2943 |
| (N20)NGG | 8 | 48697896 | + | CCCGGTGAGTTAACCTCCAGGGG | 1 | 1 | 7 | SEQ ID NO. 2944 |
| (N20)NGG | 8 | 48697758 | - | CATTTTAAAAGTAGCATGTTGG | 2 | 14 | 210 | SEQ ID NO. 2945 |

FIG. 12 cont.

| site_type | site_chr omosome | site_start_ nucleotide | site_s trand | target_site_sequence_wi th NGG | genome_wide_ hits_with_1_ or_less_mism atches | genome_wide_ hits_with_ 2_or_less_m ismatches | genome_wide_ hits_with_ or_less_m atches | genome_wide_ hits_with_3_ or_less_mism atches | |
|---|---|---|---|---|---|---|---|---|---|
| (N20)NGG | 8 | 48697796 | - | CATTCTTTCAGATTCCCAGGGGG | | 3 | 10 | 80 | SEQ ID NO. 2946 |
| (N20)NGG | 8 | 48697797 | - | ACATTCTTTCAGATTCCCAGGGG | | 1 | 8 | 82 | SEQ ID NO. 2947 |
| (N20)NGG | 8 | 48697798 | - | AACATTCTTTCAGATTCCCAGGG | | 1 | 6 | 85 | SEQ ID NO. 2948 |
| (N20)NGG | 8 | 48697799 | - | GAACATTCTTTCAGATTCCCAGG | | 1 | 4 | 65 | SEQ ID NO. 2949 |
| (N20)NGG | 8 | 48697823 | - | ACTTTGAAGTCGCTCATCCAGGG | | 1 | 3 | 17 | SEQ ID NO. 2950 |
| (N20)NGG | 8 | 48697824 | - | CACTTTGAAGTCGCTCATCCAGG | | 1 | 1 | 9 | SEQ ID NO. 2951 |
| (N20)NGG | 8 | 48697852 | - | GAATCTCCAGCTCATTTCTCAGG | | 1 | 6 | 53 | SEQ ID NO. 2952 |
| (N20)NGG | 8 | 48697874 | - | CCCCTGGAGTTAACTCACCGGG | | 1 | 1 | 19 | SEQ ID NO. 2953 |
| (N20)NGG | 8 | 48697875 | - | ACCCCTGGAGTTAACTCACCGG | | 1 | 1 | 12 | SEQ ID NO. 2954 |
| (N20)NGG | 8 | 48701466 | + | TACTTTTTTTCCCCTGACAGG | | 2 | 15 | 278 | SEQ ID NO. 2955 |
| (N20)NGG | 8 | 48701471 | + | TTTTTTTCCCTGACAGGATTGG | | 2 | 10 | 115 | SEQ ID NO. 2956 |
| (N20)NGG | 8 | 48701559 | + | TGAAAGAATGTATGCAGCCTTGG | | 1 | 5 | 69 | SEQ ID NO. 2957 |
| (N20)NGG | 8 | 48701560 | + | GAAAGAATGTATGCAGCCTTGGG | | 2 | 6 | 73 | SEQ ID NO. 2958 |
| (N20)NGG | 8 | 48701571 | + | TGCAGCCTTGGGTGACCAAAGG | | 1 | 1 | 34 | SEQ ID NO. 2959 |
| (N20)NGG | 8 | 48701578 | + | TTGGGTGACCAAAGGCTCCAGG | | 1 | 1 | 22 | SEQ ID NO. 2960 |
| (N20)NGG | 8 | 48701583 | + | TGACCCAAAGGCTCCAGGCCTGG | | 1 | 1 | 51 | SEQ ID NO. 2961 |
| (N20)NGG | 8 | 48701584 | + | GACCCAAAGGCTCCAGGCCTGGG | | 1 | 6 | 60 | SEQ ID NO. 2962 |
| (N20)NGG | 8 | 48701585 | + | ACCCAAAGGCTCCAGGCCTGGGG | | 1 | 7 | 91 | SEQ ID NO. 2963 |
| (N20)NGG | 8 | 48701586 | + | CCCAAAGGCTCCAGGCCTGGGGG | | 2 | 7 | 103 | SEQ ID NO. 2964 |
| (N20)NGG | 8 | 48701597 | + | CAGGCCTGGGGGCCTTTAGAAGG | | 3 | 9 | 59 | SEQ ID NO. 2965 |
| (N20)NGG | 8 | 48701610 | + | CTTTAGAAGGAAGTTTATTCAGG | | 1 | 7 | 78 | SEQ ID NO. 2966 |
| (N20)NGG | 8 | 48701615 | + | GAAGAAGTTTATTCAGGTATGG | | 1 | 3 | 69 | SEQ ID NO. 2967 |
| (N20)NGG | 8 | 48701620 | + | AAGTTTATTCAGTATGGACTGG | | 1 | 4 | 19 | SEQ ID NO. 2968 |
| (N20)NGG | 8 | 48701456 | - | CATTGCTCCAATCCTGTCAGGG | | 1 | 2 | 38 | SEQ ID NO. 2969 |
| (N20)NGG | 8 | 48701457 | - | TCATTGCTCCAATCCTGTCAGG | | 1 | 3 | 21 | SEQ ID NO. 2970 |
| (N20)NGG | 8 | 48701458 | - | ATCATTGCTCCAATCCTGTCAG | | 1 | 2 | 36 | SEQ ID NO. 2971 |
| (N20)NGG | 8 | 48701503 | - | AATGTTTTTTTTTATTTACAGGG | | 1 | 47 | 1234 | SEQ ID NO. 2972 |
| (N20)NGG | 8 | 48701504 | - | CAATGTTTTTTTTATTTACAGG | | 1 | 22 | 559 | SEQ ID NO. 2973 |
| (N20)NGG | 8 | 48701505 | - | TCAATGTTTTTTTTATTTACAG | | 1 | 14 | 413 | SEQ ID NO. 2974 |
| (N20)NGG | 8 | 48701554 | - | TGGAGCCTTTGGGTCACCCAAGG | | 1 | 4 | 40 | SEQ ID NO. 2975 |
| (N20)NGG | 8 | 48701564 | - | CCCCAGGCCTGGAGCCTTTGGG | | 2 | 8 | 86 | SEQ ID NO. 2976 |
| (N20)NGG | 8 | 48701565 | - | GCCCCAGGCCTGGAGCCTTTGG | | 1 | 10 | 133 | SEQ ID NO. 2977 |
| (N20)NGG | 8 | 48701574 | - | CTTCTAAAGGCCCCCAGGCCTGG | | 1 | 3 | 36 | SEQ ID NO. 2978 |

FIG. 12 cont.

| site_type | site_chr omosome | site_start_ nucleotide | site_s trand | target_site_sequence_wi th_NGG | genome_wide_ hits_with_1_ or_less_mism atches | genome_wide_ hits_with_ 2_or_less_m ismatches | genome_wide_ hits_with_3 _or_less_mism atches | | |
|---|---|---|---|---|---|---|---|---|---|
| (N20)NGG | 8 | 48701579 | - | ACTTCCTTCTAAAGGCCCCAGG | 1 | 2 | 39 | SEQ ID NO. | 2979 |
| (N20)NGG | 8 | 48701587 | - | CTGAATAAACTTCCTTCTAAAGG | 1 | 4 | 60 | SEQ ID NO. | 2980 |
| (N20)NGG | 8 | 48701711 | + | CTTTGTAAATTTTTTTAAATAGG | 3 | 81 | 973 | SEQ ID NO. | 2981 |
| (N20)NGG | 8 | 48701727 | + | AAATAGGATTAAAAGTAAGTTGG | 1 | 6 | 140 | SEQ ID NO. | 2982 |
| (N20)NGG | 8 | 48701734 | + | ATTAAAAGTAAGTTGGATCAAGG | 1 | 8 | 84 | SEQ ID NO. | 2983 |
| (N20)NGG | 8 | 48701737 | + | AAAAGTAAGTTGGATCAAGGAGG | 1 | 4 | 54 | SEQ ID NO. | 2984 |
| (N20)NGG | 8 | 48701799 | + | TAATCCTGAACTGCTCTTTAAGG | 1 | 3 | 37 | SEQ ID NO. | 2985 |
| (N20)NGG | 8 | 48701813 | + | TCTTTAAGGTAATGATAGAACGG | 1 | 4 | 110 | SEQ ID NO. | 2986 |
| (N20)NGG | 8 | 48701820 | + | GGTAATGATAGAACGGCTTCTGG | 1 | 1 | 3 | SEQ ID NO. | 2987 |
| (N20)NGG | 8 | 48701761 | - | AGGATTAGAGAGCTGATCTAAGG | 1 | 2 | 27 | SEQ ID NO. | 2988 |
| (N20)NGG | 8 | 48701781 | - | ATTACCTTAAAGAGCAGTTCAGG | 1 | 1 | 37 | SEQ ID NO. | 2989 |
| (N20)NGG | 8 | 48706870 | + | AGATCTCTTCCGTTCCTCTGCTGG | 1 | 1 | 22 | SEQ ID NO. | 2990 |
| (N20)NGG | 8 | 48706885 | + | CCTGCTGGCAGTTCATCAGCTGG | 1 | 2 | 28 | SEQ ID NO. | 2991 |
| (N20)NGG | 8 | 48706898 | + | CATCAGCTGGATCAGCCACATGG | 1 | 6 | 39 | SEQ ID NO. | 2992 |
| (N20)NGG | 8 | 48706901 | + | CAGCTGGATCAGCCACATGTGG | 1 | 3 | 53 | SEQ ID NO. | 2993 |
| (N20)NGG | 8 | 48706910 | + | CAGCCACATGTGGCCTTACTGG | 1 | 5 | 51 | SEQ ID NO. | 2994 |
| (N20)NGG | 8 | 48706946 | + | CGTTGCTGTTCAGCACTCTGTGG | 1 | 3 | 17 | SEQ ID NO. | 2995 |
| (N20)NGG | 8 | 48706973 | + | AATCACTGATAACTACCCGCAGG | | 1 | 6 | SEQ ID NO. | 2996 |
| (N20)NGG | 8 | 48707021 | + | CAGCGAAAGCTATTCCTTCAAGG | | 2 | 21 | SEQ ID NO. | 2997 |
| (N20)NGG | 8 | 48707034 | + | TCCTTCAAGGATAACTTCTACTGG | | 2 | 23 | SEQ ID NO. | 2998 |
| (N20)NGG | 8 | 48707048 | + | TTCTACTGGTCATAAGAATAAGG | | 1 | 31 | SEQ ID NO. | 2999 |
| (N20)NGG | 8 | 48707057 | + | TCATAAGAATAAGGAGTTTGTGG | | 3 | 66 | SEQ ID NO. | 3000 |
| (N20)NGG | 8 | 48707062 | + | AGAATAAGGAGTTTGTGGCAAGG | | 7 | 95 | SEQ ID NO. | 3001 |
| (N20)NGG | 8 | 48707066 | + | TAAGGAGTTTGTGGCAAGGTAGG | 1 | 3 | 51 | SEQ ID NO. | 3002 |
| (N20)NGG | 8 | 48707081 | + | AAGGTAGGTAATATTACAGAAGG | 2 | 5 | 71 | SEQ ID NO. | 3003 |
| (N20)NGG | 8 | 48706857 | - | GATGAACTGCCAGCAGGGAACGG | 2 | 4 | 64 | SEQ ID NO. | 3004 |
| (N20)NGG | 8 | 48706862 | - | CAGCTGATGAACTGCCAGCAGG | 1 | 2 | 78 | SEQ ID NO. | 3005 |
| (N20)NGG | 8 | 48706863 | - | CCAGCTGATGAACTGCCAGCAGG | 1 | 2 | 35 | SEQ ID NO. | 3006 |
| (N20)NGG | 8 | 48706891 | - | TGTCCAGTAAGGCCACCATGTGG | 1 | 3 | 31 | SEQ ID NO. | 3007 |
| (N20)NGG | 8 | 48706902 | - | GGCTTGGTCTTTGTCCAGTAAGG | 1 | 3 | 28 | SEQ ID NO. | 3008 |
| (N20)NGG | 8 | 48706918 | - | AGTGCTGAACAGCAACGGCTTGG | 1 | 2 | 14 | SEQ ID NO. | 3009 |
| (N20)NGG | 8 | 48706923 | - | CACAGAGTGCTGAACAGCAACGG | 1 | 6 | 66 | SEQ ID NO. | 3010 |
| (N20)NGG | 8 | 48706966 | - | AGGGATAAACAATAGCCTGCGGG | 1 | 1 | 24 | SEQ ID NO. | 3011 |

FIG. 12 cont.

| site_type | site_chr omosome | site_start_ nucleotide | site_s trand | target_site_sequence_wi th_NGG | genome_wide_ hits_with_1 or_less_mism atches | genome_wide_ hits_with_2_or_less_m ismatches | genome_wide_ hits_with_3_or_less_mism atches | |
|---|---|---|---|---|---|---|---|---|
| (N20)NGG | 8 | 48706967 | - | AAGGGATAAACAATAGCCTGCGG | | 1 | 5 | 37 SEQ ID NO. 3012 |
| (N20)NGG | 8 | 48706985 | - | CTTTCGCTGCTTATGATGAAGGG | | 1 | 1 | 11 SEQ ID NO. 3013 |
| (N20)NGG | 8 | 48706986 | - | GCTTTCGCTGCTTATGATGAAGG | | 1 | 1 | 15 SEQ ID NO. 3014 |
| (N20)NGG | 8 | 48707013 | - | ACCAGTAGAAGTATCCTTGAAGG | | 1 | 1 | 18 SEQ ID NO. 3015 |
| (N20)NGG | 8 | 48710820 | + | TATTGATTCTGCAGAACTGCAGG | | 1 | 2 | 62 SEQ ID NO. 3016 |
| (N20)NGG | 8 | 48710838 | + | GCAGGCGTATCCAGCACTTGTGG | | 1 | 2 | 12 SEQ ID NO. 3017 |
| (N20)NGG | 8 | 48710841 | + | GGCGTATCCAGCACTTGTGGTGG | | 1 | 1 | 3 SEQ ID NO. 3018 |
| (N20)NGG | 8 | 48710921 | + | GATTACTTCAGATTATAGAACGG | | 1 | 5 | 80 SEQ ID NO. 3019 |
| (N20)NGG | 8 | 48710931 | + | GATTATAGAACGGTATCCAGAGG | | 1 | 1 | 10 SEQ ID NO. 3020 |
| (N20)NGG | 8 | 48710958 | + | TTTGAGCCTCATGACAAAAGAGG | | 1 | 4 | 43 SEQ ID NO. 3021 |
| (N20)NGG | 8 | 48710962 | + | AGCCTCATGACAAAAGAGGTTGG | | 1 | 3 | 30 SEQ ID NO. 3022 |
| (N20)NGG | 8 | 48710980 | + | GTTGGTGTCTTTATTCTACTTGG | | 1 | 2 | 45 SEQ ID NO. 3023 |
| (N20)NGG | 8 | 48710788 | - | TGCAGAATCAATAACTATCAAGG | | 2 | 3 | 45 SEQ ID NO. 3024 |
| (N20)NGG | 8 | 48710826 | - | ATTTTCTCCACCACAAGTGCTGG | | 1 | 1 | 39 SEQ ID NO. 3025 |
| (N20)NGG | 8 | 48710872 | - | AAACTTCAATCTGGCTTCATTGG | | 1 | 3 | 56 SEQ ID NO. 3026 |
| (N20)NGG | 8 | 48710881 | - | TAACTTAGGAAACTTCAATCTGG | | 1 | 3 | 49 SEQ ID NO. 3027 |
| (N20)NGG | 8 | 48710895 | - | TCTATAATCTGAAGTAATCTAGG | | 2 | 6 | 57 SEQ ID NO. 3028 |
| (N20)NGG | 8 | 48710925 | - | ATGAGGCTCAAAGTCTCCTCTGG | | 1 | 2 | 36 SEQ ID NO. 3029 |
| (N20)NGG | 8 | 48710942 | - | CACCAACCTCTTTTGTCATGAGG | | 1 | 3 | 37 SEQ ID NO. 3030 |
| (N20)NGG | 8 | 48711770 | + | TTTAGGTCTCTGTGAATTCCAGG | | 1 | 2 | 50 SEQ ID NO. 3031 |
| (N20)NGG | 8 | 48711779 | + | CTGTGAATTCCAGTGATCGCGG | | 1 | 3 | 22 SEQ ID NO. 3032 |
| (N20)NGG | 8 | 48711780 | + | TGTGAATTCCAGTGATCGCGGG | | 1 | 2 | 16 SEQ ID NO. 3033 |
| (N20)NGG | 8 | 48711815 | + | AGCATTCCAGCACCTCTCTGAGG | | 1 | 4 | 50 SEQ ID NO. 3034 |
| (N20)NGG | 8 | 48711824 | + | GCACCTCTCTGAGGCTGTGCAGG | | 1 | 1 | 68 SEQ ID NO. 3035 |
| (N20)NGG | 8 | 48711827 | + | CCTCTCTGAGGCTGTGCAGGCGG | | 1 | 12 | 134 SEQ ID NO. 3036 |
| (N20)NGG | 8 | 48711833 | + | TGAGGCTGTGCAGGCGGCTGAGG | | 1 | 6 | 97 SEQ ID NO. 3037 |
| (N20)NGG | 8 | 48711836 | + | GGCTGTGCAGGCGGCTGAGGAGG | | 1 | 37 | 893 SEQ ID NO. 3038 |
| (N20)NGG | 8 | 48711839 | + | TGTGCAGGCGGCTGAGGAGGAGG | | 1 | 18 | 407 SEQ ID NO. 3039 |
| (N20)NGG | 8 | 48711856 | + | AGGAGGCCCAGCCTCCCTCCTGG | | 6 | 14 | 129 SEQ ID NO. 3040 |
| (N20)NGG | 8 | 48711864 | + | CAGCCTCCCTCCTGGAGCTGTGG | | 3 | 18 | 180 SEQ ID NO. 3041 |
| (N20)NGG | 8 | 48711865 | + | AGCCTCCCTCCTGGAGCTGTGGG | | 2 | 14 | 98 SEQ ID NO. 3042 |
| (N20)NGG | 8 | 48711876 | + | TGGAGCTGTGGGCCTGCAGCTGG | | 2 | 14 | 122 SEQ ID NO. 3043 |
| (N20)NGG | 8 | 48711877 | + | GGAGCTGTGGGCCTGCAGCTGGG | | 1 | 19 | 138 SEQ ID NO. 3044 |

FIG. 12 cont.

| site_type | site_chr omosome | site_start_ nucleotide | site_s trand | target_site_sequence_wi th NGG | genome_wide_ hits_with_1_ or_less_mism atches | genome_wide_ hits_with_ 2_or_less_m ismatches | genome_wide_ hits_with_3_ or_less_mism atches | | |
|---|---|---|---|---|---|---|---|---|---|
| (N20)NGG | 8 | 48711878 | + | GAGCTGTGGGCCTGCAGCTGGGG | | 1 | 10 | 148 | SEQ ID NO. 3045 |
| (N20)NGG | 8 | 48711902 | + | GATTGATGTTACATGACGCTGG | 1 | | 1 | 7 | SEQ ID NO. 3046 |
| (N20)NGG | 8 | 48711932 | + | CTGTGACCAACAGCTGCGCAAGG | 1 | | 2 | 29 | SEQ ID NO. 3047 |
| (N20)NGG | 8 | 48711935 | + | TGACCAACAGCTGCGCAAGGAGG | 1 | | 2 | 23 | SEQ ID NO. 3048 |
| (N20)NGG | 8 | 48711951 | + | AAGGAGGAAGAGAATGCATCAGG | 1 | | 6 | 147 | SEQ ID NO. 3049 |
| (N20)NGG | 8 | 48711766 | - | GGTACAGACCCGCGATCACCTGG | 1 | | 1 | 3 | SEQ ID NO. 3050 |
| (N20)NGG | 8 | 48711787 | - | AGAGGTGCTGAAATGCTCTCTGG | 1 | | 4 | 32 | SEQ ID NO. 3051 |
| (N20)NGG | 8 | 48711799 | - | GCACAGCCTCAGAGAGGTGCTGG | 1 | | 4 | 84 | SEQ ID NO. 3052 |
| (N20)NGG | 8 | 48711805 | - | CCGCCTGCACAGCCTCAGAGAGG | 1 | | 3 | 61 | SEQ ID NO. 3053 |
| (N20)NGG | 8 | 48711840 | - | ACAGCTCCAGAGGGAGGCTGGG | 2 | | 13 | 114 | SEQ ID NO. 3054 |
| (N20)NGG | 8 | 48711841 | - | CACAGCTCCAGGAGGGAGGCTGG | 2 | | 14 | 149 | SEQ ID NO. 3055 |
| (N20)NGG | 8 | 48711845 | - | GGCCCACAGCTCCAGGAGGGAGG | 1 | | 18 | 172 | SEQ ID NO. 3056 |
| (N20)NGG | 8 | 48711848 | - | GCAGGCCCACAGCTCCAGGAGGG | 1 | | 8 | 101 | SEQ ID NO. 3057 |
| (N20)NGG | 8 | 48711849 | - | TGCAGGCCCACAGCTCCAGGAGG | 2 | | 11 | 104 | SEQ ID NO. 3058 |
| (N20)NGG | 8 | 48711852 | - | AGCTGCAGGCCCACAGCTCCAGG | 2 | | 17 | 119 | SEQ ID NO. 3059 |
| (N20)NGG | 8 | 48711866 | - | GCATCAATCACCCCAGCTGCAGG | 1 | | 1 | 32 | SEQ ID NO. 3060 |
| (N20)NGG | 8 | 48711916 | - | CTTCCTCCTTGCGCAGCTGTTGG | 1 | | 2 | 55 | SEQ ID NO. 3061 |
| (N20)NGG | 8 | 48713394 | + | CTACTTAAGCAAAATATTCTGG | 1 | | 7 | 87 | SEQ ID NO. 3062 |
| (N20)NGG | 8 | 48713421 | + | CCGTGACCAGAACATTCTCTTGG | 2 | | 6 | 31 | SEQ ID NO. 3063 |
| (N20)NGG | 8 | 48713422 | + | CGTGACCAGAACATTCTCTTGGG | 1 | | 5 | 33 | SEQ ID NO. 3064 |
| (N20)NGG | 8 | 48713435 | + | TTCTCTTGGGTACAACTTACAGG | 1 | | 3 | 35 | SEQ ID NO. 3065 |
| (N20)NGG | 8 | 48713487 | + | AGCCTGCCTTGCTGAAATCGAGG | 1 | | 2 | 21 | SEQ ID NO. 3066 |
| (N20)NGG | 8 | 48713490 | + | CTGCCTTGCTGAAATCGAGGAGG | 1 | | 1 | 24 | SEQ ID NO. 3067 |
| (N20)NGG | 8 | 48713496 | + | TGCTGAAATCGAGGAGGACAAGG | 1 | | 3 | 23 | SEQ ID NO. 3068 |
| (N20)NGG | 8 | 48713521 | + | AGAAGAATCTTAGAGCTTTCTGG | 1 | | 6 | 67 | SEQ ID NO. 3069 |
| (N20)NGG | 8 | 48713535 | + | GCTTTCTGGATCCAGTTCAGAGG | 1 | | 2 | 39 | SEQ ID NO. 3070 |
| (N20)NGG | 8 | 48713547 | + | CAGTTCAGAGATTCAGAGAAGG | 1 | | 5 | 92 | SEQ ID NO. 3071 |
| (N20)NGG | 8 | 48713556 | + | GGATTCAGAGAAGGTAATACTGG | 1 | | 3 | 47 | SEQ ID NO. 3072 |
| (N20)NGG | 8 | 48713559 | + | TTCAGAGAAGGTAATACTGGAGG | 1 | | 4 | 64 | SEQ ID NO. 3073 |
| (N20)NGG | 8 | 48713346 | - | GACACGTTGTTCTCATCTGTTGG | 1 | | 2 | 26 | SEQ ID NO. 3074 |
| (N20)NGG | 8 | 48713399 | - | CCAAGAATGTTCTGGTCACGG | 1 | | 7 | 53 | SEQ ID NO. 3075 |
| (N20)NGG | 8 | 48713405 | - | TTGTACCCAAGAATGTTCTGG | | 1 | 3 | 36 | SEQ ID NO. 3076 |
| (N20)NGG | 8 | 48713463 | - | TCGATTTCAGCAAGGCAGGCTGG | 1 | | 2 | 17 | SEQ ID NO. 3077 |

FIG. 12 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 8 | 48713467 | - | CTCCTCGATTTCAGCAAGGCAGG | 1 | 1 | 19 | SEQ ID NO. 3078 |
| (N20)NGG | 8 | 48713471 | - | TGTCCTCCTCGATTTCAGCAAGG | 1 | 2 | 17 | SEQ ID NO. 3079 |
| (N20)NGG | 8 | 48713524 | - | CTTCTCTGAATCCTCTGAACTGG | 2 | 5 | 57 | SEQ ID NO. 3080 |
| (N20)NGG | 8 | 48715899 | + | ACTTGCTATGAAACTACTGAAGG | 1 | 4 | 45 | SEQ ID NO. 3081 |
| (N20)NGG | 8 | 48715934 | + | AGTCAAAAACCAGAGACGATTGG | 1 | 2 | 43 | SEQ ID NO. 3082 |
| (N20)NGG | 8 | 48715938 | + | AAAAACCAGACGATTGGCTGG | 1 | 3 | 30 | SEQ ID NO. 3083 |
| (N20)NGG | 8 | 48715946 | + | GAGACGATTGGCTGCTGAGCTGG | 1 | 1 | 30 | SEQ ID NO. 3084 |
| (N20)NGG | 8 | 48715947 | + | AGACGATTGGCTGGTGAGCTGGG | 1 | 2 | 21 | SEQ ID NO. 3085 |
| (N20)NGG | 8 | 48715979 | + | ACTGCGCCTGAGCCACTGCCGG | 1 | 3 | 39 | SEQ ID NO. 3086 |
| (N20)NGG | 8 | 48715985 | + | GCCTGAGCCACTGCCGGAGCCGG | 1 | 20 | 98 | SEQ ID NO. 3087 |
| (N20)NGG | 8 | 48715992 | + | CCACTGCCGGAGCCGGTCCCAGG | 1 | 2 | 14 | SEQ ID NO. 3088 |
| (N20)NGG | 8 | 48715993 | + | CACTGCCGGAGCCGGTCCCAGGG | 1 | 3 | 24 | SEQ ID NO. 3089 |
| (N20)NGG | 8 | 48716007 | + | GTCCCAGGGCTGCTCTGAGCAGG | 2 | 15 | 239 | SEQ ID NO. 3090 |
| (N20)NGG | 8 | 48716040 | + | GCTGAAAACAGTCTCTTTGTTGG | 1 | 7 | 89 | SEQ ID NO. 3091 |
| (N20)NGG | 8 | 48716041 | + | CTGAAAACAGTCTCTTTTGTTGGG | 1 | 8 | 89 | SEQ ID NO. 3092 |
| (N20)NGG | 8 | 48715921 | - | GCTCACCAGCCAATCGTCTCTGG | 1 | 1 | 14 | SEQ ID NO. 3093 |
| (N20)NGG | 8 | 48715961 | - | GGCTCCGGCCAGTGGCTCAGGCGG | 1 | 20 | 66 | SEQ ID NO. 3094 |
| (N20)NGG | 8 | 48715964 | - | ACCGGCTCCGGCCAGTGGCTCAGG | 1 | 4 | 40 | SEQ ID NO. 3095 |
| (N20)NGG | 8 | 48715970 | - | CCTGGACCGGCTCCGGCAGTGG | 2 | 5 | 33 | SEQ ID NO. 3096 |
| (N20)NGG | 8 | 48715976 | - | AGCAGCCCTGGACCGGCTCCGG | 1 | 3 | 56 | SEQ ID NO. 3097 |
| (N20)NGG | 8 | 48715982 | - | GCTCAGAGCAGCCCTGGGACCGG | 1 | 7 | 141 | SEQ ID NO. 3098 |
| (N20)NGG | 8 | 48715987 | - | CACCTGCTCAGAGCAGCCCTGGG | 2 | 11 | 145 | SEQ ID NO. 3099 |
| (N20)NGG | 8 | 48715988 | - | GCACCTGCTCAGAGCAGCCCTGG | 1 | 5 | 98 | SEQ ID NO. 3100 |
| (N20)NGG | 8 | 48719722 | + | TTTCTTTCTCAGCAAAATAGAGG | 2 | 19 | 253 | SEQ ID NO. 3101 |
| (N20)NGG | 8 | 48719764 | + | AGAAGATAATAGTATGAATGTGG | 1 | 6 | 95 | SEQ ID NO. 3102 |
| (N20)NGG | 8 | 48719774 | + | AGTATGAATGTGATCAAGATGG | 2 | 3 | 58 | SEQ ID NO. 3103 |
| (N20)NGG | 8 | 48719790 | + | AAGATGGACCCCAGTGACAGG | 1 | 3 | 40 | SEQ ID NO. 3104 |
| (N20)NGG | 8 | 48719794 | + | TGGAGACCCCAGTGACAGGATGG | 2 | 9 | 81 | SEQ ID NO. 3105 |
| (N20)NGG | 8 | 48719809 | + | CAGGATGGAAGTGCAAGAGCAGG | 2 | 8 | 126 | SEQ ID NO. 3106 |
| (N20)NGG | 8 | 48719835 | + | AAGATATCAGCTCCCTGATCAGG | 1 | 1 | 23 | SEQ ID NO. 3107 |
| (N20)NGG | 8 | 48719880 | + | TGAAGATAGACAGTGCCCGG | 1 | 3 | 40 | SEQ ID NO. 3108 |
| (N20)NGG | 8 | 48719887 | + | GATAGACAGTGCCCGGAAGCAGG | 1 | 1 | 11 | SEQ ID NO. 3109 |
| (N20)NGG | 8 | 48719890 | + | AGACAGTGCCCGGAAGCAGGTGG | 1 | 4 | 45 | SEQ ID NO. 3110 |

FIG. 12 cont.

| site type | site_chr omosome | site_start_ nucleotide | site s trand | target_site_sequence_wi th NGG | genome_wide_ hits_with_1_ or_less_mism atches | genome_wide_ hits_with_ 2_or_less_m ismatches | genome_wide_ hits_with_3_ or_less_mism atches | | |
|---|---|---|---|---|---|---|---|---|---|
| (N20)NGG | 8 | 48719891 | + | GACAGTGCCCGAAGCAGTGG | | 1 | 2 | 29 | SEQ ID NO. 3111 |
| (N20)NGG | 8 | 48719732 | - | ACTATTATCTTCTGGAAGAGGG | | 1 | 10 | 71 | SEQ ID NO. 3112 |
| (N20)NGG | 8 | 48719733 | - | TACTATTATCTTCTGGAAGAGG | | 1 | 4 | 79 | SEQ ID NO. 3113 |
| (N20)NGG | 8 | 48719734 | - | ATACTATTATCTTCTGGAAGAG | | 1 | 3 | 56 | SEQ ID NO. 3114 |
| (N20)NGG | 8 | 48719740 | - | ACATTCATACTATTATCTTCTG | | 1 | 6 | 173 | SEQ ID NO. 3115 |
| (N20)NGG | 8 | 48719778 | - | GCACTTCCATCCTGTCACTGGG | | 1 | 3 | 33 | SEQ ID NO. 3116 |
| (N20)NGG | 8 | 48719779 | - | TGCACTTCCATCCTGTCACTGG | | 1 | 2 | 25 | SEQ ID NO. 3117 |
| (N20)NGG | 8 | 48719780 | - | TTGCACTTCCATCCTGTCACTG | | 2 | 4 | 26 | SEQ ID NO. 3118 |
| (N20)NGG | 8 | 48719825 | - | AAACTTGCAACTCCTGATCAGG | | 1 | 1 | 30 | SEQ ID NO. 3119 |
| (N20)NGG | 8 | 48719826 | - | AAAACTTGCAACTCCTGATCAG | | 1 | 3 | 23 | SEQ ID NO. 3120 |
| (N20)NGG | 8 | 48719849 | - | GTCTATCATCTTCATTTTCATGG | | 1 | 10 | 115 | SEQ ID NO. 3121 |
| (N20)NGG | 8 | 48719876 | - | ACGAGTACCCACCTGCTTCCGG | | 1 | 1 | 11 | SEQ ID NO. 3122 |
| (N20)NGG | 8 | 48719877 | - | CACGAGTACCCACCTGCTTCCG | | 1 | 1 | 12 | SEQ ID NO. 3123 |
| (N20)NGG | 8 | 48730010 | + | CACCCTCTAATACTATTTTAGG | | 1 | 4 | 61 | SEQ ID NO. 3124 |
| (N20)NGG | 8 | 48730056 | + | TTAAGAGACTTCTGAACACCTGG | | 1 | 5 | 47 | SEQ ID NO. 3125 |
| (N20)NGG | 8 | 48730084 | + | CAGATATCCAGATGCTAAAATGG | | 1 | 2 | 78 | SEQ ID NO. 3126 |
| (N20)NGG | 8 | 48730101 | + | AAATGGACCCAATGAACATCTG | | 1 | 3 | 67 | SEQ ID NO. 3127 |
| (N20)NGG | 8 | 48730102 | + | AATGGACCCAATGAACATCTGG | | 1 | 3 | 39 | SEQ ID NO. 3128 |
| (N20)NGG | 8 | 48730122 | + | GGGATGACATCATCACACAAATCGG | | 1 | 2 | 37 | SEQ ID NO. 3129 |
| (N20)NGG | 8 | 48730132 | + | CATCACAAATCGTAAGACGTGG | | 1 | 1 | 9 | SEQ ID NO. 3130 |
| (N20)NGG | 8 | 48729990 | - | TGCCTAAAAATAGTATTAGAGGG | | 1 | 4 | 74 | SEQ ID NO. 3131 |
| (N20)NGG | 8 | 48729991 | - | TTGCCTAAAAATAGTATTAGAG | | 1 | 2 | 75 | SEQ ID NO. 3132 |
| (N20)NGG | 8 | 48730030 | - | GTGTTCAGAAGTCTCTTAAGGG | | 1 | 3 | 45 | SEQ ID NO. 3133 |
| (N20)NGG | 8 | 48730031 | - | GGTGTTCAGAAGTCTCTTAAGG | | 1 | 3 | 34 | SEQ ID NO. 3134 |
| (N20)NGG | 8 | 48730032 | - | AGGTGTTCAGAAGTCTCTTAAG | | 1 | 8 | 49 | SEQ ID NO. 3135 |
| (N20)NGG | 8 | 48730052 | - | ATCTGGATATCTGTTTGTCCAGG | | 1 | 6 | 143 | SEQ ID NO. 3136 |
| (N20)NGG | 8 | 48730069 | - | ATTGGGTCCATTTTAGCATCTGG | | 1 | 1 | 19 | SEQ ID NO. 3137 |
| (N20)NGG | 8 | 48730086 | - | TGTCATCCCAGATGTTCATTGGG | | 1 | 3 | 30 | SEQ ID NO. 3138 |
| (N20)NGG | 8 | 48730087 | - | ATGTCATCCCAGATGTTCATTGG | | 1 | 1 | 34 | SEQ ID NO. 3139 |
| (N20)NGG | 8 | 48732025 | + | CACCAAATTGCAGTCTGTACAGG | | 1 | 1 | 26 | SEQ ID NO. 3140 |
| (N20)NGG | 8 | 48732043 | + | ACAGGCTTTAACAGAAATTCAGG | | 1 | 2 | 51 | SEQ ID NO. 3141 |
| (N20)NGG | 8 | 48732071 | + | ATCAGCTTTATAAGCAAACAAGG | | 1 | 4 | 65 | SEQ ID NO. 3142 |
| (N20)NGG | 8 | 48732087 | + | AACAAGGTAATTTTTTCATCGG | | 1 | 17 | 171 | SEQ ID NO. 3143 |

FIG. 12 cont.

| site_type | site_chr omosome | site_start_ nucleotide | site s trand | target_site_sequence wi th NGG | genome_wide_ hits_with_1_ or_less_mism atches | genome_wide_ hits_with_ 2_or_less_m ismatches | genome_wide_ hits_with_3_ or_less_mism atches | | |
|---|---|---|---|---|---|---|---|---|---|
| (N20)NGG | 8 | 48731982 | - | TGAGTCTACTTTGGTGTAAGAGG | 1 | 3 | 26 | SEQ ID NO. | 3144 |
| (N20)NGG | 8 | 48731991 | - | GCAATTTGGTGAGTCTACTTTGG | 1 | 4 | 21 | SEQ ID NO. | 3145 |
| (N20)NGG | 8 | 48732005 | - | AGCCTGTACAGACTGCAATTTGG | 1 | 3 | 21 | SEQ ID NO. | 3146 |
| (N20)NGG | 8 | 48733279 | + | AGTATATTTTATGTTCCTTAGG | 3 | 21 | 253 | SEQ ID NO. | 3147 |
| (N20)NGG | 8 | 48733330 | + | CAAGCTGAAGCTGCTGCTCCAGG | 2 | 13 | 138 | SEQ ID NO. | 3148 |
| (N20)NGG | 8 | 48733331 | + | AAGCTGAAGCTGCTGCTCCAGG | 4 | 30 | 315 | SEQ ID NO. | 3149 |
| (N20)NGG | 8 | 48733336 | + | GAAGCTGCTGCTCCAGGAGAGG | 2 | 9 | 186 | SEQ ID NO. | 3150 |
| (N20)NGG | 8 | 48733379 | + | TTTATTGACAAAGCTATGCACGG | 1 | 6 | 76 | SEQ ID NO. | 3151 |
| (N20)NGG | 8 | 48733380 | + | TTATTGACAAAGCTATGCACGGG | 1 | 1 | 29 | SEQ ID NO. | 3152 |
| (N20)NGG | 8 | 48733381 | + | TATTGACAAAGCTATGCACGGGG | 1 | 1 | 18 | SEQ ID NO. | 3153 |
| (N20)NGG | 8 | 48733393 | + | TATGCACGGGGAGCTCCAGAGG | 1 | 5 | 26 | SEQ ID NO. | 3154 |
| (N20)NGG | 8 | 48733484 | + | GCCAAATATTACATTCAAAATGG | 1 | 7 | 127 | SEQ ID NO. | 3155 |
| (N20)NGG | 8 | 48733504 | + | TGGCATTCAGAGTTTTATGCAGG | 1 | 4 | 34 | SEQ ID NO. | 3156 |
| (N20)NGG | 8 | 48733273 | - | TAAGGTAGATATGTTCCTAAGG | 1 | 3 | 54 | SEQ ID NO. | 3157 |
| (N20)NGG | 8 | 48733291 | - | AGCTTGCTGCGGATCATGTAAGG | 1 | 1 | 7 | SEQ ID NO. | 3158 |
| (N20)NGG | 8 | 48733302 | - | GCAGCAGCTTCAGCTTGCTGCGG | 1 | 8 | 96 | SEQ ID NO. | 3159 |
| (N20)NGG | 8 | 48733326 | - | GGGACTGGTCAGCCTCTCCCTGG | 1 | 4 | 41 | SEQ ID NO. | 3160 |
| (N20)NGG | 8 | 48733341 | - | CAATAAATGTCAGCAGGGACTGG | 1 | 5 | 56 | SEQ ID NO. | 3161 |
| (N20)NGG | 8 | 48733346 | - | TTTGTCAATAAATGTCAGCAGGG | 1 | 7 | 80 | SEQ ID NO. | 3162 |
| (N20)NGG | 8 | 48733347 | - | CTTTGTCAATAAATGTCAGCAGG | 1 | 6 | 51 | SEQ ID NO. | 3163 |
| (N20)NGG | 8 | 48733386 | - | GAAGCTCTAGAATCGCCTTCTGG | 1 | 1 | 14 | SEQ ID NO. | 3164 |
| (N20)NGG | 8 | 48733437 | - | TGTCAACATCATCTTGCAGGAGG | 1 | 3 | 37 | SEQ ID NO. | 3165 |
| (N20)NGG | 8 | 48733440 | - | CTCTGTCAACATCATCTTGCAGG | 1 | 6 | 41 | SEQ ID NO. | 3166 |
| (N20)NGG | 8 | 48733463 | - | GCCATTTTGAATGTAATATTTGG | 1 | 4 | 97 | SEQ ID NO. | 3167 |
| (N20)NGG | 8 | 48734164 | + | TTTTATTAACTTTTTCTCCACTAGG | 1 | 9 | 169 | SEQ ID NO. | 3168 |
| (N20)NGG | 8 | 48734184 | + | AGGCTCTCAATAAACAAGACTGG | 1 | 3 | 34 | SEQ ID NO. | 3169 |
| (N20)NGG | 8 | 48734185 | + | GGCTCTCAATAAACAAGACTGGG | 1 | 5 | 31 | SEQ ID NO. | 3170 |
| (N20)NGG | 8 | 48734192 | + | AATAAACAAGACTGGGTAGATGG | 1 | 5 | 73 | SEQ ID NO. | 3171 |
| (N20)NGG | 8 | 48734215 | + | TGAGCCCACAGAAGCCGAGAAGG | 1 | 5 | 67 | SEQ ID NO. | 3172 |
| (N20)NGG | 8 | 48734223 | + | CAGAAGCCGAGAAGGATTTTTGG | 1 | 3 | 40 | SEQ ID NO. | 3173 |
| (N20)NGG | 8 | 48734224 | + | AGAAGCCGAGAAGGATTTTTGGG | 1 | 2 | 44 | SEQ ID NO. | 3174 |
| (N20)NGG | 8 | 48734265 | + | GTTACAACCACCTTGCTGAGTGG | 2 | 3 | 22 | SEQ ID NO. | 3175 |
| (N20)NGG | 8 | 48734334 | + | CCCCAGACCTAAATAAAATCTGG | 1 | 2 | 38 | SEQ ID NO. | 3176 |

FIG. 12 cont.

| site_type | site_chr omosome | site_start_ nucleotide | site_s trand | target_site_sequence wi th NGG | genome_wide_ hits_with_1_ or_less_mism atches | genome_wide_ hits_with_ 2_or_less_m ismatches | genome_wide_ hits_with_3_ or_less_mism atches | |
|---|---|---|---|---|---|---|---|---|
| (N20)NGG | 8 | 48734353 | + | CTGGAGTGAACCATTTTATCAGG | 1 | 1 | 5 | 41 SEQ ID NO. 3177 |
| (N20)NGG | 8 | 48734356 | + | GAGTGAACCATTTTATCAGGTGG | 1 | 1 | 2 | 42 SEQ ID NO. 3178 |
| (N20)NGG | 8 | 48734357 | + | AGTGAACCATTTTATCAGGTGGG | 1 | 1 | 3 | 42 SEQ ID NO. 3179 |
| (N20)NGG | 8 | 48734157 | - | CTTGTTTATTGAGAGCCTAGTGG | 1 | 1 | 2 | 39 SEQ ID NO. 3180 |
| (N20)NGG | 8 | 48734197 | - | AAATCCTTCTCGGCTTCTGTGGG | 1 | 1 | 2 | 29 SEQ ID NO. 3181 |
| (N20)NGG | 8 | 48734198 | - | AAAATCCTTCTCGGCTTCTGTGG | 1 | 1 | 1 | 39 SEQ ID NO. 3182 |
| (N20)NGG | 8 | 48734207 | - | AAGTTCCCAAAAATCCTTCTCGG | 1 | 1 | 4 | 67 SEQ ID NO. 3183 |
| (N20)NGG | 8 | 48734234 | - | AAGGTTGTTGTAACAGTCAAGGG | 1 | 1 | 3 | 29 SEQ ID NO. 3184 |
| (N20)NGG | 8 | 48734235 | - | AAGGTGGTTGTAACAGTCAAGG | 1 | 1 | 2 | 39 SEQ ID NO. 3185 |
| (N20)NGG | 8 | 48734250 | - | GTGATTTCCACTCAGCAAGGTGG | 1 | 1 | 2 | 36 SEQ ID NO. 3186 |
| (N20)NGG | 8 | 48734253 | - | CAAGTGCATTTCCACTCAGCAAGG | 1 | 1 | 2 | 36 SEQ ID NO. 3187 |
| (N20)NGG | 8 | 48734291 | - | GGGGTTCTCACTGTCTATACTGG | 1 | 1 | 1 | 24 SEQ ID NO. 3188 |
| (N20)NGG | 8 | 48734310 | - | AGATTTTATTTAGGTCTGGGGGG | 1 | 1 | 2 | 44 SEQ ID NO. 3189 |
| (N20)NGG | 8 | 48734311 | - | CAGATTTTATTTAGGTCTGGGGG | 2 | 2 | 3 | 58 SEQ ID NO. 3190 |
| (N20)NGG | 8 | 48734312 | - | CCAGATTTTATTTAGGTCTGGGG | 1 | 1 | 1 | 49 SEQ ID NO. 3191 |
| (N20)NGG | 8 | 48734313 | - | TCCAGATTTTATTTAGGTCTGGG | 1 | 1 | 3 | 83 SEQ ID NO. 3192 |
| (N20)NGG | 8 | 48734314 | - | CTCCAGATTTTATTTAGGTCTGG | 1 | 1 | 5 | 43 SEQ ID NO. 3193 |
| (N20)NGG | 8 | 48734319 | - | GTTCACTCCAGATTTTATTTAGG | 2 | 2 | 6 | 102 SEQ ID NO. 3194 |
| (N20)NGG | 8 | 48734341 | - | ATTTTACCACCTGATAAAATGG | 1 | 1 | 5 | 95 SEQ ID NO. 3195 |
| (N20)NGG | 8 | 48736418 | + | GCCTTTTTGATTGTTTTCTAGG | 1 | 1 | 19 | 440 SEQ ID NO. 3196 |
| (N20)NGG | 8 | 48736435 | + | TGTAGGCTGTATAGATCAATTGG | 1 | 1 | 2 | 24 SEQ ID NO. 3197 |
| (N20)NGG | 8 | 48736456 | + | GGAGAATACGACGTCCTCCGTGG | 1 | 1 | 1 | 3 SEQ ID NO. 3198 |
| (N20)NGG | 8 | 48736457 | + | GAGAATACGACGTCCTCCGTGGG | 1 | 1 | 1 | 2 SEQ ID NO. 3199 |
| (N20)NGG | 8 | 48736477 | + | GGGATTTTTACCAGTGAGATAGG | 1 | 1 | 5 | 46 SEQ ID NO. 3200 |
| (N20)NGG | 8 | 48736557 | + | AGCTCGTAAGCAGTATGATGAGG | 1 | 1 | 3 | 41 SEQ ID NO. 3201 |
| (N20)NGG | 8 | 48736573 | + | GATGAGGTAAAATTGATCTCTGG | 1 | 1 | 2 | 48 SEQ ID NO. 3202 |
| (N20)NGG | 8 | 48736397 | - | GCCTACAAAACAAATCAAAAAGG | 1 | 1 | 12 | 260 SEQ ID NO. 3203 |
| (N20)NGG | 8 | 48736448 | - | CACTGGTAAAAATCCCACGAGG | 1 | 1 | 2 | 19 SEQ ID NO. 3204 |
| (N20)NGG | 8 | 48736451 | - | TCTCACTGGTAAAAATCCCACGG | 1 | 1 | 7 | 62 SEQ ID NO. 3205 |
| (N20)NGG | 8 | 48736465 | - | TTGCTTTGTTCCTATCTCACTGG | 2 | 2 | 3 | 79 SEQ ID NO. 3206 |
| (N20)NGG | 8 | 48736516 | - | AGCTTCAGAATAATCACTTCTGG | 1 | 1 | 3 | 60 SEQ ID NO. 3207 |
| (N20)NGG | 8 | 48739216 | + | GGTTGTATGTGTGGTTTCACAGG | 1 | 1 | 2 | 41 SEQ ID NO. 3208 |
| (N20)NGG | 8 | 48739261 | + | CCTGCTGAGCCTCGACCCAGCGG | 1 | 1 | 2 | 42 SEQ ID NO. 3209 |

FIG. 12 cont.

| site_type | site_chr omosome | site_start_ nucleotide | site_s trand | target_site_sequence_wi th_NGG | genome_wide_ hits_with_1 or_less_mism atches | genome_wide_ hits_with_ 2_or_less_m ismatches | genome_wide_ hits_with_3_ or_less_mism atches | |
|---|---|---|---|---|---|---|---|---|
| (N20)NGG | 8 | 48739274 | + | GACCCAGCGCTGTTAGCGCTGG | | 1 | 3 | SEQ ID NO. 3210 |
| (N20)NGG | 8 | 48739282 | + | GGCTGTTAGCGCTGGTTGCCTGG | 1 | 1 | 6 | SEQ ID NO. 3211 |
| (N20)NGG | 8 | 48739303 | + | GGCAGCCTACAGCAGCCCGTGG | 1 | 2 | 30 | SEQ ID NO. 3212 |
| (N20)NGG | 8 | 48739304 | + | GCCAGCCTACAGCAGCCCGTGGG | 1 | 2 | 17 | SEQ ID NO. 3213 |
| (N20)NGG | 8 | 48739321 | + | CGTGGGCATCCGCCTGCTAGAGG | 1 | 6 | 20 | SEQ ID NO. 3214 |
| (N20)NGG | 8 | 48739324 | + | GGGCATCCGCCTGCTAGAGGAGG | 1 | 8 | 30 | SEQ ID NO. 3215 |
| (N20)NGG | 8 | 48739373 | + | CTGCCTGCCAAGCGAGTCCGTGG | 1 | 1 | 8 | SEQ ID NO. 3216 |
| (N20)NGG | 8 | 48739374 | + | TGCCTGCCAAGCGAGTCCGTGGG | 1 | 1 | 5 | SEQ ID NO. 3217 |
| (N20)NGG | 8 | 48739378 | + | TGCCAAGCGAGTCCGTGGGAAGG | 1 | 1 | 9 | SEQ ID NO. 3218 |
| (N20)NGG | 8 | 48739407 | + | TCCCTCCTGATGTCCTCAGATGG | 1 | 2 | 55 | SEQ ID NO. 3219 |
| (N20)NGG | 8 | 48739408 | + | CCCTCCTGATGTCCTCAGATGGG | 1 | 3 | 39 | SEQ ID NO. 3220 |
| (N20)NGG | 8 | 48739411 | + | TCCTGATGTCCTCAGATGGGTGG | 1 | 5 | 46 | SEQ ID NO. 3221 |
| (N20)NGG | 8 | 48739433 | + | GAGCTTGCTAAGTAAGTGTGAGG | 1 | 6 | 26 | SEQ ID NO. 3222 |
| (N20)NGG | 8 | 48739438 | + | TGCTAAGTAAGTGTGAGGTCAGG | 1 | 1 | 35 | SEQ ID NO. 3223 |
| (N20)NGG | 8 | 48739238 | - | CGCTGGGTCGAGGCTCAGCAGGG | 1 | 1 | 26 | SEQ ID NO. 3224 |
| (N20)NGG | 8 | 48739239 | - | CCGCTGGGTCGAGGCTCAGCAGG | 1 | 1 | 17 | SEQ ID NO. 3225 |
| (N20)NGG | 8 | 48739248 | - | CGCTAACAGCGCTGGGCTCGAGG | 1 | 1 | 2 | SEQ ID NO. 3226 |
| (N20)NGG | 8 | 48739254 | - | AACCAGCGCTAACAGCCGCTGGG | 1 | 2 | 4 | SEQ ID NO. 3227 |
| (N20)NGG | 8 | 48739255 | - | CAACAGCGCTAACAGCCGCTGG | 1 | 2 | 4 | SEQ ID NO. 3228 |
| (N20)NGG | 8 | 48739278 | - | CGGGCTGCTGTAGGCTGGCAGG | 1 | 1 | 26 | SEQ ID NO. 3229 |
| (N20)NGG | 8 | 48739283 | - | GCCCACGGGCTGCTGTAGGCTGG | 1 | 2 | 25 | SEQ ID NO. 3230 |
| (N20)NGG | 8 | 48739287 | - | GGATGCCCACGGGCTGCTGTAGG | 1 | 2 | 38 | SEQ ID NO. 3231 |
| (N20)NGG | 8 | 48739297 | - | TCTAGCAGGCGATGCCCACGGG | 1 | 3 | 28 | SEQ ID NO. 3232 |
| (N20)NGG | 8 | 48739298 | - | CTCTAGCAGGCGATGCCCACGG | 1 | 7 | 13 | SEQ ID NO. 3233 |
| (N20)NGG | 8 | 48739308 | - | GCAGAGCCTCCTCTAGCAGGCGG | 1 | 5 | 72 | SEQ ID NO. 3234 |
| (N20)NGG | 8 | 48739311 | - | GCAGCAGAGCCTCCTCTAGCAGG | 1 | 4 | 43 | SEQ ID NO. 3235 |
| (N20)NGG | 8 | 48739332 | - | GCAGCTCAGCAGGCAGCAGGCGG | 2 | 14 | 212 | SEQ ID NO. 3236 |
| (N20)NGG | 8 | 48739335 | - | CAGGCAGCTCAGCAGGCAGCAGG | 2 | 28 | 218 | SEQ ID NO. 3237 |
| (N20)NGG | 8 | 48739342 | - | CGCTTGGCAGGCAGCTCAGCAGG | 2 | 5 | 47 | SEQ ID NO. 3238 |
| (N20)NGG | 8 | 48739354 | - | TTCCCACGGACTGCTTGGCAGG | 1 | 1 | 7 | SEQ ID NO. 3239 |
| (N20)NGG | 8 | 48739358 | - | GGCCTTCCCACGGACTGCTTGG | 1 | 2 | 6 | SEQ ID NO. 3240 |
| (N20)NGG | 8 | 48739368 | - | GAGGGAGGCGGCCTTCCCACGG | 2 | 5 | 57 | SEQ ID NO. 3241 |
| (N20)NGG | 8 | 48739379 | - | GAGGACATCAGGAGGAGGCGG | 1 | 7 | 124 | SEQ ID NO. 3242 |

FIG. 12 cont.

| site_type | site_chr omosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 8 | 48739380 | - | TGAGGACATCAGGAGGGAGGCGG | 2 | 17 | 168 | SEQ ID NO. 3243 |
| (N20)NGG | 8 | 48739383 | - | ATCTGAGGACATCAGGAGGGAGG | 1 | 3 | 71 | SEQ ID NO. 3244 |
| (N20)NGG | 8 | 48739386 | - | CCCATCTGAGGACATCAGGAGGG | 1 | 2 | 52 | SEQ ID NO. 3245 |
| (N20)NGG | 8 | 48739387 | - | ACCCATCTGAGGACATCAGGAGG | 1 | 1 | 33 | SEQ ID NO. 3246 |
| (N20)NGG | 8 | 48739390 | - | TCCACCCATCTGAGGACATCAGG | 1 | 1 | 35 | SEQ ID NO. 3247 |
| (N20)NGG | 8 | 48739398 | - | TAGCAAGCTCCACCCATCTGAGG | 1 | 2 | 24 | SEQ ID NO. 3248 |
| (N20)NGG | 8 | 48740730 | + | TTGTTTTGAATTTTTTACAGAGG | 1 | 38 | 467 | SEQ ID NO. 3249 |
| (N20)NGG | 8 | 48740731 | + | TGTTTTGAATTTTTTACAGAGGG | 3 | 24 | 669 | SEQ ID NO. 3250 |
| (N20)NGG | 8 | 48740774 | + | CTCTTTAGCAGCTTGTTTTCTGG | 1 | 6 | 55 | SEQ ID NO. 3251 |
| (N20)NGG | 8 | 48740791 | + | TTCTGGAATTTTGAAAGAGATGG | 3 | 15 | 244 | SEQ ID NO. 3252 |
| (N20)NGG | 8 | 48740908 | + | ACCCTTTGTCTCTTGTATTCAGG | 1 | 3 | 89 | SEQ ID NO. 3253 |
| (N20)NGG | 8 | 48740733 | - | AGAGCTGTTTTGCAATTATTGGG | 2 | 4 | 87 | SEQ ID NO. 3254 |
| (N20)NGG | 8 | 48740737 | - | AAGAGCTGTTTTGCAATTATTGG | 1 | 5 | 73 | SEQ ID NO. 3255 |
| (N20)NGG | 8 | 48740867 | - | GGGTGGAAAGAAAGAGAAGGTGG | 6 | 51 | 772 | SEQ ID NO. 3256 |
| (N20)NGG | 8 | 48740870 | - | AAAGGGTGGAAAGAAAGAGAAGG | 4 | 94 | 1695 | SEQ ID NO. 3257 |
| (N20)NGG | 8 | 48740884 | - | TGAATACAAGAGACAAAGGGTGG | 1 | 5 | 118 | SEQ ID NO. 3258 |
| (N20)NGG | 8 | 48740887 | - | ACCTGAATACAAGAGACAAAGGG | 1 | 2 | 67 | SEQ ID NO. 3259 |
| (N20)NGG | 8 | 48740888 | - | TACCTGAATACAAGAGACAAAGG | 1 | 6 | 51 | SEQ ID NO. 3260 |
| (N20)NGG | 8 | 48743165 | + | TCTTTGGTTCTGGTGCTTATAGG | 1 | 2 | 51 | SEQ ID NO. 3261 |
| (N20)NGG | 8 | 48743195 | + | GAGTGAGTTAAAAATGAAGCAGG | 1 | 4 | 76 | SEQ ID NO. 3262 |
| (N20)NGG | 8 | 48743204 | + | AAAAATGAAGCAGGATGCCCAGG | 1 | 3 | 93 | SEQ ID NO. 3263 |
| (N20)NGG | 8 | 48743227 | + | TCGTTCTGTACAGAAGCTACCGG | 1 | 1 | 13 | SEQ ID NO. 3264 |
| (N20)NGG | 8 | 48743232 | + | CTGTACAGAAGCTACCGGCACGG | 1 | 3 | 14 | SEQ ID NO. 3265 |
| (N20)NGG | 8 | 48743285 | + | CAGCCTCATCACCCCGTTACAGG | 1 | 2 | 18 | SEQ ID NO. 3266 |
| (N20)NGG | 8 | 48743291 | + | CATCACCCCGTTACAGGCCGTGG | 1 | 1 | 28 | SEQ ID NO. 3267 |
| (N20)NGG | 8 | 48743297 | + | CCCGTTACAGGCCGTGGCCCAGG | 1 | 1 | 5 | SEQ ID NO. 3268 |
| (N20)NGG | 8 | 48743199 | - | GCTTCTGTACAGAACGACCTGGG | 1 | 1 | 19 | SEQ ID NO. 3269 |
| (N20)NGG | 8 | 48743200 | - | AGCTTCTGTACAGAACGACCTGG | 1 | 1 | 7 | SEQ ID NO. 3270 |
| (N20)NGG | 8 | 48743224 | - | TGTTCAGGAAGGTCTCCGTGCGG | 1 | 3 | 23 | SEQ ID NO. 3271 |
| (N20)NGG | 8 | 48743236 | - | GCTTGATCTGAATGTCAGGAAGG | 1 | 5 | 42 | SEQ ID NO. 3272 |
| (N20)NGG | 8 | 48743240 | - | CTGTGCTTGATCTGAATGTCAGG | 1 | 2 | 28 | SEQ ID NO. 3273 |
| (N20)NGG | 8 | 48743266 | - | CGGCCTGTAACGGGGTGATGAGG | 1 | 1 | 7 | SEQ ID NO. 3274 |
| (N20)NGG | 8 | 48743274 | - | CTGGGCCACGGCCTGTAACGGGG | 1 | 1 | 8 | SEQ ID NO. 3275 |

FIG. 12 cont.

| site_type | site_chr omosome | site_start_ nucleotide | site_s trand | target_site_sequence_wi th NGG | genome_wide_ hits_with_1_ or_less_mism atches | genome_wide_ hits_with_ 2_or_less_m ismatches | genome_wide_ hits_with_3_ or_less_mism atches | |
|---|---|---|---|---|---|---|---|---|
| (N20)NGG | 8 | 48743275 | - | CCTGGGCCACGGCCTGTAACGGG | | 1 | 31 | SEQ ID NO. 3276 |
| (N20)NGG | 8 | 48743276 | - | ACCTGGGCCACGGCCTGTAACGG | | 2 | 11 | SEQ ID NO. 3277 |
| (N20)NGG | 8 | 48743286 | - | GCAAAAACTGACCTGGGCCACGG | | 3 | 40 | SEQ ID NO. 3278 |
| (N20)NGG | 8 | 48743292 | - | GCAGCGGCAAAAACTGACCTGGG | | 2 | 19 | SEQ ID NO. 3279 |
| (N20)NGG | 8 | 48743293 | - | CGCAGCGGCAAAAACTGACCTGG | | 1 | 12 | SEQ ID NO. 3280 |
| (N20)NGG | 8 | 48744374 | + | TGGCCTGCTTTCCCTCTCCAGG | | 8 | 68 | SEQ ID NO. 3281 |
| (N20)NGG | 8 | 48744379 | + | CTGCTTTCCCTCTCCAGGTGCGG | 2 | 12 | 111 | SEQ ID NO. 3282 |
| (N20)NGG | 8 | 48744383 | + | TTTCCCTCTCCAGGTGCGGCCGG | 1 | 2 | 30 | SEQ ID NO. 3283 |
| (N20)NGG | 8 | 48744387 | + | CCTCTCCAGGTGCGGCCGGCCGG | 1 | 3 | 25 | SEQ ID NO. 3284 |
| (N20)NGG | 8 | 48744391 | + | TCCAGGTGCGGCCGGCCGGACGG | 1 | 2 | 23 | SEQ ID NO. 3285 |
| (N20)NGG | 8 | 48744414 | + | ACCTACTACGACTGCGCAGACGG | 1 | 1 | 5 | SEQ ID NO. 3286 |
| (N20)NGG | 8 | 48744423 | + | GACTGCGCAGACGGTTTATGAGG | 1 | 1 | 3 | SEQ ID NO. 3287 |
| (N20)NGG | 8 | 48744424 | + | ACTGCGCAGACGGTTTATGAGGG | 1 | 1 | 2 | SEQ ID NO. 3288 |
| (N20)NGG | 8 | 48744430 | + | CAGACGGTTTATGAGGGACCAGG | 1 | 1 | 10 | SEQ ID NO. 3289 |
| (N20)NGG | 8 | 48744461 | + | AGTTTGATGTATGCCAGAAAAGG | 1 | 1 | 77 | SEQ ID NO. 3290 |
| (N20)NGG | 8 | 48744487 | + | TGCTGAGCAAAAACGAGAGAAGG | 1 | 4 | 56 | SEQ ID NO. 3291 |
| (N20)NGG | 8 | 48744356 | - | CGCACCTGAGAGGGAAAGCAGG | 1 | 3 | 41 | SEQ ID NO. 3292 |
| (N20)NGG | 8 | 48744364 | - | CGGCCAGCCGCCACCTGGAGAGG | 1 | 4 | 22 | SEQ ID NO. 3293 |
| (N20)NGG | 8 | 48744365 | - | CCGGCCAGCCGCCACCTGGAGAG | 1 | 3 | 35 | SEQ ID NO. 3294 |
| (N20)NGG | 8 | 48744370 | - | TCCGTCCGGCCAGCCGCCACCTGG | 1 | 2 | 25 | SEQ ID NO. 3295 |
| (N20)NGG | 8 | 48744380 | - | TCGTAGTAGTCCGTCCGGCCGG | 1 | 1 | 1 | SEQ ID NO. 3296 |
| (N20)NGG | 8 | 48744384 | - | GCAGTCGTAGTAGTCCGTCCGG | 1 | 1 | 1 | SEQ ID NO. 3297 |
| (N20)NGG | 8 | 48744393 | - | ACCGTCTGCGCCAGTCGTAGTAGG | 1 | 1 | 3 | SEQ ID NO. 3298 |
| (N20)NGG | 8 | 48744426 | - | ACATCAAACTGAGCTTCTCCTGG | 1 | 3 | 41 | SEQ ID NO. 3299 |
| (N20)NGG | 8 | 48744452 | - | TTGCTCAGCAACGCCTTTTCTGG | 1 | 2 | 26 | SEQ ID NO. 3300 |
| (N20)NGG | 8 | 48746759 | + | CTCTGATTGCATGTCACAGATGG | 1 | 2 | 46 | SEQ ID NO. 3301 |
| (N20)NGG | 8 | 48746778 | + | ATGGAAGAAGCTCATTTGATTGG | 1 | 2 | 51 | SEQ ID NO. 3302 |
| (N20)NGG | 8 | 48746786 | + | AGCTCATTTGATTGGCTGACCGG | 1 | 1 | 28 | SEQ ID NO. 3303 |
| (N20)NGG | 8 | 48746787 | + | GCTCATTTGATTGGCTGACCGGG | 1 | 1 | 13 | SEQ ID NO. 3304 |
| (N20)NGG | 8 | 48746806 | + | GCGGAGCAGCACTGACCCGCTGG | 2 | 2 | 18 | SEQ ID NO. 3305 |
| (N20)NGG | 8 | 48746856 | + | CCTTGCTGTTTGCCCACACAAGAGG | 1 | 4 | 45 | SEQ ID NO. 3306 |
| (N20)NGG | 8 | 48746865 | + | TTGCCACAAGAGGAGTGAAAGG | 1 | 3 | 47 | SEQ ID NO. 3307 |
| (N20)NGG | 8 | 48746893 | + | GAGAGCACCCTTGAAGTCAGTGG | 1 | 2 | 38 | SEQ ID NO. 3308 |

FIG. 12 cont.

| site type | site_chr omosome | site_start_ nucleotide | site_s trand | target_site_sequence_wi th_NGG | genome_wide_ hits_with_1 or_less_mism atches | genome_wide_ hits_with_ 2_or_less_m ismatches | genome_wide_ hits_with_3 or_less_mism atches | |
|---|---|---|---|---|---|---|---|---|
| (N20)NGG | 8 | 48746894 | + | AGAGCACCCTTGAAGTCAGTGGG | | 1 | 29 | SEQ ID NO. 3309 |
| (N20)NGG | 8 | 48746895 | + | GAGCACCCTTGAAGTCAGTGGGG | | 1 | 36 | SEQ ID NO. 3310 |
| (N20)NGG | 8 | 48746906 | + | AAGTCAGTGGGGCCTGATTTTGG | | 1 | 40 | SEQ ID NO. 3311 |
| (N20)NGG | 8 | 48746907 | + | AGTCAGTGGGGCCTGATTTTTGG | | 1 | 42 | SEQ ID NO. 3312 |
| (N20)NGG | 8 | 48746916 | + | GGCCTGATTTTGGGAAAAAAAGG | | 1 | 82 | SEQ ID NO. 3313 |
| (N20)NGG | 8 | 48746920 | + | TGATTTTGGGAAAAAAAGGCTGG | | 4 | 128 | SEQ ID NO. 3314 |
| (N20)NGG | 8 | 48746921 | + | GATTTTGGGAAAAAAAGGCTGGG | | 2 | 11 | 103 | SEQ ID NO. 3315 |
| (N20)NGG | 8 | 48746930 | + | AAAAAAGGCTGGGCCTTCCAGG | | 1 | 9 | 87 | SEQ ID NO. 3316 |
| (N20)NGG | 8 | 48746931 | + | AAAAAAGGCTGGGCCTTCCAGGG | | 1 | 6 | 46 | SEQ ID NO. 3317 |
| (N20)NGG | 8 | 48746932 | + | AAAAAGGCTGGGCCTTCCAGGGG | | 1 | 3 | 54 | SEQ ID NO. 3318 |
| (N20)NGG | 8 | 48746938 | + | GCTGGGCCTTCCAGGGGACGAGG | | 2 | 3 | 58 | SEQ ID NO. 3319 |
| (N20)NGG | 8 | 48746941 | + | GGGCCTTCCAGGGGACGAGGTGG | | 1 | 6 | 63 | SEQ ID NO. 3320 |
| (N20)NGG | 8 | 48746957 | + | GAGGTGGATAACAAAGTGAAAGG | | 1 | 5 | 104 | SEQ ID NO. 3321 |
| (N20)NGG | 8 | 48746965 | + | TAACAAAGTGAAAGGTAAGCTGG | | 1 | 3 | 64 | SEQ ID NO. 3322 |
| (N20)NGG | 8 | 48746966 | + | AACAAAGTGAAAGGTAAGCTGGG | | 1 | 7 | 103 | SEQ ID NO. 3323 |
| (N20)NGG | 8 | 48746734 | − | TCTGTGACATGCAATCAGAGAGG | | 1 | 8 | 56 | SEQ ID NO. 3324 |
| (N20)NGG | 8 | 48746783 | − | CAGCGGGTCAGTGCTGCTCCCGG | | 1 | 2 | 31 | SEQ ID NO. 3325 |
| (N20)NGG | 8 | 48746799 | − | GACTGGTGTGTGTCGACCAGCGG | | 1 | 3 | 5 | SEQ ID NO. 3326 |
| (N20)NGG | 8 | 48746800 | − | GGACTGGTGTGTCGACCAGCGG | | 1 | 1 | 11 | SEQ ID NO. 3327 |
| (N20)NGG | 8 | 48746811 | − | AGTCAGATGAGGGACTGGTGTGG | | 1 | 2 | 64 | SEQ ID NO. 3328 |
| (N20)NGG | 8 | 48746816 | − | CAAGGAGTCAGATGAGGGACTGG | | 2 | 4 | 50 | SEQ ID NO. 3329 |
| (N20)NGG | 8 | 48746821 | − | AACAGCAAGGAGTCAGATGAGGG | | 1 | 2 | 57 | SEQ ID NO. 3330 |
| (N20)NGG | 8 | 48746822 | − | AAACAGCAAGGAGTCAGATGAGG | | 2 | 5 | 103 | SEQ ID NO. 3331 |
| (N20)NGG | 8 | 48746834 | − | CCTCTTGTGTGGCAAACAGCAGG | | 1 | 5 | 45 | SEQ ID NO. 3332 |
| (N20)NGG | 8 | 48746846 | − | TAACCTTTCACTCCTCTTGTGGG | | 1 | 4 | 51 | SEQ ID NO. 3333 |
| (N20)NGG | 8 | 48746847 | − | GTAACCTTTCACTCCTCTTGTGG | | 1 | 1 | 20 | SEQ ID NO. 3334 |
| (N20)NGG | 8 | 48746878 | − | TCAGGCCCCACTGACTTCAAGGG | | 1 | 5 | 50 | SEQ ID NO. 3335 |
| (N20)NGG | 8 | 48746879 | − | ATCAGGCCCCACTGACTTCAAGG | | 1 | 3 | 47 | SEQ ID NO. 3336 |
| (N20)NGG | 8 | 48746896 | − | AGCCTTTTTTTCCCAAAATCAGG | | 1 | 6 | 84 | SEQ ID NO. 3337 |
| (N20)NGG | 8 | 48746922 | − | TATCCACCTCGTCCCCTGGAAGG | | 1 | 2 | 13 | SEQ ID NO. 3338 |
| (N20)NGG | 8 | 48746926 | − | TTGTTATCCACCTCGTCCCCTGG | | 1 | 1 | 18 | SEQ ID NO. 3339 |
| (N20)NGG | 8 | 48748898 | + | TTTGAAACTTTCTTATGTACAGG | | 1 | 5 | 95 | SEQ ID NO. 3340 |
| (N20)NGG | 8 | 48748921 | + | AATATACCATTGATTCTGATTGG | | 2 | 2 | 58 | SEQ ID NO. 3341 |

FIG. 12 cont.

| site_type | site_chr omosome | site_start_ nucleotide | site_s trand | target_site_sequence_wi th_NGG | genome_wide_ hits_with_1_ or_less_mism atches | genome_wide_ hits_with_ 2_or_less_m ismatches | genome_wide_ hits_with_3_ or_less_mism atches | |
|---|---|---|---|---|---|---|---|---|
| (N20)NGG | 8 | 48748958 | + | TGTTCTCACTCCGATGTTTGTGG | 1 | 2 | 18 | SEQ ID NO. 3342 |
| (N20)NGG | 8 | 48748967 | + | TCCGATGTTTGTGAGACCCAGG | | 3 | 17 | SEQ ID NO. 3343 |
| (N20)NGG | 8 | 48748976 | + | TGTGGAGACCCAGGCCTCCCAGG | 1 | 11 | 71 | SEQ ID NO. 3344 |
| (N20)NGG | 8 | 48748977 | + | GTGGAGACCCAGGCCTCCCAGGG | 2 | 8 | 79 | SEQ ID NO. 3345 |
| (N20)NGG | 8 | 48749000 | + | CACTCTCCAGACCCGTACCCAGG | 1 | 3 | 19 | SEQ ID NO. 3346 |
| (N20)NGG | 8 | 48749004 | + | CTCCAGACCCGTACCCAGGAAGG | 1 | 2 | 27 | SEQ ID NO. 3347 |
| (N20)NGG | 8 | 48749005 | + | TCCAGACCCGTACCCAGGAAGGG | 1 | 2 | 41 | SEQ ID NO. 3348 |
| (N20)NGG | 8 | 48749023 | + | AAGGGTCCCTCTCAGCTCGCTGG | 1 | 3 | 26 | SEQ ID NO. 3349 |
| (N20)NGG | 8 | 48749030 | + | CCTCTCAGCTCGCTGGCCAGTGG | 1 | 3 | 38 | SEQ ID NO. 3350 |
| (N20)NGG | 8 | 48749034 | + | TCAGCTCGCTGGCCAGTGGCAGG | 1 | 3 | 26 | SEQ ID NO. 3351 |
| (N20)NGG | 8 | 48749035 | + | CAGCTCGCTGGCCAGTGGCAGGG | 2 | 10 | 62 | SEQ ID NO. 3352 |
| (N20)NGG | 8 | 48749044 | + | GGCCAGTGGCAGGGCAGATAAGG | 1 | 6 | 71 | SEQ ID NO. 3353 |
| (N20)NGG | 8 | 48749045 | + | GCCAGTGGCAGGGCAGATAAGGG | 1 | 7 | 75 | SEQ ID NO. 3354 |
| (N20)NGG | 8 | 48749088 | + | TTCACACTGACACAGACTGCAGG | 2 | 2 | 53 | SEQ ID NO. 3355 |
| (N20)NGG | 8 | 48749110 | + | GTAACAGTGACCCTGCCCGCTGG | 1 | 1 | 13 | SEQ ID NO. 3356 |
| (N20)NGG | 8 | 48748905 | - | GAAACGCCAATGACAGAATCAATGG | 1 | 2 | 35 | SEQ ID NO. 3357 |
| (N20)NGG | 8 | 48748927 | - | TCGGAGTGAGAACAGTACTTCGG | 1 | 3 | 19 | SEQ ID NO. 3358 |
| (N20)NGG | 8 | 48748946 | - | GCCTGGGTCTCCACAAACATCGG | 2 | 4 | 55 | SEQ ID NO. 3359 |
| (N20)NGG | 8 | 48748962 | - | GAGAGTGCCCTGGGAGGCCTGG | 1 | 6 | 76 | SEQ ID NO. 3360 |
| (N20)NGG | 8 | 48748963 | - | GGAGAGTGCCCTGGGAGGCCTGG | 1 | 13 | 140 | SEQ ID NO. 3361 |
| (N20)NGG | 8 | 48748968 | - | GGTCTGGAGAGTGCCCTGGGAGG | 1 | 5 | 107 | SEQ ID NO. 3362 |
| (N20)NGG | 8 | 48748971 | - | ACGGGTCTGGAGAGTGCCCTGGG | 1 | 1 | 22 | SEQ ID NO. 3363 |
| (N20)NGG | 8 | 48748972 | - | TACGGGTCTGGAGAGTGCCCTGG | 1 | 1 | 12 | SEQ ID NO. 3364 |
| (N20)NGG | 8 | 48748984 | - | ACCCTTCCTGGGTACGGGTCTGG | 1 | 1 | 17 | SEQ ID NO. 3365 |
| (N20)NGG | 8 | 48748989 | - | GAGGGACCCTTCCTGGGTACGG | 1 | 3 | 35 | SEQ ID NO. 3366 |
| (N20)NGG | 8 | 48748990 | - | AGAGGGACCCTTCCTGGGTACGG | 1 | 3 | 41 | SEQ ID NO. 3367 |
| (N20)NGG | 8 | 48748995 | - | AGCTGAGAGGGACCCTTCCTGGG | 1 | 4 | 47 | SEQ ID NO. 3368 |
| (N20)NGG | 8 | 48748996 | - | GAGCTGAGAGGGACCCTTCCTGG | 1 | 6 | 49 | SEQ ID NO. 3369 |
| (N20)NGG | 8 | 48749007 | - | CACTGGCCAGCGAGCTGAGAGGG | 1 | 5 | 25 | SEQ ID NO. 3370 |
| (N20)NGG | 8 | 48749008 | - | CCACTGGCCAGCGAGCTGAGAGG | 1 | 2 | 38 | SEQ ID NO. 3371 |
| (N20)NGG | 8 | 48749024 | - | GCCCTTATCTGCCCTGCCACTGG | 1 | 3 | 44 | SEQ ID NO. 3372 |
| (N20)NGG | 8 | 48749046 | - | GAAGTCATGCTGCTGCTGGGTTGG | 1 | 9 | 71 | SEQ ID NO. 3373 |
| (N20)NGG | 8 | 48749049 | - | TGTGAAGTCATGCTGCTGCTGGG | 1 | 2 | 53 | SEQ ID NO. 3374 |

FIG. 12 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 8 | 48749050 | - | GTGTGAAGTCATGCTGCTGCTGG | | 1 | 3 | 34 SEQ ID NO. 3375 |
| (N20)NGG | 8 | 48749793 | + | GATTAATTATTCGAAATTTCTGG | | 1 | 2 | 34 SEQ ID NO. 3376 |
| (N20)NGG | 8 | 48749808 | + | ATTTCTGGAGCATGAAACTAGG | | 1 | 5 | 94 SEQ ID NO. 3377 |
| (N20)NGG | 8 | 48749827 | + | TAGGTTACCTTCAAATACCTTGG | | 1 | 1 | 22 SEQ ID NO. 3378 |
| (N20)NGG | 8 | 48749832 | + | TACCTTCAAATACCTTGGACCGG | | 1 | 1 | 27 SEQ ID NO. 3379 |
| (N20)NGG | 8 | 48749839 | + | AAATACCTTGGACCGGTTGCTGG | | 1 | 1 | 6 SEQ ID NO. 3380 |
| (N20)NGG | 8 | 48749980 | + | TCTGTCAGAATGCGAATTTCAGG | | 1 | 1 | 22 SEQ ID NO. 3381 |
| (N20)NGG | 8 | 48749988 | + | AATGCGAATTTCAGGTAATGTGG | | 1 | 5 | 40 SEQ ID NO. 3382 |
| (N20)NGG | 8 | 48749796 | - | TTGAAGGTAACCTAGTTTCATGG | | 1 | 3 | 31 SEQ ID NO. 3383 |
| (N20)NGG | 8 | 48749812 | - | AACCGGTCCAAGGTATTTGAAGG | | 1 | 1 | 6 SEQ ID NO. 3384 |
| (N20)NGG | 8 | 48749822 | - | TAGTGCCAAGCAACCGGTCCAAGG | | 1 | 1 | 10 SEQ ID NO. 3385 |
| (N20)NGG | 8 | 48749829 | - | AGGAATTTAGTGCCAGCAACCGG | | 1 | 5 | 51 SEQ ID NO. 3386 |
| (N20)NGG | 8 | 48749849 | - | TTCTATCTTAGGAGAATATAAGG | | 1 | 5 | 95 SEQ ID NO. 3387 |
| (N20)NGG | 8 | 48749860 | - | AAAAAGTGCACTTCTATCTTAGG | | 1 | 4 | 72 SEQ ID NO. 3388 |
| (N20)NGG | 8 | 48749915 | - | TGGATAATCTGGGCTCATGCTGG | | 1 | 2 | 12 SEQ ID NO. 3389 |
| (N20)NGG | 8 | 48749925 | - | ACATGGGGTTTGATAATCTGG | | 2 | 2 | 30 SEQ ID NO. 3390 |
| (N20)NGG | 8 | 48749926 | - | AACATGGGGTTTGATAATCTGG | | 1 | 4 | 28 SEQ ID NO. 3391 |
| (N20)NGG | 8 | 48749935 | - | GGATGCTCGAACATGGGGTTTGG | | 1 | 3 | 14 SEQ ID NO. 3392 |
| (N20)NGG | 8 | 48749940 | - | ACAGAGGATGCTCGAACATGGGG | | 1 | 1 | 18 SEQ ID NO. 3393 |
| (N20)NGG | 8 | 48749941 | - | GACAGAGGATGCTCGAACATGG | | 1 | 2 | 6 SEQ ID NO. 3394 |
| (N20)NGG | 8 | 48749942 | - | TGACAGAGGATGCTCGAACATGG | | 1 | 2 | 14 SEQ ID NO. 3395 |
| (N20)NGG | 8 | 48749956 | - | TGAAATTCGCATTCTGACAGAGG | | 1 | 2 | 25 SEQ ID NO. 3396 |
| (N20)NGG | 8 | 48751742 | + | TGAGACAGATAATGACTCCCAGG | | 1 | 4 | 36 SEQ ID NO. 3397 |
| (N20)NGG | 8 | 48751757 | + | CTCCAGGAAATATTTAAGTTGG | | 1 | 4 | 69 SEQ ID NO. 3398 |
| (N20)NGG | 8 | 48751779 | + | GCAAAGATGTGCTGATTCAAGG | | 1 | 1 | 50 SEQ ID NO. 3399 |
| (N20)NGG | 8 | 48751800 | + | GGATTGATCGATGAGAACCCTGG | | 1 | 1 | 5 SEQ ID NO. 3400 |
| (N20)NGG | 8 | 48751822 | + | GACTTCAGTACGTGAATAACTGG | | 1 | 4 | 17 SEQ ID NO. 3401 |
| (N20)NGG | 8 | 48751823 | + | ACTTCAGTACGTGAATAACTGGG | | 1 | 2 | 16 SEQ ID NO. 3402 |
| (N20)NGG | 8 | 48751827 | + | CAGTACGTGAATAACTGGGCTGG | | 1 | 1 | 6 SEQ ID NO. 3403 |
| (N20)NGG | 8 | 48751828 | + | AGTACGTGAATAACTGGGCTGG | | 1 | 1 | 14 SEQ ID NO. 3404 |
| (N20)NGG | 8 | 48751712 | - | TCATTATCTGTCTCACTTTCTGG | | 1 | 29 | 133 SEQ ID NO. 3405 |
| (N20)NGG | 8 | 48751737 | - | TGCCAACTTAAATATTTCCTGG | | 1 | 2 | 82 SEQ ID NO. 3406 |
| (N20)NGG | 8 | 48751738 | - | TTGCCAACTTAAATATTTCCTGG | | 1 | 6 | 76 SEQ ID NO. 3407 |

FIG. 12 cont.

| site_type | site_chr omosome | site_start_ nucleotide | site_s trand | target_site_sequence_wi th_NGG | genome_wide_ hits_with_1_ or_less_mism atches | genome_wide_ hits_with_ 2_or_less_m ismatches | genome_wide_ hits_with_3_ or_less_mism atches | |
|---|---|---|---|---|---|---|---|---|
| (N20)NGG | 8 | 48751795 | - | TATTCACGTACTGAAGTCCAGGG | | 1 | 16 | SEQ ID NO. 3408 |
| (N20)NGG | 8 | 48751796 | - | TTATTCACGTACTGAAGTCCAGG | | 1 | 14 | SEQ ID NO. 3409 |
| (N20)NGG | 8 | 48752604 | + | TGAAAGACAAAAAGTATGTTTGG | | 2 | 184 | SEQ ID NO. 3410 |
| (N20)NGG | 8 | 48752673 | + | AGAACTTCTGAACCCGTTGTGG | 1 | | 15 | SEQ ID NO. 3411 |
| (N20)NGG | 8 | 48752705 | + | CCCATCCTTCTACAACATGTAGG | | 3 | 24 | SEQ ID NO. 3412 |
| (N20)NGG | 8 | 48752706 | + | CCATCCTTCTACAACATGTAGGG | | 2 | 28 | SEQ ID NO. 3413 |
| (N20)NGG | 8 | 48752732 | + | AAATGTATAATATTCTCATGTGG | | 2 | 185 | SEQ ID NO. 3414 |
| (N20)NGG | 8 | 48752750 | + | TGTGGATTCATGATAATTACAGG | 1 | | 31 | SEQ ID NO. 3415 |
| (N20)NGG | 8 | 48752569 | - | TTGTCTTTCATCATCTCTATGGG | | 2 | 7 | SEQ ID NO. 3416 |
| (N20)NGG | 8 | 48752570 | - | TTTGTCTTTCATCATCTCTATGG | 3 | | 124 | SEQ ID NO. 3417 |
| (N20)NGG | 8 | 48752625 | - | AGTTCTACTGGTTTTAACTTTGG | 1 | | 151 | SEQ ID NO. 3418 |
| (N20)NGG | 8 | 48752637 | - | AGAAGTTCTCGGAGTTCTACTGG | 1 | | 62 | SEQ ID NO. 3419 |
| (N20)NGG | 8 | 48752648 | - | CAACGGGTTCAGAAGTTCTCGG | | 3 | 26 | SEQ ID NO. 3420 |
| (N20)NGG | 8 | 48752663 | - | GGGAAACGAATTCCACAACGGGG | 1 | | 11 | SEQ ID NO. 3421 |
| (N20)NGG | 8 | 48752664 | - | TGGGAAACGAATTCCACAACGGG | 1 | | 7 | SEQ ID NO. 3422 |
| (N20)NGG | 8 | 48752665 | - | ATGGGAAACGAATTCCACAACGG | 1 | | 20 | SEQ ID NO. 3423 |
| (N20)NGG | 8 | 48752683 | - | CCTACACATGTTGTAGAAGGATGG | 1 | | 25 | SEQ ID NO. 3424 |
| (N20)NGG | 8 | 48752684 | - | CCCTACACATGTTGTAGAAGGATG | 1 | | 28 | SEQ ID NO. 3425 |
| (N20)NGG | 8 | 48752688 | - | TGTTCCCTACACATGTTGTAGAAGG | 1 | | 39 | SEQ ID NO. 3426 |
| (N20)NGG | 8 | 48761714 | + | CACCAGTTCCCTTCCCGCCAGG | 1 | | 34 | SEQ ID NO. 3427 |
| (N20)NGG | 8 | 48761755 | + | TTTCTGCTGCCAAAATTTCATGG | 1 | | 48 | SEQ ID NO. 3428 |
| (N20)NGG | 8 | 48761778 | + | AGTGTTGAAAACACTCTGTCTGG | 1 | | 114 | SEQ ID NO. 3429 |
| (N20)NGG | 8 | 48761781 | + | GTTGAAAACACTCTGTCTGGAGG | 1 | | 35 | SEQ ID NO. 3430 |
| (N20)NGG | 8 | 48761784 | + | GAAAACACTCTGTCTGGAGGTGG | 1 | | 93 | SEQ ID NO. 3431 |
| (N20)NGG | 8 | 48761799 | + | GGAGGTGGTACTTTGTCGTGTGG | 1 | | 68 | SEQ ID NO. 3432 |
| (N20)NGG | 8 | 48761802 | + | GGTGGTACTTTGTCGTGTGGAGG | 1 | | 25 | SEQ ID NO. 3433 |
| (N20)NGG | 8 | 48761803 | + | GTGGTACTTTGTCGTGTGGAGGG | 1 | | 8 | SEQ ID NO. 3434 |
| (N20)NGG | 8 | 48761838 | + | GTACTTCCAGTTAAAGAGCAAGG | 1 | | 16 | SEQ ID NO. 3435 |
| (N20)NGG | 8 | 48761864 | + | TCGTTCAAGTCATGAGACATAGG | 1 | | 77 | SEQ ID NO. 3436 |
| (N20)NGG | 8 | 48761694 | - | AACCTGCGGGAAGGGAACTGG | | 3 | 20 | SEQ ID NO. 3437 |
| (N20)NGG | 8 | 48761700 | - | TTCATGAACCTGCGGGGAAGGG | | 4 | 36 | SEQ ID NO. 3438 |
| (N20)NGG | 8 | 48761701 | - | ATTCATGAACCTGCGCGGGAAGG | | 2 | 28 | SEQ ID NO. 3439 |
| (N20)NGG | 8 | 48761705 | - | CAGCATTCATGAACCTGGCGGGG | | 2 | 36 | SEQ ID NO. 3440 |

FIG. 12 cont.

| site_type | site_chr omosome | site_start_ nucleotide | site_s trand | target_site_sequence_with NGG | genome_wide hits_with_1_ or_less_mism atches | genome_wide hits_with_ 2_or_less_m ismatches | genome_wide hits_with_ 3_or_less_mism atches | |
|---|---|---|---|---|---|---|---|---|
| (N20)NGG | 8 | 48761706 | - | ACAGCATTCATGAACCTGCGGG | 1 | | 50 | SEQ ID NO. 3441 |
| (N20)NGG | 8 | 48761707 | - | CACAGCATTCATGAACCTGCGG | 2 | 15 | 179 | SEQ ID NO. 3442 |
| (N20)NGG | 8 | 48761710 | - | GAACACAGCATTCATGAACCTGG | 1 | 7 | 49 | SEQ ID NO. 3443 |
| (N20)NGG | 8 | 48761742 | - | TTCAACACTCCATGAAATTTTGG | | 2 | 60 | SEQ ID NO. 3444 |
| (N20)NGG | 8 | 48761822 | - | CGAAGTCCTTGCTCTTTAACTGG | 2 | 3 | 19 | SEQ ID NO. 3445 |
| (N20)NGG | 8 | 48761945 | + | AAACTTAATTTTCAGATACTGG | | 12 | 154 | SEQ ID NO. 3446 |
| (N20)NGG | 8 | 48761948 | + | CTTAATTTTCAGATACTGGAGG | 1 | 2 | 75 | SEQ ID NO. 3447 |
| (N20)NGG | 8 | 48761966 | + | GGAGGAGTCTCTGTGTGAACTGG | 1 | 3 | 99 | SEQ ID NO. 3448 |
| (N20)NGG | 8 | 48762002 | + | GAAGCAACATCAGAATACTATGG | 1 | 1 | 45 | SEQ ID NO. 3449 |
| (N20)NGG | 8 | 48762005 | + | GCAACATCAGAATACTATGAGG | 1 | 3 | 34 | SEQ ID NO. 3450 |
| (N20)NGG | 8 | 48762064 | + | GCTTCCCTCCTCTTGCAGACAGG | 1 | 4 | 48 | SEQ ID NO. 3451 |
| (N20)NGG | 8 | 48762069 | + | CCTCCTCTTGCAGACAGGTATGG | 1 | 2 | 33 | SEQ ID NO. 3452 |
| (N20)NGG | 8 | 48762070 | + | CTCCTCTTGCAGACAGGTATGGG | 1 | 2 | 21 | SEQ ID NO. 3453 |
| (N20)NGG | 8 | 48762079 | + | CAGACAGGTATGGGCTGTCCAGG | 1 | 2 | 36 | SEQ ID NO. 3454 |
| (N20)NGG | 8 | 48762080 | + | AGACAGGTATGGGCTGTCCAGGG | 1 | 2 | 32 | SEQ ID NO. 3455 |
| (N20)NGG | 8 | 48762036 | - | TGCAAGAGGAGGGAAGCTCTTGG | 1 | 6 | 49 | SEQ ID NO. 3456 |
| (N20)NGG | 8 | 48762046 | - | CATACCTGTCTGCAAGAGGAGGG | 1 | 3 | 29 | SEQ ID NO. 3457 |
| (N20)NGG | 8 | 48762047 | - | CCATACCTGTCTGCAAGAGGAGG | 1 | 2 | 40 | SEQ ID NO. 3458 |
| (N20)NGG | 8 | 48762050 | - | AGCCCATACCTGTCTGCAAGAGG | 1 | 2 | 25 | SEQ ID NO. 3459 |
| (N20)NGG | 8 | 48765243 | + | TGTTTATTGTAGATACTTCCAGG | 1 | 14 | 73 | SEQ ID NO. 3460 |
| (N20)NGG | 8 | 48765249 | + | TTGTAGATACTTCCAGGCTTTGG | 1 | 2 | 27 | SEQ ID NO. 3461 |
| (N20)NGG | 8 | 48765310 | + | GCCGCTGCAGCAGAAGTTCTAGG | 1 | 2 | 25 | SEQ ID NO. 3462 |
| (N20)NGG | 8 | 48765333 | + | ACTTATACTTCGATATGTTATGG | 1 | 2 | 23 | SEQ ID NO. 3463 |
| (N20)NGG | 8 | 48765239 | - | ACATATTATTCACCAAAGCCTGG | 3 | 3 | 54 | SEQ ID NO. 3464 |
| (N20)NGG | 8 | 48765262 | - | CACTTCTTTATATCTTACAAAGG | 1 | 3 | 83 | SEQ ID NO. 3465 |
| (N20)NGG | 8 | 48765289 | - | TCCTAGAACTTCTGCTGCAGCGG | 1 | 4 | 71 | SEQ ID NO. 3466 |
| (N20)NGG | 8 | 48766643 | + | CTCCTTTGTGCTTATGTTTCAGG | 3 | 8 | 74 | SEQ ID NO. 3467 |
| (N20)NGG | 8 | 48766666 | + | TTAATATTTGAAAAGTTTTCCGG | 3 | 30 | 414 | SEQ ID NO. 3468 |
| (N20)NGG | 8 | 48766699 | + | AATTCTAAAGACAACTCAGTAGG | 1 | 7 | 92 | SEQ ID NO. 3469 |
| (N20)NGG | 8 | 48766700 | + | ATTCTAAAGACAACTCAGTAGGG | 1 | 6 | 74 | SEQ ID NO. 3470 |
| (N20)NGG | 8 | 48766714 | + | TCAGTAGGGATTCAATTGCTAGG | 1 | 2 | 25 | SEQ ID NO. 3471 |
| (N20)NGG | 8 | 48766725 | + | TCAATTGCTAGCATCGTGATGG | 1 | 2 | 12 | SEQ ID NO. 3472 |
| (N20)NGG | 8 | 48766759 | + | CCTCCCTATGACCCACAGTGTGG | 1 | 5 | 40 | SEQ ID NO. 3473 |

FIG. 12 cont.

| site_type | site_chromosome | site_start_nucleotide | site_strand | target_site_sequence_with NGG | genome_wide_hits_with_1_or_less_mismatches | genome_wide_hits_with_2_or_less_mismatches | genome_wide_hits_with_3_or_less_mismatches | | |
|---|---|---|---|---|---|---|---|---|---|
| (N20)NGG | 8 | 48766623 | - | AACCTGAAACATAAGCACAAAGG | | 1 | 4 | 105 | SEQ ID NO. 3474 |
| (N20)NGG | 8 | 48766663 | - | TTTAGAATTAGGATCTTTACCGG | | 1 | 11 | 138 | SEQ ID NO. 3475 |
| (N20)NGG | 8 | 48766674 | - | ACTGAGTTGTCTTTAGAATTAGG | | 1 | 4 | 65 | SEQ ID NO. 3476 |
| (N20)NGG | 8 | 48766726 | - | GTCATAGGGAGGCAGGTCATTGG | | 1 | 1 | 30 | SEQ ID NO. 3477 |
| (N20)NGG | 8 | 48766733 | - | ACTGTGGGTCATAGGGAGGCAGG | | 1 | 1 | 47 | SEQ ID NO. 3478 |
| (N20)NGG | 8 | 48766737 | - | CCACACTGTGGGTCATAGGGAGG | | 1 | 5 | 35 | SEQ ID NO. 3479 |
| (N20)NGG | 8 | 48766740 | - | ATGCCACACTGTGGGTCATAGG | | 1 | 7 | 33 | SEQ ID NO. 3480 |
| (N20)NGG | 8 | 48766741 | - | GATGCCACACTGTGGGTCATAGG | | 1 | 2 | 36 | SEQ ID NO. 3481 |
| (N20)NGG | 8 | 48766748 | - | TACTCTGGATGCCACACTGTGG | | 1 | 1 | 35 | SEQ ID NO. 3482 |
| (N20)NGG | 8 | 48766749 | - | CTACTCTGGATGCCACACTGTGG | | 1 | 2 | 41 | SEQ ID NO. 3483 |
| (N20)NGG | 8 | 48766763 | - | CAAACACGTACTCGCTACTCTGG | | 1 | 1 | 2 | SEQ ID NO. 3484 |
| (N20)NGG | 8 | 48767782 | + | CAGAATTTCTGTACCTTTTCAGGG | | 1 | 9 | 243 | SEQ ID NO. 3485 |
| (N20)NGG | 8 | 48767783 | + | AGAATTTCTGTACCTTTTCAGGG | | 1 | 8 | 278 | SEQ ID NO. 3486 |
| (N20)NGG | 8 | 48767784 | + | GAATTTCTGTACCTTTTCAGGGG | | 1 | 11 | 112 | SEQ ID NO. 3487 |
| (N20)NGG | 8 | 48767785 | + | AATTTCTGTACCTTTTCAGGGGG | | 1 | 9 | 110 | SEQ ID NO. 3488 |
| (N20)NGG | 8 | 48767907 | + | TAAAGACCCTGTCGAGTGCTGG | | 1 | 1 | 10 | SEQ ID NO. 3489 |
| (N20)NGG | 8 | 48767911 | + | GACCCTGTCGAGTGCTGGAAGG | | 1 | 1 | 10 | SEQ ID NO. 3490 |
| (N20)NGG | 8 | 48767934 | + | ATTGTTTATCCATCCCTTATAGG | | 1 | 5 | 57 | SEQ ID NO. 3491 |
| (N20)NGG | 8 | 48767946 | - | TCCCTTATAGGTATGTTTACTGG | | 1 | 3 | 22 | SEQ ID NO. 3492 |
| (N20)NGG | 8 | 48767773 | - | TCTTTAGGGACCCCCTGAAAAGG | | 1 | 1 | 26 | SEQ ID NO. 3493 |
| (N20)NGG | 8 | 48767787 | - | TTGCTAACACTTCATCTTTAGG | | 1 | 5 | 57 | SEQ ID NO. 3494 |
| (N20)NGG | 8 | 48767788 | - | TTTGCTAACACTTCATCTTTAGG | | 1 | 3 | 81 | SEQ ID NO. 3495 |
| (N20)NGG | 8 | 48767826 | - | GATGAAAGACATGTTTCATTAGG | | 1 | 6 | 92 | SEQ ID NO. 3496 |
| (N20)NGG | 8 | 48767848 | - | TGTCTAAACACAGCTCTTTTTGG | | 1 | 1 | 59 | SEQ ID NO. 3497 |
| (N20)NGG | 8 | 48767874 | - | CAAGGTCTTTTATAATTTCAAGG | | 1 | 7 | 88 | SEQ ID NO. 3498 |
| (N20)NGG | 8 | 48767891 | - | ATCCTTCCAGCACTCGACAAGGG | | 1 | 2 | 12 | SEQ ID NO. 3499 |
| (N20)NGG | 8 | 48767892 | - | AATCCTTCCAGCACTCGACAAGG | | 1 | 1 | 19 | SEQ ID NO. 3500 |
| (N20)NGG | 8 | 48767921 | - | GTAAACATACCTATAAGGGATGG | | 1 | 2 | 25 | SEQ ID NO. 3501 |
| (N20)NGG | 8 | 48767925 | - | ACCAGTAAACATACCTATAAGGG | | 1 | 1 | 33 | SEQ ID NO. 3502 |
| (N20)NGG | 8 | 48767926 | - | AACCAGTAAACATACCTATAAGG | | 1 | 5 | 51 | SEQ ID NO. 3503 |
| (N20)NGG | 8 | 48769716 | + | TGACTTTTACATCTCTTGTAGG | | 1 | 7 | 62 | SEQ ID NO. 3504 |
| (N20)NGG | 8 | 48769742 | + | TTCGCCCTTACGCGAAGCACTGG | | 1 | 1 | 1 | SEQ ID NO. 3505 |
| (N20)NGG | 8 | 48769764 | + | GCTTAGCCCCTTGCTGCAGCTGG | | 1 | 2 | 28 | SEQ ID NO. 3506 |

FIG. 12 cont.

| site type | site_chr omosome | site_start_ nucleotide | site_s trand | target_site_sequence_wi th NGG | genome_wide_ hits_with_1_ or_less_mism atches | genome_wide_ hits_with_ 2_or_less_m ismatches | genome_wide_ hits_with_3_ or_less_mism atches | |
|---|---|---|---|---|---|---|---|---|
| (N20)NGG | 8 | 48769783 | + | CTGGCTGCTTCTGAAAACAATGG | | 2 | 12 | 98 SEQ ID NO. 3507 |
| (N20)NGG | 8 | 48769786 | + | GCTGCTTCTGAAAACAATGGAGG | | 1 | 6 | 80 SEQ ID NO. 3508 |
| (N20)NGG | 8 | 48769792 | + | TCTGAAAACAATGGAGGAGAAGG | | 1 | 13 | 150 SEQ ID NO. 3509 |
| (N20)NGG | 8 | 48769806 | + | AGGAGAAGGAATTCACTACATGG | | 1 | 5 | 110 SEQ ID NO. 3510 |
| (N20)NGG | 8 | 48769809 | + | AGAAGGAATTCACTACATGTGG | | 1 | 2 | 66 SEQ ID NO. 3511 |
| (N20)NGG | 8 | 48769821 | + | CTACATGGTGTTGAGATAGTGG | | 1 | 3 | 47 SEQ ID NO. 3512 |
| (N20)NGG | 8 | 48769838 | + | TAGTGGCCACTATTCTTTTCATGG | | 1 | 4 | 31 SEQ ID NO. 3513 |
| (N20)NGG | 8 | 48769843 | + | GCCACTATTCTTTCATGGACAGG | | 1 | 1 | 13 SEQ ID NO. 3514 |
| (N20)NGG | 8 | 48769848 | + | TATTCTTTCATGGACAGGCTTGG | | 1 | 4 | 42 SEQ ID NO. 3515 |
| (N20)NGG | 8 | 48769865 | + | GCTTGGCCACTCCAACAGTAAGG | | 1 | 2 | 18 SEQ ID NO. 3516 |
| (N20)NGG | 8 | 48769706 | − | AAGGGCGAAAGACCTACAAGAGG | | 1 | 1 | 19 SEQ ID NO. 3517 |
| (N20)NGG | 8 | 48769724 | − | TAAGCCAGTGCTTCGCGTAAGG | | 1 | 1 | 3 SEQ ID NO. 3518 |
| (N20)NGG | 8 | 48769725 | − | CTAAGCCAGTGCTTCGCGTAAG | | 1 | 1 | 7 SEQ ID NO. 3519 |
| (N20)NGG | 8 | 48769748 | − | AAGCAGCCAGCTGCAGCAAGGG | | 1 | 1 | 83 SEQ ID NO. 3520 |
| (N20)NGG | 8 | 48769749 | − | GAAGCAGCCAGCTGCAGCAAGG | | 3 | 3 | 92 SEQ ID NO. 3521 |
| (N20)NGG | 8 | 48769750 | − | AGAAGCAGCCAGCTGCAGCAAGG | | 1 | 11 | 114 SEQ ID NO. 3522 |
| (N20)NGG | 8 | 48769822 | − | GCCTGTCCATGAAAGAATAGTGG | | 1 | 6 | 25 SEQ ID NO. 3523 |
| (N20)NGG | 8 | 48769849 | − | ATCAATCCTTACTGTTGGAGTGG | | 1 | 1 | 22 SEQ ID NO. 3524 |
| (N20)NGG | 8 | 48769854 | − | GATGCATCAATCCTTACTGTTGG | | 1 | 1 | 23 SEQ ID NO. 3525 |
| (N20)NGG | 8 | 48771076 | + | AATTTTGAATGTTTTATTTTAGG | | 2 | 82 | 1250 SEQ ID NO. 3526 |
| (N20)NGG | 8 | 48771105 | + | TGCCAAGAGATCTTCCTTCTTGG | | 1 | 4 | 62 SEQ ID NO. 3527 |
| (N20)NGG | 8 | 48771122 | + | TCTTGGATGAAATTCCTCCATGG | | 1 | 5 | 66 SEQ ID NO. 3528 |
| (N20)NGG | 8 | 48771130 | + | GAAATTCCTCCATGGCAAACTGG | | 1 | 2 | 34 SEQ ID NO. 3529 |
| (N20)NGG | 8 | 48771131 | + | AAATTCCTCCATGGCAAACTGGG | | 1 | 1 | 40 SEQ ID NO. 3530 |
| (N20)NGG | 8 | 48771196 | + | GCTTGTTATTAATACAGAAGAGG | | 1 | 3 | 56 SEQ ID NO. 3531 |
| (N20)NGG | 8 | 48771085 | − | ATCCAAGAAGGAAGATCTCTTGG | | 1 | 1 | 70 SEQ ID NO. 3532 |
| (N20)NGG | 8 | 48771097 | − | TGGAGGAATTCATCCAAGAAGG | | 2 | 7 | 77 SEQ ID NO. 3533 |
| (N20)NGG | 8 | 48771114 | − | GATTTCCCAGTTTGCCATGGAGG | | 1 | 4 | 27 SEQ ID NO. 3534 |
| (N20)NGG | 8 | 48771117 | − | TTGGATTTCCCAGTTTGCCATGG | | 1 | 4 | 70 SEQ ID NO. 3535 |
| (N20)NGG | 8 | 48771136 | − | CGGATATTTAATGGTACTATTGG | | 1 | 1 | 17 SEQ ID NO. 3536 |
| (N20)NGG | 8 | 48771145 | − | AAGAAGAGACGGATATTTAATGG | | 1 | 2 | 74 SEQ ID NO. 3537 |
| (N20)NGG | 8 | 48771156 | − | CAAGCTTGGTAAGAAGAGACGG | | 1 | 9 | 65 SEQ ID NO. 3538 |
| (N20)NGG | 8 | 48771170 | − | TTCTGTATTAATAACAAGCTTGG | | 2 | 4 | 79 SEQ ID NO. 3539 |

FIG. 12 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 8 | 48771409 | + | TCCTGGGCCCTCCCTTTCGCAGG | 1 | 1 | 12 | 59 SEQ ID NO. 3540 |
| (N20)NGG | 8 | 48771417 | + | CCTCCCTTTCGCAGGAGCAGCGG | 1 | | 4 | 40 SEQ ID NO. 3541 |
| (N20)NGG | 8 | 48771418 | + | CTCCCTTTCGCAGGAGCAGCGGG | 1 | | 4 | 41 SEQ ID NO. 3542 |
| (N20)NGG | 8 | 48771427 | + | GCAGGAGCAGCGGGACCCCACGG | 1 | | 5 | 67 SEQ ID NO. 3543 |
| (N20)NGG | 8 | 48771445 | + | CACGGTGCATGATGATGTGCTGG | 1 | | 2 | 10 SEQ ID NO. 3544 |
| (N20)NGG | 8 | 48771451 | + | GCATGATGATGTGCTGGAGCTGG | 2 | | 2 | 33 SEQ ID NO. 3545 |
| (N20)NGG | 8 | 48771457 | + | TGATGTGCTGGAGCTGGAGATGG | 1 | | 8 | 102 SEQ ID NO. 3546 |
| (N20)NGG | 8 | 48771471 | + | TGGAGATGGACGAGCTCAATCGG | 1 | | 2 | 30 SEQ ID NO. 3547 |
| (N20)NGG | 8 | 48771484 | + | GCTCAATCGGCATGAGTGCATGG | 1 | | 1 | 7 SEQ ID NO. 3548 |
| (N20)NGG | 8 | 48771496 | + | TGAGTGCATGGCGCCCCTGACGG | 1 | | 1 | 14 SEQ ID NO. 3549 |
| (N20)NGG | 8 | 48771502 | + | CATGGCGCCCCTGACGGCCCTGG | 1 | | 1 | 14 SEQ ID NO. 3550 |
| (N20)NGG | 8 | 48771526 | + | CAAGCACATGCACAGAAGCCTGG | 1 | | 3 | 95 SEQ ID NO. 3551 |
| (N20)NGG | 8 | 48771527 | + | AAGCACATGCACAGAAGCCTGGG | 1 | | 2 | 71 SEQ ID NO. 3552 |
| (N20)NGG | 8 | 48771539 | + | AGAAGCCTGGCCCGCCCTCAAGG | 1 | | 1 | 36 SEQ ID NO. 3553 |
| (N20)NGG | 8 | 48771547 | + | GGGCCCGCCCTCAAGGAGAAGAGG | 1 | | 2 | 33 SEQ ID NO. 3554 |
| (N20)NGG | 8 | 48771388 | - | TCCTGCGAAAGGGAGGGCCCAGG | 1 | | 2 | 39 SEQ ID NO. 3555 |
| (N20)NGG | 8 | 48771394 | - | CGCTGCTCCTGCGAAAGGGAGGG | 1 | | 3 | 21 SEQ ID NO. 3556 |
| (N20)NGG | 8 | 48771395 | - | CCGCTGCTCCTGCGAAAGGGAGG | 1 | | 2 | 19 SEQ ID NO. 3557 |
| (N20)NGG | 8 | 48771398 | - | GTCCCGCTGCTCCTGCGAAAGGG | 1 | | 2 | 16 SEQ ID NO. 3558 |
| (N20)NGG | 8 | 48771399 | - | GGTCCCGCTGCTCCTGCGAAAGG | 1 | | 3 | 19 SEQ ID NO. 3559 |
| (N20)NGG | 8 | 48771420 | - | GCACATCATCATGCACCGTGGG | 1 | | 2 | 9 SEQ ID NO. 3560 |
| (N20)NGG | 8 | 48771421 | - | AGCACATCATCATGCACCGTGGG | 1 | | 2 | 12 SEQ ID NO. 3561 |
| (N20)NGG | 8 | 48771422 | - | CAGCACATCATCATGCACCGTGG | 1 | | 2 | 11 SEQ ID NO. 3562 |
| (N20)NGG | 8 | 48771487 | - | TGCTTGACCAGGGCCGTCAGGGG | 1 | | 1 | 19 SEQ ID NO. 3563 |
| (N20)NGG | 8 | 48771488 | - | GTGCTTGACCAGGGCCGTCAGGG | 1 | | 2 | 13 SEQ ID NO. 3564 |
| (N20)NGG | 8 | 48771489 | - | TGTGCTTGACCAGGGCCGTCAGG | 1 | | 1 | 7 SEQ ID NO. 3565 |
| (N20)NGG | 8 | 48771497 | - | TCTGTGCATGTGCTTGACCAGGG | 1 | | 3 | 59 SEQ ID NO. 3566 |
| (N20)NGG | 8 | 48771498 | - | TTCTGTGCATGTGCTTGACCAGG | 1 | | 3 | 47 SEQ ID NO. 3567 |
| (N20)NGG | 8 | 48771522 | - | CTTCTCCTTGAGGGGCCCAGG | 1 | | 4 | 34 SEQ ID NO. 3568 |
| (N20)NGG | 8 | 48771528 | - | GCACCTCTTCTCCTTGAGGCGG | 1 | | 4 | 34 SEQ ID NO. 3569 |
| (N20)NGG | 8 | 48771529 | - | AGCACCTCTTCTCCTTGAGGCGG | 1 | | 3 | 58 SEQ ID NO. 3570 |
| (N20)NGG | 8 | 48771532 | - | AAAAGCACCTCTTCTCCTTGAGG | 1 | | 5 | 79 SEQ ID NO. 3571 |
| (N20)NGG | 8 | 48772174 | + | CTCCTTTTTTATATTTCAGATGG | 2 | | 15 | 386 SEQ ID NO. 3572 |

FIG. 12 cont.

| site_type | site_chr omosome | site_start_ nucleotide | site_s trand | target_site_sequence_wi th_NGG | genome_wide_ hits_with_1 or_less_mism atches | genome_wide_ hits_with_ 2_or_less_m ismatches | genome_wide_ hits_with_ 3_or_less_mism atches | | |
|---|---|---|---|---|---|---|---|---|---|
| (N20)NGG | 8 | 48772206 | + | TATGTCTCCCTGTCATATTTGG | 1 | 1 | 6 | 55 | SEQ ID NO. 3573 |
| (N20)NGG | 8 | 48772227 | + | GGCAGACAGTACCCTGAGTGAGG | | 1 | 5 | 35 | SEQ ID NO. 3574 |
| (N20)NGG | 8 | 48772255 | + | AGTCAATTGATTTCTCAACCGG | 1 | 1 | 5 | 62 | SEQ ID NO. 3575 |
| (N20)NGG | 8 | 48772303 | + | CAAGACCCTAGACCTGCCACTGG | 1 | 1 | 3 | 55 | SEQ ID NO. 3576 |
| (N20)NGG | 8 | 48772313 | + | GACCTGCCACTGGTCGTTTTCGG | 1 | 1 | 1 | 6 | SEQ ID NO. 3577 |
| (N20)NGG | 8 | 48772319 | + | CCACTGGTCGTTTTCGGAGACGG | 1 | 1 | 2 | 9 | SEQ ID NO. 3578 |
| (N20)NGG | 8 | 48772320 | + | CACTGGTCGTTTTCGGAGACGGG | 1 | 1 | 1 | 5 | SEQ ID NO. 3579 |
| (N20)NGG | 8 | 48772154 | - | GACCATCTGAAATATAAAAAGG | 1 | 1 | 5 | 183 | SEQ ID NO. 3580 |
| (N20)NGG | 8 | 48772176 | - | GACAGGGAAGACATATAGGAAGG | 1 | 1 | 8 | 70 | SEQ ID NO. 3581 |
| (N20)NGG | 8 | 48772180 | - | ATATGACAGGGAAGACATATAGG | 1 | 1 | 2 | 55 | SEQ ID NO. 3582 |
| (N20)NGG | 8 | 48772192 | - | ACTGTCTGCCAAATATGACAGGG | 1 | 1 | 3 | 47 | SEQ ID NO. 3583 |
| (N20)NGG | 8 | 48772193 | - | TACTGTCTGCCAAATATGACAGG | 1 | 1 | 4 | 37 | SEQ ID NO. 3584 |
| (N20)NGG | 8 | 48772216 | - | TTGACTCATTTCCTCACTCAGGG | 1 | 1 | 8 | 81 | SEQ ID NO. 3585 |
| (N20)NGG | 8 | 48772217 | - | ATTGACTCATTTCCTCACTCAGG | 1 | 1 | 5 | 81 | SEQ ID NO. 3586 |
| (N20)NGG | 8 | 48772252 | - | GTATGAATAGCTCTGAACTCCGG | 1 | 1 | 1 | 28 | SEQ ID NO. 3587 |
| (N20)NGG | 8 | 48772279 | - | AGTGGCAGGTCTAGGGTCTTTGG | 1 | 1 | 1 | 26 | SEQ ID NO. 3588 |
| (N20)NGG | 8 | 48772280 | - | CAGTGGCAGGTCTAGGGTCTTGG | 1 | 1 | 2 | 41 | SEQ ID NO. 3589 |
| (N20)NGG | 8 | 48772286 | - | AACGACCAGTGGCAGGTCTAGGG | 1 | 1 | 1 | 5 | SEQ ID NO. 3590 |
| (N20)NGG | 8 | 48772287 | - | AAACGACCAGTGGCAGGTCTAGG | 1 | 1 | 1 | 15 | SEQ ID NO. 3591 |
| (N20)NGG | 8 | 48772293 | - | CTCCGAAAACGACCAGTGGCAGG | 1 | 1 | 1 | 3 | SEQ ID NO. 3592 |
| (N20)NGG | 8 | 48772297 | - | CCGTCTCCGAAAACGACCAGTGG | 1 | 1 | 1 | 3 | SEQ ID NO. 3593 |
| (N20)NGG | 8 | 48773459 | + | GTTTATTTGTTCTTTCCAATAGG | 1 | 1 | 2 | 105 | SEQ ID NO. 3594 |
| (N20)NGG | 8 | 48773468 | + | TTCTTTCCAATAGGTTCCTATGG | 1 | 1 | 2 | 38 | SEQ ID NO. 3595 |
| (N20)NGG | 8 | 48773497 | + | AGAAAAGTACATTGAAATTAGG | 1 | 1 | 19 | 349 | SEQ ID NO. 3596 |
| (N20)NGG | 8 | 48773523 | + | GAAGCCAGAGAAGCAGCAAATGG | 1 | 1 | 14 | 212 | SEQ ID NO. 3597 |
| (N20)NGG | 8 | 48773524 | + | AAGCCAGAGAAGCAGCAAATGGG | 1 | 2 | 7 | 141 | SEQ ID NO. 3598 |
| (N20)NGG | 8 | 48773525 | + | AGCCAGAGAAGCAGCAAATGGG | 1 | 1 | 9 | 150 | SEQ ID NO. 3599 |
| (N20)NGG | 8 | 48773532 | + | GAAGCAGCAAATGGGGATTCGG | 1 | 1 | 7 | 39 | SEQ ID NO. 3600 |
| (N20)NGG | 8 | 48773536 | + | CAGCAAATGGGGATTCAGGTAGG | 1 | 1 | 2 | 43 | SEQ ID NO. 3601 |
| (N20)NGG | 8 | 48773451 | - | TCTTTCCATAGGAACCTATTGGG | 1 | 1 | 3 | 50 | SEQ ID NO. 3602 |
| (N20)NGG | 8 | 48773452 | - | TTCTTTCCATAGGAACCTATTGG | 1 | 1 | 3 | 42 | SEQ ID NO. 3603 |
| (N20)NGG | 8 | 48773462 | - | TACTTTTCTTTCTTTCCATAGG | 1 | 5 | 51 | 869 | SEQ ID NO. 3604 |
| (N20)NGG | 8 | 48773505 | - | ATCCCCATTTGTGCTTCTCTGG | 1 | 1 | 3 | 52 | SEQ ID NO. 3605 |

FIG. 12 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 8 | 48774688 | + | TAATTTTCTGTAGAAGTTGAGG |   | 1 | 8 | 83 SEQ ID NO. 3606 |
| (N20)NGG | 8 | 48774651 | - | GAAAATTATAGCGGCGCTTCAG | 1 | 1 | 1 | 2 SEQ ID NO. 3607 |
| (N20)NGG | 8 | 48774660 | - | CTTCTACAGGAAAATTATAGCGG |   | 1 | 3 | 50 SEQ ID NO. 3608 |
| (N20)NGG | 8 | 48774673 | - | TCACTCACCTCAACTTCTACAGG |   | 1 | 2 | 33 SEQ ID NO. 3609 |
| (N20)NGG | 8 | 48774964 | + | CGATGCATTTACAGAGAACATGG |   | 1 | 2 | 25 SEQ ID NO. 3610 |
| (N20)NGG | 8 | 48774968 | + | GCATTTACAGAGAACATGGCAGG |   | 1 | 6 | 58 SEQ ID NO. 3611 |
| (N20)NGG | 8 | 48774985 | + | GGCAGGAGAATCAGCTGCTGG |   | 1 | 5 | 74 SEQ ID NO. 3612 |
| (N20)NGG | 8 | 48774990 | + | GAGAGAATCAGCTGCTGGAGAGG |   | 1 | 7 | 88 SEQ ID NO. 3613 |
| (N20)NGG | 8 | 48775073 | + | AATGAGTTAAAATTTTACCAAGG |   | 1 | 14 | 204 SEQ ID NO. 3614 |
| (N20)NGG | 8 | 48775102 | + | GTTTAGTGAAAAACCAGAAAAGG |   | 2 | 12 | 108 SEQ ID NO. 3615 |
| (N20)NGG | 8 | 48775106 | + | AGTGAAAAACCAGAAAAGTAGG |   | 1 | 10 | 137 SEQ ID NO. 3616 |
| (N20)NGG | 8 | 48775118 | + | GAAAAGTAGGCCACTCCTACGG |   | 1 | 1 | 31 SEQ ID NO. 3617 |
| (N20)NGG | 8 | 48775002 | - | CGCAGTTGTATGCTGCACAATGG |   | 1 | 5 | 16 SEQ ID NO. 3618 |
| (N20)NGG | 8 | 48775025 | - | GACACAGCAGATGACAGATATGG |   | 1 | 6 | 62 SEQ ID NO. 3619 |
| (N20)NGG | 8 | 48775068 | - | TTTCACTAAAACAGAAAACCTTGG |   | 3 | 6 | 131 SEQ ID NO. 3620 |
| (N20)NGG | 8 | 48775093 | - | TAGGAGTGGCCTACCTTTTCTGG |   | 1 | 2 | 14 SEQ ID NO. 3621 |
| (N20)NGG | 8 | 48776001 | + | TACTCAAATCACCAAGAAGATGG |   | 1 | 5 | 106 SEQ ID NO. 3622 |
| (N20)NGG | 8 | 48776002 | + | ACTCAAATCACCAAGAAGATGGG |   | 1 | 5 | 87 SEQ ID NO. 3623 |
| (N20)NGG | 8 | 48776064 | + | CAAAGATGATGTTCATGCTAAGG |   | 1 | 2 | 46 SEQ ID NO. 3624 |
| (N20)NGG | 8 | 48776092 | + | AAAATTAATCAAGTTTTCCATGG |   | 1 | 16 | 209 SEQ ID NO. 3625 |
| (N20)NGG | 8 | 48776110 | + | CATGGCTCGTGTATTACAGAAGG |   | 1 | 1 | 14 SEQ ID NO. 3626 |
| (N20)NGG | 8 | 48776159 | + | AGTAAGATTTTACTTAATTTTGG |   | 1 | 19 | 212 SEQ ID NO. 3627 |
| (N20)NGG | 8 | 48775948 | - | AGATTCATTTAGCTTCAAAAAGG |   | 1 | 7 | 113 SEQ ID NO. 3628 |
| (N20)NGG | 8 | 48775972 | - | CTTGGTGATTTGAGTATCAAAGG |   | 1 | 4 | 37 SEQ ID NO. 3629 |
| (N20)NGG | 8 | 48775990 | - | CTTATAGTAGCCCATCTTCTTGG |   | 1 | 2 | 16 SEQ ID NO. 3630 |
| (N20)NGG | 8 | 48776036 | - | CATGAACATCATCTTTGGAAGG |   | 1 | 2 | 53 SEQ ID NO. 3631 |
| (N20)NGG | 8 | 48776040 | - | TTAGCATGAACATCATCTTTGG |   | 1 | 7 | 75 SEQ ID NO. 3632 |
| (N20)NGG | 8 | 48776041 | - | CTTAGCATGAACATCATCTTTGG |   | 1 | 4 | 43 SEQ ID NO. 3633 |
| (N20)NGG | 8 | 48776087 | - | CTTCTGTAATACACGAGCCATGG |   | 1 | 2 | 12 SEQ ID NO. 3634 |
| (N20)NGG | 8 | 48777116 | + | TAATTTTATCTGTTTTCTTAGG |   | 2 | 39 | 787 SEQ ID NO. 3635 |
| (N20)NGG | 8 | 48777117 | + | AATTTTATCTGTTTTTCTTAGGG |   | 3 | 43 | 561 SEQ ID NO. 3636 |
| (N20)NGG | 8 | 48777118 | + | ATTTTATCTGTTTTTCTTAGGGG |   | 2 | 25 | 472 SEQ ID NO. 3637 |
| (N20)NGG | 8 | 48777139 | + | GGTTCATGTGTCACACAAGTAGG | 1 | 1 | 1 | 27 SEQ ID NO. 3638 |

FIG. 12 cont.

| site_type | site_chr omosome | site_start_ nucleotide | site_s trand | target_site_sequence_wi th NGG | genome_wide_ hits_with_1_ or_less_mism atches | genome_wide_ hits_with_ 2_or_less_m ismatches | genome_wide_ hits_with_3_ or_less_mism atches | | |
|---|---|---|---|---|---|---|---|---|---|
| (N20)NGG | 8 | 48777147 | + | TGTCACACAAGTAGGCCTTCTGG | | 1 | 3 | 26 | SEQ ID NO. 3639 |
| (N20)NGG | 8 | 48777170 | + | AAAGCGTGTATGAAATGTTCAGG | | 1 | 1 | 15 | SEQ ID NO. 3640 |
| (N20)NGG | 8 | 48777174 | + | CGTGTATGAAATGTTCAGGAAGG | | 2 | 9 | 99 | SEQ ID NO. 3641 |
| (N20)NGG | 8 | 48777213 | + | TTTCACACGCCAGTCCTTTGTGG | | 1 | 1 | 18 | SEQ ID NO. 3642 |
| (N20)NGG | 8 | 48777239 | + | GCTCCCTCCTCACTCTGCTGTGG | | 2 | 13 | 147 | SEQ ID NO. 3643 |
| (N20)NGG | 8 | 48777252 | + | TCTGCTGTGGCACTGTAGCCTGG | | 1 | 4 | 58 | SEQ ID NO. 3644 |
| (N20)NGG | 8 | 48777285 | + | AGAATTCTTCAGCACAATTGTGG | | 1 | 2 | 52 | SEQ ID NO. 3645 |
| (N20)NGG | 8 | 48777288 | + | ATTCTTCAGCACAATTGTGGTGG | | 2 | 3 | 39 | SEQ ID NO. 3646 |
| (N20)NGG | 8 | 48777314 | + | CCATTGATGTGTTGAAGTCCAGG | | 1 | 3 | 62 | SEQ ID NO. 3647 |
| (N20)NGG | 8 | 48777324 | + | GTTGAAGTCCAGGTTTACAAAGG | | 1 | 2 | 29 | SEQ ID NO. 3648 |
| (N20)NGG | 8 | 48777140 | - | TTTCATACACGCTTTCCAGAAGG | | 1 | 4 | 28 | SEQ ID NO. 3649 |
| (N20)NGG | 8 | 48777179 | - | GGCGTGTGAAACTTAGGCGGGGG | | 1 | 3 | 6 | SEQ ID NO. 3650 |
| (N20)NGG | 8 | 48777180 | - | TGGCGTGTGAAACTTAGGCGGGG | | 1 | 1 | 4 | SEQ ID NO. 3651 |
| (N20)NGG | 8 | 48777181 | - | CTGGCGTGTGAAACTTAGGCGGG | | 1 | 1 | 16 | SEQ ID NO. 3652 |
| (N20)NGG | 8 | 48777182 | - | ACTGGCGTGTGAAACTTAGGCGG | | 2 | 3 | 14 | SEQ ID NO. 3653 |
| (N20)NGG | 8 | 48777185 | - | AGGACTGGCGTGTGAAACTTAGG | | 1 | 2 | 8 | SEQ ID NO. 3654 |
| (N20)NGG | 8 | 48777200 | - | GGGAGCGCGGTCCACAAGGACTGG | | 1 | 2 | 10 | SEQ ID NO. 3655 |
| (N20)NGG | 8 | 48777205 | - | GAGGAGGAGCGGTCCACAAAGG | | 1 | 2 | 48 | SEQ ID NO. 3656 |
| (N20)NGG | 8 | 48777215 | - | ACAGCAGAGTGAGGAGGAGCGG | | 1 | 30 | 331 | SEQ ID NO. 3657 |
| (N20)NGG | 8 | 48777220 | - | GTGCCACAGCAGAGTGAGGAGGG | | 1 | 9 | 88 | SEQ ID NO. 3658 |
| (N20)NGG | 8 | 48777221 | - | AGTGCCACAGCAGAGTGAGGAGG | | 1 | 6 | 74 | SEQ ID NO. 3659 |
| (N20)NGG | 8 | 48777224 | - | TACAGTGCCACAGCAGAGTGAGG | | 1 | 3 | 41 | SEQ ID NO. 3660 |
| (N20)NGG | 8 | 48777248 | - | AGAATTCTTCAAAGCATCCAGG | | 1 | 3 | 51 | SEQ ID NO. 3661 |
| (N20)NGG | 8 | 48777292 | - | CCTGGACTTCAACACATCAATGG | | 1 | 2 | 33 | SEQ ID NO. 3662 |
| (N20)NGG | 8 | 48777310 | - | GTATGATACCTTTGTAAACCTGG | | 1 | 2 | 23 | SEQ ID NO. 3663 |
| (N20)NGG | 8 | 48790299 | + | TTTCTAGTTTCTAGATGCATTGG | | 1 | 5 | 96 | SEQ ID NO. 3664 |
| (N20)NGG | 8 | 48790326 | + | ATCTCAAAGCCCTATGTTGTTGG | | 1 | 1 | 25 | SEQ ID NO. 3665 |
| (N20)NGG | 8 | 48790352 | + | TGATGACAGAAGTTCTTTGTCGG | | 2 | 4 | 59 | SEQ ID NO. 3666 |
| (N20)NGG | 8 | 48790353 | + | GATGACAGAAGTTCTTTGTCGGG | | 1 | 3 | 36 | SEQ ID NO. 3667 |
| (N20)NGG | 8 | 48790371 | + | TCGGAACAGCAGCATGTCATGG | | 1 | 1 | 17 | SEQ ID NO. 3668 |
| (N20)NGG | 8 | 48790397 | + | AATTATTTCAATCCAGTTTCAGG | | 2 | 6 | 114 | SEQ ID NO. 3669 |
| (N20)NGG | 8 | 48790400 | + | TATTTCAATCCAGTTTCAGGAGG | | 1 | 1 | 55 | SEQ ID NO. 3670 |
| (N20)NGG | 8 | 48790412 | + | GTTTCAGGAGGATTGCCAGAAGG | | 1 | 2 | 26 | SEQ ID NO. 3671 |

| site_type | site_chr omosome | site_start_ nucleotide | site_s trand | target_site_sequence_wi th NGG | genome_wide_ hits_with_1_ or_less_mism atches | genome_wide_ hits_with_ 2_or_less_m ismatches | genome_wide_ hits_with_3_ or_less_mism atches | |
|---|---|---|---|---|---|---|---|---|
| (N20)NGG | 8 | 48790425 | + | TGCCAGAAGGTAAGTCATTCTGG | 1 | 2 | 39 | SEQ ID NO. 3672 |
| (N20)NGG | 8 | 48790430 | + | GAAGGTAAGTCATTCTGGCCTGG | 1 | 5 | 28 | SEQ ID NO. 3673 |
| (N20)NGG | 8 | 48790431 | + | AAGGTAAGTCATTCTGGCCTGGG | 1 | 2 | 44 | SEQ ID NO. 3674 |
| (N20)NGG | 8 | 48790313 | - | TCATCAATTCCAACAACATAGGG | 1 | 1 | 58 | SEQ ID NO. 3675 |
| (N20)NGG | 8 | 48790314 | - | GTCATCAATTCCAACAACATAGG | 1 | 2 | 32 | SEQ ID NO. 3676 |
| (N20)NGG | 8 | 48790387 | - | TCTGGCAATCCTCCTGAAACTGG | 1 | 2 | 19 | SEQ ID NO. 3677 |
| (N20)NGG | 8 | 48790405 | - | GGCCAGAATGACTTACCTTCTGG | 1 | 3 | 28 | SEQ ID NO. 3678 |
| (N20)NGG | 8 | 48792051 | + | TTATGTCTGTCTTGCTCCACAGG | 1 | 5 | 79 | SEQ ID NO. 3679 |
| (N20)NGG | 8 | 48792052 | + | TATGTCTGTCTTGCTCCACAGGG | 1 | 6 | 71 | SEQ ID NO. 3680 |
| (N20)NGG | 8 | 48792094 | + | CCATTCTTCACCAGCCTCACTGG | 1 | 7 | 88 | SEQ ID NO. 3681 |
| (N20)NGG | 8 | 48792097 | + | TTCTTCACCAGCCTCACTGGAGG | 1 | 6 | 80 | SEQ ID NO. 3682 |
| (N20)NGG | 8 | 48792105 | + | CAGCCTCACTGGAGGCAGTCTGG | 1 | 2 | 56 | SEQ ID NO. 3683 |
| (N20)NGG | 8 | 48792108 | + | CCTCACTGGAGGCAGTCTGGAGG | 1 | 8 | 65 | SEQ ID NO. 3684 |
| (N20)NGG | 8 | 48792126 | + | GGAGGAACTTAGACGTGTTCTGG | 1 | 2 | 11 | SEQ ID NO. 3685 |
| (N20)NGG | 8 | 48792164 | + | CTCACTTCCCCATGCAGTCCAGG | 2 | 6 | 45 | SEQ ID NO. 3686 |
| (N20)NGG | 8 | 48792165 | + | TCACTTCCCCATGCAGTCCAGGG | 2 | 2 | 48 | SEQ ID NO. 3687 |
| (N20)NGG | 8 | 48792178 | + | CAGTCCAGGGAATTTCCTCCAGG | 1 | 3 | 60 | SEQ ID NO. 3688 |
| (N20)NGG | 8 | 48792188 | + | AATTTCCTCCAGGAACTCCGCGG | 1 | 2 | 25 | SEQ ID NO. 3689 |
| (N20)NGG | 8 | 48792204 | + | TCCGCGGTTCAATAATTATGTGG | 1 | 1 | 5 | SEQ ID NO. 3690 |
| (N20)NGG | 8 | 48792219 | + | TTATGTGGACTGCATGAAAAAGG | 1 | 4 | 44 | SEQ ID NO. 3691 |
| (N20)NGG | 8 | 48792045 | - | AGAGTGACAGCTTGGCCCTGTGG | 1 | 6 | 58 | SEQ ID NO. 3692 |
| (N20)NGG | 8 | 48792053 | - | ATGGAAGAAGAGTGACAGCTTGG | 1 | 5 | 75 | SEQ ID NO. 3693 |
| (N20)NGG | 8 | 48792072 | - | CCAGTGAGGCTGGTGAAGAATGG | 1 | 11 | 115 | SEQ ID NO. 3694 |
| (N20)NGG | 8 | 48792082 | - | CAGACTGCCTCCAGTGAGGCTGG | 2 | 2 | 39 | SEQ ID NO. 3695 |
| (N20)NGG | 8 | 48792086 | - | CCTCCAGACTGCCTCCAGTGAGG | 1 | 7 | 58 | SEQ ID NO. 3696 |
| (N20)NGG | 8 | 48792149 | - | GAAATTCCCTGGACTGCATGGGG | 1 | 3 | 33 | SEQ ID NO. 3697 |
| (N20)NGG | 8 | 48792150 | - | GGAAATTCCCTGGACTGCATGGG | 1 | 3 | 24 | SEQ ID NO. 3698 |
| (N20)NGG | 8 | 48792151 | - | AGGAAATTCCCTGGACTGCATGG | 1 | 5 | 49 | SEQ ID NO. 3699 |
| (N20)NGG | 8 | 48792160 | - | AGTTCCTGGAGAAATTCCCTGG | 1 | 5 | 30 | SEQ ID NO. 3700 |
| (N20)NGG | 8 | 48792171 | - | TTGAACCGCGGAGTTCCTGGAGG | 1 | 3 | 16 | SEQ ID NO. 3701 |
| (N20)NGG | 8 | 48792174 | - | TTATTGAACCGCGGAGTTCCTGG | 1 | 1 | 3 | SEQ ID NO. 3702 |
| (N20)NGG | 8 | 48792183 | - | TCCACATAATTATTGAACCGCGG | 1 | 1 | 12 | SEQ ID NO. 3703 |
| (N20)NGG | 8 | 48794010 | + | GTATCTTTTAATACAAGTCATGG | 1 | 3 | 58 | SEQ ID NO. 3704 |

| site_type | site_chr omosome | site_start_ nucleotide | site_s trand | target_site_sequence_wi th_NGG | genome_wide_ hits_with_1 or_less_mism atches | genome_wide_ hits_with_ 2_or_less_m ismatches | genome_wide_ hits_with_ 3_or_less_mism atches | | |
|---|---|---|---|---|---|---|---|---|---|
| (N20)NGG | 8 | 48794066 | + | TCTACTTGCTGACACAAAGCTGG |  |  | 2 | 39 | SEQ ID NO. 3705 |
| (N20)NGG | 8 | 48794081 | + | AAAGCTGGATCTACATTTAAAGG | 1 |  | 4 | 64 | SEQ ID NO. 3706 |
| (N20)NGG | 8 | 48793951 | - | AAAGGAAGGAAAAGAAAAACAGG | 1 | 16 | 314 | 5097 | SEQ ID NO. 3707 |
| (N20)NGG | 8 | 48793965 | - | AGATGAATCAATCTAAAGGAAGG | 1 |  | 5 | 137 | SEQ ID NO. 3708 |
| (N20)NGG | 8 | 48793969 | - | ATACAGATGAATCAATCTAAAGG |  |  | 4 | 92 | SEQ ID NO. 3709 |
| (N20)NGG | 8 | 48794017 | - | TATATGTTGTAAAGACTTCAGGG | 1 |  | 2 | 86 | SEQ ID NO. 3710 |
| (N20)NGG | 8 | 48794018 | - | ATATATGTTGTAAAGACTTCAGG | 1 |  | 6 | 66 | SEQ ID NO. 3711 |
| (N20)NGG | 8 | 48794472 | + | ACTCACAACGAAATTGTCTCAGG | 1 |  | 2 | 16 | SEQ ID NO. 3712 |
| (N20)NGG | 8 | 48794491 | + | CAGGTGAGTGCCGTTTTGAACGG | 1 |  | 1 | 17 | SEQ ID NO. 3713 |
| (N20)NGG | 8 | 48794513 | + | GCATGTTAGACCAGAGCTTCAGG | 1 |  | 1 | 21 | SEQ ID NO. 3714 |
| (N20)NGG | 8 | 48794514 | + | CATGTTAGACCAGAGCTTCAGGG | 1 |  | 1 | 30 | SEQ ID NO. 3715 |
| (N20)NGG | 8 | 48794539 | + | CGAGCAAACCAGAAACACCAAGG | 1 |  | 3 | 39 | SEQ ID NO. 3716 |
| (N20)NGG | 8 | 48794573 | + | CGACTACAATTCTGCAACACTGG | 1 |  | 2 | 10 | SEQ ID NO. 3717 |
| (N20)NGG | 8 | 48794591 | + | ACTCGAAGAAGTGTGATTCATGG | 1 |  | 2 | 62 | SEQ ID NO. 3718 |
| (N20)NGG | 8 | 48794594 | + | GGAAGAAGTGTGATTCATGGTGG | 1 |  | 6 | 100 | SEQ ID NO. 3719 |
| (N20)NGG | 8 | 48794595 | + | GAAGAAGTGTGATTCATGGTGGG | 1 |  | 4 | 68 | SEQ ID NO. 3720 |
| (N20)NGG | 8 | 48794625 | + | TTCCCCTCTGAAACTAAAATGG | 1 |  | 1 | 30 | SEQ ID NO. 3721 |
| (N20)NGG | 8 | 48794634 | - | CGAAACTAAAATGGCAGTGCTGG | 1 |  | 1 | 15 | SEQ ID NO. 3722 |
| (N20)NGG | 8 | 48794643 | - | AATGGCAGTGCTGGCCTTACTGG | 1 |  | 6 | 50 | SEQ ID NO. 3723 |
| (N20)NGG | 8 | 48794658 | + | CTTACTGGCAAAATTTTACAGG | 1 |  | 3 | 63 | SEQ ID NO. 3724 |
| (N20)NGG | 8 | 48794479 | - | GTCTAACATGCCCTTCAAAACGG | 1 |  | 1 | 7 | SEQ ID NO. 3725 |
| (N20)NGG | 8 | 48794501 | - | TTGGCTCGCTTCCCTGAAGCTCTGG | 1 |  | 2 | 27 | SEQ ID NO. 3726 |
| (N20)NGG | 8 | 48794525 | - | GTTTCAGTCCTTGGTGTTTCTGG | 2 |  | 7 | 69 | SEQ ID NO. 3727 |
| (N20)NGG | 8 | 48794534 | - | TAGTCGCAAGTTTCAGTCCTTGG | 1 |  | 1 | 14 | SEQ ID NO. 3728 |
| (N20)NGG | 8 | 48794596 | - | AGTTTCGAGAGGGAATCTTTGG | 1 |  | 1 | 17 | SEQ ID NO. 3729 |
| (N20)NGG | 8 | 48794605 | - | TGCCATTTTAGTTTCGAGAGGGG | 1 |  | 3 | 22 | SEQ ID NO. 3730 |
| (N20)NGG | 8 | 48794606 | - | CTGCCATTTTAGTTTCGAGAGGG | 1 |  | 1 | 22 | SEQ ID NO. 3731 |
| (N20)NGG | 8 | 48794607 | - | ACTGCCATTTTAGTTTCGAGAGG | 1 |  | 1 | 24 | SEQ ID NO. 3732 |
| (N20)NGG | 8 | 48794635 | - | CTGTAAAATTTTTGCCAGTAAGG | 2 |  | 5 | 93 | SEQ ID NO. 3733 |
| (N20)NGG | 8 | 48798540 | + | GAGTCTTTCTCCTGAACCAGCGG | 1 |  | 4 | 63 | SEQ ID NO. 3734 |
| (N20)NGG | 8 | 48798552 | + | GAACCCAGCGGTGCTGTCCACGG | 1 |  | 2 | 25 | SEQ ID NO. 3735 |
| (N20)NGG | 8 | 48798561 | + | GGTGCTGTCCACGCGGTCCTTGG |  |  | 2 | 19 | SEQ ID NO. 3736 |
| (N20)NGG | 8 | 48798562 | + | GTGCTGTCCACGGCGGTCCTTGGG |  |  | 1 | 5 | SEQ ID NO. 3737 |

FIG. 12 cont.

| site type | site chr omosome | site_start_ nucleotide | site s trand | target_site_sequence wi th NGG | genome wide hits with 1 or less mism atches | genome wide hits with 2 or less m ismatches | genome wide hits with m or less m ismatches | genome wide hits with 3 or less mism atches | |
|---|---|---|---|---|---|---|---|---|---|
| (N20)NGG | 8 | 48798573 | + | GGCGTCCTTGGGCAGCTCACAGG | | 1 | 4 | 27 | SEQ ID NO. 3738 |
| (N20)NGG | 8 | 48798574 | + | GCGTCCTTGGGCAGCTCACAGGG | | 1 | 5 | 35 | SEQ ID NO. 3739 |
| (N20)NGG | 8 | 48798598 | + | AGCGTCATCCACTTCTCCCATGG | | 1 | 1 | 20 | SEQ ID NO. 3740 |
| (N20)NGG | 8 | 48798599 | + | GCGTCATCCACTTCTCCCATGGG | | 1 | 2 | 13 | SEQ ID NO. 3741 |
| (N20)NGG | 8 | 48798600 | + | CGTCATCCACTTCTCCCATGGGG | | 1 | 2 | 28 | SEQ ID NO. 3742 |
| (N20)NGG | 8 | 48798639 | + | GTTCTCAGAAACGATCAACACGG | | 1 | 4 | 50 | SEQ ID NO. 3743 |
| (N20)NGG | 8 | 48798657 | + | CACGGAATTATTGAAAAATCTGG | | 1 | 2 | 61 | SEQ ID NO. 3744 |
| (N20)NGG | 8 | 48798672 | + | AAATCTGATCTTGCTGTATTGG | | 1 | 6 | 96 | SEQ ID NO. 3745 |
| (N20)NGG | 8 | 48798693 | + | GGAGCTCATGCAGTCTTCAGTGG | | 1 | 1 | 55 | SEQ ID NO. 3746 |
| (N20)NGG | 8 | 48798708 | + | TTCAGTGGATAATACCAAAATGG | | 2 | 8 | 63 | SEQ ID NO. 3747 |
| (N20)NGG | 8 | 48798488 | - | GCTCACACTGGGAAAAAGAAAGG | | 1 | 7 | 95 | SEQ ID NO. 3748 |
| (N20)NGG | 8 | 48798499 | - | ACTCACAAGGCGCTCACACTGGG | | 1 | 2 | 17 | SEQ ID NO. 3749 |
| (N20)NGG | 8 | 48798500 | - | GACTCACAAGGCGCTCACACTGG | | 1 | 1 | 8 | SEQ ID NO. 3750 |
| (N20)NGG | 8 | 48798512 | - | GGTTCAGGAGAAGACTCACAAGG | | 1 | 2 | 46 | SEQ ID NO. 3751 |
| (N20)NGG | 8 | 48798527 | - | TGGACAGCACCGCTGGGTTCAGG | | 1 | 3 | 36 | SEQ ID NO. 3752 |
| (N20)NGG | 8 | 48798533 | - | ACGCCGTGGACAGCACCGCTGGG | | 1 | 1 | 8 | SEQ ID NO. 3753 |
| (N20)NGG | 8 | 48798534 | - | GACGCCGTGGACAGCACCGCTGG | | 1 | 2 | 6 | SEQ ID NO. 3754 |
| (N20)NGG | 8 | 48798547 | - | TGAGCTGCCCAAGGACGCGTGG | | 1 | 2 | 26 | SEQ ID NO. 3755 |
| (N20)NGG | 8 | 48798556 | - | GCTGCCCTGTGAGCTGCCCAAGG | | 3 | 9 | 101 | SEQ ID NO. 3756 |
| (N20)NGG | 8 | 48798584 | - | AATACTCCCATGGAGAAGTGG | | 1 | 2 | 37 | SEQ ID NO. 3757 |
| (N20)NGG | 8 | 48798592 | - | GCTATAGAAATACTCCCATGGG | | 1 | 3 | 21 | SEQ ID NO. 3758 |
| (N20)NGG | 8 | 48798593 | - | AGCTATAGAAATACTCCCATGG | | 1 | 2 | 34 | SEQ ID NO. 3759 |
| (N20)NGG | 8 | 48798700 | - | GGGAAACTTTGTTACCATTTTGG | | 1 | 4 | 53 | SEQ ID NO. 3760 |
| (N20)NGG | 8 | 48800132 | + | ACAGATTTGCATCATTCTGTTGG | | 3 | 10 | 73 | SEQ ID NO. 3761 |
| (N20)NGG | 8 | 48800152 | + | TGGCACAGAACTTCTTTCCCTGG | | 1 | 7 | 55 | SEQ ID NO. 3762 |
| (N20)NGG | 8 | 48800162 | + | CTTCTTTCCCTGGTTTATAAAGG | | 1 | 3 | 111 | SEQ ID NO. 3763 |
| (N20)NGG | 8 | 48800174 | + | GTTTATAAAGCATTGCCCCTGG | | 1 | 1 | 27 | SEQ ID NO. 3764 |
| (N20)NGG | 8 | 48800224 | + | AGACCTCAGTTGTAAGCAGCTGG | | 1 | 4 | 21 | SEQ ID NO. 3765 |
| (N20)NGG | 8 | 48800231 | + | AGTTGTAAGCAGCTGGCCAGCGG | | 1 | 3 | 27 | SEQ ID NO. 3766 |
| (N20)NGG | 8 | 48800239 | + | GCAGCTGGCCAGCGGACTTCTGG | | 1 | 2 | 26 | SEQ ID NO. 3767 |
| (N20)NGG | 8 | 48800258 | + | CTGGAGTTAGCCTTTGCTTTTGG | | 1 | 3 | 44 | SEQ ID NO. 3768 |
| (N20)NGG | 8 | 48800261 | + | GAGTTAGCCTTTGCTTTTGGAGG | | 1 | 4 | 52 | SEQ ID NO. 3769 |
| (N20)NGG | 8 | 48800266 | + | AGCCTTTGCTTTTGGAGGACTGG | | 1 | 1 | 43 | SEQ ID NO. 3770 |

FIG. 12 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | | |
|---|---|---|---|---|---|---|---|---|---|
| (N20)NGG | 8 | 48800270 | + | TTTGCTTTTGGAGGACTGTAGG | 1 | 3 | 49 | SEQ ID NO. | 3771 |
| (N20)NGG | 8 | 48800099 | - | ATGCAAATCTGTGGACTAAAAGG | 1 | 3 | 62 | SEQ ID NO. | 3772 |
| (N20)NGG | 8 | 48800108 | - | AACAGAATGATGCAAATCTGTGG | 1 | 6 | 89 | SEQ ID NO. | 3773 |
| (N20)NGG | 8 | 48800147 | - | GGCAATGCCTTTATAAACCAGG | 1 | 2 | 45 | SEQ ID NO. | 3774 |
| (N20)NGG | 8 | 48800148 | - | GGGCAATGCCTTTATAAACCAGG | 1 | 1 | 31 | SEQ ID NO. | 3775 |
| (N20)NGG | 8 | 48800168 | - | ACACTGTCTCTCATCTCCAGGGG | 1 | 3 | 83 | SEQ ID NO. | 3776 |
| (N20)NGG | 8 | 48800169 | - | GACACTGTCTCTCATCTCCAGG | 1 | 6 | 89 | SEQ ID NO. | 3777 |
| (N20)NGG | 8 | 48800170 | - | AGACACTGTCTCTCATCTCCAGG | 1 | 3 | 99 | SEQ ID NO. | 3778 |
| (N20)NGG | 8 | 48800194 | - | TTACAACTGAGGTCTAGAGAAGG | 1 | 3 | 50 | SEQ ID NO. | 3779 |
| (N20)NGG | 8 | 48800205 | - | TGGCCAGCTGCTTACAACTGAGG | 1 | 1 | 35 | SEQ ID NO. | 3780 |
| (N20)NGG | 8 | 48800225 | - | GGCTAACTCCAGAAGTCCGCTGG | 1 | 1 | 51 | SEQ ID NO. | 3781 |
| (N20)NGG | 8 | 48800246 | - | TACCAGTCTCTCCAAAAGCAAAGG | 1 | 3 | 49 | SEQ ID NO. | 3782 |
| (N20)NGG | 8 | 48801085 | + | TTGTCACATGGCCAGCATTGAGG | 1 | 2 | 44 | SEQ ID NO. | 3783 |
| (N20)NGG | 8 | 48801110 | + | CTTTGTGCCGTCAACTTGTATGG | 1 | 1 | 11 | SEQ ID NO. | 3784 |
| (N20)NGG | 8 | 48801127 | + | GTATGGCCCTGACGCGCAAGTGG | 1 | 1 | 4 | SEQ ID NO. | 3785 |
| (N20)NGG | 8 | 48801132 | + | GCCCTGACCGCAAGTGGACAGG | 1 | 1 | 1 | SEQ ID NO. | 3786 |
| (N20)NGG | 8 | 48801138 | + | ACGCGCAAGTGGACAGGAGCAGG | 1 | 1 | 4 | SEQ ID NO. | 3787 |
| (N20)NGG | 8 | 48801142 | + | GCAAGTGGACAGGAGCAGGCTGG | 1 | 5 | 85 | SEQ ID NO. | 3788 |
| (N20)NGG | 8 | 48801182 | + | TGTAAACAGCTTCACAGAGCTGG | 1 | 4 | 64 | SEQ ID NO. | 3789 |
| (N20)NGG | 8 | 48801183 | + | GTAAACAGCTTCACAGAGCTGGG | 1 | 3 | 49 | SEQ ID NO. | 3790 |
| (N20)NGG | 8 | 48801211 | + | GCATAATATATTACCGTCTCAGG | 1 | 2 | 16 | SEQ ID NO. | 3791 |
| (N20)NGG | 8 | 48801074 | - | GGCACAAAGCTCCTCAATGCTGG | 1 | 1 | 18 | SEQ ID NO. | 3792 |
| (N20)NGG | 8 | 48801095 | - | GTCAGGGCCATACAAGTTGACGG | 1 | 1 | 18 | SEQ ID NO. | 3793 |
| (N20)NGG | 8 | 48801111 | - | TCCTGTCCACTTGCGCGTCAGG | 1 | 1 | 8 | SEQ ID NO. | 3794 |
| (N20)NGG | 8 | 48801112 | - | CTCCTGTCCACTTGCGCGTCAGG | 1 | 1 | 7 | SEQ ID NO. | 3795 |
| (N20)NGG | 8 | 48801158 | - | AGCTCTGTGAAGCTGTTTACAGG | 1 | 2 | 42 | SEQ ID NO. | 3796 |
| (N20)NGG | 8 | 48801202 | - | TAAGTTATAGTTACCTGAGACGG | 1 | 2 | 38 | SEQ ID NO. | 3797 |
| (N20)NGG | 8 | 48801586 | + | TCTGTTACAGCTCCTGAAGAAGG | 1 | 3 | 92 | SEQ ID NO. | 3798 |
| (N20)NGG | 8 | 48801619 | + | TACACCTGATGAGAGTCCTGG | 1 | 4 | 20 | SEQ ID NO. | 3799 |
| (N20)NGG | 8 | 48801650 | + | CTGTGTGACCCGCAAGCATAGG | 1 | 2 | 29 | SEQ ID NO. | 3800 |
| (N20)NGG | 8 | 48801662 | + | GCAAGCATAGGTTTCAACATCGG | 1 | 1 | 26 | SEQ ID NO. | 3801 |
| (N20)NGG | 8 | 48801673 | + | TTTCAACATGGAGACGTCCAGG | 1 | 1 | 3 | SEQ ID NO. | 3802 |
| (N20)NGG | 8 | 48801679 | + | CATCGGAGACGTCCAGGTTATGG | 1 | 1 | 13 | SEQ ID NO. | 3803 |

FIG. 12 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 8 | 48801783 | + | GAGAGAAAATAACAGCACAGAGG | 1 | 9 | 175 | SEQ ID NO. 3804 |
| (N20)NGG | 8 | 48801786 | + | AGAAATAACAGCACAGAGGTGG | 2 | 12 | 229 | SEQ ID NO. 3805 |
| (N20)NGG | 8 | 48801787 | + | GAAAATAACAGCACAGAGGTGGG | 1 | 15 | 119 | SEQ ID NO. 3806 |
| (N20)NGG | 8 | 48801794 | + | ACAGCACAGAGGTGGGTACTTGG | 1 | 4 | 50 | SEQ ID NO. 3807 |
| (N20)NGG | 8 | 48801795 | + | CAGCACAGAGGTGGGTACTTGGG | | 4 | 52 | SEQ ID NO. 3808 |
| (N20)NGG | 8 | 48801805 | + | GTGGGTACTTGGGTCACAATCGG | 1 | 1 | 14 | SEQ ID NO. 3809 |
| (N20)NGG | 8 | 48801806 | + | TGGGTACTTGGGTCACAATCGGG | 1 | 3 | 30 | SEQ ID NO. 3810 |
| (N20)NGG | 8 | 48801807 | + | GGGTACTTGGGTCACAATCGGGG | 1 | 2 | 8 | SEQ ID NO. 3811 |
| (N20)NGG | 8 | 48801576 | – | TATTACACAAGTCCTTCTTCAGG | 1 | 3 | 37 | SEQ ID NO. 3812 |
| (N20)NGG | 8 | 48801603 | – | TCTGCACCAGGACTCTCATCAGG | 1 | 3 | 38 | SEQ ID NO. 3813 |
| (N20)NGG | 8 | 48801615 | – | GCTCACACAGCGTCTGCACCAGG | 1 | 2 | 36 | SEQ ID NO. 3814 |
| (N20)NGG | 8 | 48801637 | – | ATGTTGAAACCTATGCTTGCGG | 1 | 1 | 23 | SEQ ID NO. 3815 |
| (N20)NGG | 8 | 48801638 | – | GATGTTGAAACCTATGCTTGCGG | 1 | 4 | 17 | SEQ ID NO. 3816 |
| (N20)NGG | 8 | 48801669 | – | CAGGAAGATGAGCCATAACCTGG | 2 | 8 | 38 | SEQ ID NO. 3817 |
| (N20)NGG | 8 | 48801688 | – | ATCAGATTCACACAACATCAGG | 2 | 4 | 70 | SEQ ID NO. 3818 |
| (N20)NGG | 8 | 48801728 | – | CTCTAGGATATCTTTGTATGGGG | 1 | 1 | 35 | SEQ ID NO. 3819 |
| (N20)NGG | 8 | 48801729 | – | TCTCTAGGATATCTTTGTATGG | 1 | 7 | 60 | SEQ ID NO. 3820 |
| (N20)NGG | 8 | 48801730 | – | GTCTCTAGGATATCTTTGTATGG | 1 | 2 | 32 | SEQ ID NO. 3821 |
| (N20)NGG | 8 | 48801744 | – | TCTCTCTCAGATGGGTCTCTAGG | 1 | 1 | 39 | SEQ ID NO. 3822 |
| (N20)NGG | 8 | 48801752 | – | TGTTATTTTCTCTCTCAGATGG | 1 | 13 | 157 | SEQ ID NO. 3823 |
| (N20)NGG | 8 | 48801753 | – | CTGTTATTTTCTCTCTCAGATGG | 3 | 13 | 162 | SEQ ID NO. 3824 |
| (N20)NGG | 8 | 48802817 | + | ACTTTAATATAATTGCTTCTAGG | 3 | 18 | 179 | SEQ ID NO. 3825 |
| (N20)NGG | 8 | 48802852 | + | GTCTTCACTTTTGAAAGCAGTGG | 1 | 5 | 82 | SEQ ID NO. 3826 |
| (N20)NGG | 8 | 48802910 | + | ATAGCAGCAGAAAAGTGCTTTGG | 2 | 5 | 105 | SEQ ID NO. 3827 |
| (N20)NCC | 8 | 48802916 | + | GCCAGAAAAGTGCTTTGGCACTGG | 1 | 1 | 30 | SEQ ID NO. 3828 |
| (N20)NGG | 8 | 48802917 | + | CAGAAAAGTGCTTTGGCACTGGG | 1 | 3 | 49 | SEQ ID NO. 3829 |
| (N20)NGG | 8 | 48802918 | + | AGAAAAGTGCTTTGGCACTGGGG | 2 | 4 | 61 | SEQ ID NO. 3830 |
| (N20)NGG | 8 | 48802925 | + | TGCTTTGGCACTGGGCAGCAGG | 2 | 5 | 51 | SEQ ID NO. 3831 |
| (N20)NGG | 8 | 48802948 | + | TAACAGAACAAGCCCACAAGAGG | 1 | 3 | 40 | SEQ ID NO. 3832 |
| (N20)NGG | 8 | 48802949 | + | AACAGAACAAGCCCACAAGAGGG | 1 | 4 | 62 | SEQ ID NO. 3833 |
| (N20)NGG | 8 | 48802956 | + | CAAGCCCACAAGAGGGAGAAAGG | 1 | 5 | 71 | SEQ ID NO. 3834 |
| (N20)NGG | 8 | 48802984 | + | CTACAGCAAATGCACCGTTGTGG | 1 | 2 | 8 | SEQ ID NO. 3835 |
| (N20)NGG | 8 | 48802989 | + | GCAAATGCACCGTTGTGTCCGG | 1 | 1 | 13 | SEQ ID NO. 3836 |

FIG. 12 cont.

| site_type | site_chromosome | site_start_nucleotide | site_strand | target_site_sequence_with NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 8 | 48802996 | + | CACCGTTGTGGTCCGGATTATGG | 1 | 2 | 4 | SEQ ID NO. 3837 |
| (N20)NGG | 8 | 48803029 | + | GACTCTGCTAAACACCTCCCCGG | 1 | 2 | 27 | SEQ ID NO. 3838 |
| (N20)NGG | 8 | 48803033 | + | CTGCTAAACACCTCCCCGAAGG | 1 | 1 | 15 | SEQ ID NO. 3839 |
| (N20)NGG | 8 | 48803037 | + | TAAACACCTCCCCGAAGGATGG | 1 | 1 | 35 | SEQ ID NO. 3840 |
| (N20)NGG | 8 | 48803041 | + | CACCTCCCCGAAGGATGGAAGG | 1 | 1 | 31 | SEQ ID NO. 3841 |
| (N20)NGG | 8 | 48803045 | + | TCCCCGAAGGATGGAAGGTAGG | 1 | 2 | 29 | SEQ ID NO. 3842 |
| (N20)NGG | 8 | 48803064 | + | TAGGCTGCTCTGTTAATTTGAGG | 1 | 3 | 32 | SEQ ID NO. 3843 |
| (N20)NGG | 8 | 48802826 | – | TGCTTTCAAAAGTGAAGACTGGG | 1 | 8 | 102 | SEQ ID NO. 3844 |
| (N20)NGG | 8 | 48802827 | – | CTGCTTTCAAAAGTGAAGACTGG | 1 | 2 | 82 | SEQ ID NO. 3845 |
| (N20)NGG | 8 | 48802874 | – | TGCTGCTATAATGTCATGCATGG | 1 | 1 | 57 | SEQ ID NO. 3846 |
| (N20)NGG | 8 | 48802938 | – | TGTACCTTTCTCCCCTCTTGTGG | 1 | 5 | 80 | SEQ ID NO. 3847 |
| (N20)NGG | 8 | 48802939 | – | TTGTACCTTTCTCCCCTCTTGTG | 1 | 6 | 82 | SEQ ID NO. 3848 |
| (N20)NGG | 8 | 48802976 | – | CTCCATAATCCGGACCACAACGG | 1 | 1 | 8 | SEQ ID NO. 3849 |
| (N20)NGG | 8 | 48802986 | – | TCGTGGTAAACTCCATAATCCGG | 1 | 2 | 10 | SEQ ID NO. 3850 |
| (N20)NGG | 8 | 48803003 | – | GGAGGTGTTTAGCAGAGTCCTGG | 1 | 1 | 16 | SEQ ID NO. 3851 |
| (N20)NGG | 8 | 48803021 | – | TACCTTCCATCCTTCCGGGAGG | 1 | 1 | 18 | SEQ ID NO. 3852 |
| (N20)NGG | 8 | 48803024 | – | GCCTACCTTCCATCCTTCCGGGG | 1 | 2 | 25 | SEQ ID NO. 3853 |
| (N20)NGG | 8 | 48803025 | – | AGCCTACCTTCCATCCTTCCGGG | 1 | 11 | 84 | SEQ ID NO. 3854 |
| (N20)NGG | 8 | 48803026 | – | CAGCCTACCTTCCATCCTTCCGG | 1 | 6 | 71 | SEQ ID NO. 3855 |
| (N20)NGG | 8 | 48805699 | + | TTAATTTGTTTCTTTTTAAAGG | 6 | 183 | 2613 | SEQ ID NO. 3856 |
| (N20)NGG | 8 | 48805721 | + | GCAACAGATCCCCTAATTTGTGG | 1 | 4 | 25 | SEQ ID NO. 3857 |
| (N20)NGG | 8 | 48805740 | + | GTGGCTGAAAGATGTTCTCAAGG | 1 | 2 | 48 | SEQ ID NO. 3858 |
| (N20)NGG | 8 | 48805747 | + | AAAGATGTTCTCAAGGAAGAAGG | 1 | 8 | 138 | SEQ ID NO. 3859 |
| (N20)NGG | 8 | 48805776 | + | TTTTCTCATCAACACCTTTGAGG | 2 | 7 | 90 | SEQ ID NO. 3860 |
| (N20)NGG | 8 | 48805777 | + | TTTCTCATCAACACCTTTGAGGG | 1 | 7 | 88 | SEQ ID NO. 3861 |
| (N20)NGG | 8 | 48805778 | + | TTCTCATCAACACCTTTGAGGGG | 1 | 3 | 53 | SEQ ID NO. 3862 |
| (N20)NGG | 8 | 48805779 | + | TCTCATCAACACCTTTGAGGGGG | 1 | 3 | 41 | SEQ ID NO. 3863 |
| (N20)NGG | 8 | 48805780 | + | CTCATCAACACCTTTGAGGGGGG | 2 | 5 | 35 | SEQ ID NO. 3864 |
| (N20)NGG | 8 | 48805783 | + | ATCAACACCTTTGAGGGGGGTGG | 1 | 4 | 32 | SEQ ID NO. 3865 |
| (N20)NGG | 8 | 48805789 | + | ACCTTTGAGGGGGTGGCTGTGG | 1 | 3 | 51 | SEQ ID NO. 3866 |
| (N20)NGG | 8 | 48805800 | + | GGGTGGCTGTGGCCAGCCCTCGG | 3 | 11 | 127 | SEQ ID NO. 3867 |
| (N20)NGG | 8 | 48805801 | + | GGTGGCTGTGGCCAGCCCTCGGG | 2 | 8 | 104 | SEQ ID NO. 3868 |
| (N20)NGG | 8 | 48805809 | + | TGGCCAGCCCTCGGGCATCCTG | 2 | 3 | 38 | SEQ ID NO. 3869 |

FIG. 12 cont.

| site_type | site_chr omosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 8 | 48805834 | + | CAGCCCACCCTCTTGTACTTCGG | 2 | 3 | 34 | SEQ ID NO. 3870 |
| (N20)NGG | 8 | 48805835 | + | AGCCCACCCTCTTGTACTTCGGG | 1 | 1 | 23 | SEQ ID NO. 3871 |
| (N20)NGG | 8 | 48805836 | + | GCCCACCCTCTTGTACTTCGGGG | 1 | 2 | 22 | SEQ ID NO. 3872 |
| (N20)NGG | 8 | 48805837 | + | CCCACCCTCTTGTACTTCGGGGG | 1 | 2 | 27 | SEQ ID NO. 3873 |
| (N20)NGG | 8 | 48805853 | + | TCGGGGCCATTCAGCCTGCAGG | 1 | 1 | 12 | SEQ ID NO. 3874 |
| (N20)NGG | 8 | 48805867 | + | GCCTGCAGGCCACGCTATGCTGG | 1 | 1 | 36 | SEQ ID NO. 3875 |
| (N20)NGG | 8 | 48805871 | + | GCAGGCCACGCTATGCTGGCTGG | 1 | 1 | 10 | SEQ ID NO. 3876 |
| (N20)NGG | 8 | 48805883 | + | ATGCTGGCTGGACCTGCTCCTGG | 1 | 5 | 48 | SEQ ID NO. 3877 |
| (N20)NGG | 8 | 48805892 | + | GGACCTGCTCCTGGCCGCGTTGG | 1 | 1 | 17 | SEQ ID NO. 3878 |
| (N20)NGG | 8 | 48805914 | + | GAGTGCTACAACACGTTCATTGG | 1 | 1 | 10 | SEQ ID NO. 3879 |
| (N20)NGG | 8 | 48805929 | + | TTCATTGGCGAGAGAACTGTAGG | 1 | 3 | 16 | SEQ ID NO. 3880 |
| (N20)NGG | 8 | 48805940 | + | GAGAACTGTAGGAGCGCTCCAGG | 1 | 1 | 9 | SEQ ID NO. 3881 |
| (N20)NGG | 8 | 48805947 | + | GTAGGAGCGCTCCAGGTCCTAGG | 1 | 1 | 16 | SEQ ID NO. 3882 |
| (N20)NGG | 8 | 48805951 | + | GAGCGCTCCAGGTCCTAGGTAGG | 1 | 2 | 15 | SEQ ID NO. 3883 |
| (N20)NGG | 8 | 48805971 | + | AGGTCACCCTTGCCTTATTCTGG | 1 | 6 | 87 | SEQ ID NO. 3884 |
| (N20)NGG | 8 | 48805708 | - | ATCTTTCAGCCACCACAAATTAGGG | 2 | 6 | 56 | SEQ ID NO. 3885 |
| (N20)NGG | 8 | 48805709 | - | CATCTTTCAGCCACCACAAATTAGG | 2 | 5 | 53 | SEQ ID NO. 3886 |
| (N20)NGG | 8 | 48805710 | - | ACATCTTTCAGCCACCACAAAGG | 1 | 4 | 58 | SEQ ID NO. 3887 |
| (N20)NGG | 8 | 48805768 | - | GCCACAGCCACCCCCGAGGGCTGG | 2 | 2 | 67 | SEQ ID NO. 3888 |
| (N20)NGG | 8 | 48805790 | - | GGGCCAGGATGCCCAGGAGGGCTGG | 2 | 6 | 61 | SEQ ID NO. 3889 |
| (N20)NGG | 8 | 48805794 | - | GGCTGGGCCAGGATGCCCGAGG | 1 | 2 | 45 | SEQ ID NO. 3890 |
| (N20)NGG | 8 | 48805795 | - | GGGCTGGGCCAGGATGCCCCAGG | 1 | 8 | 103 | SEQ ID NO. 3891 |
| (N20)NGG | 8 | 48805805 | - | ACAAGAGGGTGGCTGGGCCAGG | 2 | 12 | 157 | SEQ ID NO. 3892 |
| (N20)NGG | 8 | 48805810 | - | GAAGTACAAGAGGGTGGGCTGG | 2 | 5 | 49 | SEQ ID NO. 3893 |
| (N20)NGG | 8 | 48805811 | - | CGAAGTACAAGAGGGTGGGCTGG | 1 | 2 | 27 | SEQ ID NO. 3894 |
| (N20)NGG | 8 | 48805815 | - | CCCCGAAGTACAAGAGGGTGGG | 1 | 1 | 5 | SEQ ID NO. 3895 |
| (N20)NGG | 8 | 48805816 | - | CCCCCGAAGTACAAGAGGGTGG | 1 | 1 | 9 | SEQ ID NO. 3896 |
| (N20)NGG | 8 | 48805819 | - | ATGGCCCCGAAGTACAAGAGG | 1 | 1 | 14 | SEQ ID NO. 3897 |
| (N20)NGG | 8 | 48805820 | - | AATGGCCCCGAAGTACAAGAG | 1 | 1 | 13 | SEQ ID NO. 3898 |
| (N20)NGG | 8 | 48805838 | - | AGCGTGGCCTGCAGGCTGAATGG | 1 | 2 | 29 | SEQ ID NO. 3899 |
| (N20)NGG | 8 | 48805846 | - | GCCAGCATAGCGTGGCCTGCAGG | 1 | 3 | 22 | SEQ ID NO. 3900 |
| (N20)NGG | 8 | 48805854 | - | CAGGTCCAGCCAGCATAGCGTGG | 1 | 1 | 17 | SEQ ID NO. 3901 |
| (N20)NGG | 8 | 48805873 | - | ACTCCAACGCGGCCAGGAGCAGG | 1 | 1 | 16 | SEQ ID NO. 3902 |

| site type | site chromosome | site_start nucleotide | site strand | target_site_sequence_with NGG | genome wide hits with 1 or less mismatches | genome wide hits with 2 or less mismatches | genome wide hits with 3 or less mismatches | | |
|---|---|---|---|---|---|---|---|---|---|
| (N20)NGG | 8 | 48805879 | - | TGTAGCACTCCAACGCGGCCAGG | 1 | 1 | 6 | SEQ ID NO. | 3903 |
| (N20)NGG | 8 | 48805884 | - | CGTGTTGTAGCACTCCAACGCGG | 1 | 1 | 8 | SEQ ID NO. | 3904 |
| (N20)NGG | 8 | 48805936 | - | AGGGTGACCTACCTAGGACCTGG | 1 | 1 | 11 | SEQ ID NO. | 3905 |
| (N20)NGG | 8 | 48805942 | - | AAGGCAAGGTGACCTACCTAGG | 1 | 1 | 24 | SEQ ID NO. | 3906 |
| (N20)NGG | 8 | 48809722 | + | AGTATGCTGTCTCTGTGCAGAGG | 1 | 2 | 56 | SEQ ID NO. | 3907 |
| (N20)NGG | 8 | 48809754 | + | TTCCGCATCATTGTGTTTATTGG | 1 | 1 | 28 | SEQ ID NO. | 3908 |
| (N20)NGG | 8 | 48809760 | + | ATCATTGTGTTTATTGGATCTGG | 1 | 3 | 46 | SEQ ID NO. | 3909 |
| (N20)NGG | 8 | 48809768 | + | GTTTATTGGATCTGGTCAAGTGG | 1 | 2 | 25 | SEQ ID NO. | 3910 |
| (N20)NGG | 8 | 48809785 | + | AAGTGGCTTTTAGCTCATTGTGG | 1 | 1 | 31 | SEQ ID NO. | 3911 |
| (N20)NGG | 8 | 48809786 | + | AGTGGCTTTTAGCTCATTGTGGG | 1 | 1 | 36 | SEQ ID NO. | 3912 |
| (N20)NGG | 8 | 48809789 | + | GGCTTTTAGCTCATTGTGGGAGG | 1 | 1 | 28 | SEQ ID NO. | 3913 |
| (N20)NGG | 8 | 48809854 | + | AAATTCGTTCCTTTATTGCCAGG | 1 | 3 | 34 | SEQ ID NO. | 3914 |
| (N20)NGG | 8 | 48809859 | + | CGTTCCTTTATTGCCAGGTATGG | 1 | 1 | 14 | SEQ ID NO. | 3915 |
| (N20)NGG | 8 | 48809727 | - | AAACACAATGATGCGGAAGGTGG | 1 | 2 | 25 | SEQ ID NO. | 3916 |
| (N20)NGG | 8 | 48809730 | - | AATAAACACAATGATGCGGAAGG | 1 | 2 | 31 | SEQ ID NO. | 3917 |
| (N20)NGG | 8 | 48809734 | - | ATCCAATAAACACAATGATGCGG | 1 | 1 | 59 | SEQ ID NO. | 3918 |
| (N20)NGG | 8 | 48809790 | - | TTGTGTCGACATTCTGTCTGGGG | 1 | 3 | 47 | SEQ ID NO. | 3919 |
| (N20)NGG | 8 | 48809791 | - | TTTGTGTCGACATTCTGTCTGGG | 1 | 1 | 31 | SEQ ID NO. | 3920 |
| (N20)NGG | 8 | 48809792 | - | ATTTGTGTCGACATTCTGTCTGG | 1 | 1 | 16 | SEQ ID NO. | 3921 |
| (N20)NGG | 8 | 48809815 | - | GAATTTATAAAAGAGTTCAATGG | 1 | 5 | 162 | SEQ ID NO. | 3922 |
| (N20)NGG | 8 | 48809841 | - | ATTACCATACCTGGCAATAAAGG | 1 | 5 | 55 | SEQ ID NO. | 3923 |
| (N20)NGG | 8 | 48809850 | - | GATATACAGATTACCATACCTGG | 1 | 3 | 19 | SEQ ID NO. | 3924 |
| (N20)NGG | 8 | 48811029 | + | ATGTCTCTGTACTTGAGAACAGG | 1 | 5 | 46 | SEQ ID NO. | 3925 |
| (N20)NGG | 8 | 48811129 | + | CAAAGAAACGACGTTTGCCGCGG | 1 | 2 | 6 | SEQ ID NO. | 3926 |
| (N20)NGG | 8 | 48811133 | + | GAAACGACGTTTGCCGCGGTAGG | 1 | 1 | 1 | SEQ ID NO. | 3927 |
| (N20)NGG | 8 | 48811053 | - | GATGCGGCATAGGTGATCAATGG | 1 | 1 | 13 | SEQ ID NO. | 3928 |
| (N20)NGG | 8 | 48811063 | - | TCTTTTCAATGATGCGGCATAGG | 1 | 4 | 22 | SEQ ID NO. | 3929 |
| (N20)NGG | 8 | 48811069 | - | CATGCTTCTTTTCAATGATGCGG | 1 | 1 | 58 | SEQ ID NO. | 3930 |
| (N20)NGG | 8 | 48811124 | - | GGAAGCAAGATCACCTACCGCGG | 1 | 1 | 18 | SEQ ID NO. | 3931 |
| (N20)NGG | 8 | 48812932 | + | TTTCCTATTCTTTATTTTACAGG | 2 | 25 | 352 | SEQ ID NO. | 3932 |
| (N20)NGG | 8 | 48812933 | + | TTCCTATTCTTTATTTTACAGGG | 2 | 12 | 304 | SEQ ID NO. | 3933 |
| (N20)NGG | 8 | 48812948 | + | TTACAGGGAAGAAGAGTCTCTGG | 1 | 3 | 52 | SEQ ID NO. | 3934 |
| (N20)NGG | 8 | 48812951 | + | CAGGGAAGAAGAGTCTCTGGTGG | 1 | 7 | 112 | SEQ ID NO. | 3935 |

| site_type | site_chr omosome | site_start_ nucleotide | site_s trand | target_site_sequence wi th NGG | genome_wide_ hits_with_1 or_less_mism atches | genome_wide_ hits_with_ 2_or_less_m ismatches | genome_wide_ hits_with_3 or_less_mism atches | | |
|---|---|---|---|---|---|---|---|---|---|
| (N20)NGG | 8 | 48812975 | + | ACAGTTTGTGTTTGAAGCCTTGG | 1 | | 6 | 56 | SEQ ID NO. 3936 |
| (N20)NGG | 8 | 48812987 | + | TGAAGCCTTGGTGATATACATGG | 1 | | 2 | 33 | SEQ ID NO. 3937 |
| (N20)NGG | 8 | 48812996 | + | GGTGATATACATGGAGAGTCTGG | 1 | | 1 | 11 | SEQ ID NO. 3938 |
| (N20)NGG | 8 | 48813027 | + | CATGCAGATGAGAAGTCCTTAGG | 1 | | 2 | 55 | SEQ ID NO. 3939 |
| (N20)NGG | 8 | 48812913 | - | TTCCCTGTAAATAAAGAATAGG | 2 | | 16 | 246 | SEQ ID NO. 3940 |
| (N20)NGG | 8 | 48812970 | - | ACTCTCCATGTATATCACCAAGG | 1 | | 1 | 24 | SEQ ID NO. 3941 |
| (N20)NGG | 8 | 48812997 | - | CTTCCATCTGCATGTGCTAAGG | 1 | | 2 | 63 | SEQ ID NO. 3942 |
| (N20)NGG | 8 | 48813021 | - | ACTGAAGCAAAACGTACCTAAGG | 1 | | 1 | 25 | SEQ ID NO. 3943 |
| (N20)NGG | 8 | 48815128 | + | AGGTCTCTTTGTTTGTTTCAGG | 1 | | 15 | 192 | SEQ ID NO. 3944 |
| (N20)NGG | 8 | 48815132 | + | CTCTTTGTTTGTTTCAGGATGG | 1 | | 11 | 201 | SEQ ID NO. 3945 |
| (N20)NGG | 8 | 48815140 | + | TTTGTTTCAGGATGGAATTGTGG | 1 | | 4 | 85 | SEQ ID NO. 3946 |
| (N20)NGG | 8 | 48815174 | + | AGTACTTTAAGAGATTTTTGTGG | 2 | | 7 | 119 | SEQ ID NO. 3947 |
| (N20)NGG | 8 | 48815178 | + | CTTTAAGAGATTTTTGTGGTCGG | 1 | | 7 | 99 | SEQ ID NO. 3948 |
| (N20)NGG | 8 | 48815202 | + | GTATTCGAGAATTCCTTAAATGG | 1 | | 2 | 18 | SEQ ID NO. 3949 |
| (N20)NGG | 8 | 48815233 | + | GCAAATAACACCACAGCAGCAGG | 1 | | 3 | 39 | SEQ ID NO. 3950 |
| (N20)NGG | 8 | 48815310 | + | TTCACCCCAATGCTTTCAAGAGG | 1 | | 2 | 40 | SEQ ID NO. 3951 |
| (N20)NGG | 8 | 48815314 | + | CCCCAATGCTTTCAAGAGGCTGG | 1 | | 3 | 23 | SEQ ID NO. 3952 |
| (N20)NGG | 8 | 48815315 | + | CCCAATGCTTTCAAGAGGCTGGG | 1 | | 2 | 56 | SEQ ID NO. 3953 |
| (N20)NGG | 8 | 48815346 | + | TTGCCTTTAATAATATCTACAGG | 1 | | 5 | 70 | SEQ ID NO. 3954 |
| (N20)NGG | 8 | 48815347 | + | TGCCTTTAATAATATCTACAGGG | 1 | | 5 | 105 | SEQ ID NO. 3955 |
| (N20)NGG | 8 | 48815355 | + | ATAATATCTACAGGGAATTCAGG | 1 | | 4 | 53 | SEQ ID NO. 3956 |
| (N20)NGG | 8 | 48815142 | - | CTCTTAAAGTACTGTCAACAGG | 1 | | 3 | 40 | SEQ ID NO. 3957 |
| (N20)NGG | 8 | 48815143 | - | TCTCTTAAAGTACTGTCAACAGG | 1 | | 3 | 27 | SEQ ID NO. 3958 |
| (N20)NGG | 8 | 48815193 | - | TTTGCTTAATGGACCATTTAAGG | 1 | | 4 | 43 | SEQ ID NO. 3959 |
| (N20)NGG | 8 | 48815204 | - | CTGTGGTGTTATTTGCTTAATGG | 2 | | 4 | 63 | SEQ ID NO. 3960 |
| (N20)NGG | 8 | 48815221 | - | GGACTCTTCCTCCTGCTGCTGTGG | 1 | | 9 | 70 | SEQ ID NO. 3961 |
| (N20)NGG | 8 | 48815242 | - | AAAAGCGATTTGGTGTTTACTGG | 1 | | 2 | 23 | SEQ ID NO. 3962 |
| (N20)NGG | 8 | 48815252 | - | AAGTCGCTTGAAAAGCGATTTGG | 1 | | 1 | 6 | SEQ ID NO. 3963 |
| (N20)NGG | 8 | 48815280 | - | AAGCATTGGGGTGAAGCGCAAGG | 1 | | 1 | 20 | SEQ ID NO. 3964 |
| (N20)NGG | 8 | 48815292 | - | CCAGCCTCTTGAAAGCATTGGG | 1 | | 2 | 39 | SEQ ID NO. 3965 |
| (N20)NGG | 8 | 48815293 | - | CCCAGCCTCTTGAAAGCATTGG | 1 | | 5 | 60 | SEQ ID NO. 3966 |
| (N20)NGG | 8 | 48815294 | - | TCCCAGCCTCTTGAAAGCATTGG | 2 | | 5 | 147 | SEQ ID NO. 3967 |
| (N20)NGG | 8 | 48815327 | - | TTCCCTGTAGATATTATTAAAGG | 1 | | 6 | 82 | SEQ ID NO. 3968 |

FIG. 12 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 8 | 48817428 | + | TTTAATGGTATTGTTTCTTCAGG | 2 | 61 | 604 | SEQ ID NO. 3969 |
| (N20)NGG | 8 | 48817436 | + | TATTGTTTCTTCAGTGACAAGG | 1 | 1 | 63 | SEQ ID NO. 3970 |
| (N20)NGG | 8 | 48817475 | + | TAGTTATGCAGCTGATTCACTGG | 1 | 2 | 13 | SEQ ID NO. 3971 |
| (N20)NGG | 8 | 48817506 | + | CAACAAGAAATTTGAAAGTCAGG | 1 | 4 | 108 | SEQ ID NO. 3972 |
| (N20)NGG | 8 | 48817536 | + | TGCCTTACTAGAAGCTATATTGG | 1 | 3 | 16 | SEQ ID NO. 3973 |
| (N20)NGG | 8 | 48817449 | - | TGAATCAGCTGCATAACTAGTGG | 1 | 2 | 35 | SEQ ID NO. 3974 |
| (N20)NGG | 8 | 48817516 | - | TACCAATATAGCTTCTAGTAAGG | 1 | 1 | 16 | SEQ ID NO. 3975 |
| (N20)NGG | 8 | 48824969 | + | CTGACCTCCTGGTCTGTTTTAGG | 1 | 4 | 54 | SEQ ID NO. 3976 |
| (N20)NGG | 8 | 48824999 | + | CTGTGAACTTTTACATAGCATGG | 1 | 3 | 50 | SEQ ID NO. 3977 |
| (N20)NGG | 8 | 48825014 | + | TAGCATGGTTATGTTTATGTTGG | 1 | 2 | 59 | SEQ ID NO. 3978 |
| (N20)NGG | 8 | 48825015 | + | AGCATGGTTATGTTTATGTTTGG | 1 | 3 | 54 | SEQ ID NO. 3979 |
| (N20)NGG | 8 | 48825039 | + | AAAGCCACGCAGATGCCAGAAGG | 1 | 5 | 55 | SEQ ID NO. 3980 |
| (N20)NGG | 8 | 48825040 | + | AAGCCACGCAGATGCCAGAAGGG | 1 | 4 | 72 | SEQ ID NO. 3981 |
| (N20)NGG | 8 | 48825041 | + | AGCCACGCAGATGCCAGAAGGGG | 1 | 4 | 67 | SEQ ID NO. 3982 |
| (N20)NGG | 8 | 48825042 | + | GCCACGCAGATGCCAGAAGGGGG | 1 | 4 | 46 | SEQ ID NO. 3983 |
| (N20)NGG | 8 | 48825047 | + | GCAGATGCCAGAAGGGGGACAGG | 1 | 3 | 57 | SEQ ID NO. 3984 |
| (N20)NGG | 8 | 48825048 | + | CAGATGCCAGAAGGGGGACAGGG | 2 | 5 | 71 | SEQ ID NO. 3985 |
| (N20)NGG | 8 | 48825079 | + | CCATGTACCAGCTCTATAAGCGG | 1 | 3 | 21 | SEQ ID NO. 3986 |
| (N20)NGG | 8 | 48825122 | + | ACTTGCGTGTGATGTTGATCAGG | 1 | 2 | 11 | SEQ ID NO. 3987 |
| (N20)NGG | 8 | 48825127 | + | CGTGTGATGTTGATCAGGTAAGG | 1 | 2 | 7 | SEQ ID NO. 3988 |
| (N20)NGG | 8 | 48825128 | + | GTGTGATGTTGATCAGGTAAGGG | 1 | 2 | 30 | SEQ ID NO. 3989 |
| (N20)NGG | 8 | 48824951 | - | GCAACCTAAAACAGACCAGGAGG | 1 | 3 | 25 | SEQ ID NO. 3990 |
| (N20)NGG | 8 | 48824954 | - | GCTGCAACCTAAAACAGACCAGG | 1 | 3 | 23 | SEQ ID NO. 3991 |
| (N20)NGG | 8 | 48824976 | - | CATGCTATGTAAAAGTTCACAGG | 1 | 4 | 51 | SEQ ID NO. 3992 |
| (N20)NGG | 8 | 48825021 | - | TCCCCCTTCTGGCATCTGCGTGG | 1 | 2 | 22 | SEQ ID NO. 3993 |
| (N20)NGG | 8 | 48825032 | - | GGGCTCCCTGTCCCCCTTCTGG | 1 | 5 | 68 | SEQ ID NO. 3994 |
| (N20)NGG | 8 | 48825051 | - | ATAGAGCTGGTACATGGGTGGG | 1 | 1 | 24 | SEQ ID NO. 3995 |
| (N20)NGG | 8 | 48825052 | - | TATAGAGCTGGTACATGGGTGG | 1 | 2 | 22 | SEQ ID NO. 3996 |
| (N20)NGG | 8 | 48825053 | - | TTATAGAGCTGGTACATGGGTGG | 1 | 1 | 20 | SEQ ID NO. 3997 |
| (N20)NGG | 8 | 48825056 | - | CGCTTATAGAGCTGGTACATGGG | 1 | 1 | 7 | SEQ ID NO. 3998 |
| (N20)NGG | 8 | 48825057 | - | CCGTTATAGAGCTGGTACATGG | 1 | 1 | 4 | SEQ ID NO. 3999 |
| (N20)NGG | 8 | 48825064 | - | GAAACTCCGCTTATAGAGCTGG | 1 | 1 | 2 | SEQ ID NO. 4000 |
| (N20)NGG | 8 | 48825086 | - | CACGCAAGTCGAAGCAGCACAGG | 1 | 2 | 8 | SEQ ID NO. 4001 |

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 8 | 48826495 | + | TGAGATGATGAAGAGCTATGTGG | 1 | 1 | 11 | 69 SEQ ID NO. 4002 |
| (N20)NGG | 8 | 48826500 | + | TGATGAAGAGCTATGTGGCCTGG | 1 | 1 | 1 | 39 SEQ ID NO. 4003 |
| (N20)NGG | 8 | 48826501 | + | GATGAAGAGCTATGTGGCCTGGG | 1 | 8 | 8 | 59 SEQ ID NO. 4004 |
| (N20)NGG | 8 | 48826515 | + | TGGCCTGGGACAGAGAAGCGG | 2 | 9 | 9 | 195 SEQ ID NO. 4005 |
| (N20)NGG | 8 | 48826564 | + | GATGAAACCTGTCATTTTCCTGG | 1 | 5 | 5 | 54 SEQ ID NO. 4006 |
| (N20)NGG | 8 | 48826466 | − | GCTCTTCATCATCTCATCTGAGG | 2 | 3 | 3 | 57 SEQ ID NO. 4007 |
| (N20)NGG | 8 | 48826496 | − | CAGCCGCTTCTCTCTGTCCAGG | 2 | 10 | 10 | 95 SEQ ID NO. 4008 |
| (N20)NGG | 8 | 48826531 | − | ACAGGTTTCATCTCTCTAAAGG | 1 | 4 | 4 | 54 SEQ ID NO. 4009 |
| (N20)NGG | 8 | 48826532 | − | GACAGGTTTCATCTCTCTAAGG | 1 | 6 | 6 | 34 SEQ ID NO. 4010 |
| (N20)NGG | 8 | 48826549 | − | AACACATCCAGAAAATGACAGG | 1 | 5 | 5 | 92 SEQ ID NO. 4011 |
| (N20)NGG | 8 | 48826560 | − | CTCGAGGCAGGAACACATCCAGG | 1 | 2 | 2 | 33 SEQ ID NO. 4012 |
| (N20)NGG | 8 | 48826572 | − | CTAATTCTGTGACTGCGAGGCAGG | 1 | 1 | 1 | 50 SEQ ID NO. 4013 |
| (N20)NGG | 8 | 48826576 | − | AGCGCTAATTCTGTGACTCGAGG | 1 | 2 | 2 | 7 SEQ ID NO. 4014 |
| (N20)NGG | 8 | 48826604 | − | TACTTTAGTTTGTCTGTCACTGG | 1 | 1 | 1 | 37 SEQ ID NO. 4015 |
| (N20)NGG | 8 | 48827939 | + | ATTAGAGTAGTACAAATGCTTGG | 1 | 2 | 2 | 32 SEQ ID NO. 4016 |
| (N20)NGG | 8 | 48827948 | + | GTACAAATGCTTGGATCTCTAGG | 1 | 4 | 4 | 29 SEQ ID NO. 4017 |
| (N20)NGG | 8 | 48827951 | + | CAAATGCTTGGATCTCTAGGAGG | 1 | 10 | 10 | 204 SEQ ID NO. 4018 |
| (N20)NGG | 8 | 48827978 | + | ATAAACAAAAATCTTCTGACAGG | 1 | 8 | 8 | 137 SEQ ID NO. 4019 |
| (N20)NGG | 8 | 48827990 | − | TCTAATTCTTATTCTTCTAAGG | 2 | 22 | 22 | 266 SEQ ID NO. 4020 |
| (N20)NGG | 8 | 48830855 | + | TAGATGAGACCAAGAATAACTGG | 1 | 2 | 2 | 47 SEQ ID NO. 4021 |
| (N20)NGG | 8 | 48830856 | + | AGATGAGACCAAGAATAACTGGG | 1 | 6 | 6 | 61 SEQ ID NO. 4022 |
| (N20)NGG | 8 | 48830876 | + | GGGAAGTGTCAGCTCTTTCTCGG | 1 | 6 | 6 | 57 SEQ ID NO. 4023 |
| (N20)NGG | 8 | 48830877 | + | GGAAGTGTCAGCTCTTTCTCGGG | 1 | 4 | 4 | 50 SEQ ID NO. 4024 |
| (N20)NGG | 8 | 48830890 | + | CTTTCTCGGGCTGCCCAGAAAGG | 1 | 5 | 5 | 36 SEQ ID NO. 4025 |
| (N20)NGG | 8 | 48830904 | + | CCAGAAAGGATTTAATAAAGTGG | 1 | 5 | 5 | 118 SEQ ID NO. 4026 |
| (N20)NGG | 8 | 48830842 | − | TGACACTTCCCAGTTATTCTTGG | 1 | 1 | 1 | 42 SEQ ID NO. 4027 |
| (N20)NGG | 8 | 48830881 | − | CACTTTATTAAATCCTTTCTGGG | 2 | 5 | 5 | 135 SEQ ID NO. 4028 |
| (N20)NGG | 8 | 48830882 | − | CCACTTTATTAAATCCTTTCTGG | 1 | 7 | 7 | 63 SEQ ID NO. 4029 |
| (N20)NGG | 8 | 48830933 | − | AAGGACTTCTTACTGATGAAAGG | 1 | 7 | 7 | 51 SEQ ID NO. 4030 |
| (N20)NGG | 8 | 48839756 | + | TGTTTGTATTAACATACAGATGG | 1 | 7 | 7 | 123 SEQ ID NO. 4031 |
| (N20)NGG | 8 | 48839768 | + | CATACAGATGGCTTTCAAACTGG | 1 | 2 | 2 | 36 SEQ ID NO. 4032 |
| (N20)NGG | 8 | 48839769 | + | ATACAGATGGCTTTCAAACTGGG | 1 | 4 | 4 | 66 SEQ ID NO. 4033 |
| (N20)NGG | 8 | 48839789 | + | GGGCCTGAGCTATACCCCTTGG | 1 | 4 | 4 | 20 SEQ ID NO. 4034 |

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 8 | 48839799 | + | TATACCCCTTGGCAGAAGTAGG | | 1 | 1 | 14 SEQ ID NO. 4035 |
| (N20)NGG | 8 | 48839821 | + | GCCTGAATGCTCTAGAAGAATGG | | 1 | 3 | 32 SEQ ID NO. 4036 |
| (N20)NGG | 8 | 48839882 | + | CAAAGACATTCTCCCCTGCCTGG | | 1 | 2 | 42 SEQ ID NO. 4037 |
| (N20)NGG | 8 | 48839886 | + | GACATTCTCCCCTGCCTGGATGG | | 1 | 6 | 51 SEQ ID NO. 4038 |
| (N20)NGG | 8 | 48839913 | + | CTGAAGACTTCAGCCTTGTCAGG | | 1 | 4 | 39 SEQ ID NO. 4039 |
| (N20)NGG | 8 | 48839770 | - | CTGCCAAGGGGTATAGCTCAGG | | 1 | 2 | 11 SEQ ID NO. 4040 |
| (N20)NGG | 8 | 48839781 | - | CAGGCCTACTTCTGCCAAGGGGG | | 1 | 1 | 33 SEQ ID NO. 4041 |
| (N20)NGG | 8 | 48839782 | - | TCAGGCCTACTTCTGCCAAGGGG | | 1 | 1 | 31 SEQ ID NO. 4042 |
| (N20)NGG | 8 | 48839783 | - | TTCAGGCCTACTTCTGCCAAGG | | 1 | 1 | 28 SEQ ID NO. 4043 |
| (N20)NGG | 8 | 48839784 | - | ATTCAGGCCTACTTCTGCCAAGG | | 1 | 2 | 32 SEQ ID NO. 4044 |
| (N20)NGG | 8 | 48839800 | - | ACCATTCTTCTAGAGCATTCAGG | | 1 | 1 | 30 SEQ ID NO. 4045 |
| (N20)NGG | 8 | 48839852 | - | GGGAGAATGTCTTTGTAATAAGG | | 1 | 5 | 68 SEQ ID NO. 4046 |
| (N20)NGG | 8 | 48839872 | - | TCAGGTATCCATCCAGGCAGGGG | | 1 | 3 | 40 SEQ ID NO. 4047 |
| (N20)NGG | 8 | 48839873 | - | TTCAGGTATCCATCCAGGCAGG | | 1 | 3 | 36 SEQ ID NO. 4048 |
| (N20)NGG | 8 | 48839874 | - | CTTCAGGTATCCATCCAGGCAGG | | 1 | 1 | 23 SEQ ID NO. 4049 |
| (N20)NGG | 8 | 48839878 | - | AAGTCTTCAGGTATCCATCCAGG | | 1 | 2 | 27 SEQ ID NO. 4050 |
| (N20)NGG | 8 | 48839890 | - | CTGACAAGGCTGAAGTCTTCAGG | | 1 | 4 | 37 SEQ ID NO. 4051 |
| (N20)NGG | 8 | 48839904 | - | CTTCTAAACATTACCTGACAAGG | | 1 | 2 | 39 SEQ ID NO. 4052 |
| (N20)NGG | 8 | 48840330 | + | TACTGTCTTCTTTCTTGTTAAGG | | 1 | 12 | 166 SEQ ID NO. 4053 |
| (N20)NGG | 8 | 48840333 | + | TGTCTTCTTTCTTGTTAAGGTGG | | 1 | 7 | 123 SEQ ID NO. 4054 |
| (N20)NGG | 8 | 48840369 | + | GCAGTACAAAGATGAACTTTTGG | | 2 | 3 | 51 SEQ ID NO. 4055 |
| (N20)NGG | 8 | 48840450 | + | AGCCTACGTTCCTGCACTGCAGG | | 1 | 1 | 10 SEQ ID NO. 4056 |
| (N20)NGG | 8 | 48840454 | + | TACGTTCCTGCACTGCAGGTAGG | | 1 | 2 | 15 SEQ ID NO. 4057 |
| (N20)NGG | 8 | 48840370 | - | CAGAGAAAGGTCAAACAAGAGAG | | 1 | 5 | 107 SEQ ID NO. 4058 |
| (N20)NGG | 8 | 48840382 | - | GTGTGCAAGGACAGAAGAAAAGG | | 2 | 7 | 158 SEQ ID NO. 4059 |
| (N20)NGG | 8 | 48840394 | - | TTCAATGATGTTGTGTGGCAAGG | | 1 | 2 | 55 SEQ ID NO. 4060 |
| (N20)NGG | 8 | 48840399 | - | TCGAGTTCAATGATGTTGTGTGG | | 1 | 2 | 9 SEQ ID NO. 4061 |
| (N20)NGG | 8 | 48840430 | - | TACCTGCAGTGCAGGAACGTAGG | | 1 | 1 | 18 SEQ ID NO. 4062 |
| (N20)NGG | 8 | 48840438 | - | ACAACGCCTACCTGCAGTGCAGG | | 1 | 2 | 12 SEQ ID NO. 4063 |
| (N20)NGG | 8 | 48841651 | + | AACTTGCTGTTTATTTGACAGG | | 2 | 10 | 99 SEQ ID NO. 4064 |
| (N20)NGG | 8 | 48841652 | + | ACTTGCTGTTTTATTTGACAGG | | 1 | 7 | 108 SEQ ID NO. 4065 |
| (N20)NGG | 8 | 48841730 | + | TTTGCTTTATTTGTGAAATTTGG | | 1 | 15 | 363 SEQ ID NO. 4066 |
| (N20)NGG | 8 | 48841738 | + | ATTTGTGAAATTTGGCAAAGAGG | | 2 | 13 | 136 SEQ ID NO. 4067 |

FIG. 12 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 8 | 48841660 | - | GGAGAGTGTTTCAGACTCTTTGG | | 1 | 3 | 33 SEQ ID NO. 4068 |
| (N20)NGG | 8 | 48841681 | - | GAATACTTTTCTGGGTCTTCAGG | | 1 | 7 | 46 SEQ ID NO. 4069 |
| (N20)NGG | 8 | 48841689 | - | CAAAGCAAGAATACTTTTCTGGG | | 2 | 4 | 143 SEQ ID NO. 4070 |
| (N20)NGG | 8 | 48841690 | - | GCAAAGCAAGAATACTTTTCTGG | | 1 | 5 | 62 SEQ ID NO. 4071 |
| (N20)NGG | 8 | 48842454 | + | AAGCAGAATTTTTGAACCATGG | | 2 | 31 | 630 SEQ ID NO. 4072 |
| (N20)NGG | 8 | 48842455 | + | AGCAGAATTTTTGAACCATGGG | | 1 | 3 | 137 SEQ ID NO. 4073 |
| (N20)NGG | 8 | 48842496 | + | AATTAATTTTGCAATCTACAAGG | | 1 | 5 | 116 SEQ ID NO. 4074 |
| (N20)NGG | 8 | 48842513 | + | ACAAGGTTGCCCCTCATCAGTGG | | 1 | 3 | 19 SEQ ID NO. 4075 |
| (N20)NGG | 8 | 48842572 | + | CAAGAAAATAAAATATTTCGAGG | | 1 | 20 | 306 SEQ ID NO. 4076 |
| (N20)NGG | 8 | 48842589 | + | TCGAGGTGAGTCTTTCTTTGCAGG | | 2 | 4 | 38 SEQ ID NO. 4077 |
| (N20)NGG | 8 | 48842421 | - | AAAAATTCTGCTTGTTTCTCAGG | | 1 | 13 | 160 SEQ ID NO. 4078 |
| (N20)NGG | 8 | 48842422 | - | AAAAATTCTGCTTGTTTCTCAGG | | 1 | 5 | 118 SEQ ID NO. 4079 |
| (N20)NGG | 8 | 48842449 | - | TATGAAAATGAGTACACCATGG | | 1 | 5 | 50 SEQ ID NO. 4080 |
| (N20)NGG | 8 | 48842500 | - | TTGTAGAAACCACTGATGAGGGG | | 1 | 7 | 49 SEQ ID NO. 4081 |
| (N20)NGG | 8 | 48842501 | - | TTTGTAGAAACCACTGATGAGGG | | 1 | 4 | 90 SEQ ID NO. 4082 |
| (N20)NGG | 8 | 48842502 | - | ATTTGTAGAAACCACTGATGAGG | | 1 | 5 | 61 SEQ ID NO. 4083 |
| (N20)NGG | 8 | 48842549 | - | CTCGAAATATTTATTTTCTTTGG | | 1 | 21 | 221 SEQ ID NO. 4084 |
| (N20)NGG | 8 | 48843235 | + | CTACAATTACTCTCTTTAAGAATGG | | 1 | 3 | 78 SEQ ID NO. 4085 |
| (N20)NGG | 8 | 48843243 | + | ACTCTTTAAGAATGGAGATGAGG | | 1 | 7 | 67 SEQ ID NO. 4086 |
| (N20)NGG | 8 | 48843250 | + | AAGAATGGAGATGAGGCGCCTGG | | 1 | 4 | 41 SEQ ID NO. 4087 |
| (N20)NGG | 8 | 48843257 | + | GAGATGAGGCGCCTGGTGTTTGG | | 1 | 3 | 31 SEQ ID NO. 4088 |
| (N20)NGG | 8 | 48843282 | + | GATCCCAACTTCAGATCCAGCGG | | 2 | 2 | 31 SEQ ID NO. 4089 |
| (N20)NGG | 8 | 48843318 | + | AGCTAAACCTAAAGATTTTTCGG | | 1 | 9 | 84 SEQ ID NO. 4090 |
| (N20)NGG | 8 | 48843333 | + | TTTTTCGGCTTTCATTAACCTGG | | 1 | 2 | 33 SEQ ID NO. 4091 |
| (N20)NGG | 8 | 48843336 | + | TTCGGCTTTCATTAACCTGGTCG | | 1 | 2 | 18 SEQ ID NO. 4092 |
| (N20)NGG | 8 | 48843347 | + | TTAACCTGGTGGAATTTTGCAGG | | 1 | 4 | 41 SEQ ID NO. 4093 |
| (N20)NGG | 8 | 48843354 | + | GGTGGAATTTTGCAGGTATTTGG | | 1 | 4 | 39 SEQ ID NO. 4094 |
| (N20)NGG | 8 | 48843246 | - | GTTGGGATCATCCAAACACCAGG | | 1 | 2 | 24 SEQ ID NO. 4095 |
| (N20)NGG | 8 | 48843263 | - | TAGCCGCTGATCTGAAGTTGGG | | 1 | 1 | 10 SEQ ID NO. 4096 |
| (N20)NGG | 8 | 48843264 | - | TTAGCCGCTGATCTGAAGTTGG | | 1 | 1 | 14 SEQ ID NO. 4097 |
| (N20)NGG | 8 | 48843276 | - | GCTGATGCAAGTTAGCCGCTGG | | 1 | 1 | 5 SEQ ID NO. 4098 |
| (N20)NGG | 8 | 48843294 | - | GAAAATCTTTTAGGTTTAGCTGG | | 1 | 1 | 57 SEQ ID NO. 4099 |
| (N20)NGG | 8 | 48843303 | - | ATGAAAGCCGAAAAATCTTTAGG | | 1 | 2 | 39 SEQ ID NO. 4100 |

FIG. 12 cont.

| site_type | site_chromosome | site_start_nucleotide | site_strand | target_site_sequence_with NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 8 | 48843329 | - | AATACCTGCAAAATTCCACCAGG | | 1 | 3 | 53 SEQ ID NO. 4101 |
| (N20)NGG | 8 | 48845579 | + | TATTGTTTTCTTTATTTAAAGG | | 1 | 63 | 1249 SEQ ID NO. 4102 |
| (N20)NGG | 8 | 48845693 | + | TTTGAAGATTGTTGAGAAATTGG | | 1 | 6 | 137 SEQ ID NO. 4103 |
| (N20)NGG | 8 | 48845721 | + | ACACTTGAAATACAGACTGTTGG | | 1 | 3 | 40 SEQ ID NO. 4104 |
| (N20)NGG | 8 | 48845722 | + | CACTTGAAATACAGACTGTTGGG | | 1 | 2 | 54 SEQ ID NO. 4105 |
| (N20)NGG | 8 | 48845723 | + | ACTTGAAATACAGACTGTTGGGG | | 1 | 4 | 53 SEQ ID NO. 4106 |
| (N20)NGG | 8 | 48845732 | + | ACAGACTGTTGGGAACAAGAGG | | 1 | 4 | 66 SEQ ID NO. 4107 |
| (N20)NGG | 8 | 48845619 | - | ATGATTCAGACTTTCACTGGAGG | | 1 | 1 | 44 SEQ ID NO. 4108 |
| (N20)NGG | 8 | 48845622 | - | TAAATGATTCAGACTTTCACTGG | | 1 | 5 | 68 SEQ ID NO. 4109 |
| (N20)NGG | 8 | 48845667 | - | TTTCTCAACAATCTTCAAAACGG | | 1 | 7 | 153 SEQ ID NO. 4110 |
| (N20)NGG | 8 | 48846524 | + | GTCATGCTGTCTTTCTGGCCAGG | | 1 | 1 | 29 SEQ ID NO. 4111 |
| (N20)NGG | 8 | 48846525 | + | TCATGCTGTCTTTCTGGCCAGGG | | 1 | 7 | 81 SEQ ID NO. 4112 |
| (N20)NGG | 8 | 48846561 | + | TCTGAAGACCACCGTGCTTCAGG | | 1 | 2 | 22 SEQ ID NO. 4113 |
| (N20)NGG | 8 | 48846562 | + | CTGAAGACCACCGTGCTTCAGGG | | 1 | 2 | 16 SEQ ID NO. 4114 |
| (N20)NGG | 8 | 48846563 | + | TGAAGACCACCGTGCTTCAGGGG | | 1 | 1 | 18 SEQ ID NO. 4115 |
| (N20)NGG | 8 | 48846576 | + | GCTTCAGGGGAAGTCAGAACTGG | | 1 | 5 | 37 SEQ ID NO. 4116 |
| (N20)NGG | 8 | 48846583 | + | GGGAAGTCAGAACTGGCAAATGG | | 1 | 7 | 71 SEQ ID NO. 4117 |
| (N20)NGG | 8 | 48846587 | + | AGTCAGAACTGGCAAATGGAAGG | | 1 | 6 | 60 SEQ ID NO. 4118 |
| (N20)NGG | 8 | 48846611 | + | GCCCACATACAAAGACTACGTGG | | 1 | 1 | 11 SEQ ID NO. 4119 |
| (N20)NGG | 8 | 48846650 | + | CCTGAGCTCTGACCAGATGATGG | | 2 | 5 | 79 SEQ ID NO. 4120 |
| (N20)NGG | 8 | 48846520 | - | CAGATTCAGACTCAGGGCCCTGG | | 1 | 11 | 80 SEQ ID NO. 4121 |
| (N20)NGG | 8 | 48846526 | - | GGTCTTCAGATTCAGACTCAGG | | 1 | 6 | 78 SEQ ID NO. 4122 |
| (N20)NGG | 8 | 48846527 | - | TGGTCTTCAGATTCAGACTCAGG | | 1 | 4 | 50 SEQ ID NO. 4123 |
| (N20)NGG | 8 | 48846547 | - | TGACTTCCCCTGAAGCACGTGG | | 1 | 1 | 20 SEQ ID NO. 4124 |
| (N20)NGG | 8 | 48846550 | - | TTCTGACTTCCCCTGAAGCACGG | | 1 | 6 | 77 SEQ ID NO. 4125 |
| (N20)NGG | 8 | 48846590 | - | TCCACGTAGTCTTTGTATGTGG | | 1 | 2 | 18 SEQ ID NO. 4126 |
| (N20)NGG | 8 | 48846591 | - | ATCCACGTAGTCTTTGTATGTGTG | | 1 | 2 | 11 SEQ ID NO. 4127 |
| (N20)NGG | 8 | 48846628 | - | CCATCACTGGTCAGAGCTCAGG | | 1 | 3 | 26 SEQ ID NO. 4128 |
| (N20)NGG | 8 | 48846640 | - | TGGTAAATGTTACCATCACTCGG | | 2 | 3 | 48 SEQ ID NO. 4129 |
| (N20)NGG | 8 | 48847576 | + | TTTTCTTTTTTCAGTGCATCAGG | | 1 | 14 | 294 SEQ ID NO. 4130 |
| (N20)NGG | 8 | 48847577 | + | TTTCTTTTTTCAGTGCATCAGGG | | 2 | 19 | 285 SEQ ID NO. 4131 |
| (N20)NGG | 8 | 48847606 | + | CAGAATATGTTCTAAACCAGTGG | | 2 | 4 | 56 SEQ ID NO. 4132 |
| (N20)NGG | 8 | 48847618 | + | TAAACCAGTGGTCCTTCCAAAGG | | 1 | 2 | 27 SEQ ID NO. 4133 |

FIG. 12 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | | |
|---|---|---|---|---|---|---|---|---|---|
| (N20)NGG | 8 | 48847600 | - | TTTACCTTTGGAAGGACCACTGG | | 1 | 4 | 57 | SEQ ID NO. 4134 |
| (N20)NGG | 8 | 48847608 | - | ATTCAGAATTTACCTTTGAAGG | | 1 | 6 | 102 | SEQ ID NO. 4135 |
| (N20)NGG | 8 | 48847612 | - | TTAAATTCAGAATTTACCTTTGG | | 1 | 13 | 150 | SEQ ID NO. 4136 |
| (N20)NGG | 8 | 48848291 | + | GTTTGCTGATTATTTCCGGTAGG | | 1 | 2 | 15 | SEQ ID NO. 4137 |
| (N20)NGG | 8 | 48848300 | + | TTATTTCCGTAGGTTCCTGAGG | | 1 | 1 | 21 | SEQ ID NO. 4138 |
| (N20)NGG | 8 | 48848318 | + | TGAGGTGTATACTCCAGTTCTGG | | 1 | 1 | 22 | SEQ ID NO. 4139 |
| (N20)NGG | 8 | 48848330 | + | TCCAGTTCTGGAGCACCTCGTGG | | 1 | 1 | 20 | SEQ ID NO. 4140 |
| (N20)NGG | 8 | 48848378 | + | GTACAGTCCAAAAATGCAGCTGG | | 1 | 1 | 30 | SEQ ID NO. 4141 |
| (N20)NGG | 8 | 48848402 | + | GTGTTGCAGAGCCATAGTGAAGG | | 1 | 2 | 27 | SEQ ID NO. 4142 |
| (N20)NGG | 8 | 48848417 | + | AGTGAAGGTGTTCCTAGCTTTGG | | 1 | 2 | 24 | SEQ ID NO. 4143 |
| (N20)NGG | 8 | 48848427 | + | TTCCTAGCTTTGGCAGCAAAAGG | | 1 | 5 | 56 | SEQ ID NO. 4144 |
| (N20)NGG | 8 | 48848428 | + | TCCTAGCTTTGGCAGCAAAAGGG | | 1 | 7 | 62 | SEQ ID NO. 4145 |
| (N20)NGG | 8 | 48848440 | + | CAGCAAAAGGGCCAGTTCTCAGG | | 1 | 3 | 45 | SEQ ID NO. 4146 |
| (N20)NGG | 8 | 48848459 | + | CAGGAATTGCATTAGTACTGTGG | | 1 | 2 | 53 | SEQ ID NO. 4147 |
| (N20)NGG | 8 | 48848460 | + | AGGAATTGCATTAGTACTGTGGG | | 1 | 2 | 49 | SEQ ID NO. 4148 |
| (N20)NGG | 8 | 48848284 | - | TATACACCTCAGGAACCTACCG | | 1 | 2 | 14 | SEQ ID NO. 4149 |
| (N20)NGG | 8 | 48848294 | - | AGAACTGGAGTATACACCTCAGG | | 1 | 2 | 22 | SEQ ID NO. 4150 |
| (N20)NGG | 8 | 48848309 | - | ACCACGAGGTGCTCCAGAACTGG | | 1 | 4 | 9 | SEQ ID NO. 4151 |
| (N20)NGG | 8 | 48848323 | - | TGTCTATCTGCATCACCACGAGG | | 1 | 2 | 13 | SEQ ID NO. 4152 |
| (N20)NGG | 8 | 48848350 | - | GCATTTTTGGACTGTACTGTGG | | 1 | 2 | 23 | SEQ ID NO. 4153 |
| (N20)NGG | 8 | 48848351 | - | TGCATTTTTGGACTGTACTGTGG | | 1 | 4 | 39 | SEQ ID NO. 4154 |
| (N20)NGG | 8 | 48848363 | - | CAACACACCAGTGCATTTTTGG | | 2 | 5 | 47 | SEQ ID NO. 4155 |
| (N20)NGG | 8 | 48848391 | - | AGCTAGGAACACCTTCACTATGG | | 1 | 1 | 19 | SEQ ID NO. 4156 |
| (N20)NGG | 8 | 48848407 | - | GCCCTTTTGCTGCCAAAGCTAGG | | 2 | 4 | 48 | SEQ ID NO. 4157 |
| (N20)NGG | 8 | 48848429 | - | CTAATGCAATTCCTGAGAACTGG | | 2 | 5 | 31 | SEQ ID NO. 4158 |
| (N20)NGG | 8 | 48848921 | + | ACCTTTTCTAAAGCCGTGCAAGG | | 1 | 2 | 19 | SEQ ID NO. 4159 |
| (N20)NGG | 8 | 48849006 | + | TTCCTCACCCAGACAGACACTGG | | 1 | 2 | 48 | SEQ ID NO. 4160 |
| (N20)NGG | 8 | 48848900 | - | ACCTTGCGGCTTTAGAAAAGG | | 1 | 3 | 13 | SEQ ID NO. 4161 |
| (N20)NGG | 8 | 48848912 | - | TTTGCGTTTATAACCTTGCACGG | | 1 | 1 | 29 | SEQ ID NO. 4162 |
| (N20)NGG | 8 | 48848986 | - | CACCAGTGTCTCTGGGTGAGG | | 1 | 6 | 146 | SEQ ID NO. 4163 |
| (N20)NGG | 8 | 48848991 | - | GTCGTCACCAGTGTCTCTGTCTGG | | 1 | 2 | 9 | SEQ ID NO. 4164 |
| (N20)NGG | 8 | 48848992 | - | GGTCGTCACCAGTGTCTCTGTCTGG | | 1 | 1 | 13 | SEQ ID NO. 4165 |
| (N20)NGG | 8 | 48849013 | - | AGCTTGGCATCTGATAAACACGG | | 1 | 6 | 38 | SEQ ID NO. 4166 |

FIG. 12 cont.

| site_type | site_chr omosome | site_start_ nucleotide | site_s trand | target_site_sequence_wi th_NGG | genome_wide_ hits_with_1 or_less_mism atches | genome_wide_ hits_with_ 2_or_less_m ismatches | genome_wide_ hits_with_ 3_or_less_mism atches | |
|---|---|---|---|---|---|---|---|---|
| (N20)NGG | 8 | 48849029 | - | GCAACAGACTGGAGGAAGCTTGG | 1 | 1 | 3 | 62 SEQ ID NO. 4167 |
| (N20)NGG | 8 | 48849037 | - | AGACGCTTGCAACAGACTGGAGG | | 1 | 3 | 15 SEQ ID NO. 4168 |
| (N20)NGG | 8 | 48849040 | - | GCAAGACGCTTGCAACAGACTGG | | 1 | 1 | 11 SEQ ID NO. 4169 |
| (N20)NGG | 8 | 48849067 | - | TTAGTTCACTTACTGTGTCAAGG | | 1 | 5 | 63 SEQ ID NO. 4170 |
| (N20)NGG | 8 | 48852110 | + | AATAAATATTATGTATTTGCAGG | | 3 | 18 | 262 SEQ ID NO. 4171 |
| (N20)NGG | 8 | 48852122 | + | GTATTTGCAGGTTTCTAATATGG | | 1 | 6 | 100 SEQ ID NO. 4172 |
| (N20)NGG | 8 | 48852125 | + | TTTGCAGGTTTCTAATATGGTGG | | 1 | 4 | 49 SEQ ID NO. 4173 |
| (N20)NGG | 8 | 48852170 | + | AAATAAACTGCAGTACTTTATGG | | 1 | 6 | 143 SEQ ID NO. 4174 |
| (N20)NGG | 8 | 48852183 | + | TACTTTATGGAGCAGTTTTATGG | | 1 | 6 | 154 SEQ ID NO. 4175 |
| (N20)NGG | 8 | 48852200 | + | TTATGGAATCATCAGAAATGTGG | | 1 | 2 | 66 SEQ ID NO. 4176 |
| (N20)NGG | 8 | 48852215 | + | AAATGTGGATTCGAACAACAAGG | | 1 | 3 | 35 SEQ ID NO. 4177 |
| (N20)NGG | 8 | 48852237 | + | GAGTTATCTATTGCTATCCGTGG | | 1 | 1 | 5 SEQ ID NO. 4178 |
| (N20)NGG | 8 | 48852243 | + | TCTATTGCTATCCGTGGATATGG | | 1 | 2 | 10 SEQ ID NO. 4179 |
| (N20)NGG | 8 | 48852255 | - | CGTGGATATGGACTTTTTGCAGG | | 1 | 2 | 6 SEQ ID NO. 4180 |
| (N20)NGG | 8 | 48852771 | + | CTGCAAAAAGTCCATATCCACGG | | 1 | 2 | 43 SEQ ID NO. 4181 |
| (N20)NGG | 8 | 48855771 | + | ATGGCATTTGCATTTGCAGCTGG | | 1 | 4 | 65 SEQ ID NO. 4182 |
| (N20)NGG | 8 | 48855821 | + | TCAGTTTAGCACCTGCCTTCTGG | | 1 | 5 | 37 SEQ ID NO. 4183 |
| (N20)NGG | 8 | 48855859 | + | TATTTGAAGTCTTGTTAAAGTGG | | 1 | 9 | 113 SEQ ID NO. 4184 |
| (N20)NGG | 8 | 48855908 | + | AAAAGCTGCACTTTCAGCCCTGG | | 1 | 3 | 58 SEQ ID NO. 4185 |
| (N20)NGG | 8 | 48855926 | + | CCTGGAATCCTTTCTGAAACAGG | | 2 | 13 | 97 SEQ ID NO. 4186 |
| (N20)NGG | 8 | 48855778 | - | GAGATGCATGCAGGGCAAATAGG | | 1 | 3 | 33 SEQ ID NO. 4187 |
| (N20)NGG | 8 | 48855786 | - | GCTAAACTGAGATGCATGCAGG | | 1 | 1 | 16 SEQ ID NO. 4188 |
| (N20)NGG | 8 | 48855787 | - | TGCTAAACTGAGATGCATGCAGG | | 1 | 1 | 21 SEQ ID NO. 4189 |
| (N20)NGG | 8 | 48855810 | - | CACGTAGTTGTCCAGAAGGCAGG | | 1 | 1 | 11 SEQ ID NO. 4190 |
| (N20)NGG | 8 | 48855814 | - | GAGACACGTAGTTGTCCAGAAGG | | 1 | 2 | 10 SEQ ID NO. 4191 |
| (N20)NGG | 8 | 48855864 | - | TTTCAATTCTACATTTGTCTGGG | | 2 | 8 | 158 SEQ ID NO. 4192 |
| (N20)NGG | 8 | 48855865 | - | TTTTCAATTCTACATTTGTGTGG | | 1 | 10 | 148 SEQ ID NO. 4193 |
| (N20)NGG | 8 | 48855903 | - | CTGTTTCAGAAAGGATTCCAGGG | | 1 | 7 | 72 SEQ ID NO. 4194 |
| (N20)NGG | 8 | 48855904 | - | CCTGTTTCAGAAAGGATTCCAGG | | 1 | 5 | 60 SEQ ID NO. 4195 |
| (N20)NGG | 8 | 48855912 | - | TTGTGGTACCTGTTTCAGAAAGG | | 1 | 1 | 35 SEQ ID NO. 4196 |
| (N20)NGG | 8 | 48856443 | + | AAGAGATATGCTGTGCCCTCAGG | | 1 | 3 | 35 SEQ ID NO. 4197 |
| (N20)NGG | 8 | 48856447 | + | GATATGCTGTGCCCTCAGTAGG | | 1 | 2 | 21 SEQ ID NO. 4198 |
| (N20)NGG | 8 | 48856465 | + | GTAGGATTCTGTTTATAATGAGG | | 2 | 6 | 58 SEQ ID NO. 4199 |

FIG. 12 cont.

| site_type | site_chr omosome | site_start_ nucleotide | site_s trand | target_site_sequence_wi th_NGG | genome_wide_ hits_with_1 or_less_mism atches | genome_wide_ hits_with_ 2_or_less_m ismatches | genome_wide_ hits_with_3_ or_less_mism atches | | |
|---|---|---|---|---|---|---|---|---|---|
| (N20)NGG | 8 | 48856436 | - | ATAAACAGAATCCTACCTGAGGG | 1 | | 3 | 56 | SEQ ID NO. 4200 |
| (N20)NGG | 8 | 48856437 | - | TATGAACAGAATCCTACCTGAGG | 1 | | 3 | 45 | SEQ ID NO. 4201 |
| (N20)NGG | 8 | 48856549 | + | CCCTAGATCCCAGACTTCAAGG | 1 | | 5 | 61 | SEQ ID NO. 4202 |
| (N20)NGG | 8 | 48856550 | + | CCTAGATCCCCAGACTTCAAGGG | 1 | | 1 | 27 | SEQ ID NO. 4203 |
| (N20)NGG | 8 | 48856574 | + | GATTTTTAATTTTGTACTAAAGG | 1 | | 12 | 240 | SEQ ID NO. 4204 |
| (N20)NGG | 8 | 48856589 | + | ACTAAAGGCAATTCGTCCTCAGG | 1 | | 2 | 10 | SEQ ID NO. 4205 |
| (N20)NGG | 8 | 48856593 | + | AAGGCAATTCGTCCTCAGGTAGG | 1 | | 3 | 11 | SEQ ID NO. 4206 |
| (N20)NGG | 8 | 48856527 | - | CCTTGAAGTCTGGGGATCTAGGG | 1 | | 1 | 35 | SEQ ID NO. 4207 |
| (N20)NGG | 8 | 48856528 | - | CCCTTGAAGTCTGGGGATCTAGG | 1 | | 2 | 43 | SEQ ID NO. 4208 |
| (N20)NGG | 8 | 48856535 | - | AAAATCTCCCTTGAAGTCTGGGG | 1 | | 4 | 74 | SEQ ID NO. 4209 |
| (N20)NGG | 8 | 48856536 | - | AAAAATCTCCCTTGAAGTCTGGG | 1 | | 2 | 76 | SEQ ID NO. 4210 |
| (N20)NGG | 8 | 48856537 | - | TAAAAATCTCCCTTGAAGTCTGG | 1 | | 3 | 64 | SEQ ID NO. 4211 |
| (N20)NGG | 8 | 48856583 | - | AGTAATATTAATCCTACCTGAGG | 1 | | 2 | 42 | SEQ ID NO. 4212 |
| (N20)NGG | 8 | 48866218 | + | AGAGCCCAAACTACCTGTTCTGG | 1 | | 3 | 21 | SEQ ID NO. 4213 |
| (N20)NGG | 8 | 48866222 | + | CCCAAACTACCTGTTCTGCCAGG | 1 | | 3 | 26 | SEQ ID NO. 4214 |
| (N20)NGG | 8 | 48866233 | + | TGTTCTGCCAGGATGTCTGAAGG | 2 | | 2 | 31 | SEQ ID NO. 4215 |
| (N20)NGG | 8 | 48866234 | + | GTTCTGGCAGGATGTCTGAAGGG | 1 | | 5 | 78 | SEQ ID NO. 4216 |
| (N20)NGG | 8 | 48866235 | + | TTCTGGCAGGATGTCTGAAGGGG | 1 | | 3 | 60 | SEQ ID NO. 4217 |
| (N20)NGG | 8 | 48866272 | + | GTGCAACTTCACTAAGTCCATGG | 1 | | 3 | 17 | SEQ ID NO. 4218 |
| (N20)NGG | 8 | 48866279 | + | TTCACTAAGTCCATGGAAGAAGG | 2 | | 15 | 82 | SEQ ID NO. 4219 |
| (N20)NGG | 8 | 48866289 | + | CCATGGAAGAAGGTATTGCTTGG | 1 | | 3 | 32 | SEQ ID NO. 4220 |
| (N20)NGG | 8 | 48866200 | - | CCTGCCAGAACAGGTAGTTTGG | 2 | | 3 | 20 | SEQ ID NO. 4221 |
| (N20)NGG | 8 | 48866201 | - | TCCTGCCAGAACAGGTAGTTTGG | 3 | | 4 | 21 | SEQ ID NO. 4222 |
| (N20)NGG | 8 | 48866209 | - | TTCAGACATCCTGCCAGAACAGG | 1 | | 3 | 37 | SEQ ID NO. 4223 |
| (N20)NGG | 8 | 48866240 | - | AGTGAAGTTGCACAGAAGTCAGG | 2 | | 6 | 91 | SEQ ID NO. 4224 |
| (N20)NGG | 8 | 48866267 | - | CCAAGCAATACCTTCTTCCATGG | 2 | | 6 | 41 | SEQ ID NO. 4225 |
| (N20)NGG | 8 | 48866393 | + | GAAAAAGTATATGAGCTCCTAGG | 1 | | 1 | 63 | SEQ ID NO. 4226 |
| (N20)NGG | 8 | 48866401 | + | ATATGAGCTCCTAGGATTATTGG | 1 | | 5 | 34 | SEQ ID NO. 4227 |
| (N20)NGG | 8 | 48866402 | + | TATGAGCTCCTAGGATTATTGG | 2 | | 4 | 33 | SEQ ID NO. 4228 |
| (N20)NGG | 8 | 48866461 | + | AAACCTGTTCCGCGCTTTTCTGG | 1 | | 1 | 10 | SEQ ID NO. 4229 |
| (N20)NGG | 8 | 48866462 | + | AACCTGTTCCGCGCTTTTCTGGG | 1 | | 2 | 11 | SEQ ID NO. 4230 |
| (N20)NGG | 8 | 48866479 | + | TCTGGGTGAACTTAAGACCCAGG | 1 | | 2 | 19 | SEQ ID NO. 4231 |
| (N20)NGG | 8 | 48866388 | - | GAACTTCACCCAATAATCCTAGG | 1 | | 1 | 21 | SEQ ID NO. 4232 |

FIG. 12 cont.

| site_type | site_chr cmosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 8 | 48866413 | - | GCATTATTTATCATCTCACTAGG |   | 1 | 6 | 60 SEQ ID NO. 4233 |
| (N20)NGG | 8 | 48866442 | - | CACCCAGAAAAGCGCGGAACAGG |   | 1 | 1 | 8 SEQ ID NO. 4234 |
| (N20)NGG | 8 | 48866448 | - | TAAGTTCACCCAGAAAAGCGCGG |   | 1 | 2 | 21 SEQ ID NO. 4235 |
| (N20)NGG | 8 | 48866474 | - | TCATAAAGTTCATCATACCTGGG |   | 1 | 4 | 38 SEQ ID NO. 4236 |
| (N20)NGG | 8 | 48866475 | - | GTCATAAAGTTCATCATACCTGG |   | 1 | 2 | 23 SEQ ID NO. 4237 |
| (N20)NGG | 8 | 48866930 | + | TTTTAGAAGTTCTAGACTCATGG |   | 1 | 5 | 86 SEQ ID NO. 4238 |
| (N20)NGG | 8 | 48866946 | + | CTCATGGATGAATTTAAAATTGG |   | 1 | 9 | 111 SEQ ID NO. 4239 |
| (N20)NGG | 8 | 48866970 | + | GAATTATTTAGTAAATTCTATGG |   | 2 | 6 | 170 SEQ ID NO. 4240 |
| (N20)NGG | 8 | 48867006 | + | AAAAAAAATACCAGATACAGG |   | 9 | 181 | 2285 SEQ ID NO. 4241 |
| (N20)NGG | 8 | 48866996 | - | AAATGCATCTCACCTGTATCTGG |   | 1 | 3 | 35 SEQ ID NO. 4242 |
| (N20)NGG | 8 | 48868493 | + | TAAATGTAAAATTCCAGCCCTGG |   | 3 | 11 | 94 SEQ ID NO. 4243 |
| (N20)NGG | 8 | 48868508 | + | AGCCCTGGACTTTCTTATTAAGG |   | 3 | 7 | 43 SEQ ID NO. 4244 |
| (N20)NGG | 8 | 48868428 | - | AACACTGGTACAAGTGTTCTAGG |   | 1 | 7 | 53 SEQ ID NO. 4245 |
| (N20)NGG | 8 | 48868443 | - | TCTATCTTTTGTATAAACACTGG |   | 4 | 6 | 81 SEQ ID NO. 4246 |
| (N20)NGG | 8 | 48868484 | - | TTAATAAGAAGTCCAGGGCTGG |   | 2 | 6 | 50 SEQ ID NO. 4247 |
| (N20)NGG | 8 | 48868488 | - | TACCTTAATAAGAAGGTCCAGGG |   | 1 | 3 | 33 SEQ ID NO. 4248 |
| (N20)NGG | 8 | 48868489 | - | TTACCTTAATAAGAAGGTCCAGG |   | 1 | 1 | 29 SEQ ID NO. 4249 |
| (N20)NGG | 8 | 48868495 | - | ACATAATTACCTTAATAAGAAGG |   | 1 | 4 | 86 SEQ ID NO. 4250 |
| (N20)NGG | 8 | 48869787 | + | ATGTATTTTCTTTAGAAAAAATGG |   | 5 | 45 | 588 SEQ ID NO. 4251 |
| (N20)NGG | 8 | 48869788 | + | TGTATTTTCTTTAGAAAAAATGGG |   | 2 | 29 | 518 SEQ ID NO. 4252 |
| (N20)NGG | 8 | 48869823 | + | ACCTTACTCTGTTGAAATTAAGG |   | 1 | 2 | 36 SEQ ID NO. 4253 |
| (N20)NGG | 8 | 48869753 | - | AGAAAATACATAAAACTTTAGG |   | 2 | 29 | 537 SEQ ID NO. 4254 |
| (N20)NGG | 8 | 48869789 | - | CAGAGTAAGGTGCGATCTTCTGG |   | 1 | 1 | 8 SEQ ID NO. 4255 |
| (N20)NGG | 8 | 48869802 | - | ACCTTAATTTCAACAGAGTAAGG |   | 1 | 1 | 47 SEQ ID NO. 4256 |
| (N20)NGG | 8 | 48869950 | + | TTAGTTTTTTCCAGAGATTTCCG |   | 2 | 12 | 158 SEQ ID NO. 4257 |
| (N20)NGG | 8 | 48869969 | + | TCGGTTTTGCTTGTTATTTGTCCGG |   | 2 | 5 | 89 SEQ ID NO. 4258 |
| (N20)NGG | 8 | 48870008 | + | TTTGAAGTAAGTTGACAATTTTGG |   | 1 | 5 | 73 SEQ ID NO. 4259 |
| (N20)NGG | 8 | 48869938 | - | TACAAGCAAACCGAAATCTCTGG |   | 1 | 4 | 14 SEQ ID NO. 4260 |
| (N20)NGG | 8 | 48869966 | - | CAATACTGTTGAGTGACTTCCGG |   | 3 | 3 | 30 SEQ ID NO. 4261 |
| (N20)NGG | 8 | 48872530 | + | CGCGCGGGAGCGGACTCGGCGG |   | 1 | 2 | 20 SEQ ID NO. 4262 |
| (N20)NGG | 8 | 48872535 | + | GGGAGCGGGACTCGGCGGCATGG |   | 1 | 2 | 34 SEQ ID NO. 4263 |
| (N20)NGG | 8 | 48872538 | + | AGCGGGACTCGGCGGCATGGCGG |   | 1 | 2 | 8 SEQ ID NO. 4264 |
| (N20)NGG | 8 | 48872539 | + | GCGGGACTCGGCGGCATGGCGGG |   | 1 | 1 | 11 SEQ ID NO. 4265 |

FIG. 12 cont.

| site type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 8 | 48872545 | + | CTCGGCGGCATGGCGGGCTCCGG | | 1 | 2 | 11 SEQ ID NO. 4266 |
| (N20)NGG | 8 | 48872551 | + | GGCATGGCGGGCTCCGGAGCCGG | | 1 | 2 | 26 SEQ ID NO. 4267 |
| (N20)NGG | 8 | 48872573 | + | GTGTGCGTTGCTCCCTGCTGCGG | | 1 | 4 | 47 SEQ ID NO. 4268 |
| (N20)NGG | 8 | 48872580 | + | TTGCTCCCTGCTGCGGCTGCAGG | | 1 | 4 | 73 SEQ ID NO. 4269 |
| (N20)NGG | 8 | 48872598 | + | GCAGGAGACCTTGTCCGCTGCGG | | 1 | 2 | 14 SEQ ID NO. 4270 |
| (N20)NGG | 8 | 48872608 | + | TTGTCCGCTGCGGACCGCTGCGG | | 1 | 1 | 5 SEQ ID NO. 4271 |
| (N20)NGG | 8 | 48872619 | + | GGACCGCTGCGGTGCTGCCCTGG | | 1 | 1 | 23 SEQ ID NO. 4272 |
| (N20)NGG | 8 | 48872623 | + | CGCTGCGGTGCTGCCCTGGCCGG | | 1 | 4 | 30 SEQ ID NO. 4273 |
| (N20)NGG | 8 | 48872641 | + | GCCGGTCATCAACTGATCCGCGG | | 1 | 1 | 1 SEQ ID NO. 4274 |
| (N20)NGG | 8 | 48872646 | + | TCATCAACTGATCCGCGGCCTGG | | 1 | 1 | 5 SEQ ID NO. 4275 |
| (N20)NGG | 8 | 48872647 | + | CATCAACTGATCCGCGGCCTGGG | | 1 | 1 | 64 SEQ ID NO. 4276 |
| (N20)NGG | 8 | 48872648 | + | ATCAACTGATCCGCGGCCTGGGG | | 1 | 1 | 3 SEQ ID NO. 4277 |
| (N20)NGG | 8 | 48872652 | + | ACTGATCCGCGGCCTGGGGCAGG | | 1 | 1 | 23 SEQ ID NO. 4278 |
| (N20)NGG | 8 | 48872679 | + | CGTCCTGAGCAGCCCCGCGCGG | | 1 | 3 | 29 SEQ ID NO. 4279 |
| (N20)NGG | 8 | 48872685 | + | GAGCAGCCCCGCGGTGCTGG | | 2 | 5 | 34 SEQ ID NO. 4280 |
| (N20)NGG | 8 | 48872686 | + | AGCAGCCCCGCGGTGCTGCTGGG | | 1 | 4 | 35 SEQ ID NO. 4281 |
| (N20)NGG | 8 | 48872689 | + | AGCAGCCCCGCGGTGCTGGGTGG | | 1 | 4 | 57 SEQ ID NO. 4282 |
| (N20)NGG | 8 | 48872690 | + | GCAGCCCCGCGGTGCTGGGTGGG | | 1 | 2 | 36 SEQ ID NO. 4283 |
| (N20)NGG | 8 | 48872696 | + | CCGCGGTGCTGGGTGGGTACCGG | | 2 | 7 | 22 SEQ ID NO. 4284 |
| (N20)NGG | 8 | 48872706 | + | GGGTGGGTACCGGCCCGAGCTGG | | 1 | 3 | 18 SEQ ID NO. 4285 |
| (N20)NGG | 8 | 48872707 | + | GGTGGGTACCGGCCCGAGCTGGG | | 1 | 2 | 6 SEQ ID NO. 4286 |
| (N20)NGG | 8 | 48872542 | – | GGAGCAACGCACACCGGCTCCGG | | 1 | 2 | 15 SEQ ID NO. 4287 |
| (N20)NGG | 8 | 48872548 | – | CAGCAGGGAGCAACGCACACCGG | | 2 | 9 | 105 SEQ ID NO. 4288 |
| (N20)NGG | 8 | 48872563 | – | GGTCTCCTGCAGCCGCAGCAGGG | | 1 | 4 | 51 SEQ ID NO. 4289 |
| (N20)NGG | 8 | 48872564 | – | AGGTCTCCTGCAGCCGCAGCAGG | | 1 | 3 | 50 SEQ ID NO. 4290 |
| (N20)NGG | 8 | 48872584 | – | GCAGCGGTCCGCAGCGGACAAGG | | 1 | 1 | 5 SEQ ID NO. 4291 |
| (N20)NGG | 8 | 48872590 | – | AGCACCGCAGCGGTCCGCAGCGG | | 2 | 3 | 10 SEQ ID NO. 4292 |
| (N20)NGG | 8 | 48872600 | – | CCCAGGGCAGCACCGCAGCGG | | 1 | 3 | 40 SEQ ID NO. 4293 |
| (N20)NGG | 8 | 48872614 | – | GATCAGTTGATGACCGGCCAGGG | | 1 | 1 | 8 SEQ ID NO. 4294 |
| (N20)NGG | 8 | 48872615 | – | GGATCAGTTGATGACCGGCCAGG | | 1 | 2 | 15 SEQ ID NO. 4295 |
| (N20)NGG | 8 | 48872620 | – | GCCGCGGATCAGTTGATGACCGG | | 1 | 1 | 4 SEQ ID NO. 4296 |
| (N20)NGG | 8 | 48872636 | – | CCCATTCCTGCCCAGGCCGCGG | | 1 | 1 | 33 SEQ ID NO. 4297 |
| (N20)NGG | 8 | 48872642 | – | TCAGGACGCATTCCTGCCCCAGG | | 1 | 4 | 31 SEQ ID NO. 4298 |

FIG. 12 cont.

| site_type | site_chr omosome | site_start_ nucleotide | site_s trand | target_site_sequence_wi th_NGG | genome_wide_ hits_with_1_ or_less_mism atches | genome_wide_ hits_with_ 2_or_less_m ismatches | genome_wide_ hits_with_3_ or_less_mism atches | |
|---|---|---|---|---|---|---|---|---|
| (N20)NGG | 8 | 48872660 | - | GCACCGCGGGCTGCTGCTCAGG | | 1 | 32 | SEQ ID NO. 4299 |
| (N20)NGG | 8 | 48872672 | - | GGTACCCACCCAGCACCGCGGG | 1 | 1 | 18 | SEQ ID NO. 4300 |
| (N20)NGG | 8 | 48872673 | - | CGGTACCCACCCAGCACCGCGG | 1 | 1 | 15 | SEQ ID NO. 4301 |
| (N20)NGG | 8 | 48872674 | - | CCGGTACCCACCCAGCACCGCG | 1 | 1 | 16 | SEQ ID NO. 4302 |

FIG. 12 cont.

| site type | site_chr omosome | site_start_ nucleotide | site_s trand | target_site_sequence_with_NGG | genome_wide_ hits_with_1_ or_less_mism atches | genome_wide_ hits_with_2_ or_less_mism atches | genome_wide_ hits_with_3_ or_less_mism atches | | |
|---|---|---|---|---|---|---|---|---|---|
| (N20)NGG | 11 | 36594881 | + | AGCCTCTTTCCCACCCACCTTGG | 1 | 8 | 94 | SEQ ID NO. | 4303 |
| (N20)NGG | 11 | 36594882 | + | GCCTCTTTCCCACCCACCTTGGG | 1 | 2 | 65 | SEQ ID NO. | 4304 |
| (N20)NGG | 11 | 36594937 | + | CACATATTAAATTTCAGAATGG | 1 | 20 | 258 | SEQ ID NO. | 4305 |
| (N20)NGG | 11 | 36594955 | + | AATGGAAATTTAAGCTGTTCCGG | 1 | 7 | 80 | SEQ ID NO. | 4306 |
| (N20)NGG | 11 | 36594956 | + | ATGGAAATTTAAGCTGTTCCGGG | 1 | 13 | 156 | SEQ ID NO. | 4307 |
| (N20)NGG | 11 | 36594995 | + | GACACCTGAAGAGCTCAAAAGG | 1 | 2 | 47 | SEQ ID NO. | 4308 |
| (N20)NGG | 11 | 36595004 | + | AGAAGCTCAAAAGGAAAAGAAGG | 3 | 24 | 430 | SEQ ID NO. | 4309 |
| (N20)NGG | 11 | 36595016 | + | GGAAAAGAAGGATTCCTTTGAGG | 1 | 8 | 108 | SEQ ID NO. | 4310 |
| (N20)NGG | 11 | 36595017 | + | GAAAAGAAGGATTCCTTTGAGGG | 1 | 11 | 268 | SEQ ID NO. | 4311 |
| (N20)NGG | 11 | 36595018 | + | AAAAGAAGGATTCCTTTGAGGGG | 1 | 7 | 95 | SEQ ID NO. | 4312 |
| (N20)NGG | 11 | 36595031 | + | CTTTGAGGGGAAACCCTCTCTGG | 1 | 3 | 23 | SEQ ID NO. | 4313 |
| (N20)NGG | 11 | 36595052 | + | GGAGCAATCTCCAGCAGTCCTGG | 1 | 1 | 24 | SEQ ID NO. | 4314 |
| (N20)NGG | 11 | 36595058 | + | ATCTCCAGCAGTCCTGACAAGG | 1 | 3 | 46 | SEQ ID NO. | 4315 |
| (N20)NGG | 11 | 36595065 | + | GCAGTCCTGACAAGGCTGATGG | 1 | 2 | 44 | SEQ ID NO. | 4316 |
| (N20)NGG | 11 | 36595149 | + | CACGACAACGAGAAAGCAAGAGG | 1 | 1 | 19 | SEQ ID NO. | 4317 |
| (N20)NGG | 11 | 36595197 | + | CGACATCTCTGCCGCATCTGTGG | 1 | 1 | 9 | SEQ ID NO. | 4318 |
| (N20)NGG | 11 | 36595198 | + | GACATCTCTGCCGCATCTGTGGG | 1 | 1 | 14 | SEQ ID NO. | 4319 |
| (N20)NGG | 11 | 36595228 | + | TTAGAGCTGATGAGCACAACAGG | 1 | 2 | 26 | SEQ ID NO. | 4320 |
| (N20)NGG | 11 | 36595245 | + | AACAGAGATATCCAGTCCATGG | 1 | 2 | 83 | SEQ ID NO. | 4321 |
| (N20)NGG | 11 | 36595253 | + | ATATCCAGTCCATGGTCCTGTGG | 1 | 3 | 21 | SEQ ID NO. | 4322 |
| (N20)NGG | 11 | 36595257 | + | CCAGTCCATGGTCCTGTGGATGG | 1 | 5 | 41 | SEQ ID NO. | 4323 |
| (N20)NGG | 11 | 36595269 | + | CCTGTGGATGGTAAAACCCTAGG | 1 | 3 | 43 | SEQ ID NO. | 4324 |
| (N20)NGG | 11 | 36595286 | + | CCTAGGCCTTTTACGAAACAAGG | 1 | 1 | 24 | SEQ ID NO. | 4325 |
| (N20)NGG | 11 | 36595306 | + | AGGAAAAGAGAGCTACTTCCTGG | 1 | 2 | 55 | SEQ ID NO. | 4326 |
| (N20)NGG | 11 | 36595310 | + | AAAGAGAGCTACTTCCTGGCCGG | 1 | 2 | 48 | SEQ ID NO. | 4327 |
| (N20)NGG | 11 | 36595325 | + | CTGGCCGGACCTCATTGCCAAGG | 1 | 1 | 18 | SEQ ID NO. | 4328 |
| (N20)NGG | 11 | 36595333 | + | ACCTCATTGCCAAGGTTTTCCGG | 1 | 4 | 35 | SEQ ID NO. | 4329 |
| (N20)NGG | 11 | 36595346 | + | GGTTTTCCGGATCGATGTGAAGG | 1 | 1 | 1 | SEQ ID NO. | 4330 |
| (N20)NGG | 11 | 36595393 | + | CTGAGTTCTGCCATAACTGCTGG | 1 | 2 | 40 | SEQ ID NO. | 4331 |
| (N20)NGG | 11 | 36595408 | + | ACTGCTGGAGCATCATGCACAGG | 1 | 4 | 26 | SEQ ID NO. | 4332 |
| (N20)NGG | 11 | 36595433 | + | GTTTAGCAGTGCCCCATGTGAGG | 1 | 1 | 13 | SEQ ID NO. | 4333 |
| (N20)NGG | 11 | 36595447 | + | CATGTGAGGTTTACTTCCCGAGG | 1 | 1 | 12 | SEQ ID NO. | 4334 |
| (N20)NGG | 11 | 36595460 | + | CTTCCCGAGGAACGTGACCATGG | 1 | 3 | 24 | SEQ ID NO. | 4335 |

FIG. 13

| site_type | site_chr omosome | site_start_ nucleotide | site_s trand | target_site_sequence_with_NGG | genome_wide_ hits_with_1_ or_less_mism atches | genome_wide_ hits_with_2_ or_less_mism atches | genome_wide_ hits_with_3_ or_less_mism atches | |
|---|---|---|---|---|---|---|---|---|
| (N20)NGG | 11 | 36595465 | + | CGAGGAACGTGACCATGGAGTGG |   | 2 | 15 | SEQ ID NO. 4336 |
| (N20)NGG | 11 | 36595510 | + | ACATCTGCAACACTGCCCGTCGG | 1 | 1 | 12 | SEQ ID NO. 4337 |
| (N20)NGG | 11 | 36595511 | + | CATCTGCAACACTGCCCGTCGGG |   | 1 | 9 | SEQ ID NO. 4338 |
| (N20)NGG | 11 | 36595512 | + | ATCTGCAACACTGCCCGTCGGGG |   | 1 | 10 | SEQ ID NO. 4339 |
| (N20)NGG | 11 | 36595522 | + | CTGCCCGTCGGGACTCAAGAGG |   | 1 | 14 | SEQ ID NO. 4340 |
| (N20)NGG | 11 | 36595616 | + | TCAGCACAAGAGAAGAGCTCAGG |   | 6 | 78 | SEQ ID NO. 4341 |
| (N20)NGG | 11 | 36595621 | + | ACAAGAAGAGAGCTCAGGCAAGG | 1 | 9 | 140 | SEQ ID NO. 4342 |
| (N20)NGG | 11 | 36595634 | + | TCAGGCAAGATCAGCAGCAAGG |   | 2 | 57 | SEQ ID NO. 4343 |
| (N20)NGG | 11 | 36595697 | + | TAGTACCAAGCTCCTTGCAGTGG | 1 | 2 | 25 | SEQ ID NO. 4344 |
| (N20)NGG | 11 | 36595754 | + | CCAGATCTGTGAACACATTCTGG | 2 | 6 | 47 | SEQ ID NO. 4345 |
| (N20)NGG | 11 | 36595766 | + | ACACATTCTGGCTGACCCTGTGG |   | 4 | 40 | SEQ ID NO. 4346 |
| (N20)NGG | 11 | 36595795 | + | ACTGTAAGCATGTCTTTTGCCGG | 1 | 6 | 108 | SEQ ID NO. 4347 |
| (N20)NGG | 11 | 36595796 | + | CTGTAAGCATGTCTTTTGCCGGG | 1 | 2 | 51 | SEQ ID NO. 4348 |
| (N20)NGG | 11 | 36595826 | + | TCTCAGATGCCTCAAAGTCATGG | 1 | 4 | 63 | SEQ ID NO. 4349 |
| (N20)NGG | 11 | 36595827 | + | CTCAGATGCCTCAAAGTCATGGG | 1 | 3 | 49 | SEQ ID NO. 4350 |
| (N20)NGG | 11 | 36595874 | + | TCCAGTCTTCCCTACTGACCTGG | 1 | 2 | 33 | SEQ ID NO. 4351 |
| (N20)NGG | 11 | 36595919 | + | GAGCGTCTTGAATTCCCTGATGG | 1 | 1 | 19 | SEQ ID NO. 4352 |
| (N20)NGG | 11 | 36595949 | + | TCCAGCAAAGAGTGCAATGAGG | 1 | 4 | 46 | SEQ ID NO. 4353 |
| (N20)NGG | 11 | 36595952 | + | AGCAAAAGAGTCAATGAGGAGG | 2 | 4 | 92 | SEQ ID NO. 4354 |
| (N20)NGG | 11 | 36595961 | + | GTGCAATGAGGAGGTCAGTTTGG | 1 | 3 | 36 | SEQ ID NO. 4355 |
| (N20)NGG | 11 | 36595994 | + | TCACCACATCTCAAGTCACAAGG | 1 | 2 | 48 | SEQ ID NO. 4356 |
| (N20)NGG | 11 | 36596028 | + | ATTTTTGTGCACATTAATAAAGG | 1 | 11 | 171 | SEQ ID NO. 4357 |
| (N20)NGG | 11 | 36596029 | + | TTTTTGTGCACATTAATAAAGGG | 1 | 9 | 142 | SEQ ID NO. 4358 |
| (N20)NGG | 11 | 36596030 | + | TTTTGTGCACATTAATAAAGGGG | 1 | 4 | 85 | SEQ ID NO. 4359 |
| (N20)NGG | 11 | 36596031 | + | TTTGTGCACATTAATAAAGGGGG | 1 | 3 | 57 | SEQ ID NO. 4360 |
| (N20)NGG | 11 | 36596035 | + | TGCACATTAATAAAGGGGGCCGG | 1 | 1 | 18 | SEQ ID NO. 4361 |
| (N20)NGG | 11 | 36596065 | + | AACATCTTCTGTCGCTGACTCGG | 1 | 1 | 21 | SEQ ID NO. 4362 |
| (N20)NGG | 11 | 36596083 | + | CTCGGAGAGCTCAGAAGCACCGG | 2 | 2 | 28 | SEQ ID NO. 4363 |
| (N20)NGG | 11 | 36596089 | + | GAGCTCAGAAGCACCGGCTGAGG | 2 | 5 | 54 | SEQ ID NO. 4364 |
| (N20)NGG | 11 | 36596090 | + | AGCTCAGAAGCACCGGCTGAGGG | 1 | 4 | 23 | SEQ ID NO. 4365 |
| (N20)NGG | 11 | 36596133 | + | GCCTTTGCTGACAAAGAAGAAGG | 2 | 4 | 63 | SEQ ID NO. 4366 |
| (N20)NGG | 11 | 36596136 | + | TTTGCTGACAAAGAAGAAGGTGG | 2 | 11 | 153 | SEQ ID NO. 4367 |
| (N20)NGG | 11 | 36596174 | + | GTGCATGACCTTGTTCCTGCTGG | 1 | 2 | 26 | SEQ ID NO. 4368 |

FIG. 13 cont.

| site type | site chromosome | site start nucleotide | site strand | target site sequence with NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 11 | 36596182 | + | CCTTGTTCCTGCTGGCTCTGAGG | 1 | 19 | 168 | SEQ ID NO. 4369 |
| (N20)NGG | 11 | 36596183 | + | CTTGTTCCTGCTGGCTCTGAGGG | 1 | 8 | 75 | SEQ ID NO. 4370 |
| (N20)NGG | 11 | 36596188 | + | TCCTGCTGGCTCTGAGGGCGAGG | 1 | 6 | 64 | SEQ ID NO. 4371 |
| (N20)NGG | 11 | 36596200 | + | TGAGGGCGAGAATGAGCACAGG | 1 | 4 | 38 | SEQ ID NO. 4372 |
| (N20)NGG | 11 | 36596216 | + | GCACAGGCAAGCTGATGAGCTGG | 1 | 5 | 35 | SEQ ID NO. 4373 |
| (N20)NGG | 11 | 36596219 | + | CAGGCAAGCTGATGAGCTGGAGG | 1 | 5 | 67 | SEQ ID NO. 4374 |
| (N20)NGG | 11 | 36596231 | + | TGAGCTGGAGGCCATCATGCAGG | 1 | 8 | 235 | SEQ ID NO. 4375 |
| (N20)NGG | 11 | 36596232 | + | GAGCTGGAGGCCATCATGCAGGG | 3 | 247 | 3384 | SEQ ID NO. 4376 |
| (N20)NGG | 11 | 36596237 | + | GGAGGCCATCATGCAGGGAAAGG | 1 | 1 | 66 | SEQ ID NO. 4377 |
| (N20)NGG | 11 | 36596238 | + | GAGGCCATCATGCAGGGAAAGGG | 1 | 6 | 65 | SEQ ID NO. 4378 |
| (N20)NGG | 11 | 36596244 | + | ATCATGCAGGGAAAGGGCTCTGG | 1 | 3 | 42 | SEQ ID NO. 4379 |
| (N20)NGG | 11 | 36596267 | + | CCTGCAGCCAGCTGTTTGCTTGG | 2 | 7 | 76 | SEQ ID NO. 4380 |
| (N20)NGG | 11 | 36596320 | + | GTCAGTACCACAAGATGTACAGG | 1 | 1 | 13 | SEQ ID NO. 4381 |
| (N20)NGG | 11 | 36596340 | + | AGGACTGTGAAAGCCATCACAGG | 1 | 2 | 41 | SEQ ID NO. 4382 |
| (N20)NGG | 11 | 36596341 | + | GGACTGTGAAAGCCATCACAGGG | 1 | 2 | 33 | SEQ ID NO. 4383 |
| (N20)NGG | 11 | 36596374 | + | TTCAGCCTTTGCATGCCCTTCGG | 1 | 5 | 58 | SEQ ID NO. 4384 |
| (N20)NGG | 11 | 36596387 | + | TGCCCTTTCGGAATGCTGAGAAGG | 1 | 2 | 41 | SEQ ID NO. 4385 |
| (N20)NGG | 11 | 36596400 | + | GCTGAGAAGGTACTTCTGCCAGG | 1 | 2 | 53 | SEQ ID NO. 4386 |
| (N20)NGG | 11 | 36596419 | + | CAGGCTACCACCACTTTGAGTGG | 2 | 2 | 37 | SEQ ID NO. 4387 |
| (N20)NGG | 11 | 36596460 | + | GTGTCTTCCAGCACTGATGTTGG | 1 | 3 | 41 | SEQ ID NO. 4388 |
| (N20)NGG | 11 | 36596472 | + | ACTGATGTTGGCATTATTGATGG | 2 | 13 | 67 | SEQ ID NO. 4389 |
| (N20)NGG | 11 | 36596473 | + | CTGATGTTGGCATTATTGATGGG | 1 | 7 | 68 | SEQ ID NO. 4390 |
| (N20)NGG | 11 | 36596498 | + | GGCATTATTGATGGGCGTGTCTGG | 1 | 2 | 25 | SEQ ID NO. 4391 |
| (N20)NGG | 11 | 36596513 | + | GTCTGACTATCATCCTCTGTGG | 1 | 2 | 17 | SEQ ID NO. 4392 |
| (N20)NGG | 11 | 36596530 | + | CTCTGTGGATGATTACCCAGTGG | 1 | 3 | 31 | SEQ ID NO. 4393 |
| (N20)NGG | 11 | 36596552 | + | CAGTGGACACCATTGCAAAGAGG | 1 | 3 | 39 | SEQ ID NO. 4394 |
| (N20)NGG | 11 | 36596567 | + | GTTCCGCTATGATTCAGCTTTGG | 2 | 1 | 12 | SEQ ID NO. 4395 |
| (N20)NGG | 11 | 36596573 | + | AGCTTTGGTGTCTTTGATGG | 1 | 7 | 76 | SEQ ID NO. 4396 |
| (N20)NGG | 11 | 36596588 | + | GGTGTCTCTTTGATGGACATGG | 1 | 3 | 44 | SEQ ID NO. 4397 |
| (N20)NGG | 11 | 36596592 | + | GGACATGGAAGAAGACATCTTGG | 1 | 3 | 73 | SEQ ID NO. 4398 |
| (N20)NGG | 11 | 36596628 | + | ATGAAGAAGACATCTTGAAGG | 1 | 3 | 87 | SEQ ID NO. 4399 |
| (N20)NGG | 11 | 36596628 | + | GACCTTGATGATTACCTGAATGG | 1 | 3 | 23 | SEQ ID NO. 4400 |
| (N20)NGG | 11 | 36596642 | + | CCTGAATGGCCCCTTCACTGTGG | 1 | 3 | 46 | SEQ ID NO. 4401 |

| site type | site chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 11 | 36596645 | + | GAATGGCCCCTTCACTGTGTGG | 1 | 1 | 31 | SEQ ID NO. 4402 |
| (N20)NGG | 11 | 36596651 | + | CCCCTTCACTGTGGTGGTGAAGG | | 2 | 62 | SEQ ID NO. 4403 |
| (N20)NGG | 11 | 36596664 | + | GTGGTGAAGGAGTCTTGTGATGG | 1 | 2 | 30 | SEQ ID NO. 4404 |
| (N20)NGG | 11 | 36596669 | + | GAAGGAGTCTTGTGATGGAATGG | 2 | 5 | 69 | SEQ ID NO. 4405 |
| (N20)NGG | 11 | 36596670 | + | AAGGAGTCTTGTGATGGAATGGG | 1 | 4 | 63 | SEQ ID NO. 4406 |
| (N20)NGG | 11 | 36596691 | + | GGAGACGTGAGTGAGAAGCATGG | 1 | 2 | 58 | SEQ ID NO. 4407 |
| (N20)NGG | 11 | 36596692 | + | GAGACGTGAGTGAGAAGCATGGG | 1 | 3 | 33 | SEQ ID NO. 4408 |
| (N20)NGG | 11 | 36596697 | + | GTGAGTGAGAAGCATGGGACTGG | 1 | 5 | 111 | SEQ ID NO. 4409 |
| (N20)NGG | 11 | 36596698 | + | TGAGTGAAGCATGGGAGTGGG | 1 | 6 | 95 | SEQ ID NO. 4410 |
| (N20)NGG | 11 | 36596717 | + | TGGGCCTGTAGTTCCAGAAAAGG | 1 | 4 | 62 | SEQ ID NO. 4411 |
| (N20)NGG | 11 | 36596840 | + | CAAGCCATTGTGCCTTATGCTGG | 1 | 4 | 34 | SEQ ID NO. 4412 |
| (N20)NGG | 11 | 36596899 | + | TGAGTCCTCTCATTGCTGAGAGG | 1 | 12 | 64 | SEQ ID NO. 4413 |
| (N20)NGG | 11 | 36596900 | + | GAGTCCTCTCATTGCTGAGAGGG | 1 | 4 | 47 | SEQ ID NO. 4414 |
| (N20)NGG | 11 | 36596903 | + | TCCTCTCATTGCTGAGAGGGAGG | 1 | 5 | 58 | SEQ ID NO. 4415 |
| (N20)NGG | 11 | 36596936 | + | CAGTGAATTAATGCTTGAGCTGG | 1 | 3 | 44 | SEQ ID NO. 4416 |
| (N20)NGG | 11 | 36596937 | + | AGTGAATTAATGCTTGAGCTGGG | 1 | 2 | 71 | SEQ ID NO. 4417 |
| (N20)NGG | 11 | 36596940 | + | GAATTAATGCTTGAGCTGGGAGG | 1 | 3 | 74 | SEQ ID NO. 4418 |
| (N20)NGG | 11 | 36596950 | + | TTGAGCTGGGAGGCATTCTCCGG | 1 | 2 | 44 | SEQ ID NO. 4419 |
| (N20)NGG | 11 | 36596971 | + | GGACTTTCAAGTTCATCTTCAGG | 1 | 3 | 48 | SEQ ID NO. 4420 |
| (N20)NGG | 11 | 36596972 | + | GACTTTCAAGTTCATCTTCAGGG | 1 | 4 | 98 | SEQ ID NO. 4421 |
| (N20)NGG | 11 | 36596973 | + | ACTTTCAAGTTCATCTTCAGGGG | 1 | 7 | 69 | SEQ ID NO. 4422 |
| (N20)NGG | 11 | 36596979 | + | AAGTTCATCTTCAGGGGCACCGG | 1 | 3 | 35 | SEQ ID NO. 4423 |
| (N20)NGG | 11 | 36597001 | + | GCTATGATGAAAAACTTGTGCGG | 1 | 2 | 53 | SEQ ID NO. 4424 |
| (N20)NGG | 11 | 36597002 | + | CTATGATGAAAAACTTGTGCCGG | 1 | 2 | 42 | SEQ ID NO. 4425 |
| (N20)NGG | 11 | 36597008 | + | TGAAAAACTTGTGCGGGAAGTGG | 1 | 2 | 18 | SEQ ID NO. 4426 |
| (N20)NGG | 11 | 36597012 | + | AAACTTGTGCGGGAAGTGGAAGG | 1 | 1 | 20 | SEQ ID NO. 4427 |
| (N20)NGG | 11 | 36597020 | + | GCGGGAAGTGGAAGGCCTCGAGG | 1 | 1 | 27 | SEQ ID NO. 4428 |
| (N20)NGG | 11 | 36597027 | + | GTGGAAGGCCTCGAGGCTTCTGG | 1 | 1 | 17 | SEQ ID NO. 4429 |
| (N20)NGG | 11 | 36597068 | + | TCTTTGTGATGCCACCCGTCTGG | 1 | 2 | 16 | SEQ ID NO. 4430 |
| (N20)NGG | 11 | 36597125 | + | CAGAAGCCATGCTGAGAACCTGG | 3 | 7 | 92 | SEQ ID NO. 4431 |
| (N20)NGG | 11 | 36597137 | + | TGAGAACCTGGAACGTTATGAGG | 1 | 1 | 10 | SEQ ID NO. 4432 |
| (N20)NGG | 11 | 36597142 | + | ACCTGGAACGTTATGAGGTCTGG | 1 | 2 | 11 | SEQ ID NO. 4433 |
| (N20)NGG | 11 | 36597170 | + | CAACCCTTACCATGAGTCTGTGG | 1 | 1 | 19 | SEQ ID NO. 4434 |

| site_type | site_chr omosome | site_start_ nucleotide | site_s trand | target_site_sequence_with_NGG | genome_wide_ hits_with_1_ or_less_mism atches | genome_wide_ hits_with_2_ or_less_mism atches | genome_wide_ hits_with_3_ or_less_mism atches | |
|---|---|---|---|---|---|---|---|---|
| (N20)NGG | 11 | 36597181 | + | ATGAGTCTGTGGAAGAACTGCGG | | 1 | 4 | 75 SEQ ID NO. 4435 |
| (N20)NGG | 11 | 36597182 | + | TGAGTCTGTGGAAGAACTCCGGG | | 1 | 4 | 70 SEQ ID NO. 4436 |
| (N20)NGG | 11 | 36597187 | + | CTGTGGAAGAACTGCGGATCGG | | 1 | 1 | 26 SEQ ID NO. 4437 |
| (N20)NGG | 11 | 36597188 | + | TGTGGAAGAACTGCGGATCGGG | | 1 | 1 | 16 SEQ ID NO. 4438 |
| (N20)NGG | 11 | 36597195 | + | GAACTGCGGATCGGGTGAAAGG | | 1 | 1 | 29 SEQ ID NO. 4439 |
| (N20)NGG | 11 | 36597196 | + | AACTGCGGATCGGGTGAAAGGG | | 1 | 1 | 5 SEQ ID NO. 4440 |
| (N20)NGG | 11 | 36597197 | + | ACTGCGGATCGGGTGAAAGGGG | | 1 | 1 | 10 SEQ ID NO. 4441 |
| (N20)NGG | 11 | 36597258 | + | GATGCACTCCACTGTGACATTGG | | 1 | 2 | 33 SEQ ID NO. 4442 |
| (N20)NGG | 11 | 36597300 | + | AAGATCTTCCAGCTAGAGATAGG | | 1 | 3 | 39 SEQ ID NO. 4443 |
| (N20)NGG | 11 | 36597301 | + | AGATCTTCCAGCTAGAGATAGGG | | 1 | 6 | 55 SEQ ID NO. 4444 |
| (N20)NGG | 11 | 36597302 | + | GATCTTCCAGCTAGAGATAGGGG | | 2 | 5 | 50 SEQ ID NO. 4445 |
| (N20)NGG | 11 | 36597335 | + | GAATCCCAATGCTTCCAAAGAGG | | 1 | 2 | 31 SEQ ID NO. 4446 |
| (N20)NGG | 11 | 36597340 | + | CCAATGCTTCCAAAGAGGAAAGG | | 1 | 7 | 60 SEQ ID NO. 4447 |
| (N20)NGG | 11 | 36597346 | + | CTTCCAAAGAGGAAAGGAAAAGG | | 1 | 41 | 458 SEQ ID NO. 4448 |
| (N20)NGG | 11 | 36597349 | + | CCAAAGAGGAAAGGAAAAGGTGG | | 2 | 39 | 523 SEQ ID NO. 4449 |
| (N20)NGG | 11 | 36597353 | + | AGAGAAAGGAAAAGGTGCAGG | | 3 | 11 | 305 SEQ ID NO. 4450 |
| (N20)NGG | 11 | 36597362 | + | GAAAAGTGGCAGGCACAAGCATCTCCGG | | 1 | 5 | 53 SEQ ID NO. 4451 |
| (N20)NGG | 11 | 36597376 | + | CCACACTGGACAAGCATCTCCGG | | 1 | 3 | 24 SEQ ID NO. 4452 |
| (N20)NGG | 11 | 36597406 | + | TGAACCTCAAACCAATCATGAGG | | 1 | 1 | 35 SEQ ID NO. 4453 |
| (N20)NGG | 11 | 36597414 | + | AAACCAATCATGAGGATGAATGG | | 1 | 5 | 72 SEQ ID NO. 4454 |
| (N20)NGG | 11 | 36597427 | + | GGATGAATGGCAACTTTGCCAGG | | 1 | 3 | 24 SEQ ID NO. 4455 |
| (N20)NGG | 11 | 36597452 | + | GCTCATGACCAAAGAGACTGTGG | | 1 | 2 | 39 SEQ ID NO. 4456 |
| (N20)NGG | 11 | 36597482 | + | TTGTGAGTTAATTCCTTCCGAGG | | 1 | 1 | 16 SEQ ID NO. 4457 |
| (N20)NGG | 11 | 36597487 | + | AGTTAATTCCTTCCGAGGAGAGG | | 1 | 1 | 13 SEQ ID NO. 4458 |
| (N20)NGG | 11 | 36597494 | + | TCCTTCCGAGGAGGCACCAGG | | 1 | 1 | 28 SEQ ID NO. 4459 |
| (N20)NGG | 11 | 36597502 | + | AGGAGAGGCACGAGGCTCTGAGG | | 1 | 3 | 69 SEQ ID NO. 4460 |
| (N20)NGG | 11 | 36597503 | + | GGAGAGGCACGAGGCTCTGAGGG | | 1 | 1 | 43 SEQ ID NO. 4461 |
| (N20)NGG | 11 | 36597512 | + | CGAGGCTCTGAGGGAGCTCATGG | | 1 | 3 | 43 SEQ ID NO. 4462 |
| (N20)NGG | 11 | 36597541 | + | ACCTGAAGATGAAACCAGTATGG | | 1 | 3 | 36 SEQ ID NO. 4463 |
| (N20)NGG | 11 | 36597643 | + | TTTCTACGAAGTTCAAGTATAGG | | 1 | 2 | 51 SEQ ID NO. 4464 |
| (N20)NGG | 11 | 36597650 | + | GAAGTTCAAGTATAGGTATGAGG | | 2 | 3 | 35 SEQ ID NO. 4465 |
| (N20)NGG | 11 | 36597651 | + | AAGTTCAAGTATAGGTATGAGGG | | 1 | 3 | 35 SEQ ID NO. 4466 |
| (N20)NGG | 11 | 36597683 | + | CAATTATTTTCACAAAACCCTGG | | 1 | 5 | 94 SEQ ID NO. 4467 |

FIG. 13 cont.

| site type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 11 | 36597709 | + | ATGTTCCTGAAATTATTGAGAGG | 1 | 4 | 79 | SEQ ID NO. 4468 |
| (N20)NGG | 11 | 36597710 | + | TGTTCCTGAAATTATTGAGAGGG |  | 8 | 155 | SEQ ID NO. 4469 |
| (N20)NGG | 11 | 36597714 | + | CCTGAAATTATTGAGAGGGATGG | 1 | 2 | 50 | SEQ ID NO. 4470 |
| (N20)NGG | 11 | 36597723 | + | ATTGAGAGGGATGGCTCCATTGG | 1 | 2 | 17 | SEQ ID NO. 4471 |
| (N20)NGG | 11 | 36597724 | + | TTGAGAGGGATGGCTCCATTGGG | 1 | 1 | 17 | SEQ ID NO. 4472 |
| (N20)NGG | 11 | 36597725 | + | TGAGAGGGATGGCTCCATTGGGG | 1 | 4 | 41 | SEQ ID NO. 4473 |
| (N20)NGG | 11 | 36597730 | + | GGGATGGCTCCATTGGGCATGG | 1 | 4 | 21 | SEQ ID NO. 4474 |
| (N20)NGG | 11 | 36597731 | + | GGATGGCTCCATTGGGCATGGG | 1 | 1 | 19 | SEQ ID NO. 4475 |
| (N20)NGG | 11 | 36597740 | + | CATTGGGCATGGCAAGTGAGG | 1 | 3 | 33 | SEQ ID NO. 4476 |
| (N20)NGG | 11 | 36597741 | + | ATTGGGCATGGCAAGTGAGGG | 1 | 3 | 41 | SEQ ID NO. 4477 |
| (N20)NGG | 11 | 36597753 | + | GCAAGTGAGGGAAATGAGTCTGG | 1 | 5 | 114 | SEQ ID NO. 4478 |
| (N20)NGG | 11 | 36597769 | + | AGTCTGGTAACAAACTGTTTAGG | 1 | 4 | 43 | SEQ ID NO. 4479 |
| (N20)NGG | 11 | 36597778 | + | ACAAACTGTTTAGGCGCTTCCGG | 1 | 1 | 16 | SEQ ID NO. 4480 |
| (N20)NGG | 11 | 36597793 | + | GCTTCCGGAAAATGAATGCCAGG | 1 | 1 | 17 | SEQ ID NO. 4481 |
| (N20)NGG | 11 | 36597815 | + | GCAGTCCAAATGCTATGAGATGG | 1 | 3 | 34 | SEQ ID NO. 4482 |
| (N20)NGG | 11 | 36597838 | + | AAGATGTCCTGAAACACCACTGG | 1 | 1 | 36 | SEQ ID NO. 4483 |
| (N20)NGG | 11 | 36597900 | + | CATAATGCATTAAAAACCTCTGG | 1 | 3 | 60 | SEQ ID NO. 4484 |
| (N20)NGG | 11 | 36597901 | + | ATAATGCATTAAAAACCTCTGGG | 2 | 8 | 86 | SEQ ID NO. 4485 |
| (N20)NGG | 11 | 36597920 | + | TGGGTTTACCATGAACCCTCAGG | 1 | 3 | 17 | SEQ ID NO. 4486 |
| (N20)NGG | 11 | 36597930 | + | ATGAACCCTCAGGCAAGCTTAGG | 1 | 2 | 27 | SEQ ID NO. 4487 |
| (N20)NGG | 11 | 36597931 | + | TGAACCCTCAGGCAAGCTTAGGG | 1 | 1 | 17 | SEQ ID NO. 4488 |
| (N20)NGG | 11 | 36597932 | + | GAACCCTCAGGCAAGCTTAGGGG | 1 | 2 | 16 | SEQ ID NO. 4489 |
| (N20)NGG | 11 | 36597942 | + | GCAAGCTTAGGGGACCCATTAGG | 1 | 2 | 12 | SEQ ID NO. 4490 |
| (N20)NGG | 11 | 36597950 | + | AGGGGACCCATTAGGCATAGAGG | 2 | 3 | 22 | SEQ ID NO. 4491 |
| (N20)NGG | 11 | 36597959 | + | ATTAGGCATAGAGGACTCTCTGG | 1 | 1 | 20 | SEQ ID NO. 4492 |
| (N20)NGG | 11 | 36597977 | + | TCTGGAAAGCCAAGATTCAATGG | 1 | 7 | 61 | SEQ ID NO. 4493 |
| (N20)NGG | 11 | 36594861 | - | TCCCAAGGTGGGTGGGAAAGAGG | 1 | 6 | 90 | SEQ ID NO. 4494 |
| (N20)NGG | 11 | 36594868 | - | AACTGAGTCCCAAGGTGGGTGGG | 1 | 6 | 113 | SEQ ID NO. 4495 |
| (N20)NGG | 11 | 36594869 | - | GAACTGAGTCCCAAGGTGGGTGG | 2 | 6 | 82 | SEQ ID NO. 4496 |
| (N20)NGG | 11 | 36594872 | - | GCAGAACTGAGTCCCAAGGTGG | 1 | 4 | 61 | SEQ ID NO. 4497 |
| (N20)NGG | 11 | 36594873 | - | GGCAGAACTGAGTCCCAAGGTGG | 1 | 6 | 100 | SEQ ID NO. 4498 |
| (N20)NGG | 11 | 36594876 | - | TGGGGCAGAACTGAGTCCCAAGG | 1 | 5 | 98 | SEQ ID NO. 4499 |
| (N20)NGG | 11 | 36594894 | - | TGGGTGCTGAATTTCATCTGGGG | 2 | 8 | 65 | SEQ ID NO. 4500 |

FIG. 13 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 11 | 36594895 | - | GTGGGTGCTGAATTTCATCTGGG | 2 | 2 | 49 | SEQ ID NO. 4501 |
| (N20)NGG | 11 | 36594896 | - | TGTGGGTGCTGAATTTCATCTGG | 1 | 4 | 38 | SEQ ID NO. 4502 |
| (N20)NGG | 11 | 36594913 | - | ATTCTGAAAATTTAATATGTGGG | 1 | 22 | 290 | SEQ ID NO. 4503 |
| (N20)NGG | 11 | 36594914 | - | CATTCTGAAAATTTAATATGTGG | 3 | 11 | 173 | SEQ ID NO. 4504 |
| (N20)NGG | 11 | 36594952 | - | TCTTTTCAAAGGATCTCACCCGG | 1 | 2 | 51 | SEQ ID NO. 4505 |
| (N20)NGG | 11 | 36594963 | - | TTCTTCAGGTGTCTTTTCAAAGG | 2 | 12 | 161 | SEQ ID NO. 4506 |
| (N20)NGG | 11 | 36594977 | - | TTTTTCCTTTTGAGCTTCTTCAGG | 1 | 11 | 187 | SEQ ID NO. 4507 |
| (N20)NGG | 11 | 36595008 | - | CAGAGAGGGTTTCCCCTCAAAGG | 1 | 4 | 28 | SEQ ID NO. 4508 |
| (N20)NGG | 11 | 36595022 | - | GCTGGAGATTGCTCCAGAGAGGG | 1 | 4 | 56 | SEQ ID NO. 4509 |
| (N20)NGG | 11 | 36595023 | - | TGCTGGAGATTGCTCCAGAGAGG | 1 | 2 | 43 | SEQ ID NO. 4510 |
| (N20)NGG | 11 | 36595040 | - | TCAGCCTTGTCCAGGACTGCTGG | 1 | 4 | 49 | SEQ ID NO. 4511 |
| (N20)NGG | 11 | 36595048 | - | TCTGACCATCAGCCTTGTCCAGG | 2 | 2 | 47 | SEQ ID NO. 4512 |
| (N20)NGG | 11 | 36595073 | - | AACAATGGCTGAGTTGGGACTGG | 1 | 5 | 52 | SEQ ID NO. 4513 |
| (N20)NGG | 11 | 36595078 | - | CTTTTAACAATGGCTGAGTTGGG | 1 | 6 | 95 | SEQ ID NO. 4514 |
| (N20)NGG | 11 | 36595079 | - | GCTTTTAACAATGGCTGAGTTGG | 1 | 3 | 58 | SEQ ID NO. 4515 |
| (N20)NGG | 11 | 36595088 | - | TTAGGGTGGGCTTTTAACAATGG | 1 | 2 | 34 | SEQ ID NO. 4516 |
| (N20)NGG | 11 | 36595101 | - | TTTCTTTGAAAACTTAGGGTGGG | 1 | 13 | 130 | SEQ ID NO. 4517 |
| (N20)NGG | 11 | 36595102 | - | ATTTCTTTGAAAACTTAGGGTGG | 1 | 5 | 108 | SEQ ID NO. 4518 |
| (N20)NGG | 11 | 36595105 | - | GAAATTTCTTTGAAAACTTAGGG | 2 | 22 | 293 | SEQ ID NO. 4519 |
| (N20)NGG | 11 | 36595106 | - | TGAAATTTCTTTGAAAACTTAGG | 1 | 22 | 312 | SEQ ID NO. 4520 |
| (N20)NGG | 11 | 36595159 | - | GATGTCGAAGGTTGGCTTGATGG | 1 | 3 | 18 | SEQ ID NO. 4521 |
| (N20)NGG | 11 | 36595167 | - | GCGGCAGAGATGTCGAAGGTTGG | 1 | 1 | 6 | SEQ ID NO. 4522 |
| (N20)NGG | 11 | 36595171 | - | AGATGCGGCAGAGATGTCGAAGG | 1 | 2 | 15 | SEQ ID NO. 4523 |
| (N20)NGG | 11 | 36595186 | - | TAAAAGAATTCCCACAGATGCGG | 1 | 7 | 91 | SEQ ID NO. 4524 |
| (N20)NGG | 11 | 36595235 | - | CCATCCACAGGACCATGGACTGG | 1 | 5 | 75 | SEQ ID NO. 4525 |
| (N20)NGG | 11 | 36595240 | - | TTTTACCATCCACAGGACCATGG | 1 | 3 | 46 | SEQ ID NO. 4526 |
| (N20)NGG | 11 | 36595247 | - | CCTAGGGTTTTACCATCCACAGG | 1 | 2 | 16 | SEQ ID NO. 4527 |
| (N20)NGG | 11 | 36595263 | - | CTTCTTTTCGTAAAAGGCCTAGG | 1 | 5 | 27 | SEQ ID NO. 4528 |
| (N20)NGG | 11 | 36595264 | - | CCTTCTTTTCGTAAAAGGCCTAG | 1 | 1 | 19 | SEQ ID NO. 4529 |
| (N20)NGG | 11 | 36595270 | - | TCTTTTCTTCTTTTCGTAAAAGG | 1 | 10 | 194 | SEQ ID NO. 4530 |
| (N20)NGG | 11 | 36595302 | - | CTTGGCAATGAGGTCCGGCCAGG | 1 | 1 | 10 | SEQ ID NO. 4531 |
| (N20)NGG | 11 | 36595307 | - | AAAACCTTGGCAATGAGGTCCGG | 1 | 4 | 52 | SEQ ID NO. 4532 |
| (N20)NGG | 11 | 36595312 | - | TCCGAAAACCTTGGCAATGAGG | 1 | 1 | 12 | SEQ ID NO. 4533 |

FIG. 13 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 11 | 36595320 | - | CACATCGATCCGGAAAACCTTGG | 1 | 2 | 6 | SEQ ID NO. 4534 |
| (N20)NGG | 11 | 36595330 | - | CATCTGCCTTCACATCGATCCGG | 1 | 2 | 11 | SEQ ID NO. 4535 |
| (N20)NGG | 11 | 36595363 | - | TATGGCAGAACTCAGTGGGTGG | 1 | 1 | 59 | SEQ ID NO. 4536 |
| (N20)NGG | 11 | 36595366 | - | AGTTATGCAGAACTCAGTGGGG | 1 | 4 | 34 | SEQ ID NO. 4537 |
| (N20)NGG | 11 | 36595367 | - | CAGTTATGGCAGAACTCAGTGGG | 1 | 3 | 39 | SEQ ID NO. 4538 |
| (N20)NGG | 11 | 36595368 | - | GCAGTTATGGCAGAACTCAGTGG | 1 | 4 | 57 | SEQ ID NO. 4539 |
| (N20)NGG | 11 | 36595381 | - | GCATGATGCTCCAGCAGTTATGG | 1 | 1 | 19 | SEQ ID NO. 4540 |
| (N20)NGG | 11 | 36595422 | - | CGGGAAGTAAACCTCACATGGGG | 1 | 1 | 16 | SEQ ID NO. 4541 |
| (N20)NGG | 11 | 36595423 | - | TCGGGAAGTAAACCTCACATGG | 1 | 2 | 18 | SEQ ID NO. 4542 |
| (N20)NGG | 11 | 36595424 | - | CTCGGGAAGTAAACCTCACATGG | 1 | 3 | 16 | SEQ ID NO. 4543 |
| (N20)NGG | 11 | 36595441 | - | ACTCCATGTCACGTTCCTCGG | 1 | 5 | 19 | SEQ ID NO. 4544 |
| (N20)NGG | 11 | 36595442 | - | CACTCCATGTCACGTTCCTCG | 1 | 3 | 28 | SEQ ID NO. 4545 |
| (N20)NGG | 11 | 36595455 | - | TGTGTGGGGTGCCACTCCATGG | 1 | 4 | 35 | SEQ ID NO. 4546 |
| (N20)NGG | 11 | 36595468 | - | TGTCACAGGATGGTGTGTGGGG | 2 | 5 | 97 | SEQ ID NO. 4547 |
| (N20)NGG | 11 | 36595469 | - | ATGTCACAGGATGGTGTGTGGG | 1 | 5 | 63 | SEQ ID NO. 4548 |
| (N20)NGG | 11 | 36595470 | - | GATGTCACAGGATGGTGTGTGG | 1 | 4 | 48 | SEQ ID NO. 4549 |
| (N20)NGG | 11 | 36595471 | - | AGAGTCACAGGATGATGGTGTGG | 1 | 5 | 57 | SEQ ID NO. 4550 |
| (N20)NGG | 11 | 36595478 | - | GTGTTGCAGATGTCACAGGATGG | 1 | 8 | 106 | SEQ ID NO. 4551 |
| (N20)NGG | 11 | 36595482 | - | GGCAGTGTTGCAGATGTCACAGG | 2 | 2 | 39 | SEQ ID NO. 4552 |
| (N20)NGG | 11 | 36595503 | - | CTTCCTCTTGAGTCCCGACGG | 1 | 3 | 13 | SEQ ID NO. 4553 |
| (N20)NGG | 11 | 36595504 | - | TCTTCCTCTTGAGTCCCGACGG | 1 | 2 | 24 | SEQ ID NO. 4554 |
| (N20)NGG | 11 | 36595535 | - | TTTTTGCTGAGCTGCAAGTTTGG | 1 | 2 | 52 | SEQ ID NO. 4555 |
| (N20)NGG | 11 | 36595576 | - | GCTGACGGGCTTGTCTTGCTTGG | 1 | 3 | 74 | SEQ ID NO. 4556 |
| (N20)NGG | 11 | 36595590 | - | AGCTCTTCTTCTTGTGCTGACGG | 2 | 3 | 38 | SEQ ID NO. 4557 |
| (N20)NGG | 11 | 36595591 | - | GAGCTCTTCTTCTTGTGCTGACGG | 1 | 2 | 44 | SEQ ID NO. 4558 |
| (N20)NGG | 11 | 36595653 | - | AAGATGTATCTTACTGCAGTTGG | 1 | 2 | 43 | SEQ ID NO. 4559 |
| (N20)NGG | 11 | 36595680 | - | GAAGTCCACTGCAAGGAGCTTGG | 1 | 3 | 26 | SEQ ID NO. 4560 |
| (N20)NGG | 11 | 36595687 | - | GCTCTGGGAAGTCCACTGCAAGG | 1 | 4 | 41 | SEQ ID NO. 4561 |
| (N20)NGG | 11 | 36595702 | - | TGGATTTCACAAAGTGCTCTGGG | 1 | 2 | 66 | SEQ ID NO. 4562 |
| (N20)NGG | 11 | 36595703 | - | ATGGATTTCACAAAGTGCTCTGG | 1 | 3 | 41 | SEQ ID NO. 4563 |
| (N20)NGG | 11 | 36595722 | - | TTCACAGATCGGCAGGAGATGG | 1 | 13 | 151 | SEQ ID NO. 4564 |
| (N20)NGG | 11 | 36595728 | - | AATGTGTTCACAGATCTGGCAGG | 1 | 4 | 43 | SEQ ID NO. 4565 |
| (N20)NGG | 11 | 36595732 | - | CCAGAATGTGTTCACAGATCTGG | 2 | 6 | 47 | SEQ ID NO. 4566 |

FIG. 13 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 11 | 36595759 | - | GCTTACAGTTGGTCTCCACAGGG | 1 | 1 | 23 | SEQ ID NO. 4567 |
| (N20)NGG | 11 | 36595760 | - | TGCTTACAGTTGGTCTCCACAGG | | 1 | 20 | SEQ ID NO. 4568 |
| (N20)NGG | 11 | 36595770 | - | GCAAAAGACATGCTTACAGTTGG | | 2 | 51 | SEQ ID NO. 4569 |
| (N20)NGG | 11 | 36595792 | - | GGCATCTGAGAATGCAGACCCGG | | 5 | 50 | SEQ ID NO. 4570 |
| (N20)NGG | 11 | 36595813 | - | AATAGCTGCCCATGACTTTGAGG | | 7 | 48 | SEQ ID NO. 4571 |
| (N20)NGG | 11 | 36595838 | - | AAGCATGATATCGGCAAGAGGG | 1 | 1 | 23 | SEQ ID NO. 4572 |
| (N20)NGG | 11 | 36595839 | - | GAAGCATGGATATCGGCAAGAGG | | 2 | 22 | SEQ ID NO. 4573 |
| (N20)NGG | 11 | 36595846 | - | CAGTAGGGAAGCATGGATATCGG | 1 | 2 | 47 | SEQ ID NO. 4574 |
| (N20)NGG | 11 | 36595853 | - | TCCAGGTCAGTAGGGAAGCATGG | 1 | 5 | 59 | SEQ ID NO. 4575 |
| (N20)NGG | 11 | 36595861 | - | CTGGACTTCCAGGTCAGTAGGG | 1 | 3 | 39 | SEQ ID NO. 4576 |
| (N20)NGG | 11 | 36595862 | - | ACTGGACTCTCCAGGTCAGTAGG | 2 | 5 | 17 | SEQ ID NO. 4577 |
| (N20)NGG | 11 | 36595870 | - | AGGACTTCACTGGACTCTCCAGG | 1 | 3 | 35 | SEQ ID NO. 4578 |
| (N20)NGG | 11 | 36595880 | - | ACGCTCAGAAAGGACTTCACTGG | 1 | 1 | 22 | SEQ ID NO. 4579 |
| (N20)NGG | 11 | 36595890 | - | GGAATTCAAGACGCTCAGAAAGG | 1 | 1 | 23 | SEQ ID NO. 4580 |
| (N20)NGG | 11 | 36595911 | - | TGCTGGACATTTCACCATCAGGG | 1 | 3 | 48 | SEQ ID NO. 4581 |
| (N20)NGG | 11 | 36595912 | - | TTGCTGGACATTTCACCATCAGG | 1 | 2 | 30 | SEQ ID NO. 4582 |
| (N20)NGG | 11 | 36595928 | - | TCCTCATTGACTCTTTTGCTGG | 1 | 3 | 33 | SEQ ID NO. 4583 |
| (N20)NGG | 11 | 36595975 | - | ATTCCTTGTGACTTGAGATGTGG | 1 | 3 | 32 | SEQ ID NO. 4584 |
| (N20)NGG | 11 | 36596032 | - | ACAGAAGATGTTGGCGGGGCCGG | 1 | 2 | 60 | SEQ ID NO. 4585 |
| (N20)NGG | 11 | 36596036 | - | AGCGACAGAAGATGTTGGCGGGG | 1 | 2 | 21 | SEQ ID NO. 4586 |
| (N20)NGG | 11 | 36596037 | - | CAGCGACAGAAGATGTTGGCGGG | 1 | 2 | 23 | SEQ ID NO. 4587 |
| (N20)NGG | 11 | 36596038 | - | TCAGCGACAGAAGATGTTGGCGG | 1 | 2 | 30 | SEQ ID NO. 4588 |
| (N20)NGG | 11 | 36596041 | - | GAGTCAGCGACAGAAGATGTTGG | 1 | 8 | 54 | SEQ ID NO. 4589 |
| (N20)NGG | 11 | 36596080 | - | GCAGCTTGAGCTCCCTCAGCCGG | 1 | 3 | 40 | SEQ ID NO. 4590 |
| (N20)NGG | 11 | 36596112 | - | ACCTTCTTCTTTGTCAGCACAGG | 1 | 4 | 50 | SEQ ID NO. 4591 |
| (N20)NGG | 11 | 36596148 | - | CAGGAACAAGTCATGCAGGAACAAGG | 1 | 4 | 56 | SEQ ID NO. 4592 |
| (N20)NGG | 11 | 36596160 | - | CCTCAGAGCCAGCAGGAACAAGG | 2 | 19 | 201 | SEQ ID NO. 4593 |
| (N20)NGG | 11 | 36596167 | - | TCCTGCCCTCAGAGCCAGCAGG | 1 | 2 | 41 | SEQ ID NO. 4594 |
| (N20)NGG | 11 | 36596220 | - | AGAGCCCTTTCCCTGCATGATGG | 1 | 1 | 46 | SEQ ID NO. 4595 |
| (N20)NGG | 11 | 36596245 | - | CCAAGCAAAACAGCTGGCTGCAGG | 3 | 4 | 45 | SEQ ID NO. 4596 |
| (N20)NGG | 11 | 36596252 | - | CGGATGGCCAAGCAAAACAGCTGG | 1 | 1 | 16 | SEQ ID NO. 4597 |
| (N20)NGG | 11 | 36596268 | - | GAGGAAGGTGTTGACACGGATGG | 1 | 3 | 37 | SEQ ID NO. 4598 |
| (N20)NGG | 11 | 36596272 | - | AGCTGAGGAAGGTGTTGACACGG | 1 | 5 | 72 | SEQ ID NO. 4599 |

FIG. 13 cont.

| site type | site_chr omosome | site_start_ nucleotide | site_s trand | target_site_sequence_with_NGG | genome_wide_hits_with_1_or_less_mism atches | genome_wide_hits_with_2_or_less_mism atches | genome_wide_hits_with_3_or_less_mism atches | |
|---|---|---|---|---|---|---|---|---|
| (N20)NGG | 11 | 36596283 | - | GTACTGACTGCAGCTGAGGAAGG | 1 | 7 | 57 | SEQ ID NO. 4600 |
| (N20)NGG | 11 | 36596287 | - | TGTGCTACTGACTGCAGCTGAGG | 1 | 5 | 65 | SEQ ID NO. 4601 |
| (N20)NGG | 11 | 36596305 | - | TCACAGTCCTGTACATCTTGTGG | 1 | 2 | 36 | SEQ ID NO. 4602 |
| (N20)NGG | 11 | 36596331 | - | AAAAATCTGTCTCCCTGTGATGG | 1 | 2 | 100 | SEQ ID NO. 4603 |
| (N20)NGG | 11 | 36596357 | - | GCATTCCGAAGGGCATGCAAAGG | 1 | 1 | 10 | SEQ ID NO. 4604 |
| (N20)NGG | 11 | 36596367 | - | TACCTTCTCAGCATTCCGAAGGG | 1 | 1 | 35 | SEQ ID NO. 4605 |
| (N20)NGG | 11 | 36596368 | - | GTACCTTCTCAGCATTCCGAAGG | 1 | 1 | 11 | SEQ ID NO. 4606 |
| (N20)NGG | 11 | 36596396 | - | CACTCAAAGTGGTGGTAGCCTGG | 2 | 3 | 19 | SEQ ID NO. 4607 |
| (N20)NGG | 11 | 36596404 | - | GTGGCTGCCACTCAAAGTGTGG | 1 | 1 | 30 | SEQ ID NO. 4608 |
| (N20)NGG | 11 | 36596407 | - | GAGGTGGCTGCCACTCAAAGTGG | 1 | 5 | 53 | SEQ ID NO. 4609 |
| (N20)NGG | 11 | 36596423 | - | GAAGACACATTCTTCAGAGGTGG | 1 | 4 | 82 | SEQ ID NO. 4610 |
| (N20)NGG | 11 | 36596426 | - | CTGGAAGACACATTCTTCAGAGG | 2 | 5 | 70 | SEQ ID NO. 4611 |
| (N20)NGG | 11 | 36596445 | - | AATAATGCCAACATCAGTCTCGG | 1 | 4 | 41 | SEQ ID NO. 4612 |
| (N20)NGG | 11 | 36596490 | - | CACTGGGTAATCATCCACAGAGG | 2 | 2 | 27 | SEQ ID NO. 4613 |
| (N20)NGG | 11 | 36596506 | - | TCTTTGCAATGGTGTCCACTGGG | 1 | 5 | 24 | SEQ ID NO. 4614 |
| (N20)NGG | 11 | 36596507 | - | CTCTTTGCAATGGTGTCCACTGG | 1 | 2 | 24 | SEQ ID NO. 4615 |
| (N20)NGG | 11 | 36596517 | - | ATAGCGGAACCTCTTTGCAATGG | 1 | 1 | 10 | SEQ ID NO. 4616 |
| (N20)NGG | 11 | 36596533 | - | ACACCAAAGCTGAATCATAGCGG | 1 | 2 | 35 | SEQ ID NO. 4617 |
| (N20)NGG | 11 | 36596601 | - | CAGGTAATCATCAAGGTCTTGGG | 1 | 1 | 26 | SEQ ID NO. 4618 |
| (N20)NGG | 11 | 36596602 | - | TCAGGTAATCATCAAGGTCTTGG | 1 | 3 | 33 | SEQ ID NO. 4619 |
| (N20)NGG | 11 | 36596608 | - | GGCCATTCAGGTAATCATCAAGG | 1 | 1 | 17 | SEQ ID NO. 4620 |
| (N20)NGG | 11 | 36596620 | - | CCAGAGTGAAGGGGCCATTCAGG | 1 | 3 | 33 | SEQ ID NO. 4621 |
| (N20)NGG | 11 | 36596629 | - | CCTTTCACCACCAGTGAAGGGG | 1 | 3 | 62 | SEQ ID NO. 4622 |
| (N20)NGG | 11 | 36596630 | - | TCCTTCACCACCACAGTGAAGG | 1 | 2 | 52 | SEQ ID NO. 4623 |
| (N20)NGG | 11 | 36596631 | - | CTCCTTCACCACCACAGTGAAGG | 1 | 5 | 79 | SEQ ID NO. 4624 |
| (N20)NGG | 11 | 36596699 | - | ACTGCCTTTTCTGGAACTACAGG | 2 | 2 | 53 | SEQ ID NO. 4625 |
| (N20)NGG | 11 | 36596708 | - | GAAAAACGGACTGCCTTTTCTGG | 1 | 1 | 27 | SEQ ID NO. 4626 |
| (N20)NGG | 11 | 36596722 | - | TCATGATTGTGAATGAAAAACGG | 1 | 8 | 141 | SEQ ID NO. 4627 |
| (N20)NGG | 11 | 36596757 | - | TTTCACATTCTGAGAGCTGTGG | 1 | 4 | 66 | SEQ ID NO. 4628 |
| (N20)NGG | 11 | 36596758 | - | CTTTCACATTCTGAGAGCTGTGG | 3 | 9 | 85 | SEQ ID NO. 4629 |
| (N20)NGG | 11 | 36596793 | - | ACACAGTTCAGAGTTAGGTTTGG | 1 | 4 | 32 | SEQ ID NO. 4630 |
| (N20)NGG | 11 | 36596798 | - | TTGCAACACAGTTCAGAGTTAGG | 2 | 11 | 62 | SEQ ID NO. 4631 |
| (N20)NGG | 11 | 36596822 | - | TCTGCCAGCATAAGGCACAATGG | 1 | 2 | 34 | SEQ ID NO. 4632 |

FIG. 13 cont.

| site_type | site_chr onosome | site_start nucleotide | site strand | target_site_sequence with h NGG | genome_wide_ hits_with_1_ or_less_mism atches | genome_wide_ hits_with_2_ or_less_mism atches | genome_wide_ hits_with_3_ or_less_mism atches | |
|---|---|---|---|---|---|---|---|---|
| (N20)NGG | 11 | 36596830 | - | CAGACTCATCTGCCAGCATAAGG | 1 | 1 | 36 | SEQ ID NO. 4633 |
| (N20)NGG | 11 | 36596854 | - | GGATGGCAGTCAGCGTCTCGTGG | 1 | 3 | 11 | SEQ ID NO. 4634 |
| (N20)NGG | 11 | 36596871 | - | AGCAATGAGAGGACTCAGGATGG | 1 | 5 | 97 | SEQ ID NO. 4635 |
| (N20)NGG | 11 | 36596875 | - | TCTCAGCAATGAGAGGACTCAGG | 1 | 2 | 55 | SEQ ID NO. 4636 |
| (N20)NGG | 11 | 36596882 | - | GCCTCCCTCTCAGCAATGAGAGG | 1 | 2 | 42 | SEQ ID NO. 4637 |
| (N20)NGG | 11 | 36596904 | - | CATTAATTCACTGCTCTTCATGG | 1 | 4 | 108 | SEQ ID NO. 4638 |
| (N20)NGG | 11 | 36596947 | - | TGAAGATGAACTTGAAAGTCCGG | 1 | 2 | 94 | SEQ ID NO. 4639 |
| (N20)NGG | 11 | 36596976 | - | CACAAGTTTTTCATCATAGCCGG | 1 | 1 | 28 | SEQ ID NO. 4640 |
| (N20)NGG | 11 | 36597013 | - | AGACTGAGCCAGAAAGCCTCAGG | 1 | 3 | 42 | SEQ ID NO. 4641 |
| (N20)NGG | 11 | 36597057 | - | TTGAGAGGCTTCCAGACGGGTGG | 1 | 3 | 30 | SEQ ID NO. 4642 |
| (N20)NGG | 11 | 36597060 | - | ATTTTGAGAGGCTTCCAGACGGG | 1 | 4 | 31 | SEQ ID NO. 4643 |
| (N20)NGG | 11 | 36597061 | - | GATTTTGAGAGGCTTCCAGACGG | 1 | 5 | 64 | SEQ ID NO. 4644 |
| (N20)NGG | 11 | 36597072 | - | GTGGAAGACAAGATTTTGAGAGG | 1 | 3 | 81 | SEQ ID NO. 4645 |
| (N20)NGG | 11 | 36597091 | - | CATGGCTTCTGTTATAGAGTGG | 1 | 6 | 44 | SEQ ID NO. 4646 |
| (N20)NGG | 11 | 36597102 | - | CAGGTTCTCAGCATGGCTTCTGG | 1 | 5 | 76 | SEQ ID NO. 4647 |
| (N20)NGG | 11 | 36597109 | - | AACGTTCCAGGTTCTCAGCATGG | 1 | 3 | 20 | SEQ ID NO. 4648 |
| (N20)NGG | 11 | 36597121 | - | GCCAGACCTCATAACGTTCCAGG | 1 | 1 | 11 | SEQ ID NO. 4649 |
| (N20)NGG | 11 | 36597147 | - | CACAGACTCATGGTAAGGTTGG | 1 | 2 | 29 | SEQ ID NO. 4650 |
| (N20)NGG | 11 | 36597151 | - | CTTCCACAGACTCATGGTAAGG | 1 | 5 | 41 | SEQ ID NO. 4651 |
| (N20)NGG | 11 | 36597152 | - | TCTTCCACAGACTCATGGTAAGG | 1 | 5 | 38 | SEQ ID NO. 4652 |
| (N20)NGG | 11 | 36597157 | - | GCAGTTCTTCCACAGACTCATGG | 1 | 5 | 54 | SEQ ID NO. 4653 |
| (N20)NGG | 11 | 36597209 | - | GAAGGGACTGTCTCAATGAAAGG | 1 | 3 | 40 | SEQ ID NO. 4654 |
| (N20)NGG | 11 | 36597226 | - | AGTGGAGTGCATCTATGGAAGG | 1 | 2 | 31 | SEQ ID NO. 4655 |
| (N20)NGG | 11 | 36597227 | - | CAGTGGAGTGCATCTATGGAAGG | 1 | 2 | 21 | SEQ ID NO. 4656 |
| (N20)NGG | 11 | 36597231 | - | GTCACAGTGGAGTGCATCTATGG | 1 | 9 | 59 | SEQ ID NO. 4657 |
| (N20)NGG | 11 | 36597244 | - | CTGCATTGCCAATGTCACAGTGG | 1 | 5 | 50 | SEQ ID NO. 4658 |
| (N20)NGG | 11 | 36597286 | - | ACACTTCCCCTATCTCTAGCTGG | 1 | 1 | 24 | SEQ ID NO. 4659 |
| (N20)NGG | 11 | 36597317 | - | CTTTCCTCTTTGGAAGCATTGGG | 1 | 7 | 102 | SEQ ID NO. 4660 |
| (N20)NGG | 11 | 36597318 | - | CCCTTTCCTCTTTGGAAGCATTGG | 1 | 3 | 74 | SEQ ID NO. 4661 |
| (N20)NGG | 11 | 36597327 | - | CCACCTTTTCCTCTTCCTCTTTGG | 3 | 18 | 318 | SEQ ID NO. 4662 |
| (N20)NGG | 11 | 36597354 | - | CCGAGATGCTTGTCCAGTGTGG | 1 | 1 | 11 | SEQ ID NO. 4663 |
| (N20)NGG | 11 | 36597373 | - | GTTTGAGGTTCATCTTCTTCCGG | 1 | 5 | 47 | SEQ ID NO. 4664 |
| (N20)NGG | 11 | 36597388 | - | TCATCCTCATGATTGGTTTGAGG | 1 | 3 | 36 | SEQ ID NO. 4665 |

FIG. 13 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 11 | 36597395 | - | TTGCCATTCATCCTCATGATTGG |   | 2 | 34 | SEQ ID NO. 4666 |
| (N20)NGG | 11 | 36597423 | - | CTCTTTGGTCATGAGCTTCCTGG | 1 | 5 | 59 | SEQ ID NO. 4667 |
| (N20)NGG | 11 | 36597438 | - | AACTGCATCCACAGTCTCTTTGG | 1 | 6 | 70 | SEQ ID NO. 4668 |
| (N20)NGG | 11 | 36597473 | - | GCCTCGTGCCTCTCCTCGGAAGG | 1 | 3 | 21 | SEQ ID NO. 4669 |
| (N20)NGG | 11 | 36597477 | - | CAGAGCCTCGTGCCTCTCCTCGG | 1 | 4 | 45 | SEQ ID NO. 4670 |
| (N20)NGG | 11 | 36597520 | - | GCCATACTGGTTTCATCTTCAGG | 1 | 1 | 32 | SEQ ID NO. 4671 |
| (N20)NGG | 11 | 36597533 | - | GGGCATGATGATCGCCATACTGG | 1 | 2 | 5 | SEQ ID NO. 4672 |
| (N20)NGG | 11 | 36597553 | - | ATTCTGGGCACTCTTTAGCAGGG | 1 | 2 | 35 | SEQ ID NO. 4673 |
| (N20)NGG | 11 | 36597554 | - | GATTCTGGGCACTCTTTAGCAGG | 2 | 4 | 32 | SEQ ID NO. 4674 |
| (N20)NGG | 11 | 36597568 | - | TGTACTGGCAGAGGGATTCTGGG | 1 | 2 | 31 | SEQ ID NO. 4675 |
| (N20)NGG | 11 | 36597569 | - | CTGTACTGGCAGAGGGATTCTGG | 1 | 1 | 23 | SEQ ID NO. 4676 |
| (N20)NGG | 11 | 36597576 | - | ATTGAAACTGTACTGGCAGAGGG | 1 | 3 | 38 | SEQ ID NO. 4677 |
| (N20)NGG | 11 | 36597577 | - | AATTGAAACTGTACTGGCAGAGG | 1 | 7 | 44 | SEQ ID NO. 4678 |
| (N20)NGG | 11 | 36597583 | - | GCTGTGAATTGAAACTGTACTGG | 1 | 1 | 19 | SEQ ID NO. 4679 |
| (N20)NGG | 11 | 36597619 | - | TATACTTGAACTTCGTAGAAAGG | 1 | 1 | 37 | SEQ ID NO. 4680 |
| (N20)NGG | 11 | 36597660 | - | CAGGGTTTTGTGAAAATAATTGG | 1 | 7 | 98 | SEQ ID NO. 4681 |
| (N20)NGG | 11 | 36597678 | - | AATTTCAGGAACATGGGCCAGG | 1 | 4 | 44 | SEQ ID NO. 4682 |
| (N20)NGG | 11 | 36597679 | - | TAATTTCAGGAACATGGGCCAGG | 1 | 3 | 36 | SEQ ID NO. 4683 |
| (N20)NGG | 11 | 36597684 | - | CTCAATAATTTCAGGAACATGGG | 1 | 4 | 74 | SEQ ID NO. 4684 |
| (N20)NGG | 11 | 36597685 | - | TCTCAATAATTTCAGGAACATGG | 1 | 9 | 114 | SEQ ID NO. 4685 |
| (N20)NGG | 11 | 36597692 | - | CCATCCCTCTTCAATAATTTCAG | 1 | 2 | 35 | SEQ ID NO. 4686 |
| (N20)NGG | 11 | 36597717 | - | CTTCACTTGCCCATGCCCCAATGG | 1 | 3 | 38 | SEQ ID NO. 4687 |
| (N20)NGG | 11 | 36597775 | - | ACTGCCTGGCATTCATTTTCCGG | 1 | 4 | 45 | SEQ ID NO. 4688 |
| (N20)NGG | 11 | 36597789 | - | CTCATAGCATTTGGACTGCCTGG | 1 | 1 | 18 | SEQ ID NO. 4689 |
| (N20)NGG | 11 | 36597798 | - | ATCTTCCATCTCATAGCATTTGG | 1 | 4 | 51 | SEQ ID NO. 4690 |
| (N20)NGG | 11 | 36597823 | - | TGTACAACCAGTTGGTGTTTCAG | 1 | 1 | 24 | SEQ ID NO. 4691 |
| (N20)NGG | 11 | 36597832 | - | ATTTGGAGGTGTACAACCAGTGG | 1 | 1 | 24 | SEQ ID NO. 4692 |
| (N20)NGG | 11 | 36597846 | - | AAACTTCTGGAGGTATTTGGAGG | 1 | 6 | 76 | SEQ ID NO. 4693 |
| (N20)NGG | 11 | 36597849 | - | CATAAACTTCTGGAGGTATTTGG | 1 | 2 | 42 | SEQ ID NO. 4694 |
| (N20)NGG | 11 | 36597856 | - | GAGCATTCATAAACTTCTGGAGG | 1 | 5 | 79 | SEQ ID NO. 4695 |
| (N20)NGG | 11 | 36597859 | - | TATGAGCATTCATAAACTTCTGG | 1 | 4 | 38 | SEQ ID NO. 4696 |
| (N20)NGG | 11 | 36597894 | - | AGGGTTCATGTAAACCCAGAGG | 1 | 6 | 39 | SEQ ID NO. 4697 |
| (N20)NGG | 11 | 36597906 | - | TAAGCTTGCCTGAGGGTTCATGG | 1 | 1 | 25 | SEQ ID NO. 4698 |

FIG. 13 cont.

| site_type | site_chr omosome | site_start_ nucleotide | site_s trand | target_site_sequence_with NGG | genome_wide_ hits_with_1_ or_less_mism atches | genome_wide_ hits_with_2_ or_less_mism atches | genome_wide_ hits_with_3_ or_less_mism atches | | |
|---|---|---|---|---|---|---|---|---|---|
| (N20)NGG | 11 | 36597913 | - | GGTCCCCTAAGCTTGCCTGAGGG | 1 | 2 | 21 | SEQ ID NO. | 4699 |
| (N20)NGG | 11 | 36597914 | - | GGGTCCCCTAAGCTTGCCTGAGG | 1 | 3 | 18 | SEQ ID NO. | 4700 |
| (N20)NGG | 11 | 36597934 | - | GAGAGTCCTCTATGCCTAATGGG | 1 | 1 | 9 | SEQ ID NO. | 4701 |
| (N20)NGG | 11 | 36597935 | - | AGAGAGTCCTCTATGCCTAATGG | 1 | 3 | 21 | SEQ ID NO. | 4702 |

FIG. 13 cont.

| site_type | site_chr omosome | site_start_ nucleotide | site_s trand | target_site_sequence_wi th_NGG | genome_wide_ hits_with_1_ or_less_mism atches | genome_wide_ hits_with_2_ or_less_mism atches | genome_wide_ hits_with_3_ or_less_mism atches | | |
|---|---|---|---|---|---|---|---|---|---|
| (N20)NGG | 11 | 36614186 | + | AACATAGCCTTAATTCAGCCAGG | 1 | 3 | 29 | SEQ ID NO. | 4703 |
| (N20)NGG | 11 | 36614210 | + | TTCTCACTGATGAATTTTGATGG | 1 | 24 | 221 | SEQ ID NO. | 4704 |
| (N20)NGG | 11 | 36614228 | + | GATGGACAAGTTTTCTTCTTTGG | 1 | 4 | 80 | SEQ ID NO. | 4705 |
| (N20)NGG | 11 | 36614237 | + | GTTTTCTTCTTGGACAAAAAGG | 1 | 13 | 170 | SEQ ID NO. | 4706 |
| (N20)NGG | 11 | 36614241 | + | TCTTCTTTGGACAAAAGGCTGG | 1 | 8 | 67 | SEQ ID NO. | 4707 |
| (N20)NGG | 11 | 36614264 | + | CCCAAAAGATCTGCCCCACTGG | 1 | 3 | 46 | SEQ ID NO. | 4708 |
| (N20)NGG | 11 | 36614278 | + | CCCCACTGGAGTTTTCCATCTGG | 1 | 4 | 38 | SEQ ID NO. | 4709 |
| (N20)NGG | 11 | 36614326 | + | GAAGCCTACAATTTTCTCTAAGG | 1 | 5 | 38 | SEQ ID NO. | 4710 |
| (N20)NGG | 11 | 36614378 | + | CCAGCCACTTGCACATTCAAAGG | 1 | 3 | 30 | SEQ ID NO. | 4711 |
| (N20)NGG | 11 | 36614386 | + | TTGCACATTCAAAGGCAGCTTGG | 2 | 3 | 40 | SEQ ID NO. | 4712 |
| (N20)NGG | 11 | 36614417 | + | AAGCATCAATACATCATCCATGG | 1 | 2 | 28 | SEQ ID NO. | 4713 |
| (N20)NGG | 11 | 36614420 | + | CATCAATACATCATCCATGGAGG | 1 | 1 | 22 | SEQ ID NO. | 4714 |
| (N20)NGG | 11 | 36614421 | + | ATCAATACATCATCCATGGAGGG | 1 | 3 | 30 | SEQ ID NO. | 4715 |
| (N20)NGG | 11 | 36614440 | + | AGGGAAAACACCAAACAATGAGG | 1 | 3 | 105 | SEQ ID NO. | 4716 |
| (N20)NGG | 11 | 36614491 | + | TGTTTGCAAGAACAACAAAAGG | 1 | 16 | 224 | SEQ ID NO. | 4717 |
| (N20)NGG | 11 | 36614521 | + | TCGCTGCACAGAGAAAGACTTGG | 1 | 2 | 30 | SEQ ID NO. | 4718 |
| (N20)NGG | 11 | 36614525 | + | TGCACAGAGAAAGACTTGGTAGG | 1 | 4 | 54 | SEQ ID NO. | 4719 |
| (N20)NGG | 11 | 36614549 | + | GATGTTCCTGAAGCCAGATATGG | 1 | 8 | 46 | SEQ ID NO. | 4720 |
| (N20)NGG | 11 | 36614566 | + | ATATGGTCATTCCATTAATGTGG | 1 | 4 | 45 | SEQ ID NO. | 4721 |
| (N20)NGG | 11 | 36614579 | + | ATTAATGTGGTGTACAGCCGAGG | 1 | 1 | 8 | SEQ ID NO. | 4722 |
| (N20)NGG | 11 | 36614580 | + | TTAATGTGGTGTACAGCCGAGGG | 1 | 1 | 11 | SEQ ID NO. | 4723 |
| (N20)NGG | 11 | 36614590 | + | GTACAGCCGAGGGAAAAGTATGG | 1 | 5 | 223 | SEQ ID NO. | 4724 |
| (N20)NGG | 11 | 36614591 | + | TACAGCCGAGGGAAAAGTATGGG | 1 | 2 | 20 | SEQ ID NO. | 4725 |
| (N20)NGG | 11 | 36614603 | + | AAAAGTATGGGTGTTCTCTTTGG | 1 | 2 | 60 | SEQ ID NO. | 4726 |
| (N20)NGG | 11 | 36614606 | + | AGTATGGGTGTTCTCTTTGGAGG | 1 | 2 | 40 | SEQ ID NO. | 4727 |
| (N20)NGG | 11 | 36614649 | + | CCCACAGAACCACAGAAAAATGG | 3 | 11 | 170 | SEQ ID NO. | 4728 |
| (N20)NGG | 11 | 36614686 | + | CTGCCTGCCCTGTGTTTTCCTGG | 1 | 8 | 106 | SEQ ID NO. | 4729 |
| (N20)NGG | 11 | 36614689 | + | CCTGCCCTGTGTTTTCCTGGTGG | 1 | 8 | 117 | SEQ ID NO. | 4730 |
| (N20)NGG | 11 | 36614702 | + | TTCCTGGTGGATTTTGAATTTGG | 1 | 3 | 72 | SEQ ID NO. | 4731 |
| (N20)NGG | 11 | 36614703 | + | TCCTGGTGGATTTTGAATTTGGG | 1 | 7 | 123 | SEQ ID NO. | 4732 |
| (N20)NGG | 11 | 36614737 | + | ATACATTCTTCCAGAACTTCAGG | 1 | 5 | 73 | SEQ ID NO. | 4733 |
| (N20)NGG | 11 | 36614741 | + | ATTCTTCCAGAACTTCAGGATGG | 1 | 4 | 73 | SEQ ID NO. | 4734 |
| (N20)NGG | 11 | 36614742 | + | TTCTTCCAGAACTTCAGGATGGG | 1 | 4 | 69 | SEQ ID NO. | 4735 |

FIG. 14

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 11 | 36614792 | + | AATGACACCATCTATATTTTAGG | 1 | 18 | 113 | SEQ ID NO. 4736 |
| (N20)NGG | 11 | 36614795 | + | GACACCATCTATATTTTAGGAGG | 1 | 3 | 49 | SEQ ID NO. 4737 |
| (N20)NGG | 11 | 36614820 | + | ATTCACTTGCCAATATATATCCGG | 1 | 2 | 47 | SEQ ID NO. 4738 |
| (N20)NGG | 11 | 36614844 | + | CTGCCAACCTGTACAGAATAAGG | 1 | 3 | 42 | SEQ ID NO. 4739 |
| (N20)NGG | 11 | 36614845 | + | TGCCAACCTGTACAGAATAAGGG | 1 | 2 | 36 | SEQ ID NO. 4740 |
| (N20)NGG | 11 | 36614860 | + | AATAAGGGTTGATCTTCCCCTGG | 1 | 2 | 22 | SEQ ID NO. 4741 |
| (N20)NGG | 11 | 36614861 | + | ATAAGGGTTGATCTTCCCCTGGG | 1 | 1 | 27 | SEQ ID NO. 4742 |
| (N20)NGG | 11 | 36614894 | + | GTGAATTGCACAGTCTTGCCAGG | 1 | 2 | 25 | SEQ ID NO. 4743 |
| (N20)NGG | 11 | 36614897 | + | AATTGCACAGTCTTGCCAGGAGG | 1 | 5 | 39 | SEQ ID NO. 4744 |
| (N20)NGG | 11 | 36614957 | + | AATGATGAATTTGTTATTGTTGG | 2 | 8 | 158 | SEQ ID NO. 4745 |
| (N20)NGG | 11 | 36614960 | + | GATGAATTTGTTATTGTTGGTGG | 1 | 6 | 90 | SEQ ID NO. 4746 |
| (N20)NGG | 11 | 36615013 | + | CTGCAACATCATCTCTTTAGAGG | 1 | 5 | 78 | SEQ ID NO. 4747 |
| (N20)NGG | 11 | 36615040 | + | CAAGATAGAAATTCGTGAGATGG | 1 | 5 | 34 | SEQ ID NO. 4748 |
| (N20)NGG | 11 | 36615054 | + | GTGAGATGGAGACCCCAGATTGG | 1 | 1 | 40 | SEQ ID NO. 4749 |
| (N20)NGG | 11 | 36615084 | + | ACATTAAGCACAGCAAGATATGG | 1 | 7 | 62 | SEQ ID NO. 4750 |
| (N20)NGG | 11 | 36615089 | + | AAGCACAGCAAGATATGGTTTGG | 1 | 2 | 49 | SEQ ID NO. 4751 |
| (N20)NGG | 11 | 36615100 | + | GATATGGTTTGGAAGCAACATGG | 1 | 2 | 48 | SEQ ID NO. 4752 |
| (N20)NGG | 11 | 36615101 | + | ATATGGTTTGGAAGCAACATGGG | 1 | 3 | 96 | SEQ ID NO. 4753 |
| (N20)NGG | 11 | 36615107 | + | TTTGGAAGCAACATGGGAAATGG | 1 | 8 | 210 | SEQ ID NO. 4754 |
| (N20)NGG | 11 | 36615122 | + | GGAAATGGAACTGTTTTTCTTGG | 1 | 14 | 119 | SEQ ID NO. 4755 |
| (N20)NGG | 11 | 36615131 | + | ACTGTTTTTCTTGGCATACCAGG | 1 | 2 | 51 | SEQ ID NO. 4756 |
| (N20)NGG | 11 | 36615158 | + | AATAAACAAGTTGTTTCAGAAGG | 2 | 6 | 109 | SEQ ID NO. 4757 |
| (N20)NGG | 11 | 36615251 | + | CAAACATCAACAGAAGATCCAGG | 1 | 4 | 57 | SEQ ID NO. 4758 |
| (N20)NGG | 11 | 36615252 | + | AAACATCAACAGAAGATCCAGGG | 1 | 8 | 97 | SEQ ID NO. 4759 |
| (N20)NGG | 11 | 36615253 | + | AACATCAACAGAAGATCCAGGGG | 1 | 4 | 72 | SEQ ID NO. 4760 |
| (N20)NGG | 11 | 36615317 | + | GCAGAAGCAAATAGTTTTGATGG | 1 | 3 | 92 | SEQ ID NO. 4761 |
| (N20)NGG | 11 | 36615374 | + | GAAGAAGATGAGTCTGAGACAGG | 1 | 7 | 125 | SEQ ID NO. 4762 |
| (N20)NGG | 11 | 36615381 | + | ATGAGTCTGAGACAGGCTACTGG | 1 | 2 | 29 | SEQ ID NO. 4763 |
| (N20)NGG | 11 | 36615409 | + | ATGCTGCCTACTTGTGATGTGG | 1 | 5 | 48 | SEQ ID NO. 4764 |
| (N20)NGG | 11 | 36615423 | + | GTGATGTGGATATCAACACTTGG | 1 | 5 | 19 | SEQ ID NO. 4765 |
| (N20)NGG | 11 | 36615424 | + | TGATGTGGATATCAACACTTGGG | 1 | 1 | 31 | SEQ ID NO. 4766 |
| (N20)NGG | 11 | 36615479 | + | GCCATGATCTACTGCTCTCATGG | 1 | 3 | 39 | SEQ ID NO. 4767 |
| (N20)NGG | 11 | 36615480 | + | CCATGATCTACTGCTCTCATGGG | 1 | 2 | 31 | SEQ ID NO. 4768 |

FIG. 14 cont.

| site_type | site_chr omosome | site_start nucleotide | site_s trand | target_site_sequence_wi th_NGG | genome_wide_ hits_with_1_ or_less_mism atches | genome_wide_ hits_with_2_ or_less_mism atches | genome_wide_ hits_with_3_ or_less_mism atches | |
|---|---|---|---|---|---|---|---|---|
| (N20)NGG | 11 | 36615481 | + | CATGATCTACTGCTCTCATGGGG | 1 | 3 | 22 | SEQ ID NO. 4769 |
| (N20)NGG | 11 | 36615485 | + | ATCTACTGCTCTCATGGGGATGG | 1 | 2 | 37 | SEQ ID NO. 4770 |
| (N20)NGG | 11 | 36615486 | + | TCTACTGCTCTCATGGGGATGGG | 1 | 3 | 34 | SEQ ID NO. 4771 |
| (N20)NGG | 11 | 36615492 | + | GCTCTCATGGGGATGGGCACTGG | 1 | 3 | 36 | SEQ ID NO. 4772 |
| (N20)NGG | 11 | 36615493 | + | CTCTCATGGGGATGGGCACTGGG | 2 | 3 | 45 | SEQ ID NO. 4773 |
| (N20)NGG | 11 | 36615511 | + | CTGGGTCCATGCTCAGTGCATGG | 1 | 4 | 50 | SEQ ID NO. 4774 |
| (N20)NGG | 11 | 36615517 | + | CCATGCTCAGTGCATGGATCTGG | 1 | 3 | 34 | SEQ ID NO. 4775 |
| (N20)NGG | 11 | 36615548 | + | ACACTCATCCATCTGTCAGCAGG | 1 | 7 | 46 | SEQ ID NO. 4776 |
| (N20)NGG | 11 | 36615580 | + | GTATTACTGCAATGAGCATGTGG | 1 | 4 | 77 | SEQ ID NO. 4777 |
| (N20)NGG | 11 | 36615659 | + | ATGAAATCCCTCCGTAAAAAAGG | 1 | 3 | 25 | SEQ ID NO. 4778 |
| (N20)NGG | 11 | 36615665 | + | TCCCTCCGTAAAAAAGGTTCTGG | 1 | 1 | 10 | SEQ ID NO. 4779 |
| (N20)NGG | 11 | 36615705 | + | CCAAGAAATCCTTTCTTAGAAGG | 1 | 5 | 71 | SEQ ID NO. 4780 |
| (N20)NGG | 11 | 36614171 | - | TGAGAAGCCTGGCTGAAGAAGG | 1 | 5 | 54 | SEQ ID NO. 4781 |
| (N20)NGG | 11 | 36614182 | - | AAATTCATCAGTGAGAAGCCTGG | 2 | 3 | 61 | SEQ ID NO. 4782 |
| (N20)NGG | 11 | 36614242 | - | CCAGTGGGCAGGATCTTTTTGG | 1 | 3 | 50 | SEQ ID NO. 4783 |
| (N20)NGG | 11 | 36614243 | - | TCCAGTGGGCAGGATCTTTTTGG | 1 | 1 | 27 | SEQ ID NO. 4784 |
| (N20)NGG | 11 | 36614252 | - | ATGGAAAACTCCAGTGGGCAGG | 1 | 6 | 47 | SEQ ID NO. 4785 |
| (N20)NGG | 11 | 36614256 | - | CCAGATGGAAAACTCCAGTGGGG | 1 | 3 | 58 | SEQ ID NO. 4786 |
| (N20)NGG | 11 | 36614257 | - | TCCAGATGGAAAACTCCAGTGGG | 1 | 3 | 70 | SEQ ID NO. 4787 |
| (N20)NGG | 11 | 36614258 | - | ATCCAGATGGAAAACTCCAGTGG | 1 | 7 | 85 | SEQ ID NO. 4788 |
| (N20)NGG | 11 | 36614271 | - | GGTTATGCTTTACATCCAGATGG | 1 | 2 | 21 | SEQ ID NO. 4789 |
| (N20)NGG | 11 | 36614292 | - | TTGTAGGCTTCAGTTTGACATGG | 1 | 3 | 44 | SEQ ID NO. 4790 |
| (N20)NGG | 11 | 36614308 | - | GAATCCTTAGAGAAAATTGTAGG | 1 | 6 | 86 | SEQ ID NO. 4791 |
| (N20)NGG | 11 | 36614330 | - | GCGAAGAGGAGGGAGGTAGCAGG | 1 | 9 | 101 | SEQ ID NO. 4792 |
| (N20)NGG | 11 | 36614337 | - | CTGGGTAGCGAAGAGGAGGGAGG | 1 | 6 | 94 | SEQ ID NO. 4793 |
| (N20)NGG | 11 | 36614340 | - | TGGCTGGGTAGCGAAGAGGAGGG | 1 | 3 | 67 | SEQ ID NO. 4794 |
| (N20)NGG | 11 | 36614341 | - | GTGGCTGGGTAGCGAAGAGGAGG | 1 | 4 | 55 | SEQ ID NO. 4795 |
| (N20)NGG | 11 | 36614344 | - | CAAGTGGCTGGGTAGCGAAGAGG | 1 | 3 | 21 | SEQ ID NO. 4796 |
| (N20)NGG | 11 | 36614355 | - | CTTTGAATGTGCAAGTGGCTGGG | 1 | 4 | 37 | SEQ ID NO. 4797 |
| (N20)NGG | 11 | 36614356 | - | CCTTTGAATGTGCAAGTGGCTGG | 1 | 2 | 29 | SEQ ID NO. 4798 |
| (N20)NGG | 11 | 36614360 | - | GCTGCCTTTGAATGTGCAAGTGG | 1 | 7 | 72 | SEQ ID NO. 4799 |
| (N20)NGG | 11 | 36614412 | - | TGTTTGGTGTTTCCCTCCATGG | 1 | 5 | 88 | SEQ ID NO. 4800 |
| (N20)NGG | 11 | 36614428 | - | TTATCTGAAACCTCATTGTTTGG | 1 | 7 | 60 | SEQ ID NO. 4801 |

FIG. 14 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | | |
|---|---|---|---|---|---|---|---|---|---|
| (N20) NGG | 11 | 36614533 | - | GAATGACCATATCTGGCTTCAGG | 2 | 3 | 36 | SEQ ID NO. | 4802 |
| (N20) NGG | 11 | 36614540 | - | ATTAATGGAATGACCATATCTGG | 1 | 2 | 35 | SEQ ID NO. | 4803 |
| (N20) NGG | 11 | 36614555 | - | TCGGCTGTACACCACATTAATGG | 1 | 2 | 5 | SEQ ID NO. | 4804 |
| (N20) NGG | 11 | 36614574 | - | GAACACCCATACTTTTCCCTCGG | 1 | 2 | 29 | SEQ ID NO. | 4805 |
| (N20) NGG | 11 | 36614620 | - | TCTGTGGTTCTGTGGGTAGAAGG | 1 | 5 | 78 | SEQ ID NO. | 4806 |
| (N20) NGG | 11 | 36614627 | - | CCATTTTCTGTGGTTCTGTGGG | 1 | 6 | 144 | SEQ ID NO. | 4807 |
| (N20) NGG | 11 | 36614628 | - | TCCATTTTCTGTGGTTCTGTGG | 1 | 9 | 120 | SEQ ID NO. | 4808 |
| (N20) NGG | 11 | 36614636 | - | TACACTATTCCATTTTCTGTGG | 1 | 8 | 105 | SEQ ID NO. | 4809 |
| (N20) NGG | 11 | 36614667 | - | CCACCAGGAAAACACAGGGCAGG | 1 | 7 | 95 | SEQ ID NO. | 4810 |
| (N20) NGG | 11 | 36614671 | - | AAATCCACCAGGAAAACACAGG | 1 | 12 | 140 | SEQ ID NO. | 4811 |
| (N20) NGG | 11 | 36614672 | - | AAAATCCACCAGGAAAACACAGG | 1 | 8 | 96 | SEQ ID NO. | 4812 |
| (N20) NGG | 11 | 36614682 | - | ACCCAAATTCAAAATCCACCAGG | 1 | 6 | 79 | SEQ ID NO. | 4813 |
| (N20) NGG | 11 | 36614725 | - | GATAGCCCATCCTGAAGTTCTGG | 1 | 1 | 16 | SEQ ID NO. | 4814 |
| (N20) NGG | 11 | 36614765 | - | AATATAGATGGTGTCATTTTTGG | 2 | 3 | 110 | SEQ ID NO. | 4815 |
| (N20) NGG | 11 | 36614777 | - | ATGTCCCTCCTAAAATATAGATGG | 1 | 8 | 100 | SEQ ID NO. | 4816 |
| (N20) NGG | 11 | 36614807 | - | GTTGGCAGGCCGGATATTATTGG | 1 | 1 | 7 | SEQ ID NO. | 4817 |
| (N20) NGG | 11 | 36614817 | - | TTCTGTACAGGTTGGCAGGCCGG | 1 | 8 | 194 | SEQ ID NO. | 4818 |
| (N20) NGG | 11 | 36614821 | - | CTTATTCTGTACAGGTTGGCAGG | 1 | 1 | 23 | SEQ ID NO. | 4819 |
| (N20) NGG | 11 | 36614825 | - | AACCCTTATTCTGTACAGGTTGG | 1 | 2 | 21 | SEQ ID NO. | 4820 |
| (N20) NGG | 11 | 36614829 | - | GATCAAACCCTTATTCTGTACAGG | 2 | 1 | 11 | SEQ ID NO. | 4821 |
| (N20) NGG | 11 | 36614854 | - | TTCACAGCTGGGCTACCAGGGG | 1 | 4 | 54 | SEQ ID NO. | 4822 |
| (N20) NGG | 11 | 36614855 | - | ATTCACAGCTGGGCTACCCAGG | 1 | 1 | 32 | SEQ ID NO. | 4823 |
| (N20) NGG | 11 | 36614856 | - | AATTCACAGCTGGGCTACCCAGG | 1 | 2 | 25 | SEQ ID NO. | 4824 |
| (N20) NGG | 11 | 36614865 | - | AGACTGTGCAATTCACAGCTGGG | 1 | 1 | 42 | SEQ ID NO. | 4825 |
| (N20) NGG | 11 | 36614866 | - | AAGACTGTGCAATTCACAGCTGG | 1 | 2 | 43 | SEQ ID NO. | 4826 |
| (N20) NGG | 11 | 36614890 | - | CTGGAGACAGAGATTCCTCCTGG | 1 | 4 | 80 | SEQ ID NO. | 4827 |
| (N20) NGG | 11 | 36614909 | - | AGTTTGAGTCAGGATTGCACTGG | 1 | 4 | 23 | SEQ ID NO. | 4828 |
| (N20) NGG | 11 | 36614919 | - | CATCATTGTTAGTTTGAGTCAGG | 1 | 1 | 31 | SEQ ID NO. | 4829 |
| (N20) NGG | 11 | 36615044 | - | AATGTCTGGGGTCCAATCTGGG | 1 | 5 | 30 | SEQ ID NO. | 4830 |
| (N20) NGG | 11 | 36615045 | - | TAATGTCTGGGGTCCAATCTGG | 1 | 3 | 22 | SEQ ID NO. | 4831 |
| (N20) NGG | 11 | 36615046 | - | TTAATGTCTGGGGTCCAATCTG | 1 | 2 | 21 | SEQ ID NO. | 4832 |
| (N20) NGG | 11 | 36615056 | - | CTTGCTGTGCTTAATGTCTGGGG | 1 | 5 | 54 | SEQ ID NO. | 4833 |
| (N20) NGG | 11 | 36615057 | - | TCTTGCTGTGCTTAATGTCTGGG | 1 | 2 | 70 | SEQ ID NO. | 4834 |

FIG. 14 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 11 | 36615058 | - | ATCTTGCTGTGCTTAATGTCTGG | 1 | 1 | 36 | SEQ ID NO. 4835 |
| (N20)NGG | 11 | 36615127 | - | ACAACTTGTTTATTGTCTCCTGG | 1 | 5 | 70 | SEQ ID NO. 4836 |
| (N20)NGG | 11 | 36615247 | - | TCAAAGGAGTGGAATCCCCTGG | 1 | 3 | 23 | SEQ ID NO. 4837 |
| (N20)NGG | 11 | 36615257 | - | TTCAGAGTCTTCAAAGGAGTGG | 1 | 6 | 79 | SEQ ID NO. 4838 |
| (N20)NGG | 11 | 36615262 | - | AATTCTTCAGAGTCTTCAAAGG | 1 | 13 | 151 | SEQ ID NO. 4839 |
| (N20)NGG | 11 | 36615263 | - | AAATTCTTCAGAGTCTTCAAAGG | 1 | 7 | 122 | SEQ ID NO. 4840 |
| (N20)NGG | 11 | 36615335 | - | TTCTTCATCATCTTCATTATAGG | 2 | 21 | 338 | SEQ ID NO. 4841 |
| (N20)NGG | 11 | 36615393 | - | TGATATCCACATCACAAGTAGGG | 1 | 2 | 30 | SEQ ID NO. 4842 |
| (N20)NGG | 11 | 36615394 | - | TTGAGCTCAGTTGAATAGAATGG | 1 | 5 | 26 | SEQ ID NO. 4843 |
| (N20)NGG | 11 | 36615427 | - | TTGAGCTCAGTTGAATAGAATGG | 1 | 3 | 42 | SEQ ID NO. 4844 |
| (N20)NGG | 11 | 36615454 | - | TGAGAGCAGTAGATCATGGCGG | 1 | 3 | 43 | SEQ ID NO. 4845 |
| (N20)NGG | 11 | 36615455 | - | ATGAGACAGTAGATCATGGCGG | 1 | 4 | 44 | SEQ ID NO. 4846 |
| (N20)NGG | 11 | 36615458 | - | CCCATGAGACCAGTAGATCATGG | 1 | 3 | 29 | SEQ ID NO. 4847 |
| (N20)NGG | 11 | 36615495 | - | CCAGATCCATGCCACTGAGCATGG | 1 | 1 | 44 | SEQ ID NO. 4848 |
| (N20)NGG | 11 | 36615534 | - | TGTTGCTTCCTGCTGACAGATGG | 1 | 3 | 89 | SEQ ID NO. 4849 |
| (N20)NGG | 11 | 36615604 | - | TTTAAGGGTAGGACTCTTTGGGG | 1 | 2 | 36 | SEQ ID NO. 4850 |
| (N20)NGG | 11 | 36615605 | - | TTTAAGGGTAGGACTCTTTTGG | 1 | 8 | 46 | SEQ ID NO. 4851 |
| (N20)NGG | 11 | 36615606 | - | TTTTTAAGGGTAGGACTCTTTGG | 1 | 2 | 54 | SEQ ID NO. 4852 |
| (N20)NGG | 11 | 36615615 | - | TTGGAGGCTTTTTAAGGGTAGG | 1 | 5 | 52 | SEQ ID NO. 4853 |
| (N20)NGG | 11 | 36615619 | - | TTCATTGGAGCTTTTTAAGGG | 2 | 9 | 98 | SEQ ID NO. 4854 |
| (N20)NGG | 11 | 36615620 | - | TTTCATTGGAGCTTTTTAAGG | 2 | 11 | 101 | SEQ ID NO. 4855 |
| (N20)NGG | 11 | 36615631 | - | TTACGGAGGATTTCATTGGAGG | 1 | 2 | 11 | SEQ ID NO. 4856 |
| (N20)NGG | 11 | 36615634 | - | TTTTTACGGAGGGATTTCATTGG | 1 | 3 | 24 | SEQ ID NO. 4857 |
| (N20)NGG | 11 | 36615644 | - | TCCAGAACCTTTTTACGGAGGG | 1 | 1 | 20 | SEQ ID NO. 4858 |
| (N20)NGG | 11 | 36615645 | - | TTCCAGAACCTTTTTACGGAGG | 1 | 2 | 19 | SEQ ID NO. 4859 |
| (N20)NGG | 11 | 36615648 | - | TTTTTCCAGAACCTTTTTACGG | 1 | 12 | 219 | SEQ ID NO. 4860 |
| (N20)NGG | 11 | 36615679 | - | CTAAGAAAGATTTCTTGGCAGG | 2 | 4 | 86 | SEQ ID NO. 4861 |
| (N20)NGG | 11 | 36615683 | - | CCTTCTAAGAAAGGATTTCTTGG | 1 | 8 | 100 | SEQ ID NO. 4862 |
| (N20)NGG | 11 | 36615692 | - | ATCAAACAACCTTCTAAGAAAGG | 1 | 5 | 63 | SEQ ID NO. 4863 |

FIG. 14 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 2 | 98340496 | + | GCAGGTTTCGGAGGCCCAGGGG | 1 | | 3 | 38 SEQ ID NO. 4864 |
| (N20)NGG | 2 | 98340514 | + | AGGGGCGATGCCAGACCCGCGG | 1 | | 1 | 18 SEQ ID NO. 4865 |
| (N20)NGG | 2 | 98340536 | + | GCGCACCTGCCCTTCTTCTACG | 1 | | 1 | 16 SEQ ID NO. 4866 |
| (N20)NGG | 2 | 98340556 | + | CGGCAGCATCTCGCGTGCCGAGG | 1 | | 1 | 5 SEQ ID NO. 4867 |
| (N20)NGG | 2 | 98340562 | + | CATCTCGCGTGCCGAGGCGAGG | 1 | | 1 | 3 SEQ ID NO. 4868 |
| (N20)NGG | 2 | 98340577 | + | GGCCGAGGAGCACCTGAAGCTGG | 1 | | 5 | 72 SEQ ID NO. 4869 |
| (N20)NGG | 2 | 98340580 | + | CGAGGAGCACCTGAAGCTGGCGG | 1 | | 17 | 373 SEQ ID NO. 4870 |
| (N20)NGG | 2 | 98340581 | + | GAGGAGCACCTGAAGCTGGCGG | 1 | | 11 | 352 SEQ ID NO. 4871 |
| (N20)NGG | 2 | 98340586 | + | GCACCTGAAGCTGGCGGGCATGG | 1 | | 3 | 69 SEQ ID NO. 4872 |
| (N20)NGG | 2 | 98340589 | + | CCTGAAGCTGGCGGGCATGGCGG | 1 | | 2 | 52 SEQ ID NO. 4873 |
| (N20)NGG | 2 | 98340593 | + | AAGCTGGCGGGCATGGCGACGG | 1 | | 2 | 20 SEQ ID NO. 4874 |
| (N20)NGG | 2 | 98340594 | + | AGCTGGCGGGCATGGCGACGG | 1 | | 2 | 18 SEQ ID NO. 4875 |
| (N20)NGG | 2 | 98340628 | + | GCGCCAGTGCCTCGCGCTCGCTGG | 1 | | 2 | 13 SEQ ID NO. 4876 |
| (N20)NGG | 2 | 98340629 | + | CGCCAGTGCCTCGCGCTCGCTGGG | 1 | | 2 | 17 SEQ ID NO. 4877 |
| (N20)NGG | 2 | 98340632 | + | CAGTGCCTCGCGCTCGCTGGGCGG | 1 | | 1 | 19 SEQ ID NO. 4878 |
| (N20)NGG | 2 | 98340698 | + | CCCATCGAGGCCAGCTCAACGG | 1 | | 3 | 14 SEQ ID NO. 4879 |
| (N20)NGG | 2 | 98340716 | + | AACGGCACCTACGCCATTGCCGG | 1 | | 2 | 4 SEQ ID NO. 4880 |
| (N20)NGG | 2 | 98340719 | + | GGCACCTACGCCATTGCCGGCGG | 2 | | 2 | 10 SEQ ID NO. 4881 |
| (N20)NGG | 2 | 98340734 | + | GCCGGCGGCAAAGCGCACTGTGG | 1 | | 2 | 10 SEQ ID NO. 4882 |
| (N20)NGG | 2 | 98340739 | + | CGGCAAAGCGCACTGTGGACCGG | 1 | | 1 | 7 SEQ ID NO. 4883 |
| (N20)NGG | 2 | 98340776 | + | TTCTACTCGCGCGACCCCGACGG | 1 | | 1 | 1 SEQ ID NO. 4884 |
| (N20)NGG | 2 | 98340777 | + | TCTACTCGCGCGACCCCGACGGG | 1 | | 1 | 1 SEQ ID NO. 4885 |
| (N20)NGG | 2 | 98340810 | + | ACCTGCGCAAGCCGTGCAACCGG | 1 | | 1 | 9 SEQ ID NO. 4886 |
| (N20)NGG | 2 | 98340817 | + | CAAGCCGTGCAACCGGCCGTCGG | 1 | | 1 | 3 SEQ ID NO. 4887 |
| (N20)NGG | 2 | 98340818 | + | AAGCCGTGCAACCGGCCGTCGGG | 1 | | 1 | 1 SEQ ID NO. 4888 |
| (N20)NGG | 2 | 98340835 | + | GTCGGGCCTCGAGCCCAGCCGG | 1 | | 21 | 58 SEQ ID NO. 4889 |
| (N20)NGG | 2 | 98340836 | + | TCGGGCCTCGAGCCCAGCCGGG | 1 | | 20 | 58 SEQ ID NO. 4890 |
| (N20)NGG | 2 | 98340837 | + | CGGGCCTCGAGCCCAGCCGGGG | 1 | | 2 | 49 SEQ ID NO. 4891 |
| (N20)NGG | 2 | 98340838 | + | GGGCCTCGAGCCCAGCCGGGGG | 1 | | 22 | 81 SEQ ID NO. 4892 |
| (N20)NGG | 2 | 98340865 | + | CGACTGCCTGCCGAGACGCCATGG | 1 | | 1 | 8 SEQ ID NO. 4893 |
| (N20)NGG | 2 | 98340891 | + | GTGACTACGTGCCCAGACGTGG | 1 | | 1 | 3 SEQ ID NO. 4894 |
| (N20)NGG | 2 | 98340898 | + | CGTGCGCCAGACGTGGAAGCTGG | 1 | | 1 | 6 SEQ ID NO. 4895 |
| (N20)NGG | 2 | 98340901 | + | GCGCCAGACGTGGAAGCTGGAGG | 1 | | 1 | 18 SEQ ID NO. 4896 |

FIG. 15

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 2 | 98340917 | + | CTGAGGTGAGAGCCAGCCTGG | 1 | 2 | 78 | SEQ ID NO. 4897 |
| (N20)NGG | 2 | 98340918 | + | TGGAGGTGAGAGCCAGCCTGGG | 1 | 6 | 72 | SEQ ID NO. 4898 |
| (N20)NGG | 2 | 98340919 | + | GGAGGTGAGAGCCAGCCTGGGG | 1 | 6 | 109 | SEQ ID NO. 4899 |
| (N20)NGG | 2 | 98340924 | + | TGAGAGCGCAGCCTGGGGCGCGG | 1 | 1 | 51 | SEQ ID NO. 4900 |
| (N20)NGG | 2 | 98340925 | + | GAGAGCGCAGCCTGGGGCGCGG | 1 | 5 | 53 | SEQ ID NO. 4901 |
| (N20)NGG | 2 | 98340489 | - | CGGGTCTGGCATCGCCCCTGG | 1 | 3 | 22 | SEQ ID NO. 4902 |
| (N20)NGG | 2 | 98340490 | - | GCGGGTCTGGCATCGCCCCTG | 1 | 1 | 13 | SEQ ID NO. 4903 |
| (N20)NGG | 2 | 98340502 | - | GGCAGTGCGCCGCGGGGTCTGG | 1 | 2 | 34 | SEQ ID NO. 4904 |
| (N20)NGG | 2 | 98340507 | - | AGAAGGGCAGGTGCCGCCGGG | 1 | 1 | 23 | SEQ ID NO. 4905 |
| (N20)NGG | 2 | 98340508 | - | AAGAAGGGCAGGTGCCGCCGGG | 1 | 3 | 19 | SEQ ID NO. 4906 |
| (N20)NGG | 2 | 98340509 | - | GAAGAAGGGCAGGTGCGCCGG | 1 | 5 | 35 | SEQ ID NO. 4907 |
| (N20)NGG | 2 | 98340519 | - | TGCTGCCGTAGAAGAGGGCAGG | 1 | 1 | 24 | SEQ ID NO. 4908 |
| (N20)NGG | 2 | 98340523 | - | GAGATGCTGCCGTAGAAGAAGG | 1 | 3 | 41 | SEQ ID NO. 4909 |
| (N20)NGG | 2 | 98340524 | - | CGAGATGCTGCCGTAGAAGAAG | 1 | 1 | 10 | SEQ ID NO. 4910 |
| (N20)NGG | 2 | 98340551 | - | CTTCAGGTGCTCTCCGGCCTCG | 1 | 1 | 94 | SEQ ID NO. 4911 |
| (N20)NGG | 2 | 98340557 | - | CGCCAGCTTCAGGTGCTCCTCG | 1 | 5 | 47 | SEQ ID NO. 4912 |
| (N20)NGG | 2 | 98340567 | - | CCGCCATGCCCGCCAGCTTCAGG | 1 | 3 | 34 | SEQ ID NO. 4913 |
| (N20)NGG | 2 | 98340600 | - | AGCGCAGGCACTGCCGCCAGCAGG | 1 | 2 | 21 | SEQ ID NO. 4914 |
| (N20)NGG | 2 | 98340609 | - | CGCCCAGCGAGCGCAGGCACTGG | 1 | 1 | 18 | SEQ ID NO. 4915 |
| (N20)NGG | 2 | 98340615 | - | CATAGCCGCCCAGCGAGCGCAGG | 1 | 1 | 7 | SEQ ID NO. 4916 |
| (N20)NGG | 2 | 98340666 | - | GGCGCTCGATGGGAAAGTGGTGG | 1 | 2 | 17 | SEQ ID NO. 4917 |
| (N20)NGG | 2 | 98340669 | - | GCTGGCGCTCGATGGGAAAGTGG | 1 | 2 | 8 | SEQ ID NO. 4918 |
| (N20)NGG | 2 | 98340676 | - | CCGTTGAGCTGGCGCTCGATGG | 1 | 1 | 3 | SEQ ID NO. 4919 |
| (N20)NGG | 2 | 98340677 | - | GCCGTTGAGCTGGCCGTTGAGCTGG | 1 | 1 | 9 | SEQ ID NO. 4920 |
| (N20)NGG | 2 | 98340687 | - | TGGCGTAGGTGCCGTTGAGCTGG | 1 | 1 | 11 | SEQ ID NO. 4921 |
| (N20)NGG | 2 | 98340701 | - | TTTGCCGCCGGCAATGGCGTAGG | 1 | 1 | 2 | SEQ ID NO. 4922 |
| (N20)NGG | 2 | 98340707 | - | GTGCGCTTTGCCGCCGGCAATGG | 1 | 1 | 1 | SEQ ID NO. 4923 |
| (N20)NGG | 2 | 98340713 | - | TCCACAGTGCGCTTTGCCGCCGG | 1 | 2 | 15 | SEQ ID NO. 4924 |
| (N20)NGG | 2 | 98340736 | - | TAGAACTCGCAGAGCTCTGCCGG | 1 | 2 | 17 | SEQ ID NO. 4925 |
| (N20)NGG | 2 | 98340768 | - | GGTTGCAGGGCAGCCCCTCGGGG | 1 | 2 | 14 | SEQ ID NO. 4926 |
| (N20)NGG | 2 | 98340769 | - | AGGTTGCAGGGCAGCCCGTCGG | 1 | 1 | 20 | SEQ ID NO. 4927 |
| (N20)NGG | 2 | 98340770 | - | CAGGTTGCAGGGCAGCCCGTCGG | 1 | 4 | 23 | SEQ ID NO. 4928 |
| (N20)NGG | 2 | 98340781 | - | CACGGCTTGCGCAGGTTGCAGGG | 1 | 1 | 10 | SEQ ID NO. 4929 |

FIG. 15 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 2 | 98340782 | - | GCACGGCTTGCGCAGGTTGCAGG | 1 | 1 | 8 | SEQ ID NO. 4930 |
| (N20)NGG | 2 | 98340789 | - | GCCGGTTGCACGGCTTGCGCAGG | 1 | 1 | 5 | SEQ ID NO. 4931 |
| (N20)NGG | 2 | 98340799 | - | AGGCCCGACACGCCGGTTGCACGG | 1 | 1 | 4 | SEQ ID NO. 4932 |
| (N20)NGG | 2 | 98340807 | - | GCGGCTCGAGGCCCGACGGCCGG | 1 | 1 | 12 | SEQ ID NO. 4933 |
| (N20)NGG | 2 | 98340811 | - | GGGCTGCGGCTCGAGGCCCGACGG | 1 | 2 | 28 | SEQ ID NO. 4934 |
| (N20)NGG | 2 | 98340819 | - | AGACCCCGGCTGCGGCTCGAGG | 1 | 3 | 13 | SEQ ID NO. 4935 |
| (N20)NGG | 2 | 98340826 | - | CAGTGCAAGACCCCGGCTGCGG | 1 | 2 | 7 | SEQ ID NO. 4936 |
| (N20)NGG | 2 | 98340832 | - | CGCAGGCAGTGCAAGACCCCGG | 1 | 1 | 12 | SEQ ID NO. 4937 |
| (N20)NGG | 2 | 98340849 | - | CACGCACCATGGCGTCTGCAGG | 1 | 1 | 9 | SEQ ID NO. 4938 |
| (N20)NGG | 2 | 98340860 | - | GCGCACGTAGTCACGCACCATGG | 1 | 1 | 4 | SEQ ID NO. 4939 |
| (N20)NGG | 2 | 98340882 | - | TCACCTCCAGTTCCACGTCTGG | 2 | 3 | 41 | SEQ ID NO. 4940 |
| (N20)NGG | 2 | 98341554 | + | CTCCTCGCCTCTCCTTTTCTAGG | 1 | 7 | 162 | SEQ ID NO. 4941 |
| (N20)NGG | 2 | 98341555 | + | TCCTCGCCTCTCCTTTTCTAGGG | 1 | 2 | 71 | SEQ ID NO. 4942 |
| (N20)NGG | 2 | 98341560 | + | GCCTCTCCTTTTCTAGGGCGAGG | 1 | 1 | 33 | SEQ ID NO. 4943 |
| (N20)NGG | 2 | 98341566 | + | CCTTTTCTAGGGCGAGGCCCTGG | 1 | 4 | 21 | SEQ ID NO. 4944 |
| (N20)NGG | 2 | 98341572 | + | CTAGGGCGAGGCCCTGAGCAGG | 1 | 2 | 38 | SEQ ID NO. 4945 |
| (N20)NGG | 2 | 98341587 | + | GGAGCAGGCCATCATCAGCCAGG | 1 | 5 | 39 | SEQ ID NO. 4946 |
| (N20)NGG | 2 | 98341596 | + | CATCATCAGCCAGGCCCCGCAGG | 1 | 2 | 32 | SEQ ID NO. 4947 |
| (N20)NGG | 2 | 98341599 | + | CATCAGCCAGGCCCCGCAGGTGG | 2 | 6 | 80 | SEQ ID NO. 4948 |
| (N20)NGG | 2 | 98341620 | + | GGAGAAGCTCATTGCTACGACGG | 1 | 2 | 19 | SEQ ID NO. 4949 |
| (N20)NGG | 2 | 98341631 | + | TTGCTACGACGGCCCACGAGCGG | 1 | 1 | 1 | SEQ ID NO. 4950 |
| (N20)NGG | 2 | 98341640 | + | CGGCCCACGAGCGGATGCCCTGG | 1 | 1 | 4 | SEQ ID NO. 4951 |
| (N20)NGG | 2 | 98341665 | + | CCACAGCAGCCTGACGCGTGAGG | 1 | 2 | 24 | SEQ ID NO. 4952 |
| (N20)NGG | 2 | 98341668 | + | CAGCAGCCTGACGCGTGAGGAGG | 2 | 3 | 18 | SEQ ID NO. 4953 |
| (N20)NGG | 2 | 98341690 | + | GCCGAGCGCAAACTTTACTCTGG | 1 | 1 | 3 | SEQ ID NO. 4954 |
| (N20)NGG | 2 | 98341691 | + | CCGAGCGCAAACTTTACTCTGGG | 1 | 1 | 2 | SEQ ID NO. 4955 |
| (N20)NGG | 2 | 98341692 | + | CGAGCGCAAACTTTACTCTGGGG | 1 | 1 | 5 | SEQ ID NO. 4956 |
| (N20)NGG | 2 | 98341705 | + | TACTCTGGGGCGCAGACCGACGG | 1 | 1 | 6 | SEQ ID NO. 4957 |
| (N20)NGG | 2 | 98341722 | + | CGACGGCAAGTTCCTGTATGTGG | 1 | 4 | 7 | SEQ ID NO. 4958 |
| (N20)NGG | 2 | 98341723 | + | GACGGCAAGTTCCTGTATGTGGG | 1 | 1 | 9 | SEQ ID NO. 4959 |
| (N20)NGG | 2 | 98341724 | + | ACGGCAAGTTCCTGTATGTGGGG | 1 | 3 | 16 | SEQ ID NO. 4960 |
| (N20)NGG | 2 | 98341729 | + | AAGTTCCTGTATGTGGGGCCCGG | 1 | 2 | 26 | SEQ ID NO. 4961 |
| (N20)NGG | 2 | 98341730 | + | AGTTCCTGTATGTGGGGCCCGGG | 1 | 4 | 45 | SEQ ID NO. 4962 |

FIG. 15 cont.

| site type | site chromosome | site start nucleotide | site strand | target site sequence with NGG | genome wide hits with 1 or less mismatches | genome wide hits with 2 or less mismatches | genome wide hits with 3 or less mismatches | SEQ ID NO. |
|---|---|---|---|---|---|---|---|---|
| (N20)NGG | 2 | 98341736 | + | TGTATGTGGGCCCGGGATTTGG |  |  | 2 | 26 SEQ ID NO. 4963 |
| (N20)NGG | 2 | 98341737 | + | GTATGTGGGCCCGGGATTTGGG | 1 |  | 2 | 21 SEQ ID NO. 4964 |
| (N20)NGG | 2 | 98341531 | - | CTAGAAAAGGAGAGGCGAGAGG | 1 |  | 6 | 100 SEQ ID NO. 4965 |
| (N20)NGG | 2 | 98341534 | - | GCCCTAGAAAAGGAGAGGCGAGG | 1 |  | 1 | 30 SEQ ID NO. 4966 |
| (N20)NGG | 2 | 98341539 | - | GCCTCGCCTAGAAAAGGAGAGG | 1 |  | 2 | 23 SEQ ID NO. 4967 |
| (N20)NGG | 2 | 98341544 | - | CCAGGGCCTCGCCTAGAAAAGG | 1 |  | 3 | 30 SEQ ID NO. 4968 |
| (N20)NGG | 2 | 98341561 | - | GCTGATGATGGCCTGCTCCAGG | 3 |  | 6 | 53 SEQ ID NO. 4969 |
| (N20)NGG | 2 | 98341562 | - | GGCTGATGATGGCCTGCTCCAG | 1 |  | 7 | 52 SEQ ID NO. 4970 |
| (N20)NGG | 2 | 98341573 | - | CTGCGGGCCTGGCTGATGATGG | 1 |  | 1 | 41 SEQ ID NO. 4971 |
| (N20)NGG | 2 | 98341583 | - | GCTTCTCCACCTGCGGGGCCTGG | 1 |  | 7 | 75 SEQ ID NO. 4972 |
| (N20)NGG | 2 | 98341588 | - | AATGAGCTTCTCCACCTGCGGG | 1 |  | 2 | 33 SEQ ID NO. 4973 |
| (N20)NGG | 2 | 98341589 | - | CAATGAGCTTCTCTCCACCTGCGG | 2 |  | 11 | 57 SEQ ID NO. 4974 |
| (N20)NGG | 2 | 98341590 | - | GCAATGAGCTTCTCTCCACCTGCG | 2 |  | 6 | 33 SEQ ID NO. 4975 |
| (N20)NGG | 2 | 98341621 | - | GTACCAGGGCATCCGCTCGTGG | 1 |  | 1 | 5 SEQ ID NO. 4976 |
| (N20)NGG | 2 | 98341622 | - | GGTACCAGGGCATCCGCTCGTG | 1 |  | 1 | 9 SEQ ID NO. 4977 |
| (N20)NGG | 2 | 98341635 | - | GTCAGGCTGCTGTGGTACCAGG | 1 |  | 2 | 53 SEQ ID NO. 4978 |
| (N20)NGG | 2 | 98341636 | - | CGTCAGGCTGCTGTGGTACCAG | 1 |  | 2 | 49 SEQ ID NO. 4979 |
| (N20)NGG | 2 | 98341643 | - | CCTCACGCGTCAGGCTGCTGTG | 1 |  | 2 | 25 SEQ ID NO. 4980 |
| (N20)NGG | 2 | 98341652 | - | GCTCGGCCTCCTCACGCGTCAG | 1 |  | 4 | 9 SEQ ID NO. 4981 |
| (N20)NGG | 2 | 98341669 | - | CCCAGAGTAAAGTTTGCGCTCGG | 1 |  | 1 | 6 SEQ ID NO. 4982 |
| (N20)NGG | 2 | 98341699 | - | CACATACAGGAACTTGCCGTCG | 1 |  | 2 | 19 SEQ ID NO. 4983 |
| (N20)NGG | 2 | 98341712 | - | AAATCCGGGCCCCACATACAGG | 1 |  | 2 | 12 SEQ ID NO. 4984 |
| (N20)NGG | 2 | 98349345 | + | ATCCCTCCCTTCCCTGCCAGG | 1 |  | 19 | 323 SEQ ID NO. 4985 |
| (N20)NGG | 2 | 98349351 | + | TCCCTTCCCCTGCCAGGCTGAGG | 4 |  | 40 | 380 SEQ ID NO. 4986 |
| (N20)NGG | 2 | 98349357 | + | CCCTGCCAGGCTGAGGCCGCGG | 1 |  | 8 | 116 SEQ ID NO. 4987 |
| (N20)NGG | 2 | 98349361 | + | TGCCAGGCTGAGGCCGCGGAAGG | 1 |  | 2 | 53 SEQ ID NO. 4988 |
| (N20)NGG | 2 | 98349367 | + | GCTGAGGCCGCGGAAGGAGCAGG | 1 |  | 4 | 92 SEQ ID NO. 4989 |
| (N20)NGG | 2 | 98349368 | + | CTGAGGCCGCGGAAGGAGCAGG | 1 |  | 4 | 72 SEQ ID NO. 4990 |
| (N20)NGG | 2 | 98349395 | + | TACGCCCTGTCCCTCATCTATGG | 1 |  | 4 | 10 SEQ ID NO. 4991 |
| (N20)NGG | 2 | 98349396 | + | ACGCCCTGTCCCTCATCTATGGG | 1 |  | 1 | 12 SEQ ID NO. 4992 |
| (N20)NGG | 2 | 98349403 | + | GTCCCTCATCTATGGGAAGACGG | 1 |  | 4 | 37 SEQ ID NO. 4993 |
| (N20)NGG | 2 | 98349433 | + | CTACCTCATCAGCCAAGACAAGG | 1 |  | 1 | 45 SEQ ID NO. 4994 |
| (N20)NGG | 2 | 98349436 | + | CCTCATCAGCCAAGACAAGGCCGG | 2 |  | 4 | 58 SEQ ID NO. 4995 |

FIG. 15 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 2 | 98349437 | + | CTCATCAGCCAAGACAAGGCGGG | 1 | 4 | 45 | SEQ ID NO. 4996 |
| (N20)NGG | 2 | 98349457 | + | GGGCAAGTACTGCATTCCCGAGG | 1 | 2 | 10 | SEQ ID NO. 4997 |
| (N20)NGG | 2 | 98349458 | + | GGCAAGTACTGCATTCCCGAGGG | 1 | 2 | 12 | SEQ ID NO. 4998 |
| (N20)NGG | 2 | 98349480 | + | GCACCAAGTTTGACACGCTCTGG | 1 | 1 | 6 | SEQ ID NO. 4999 |
| (N20)NGG | 2 | 98349484 | + | CAAGTTTGACACGCTCTGGCAGG | 1 | 2 | 14 | SEQ ID NO. 5000 |
| (N20)NGG | 2 | 98349488 | + | TTTGACACGCTCTGGCAGGTAGG | 1 | 1 | 18 | SEQ ID NO. 5001 |
| (N20)NGG | 2 | 98349325 | - | AGCCTGGCAGGGGAAGGGAGGGG | 2 | 25 | 373 | SEQ ID NO. 5002 |
| (N20)NGG | 2 | 98349326 | - | CAGCCTGGCAGGGGAAGGGAGGG | 3 | 31 | 429 | SEQ ID NO. 5003 |
| (N20)NGG | 2 | 98349327 | - | TCAGCCTGGCAGGGGAAGGGAGG | 3 | 26 | 293 | SEQ ID NO. 5004 |
| (N20)NGG | 2 | 98349330 | - | GCCTCAGCCTGGCAGGGGAAGGG | 1 | 17 | 236 | SEQ ID NO. 5005 |
| (N20)NGG | 2 | 98349331 | - | GGCCTCAGCCTGGCAGGGGAAGG | 1 | 20 | 289 | SEQ ID NO. 5006 |
| (N20)NGG | 2 | 98349335 | - | CCGGCGGCCTCAGCCTGGCAGGG | 1 | 8 | 55 | SEQ ID NO. 5007 |
| (N20)NGG | 2 | 98349336 | - | TCCGCGGCCTCAGCCTGGCAGGG | 1 | 6 | 108 | SEQ ID NO. 5008 |
| (N20)NGG | 2 | 98349337 | - | TTCCGCGGCCTCAGCCTGGCAGG | 1 | 2 | 211 | SEQ ID NO. 5009 |
| (N20)NGG | 2 | 98349341 | - | CTCCTTCCGCGGCCTCAGCCTGG | 2 | 3 | 38 | SEQ ID NO. 5010 |
| (N20)NGG | 2 | 98349352 | - | TATGTCCCTGCTCTCTTCCGCGG | 1 | 1 | 23 | SEQ ID NO. 5011 |
| (N20)NGG | 2 | 98349377 | - | CTTCCATAGATGAGGGACAGGG | 1 | 4 | 42 | SEQ ID NO. 5012 |
| (N20)NGG | 2 | 98349378 | - | TCTTCCATAGATGAGGGACAGG | 1 | 4 | 39 | SEQ ID NO. 5013 |
| (N20)NGG | 2 | 98349383 | - | CACCGTCTTCCCATAGATGAGGG | 1 | 2 | 15 | SEQ ID NO. 5014 |
| (N20)NGG | 2 | 98349384 | - | ACACCGTCTTCCCATAGATGAGG | 1 | 2 | 16 | SEQ ID NO. 5015 |
| (N20)NGG | 2 | 98349408 | - | TGTCTTGGCTGATGAGGTAGTGG | 1 | 1 | 46 | SEQ ID NO. 5016 |
| (N20)NGG | 2 | 98349414 | - | CCGGCTTGTCTTGGCTGATGAGG | 1 | 3 | 27 | SEQ ID NO. 5017 |
| (N20)NGG | 2 | 98349423 | - | AGTACTTGCCCGCCTGTCTTGG | 1 | 2 | 7 | SEQ ID NO. 5018 |
| (N20)NGG | 2 | 98349451 | - | GTGTCAAACTTGGTGCCCTCGG | 1 | 2 | 24 | SEQ ID NO. 5019 |
| (N20)NGG | 2 | 98349452 | - | CGTGTCAAACTTGGTGCCCTCG | 1 | 1 | 9 | SEQ ID NO. 5020 |
| (N20)NGG | 2 | 98349461 | - | CTGCCAGAGCGTGTCAAACTTGG | 1 | 1 | 11 | SEQ ID NO. 5021 |
| (N20)NGG | 2 | 98349590 | + | AGCTGCCTGCTCCCTGCAGCTGG | 3 | 18 | 173 | SEQ ID NO. 5022 |
| (N20)NGG | 2 | 98349593 | + | TGCCTGCTCCCTGCAGCTGGTGG | 2 | 17 | 246 | SEQ ID NO. 5023 |
| (N20)NGG | 2 | 98349611 | + | GGTGAAGTATCTGAAGCTGAAGG | 1 | 2 | 37 | SEQ ID NO. 5024 |
| (N20)NGG | 2 | 98349614 | + | GGAGTATCTGAAGCTGAAGGCGG | 1 | 8 | 102 | SEQ ID NO. 5025 |
| (N20)NGG | 2 | 98349618 | + | TATCTGAAGCTGAAGGCGGACGG | 1 | 1 | 26 | SEQ ID NO. 5026 |
| (N20)NGG | 2 | 98349619 | + | ATCTGAAGCTGAAGGCGGACGGG | 1 | 1 | 15 | SEQ ID NO. 5027 |
| (N20)NGG | 2 | 98349638 | + | CGGGCTCATCTACTGCCTGAAGG | 1 | 2 | 15 | SEQ ID NO. 5028 |

FIG. 15 cont.

| site type | site_chromosome | site_start_nucleotide | site_strand | target_site_sequence_with NGG | genome_wide_hits_with_1_or_less_mismatches | genome_wide_hits_with_2_or_less_mismatches | genome_wide_hits_with_3_or_less_mismatches | | |
|---|---|---|---|---|---|---|---|---|---|
| (N20)NGG | 2 | 98349641 | + | GCTCATCTACTGCCTGAAGGAGG | 1 | 1 | 25 | SEQ ID NO. | 5029 |
| (N20)NGG | 2 | 98349675 | + | AGCAGTGCCAGCAACGCCTCAGG | 1 | 2 | 25 | SEQ ID NO. | 5030 |
| (N20)NGG | 2 | 98349681 | + | GCCAGCAACGCCTCAGTGACGG | 1 | 2 | 27 | SEQ ID NO. | 5031 |
| (N20)NGG | 2 | 98349688 | + | ACGCCTCAGTGACGCCAGCAGG | 1 | 2 | 18 | SEQ ID NO. | 5032 |
| (N20)NGG | 2 | 98349691 | + | CCTCAGTGACGGCAGCAGGCGG | 1 | 8 | 67 | SEQ ID NO. | 5033 |
| (N20)NGG | 2 | 98349692 | + | CTCAGGTGACGGCAGCAGGCGG | 1 | 5 | 55 | SEQ ID NO. | 5034 |
| (N20)NGG | 2 | 98349695 | + | AGTGACGGCAGCAGGCGGCGG | 1 | 1 | 57 | SEQ ID NO. | 5035 |
| (N20)NGG | 2 | 98349696 | + | GGTGACGCGGCAGCAGGCGGCGG | 1 | 3 | 65 | SEQ ID NO. | 5036 |
| (N20)NGG | 2 | 98349699 | + | GACGGCAGCAGGCGGGCGGCGG | 1 | 8 | 90 | SEQ ID NO. | 5037 |
| (N20)NGG | 2 | 98349573 | - | CTCCACCAGCTGCAGGAGCAGG | 1 | 9 | 119 | SEQ ID NO. | 5038 |
| (N20)NGG | 2 | 98349579 | - | CAGATACTCCACCAGCTGCAGG | 1 | 6 | 51 | SEQ ID NO. | 5039 |
| (N20)NGG | 2 | 98349580 | - | TCAGATACTCCACCAGCTGCAG | 1 | 2 | 30 | SEQ ID NO. | 5040 |
| (N20)NGG | 2 | 98349631 | - | TGTTGGGGCAGGCCTCCTTCAGG | 1 | 3 | 55 | SEQ ID NO. | 5041 |
| (N20)NGG | 2 | 98349642 | - | GCTGGCACTGCTGTTGGGGCAGG | 2 | 14 | 102 | SEQ ID NO. | 5042 |
| (N20)NGG | 2 | 98349646 | - | CGTTGCTGGCACTGCTGTTGGGG | 1 | 3 | 37 | SEQ ID NO. | 5043 |
| (N20)NGG | 2 | 98349647 | - | GCGTTGCTGGCACTGCTGTTGGG | 1 | 2 | 10 | SEQ ID NO. | 5044 |
| (N20)NGG | 2 | 98349648 | - | GGCGTTGCTGGCACTGCTGTTGG | 1 | 2 | 37 | SEQ ID NO. | 5045 |
| (N20)NGG | 2 | 98349660 | - | GCCGTCACCTGAGGCGTTGCTGG | 1 | 3 | 7 | SEQ ID NO. | 5046 |
| (N20)NGG | 2 | 98349669 | - | CCGCCTGCGTCACCTGAGG | 2 | 2 | 41 | SEQ ID NO. | 5047 |
| (N20)NGG | 2 | 98349759 | + | ACTGTCCCTTCTGCTCCCCCAGG | 1 | 2 | 83 | SEQ ID NO. | 5048 |
| (N20)NGG | 2 | 98349760 | + | CTGTCCCTTCTGCTCCCCCAGGG | 1 | 15 | 191 | SEQ ID NO. | 5049 |
| (N20)NGG | 2 | 98349761 | + | TGTCCCTTCTGCTCCCCCAGGGG | 1 | 9 | 119 | SEQ ID NO. | 5050 |
| (N20)NGG | 2 | 98349814 | + | CCAACGTTGACTCATGTGAGTTGG | 1 | 1 | 15 | SEQ ID NO. | 5051 |
| (N20)NGG | 2 | 98349815 | + | CACGTTGACTCATGTGAGTTGGG | 1 | 1 | 21 | SEQ ID NO. | 5052 |
| (N20)NGG | 2 | 98349816 | + | ACGTTGACTCATGTGAGTTGGGG | 1 | 1 | 11 | SEQ ID NO. | 5053 |
| (N20)NGG | 2 | 98349817 | + | CGTTGACTCATGTGAGTTGGGGG | 1 | 1 | 14 | SEQ ID NO. | 5054 |
| (N20)NGG | 2 | 98349824 | + | TCATGTGAGTTGGGGGCACCTGG | 1 | 3 | 19 | SEQ ID NO. | 5055 |
| (N20)NGG | 2 | 98349742 | - | CAGCCCCTGGGGGAGCAGAAGGG | 3 | 9 | 111 | SEQ ID NO. | 5056 |
| (N20)NGG | 2 | 98349743 | - | GCAGCCCCTGGGGGAGCAGAAGG | 1 | 17 | 144 | SEQ ID NO. | 5057 |
| (N20)NGG | 2 | 98349752 | - | GTGGGAGCAGCAGCCCCTGGGGG | 2 | 13 | 169 | SEQ ID NO. | 5058 |
| (N20)NGG | 2 | 98349753 | - | TGTGGGAGCAGCAGCCCCTGGGG | 4 | 17 | 142 | SEQ ID NO. | 5059 |
| (N20)NGG | 2 | 98349754 | - | GTGTGGGAGCAGCAGCCCCTGGG | 2 | 10 | 79 | SEQ ID NO. | 5060 |
| (N20)NGG | 2 | 98349755 | - | AGTGTGGGAGCAGCAGCCCCTGG | 1 | 7 | 80 | SEQ ID NO. | 5061 |

FIG. 15 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 2 | 98349770 | - | GATGGGTGGGCTGGGAGTGTGGG | | 1 | 13 | 158 SEQ ID NO. 5062 |
| (N20)NGG | 2 | 98349771 | - | GGATGGGTGGGCTGGGAGTGTGG | | 3 | 30 | 323 SEQ ID NO. 5063 |
| (N20)NGG | 2 | 98349778 | - | TCAACGTGGATGGGTGGGCTGGG | | 1 | 3 | 15 SEQ ID NO. 5064 |
| (N20)NGG | 2 | 98349779 | - | GTCAACGTGGATGGGTGGGCTGG | | 1 | 1 | 22 SEQ ID NO. 5065 |
| (N20)NGG | 2 | 98349783 | - | ATGAGTCAACGTGGATGGGTGGG | | 1 | 2 | 16 SEQ ID NO. 5066 |
| (N20)NGG | 2 | 98349784 | - | CATGAGTCAACGTGGATGGGTGG | | 1 | 2 | 20 SEQ ID NO. 5067 |
| (N20)NGG | 2 | 98349787 | - | TCACATGAGTCAACGTGGATGGG | | 1 | 2 | 22 SEQ ID NO. 5068 |
| (N20)NGG | 2 | 98349788 | - | CTCACATGAGTCAACGTGGATGG | | 1 | 1 | 29 SEQ ID NO. 5069 |
| (N20)NGG | 2 | 98349792 | - | CCAACTCACATGAGTCAACGTGG | | 1 | 1 | 14 SEQ ID NO. 5070 |
| (N20)NGG | 2 | 98350040 | + | ATGCACACCCTCAACTCAGATGG | | 1 | 1 | 8 SEQ ID NO. 5071 |
| (N20)NGG | 2 | 98350058 | + | GATGGATACACCCTGAGCCAGG | | 1 | 2 | 16 SEQ ID NO. 5072 |
| (N20)NGG | 2 | 98350065 | + | ACACCCCTGAGCCAGGTGAGCGG | | 2 | 9 | 67 SEQ ID NO. 5073 |
| (N20)NGG | 2 | 98350066 | + | CACCCCTGAGCCAGGTGAGCGGG | | 1 | 7 | 84 SEQ ID NO. 5074 |
| (N20)NGG | 2 | 98350072 | + | TGAGCCAGGTGAGCGGGCAGAGG | | 3 | 13 | 83 SEQ ID NO. 5075 |
| (N20)NGG | 2 | 98350075 | + | GCCAGGTGAGCGGGCAGAGGTGG | | 1 | 7 | 113 SEQ ID NO. 5076 |
| (N20)NGG | 2 | 98350076 | + | CCAGGTGAGCGGGCAGAGGTGGG | | 1 | 5 | 102 SEQ ID NO. 5077 |
| (N20)NGG | 2 | 98350077 | + | CAGGTGAGCGGGCAGAGGTGGGG | | 1 | 21 | 161 SEQ ID NO. 5078 |
| (N20)NGG | 2 | 98349982 | - | TAAAGGCCACACAGGGTCAGCAAGG | | 1 | 5 | 59 SEQ ID NO. 5079 |
| (N20)NGG | 2 | 98349991 | - | CTCTGAGGCTAAAGGCCACAGGG | | 1 | 1 | 57 SEQ ID NO. 5080 |
| (N20)NGG | 2 | 98349992 | - | TCTCTGAGGCTAAAGGCCACAGG | | 1 | 5 | 54 SEQ ID NO. 5081 |
| (N20)NGG | 2 | 98349999 | - | CGATTCGTCTCTGAGGCTAAAGG | | 1 | 1 | 6 SEQ ID NO. 5082 |
| (N20)NGG | 2 | 98350006 | - | AGGTGTCGATTCGTCTCTGAGG | | 1 | 1 | 9 SEQ ID NO. 5083 |
| (N20)NGG | 2 | 98350025 | - | GGTGTATCCATCTGAGTTGAGGG | | 1 | 2 | 18 SEQ ID NO. 5084 |
| (N20)NGG | 2 | 98350026 | - | GGGTGTATCCATCTGAGTTGAGG | | 1 | 2 | 13 SEQ ID NO. 5085 |
| (N20)NGG | 2 | 98350046 | - | TGCCCGCTCACCTGGCTCAGGGG | | 2 | 10 | 61 SEQ ID NO. 5086 |
| (N20)NGG | 2 | 98350047 | - | CTGCCCGCTCACCTGGCTCAGGG | | 5 | 7 | 48 SEQ ID NO. 5087 |
| (N20)NGG | 2 | 98350048 | - | TCTGCCCGCTCACCTGGCTCAGG | | 1 | 3 | 45 SEQ ID NO. 5088 |
| (N20)NGG | 2 | 98350054 | - | CCCACCTCTGCCCGCTCACCTGG | | 1 | 6 | 108 SEQ ID NO. 5089 |
| (N20)NGG | 2 | 98351010 | + | TAACGTCCCAGACAAACCGCGG | | 1 | 1 | 10 SEQ ID NO. 5090 |
| (N20)NGG | 2 | 98351023 | + | CAAACCGCGGCGATGCCCATGG | | 1 | 1 | 3 SEQ ID NO. 5091 |
| (N20)NGG | 2 | 98351062 | + | GAGCCCTACAGCGACCCAGAGG | | 1 | 4 | 27 SEQ ID NO. 5092 |
| (N20)NGG | 2 | 98351071 | + | CAGCGACCCAGAGGAGCTCAAGG | | 2 | 2 | 45 SEQ ID NO. 5093 |
| (N20)NGG | 2 | 98351126 | + | CTCATAGCTGACATTGAACTTGG | | 1 | 9 | 44 SEQ ID NO. 5094 |

FIG. 15 cont.

| site type | site chromosome | site start nucleotide | site strand | target_site_sequence with NGG | genome_wide_hits with 1 or less mismatches | genome_wide_hits with 2 or less mismatches | genome_wide_hits with 3 or less mismatches | | |
|---|---|---|---|---|---|---|---|---|---|
| (N20)NGG | 2 | 98351132 | + | GCTGACATTGAACTTGGCTGCGG | 1 | | 51 | SEQ ID NO. | 5095 |
| (N20)NGG | 2 | 98351141 | + | GAACTTGGCTGCGGCAACTTTGG | 1 | 1 | 18 | SEQ ID NO. | 5096 |
| (N20)NGG | 2 | 98351155 | + | CAACTTTGGCTCAGTGCGCCAGG | 1 | 1 | 10 | SEQ ID NO. | 5097 |
| (N20)NGG | 2 | 98351156 | + | AACTTTGGCTCAGTGCGCCAGGG | 1 | 1 | 9 | SEQ ID NO. | 5098 |
| (N20)NGG | 2 | 98351180 | + | GTGTACCGCATGCGCAAGTATGG | 1 | 1 | 2 | SEQ ID NO. | 5099 |
| (N20)NGG | 2 | 98351195 | + | AAGTATGGCCGCCCCTGCCGTGG | 1 | 1 | 5 | SEQ ID NO. | 5100 |
| (N20)NGG | 2 | 98351198 | + | TATGGCCGCCCCTGCCGTGGTGG | 1 | 1 | 8 | SEQ ID NO. | 5101 |
| (N20)NGG | 2 | 98351199 | + | ATGGCCGCCCCTGCCGTGGTGGG | 1 | 1 | 11 | SEQ ID NO. | 5102 |
| (N20)NGG | 2 | 98350965 | - | TGCGTGCTGGGCACACACAGCCG | 2 | 11 | 66 | SEQ ID NO. | 5103 |
| (N20)NGG | 2 | 98350977 | - | CTGGGACGTTATGCGTGCTGGG | 1 | 1 | 5 | SEQ ID NO. | 5104 |
| (N20)NGG | 2 | 98350978 | - | TCTGGGACGTTATGCGTGCTGG | 1 | 1 | 4 | SEQ ID NO. | 5105 |
| (N20)NGG | 2 | 98350994 | - | CATCGGCGCGGTTTGTCTGGG | 1 | 1 | 4 | SEQ ID NO. | 5106 |
| (N20)NGG | 2 | 98350995 | - | GCATCGGCGCGCGGTTTGTCTGG | 1 | 1 | 1 | SEQ ID NO. | 5107 |
| (N20)NGG | 2 | 98350996 | - | GGCATCGGCGCGCGGTTTGTCTG | 1 | 1 | 4 | SEQ ID NO. | 5108 |
| (N20)NGG | 2 | 98351005 | - | GTGTCCATGGGCATCGGCGCGG | 1 | 2 | 14 | SEQ ID NO. | 5109 |
| (N20)NGG | 2 | 98351011 | - | ACGCTGTGTCCATGGGCATCGG | 1 | 3 | 8 | SEQ ID NO. | 5110 |
| (N20)NGG | 2 | 98351017 | - | TCATACACGCTCGTGTCCATGG | 1 | 1 | 3 | SEQ ID NO. | 5111 |
| (N20)NGG | 2 | 98351018 | - | CTCATACACGCTCGTGTCCATG | 1 | 1 | 4 | SEQ ID NO. | 5112 |
| (N20)NGG | 2 | 98351043 | - | GCTCCTCTGGGTCGCTGTAGGGG | 1 | 1 | 17 | SEQ ID NO. | 5113 |
| (N20)NGG | 2 | 98351044 | - | AGCTCCTCTGGGTCGCTGTAGG | 1 | 1 | 14 | SEQ ID NO. | 5114 |
| (N20)NGG | 2 | 98351045 | - | GAGCTCCTCTGGGTCGCTGTAG | 2 | 1 | 18 | SEQ ID NO. | 5115 |
| (N20)NGG | 2 | 98351055 | - | TCTTGTCCTTGAGCTCCTCTGG | 1 | 4 | 50 | SEQ ID NO. | 5116 |
| (N20)NGG | 2 | 98351056 | - | TTCTTGTCCTTGAGCTCCTCTG | 1 | 4 | 76 | SEQ ID NO. | 5117 |
| (N20)NGG | 2 | 98351085 | - | TGAGGAGGTTATCGCGCTTCAGG | 1 | 1 | 5 | SEQ ID NO. | 5118 |
| (N20)NGG | 2 | 98351100 | - | GTTCAATGTCAGCTATGAGGAGG | 2 | 2 | 39 | SEQ ID NO. | 5119 |
| (N20)NGG | 2 | 98351103 | - | CAAGTTCAATGTCAGCTATGAGG | 1 | 4 | 82 | SEQ ID NO. | 5120 |
| (N20)NGG | 2 | 98351151 | - | TGCGCATGCGGTACACGCCCTGG | 1 | 1 | 6 | SEQ ID NO. | 5121 |
| (N20)NGG | 2 | 98351163 | - | GGCGGCCATACTTGCGCATGCGG | 1 | 1 | 3 | SEQ ID NO. | 5122 |
| (N20)NGG | 2 | 98351712 | + | CTCCGTGGCCGGTCGGGCAGG | 1 | 4 | 22 | SEQ ID NO. | 5123 |
| (N20)NGG | 2 | 98351728 | + | GGGCAGGAAGCAGATCGACGTGG | 1 | 1 | 11 | SEQ ID NO. | 5124 |
| (N20)NGG | 2 | 98351737 | + | GCAGATCGACGTGGCCATCAAGG | 1 | 1 | 12 | SEQ ID NO. | 5125 |
| (N20)NGG | 2 | 98351749 | + | GGCCATCAAGGTCGTGAAGCAGG | 1 | 3 | 46 | SEQ ID NO. | 5126 |
| (N20)NGG | 2 | 98351750 | + | GCCATCAAGGTCGTGAAGCAGGG | 1 | 4 | 59 | SEQ ID NO. | 5127 |

FIG. 15 cont.

| site_type | site_chromosome | site_start_nucleotide | site_strand | target_site_sequence_with NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 2 | 98351755 | + | CAAGGTGCTGAAGCAGGGCACCG | 1 | | 6 | 83 SEQ ID NO. 5128 |
| (N20)NGG | 2 | 98351761 | + | GCTGAAGCAGGGCACGGAGAAGG | 1 | | 5 | 75 SEQ ID NO. 5129 |
| (N20)NGG | 2 | 98351770 | + | GGGCACGGAGAAGGCAGACACGG | 2 | | 6 | 109 SEQ ID NO. 5130 |
| (N20)NGG | 2 | 98351788 | + | CACGGAAAGATGATGCGCAGG | 1 | | 1 | 6 SEQ ID NO. 5131 |
| (N20)NGG | 2 | 98351809 | + | GGGCAGATCATGCACCAGCTGG | 1 | | 1 | 11 SEQ ID NO. 5132 |
| (N20)NGG | 2 | 98351829 | + | TGGACAACCCTACATCGTCGG | 2 | | 2 | 12 SEQ ID NO. 5133 |
| (N20)NGG | 2 | 98351837 | + | CCCTACATCGTCGGGCTCATTGG | 1 | | 2 | 8 SEQ ID NO. 5134 |
| (N20)NGG | 2 | 98351848 | + | GCGGCTCATTGGCGTCTGCCAGG | 1 | | 1 | 7 SEQ ID NO. 5135 |
| (N20)NGG | 2 | 98351854 | + | CATTGGCGTCTGCCAGGCCGAGG | 1 | | 1 | 13 SEQ ID NO. 5136 |
| (N20)NGG | 2 | 98351866 | + | CCAGGCCGAGGCCCTCATGCTGG | 1 | | 4 | 40 SEQ ID NO. 5137 |
| (N20)NGG | 2 | 98351872 | + | CGAGGCCCTCATGCTGGTCATGG | 1 | | 5 | 28 SEQ ID NO. 5138 |
| (N20)NGG | 2 | 98351878 | + | CCTCATGCTGGTCATGGAGATGG | 1 | | 3 | 47 SEQ ID NO. 5139 |
| (N20)NGG | 2 | 98351882 | + | ATGCTGGTCATGGAGATGGCTGG | 1 | | 5 | 46 SEQ ID NO. 5140 |
| (N20)NGG | 2 | 98351883 | + | TGCTGGTCATGGAGATGGCTGGG | 1 | | 2 | 54 SEQ ID NO. 5141 |
| (N20)NGG | 2 | 98351884 | + | GCTGGTCATGGAGATGGCTGGGG | 1 | | 6 | 80 SEQ ID NO. 5142 |
| (N20)NGG | 2 | 98351885 | + | CTGGTCATGGAGATGGCTGGGGG | 1 | | 4 | 70 SEQ ID NO. 5143 |
| (N20)NGG | 2 | 98351888 | + | GTCATGGAGATGGCTGGGGGCGG | 1 | | 7 | 115 SEQ ID NO. 5144 |
| (N20)NGG | 2 | 98351889 | + | TCATGGAGATGGCTGGGGGCGGG | 1 | | 8 | 89 SEQ ID NO. 5145 |
| (N20)NGG | 2 | 98351908 | + | CGGGCCGCTGCACAAGTTCCTGG | 1 | | 2 | 7 SEQ ID NO. 5146 |
| (N20)NGG | 2 | 98351912 | + | CCGCTGCACAAGTTCCTGGTCGG | 1 | | 1 | 14 SEQ ID NO. 5147 |
| (N20)NGG | 2 | 98351919 | + | ACAAGTTCCTGGTCGGCAAGAGG | 1 | | 2 | 23 SEQ ID NO. 5148 |
| (N20)NGG | 2 | 98351929 | + | GGTCGGCAAGAGGTGAGCACCGG | 2 | | 5 | 15 SEQ ID NO. 5149 |
| (N20)NGG | 2 | 98351930 | + | GTCGGCAAGAGGTGAGCACCGGG | 1 | | 1 | 16 SEQ ID NO. 5150 |
| (N20)NGG | 2 | 98351933 | + | GGCAAGAGGTGAGCACCGGGTGG | 1 | | 6 | 79 SEQ ID NO. 5151 |
| (N20)NGG | 2 | 98351934 | + | GCAAGAGGTGAGCACCGGGTGGG | 2 | | 52 | 403 SEQ ID NO. 5152 |
| (N20)NGG | 2 | 98351939 | + | AGGTGAGCACCGGGTGGGCCCGG | 2 | | 3 | 70 SEQ ID NO. 5153 |
| (N20)NGG | 2 | 98351689 | - | CTGCCCGACCCGGCCACGGGAGG | 1 | | 4 | 29 SEQ ID NO. 5154 |
| (N20)NGG | 2 | 98351692 | - | TTCCTGCCCGACCCGGCCACCGG | 1 | | 3 | 22 SEQ ID NO. 5155 |
| (N20)NGG | 2 | 98351693 | - | CTTCCTGCCCGACCCGGCCACGG | 1 | | 2 | 31 SEQ ID NO. 5156 |
| (N20)NGG | 2 | 98351699 | - | GATCTGCTTCCTGCCCGACCCGG | 1 | | 2 | 16 SEQ ID NO. 5157 |
| (N20)NGG | 2 | 98351729 | - | GCCCTGCTTCAGCACCTTGATGG | 1 | | 12 | 54 SEQ ID NO. 5158 |
| (N20)NGG | 2 | 98351802 | - | CGATGTAGGGTTGTCCAGCTGG | 1 | | 2 | 14 SEQ ID NO. 5159 |
| (N20)NGG | 2 | 98351814 | - | CAATGAGCCGCACGATGTAGGGG | 1 | | 2 | 10 SEQ ID NO. 5160 |

FIG. 15 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 2 | 98351815 | - | CCAATGAGCCGCACGATGTAGGG | | 1 | 2 | 7 SEQ ID NO. 5161 |
| (N20)NGG | 2 | 98351816 | - | GCCAATGAGCCGCACGATGTAGG | | 1 | 2 | 6 SEQ ID NO. 5162 |
| (N20)NGG | 2 | 98351844 | - | CCAGCATGAGGGCCTCGGCCTGG | | 2 | 4 | 42 SEQ ID NO. 5163 |
| (N20)NGG | 2 | 98351849 | - | CATGACCAGCATGAGGGCCTCGG | | 5 | 9 | 61 SEQ ID NO. 5164 |
| (N20)NGG | 2 | 98351855 | - | CATCTCATGACCAGCATGAGGG | | 1 | 6 | 51 SEQ ID NO. 5165 |
| (N20)NGG | 2 | 98351856 | - | CCATCTCATGACCAGCATGAGG | | 1 | 3 | 58 SEQ ID NO. 5166 |
| (N20)NGG | 2 | 98351890 | - | CCGACCAGAACTTGTGCAGCGG | | 1 | 1 | 11 SEQ ID NO. 5167 |
| (N20)NGG | 2 | 98351904 | - | GTGCTCACCTCTTGCCGACCAGG | | 1 | 2 | 13 SEQ ID NO. 5168 |
| (N20)NGG | 2 | 98353935 | + | CCCGCCTTCCCCGCCACCCCAGG | | 1 | 18 | 237 SEQ ID NO. 5169 |
| (N20)NGG | 2 | 98353936 | + | CCGCCTTCCCCGCCACCCCAGGG | | 1 | 12 | 127 SEQ ID NO. 5170 |
| (N20)NGG | 2 | 98353939 | + | CCTTCCCCGCCACCCCAGGGAGG | | 1 | 18 | 120 SEQ ID NO. 5171 |
| (N20)NGG | 2 | 98353960 | + | GGAGATCCCTGTGAGCAATGTGG | | 1 | 2 | 40 SEQ ID NO. 5172 |
| (N20)NGG | 2 | 98353978 | + | TGTGGCCGAGCTGCTGCACCAGG | | 1 | 4 | 32 SEQ ID NO. 5173 |
| (N20)NGG | 2 | 98353987 | + | GCTGCTGCACCAGGTGTCCATGG | | 1 | 4 | 54 SEQ ID NO. 5174 |
| (N20)NGG | 2 | 98353988 | + | CTGCTGCACCAGGTGTCCATGGG | | 1 | 3 | 44 SEQ ID NO. 5175 |
| (N20)NGG | 2 | 98353989 | + | TGCTGCACCAGGTGTCCATGGGG | | 1 | 2 | 43 SEQ ID NO. 5176 |
| (N20)NGG | 2 | 98354002 | + | GTCCATGGGGATGAAGTACCTGG | | 1 | 1 | 14 SEQ ID NO. 5177 |
| (N20)NGG | 2 | 98354005 | + | CATGGGGATGAAGTACCTGGAGG | | 1 | 5 | 46 SEQ ID NO. 5178 |
| (N20)NGG | 2 | 98354032 | + | GAACTTTGTGCACCGTGACCTGG | | 2 | 5 | 25 SEQ ID NO. 5179 |
| (N20)NGG | 2 | 98354035 | + | CTTTGTGCACCGTGACCTGGCGG | | 1 | 3 | 28 SEQ ID NO. 5180 |
| (N20)NGG | 2 | 98354053 | + | GGCGGCCCGCAACGTCCTGCTGG | | 1 | 1 | 10 SEQ ID NO. 5181 |
| (N20)NGG | 2 | 98354061 | + | GCAACGTCCTGCTGGTTAACCGG | | 1 | 1 | 5 SEQ ID NO. 5182 |
| (N20)NGG | 2 | 98354087 | + | TACGCCAAGATCAGCGACTTTGG | | 1 | 2 | 4 SEQ ID NO. 5183 |
| (N20)NGG | 2 | 98354104 | + | CTTTGGCCTTCCAAAGCACTGG | | 3 | 15 | 103 SEQ ID NO. 5184 |
| (N20)NGG | 2 | 98354105 | + | TTTGGCCTTCCAAAGCACTGGG | | 2 | 15 | 169 SEQ ID NO. 5185 |
| (N20)NGG | 2 | 98353912 | - | CTGGGGTGGCGGGGAAGGCGGGG | | 2 | 10 | 188 SEQ ID NO. 5186 |
| (N20)NGG | 2 | 98353913 | - | CCTGGGGTGGCGGGGAAGGCGGG | | 1 | 11 | 172 SEQ ID NO. 5187 |
| (N20)NGG | 2 | 98353914 | - | CCCTGGGGTGGCGGGGAAGGCGG | | 1 | 13 | 216 SEQ ID NO. 5188 |
| (N20)NGG | 2 | 98353917 | - | CCTCCCTGGGGTGGCGGGAAGG | | 1 | 14 | 129 SEQ ID NO. 5189 |
| (N20)NGG | 2 | 98353921 | - | ATCTCCTCCCTGGGGTGGCGGGG | | 1 | 3 | 59 SEQ ID NO. 5190 |
| (N20)NGG | 2 | 98353922 | - | GATCTCCTCCCTGGGGTGGCGGG | | 1 | 3 | 48 SEQ ID NO. 5191 |
| (N20)NGG | 2 | 98353923 | - | GGATCTCCTCCCTGGGGTGGCGG | | 1 | 8 | 75 SEQ ID NO. 5192 |
| (N20)NGG | 2 | 98353926 | - | CAGGGATCTCCTCCCTGGGGTGG | | 3 | 6 | 79 SEQ ID NO. 5193 |

FIG. 15 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | | |
|---|---|---|---|---|---|---|---|---|---|
| (N20)NGG | 2 | 98353929 | - | TCACAGGGATCTCCTCCCTGGGG | | 1 | 4 | 63 | SEQ ID NO. 5194 |
| (N20)NGG | 2 | 98353930 | - | CTCACAGGGATCTCCTCCCTGGG | | 1 | 4 | 54 | SEQ ID NO. 5195 |
| (N20)NGG | 2 | 98353931 | - | GCTCACAGGGATCTCCTCCCTGG | | 1 | 3 | 66 | SEQ ID NO. 5196 |
| (N20)NGG | 2 | 98353944 | - | GCTCGGCCACATTGCTCACAGGG | | 1 | 2 | 15 | SEQ ID NO. 5197 |
| (N20)NGG | 2 | 98353945 | - | AGCTCGGCCACATTGCTCACAGG | | 1 | 2 | 11 | SEQ ID NO. 5198 |
| (N20)NGG | 2 | 98353961 | - | GGACACCTGGTGCAGCAGCTCGG | | 1 | 1 | 44 | SEQ ID NO. 5199 |
| (N20)NGG | 2 | 98353974 | - | ACTTCATCCCCATGGACACCTGG | | 1 | 1 | 34 | SEQ ID NO. 5200 |
| (N20)NGG | 2 | 98353982 | - | CTCCAGGTACTTCATCCCCATGG | | 1 | 3 | 62 | SEQ ID NO. 5201 |
| (N20)NGG | 2 | 98353998 | - | GCACAAAGTTCTTCTCCTCCAGG | | 1 | 1 | 59 | SEQ ID NO. 5202 |
| (N20)NGG | 2 | 98354022 | - | CGTTGCGGGCCGCCAGGTCACGG | | 1 | 4 | 17 | SEQ ID NO. 5203 |
| (N20)NGG | 2 | 98354028 | - | GCAGGACGTTGCGGGCCGCCAGG | | 1 | 2 | 12 | SEQ ID NO. 5204 |
| (N20)NGG | 2 | 98354036 | - | GTTAACCAGCAGGACGTTGCGGG | | 1 | 1 | 8 | SEQ ID NO. 5205 |
| (N20)NGG | 2 | 98354037 | - | GGTTAACCAGCAGGACGTTGCGG | | 1 | 2 | 13 | SEQ ID NO. 5206 |
| (N20)NGG | 2 | 98354046 | - | CGTAGTGCCGGTTAACCAGCAGG | | 1 | 1 | 4 | SEQ ID NO. 5207 |
| (N20)NGG | 2 | 98354058 | - | CGCTGATCTTGGCGTAGTGCCGG | | 1 | 1 | 5 | SEQ ID NO. 5208 |
| (N20)NGG | 2 | 98354069 | - | GAGGCCAAAGTCGCTGATCTTGG | | 1 | 4 | 21 | SEQ ID NO. 5209 |
| (N20)NGG | 2 | 98354088 | - | CGGCACCCAGTGCTTTGGAGAGG | | 1 | 1 | 22 | SEQ ID NO. 5210 |
| (N20)NGG | 2 | 98354093 | - | GTCGTCGGCACCCAGTGCTTTGG | | 1 | 1 | 2 | SEQ ID NO. 5211 |
| (N20)NGG | 2 | 98354108 | - | TACAGTGTAGTAGCTGTGTCGTCGG | | 1 | 1 | 6 | SEQ ID NO. 5212 |
| (N20)NGG | 2 | 98354219 | + | AGCAGCATCTCCCCCTCCCCAGG | | 1 | 12 | 172 | SEQ ID NO. 5213 |
| (N20)NGG | 2 | 98354232 | + | CCTCCCCAGGCCCGCTCAGCAGG | | 2 | 5 | 89 | SEQ ID NO. 5214 |
| (N20)NGG | 2 | 98354233 | + | CTCCCCAGGCCCGCTCAGCAGGG | | 2 | 3 | 65 | SEQ ID NO. 5215 |
| (N20)NGG | 2 | 98354239 | + | AGGCCCGCTCAGCAGGGAAGTGG | | 1 | 9 | 57 | SEQ ID NO. 5216 |
| (N20)NGG | 2 | 98354251 | + | CAGGGAAGTGGCCGCTCAAGTGG | | 1 | 2 | 25 | SEQ ID NO. 5217 |
| (N20)NGG | 2 | 98354305 | + | TCTCCAGCCGCAGCGATGTCTGG | | 1 | 1 | 16 | SEQ ID NO. 5218 |
| (N20)NGG | 2 | 98354313 | + | CGCAGCGATGTCTGGAGCTATGG | | 1 | 3 | 16 | SEQ ID NO. 5219 |
| (N20)NGG | 2 | 98354314 | + | GCAGCGATGTCTGGAGCTATGGG | | 1 | 1 | 18 | SEQ ID NO. 5220 |
| (N20)NGG | 2 | 98354315 | + | CAGCGATGTCTGGAGCTATGGGG | | 1 | 2 | 22 | SEQ ID NO. 5221 |
| (N20)NGG | 2 | 98354326 | + | GGAGCTATGGGGTCACCATGTGG | | 1 | 4 | 27 | SEQ ID NO. 5222 |
| (N20)NGG | 2 | 98354327 | + | GAGCTATGGGGTCACCATGTGGG | | 1 | 4 | 146 | SEQ ID NO. 5223 |
| (N20)NGG | 2 | 98354330 | + | CTATGGGGTCACCATGTGGGAGG | | 1 | 4 | 33 | SEQ ID NO. 5224 |
| (N20)NGG | 2 | 98354343 | + | ATGTGGGAGGCCTTGTCCTACGG | | 1 | 4 | 43 | SEQ ID NO. 5225 |
| (N20)NGG | 2 | 98354360 | + | CTACGGCCAGAAGCCCTACAAGG | | 1 | 1 | 15 | SEQ ID NO. 5226 |

FIG. 15 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | |
|---|---|---|---|---|---|---|---|---|
| (N20)NGG | 2 | 98354364 | + | GGCCAGAAGCCCTACAAGGCAGG | 1 | 1 | 28 | SEQ ID NO. 5227 |
| (N20)NGG | 2 | 98354369 | + | GAAGCCCTACAAGGCAGGCGCGG | 1 | 1 | 29 | SEQ ID NO. 5228 |
| (N20)NGG | 2 | 98354370 | + | AAGCCCTACAAGGCAGGCGCGGG | 1 | 3 | 29 | SEQ ID NO. 5229 |
| (N20)NGG | 2 | 98354376 | + | TACAAGGCAGGCGCGGGCAGAGG | 1 | 1 | 24 | SEQ ID NO. 5230 |
| (N20)NGG | 2 | 98354380 | + | AGGCAGGCGCGGGCAGAGGCAGG | 2 | 10 | 164 | SEQ ID NO. 5231 |
| (N20)NGG | 2 | 98354383 | + | CAGGCGCGGGCAGAGGCAGGTGG | 1 | 13 | 325 | SEQ ID NO. 5232 |
| (N20)NGG | 2 | 98354384 | + | AGGCGCGGGCAGAGGCAGGTGGG | 2 | 7 | 89 | SEQ ID NO. 5233 |
| (N20)NGG | 2 | 98354195 | - | TGGGGAGGGGAGATGCTGCTGG | 2 | 16 | 233 | SEQ ID NO. 5234 |
| (N20)NGG | 2 | 98354207 | - | GCTGAGCGGGCCTGGGGAGGGGG | 1 | 11 | 178 | SEQ ID NO. 5235 |
| (N20)NGG | 2 | 98354208 | - | TGCTGAGCGGGCCTGGGGAGGGG | 1 | 6 | 97 | SEQ ID NO. 5236 |
| (N20)NGG | 2 | 98354209 | - | CTGCTGAGCGGGCCTGGGGAGG | 1 | 8 | 98 | SEQ ID NO. 5237 |
| (N20)NGG | 2 | 98354210 | - | CCTGCTGAGCGGGCCTGGGGAGG | 2 | 6 | 88 | SEQ ID NO. 5238 |
| (N20)NGG | 2 | 98354213 | - | TTCCCTGCTGAGCGGGCCTGGGG | 2 | 5 | 35 | SEQ ID NO. 5239 |
| (N20)NGG | 2 | 98354214 | - | CTTCCCTGCTGAGCGGGCCTGGG | 1 | 4 | 29 | SEQ ID NO. 5240 |
| (N20)NGG | 2 | 98354215 | - | ACTTCCCTGCTGAGCGGGCCTGG | 2 | 3 | 19 | SEQ ID NO. 5241 |
| (N20)NGG | 2 | 98354220 | - | CGGCCACTTCCCTGCTGAGCGGG | 1 | 7 | 53 | SEQ ID NO. 5242 |
| (N20)NGG | 2 | 98354221 | - | GCGGCCACTTCCCTGCTGAGCGG | 1 | 2 | 38 | SEQ ID NO. 5243 |
| (N20)NGG | 2 | 98354240 | - | TCGGGTGCGTACCACTTGAGCGG | 1 | 1 | 3 | SEQ ID NO. 5244 |
| (N20)NGG | 2 | 98354258 | - | TTGCGGAAGTTGATGCATTCGG | 1 | 1 | 8 | SEQ ID NO. 5245 |
| (N20)NGG | 2 | 98354259 | - | CTTGCGGAAGTTGATGCATTCGG | 1 | 1 | 14 | SEQ ID NO. 5246 |
| (N20)NGG | 2 | 98354275 | - | CGCTGCGGCTGGAGAACTTGCGG | 1 | 2 | 28 | SEQ ID NO. 5247 |
| (N20)NGG | 2 | 98354286 | - | GCTCCAGACATCGCTGCGGCTGG | 1 | 1 | 18 | SEQ ID NO. 5248 |
| (N20)NGG | 2 | 98354290 | - | CATAGCTCCAGACATCGCTGCGG | 1 | 3 | 32 | SEQ ID NO. 5249 |
| (N20)NGG | 2 | 98354319 | - | GTAGGACAAGGCCTCCCACATGG | 1 | 5 | 35 | SEQ ID NO. 5250 |
| (N20)NGG | 2 | 98354331 | - | GGGCTTCTGCCGTAGGACAAGG | 1 | 1 | 13 | SEQ ID NO. 5251 |
| (N20)NGG | 2 | 98354337 | - | CTTGTAGGGCTTCTGCCGTAGG | 1 | 2 | 30 | SEQ ID NO. 5252 |
| (N20)NGG | 2 | 98354344 | - | CGCCTGCCTTGTAGGGCTTCTGG | 1 | 4 | 32 | SEQ ID NO. 5253 |
| (N20)NGG | 2 | 98354351 | - | TGCCCGCGCCTGCCTTGTAGG | 1 | 1 | 16 | SEQ ID NO. 5254 |
| (N20)NGG | 2 | 98354352 | - | TCTGCCCGCGCCTGCCTTGTAGG | 1 | 1 | 13 | SEQ ID NO. 5255 |
| (N20)NGG | 2 | 98354467 | + | CGGCTTGAGCAGAAGATGAAAGG | 1 | 1 | 28 | SEQ ID NO. 5256 |
| (N20)NGG | 2 | 98354468 | + | GGCTTGAGCAGAAGATGAAAGGG | 1 | 4 | 67 | SEQ ID NO. 5257 |
| (N20)NGG | 2 | 98354472 | + | TGAGCAGAAGATGAAAGGGCCGG | 1 | 13 | 112 | SEQ ID NO. 5258 |
| (N20)NGG | 2 | 98354475 | + | GCAGAAGATGAAAGGGCCGGAGG | 1 | 5 | 89 | SEQ ID NO. 5259 |

FIG. 15 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | | |
|---|---|---|---|---|---|---|---|---|---|
| (N20)NGG | 2 | 98354481 | + | GATGAAAGGCCGGAGTCATGG |   |   | 3 | 32 | SEQ ID NO. 5260 |
| (N20)NGG | 2 | 98354496 | + | GGTCATGGCCTTCATCGAGCAGG | 1 |   | 1 | 11 | SEQ ID NO. 5261 |
| (N20)NGG | 2 | 98354497 | + | GTCATGGCCTTCATCGAGCAGGG |   | 2 | 3 | 15 | SEQ ID NO. 5262 |
| (N20)NGG | 2 | 98354504 | + | CCTTCATCGAGCAGGGCAAGCGG |   | 1 | 1 | 22 | SEQ ID NO. 5263 |
| (N20)NGG | 2 | 98354508 | + | CATCGAGCAGGGCAAGCGGATGG |   |   | 1 | 9 | SEQ ID NO. 5264 |
| (N20)NGG | 2 | 98354561 | + | ACGCACTCATGAGTGACTGCTGG |   |   | 2 | 16 | SEQ ID NO. 5265 |
| (N20)NGG | 2 | 98354583 | + | GATCTACAAGTGAGTGCCAGTGG |   |   | 1 | 24 | SEQ ID NO. 5266 |
| (N20)NGG | 2 | 98354584 | + | ATCTACAAGTGAGTGCCAGTGGG |   |   | 1 | 15 | SEQ ID NO. 5267 |
| (N20)NGG | 2 | 98354585 | + | TCTACAAGTGAGTGCCAGTGGGG |   |   | 3 | 24 | SEQ ID NO. 5268 |
| (N20)NGG | 2 | 98354588 | + | ACAAGTGAGTGCCAGTGGGGAGG |   | 1 | 5 | 47 | SEQ ID NO. 5269 |
| (N20)NGG | 2 | 98354589 | + | CAAGTGAGTGCCAGTGGGGAGGG |   | 2 | 8 | 87 | SEQ ID NO. 5270 |
| (N20)NGG | 2 | 98354590 | + | AAGTGAGTGCCAGTGGGGAGGGG |   | 1 | 9 | 90 | SEQ ID NO. 5271 |
| (N20)NGG | 2 | 98354442 | - | TTCATCTTCTGCTCAAGCCGGGG |   | 1 | 2 | 24 | SEQ ID NO. 5272 |
| (N20)NGG | 2 | 98354443 | - | TTTCATCTTCTGCTCAAGCCGGG |   | 1 | 2 | 63 | SEQ ID NO. 5273 |
| (N20)NGG | 2 | 98354444 | - | CTTTCATCTTCTGCTCAAGCCGG |   | 1 | 4 | 60 | SEQ ID NO. 5274 |
| (N20)NGG | 2 | 98354469 | - | TCGATGAAGGCCATGACCTCCGG |   | 1 | 2 | 22 | SEQ ID NO. 5275 |
| (N20)NGG | 2 | 98354482 | - | CCGCTTGCCCTGCTCGATGAAGG |   | 1 | 1 | 8 | SEQ ID NO. 5276 |
| (N20)NGG | 2 | 98354513 | - | GTTCGGGTGGACACTTCTGTGGG |   | 1 | 2 | 11 | SEQ ID NO. 5277 |
| (N20)NGG | 2 | 98354514 | - | AGTTCGGGTGGACACTCTGTGG |   | 1 | 1 | 12 | SEQ ID NO. 5278 |
| (N20)NGG | 2 | 98354517 | - | TACAGTTCGGGTGGACACTCTGG |   | 1 | 1 | 6 | SEQ ID NO. 5279 |
| (N20)NGG | 2 | 98354526 | - | ATGAGTGCTACAGTTCGGGTGG |   | 1 | 3 | 8 | SEQ ID NO. 5280 |
| (N20)NGG | 2 | 98354529 | - | CTCAGTAGTGCTACAGTTCGGG |   | 1 | 1 | 10 | SEQ ID NO. 5281 |
| (N20)NGG | 2 | 98354530 | - | ACTCATGAGTGCGTACAGTTCG |   | 1 | 1 | 8 | SEQ ID NO. 5282 |
| (N20)NGG | 2 | 98355837 | + | GGATGTACCCCACGCCCCACAGG |   | 1 | 1 | 14 | SEQ ID NO. 5283 |
| (N20)NGG | 2 | 98355840 | + | TGTACCCCACGCCCCACAGGTGG |   | 1 | 2 | 36 | SEQ ID NO. 5284 |
| (N20)NGG | 2 | 98355841 | + | GTACCCCACGCCCCACAGGTGGG |   | 1 | 1 | 27 | SEQ ID NO. 5285 |
| (N20)NGG | 2 | 98355844 | + | CCCCACGCCCCACAGGTGGGAGG |   | 1 | 6 | 68 | SEQ ID NO. 5286 |
| (N20)NGG | 2 | 98355868 | + | TCGCCCGACTTCCTGACCGTGG |   | 1 | 1 | 11 | SEQ ID NO. 5287 |
| (N20)NGG | 2 | 98355901 | + | GCGAGCCTGTTACTACAGCCTGG |   | 1 | 2 | 9 | SEQ ID NO. 5288 |
| (N20)NGG | 2 | 98355910 | + | TTACTACAGCCTGGCCAGCAAGG |   | 1 | 23 | 811 | SEQ ID NO. 5289 |
| (N20)NGG | 2 | 98355913 | + | CTACAGCCTGGCCAGCAAGGTGG |   | 1 | 8 | 291 | SEQ ID NO. 5290 |
| (N20)NGG | 2 | 98355917 | + | AGCCTGGCCAGCAAGGTGAAGG |   | 1 | 21 | 551 | SEQ ID NO. 5291 |
| (N20)NGG | 2 | 98355918 | + | GCCTGGCCAGCAAGGTGGAAGGG |   | 1 | 18 | 453 | SEQ ID NO. 5292 |

FIG. 15 cont.

| site_type | site_chromosome | site_start_nucleotide | site_strand | target_site_sequence_with_NGG | genome_wide_hits_with_1_or_less_mismatches | genome_wide_hits_with_2_or_less_mismatches | genome_wide_hits_with_3_or_less_mismatches | | |
|---|---|---|---|---|---|---|---|---|---|
| (N20)NGG | 2 | 98355926 | + | AGCAAGGTGAAGGCCCCCAGG | 1 | 3 | 41 | SEQ ID NO. | 5293 |
| (N20)NGG | 2 | 98355940 | + | GCCCCCAGGCAGCACACAGAAGG | 3 | 6 | 109 | SEQ ID NO. | 5294 |
| (N20)NGG | 2 | 98355946 | + | AGGCAGCACACAGAAGGCTGAGG | 1 | 9 | 127 | SEQ ID NO. | 5295 |
| (N20)NGG | 2 | 98355976 | + | TGCCTGAGCTCCCGCTGCCCAGG | 2 | 5 | 59 | SEQ ID NO. | 5296 |
| (N20)NGG | 2 | 98355977 | + | GCCTGAGCTCCCGCTGCCCAGGG | 1 | 10 | 89 | SEQ ID NO. | 5297 |
| (N20)NGG | 2 | 98355978 | + | CCTGAGCTCCCGCTGCCCAGGGG | 1 | 6 | 83 | SEQ ID NO. | 5298 |
| (N20)NGG | 2 | 98355812 | – | GTGGGGCGTGGGGTACATCCAGG | 1 | 1 | 28 | SEQ ID NO. | 5299 |
| (N20)NGG | 2 | 98355822 | – | CCTCCCACCTGTGGGGCGTGGGG | 1 | 3 | 58 | SEQ ID NO. | 5300 |
| (N20)NGG | 2 | 98355823 | – | TCCTCCCACCTGTGGGGCGTGGG | 1 | 2 | 33 | SEQ ID NO. | 5301 |
| (N20)NGG | 2 | 98355824 | – | ATCTCCCACCTGTGGGGCGTGG | 1 | 2 | 30 | SEQ ID NO. | 5302 |
| (N20)NGG | 2 | 98355829 | – | GGGCGATCCTCCCACCTGTGGGG | 1 | 1 | 27 | SEQ ID NO. | 5303 |
| (N20)NGG | 2 | 98355830 | – | GGGGCGATCCTCCCACCTGTGGG | 1 | 2 | 16 | SEQ ID NO. | 5304 |
| (N20)NGG | 2 | 98355831 | – | CGGGGCGATCCTCCCACCTGTGG | 1 | 2 | 28 | SEQ ID NO. | 5305 |
| (N20)NGG | 2 | 98355849 | – | GCTCCACGGTCAGGAAGTCGGGG | 1 | 1 | 13 | SEQ ID NO. | 5306 |
| (N20)NGG | 2 | 98355850 | – | TGCTCCACGGTCAGGAAGTCGG | 1 | 2 | 15 | SEQ ID NO. | 5307 |
| (N20)NGG | 2 | 98355851 | – | CTGCTCCACGGTCAGGAAGTCGG | 1 | 2 | 26 | SEQ ID NO. | 5308 |
| (N20)NGG | 2 | 98355858 | – | GCATGCGCTGCTCCACGGTCAGG | 1 | 2 | 9 | SEQ ID NO. | 5309 |
| (N20)NGG | 2 | 98355863 | – | GGCTCGCATGCGCTGCTCCACGG | 1 | 2 | 11 | SEQ ID NO. | 5310 |
| (N20)NGG | 2 | 98355884 | – | GCTGCCAGGCTGTAGTAACAGG | 1 | 2 | 38 | SEQ ID NO. | 5311 |
| (N20)NGG | 2 | 98355897 | – | GCCCTTCCACCTTGCTGGCCAGG | 1 | 5 | 65 | SEQ ID NO. | 5312 |
| (N20)NGG | 2 | 98355902 | – | TGGGGCCCTTCCACCTTGCTGG | 1 | 3 | 41 | SEQ ID NO. | 5313 |
| (N20)NGG | 2 | 98355919 | – | GCCTTCTGTGTGTGCTGCCTGGGG | 1 | 5 | 102 | SEQ ID NO. | 5314 |
| (N20)NGG | 2 | 98355920 | – | AGCCTTCTGTGTGTGCTGCCTGGG | 1 | 6 | 93 | SEQ ID NO. | 5315 |
| (N20)NGG | 2 | 98355921 | – | CAGCCTTCTGTGTGTGCTGCCTGG | 1 | 7 | 119 | SEQ ID NO. | 5316 |
| (N20)NGG | 2 | 98355922 | – | TCAGCCTTCTGTGTGTGCTGCCTGG | 1 | 5 | 76 | SEQ ID NO. | 5317 |
| (N20)NGG | 2 | 98355950 | – | GGCAGCGGGAGCTCAGGCACAGG | 1 | 6 | 57 | SEQ ID NO. | 5318 |
| (N20)NGG | 2 | 98355956 | – | CCCCTGGGCAGCGGGAGCTCAGG | 1 | 3 | 66 | SEQ ID NO. | 5319 |

FIG. 15 cont.

1 MDKKYSIGLD IGTNSVGWAV ITDEYKVPSK KFKVLGNTDR HSIKKNLIGA LLFDSGETAE

61 ATRLKRTARR RYTRRKNRIC YLQEIFSNEM AKVDDSFFHR LEESFLVEED KKHERHPIFG

121 NIVDEVAYHE KYPTIYHLRK KLVDSTDKAD LRLIYLALAH MIKFRGHFLI EGDLNPDNSD

181 VDKLFIQLVQ TYNQLFEENP INASGVDAKA ILSARLSKSR RLENLIAQLP GEKKNGLFGN

241 LIALSLGLTP NFKSNFDLAE DAKLQLSKDT YDDDLDNLLA QIGDQYADLF LAAKNLSDAI

301 LLSDILRVNT EITKAPLSAS MIKRYDEHHQ DLTLLKALVR QQLPEKYKEI FFDQSKNGYA

361 GYIDGGASQE EFYKFIKPIL EKMDGTEELL VKLNREDLLR KQRTFDNGSI PHQIHLGELH

421 AILRRQEDFY PFLKDNREKI EKILTFRIPY YVGPLARGNS RFAWMTRKSE ETITPWNFEE

481 VVDKGASAQS FIERMTNFDK NLPNEKVLPK HSLLYEYFTV YNELTKVKYV TEGMRKPAFL

541 SGEQKKAIVD LLFKTNRKVT VKQLKEDYFK KIECFDSVEI SGVEDRFNAS LGTYHDLLKI

601 IKDKDFLDNE ENEDILEDIV LTLTLFEDRE MIEERLKTYA HLFDDKVMKQ LKRRRYTGWG

661 RLSRKLINGI RDKQSGKTIL DFLKSDGFAN RNFMQLIHDD SLTFKEDIQK AQVSGQGDSL

721 HEHIANLAGS PAIKKGILQT VKVVDELVKV MGRHKPENIV IEMARENQTT QKGQKNSRER

781 MKRIEEGIKE LGSQILKEHP VENTQLQNEK LYLYYLQNGR DMYVDQELDI NRLSDYDVDH

841 IVPQSFLKDD SIDNKVLTRS DKNRGKSDNV PSEEVVKKMK NYWRQLLNAK LITQRKFDNL

901 TKAERGGLSE LDKAGFIKRQ LVETRQITKH VAQILDSRMN TKYDENDKLI REVKVITLKS

961 KLVSDFRKDF QFYKVREINN YHHAHDAYLN AVVGTALIKK YPKLESEFVY GDYKVYDVRK

1021 MIAKSEQEIG KATAKYFFYS NIMNFFKTEI TLANGEIRKR PLIETNGETG EIVWDKGRDF

1081 ATVRKVLSMP QVNIVKKTEV QTGGFSKESI LPKRNSDKLI ARKKDWDPKK YGGFDSPTVA

1141 YSVLVVAKVE KGKSKKLKSV KELLGITIME RSSFEKNPID FLEAKGYKEV KKDLIIKLPK

1201 YSLFELENGR KRMLASAGEL QKGNELALPS KYVNFLYLAS HYEKLKGSPE DNEQKQLFVE

1261 QHKHYLDEII EQISEFSKRV ILADANLDKV LSAYNKHRDK PIREQAENII HLFTLTNLGA

1321 PAAFKYFDTT IDRKRYTSTK EVLDATLIHQ SITGLYETRI DLSQLGGD (SEQ ID NO: 5320)

17B)

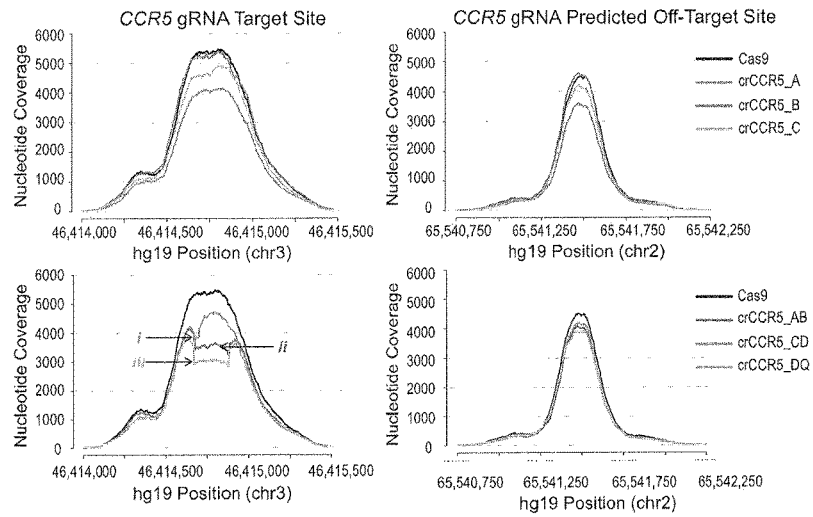

17C)

|  | crCCR5 | | | | | |
|---|---|---|---|---|---|---|
| Mutation Class | A | B | C | AB | CD | DQ |
| Predicted deletion | - | - | - | 19.95% | 20.45% | 42.13% |
| Small InDel | 5.10% | 13.54% | 13.30% | 3.06% | 0.50% | 2.95% |
| Inversion | - | - | - | 3.12% | - | 2.48% |
| Single Nucleotide Substitution | 0.03% | 0.02% | 0.00% | 0.05% | 0.15% | 0.04% |
| Others | 0.66% | 3.09% | 3.72% | 0.05% | 0.08% | 0.39% |
| Total On-Target | 5.79% | 16.65% | 17.02% | 26.23% | 21.19% | 47.99% |

17D)

| crCCR5 | Off-Target Sites | | N-Fold Enrichment of Reads with Variants (Treatment compared to Control) | | | |
|---|---|---|---|---|---|---|
|  | Total Sites | Significant Sites** | Off-Target InDel | Off-Target Other | Off-Target Combined | On-Target Combined** |
| A | 19 | 0 | 0.83 | 1.16 | 1.06 | 39.87 |
| B | 30 | 1* | 1.14* | 1.28 | 1.22 | 63 |
| C | 23 | 0 | 1.07 | 0.94 | 0.96 | 23.78 |
| D | 18 | 0 | 1.08 | 0.84 | 0.88 | 40.35 |
| Q | 36 | 0 | 0.98 | 0.78 | 0.85 | 57.66 |

```
crCCR5_A:  "GCTGCCGCCCAGTGGGACTTTGG           (SEQ ID NO: 5335)
""""""CCR2: ACTGTCTCCCTGTAGAAAACTGG           (SEQ ID NO: 5336)

crCCR5_B:  "GATCTGGTAAAGATGATTCCTGG           (SEQ ID NO: 5337)
""""""CCR2: CATTTAGTAAAGATGATTCCTGG           (SEQ ID NO: 5338)

crCCR5_C:  "ACAATGTGTCAACTCTTGACAGG           (SEQ ID NO: 5339)
""""""CCR2: GCATTTTCTGTTCTC-TGA-AGT           (SEQ ID NO: 5340)

crCCR5_D:  "TCACTATGC-TGCCGCCCAGTGG           (SEQ ID NO: 5341)
""""""CCR2: TCACTAGGCATGCTGCC-AGAGC           (SEQ ID NO: 5342)

crCCR5_Q:  "GCTGTGTTTGCGTCTCTCCAGG            (SEQ ID NO: 5343)
""""""CCR2: GCTGTGTTTGCTTGCTTCTGTCCCAGG       (SEQ ID NO: 5344)
```

18B)

| | crCCR5 treatment ||||||| |
| Mutation | B ||| AB ||| A ||
| | Reads Supporting Mutation | Total Reads at Site | Frequency | Reads Supporting Mutation | Total Reads at Site | Frequency | Reads Supporting Mutation | Total Reads at Site | Frequency |
|---|---|---|---|---|---|---|---|---|---|
| One Base Insertion | 30 | 5,963 | 0.50% | 2 | 5,339 | 0.04% | 0 | 4,678 | 0.00% |
| Two Base Insertion | 0 | 5,963 | 0.00% | 1 | 5,339 | 0.02% | 0 | 4,678 | 0.00% |
| One Base Deletion | 5 | 5,963 | 0.08% | 9 | 5,339 | 0.17% | 4 | 4,678 | 0.09% |
| Two Base Deletion | 1 | 5,963 | 0.02% | 1 | 5,339 | 0.02% | 0 | 4,678 | 0.00% |
| Total | 36 | 5,963 | 0.60% | 13 | 5,339 | 0.24% | 4 | 4,678 | 0.09% |

FIGS. 18A-18B

Table T1. Predicted gRNA mapping in Ensembl GRCh37v71

| Site | Chr | Start | End | Sequence | |
|---|---|---|---|---|---|
| guideD_OT15 | 1 | 7,721,536 | 7,721,559 | CTCCCTGGGCTGCGACCATAGTGA | SEQ ID NO. 5356 |
| guideB_OT23 | 1 | 26,857,084 | 26,857,107 | GACCTTGTGAAGATGATTCCTGG | SEQ ID NO. 5357 |
| guideB_OT17 | 1 | 40,109,230 | 40,109,253 | GATCTGGGAAAGAGGATTCCAGG | SEQ ID NO. 5358 |
| guideC_OT7 | 1 | 88,021,569 | 88,021,592 | AGATTGTGTATACTTCTTGACTAG | SEQ ID NO. 5359 |
| guideB_OT6 | 1 | 95,257,842 | 95,257,865 | CCAGGAATCATCTCTACGATATC | SEQ ID NO. 5360 |
| guideB_OT26 | 1 | 95,257,842 | 95,257,865 | CCAGGAATCATCTCTACGATATC | SEQ ID NO. 5361 |
| guideB_OT11 | 1 | 102,027,511 | 102,027,534 | CCTGGAATTCTCTTTACTAGATC | SEQ ID NO. 5362 |
| guideQ_OT35 | 1 | 109,838,856 | 109,838,879 | CCGGGAGAGGCGCGGACACAGC | SEQ ID NO. 5363 |
| guideQ_OT10 | 1 | 234,728,097 | 234,728,120 | CCAGGGAGAGACGAACCAAAAC | SEQ ID NO. 5364 |
| guideB_OT22 | 2 | 34,792,091 | 34,792,114 | GATCTGATACAGATGATTCATGG | SEQ ID NO. 5365 |
| guideB_OT2 | 2 | 55,610,332 | 55,610,355 | CTGGAATCATCTTTACAAGATG | SEQ ID NO. 5366 |
| guideD_OT4 | 2 | 65,541,463 | 65,541,486 | TGAATATCCTGTGCGCCAGTCAG | SEQ ID NO. 5367 |
| guideP_OT6 | 2 | 87,822,849 | 87,822,872 | CCACCCAAGTGATCACTCTTCCT | SEQ ID NO. 5368 |
| guideP_OT7 | 2 | 87,822,849 | 87,822,871 | AGGAAGAGTGATCACTTGGGTGG | SEQ ID NO. 5369 |
| guideQ_OT4 | 2 | 105,475,698 | 105,475,721 | TCTGTGTTTTTGTCTCTCCCCAG | SEQ ID NO. 5370 |
| guideQ_OT32 | 2 | 105,475,698 | 105,475,721 | TCTGTGTTTTTGTCTCTCCCCAG | SEQ ID NO. 5371 |
| guideP_OT7 | 2 | 112,185,053 | 112,185,076 | AGGAAGAGTGATCACTTGGGTGG | SEQ ID NO. 5372 |
| guideP_OT6 | 2 | 112,185,053 | 112,185,075 | CCACCCAAGTGATCACTCTTCCT | SEQ ID NO. 5373 |
| guideB_OT4 | 2 | 113,069,812 | 113,069,835 | CTAGGAATCATCTTCCCCAGATG | SEQ ID NO. 5374 |
| guideB_OT7 | 2 | 175,176,760 | 175,176,783 | TCTGTGGAAAAGATGATTCCAAG | SEQ ID NO. 5375 |
| guideB_OT10 | 2 | 225,356,045 | 225,356,068 | GTTCTTGTTAAGATGATTCCTGG | SEQ ID NO. 5376 |
| guideB_OT21 | 2 | 225,356,045 | 225,356,068 | GTTCTTGTTAAGATGATTCCTGG | SEQ ID NO. 5377 |
| guideP_OT3 | 2 | 239,253,476 | 239,253,499 | GGCATGTTTCATCACTTGGGGGG | SEQ ID NO. 5378 |
| guideB_OT14 | 2 | 239,332,511 | 239,332,534 | GGGCTGGTAAAGATGTTTCCAGG | SEQ ID NO. 5379 |
| guideP_OT20 | 3 | 46,399,495 | 46,399,518 | GACAAGTGTGATCACCTGGTTGG | SEQ ID NO. 5380 |
| guideQ_OT15 | 3 | 46,399,520 | 46,399,543 | GCTGTGTTTGCTTCTGTCCCAGG | SEQ ID NO. 5381 |

FIG. 20

| Name | # | Pos1 | Pos2 | Sequence | SEQ ID |
|---|---|---|---|---|---|
| guideB_OT5 | 3 | 46,399,538 | 46,399,561 | CCAGGAATCATCTTTACTAAATG | SEQ ID NO. 5382 |
| guideB_OT24 | 3 | 46,399,538 | 46,399,561 | CCAGGAATCATCTTTACTAAATG | SEQ ID NO. 5383 |
| guideD_TARGET | 3 | 46,414,654 | 46,414,677 | TCACTATGCTGCCGCCAGTGGG | SEQ ID NO. 5384 |
| guideA_TARGET | 3 | 46,414,661 | 46,414,684 | GCTGCCGCCCAGTGGGACTTTGG | SEQ ID NO. 5385 |
| guideC_TARGET | 3 | 46,414,688 | 46,414,711 | ACAATGTGTCAACTCTTGACAGG | SEQ ID NO. 5386 |
| guideP_TARGET | 3 | 46,414,834 | 46,414,857 | GACAAGTGTGATCACTTGGGTGG | SEQ ID NO. 5387 |
| guideQ_TARGET | 3 | 46,414,859 | 46,414,882 | GCTGTGTTTGCTCTCTCCCAGG | SEQ ID NO. 5388 |
| guideB_TARGET | 3 | 46,414,877 | 46,414,900 | CCAGGAATCATCTTTACCAGATC | SEQ ID NO. 5389 |
| guideC_OT6 | 3 | 51,505,036 | 51,505,059 | ACAAGGGTCAACTCTGGACAAG | SEQ ID NO. 5390 |
| guideC_OT12 | 3 | 51,505,036 | 51,505,059 | ACAAGGGGTCAACTCTGGACAAG | SEQ ID NO. 5391 |
| guideD_OT5 | 3 | 53,110,172 | 53,110,195 | CCCACTGGGCTGCAGCATCCTGG | SEQ ID NO. 5392 |
| guideQ_OT28 | 3 | 64,142,989 | 64,143,012 | CCAGCGCGTGACGCAAACACAGC | SEQ ID NO. 5393 |
| guideC_OT21 | 3 | 94,180,887 | 94,180,910 | ACAATGTGTCACCTTTTAACTGG | SEQ ID NO. 5394 |
| guideC_OT13 | 3 | 162,087,348 | 162,087,371 | ACAATATTTCAACACTTGACAAG | SEQ ID NO. 5395 |
| guideB_OT8 | 4 | 85,489,957 | 85,489,980 | CTTGGAGTCATCTTTGCCACATC | SEQ ID NO. 5396 |
| guideP_OT24 | 4 | 104,977,831 | 104,977,854 | GACAAGCGTGATCCCATGGGGAG | SEQ ID NO. 5397 |
| guideP_OT17 | 4 | 136,511,965 | 136,511,988 | CCTCCAAGTAATCACCCTTTC | SEQ ID NO. 5398 |
| guideA_OT10 | 5 | 13,378,669 | 13,378,692 | CCCAAGTCCCACTGGCAGGTGGC | SEQ ID NO. 5399 |
| guideC_OT2 | 5 | 32,668,507 | 32,668,530 | GCTATGTGTTAACTCTTGACAAG | SEQ ID NO. 5400 |
| guideC_OT11 | 5 | 32,668,507 | 32,668,530 | GCTATGTGTTAACTCTTGACAAG | SEQ ID NO. 5401 |
| guideD_OT13 | 5 | 112,310,301 | 112,310,324 | CCACTATGGTGCCTCCCAGTCAG | SEQ ID NO. 5402 |
| guideD_OT17 | 5 | 154,708,103 | 154,708,126 | TCACTCTGCTCTGTCCAGTGGG | SEQ ID NO. 5403 |
| guideD_OT1 | 5 | 157,424,997 | 157,425,020 | ACTCTGTCCTGCCGCCCAGTGAG | SEQ ID NO. 5404 |
| guideB_OT3 | 6 | 50,082,676 | 50,082,699 | CTTGGAATCATCTCTACCTGATT | SEQ ID NO. 5405 |
| guideA_OT7 | 6 | 95,560,697 | 95,560,720 | CCCAAGTCCCACTGGGTGACATG | SEQ ID NO. 5406 |
| guideQ_OT23 | 6 | 149,309,103 | 149,309,126 | CTAAGGAGAGGACCACACAGC | SEQ ID NO. 5407 |
| guideQ_OT1 | 6 | 151,120,563 | 151,120,586 | CCAGGAGGACGCAAACCCAGC | SEQ ID NO. 5408 |
| guideQ_OT24 | 6 | 151,120,563 | 151,120,586 | CCAGGAGGACGCAAACCCAGC | SEQ ID NO. 5409 |
| guideP_OT13 | 7 | 9,489,995 | 9,490,018 | CTTCTCAAGTGATCCCACTGGTC | SEQ ID NO. 5410 |

FIG. 20 cont.

| | | | | |
|---|---|---|---|---|
| guideQ_OT19 | 7 | 19,938,370 | 19,938,393 | CCTGAGAGAAGCAAACACAGA | SEQ ID NO. 5411 |
| guideQ_OT13 | 7 | 26,697,753 | 26,697,776 | CTTAGGAAAGACGCAAACATAGC | SEQ ID NO. 5412 |
| guideC_OT4 | 7 | 88,108,793 | 88,108,816 | ACATTGATTAAACTCTTGACTAG | SEQ ID NO. 5413 |
| guideC_OT9 | 7 | 120,487,950 | 120,487,973 | ACAAAGTTAAACTCTTGAGCAG | SEQ ID NO. 5414 |
| guideP_OT2 | 7 | 140,990,691 | 140,990,714 | CTTCCCAAGTGATTACACTTTAT | SEQ ID NO. 5415 |
| guideD_OT16 | 7 | 141,828,674 | 141,828,697 | CCCACTGGGCGCAGCCTAGTGA | SEQ ID NO. 5416 |
| guideC_OT8 | 7 | 145,843,581 | 145,843,604 | CTTGTCAAGATTTGCCACATTAT | SEQ ID NO. 5417 |
| guideC_OT14 | 7 | 145,843,581 | 145,843,604 | CTTGTCAAGATTTGCCACATTAT | SEQ ID NO. 5418 |
| guideQ_OT17 | 7 | 158,285,285 | 158,285,308 | CCTTGTGAGAGGCAAACACAGC | SEQ ID NO. 5419 |
| guideD_OT9 | 8 | 1,379,562 | 1,379,585 | CCTACTGGGCCTCAGCACTGTGT | SEQ ID NO. 5420 |
| guideD_OT18 | 8 | 23,095,380 | 23,095,403 | TCACTATGCAGCACCCCAGTGGG | SEQ ID NO. 5421 |
| guideB_OT28 | 8 | 104,258,547 | 104,258,570 | CCAGCCATCTCTTTACCAGCTC | SEQ ID NO. 5422 |
| guideD_OT6 | 8 | 142,638,679 | 142,638,702 | CTCACTGGGCTGCAGCATTGGGG | SEQ ID NO. 5423 |
| guideQ_OT2 | 9 | 2,427,359 | 2,427,382 | CCAGGAGAGACGCAGAAACAAC | SEQ ID NO. 5424 |
| guideQ_OT27 | 9 | 2,427,359 | 2,427,382 | CCAGGAGAGACGCAGAAACAAC | SEQ ID NO. 5425 |
| guideP_OT8 | 9 | 42,760,292 | 42,760,314 | TACATGAGTAATGATTACTCATGTA | SEQ ID NO. 5426 |
| guideP_OT9 | 9 | 42,760,292 | 42,760,314 | CTCCCAAGTGATTACTCATGTA | SEQ ID NO. 5427 |
| guideP_OT10 | 9 | 42,760,292 | 42,760,314 | CTCCCAAGTGATTACTCATGTA | SEQ ID NO. 5428 |
| guideP_OT8 | 9 | 69,769,168 | 69,769,190 | TACATGAGTAATGATTACTTGGGAG | SEQ ID NO. 5429 |
| guideP_OT9 | 9 | 69,769,168 | 69,769,190 | CTCCCAAGTGATTACTCATGTA | SEQ ID NO. 5430 |
| guideP_OT10 | 9 | 69,769,168 | 69,769,190 | CTCCCAAGTGATTACTCATGTA | SEQ ID NO. 5431 |
| guideP_OT8 | 9 | 70,135,845 | 70,135,867 | TACATGAGTAATGATTACTTGGGAG | SEQ ID NO. 5432 |
| guideP_OT9 | 9 | 70,135,845 | 70,135,867 | CTCCCAAGTGATTACTCATGTA | SEQ ID NO. 5433 |
| guideP_OT10 | 9 | 70,135,845 | 70,135,867 | CTCCCAAGTGATTACTCATGTA | SEQ ID NO. 5434 |
| guideP_OT8 | 9 | 70,386,317 | 70,386,340 | TACATGAGTAATGATTACTTGGGAG | SEQ ID NO. 5435 |
| guideP_OT9 | 9 | 70,386,317 | 70,386,339 | CTCCCAAGTGATTACTCATGTA | SEQ ID NO. 5436 |
| guideP_OT10 | 9 | 70,386,317 | 70,386,339 | CTCCCAAGTGATTACTCATGTA | SEQ ID NO. 5437 |
| guideP_OT1 | 9 | 80,982,901 | 80,982,924 | CAGAGGTGTGATCACTTGGGCAG | SEQ ID NO. 5438 |
| guideP_OT21 | 9 | 80,982,901 | 80,982,924 | CAGAGGTGTGATCACTTGGGCAG | SEQ ID NO. 5439 |

FIG. 20 cont.

| | | | | | |
|---|---|---|---|---|---|
| guideP_OT5 | 9 | 117,954,855 | 117,954,878 | CTTCCCATGTGATAACACTTGTC | SEQ ID NO. 5440 |
| guideP_OT11 | 9 | 117,954,855 | 117,954,878 | CTTCCCATGTGATAACACTTGTC | SEQ ID NO. 5441 |
| guideQ_OT20 | 10 | 3,031,086 | 3,031,109 | CCTGAGAGAGGCAAACACATC | SEQ ID NO. 5442 |
| guideB_OT19 | 10 | 20,040,235 | 20,040,258 | CCACGAATCCTCTTTACCAAATC | SEQ ID NO. 5443 |
| guideP_OT9 | 10 | 42,689,588 | 42,689,611 | CTCCCAAGTGATTACTCATGTA | SEQ ID NO. 5444 |
| guideP_OT8 | 10 | 42,689,588 | 42,689,610 | TACATGAGTAATCACTTGGGAG | SEQ ID NO. 5445 |
| guideP_OT10 | 10 | 42,689,588 | 42,689,610 | CTCCCAAGTGATTACTCATGTA | SEQ ID NO. 5446 |
| guideQ_OT9 | 10 | 47,655,769 | 47,655,792 | CCTGAGGGTGCCTCTCTCCCGGG | SEQ ID NO. 5447 |
| guideQ_OT7 | 10 | 77,358,062 | 77,358,085 | GCTGTGTGCTCGTCTCTCCCTGG | SEQ ID NO. 5448 |
| guideQ_OT31 | 10 | 77,358,062 | 77,358,085 | GCTGTGTGCTGCTCTCTCCCTGG | SEQ ID NO. 5449 |
| guideA_OT15 | 10 | 88,295,312 | 88,295,335 | GCGGCCCAGCGGGACCTGGG | SEQ ID NO. 5450 |
| guideQ_OT34 | 10 | 98,895,438 | 98,895,461 | GCTGTACTTGGGTCTCTCCCCAG | SEQ ID NO. 5451 |
| guideQ_OT8 | 10 | 117,958,114 | 117,958,137 | GCCGTGTTTTCCTCTCTCCCAAG | SEQ ID NO. 5452 |
| guideQ_OT11 | 10 | 117,958,114 | 117,958,137 | GCCGTGTTTTCCTCTCTCCCAAG | SEQ ID NO. 5453 |
| guideD_OT7 | 10 | 129,722,982 | 129,723,005 | CCCACTGGGCTGCAGAATACAGA | SEQ ID NO. 5454 |
| guideP_OT25 | 10 | 131,328,679 | 131,328,702 | CCCCCAGGAGACATCACATTTGTC | SEQ ID NO. 5455 |
| guideA_OT16 | 11 | 2,952,375 | 2,952,398 | GCTGCCGGACAGTGGGACCTGGG | SEQ ID NO. 5456 |
| guideD_OT14 | 11 | 36,441,686 | 36,441,709 | CTGACTGGACCGCACCTTAGTGA | SEQ ID NO. 5457 |
| guideQ_OT25 | 11 | 45,632,027 | 45,632,050 | GCTGTCTTTTCCTCTCTCCCTGG | SEQ ID NO. 5458 |
| guideB_OT25 | 11 | 58,575,305 | 58,575,328 | CCAGAAATAATCTTTACCAGCTC | SEQ ID NO. 5459 |
| guideQ_OT22 | 11 | 62,783,309 | 62,783,332 | GCTGTGTTGTGTCCCTCCCCAGG | SEQ ID NO. 5460 |
| guideC_OT10 | 11 | 77,709,742 | 77,709,765 | ACAAATGTGTTGGCTCTTGACTAG | SEQ ID NO. 5461 |
| guideC_OT19 | 11 | 77,709,742 | 77,709,765 | ACAATGTGTTGGCTCTTGACTAG | SEQ ID NO. 5462 |
| guideP_OT26 | 11 | 115,496,055 | 115,496,078 | GACAAGTCTGATCATTTTGGGG | SEQ ID NO. 5463 |
| guideQ_OT26 | 12 | 4,379,332 | 4,379,355 | CCACGGAGAAACACAAACACAGC | SEQ ID NO. 5464 |
| guideC_OT1 | 12 | 12,976,312 | 12,976,335 | AAAATGTGTCAACTCTTGATTAG | SEQ ID NO. 5465 |
| guideC_OT16 | 12 | 12,976,312 | 12,976,335 | AAAATGTGTCAACTCTTGATTAG | SEQ ID NO. 5466 |
| guideQ_OT21 | 12 | 19,270,661 | 19,270,684 | TCTGTGTTTGCCTCTCTCTCAGG | SEQ ID NO. 5467 |
| guideC_OT18 | 12 | 53,711,726 | 53,711,749 | ACAATGTGCCAGCTCTGACTAG | SEQ ID NO. 5468 |

FIG. 20 cont.

| | | | | |
|---|---|---|---|---|
| guideP_OT12 | 12 | 81,881,220 | 81,881,243 | GACAAGTATCAGCACTTGGTAAG | SEQ ID NO. 5469 |
| guideP_OT14 | 12 | 94,428,361 | 94,428,384 | GACTAGTGTGTTCTCTTGGAAG | SEQ ID NO. 5470 |
| guideP_OT4 | 12 | 98,582,748 | 98,582,771 | GACATGTGTAAACACTTGGAAG | SEQ ID NO. 5471 |
| guideP_OT16 | 12 | 98,582,748 | 98,582,771 | GACATGTGTAAACACTTGGAAG | SEQ ID NO. 5472 |
| guideA_OT3 | 12 | 108,460,819 | 108,460,842 | CCAAAGTCCCACTGGGTGACATC | SEQ ID NO. 5473 |
| guideA_OT13 | 12 | 108,460,819 | 108,460,842 | CCAAAGTCCCACTGGGTGACATC | SEQ ID NO. 5474 |
| guideQ_OT18 | 13 | 20,693,503 | 20,693,526 | CCTGTGAGAGGCTCAAACACAGC | SEQ ID NO. 5475 |
| guideA_OT9 | 13 | 21,047,396 | 21,047,419 | CCGCAGTCCCACTGTGCGGCACC | SEQ ID NO. 5476 |
| guideA_OT14 | 13 | 21,047,396 | 21,047,419 | CCGCAGTCCCACTGTGCGGCACC | SEQ ID NO. 5477 |
| guideP_OT22 | 13 | 25,242,593 | 25,242,616 | GACAAGTGTGTTCACTTCTGCAG | SEQ ID NO. 5478 |
| guideB_OT15 | 13 | 42,388,792 | 42,388,815 | GATTTGGGAAAGATCATTCCAGG | SEQ ID NO. 5479 |
| guideB_OT9 | 13 | 69,477,970 | 69,477,993 | GCTTTGGTAAAGTTGATTCCTAG | SEQ ID NO. 5480 |
| guideC_OT5 | 13 | 94,575,221 | 94,575,244 | AAACTGTGATAACTCTTGACTGG | SEQ ID NO. 5481 |
| guideA_OT6 | 14 | 56,740,798 | 56,740,821 | CCTAAGTCCCACTGGCCGAAAGT | SEQ ID NO. 5482 |
| guideB_OT20 | 14 | 73,729,934 | 73,729,957 | GTTCTGGTCAAGATGACTCCTGG | SEQ ID NO. 5483 |
| guideA_OT17 | 14 | 76,844,953 | 76,844,976 | CCCAGGACCCACTGGGCCAGCAGC | SEQ ID NO. 5484 |
| guideC_OT3 | 14 | 98,955,845 | 98,955,868 | AAAATCTGTCAACTCTTGAATAG | SEQ ID NO. 5485 |
| guideC_OT17 | 14 | 98,955,845 | 98,955,868 | AAAATCTGTCAACTCTTGAATAG | SEQ ID NO. 5486 |
| guideC_OT23 | 14 | 103,419,411 | 103,419,434 | CTCATTCAGGAGTGGACACATTGT | SEQ ID NO. 5487 |
| guideQ_OT30 | 14 | 105,212,041 | 105,212,064 | CCAGGGGACACGCAAACACTGC | SEQ ID NO. 5488 |
| guideD_OT11 | 15 | 27,937,804 | 27,937,827 | TCACTTGTGCTGCCAGCCAGTTGG | SEQ ID NO. 5489 |
| guideA_OT8 | 15 | 28,812,084 | 28,812,107 | CTGAAGTCCCACTACTGGGTGGTGT | SEQ ID NO. 5490 |
| guideA_OT4 | 15 | 30,815,609 | 30,815,631 | GCACCAGCCCAGTGGGACTTCAG | SEQ ID NO. 5491 |
| guideA_OT5 | 15 | 30,815,609 | 30,815,631 | GCACCAGCCCAGTGGGACTTCAG | SEQ ID NO. 5492 |
| guideA_OT4 | 15 | 32,776,439 | 32,776,462 | GCACCAGCCCAGTGGGACTTCAG | SEQ ID NO. 5493 |
| guideA_OT5 | 15 | 32,776,439 | 32,776,462 | GCACCAGCCCAGTGGGACTTCAG | SEQ ID NO. 5494 |
| guideQ_OT29 | 15 | 58,817,723 | 58,817,746 | CCAGGAAAGAGGCAAGCACAGC | SEQ ID NO. 5495 |
| guideD_OT3 | 16 | 17,377,804 | 17,377,827 | CCACTATACACCGCCCAGTCAG | SEQ ID NO. 5496 |
| guideD_OT10 | 16 | 34,381,274 | 34,381,297 | CCATTGTGCTGCCGCCCAGCCAG | SEQ ID NO. 5497 |

FIG. 20 cont.

| | | | | | |
|---|---|---|---|---|---|
| guideB_OT1 | 16 | 66,123,576 | 66,123,599 | GATCTGGAAGAGATGATTCCAAG | SEQ ID NO. 5498 |
| guideQ_OT36 | 17 | 11,833,418 | 11,833,441 | CCCGGGAGGCAGGCAAAAACAGC | SEQ ID NO. 5499 |
| guideQ_OT6 | 17 | 18,078,932 | 18,078,955 | GCTCAGTCTGGGTCTCTCCCCAG | SEQ ID NO. 5500 |
| guideQ_OT33 | 17 | 18,078,932 | 18,078,955 | GCTGAGTCTGGGTCTCTCCCCAG | SEQ ID NO. 5501 |
| guideB_OT12 | 17 | 21,284,881 | 21,284,903 | CCTGGAATGTTCTTTCCCAGATC | SEQ ID NO. 5502 |
| guideB_OT13 | 17 | 21,284,881 | 21,284,903 | CCTGGAATGTTCTTTCCCAGATC | SEQ ID NO. 5503 |
| guideP_OT23 | 17 | 59,879,562 | 59,879,585 | GACAGGTGTGAGCACTTTGGAG | SEQ ID NO. 5504 |
| guideP_OT18 | 17 | 65,415,053 | 65,415,076 | GACACTTGTGATGACTTGGGTAG | SEQ ID NO. 5505 |
| guideQ_OT5 | 18 | 11,204,603 | 11,204,626 | CTTTGGAGAGACCGCAGACACTGC | SEQ ID NO. 5506 |
| guideQ_OT12 | 18 | 11,204,603 | 11,204,626 | CTTTGGAGAGACCGCAGACACTGC | SEQ ID NO. 5507 |
| guideB_OT12 | 18 | 12,705,728 | 12,705,751 | CCTGGAATGTTCTTTCCCAGATC | SEQ ID NO. 5508 |
| guideB_OT13 | 18 | 12,705,728 | 12,705,751 | CCTGGAATGTTCTTTCCCAGATC | SEQ ID NO. 5509 |
| guideP_OT19 | 18 | 41,187,999 | 41,188,022 | CTACCCAAGTGTTCATATTTGTC | SEQ ID NO. 5510 |
| guideB_OT27 | 18 | 69,924,495 | 69,924,518 | CCAGAAATCATGTTTACCAGCTC | SEQ ID NO. 5511 |
| guideA_OT2 | 19 | 35,800,794 | 35,800,817 | CTGAGTCCCACTGCGCGGCAGC | SEQ ID NO. 5512 |
| guideQ_OT14 | 20 | 23,302,200 | 23,302,223 | CCTGGGAAAGGCGCAAACACAGC | SEQ ID NO. 5513 |
| guideB_OT18 | 20 | 23,472,840 | 23,472,863 | GATCTGATAAAGTGAGTCCAGG | SEQ ID NO. 5514 |
| guideD_OT2 | 20 | 37,102,053 | 37,102,076 | GCAGTTGCTGCCGCCAGTGGG | SEQ ID NO. 5515 |
| guideP_OT8 | 21 | 9,588,789 | 9,588,811 | TACATGAGTAATCACTTGGGAG | SEQ ID NO. 5516 |
| guideP_OT9 | 21 | 9,588,789 | 9,588,811 | CTCCCCAAGTGATTACTCATGTA | SEQ ID NO. 5517 |
| guideP_OT10 | 21 | 9,588,789 | 9,588,811 | CTCCCCAAGTGATTACTCATGTA | SEQ ID NO. 5518 |
| guideQ_OT3 | 21 | 32,760,114 | 32,760,137 | GCAGTGTGTGGGTCTCTCCCAGG | SEQ ID NO. 5519 |
| guideQ_OT16 | 21 | 32,760,114 | 32,760,137 | GCAGTGTGTGGGTCTCTCCCAGG | SEQ ID NO. 5520 |
| guideP_OT8 | 22 | 17,376,827 | 17,376,849 | TACATGAGTAATCACTTGGGAG | SEQ ID NO. 5521 |
| guideP_OT9 | 22 | 17,376,827 | 17,376,849 | CTCCCCAAGTGATTACTCATGTA | SEQ ID NO. 5522 |
| guideP_OT10 | 22 | 17,376,827 | 17,376,849 | CTCCCCAAGTGATTACTCATGTA | SEQ ID NO. 5523 |
| guideA_OT12 | 22 | 30,136,704 | 30,136,727 | CCAAAGTCGCACTGGCCTGCAGC | SEQ ID NO. 5524 |
| guideB_OT16 | 22 | 45,907,886 | 45,907,909 | GATCTGGGAGAGAAGATTCCAGG | SEQ ID NO. 5525 |
| guideC_OT20 | X | 6,258,801 | 6,258,824 | CCAGAAAAGAGTTGACACATAGT | SEQ ID NO. 5526 |

FIG. 20 cont.

| | | | | |
|---|---|---|---|---|
| guideC_OT15 | | 21,926,730 | 21,926,753 | CCTGCCAAGGGTTGACACATGGT | SEQ ID NO. 5527 |
| guideP_OT15 | X | 32,405,319 | 32,405,342 | GACAAGTGTCATAACTTTGGAAG | SEQ ID NO. 5528 |
| guideC_OT22 | X | 64,736,013 | 64,736,036 | ATAATGTGTCAACCCTGGACCAG | SEQ ID NO. 5529 |
| guideA_OT1 | X | 70,836,963 | 70,836,986 | CCAAAGACCCACTGGACGGCAGC | SEQ ID NO. 5530 |
| guideA_OT11 | X | 70,836,963 | 70,836,986 | CCAAAGACCCACTGGACGGCAGC | SEQ ID NO. 5531 |
| guideD_OT8 | X | 106,847,189 | 106,847,212 | CCAACTGGCCGGCAGCCTGGTGA | SEQ ID NO. 5532 |
| guideD_OT12 | X | 106,847,189 | 106,847,212 | CCAACTGGCCGGCAGCCTGGTGA | SEQ ID NO. 5533 |

FIG. 20 cont.

Table T2. Guide Pair crCCR5_A+B On-Target Alleles

| Allele | Cas9 Guide Site | Sequence | Split Reads (+) Strand | Split Reads (-) Strand | Split Reads TOTAL | Estimated Allele Frequency |
|---|---|---|---|---|---|---|
| Reference | A (Distal) | TATGCTGCCCGCCCAGTGGGACTTTGGAAATACAATGTGTCAACTC | 1836 | 1728 | 3564 | 76.78% (SEQ ID NO. 5534) |
| Reference | B (Proximal) | GGCTGTGTTTGCGTCTCTCCCAGGAATCATCTTTACCAGATCTCA | 1340 | 1753 | 3093 | 73.80% (SEQ ID NO. 5535) |
| 206bp deletion | AB (Both) | TATGCTGCCCGCCCAGTGGGA \| ATCATCTTTACCAGATCTCAAAAAG | 411 | 411 | 822 | 18.61% (SEQ ID NOS. 5536, 5537) |
| 205bp inversion | AB (Both) | GAGTTGACACATTGTATTTCCAAAG \| ATCATCTTTACCAGATCTCA | 60 | 78 | 138 | 3.12% (SEQ ID NOS. 5538, 5539) (SEQ ID NOS. 5540, 5541) |
| | | TATGCTGCCCGCCCAGTGGGA \| TCCTGGGAGAGACCGAAACACAGCC | | | | |
| 1bp deletion | B (Proximal) | TGGCTGTGTTTGCGTCTCTCCCAGG \| ATCATCTTTACCAGATCTCA | 23 | 27 | 50 | 1.19% (SEQ ID NOS. 5542, 5543) |
| 206bp deletion with C insertion at break | AB (Both) | TATGCTGCCCGCCCAGTGGGA \| CATCATCTTTACCAGATCTCAAAAA | 19 | 8 | 27 | 0.61% (SEQ ID NOS. 5544, 5545) |
| 1bp deletion | A (Distal) | TATGCTGCCCGCCCAGTGGGA \| TTTGGAAATACAATGTGTCAACTCT | 14 | 11 | 25 | 0.54% (SEQ ID NOS. 5546, 5547) |
| 207bp deletion | AB (Both) | TATGCTGCCCGCCCAGTGGGA \| TCATCTTTACCAGATCTCAAAAGA | 10 | 8 | 18 | 0.41% (SEQ ID NOS. 5548, 5549) |
| A insertion | B (Proximal) | GCTGTGTTTGCGTCTCTCCCAGGAA \| ATCATCTTTACCAGATCTCA | 7 | 8 | 15 | 0.36% (SEQ ID NOS. 5550, 5551) |
| A insertion | A (Distal) | TATGCTGCCCGCCCAGTGGGA \| ACTTTGAAAATACAATGTGTCAACT | 4 | 7 | 11 | 0.24% (SEQ ID NOS. 5552, 5553) |
| 3bp deletion | A (Distal) | TATGCTGCCCGCCCAGTGGGA \| TGGAAAATACAATGTGTCAACTCTTG | 7 | 0 | 7 | 0.15% (SEQ ID NOS. 5554, 5555) |
| 2bp deletion | B (Proximal) | GTGCTGTGTTTGCGTCTCTCCCAG \| ATCATCTTTACCAGATCTCA | 4 | 2 | 6 | 0.14% (SEQ ID NOS. 5556, 5557) |
| TC insertion | A (Distal) | TATGCTGCCCGCCCAGTGGGA \| TCCTTTGGAAATACAATGTGTCAAC | 3 | 3 | 6 | 0.13% (SEQ ID NOS. 5558, 5559) |
| 209bp deletion | AB (Both) | TATGCTGCCCGCCCAGTGGGA \| ATCTTTACCAGATCTCAAAAGAAG | 1 | 4 | 5 | 0.11% (SEQ ID NOS. 5560, 5561) |
| 4bp deletion | B (Proximal) | TGGTGGCTGTGTTTGCGTCTCTCCC \| ATCATCTTTACCAGATCTCA | 4 | 0 | 4 | 0.10% (SEQ ID NOS. 5562, 5563) |
| 205bp deletion | AB (Both) | TATGCTGCCCGCCCAGTGGGA \| AATCATCTTTACCAGATCTCAAAAA | 2 | 2 | 4 | 0.09% (SEQ ID NOS. 5564, 5565) |
| 206bp deletion with A insertion at break | AB (Both) | TCACTATGCTGCCCGCCCAGTGGGAA \| ATCATCTTTACCAGATCTCA | 2 | 2 | 4 | 0.09% (SEQ ID NOS. 5566, 5567) |
| 12bp deletion | A (Distal) | TATGCTGCCCGCCCAGTGGGA \| AATGTGTCAACTCTTGACAGGGCTC | 4 | 0 | 4 | 0.09% (SEQ ID NOS. 5568, 5569) |
| 2bp deletion | A (Distal) | TATGCTGCCCGCCCAGTGGGA \| TTGGAAATACAATGTGTCAACTCTT | 2 | 1 | 3 | 0.06% (SEQ ID NOS. 5570, 5571) |

FIG. 21

| | | | | | |
|---|---|---|---|---|---|
| Unidentifiable novel sequence insertion | B (Proximal) | GAGTTACATGATCCCCATCTTGTG \| ATCATCTTTACCAGATCTCA | 2 | 2 | 0.05% (SEQ ID NOS. 5572, 5573) |
| 5bp deletion | B (Proximal) | GTGGTGGCTGTGTTGCGTCTCCCC \| ATCATCTTTACCAGATCTCA | 1 | 1 | 0.02% (SEQ ID NOS. 5574, 5575) |
| A->T transversion | B (Proximal) | GGCTGTGTTTGCGTCTCTCCCAGGTATCATCTTTACCAGATCTCA | 0 | 1 | 0.02% (SEQ ID NOS. 5576) |
| 208bp deletion | AB (Both) | TATGCTGCCGCCCAGTGGGA \| CATCTTTACCAGATCTCAAAAAGAA | 1 | 1 | 0.02% (SEQ ID NOS. 5577, 5578) |
| 7bp deletion | A (Distal) | TATGCTGCCGCCCAGTGGGA \| AATACAATGTGTCAACTCTTGACAG | 0 | 1 | 0.02% (SEQ ID NOS. 5579, 5580) |
| 8bp deletion | A (Distal) | TATGCTGCCGCCCAGTGGGA \| ATACAATGTGTCAACTCTTGACAGG | 0 | 1 | 0.02% (SEQ ID NOS. 5581, 5582) |
| C->T transition | A (Distal) | TATGCTGCCGCCAGTGGGATTTTGGAAATACAATGTTTCAACTC | 1 | 1 | 0.02% (SEQ ID NOS. 5583) |

FIG. 21 cont.

Table T3. Guide Pair crCCR5_C+D On-Target Alleles

| Allele | Cas9 Guide Site | Sequence | Split Reads | | | Estimated Allele Frequency |
|---|---|---|---|---|---|---|
| | | | (+) Strand | (-) Strand | TOTAL | |
| Reference | C (Proximal) | ATACAATGTGTCAACTCTTGACAGGGCTCTATTTATAGGCTTCT | 1704 | 1457 | 3161 | 79.72% (SEQ ID NO. 5584) |
| Reference | D (Distal) | GGCTCACTATGCTGCCCGCCCAGTGGGACTTTGGAAATACAATGTG | 1659 | 1459 | 3118 | 78.64% (SEQ ID NO. 5585) |
| 35bp deletion | CD (Both) | GGCTCACTATGCTGCCGCCCC \| GACAGGGCTCTATTTATAGGCTTC | 310 | 270 | 580 | 14.63% (SEQ ID NO. 5586, 5587) |
| 34bp deletion | CD (Both) | GGCTCACTATGCTGCCGCCC \| TGACAGGGCTCTATTTATAGGCTT | 97 | 99 | 196 | 4.94% (SEQ ID NO. 5588, 5589) |
| 33bp deletion | CD (Both) | GGCTCACTATGCTGCCGCCC \| TTGACAGGGCTCTATTTATAGGCT | 23 | 11 | 34 | 0.86% (SEQ ID NO. 5590, 5591) |
| 1bp deletion | C (Proximal) | AATACAATGTGTCAACTCT \| GACAGGGCTCTATTTATAGGCTTCT | 6 | 3 | 9 | 0.23% (SEQ ID NO. 5592, 5593) |
| T->G transversion 1bp 5' of PAM | D (Distal) | GGCTCACTATGCTGCCGCCCAGGGGACTTTGGAAATACAATGTG | 3 | 0 | 3 | 0.08% (SEQ ID NO. 5594) |
| 3bp deletion | D (Distal) | GGCTCACTATGCTGCCGCCC \| GGGACTTTGGAAATACAATGTCA | 3 | 0 | 3 | 0.08% (SEQ ID NO. 5595, 5596) |
| Unidentifiable novel sequence insertion | C (Proximal) | CCGGCAAACAAACCACCGC \| GACAGGGCTCTATTTATAGGCTTCT | 3 | 0 | 3 | 0.08% (SEQ ID NO. 5597, 5598) |
| 3bp deletion | C (Proximal) | GAAATACAATGTGTCAACT \| GACAGGGCTCTATTTATAGGCTTCT | 3 | 0 | 3 | 0.08% (SEQ ID NO. 5599, 5600) |
| 5bp deletion | C (Proximal) | TCACTATACAATGTGTCAAGAC \| AGGGCTCTATTTATAGGCTTCT | 2 | 0 | 2 | 0.05% (SEQ ID NO. 5601, 5602) |
| 2bp deletion | C (Proximal) | AAATACAATGTGTCAACTC \| GACAGGGCTCTATTTATAGGCTTCT | 0 | 2 | 2 | 0.05% (SEQ ID NO. 5603, 5604) |
| 34bp deletion; breaks offset 1bp 3' of both Cas9 sites | CD (Both) | GGCTCACTATGCTGCCGCCC \| AACAGGGCTCTATTTATAGGCTTC | 1 | 0 | 1 | 0.03% (SEQ ID NO. 5605, 5606) |
| G->A transition middle base of PAM | C (Proximal) | ATACAATGTGTCAACTCTTGACAGAGCCTCTATTTATAGGCTTCT | 1 | 0 | 1 | 0.03% (SEQ ID NO. 5607) |
| 19bp deletion | C (Proximal) | CCCAGTGGGACTTTGGAAAA \| ACAGGGCTCTATTTATAGGCTTCT | 1 | 0 | 1 | 0.03% (SEQ ID NO. 5608, 5609) |
| T->C transition 2bp 5' of Cas9 site | C (Proximal) | ATACAATGTGTCAACTCCT \| GACAGGGCTCTATTTATAGGCTTCT | 1 | 0 | 1 | 0.03% (SEQ ID NO. 5610, 5611) |
| T->C transition | C (Proximal) | ATACAATGTGTCAACTCTC \| GACAGGGCTCTATTTATAGGCTTCT | 0 | 1 | 1 | 0.03% (SEQ ID NO. 5612, 5613) |

FIG. 22

Table T4. Guide Pair crCCR5_D+Q On-Target Alleles

| Allele | Cas9 Guide Site | Sequence | Split Reads (+) Strand | Split Reads (-) Strand | Split Reads TOTAL | Estimated Allele Frequency |
|---|---|---|---|---|---|---|
| Reference | D (Distal) | GGCTCACTATGCTGCGCCCAGTGGGACTTTGGAAATACAATGTG | 1662 | 1261 | 2923 | 54.53% (SEQ ID NO. 5614) |
| Reference | Q (Proximal) | GGGTGGTGGCTGTGTTTGCGTTCTCCCAGGAATCATCTTTACCA | 1296 | 1535 | 2831 | 52.82% (SEQ ID NO. 5615) |
| 205bp deletion | DQ (Both) | TTCTGGGCTCACTATGCTGCCGCCC \| CCCAGGAATCATCTTTACCA | 332 | 269 | 601 | 11.21% (SEQ ID NO. 5616, 5617) |
| 205bp deletion | DQ (Both) | GGCTCACTATGCTGCCGCCC \| CCCAGGAATCATCTTACCAGATCT | 321 | 248 | 569 | 10.62% (SEQ ID NO. 5618, 5619) |
| 204bp deletion | DQ (Both) | GGCTCACTATGCTGCCGCCC \| TCCCAGGAATCATCTTACCAGATC | 235 | 278 | 513 | 9.57% (SEQ ID NO. 5620, 5621) |
| 204bp deletion | DQ (Both) | TCTGGGCTCACTATGCTGCCGCCT \| CCCAGGAATCATCTTTACCA | 223 | 273 | 496 | 9.25% (SEQ ID NO. 5622, 5623) |
| 205bp inversion | DQ (Both) | GGCTCACTATGCTGCCGCCC \| AGAGACGCAAACACAGCCACCACC | 48 | 41 | 89 | 1.66% (SEQ ID NO. 5624, 5625) |
| 19bp deletion | D (Distal) | CACATTGTATTTCCAAAGTCCCACT \| CCCAGGAATCATCTTTACCA | | | | (SEQ ID NO. 5626, 5627) |
| 206bp inversion | DQ (Both) | GGCTCACTATGCTGCCGCCC \| AATGTGTCAACTCTTGACAGGCTC | 41 | 24 | 65 | 1.21% (SEQ ID NO. 5628, 5629) |
| | | GGCTCACTATGCTGCCGCCC \| AGAGACGCAAACAGCCACCACCC | | | | (SEQ ID NO. 5630, 5631) |
| 206bp inversion | DQ (Both) | ACATTGTATTTCCAAAGTCCCACTT \| CCCAGGAATCATCTTTACCA | 26 | 18 | 44 | 0.82% (SEQ ID NO. 5632, 5633) |
| T insertion | D (Distal) | GGCTCACTATGCTGCCGCCC \| TAGTGGGACTTTGGAAATACAATGT | 8 | 9 | 17 | 0.32% (SEQ ID NO. 5634, 5635) |
| T insertion | Q (Proximal) | GGTGGTGGCTGTGTTTGCGTCTCTT \| CCCAGGAATCATCTTTACCA | 7 | 8 | 15 | 0.28% (SEQ ID NO. 5636, 5637) |
| 206bp deletion | DQ (Both) | CTTCTGGGCTCACTATGCTGCCGCC \| CCCAGGAATCATCTTTACCA | 4 | 9 | 13 | 0.24% (SEQ ID NO. 5638, 5639) |
| Unidentifiable novel sequence insertion | Q (Proximal) | GCTGTTTCCTGCTGTGTGAATTGTTAT \| CCCAGGAATCATCTTTACCA | 5 | 7 | 12 | 0.22% (SEQ ID NO. 5640, 5641) |
| 208bp deletion | DQ (Both) | CCCTTCTGGGCTCACTATGCTGCCG \| CCCAGGAATCATCTTTACCA | 4 | 6 | 10 | 0.19% (SEQ ID NO. 5642, 5643) |
| 208bp deletion | DQ (Both) | GGCTCACTATGCTGCCGCCC \| AGGAATCATCTTACCAGATCTTCAA | 4 | 5 | 9 | 0.17% (SEQ ID NO. 5644, 5645) |
| 207bp deletion | DQ (Both) | GGCTCACTATGCTGCCGCCC \| CCAAGGAATCATCTTTACCAGATCTC | 2 | 7 | 9 | 0.17% (SEQ ID NO. 5646, 5647) |
| 109bp deletion w/ TTA insertion | D (Distal) | GGCTCACTATGCTGCCGCCC \| TTACTGTCCTCCATGCTGTGTTTGC | 5 | 3 | 8 | 0.15% (SEQ ID NO. 5648, 5649) |
| 205bp deletion | DQ (Both) | TTCTGGGCTCACTATGCTGCCGCCC \| TCCCAGGAATCATCTTTACCA | 4 | 3 | 7 | 0.13% (SEQ ID NO. 5650, 5651) |
| 219bp deletion | DQ (Both) | GGCTCACTATGCTGCCGCCC \| TTACCAGATCTCAAAAAGAAGGTCT | 3 | 4 | 7 | 0.13% (SEQ ID NO. 5652, 5653) |
| Unidentifiable novel sequence insertion | D (Distal) | GGCTCACTATGCTGCCGCCC \| TGTATACCGTCGACCTCTAGCTAGA | 3 | 3 | 6 | 0.11% (SEQ ID NO. 5654, 5655) |
| C insertion | D (Distal) | GGCTCACTATGCTGCCGCCC \| CAGTGGGACTTTGGAAATACAATGT | 2 | 3 | 5 | 0.09% (SEQ ID NO. 5656, 5657) |
| 2bp deletion | D (Distal) | GGCTCACTATGCTGCCGCCC \| TGGGACTTTGGAAACACAATGTC | 2 | 3 | 5 | 0.09% (SEQ ID NO. 5658, 5659) |
| 14bp deletion | D (Distal) | GGCTCACTATGCTGCCGCCC \| AATACAATGTGTCAACTCTTGACAG | 0 | 5 | 5 | 0.09% (SEQ ID NO. 5660, 5661) |
| 202bp deletion | DQ (Both) | GGCTCACTATGCTGCCGCCC \| TCTCCCAGGAATCATCTTTACCAG | 0 | 5 | 5 | 0.09% (SEQ ID NO. 5662, 5663) |
| 202bp deletion | DQ (Both) | TGGGCTCACTATGCTGCGGCCCT \| CCCAGGAATCATCTTTACCA | 0 | 5 | 5 | 0.09% (SEQ ID NO. 5664, 5665) |
| 215bp deletion | DQ (Both) | TACTGTCCCCTTCTGGGCTCACTAT \| CCCAGGAATCATCTTTACCA | 2 | 2 | 4 | 0.07% (SEQ ID NO. 5666, 5667) |

FIG. 23

| Mutation | Guide | Sequence | | | Count1 | Count2 | Count3 | Frequency |
|---|---|---|---|---|---|---|---|---|
| 1bp deletion | Q (Proximal) | TGGGTGGTGGCTGTGTGTTTGCGTCTT | ; | CCCAGGAATCATCTTTACCA | 2 | 2 | 4 | 0.07% (SEQ ID NO. 5668, 5669) |
| 4bp deletion | Q (Proximal) | ACTTGGGTGGTGGCTGTGTTTGCGT | ; | CCCAGGAATCATCTTTACCA | 1 | 3 | 4 | 0.07% (SEQ ID NO. 5670, 5671) |
| A insertion | D (Distal) | GGCTCACTATGCTGCCGCCC | ; | AAGTGGGACTTTGGAAATACAATGT | 3 | 0 | 3 | 0.06% (SEQ ID NO. 5672, 5673) |
| 1bp deletion | D (Distal) | GGCTCACTATGCTGCCGCCC | ; | GTGGGACTTTGGAAATACAATGTGT | 3 | 0 | 3 | 0.06% (SEQ ID NO. 5674, 5675) |
| 72bp deletion | D (Distal) | GGCTCACTATGCTGCCGCCC | ; | TCTTCATCATCCTCCTGACAATCGA | 3 | 0 | 3 | 0.06% (SEQ ID NO. 5676, 5677) |
| 48bp deletion | D (Distal) | GGCTCACTATGCTGCCGCCC | ; | TTATAGGCTTCTTCTCTGGAATCTT | 3 | 0 | 3 | 0.06% (SEQ ID NO. 5678, 5679) |
| Unidentifiable novel sequence insertion | Q (Proximal) | TTCTTCGATCAGTCTAAAAATGGCT | ; | CCCAGGAATCATCTTTACCA | 3 | 0 | 3 | 0.06% (SEQ ID NO. 5680, 5681) |
| 214bp deletion | DQ (Both) | GGCTCACTATGCTGCCGCCC | ; | CATCTTTACCAGATCTCAAAAGAA | 2 | 1 | 3 | 0.06% (SEQ ID NO. 5682, 5683) |
| 50bp deletion | D (Distal) | GGCTCACTATGCTGCCGCCC | ; | AATAGGCTTCTTCTTCTGGAATCTTC | 0 | 3 | 3 | 0.06% (SEQ ID NO. 5684, 5685) |
| 152bp deletion | D (Distal) | GGCTCACTATGCTGCCGCCC | ; | TTTGGGGTGGTGACAAGTGTGATCA | 0 | 3 | 3 | 0.06% (SEQ ID NO. 5686, 5687) |
| 181bp deletion | DQ (Both) | GGCTCACTATGCTGCCGCCC | ; | TTAAAAGCAGGACGGTCACCTTTG | 0 | 3 | 3 | 0.06% (SEQ ID NO. 5688, 5689) |
| 192bp deletion | DQ (Both) | GGCTCACTATGCTGCCGCCC | ; | TGTTTGCCTCTCCCAGGAATCAT | 1 | 1 | 2 | 0.04% (SEQ ID NO. 5690, 5691) |
| 13bp deletion | Q (Proximal) | AGTGTGATCACTTGGGTGTGCTG | ; | CCCAGGAATCATCTTTACCA | 1 | 1 | 2 | 0.04% (SEQ ID NO. 5692, 5693) |
| 62bp deletion | D (Distal) | GGCTCACTATGCTGCCGCCC | ; | TCTGGAATCTTCTCATCATCCTCC | 0 | 2 | 2 | 0.04% (SEQ ID NO. 5694, 5695) |
| A->T transversion | D (Distal) | GGCTCACTATGCTGCCGCCCTGTGGGACTTTGGAAATACAATGTG | | | 0 | 2 | 2 | 0.04% (SEQ ID NO. 5696) |
| 8bp deletion | D (Distal) | GGCTCACTATGCTGCCGCCC | ; | TTTGGAAATACAATGTGTCAACTCT | 1 | 0 | 1 | 0.02% (SEQ ID NO. 5697, 5698) |
| 195bp deletion | DQ (Both) | GGCTCACTATGCTGCCGCCC | ; | CCCAAGATCATCTTTACCAGATCT | 1 | 0 | 1 | 0.02% (SEQ ID NO. 5699, 5700) |
| 207bp deletion | DQ (Both) | CCTTCGGCTCACTATGCTGCCGC | ; | CCCAGGAATCATCTTTACCA | 1 | 0 | 1 | 0.02% (SEQ ID NO. 5701, 5702) |
| 1bp deletion | Q (Proximal) | TGGGTGGTGGCTGTGTTTGCGTCTC | ; | CCCAGGAATCATCTTTACCA | 1 | 0 | 1 | 0.02% (SEQ ID NO. 5703, 5704) |
| 17bp deletion | D (Distal) | GGCTCACTATGCTGCCGCCC | ; | ACAATGTCAACTCTTGACAGGGC | 0 | 1 | 1 | 0.02% (SEQ ID NO. 5705, 5706) |
| A deletion | D (Distal) | GGCTCACTATGCTGCCGCCC | ; | GTGGGACTTTGGAAATTCAATGTGT | 0 | 1 | 1 | 0.02% (SEQ ID NO. 5707, 5708) |
| 205bp deletion w/ G insertion | DQ (Both) | GGCTCACTATGCTGCCGCCC | ; | GCCCAGGAATCATCTTTACCAGATC | 0 | 1 | 1 | 0.02% (SEQ ID NO. 5709, 5710) |
| 187bp deletion w/ 1bp deletion 1bp 5' of proximal guide PAM | DQ (Both) | GGCTCACTATGCTGCCGCCC | ; | GGCTGTGTTTGCGTCTCTCCAGGAA | 0 | 1 | 1 | 0.02% (SEQ ID NO. 5711, 5712) |
| 218bp deletion | DQ (Both) | TCTTACTGTCCCCTTCTGCGTCTCT | ; | CCCAGGAATCATCTTTACCA | 0 | 1 | 1 | 0.02% (SEQ ID NO. 5713, 5714) |
| C insertion | Q (Proximal) | GGTGGTGGCTGTGTTTGCGTCTCTC | ; | CCCAGGAATCATCTTTACCA | 0 | 1 | 1 | 0.02% (SEQ ID NO. 5715, 5716) |

FIG. 23 cont.

Table 5. Off-Target Sites with Statistically Significant Mutational Burden

| Guide | Degenerate Sequence | Predicted Binding Site | | | Fisher's Exact Test p | | N-Fold Enrichment | | |
|---|---|---|---|---|---|---|---|---|---|
| | | Chr | Start | End | InDel | Split | InDel | Split | |
| B | CCAGGAATCATCTTTACTAAATG | 3 | 46,399,538 | 46,399,561 | 4.4x10^-13 | 1.0000 | 3.51 | 0.47 | (SEQ ID NO. 5717) |
| B | CCAGGCATCTTCTTTACCAGCTC | 8 | 104,258,547 | 104,258,570 | 0.0165 | 1.0000 | 1.93 | 0.45 | (SEQ ID NO. 5718) |
| C | AAAATGTGTCAACTCTTGATTAG | 12 | 12,976,312 | 12,976,335 | 0.0361 | 1.0000 | 1.56 | 0.27 | (SEQ ID NO. 5719) |
| C | AAAATGTGTCAACTCTTGATTAG | 12 | 12,976,312 | 12,976,335 | 0.0361 | 1.0000 | 1.56 | 0.27 | (SEQ ID NO. 5720) |
| C | CCCACTGGGCTGCAGAATACAGA | 10 | 129,722,982 | 129,723,005 | 0.0338 | 0.9996 | 1.82 | 0.50 | (SEQ ID NO. 5721) |
| Q | TCTGTGTTGCCTCTCTCTCAGG | 12 | 19,270,661 | 19,270,684 | 0.0086 | 1.0000 | 2.08 | 0.20 | (SEQ ID NO. 5722) |
| Q | CCCGGGAGGAGGCAAAACAGC | 17 | 11,833,418 | 11,833,441 | 0.0083 | 1.0000 | 2.24 | 0.20 | (SEQ ID NO. 5723) |

FIG. 24

Table T6. Comparison of On- and Off-Target Mutational Burdens

| gRNA | gRNA Combinations Tested | On-Target Site | | Most Significant Off-Target Site | |
|---|---|---|---|---|---|
| | | Mutation Frequency | Variant Read Enrichment (Treatment vs. Control) | Variant Read Enrichment (Treatment vs. Control) | Fisher's Exact p (Treatment vs Control) |
| A | A, AB | 5.79% | 58.59 | 1.84 | 0.1616 |
| B | B, AB | 16.65% | 51.02 | 3.51 | 4.416x10^-13 |
| C | C, CD | 17.02% | 30.88 | 1.56 | 0.0361 |
| D | D, CD, DQ | 26.23% | 57.64 | 1.82 | 0.0338 |
| Q | DQ | 21.19% | 46.84 | 2.24 | 0.0083 |

FIG. 25

THERAPEUTIC USES OF GENOME EDITING WITH CRISPR/CAS SYSTEMS

RELATED APPLICATIONS

This application is a continuation-in-part of PCT Application No. PCT/US2014/46034, filed Jul. 9, 2014, which claims the benefit of U.S. Provisional Application Nos. 61/844,333, filed on Jul. 9, 2013, and 61/869,369, filed on Aug. 23, 2013. The entire teachings of the above applications are incorporated herein by reference.

GOVERNMENT SUPPORT

This invention was made with government support under HL118744, HL098364, DK095384 and HL107440 awarded by the National Institutes of Health. The government has certain rights in the invention.

BACKGROUND OF THE INVENTION

Clustered regularly interspaced short palindromic repeats (CRISPR)/CRISPR-associated (Cas) systems are a new class of genome-editing tools that target desired genomic sites in mammalian cells. Recently published type II CRISPR/Cas systems use Cas9 nuclease that is targeted to a genomic site by complexing with a synthetic guide RNA that hybridizes to a 20-nucleotide DNA sequence and immediately preceding an NGG motif recognized by Cas9 (thus, a $(N)_{20}$NGG target DNA sequence). This results in a double-strand break three nucleotides upstream of the NGG motif. The double strand break instigates either non-homologous end-joining, which is error-prone and conducive to frameshift mutations that knock out gene alleles, or homology-directed repair, which can be exploited with the use of an exogenously introduced double-strand or single-strand DNA repair template to knock in or correct a mutation in the genome. Thus, CRISPR/Cas systems could be useful tools for therapeutic applications, but unfortunately prior published reports have demonstrated an efficiency of allele targeting of only 2%-4% in human stem cells (Mali et al., *Science* 339:823-826 (2013)).

SUMMARY OF THE INVENTION

Work described herein demonstrates methods of allele targeting using CRISPR/Cas systems resulting in mutant cells with efficiencies of up to 80%. These vastly improved methods permit CRISPR/Cas systems to be utilized effectively for the first time for therapeutic purposes. Methods of delivery of CRISPR/Cas systems to human stem cells are provided. In addition, methods of specifically identifying useful RNA guide sequences are provided, along with particular guide sequences useful in targeting specific genes (e.g., ADA, AK2, CD3D, DCLRE1C, IL2RG, IL7R, JAK3, LIG4, NHEJ1, PNP, PRKDC, RAG1, RAG2, ZAP70 and HBB). Moreover, methods of treatment (e.g., severe combined immunodeficiency, sickle cell disease, e.g., sickle cell anemia, beta thalassemia, etc.) utilizing the compositions and methods disclosed herein are provided. In some aspects, disclosed herein is a method for altering a target severe combined immunodeficiency (SCID)-associated polynucleotide sequence in a cell comprising contacting the SCID-associated polynucleotide sequence with a clustered regularly interspaced short palindromic repeats-associated (Cas) protein and from one to two ribonucleic acids, wherein the ribonucleic acids direct Cas protein to and hybridize to a target motif of the target SCID-associated polynucleotide sequence, wherein the target SCID-associated polynucleotide sequence is cleaved.

In some aspects, disclosed herein is a method for treating or preventing a disorder associated with expression of a SCID-associated polynucleotide sequence in a subject, the method comprising (a) altering a target SCID-associated polynucleotide sequence in a cell ex vivo by contacting the SCID-associated polynucleotide sequence with a clustered regularly interspaced short palindromic repeats-associated (Cas) protein and from one to two ribonucleic acids, wherein the ribonucleic acids direct Cas protein to and hybridize to a target motif of the target SCID-associated polynucleotide sequence, wherein the target SCID-associated polynucleotide sequence is cleaved, and (b) introducing the cell into the subject, thereby treating or preventing a disorder associated with expression of the SCID-associated polynucleotide sequence.

In some aspects, disclosed herein is a method for treating or preventing a disorder associated with expression of a SCID-associated polynucleotide sequence in a subject, the method comprising altering a target SCID-associated polynucleotide sequence in a cell by contacting the SCID-associated polynucleotide sequence with a clustered regularly interspaced short palindromic repeats-associated (Cas) protein and from one to two ribonucleic acids, wherein the ribonucleic acids direct Cas protein to and hybridize to a target motif of the target SCID-associated polynucleotide sequence, and wherein the target SCID-associated polynucleotide sequence is cleaved, thereby treating or preventing a disorder associated with expression of the SCID-associated polynucleotide sequence.

In some aspects, disclosed herein is a method for simultaneously altering multiple target SCID-associated polynucleotide sequences in a cell comprising contacting the SCID-associated polynucleotide sequences with a clustered regularly interspaced short palindromic repeats-associated (Cas) protein and multiple ribonucleic acids, wherein the ribonucleic acids direct Cas protein to and hybridize to target motifs of the target SCID-associated polynucleotide sequences, wherein the target SCID-associated polynucleotide sequences are cleaved.

In some aspects, disclosed herein is a method for treating or preventing a disorder associated with expression of SCID-associated polynucleotide sequences in a subject, the method comprising (a) altering target SCID-associated polynucleotide sequences in a cell ex vivo by contacting the SCID-associated polynucleotide sequences with a clustered regularly interspaced short palindromic repeats-associated (Cas) protein and multiple ribonucleic acids, wherein the ribonucleic acids direct Cas protein to and hybridize to target motifs of the target SCID-associated polynucleotide sequences, wherein the target SCID-associated polynucleotide sequences are cleaved, and (b) introducing the cell into the subject, thereby treating or preventing a disorder associated with expression of the SCID-associated polynucleotide sequences.

In some aspects, disclosed herein is a method for treating or preventing a disorder associated with expression of SCID-associated polynucleotide sequences in a subject, the method comprising altering target SCID-associated polynucleotide sequences in a cell by contacting the SCID-associated polynucleotide sequences with a clustered regularly interspaced short palindromic repeats-associated (Cas) protein and multiple ribonucleic acids, wherein the ribonucleic acids direct Cas protein to and hybridize to target moieties of the target SCID-associated polynucleotide sequences, and wherein the target SCID-associated polynucleotide sequences are cleaved, thereby treating or preventing a disorder associated with expression of the SCID-associated polynucleotide sequences.

In some aspects, disclosed herein is a method for altering a target sickle cell disease (SCD)-associated polynucleotide sequence in a cell comprising contacting the SCD-associated polynucleotide sequence with a clustered regularly interspaced short palindromic repeats-associated (Cas) protein and from one to two ribonucleic acids, wherein the ribonucleic acids direct Cas protein to and hybridize to a target motif of the target SCD-associated polynucleotide sequence, wherein the target SCD-associated polynucleotide sequence is cleaved.

In some aspects, disclosed herein is a method for treating or preventing a disorder associated with expression of a SCD-associated polynucleotide sequence in a subject, the method comprising (a) altering a target SCD-associated polynucleotide sequence in a cell ex vivo by contacting the SCD-associated polynucleotide sequence with a clustered regularly interspaced short palindromic repeats-associated (Cas) protein and from one to two ribonucleic acids, wherein the ribonucleic acids direct Cas protein to and hybridize to a target motif of the target SCD-associated polynucleotide sequence, wherein the target SCD-associated polynucleotide sequence is cleaved, and (b) introducing the cell into the subject, thereby treating or preventing a disorder associated with expression of the SCD-associated polynucleotide sequence.

In some aspects, disclosed herein is a method for treating or preventing a disorder associated with expression of a SCD-associated polynucleotide sequence in a subject, the method comprising altering a target SCD-associated polynucleotide sequence in a cell by contacting the SCD-associated polynucleotide sequence with a clustered regularly interspaced short palindromic repeats-associated (Cas) protein and from one to two ribonucleic acids, wherein the ribonucleic acids direct Cas protein to and hybridize to a target motif of the target SCD-associated polynucleotide sequence, and wherein the target SCD-associated polynucleotide sequence is cleaved, thereby treating or preventing a disorder associated with expression of the SCD-associated polynucleotide sequence.

In some aspects, disclosed herein is a method for simultaneously altering multiple target SCD-associated polynucleotide sequences in a cell comprising contacting the SCD-associated polynucleotide sequences with a clustered regularly interspaced short palindromic repeats-associated (Cas) protein and multiple ribonucleic acids, wherein the ribonucleic acids direct Cas protein to and hybridize to target motifs of the target SCD-associated polynucleotide sequences, wherein the target SCD-associated polynucleotide sequences are cleaved.

In some aspects, disclosed herein is a method for treating or preventing a disorder associated with expression of SCD-associated polynucleotide sequences in a subject, the method comprising (a) altering target SCD-associated polynucleotide sequences in a cell ex vivo by contacting the SCD-associated polynucleotide sequences with a clustered regularly interspaced short palindromic repeats-associated (Cas) protein and multiple ribonucleic acids, wherein the ribonucleic acids direct Cas protein to and hybridize to target motifs of the target SCD-associated polynucleotide sequences, wherein the target SCD-associated polynucleotide sequences are cleaved, and (b) introducing the cell into the subject, thereby treating or preventing a disorder associated with expression of the SCD-associated polynucleotide sequences.

In some aspects, disclosed herein is a method for treating or preventing a disorder associated with expression of SCD-associated polynucleotide sequences in a subject, the method comprising altering target SCD-associated polynucleotide sequences in a cell by contacting the SCD-associated polynucleotide sequences with a clustered regularly interspaced short palindromic repeats-associated (Cas) protein and multiple ribonucleic acids, wherein the ribonucleic acids direct Cas protein to and hybridize to target moieties of the target SCD-associated polynucleotide sequences, and wherein the target SCD-associated polynucleotide sequences are cleaved, thereby treating or preventing a disorder associated with expression of the SCD-associated polynucleotide sequences.

In some aspects, disclosed herein is a method for altering a target beta thalassemia-associated polynucleotide sequence in a cell comprising contacting the beta thalassemia-associated polynucleotide sequence with a clustered regularly interspaced short palindromic repeats-associated (Cas) protein and from one to two ribonucleic acids, wherein the ribonucleic acids direct Cas protein to and hybridize to a target motif of the target beta thalassemia-associated polynucleotide sequence, wherein the target beta thalassemia-associated polynucleotide sequence is cleaved.

In some aspects, disclosed herein is a method for treating or preventing a disorder associated with expression of a beta thalassemia-associated polynucleotide sequence in a subject, the method comprising (a) altering a target beta thalassemia-associated polynucleotide sequence in a cell ex vivo by contacting the beta thalassemia-associated polynucleotide sequence with a clustered regularly interspaced short palindromic repeats-associated (Cas) protein and from one to two ribonucleic acids, wherein the ribonucleic acids direct Cas protein to and hybridize to a target motif of the target beta thalassemia-associated polynucleotide sequence, wherein the target beta thalassemia-associated polynucleotide sequence is cleaved, and (b) introducing the cell into the subject, thereby treating or preventing a disorder associated with expression of the beta thalassemia-associated polynucleotide sequence.

In some aspects, disclosed herein is a method for treating or preventing a disorder associated with expression of a beta thalassemia-associated polynucleotide sequence in a subject, the method comprising altering a target beta thalassemia-associated polynucleotide sequence in a cell by contacting the beta thalassemia-associated polynucleotide sequence with a clustered regularly interspaced short palindromic repeats-associated (Cas) protein and from one to two ribonucleic acids, wherein the ribonucleic acids direct Cas protein to and hybridize to a target motif of the target beta thalassemia-associated polynucleotide sequence, and wherein the target beta thalassemia-associated polynucleotide sequence is cleaved, thereby treating or preventing a disorder associated with expression of the beta thalassemia-associated polynucleotide sequence.

In some aspects, disclosed herein is a method for simultaneously altering multiple target beta thalassemia-associated polynucleotide sequences in a cell comprising contacting the beta thalassemia-associated polynucleotide sequences with a clustered regularly interspaced short palindromic repeats-associated (Cas) protein and multiple ribonucleic acids, wherein the ribonucleic acids direct Cas protein to and hybridize to target motifs of the target beta thalassemia-associated polynucleotide sequences, wherein the target beta thalassemia-associated polynucleotide sequences are cleaved.

In some aspects, disclosed herein is a method for treating or preventing a disorder associated with expression of beta thalassemia-associated polynucleotide sequences in a subject, the method comprising (a) altering target beta thalassemia-associated polynucleotide sequences in a cell ex vivo by contacting the beta thalassemia-associated polynucleotide sequences with a clustered regularly interspaced short palindromic repeats-associated (Cas) protein and multiple ribonucleic acids, wherein the ribonucleic acids direct Cas protein to and hybridize to target motifs of the target beta thalassemia-associated polynucleotide sequences, wherein the target beta thalassemia-associated polynucleotide sequences are cleaved, and (b) introducing the cell into the subject, thereby treating or preventing a disorder associated with expression of the beta thalassemia-associated polynucleotide sequences.

In some aspects, disclosed herein is a method for treating or preventing a disorder associated with expression of beta thalassemia-associated polynucleotide sequences in a subject, the method comprising altering target beta thalassemia-associated polynucleotide sequences in a cell by contacting the beta thalassemia-associated polynucleotide sequences with a clustered regularly interspaced short palindromic repeats-associated (Cas) protein and multiple ribonucleic acids, wherein the ribonucleic acids direct Cas protein to and hybridize to target moieties of the target beta thalassemia-associated polynucleotide sequences, and wherein the target beta thalassemia-associated polynucleotide sequences are cleaved, thereby treating or preventing a disorder associated with expression of the beta thalassemia-associated polynucleotide sequences.

In some embodiments, the Cas protein is *Streptococcus pyogenes* Cas9 protein or a functional portion thereof. In some embodiments, the functional portion comprises a combination of operably linked Cas9 protein functional domains selected from the group consisting of a DNA binding domain, at least one RNA binding domain, a helicase domain, and an endonuclease domain. In some embodiments, the functional domains form a complex. In some embodiments, the Cas protein is Cas9 protein from any bacterial species or functional portion thereof. In some embodiments, the functional portion comprises a combination of operably linked Cas9 protein functional domains selected from the group consisting of a DNA binding domain, at least one RNA binding domain, a helicase domain, and an endonuclease domain. In some embodiments, the functional domains form a complex.

In some embodiments, the Cas protein is complexed with the one to two ribonucleic acids. In some embodiments, the Cas protein is complexed with the multiple ribonucleic acids.

In some embodiments, the target motif is a 20-nucleotide DNA sequence. In some embodiments, each target motif is a 20-nucleotide DNA sequence. In some embodiments, the target motif is a 20-nucleotide DNA sequence beginning with G and immediately precedes an NGG motif recognized by the Cas protein. In some embodiments, each target motif is a 20-nucleotide DNA sequence beginning with G and immediately precedes an NGG motif recognized by the Cas protein. In some embodiments, the target motif is a 20-nucleotide DNA sequence and immediately precedes an NGG motif recognized by the Cas protein. In some embodiments, each target motif is a 20-nucleotide DNA sequence and immediately precedes an NGG motif recognized by the Cas protein. In some embodiments, the target motif is $G(N)_{19}NGG$. In some embodiments, each target motif is $G(N)_{19}NGG$. In some embodiments, the target motif is $(N)_{20}NGG$. In some embodiments, each target motif is $(N)_{20}NGG$.

In some embodiments, the target polynucleotide sequence is cleaved such that a double-strand break results. In some embodiments, each target polynucleotide sequence is cleaved such that a double-strand break results. In some embodiments, the target polynucleotide sequence is cleaved such that a single-strand break results. In some embodiments, each target polynucleotide sequence is cleaved such that a single-strand break results.

In some embodiments, the alteration is an indel. In some embodiments, the alteration results in reduced expression of the target polynucleotide sequence. In some embodiments, the alteration results in reduced expression of the target polynucleotide sequences. In some embodiments, the alteration results in a knock out of the target polynucleotide sequence. In some embodiments, the alteration results in a knock out of the target polynucleotide sequences. In some embodiments, the alteration results in correction of the target polynucleotide sequence from an undesired sequence to a desired sequence. In some embodiments, the alteration results in correction of the target polynucleotide sequences from undesired sequences to desired sequences. In some embodiments, the alteration is a homozygous alteration. In some embodiments, each alteration is a homozygous alteration.

In some embodiments, subsequent to cleavage of the target polynucleotide sequence, homology-directed repair occurs. In some embodiments, homology-directed repair is performed using an exogenously introduced DNA repair template. In some embodiments, the exogenously introduced DNA repair template is single-stranded. In some embodiments, the exogenously introduced DNA repair template is double-stranded. In some embodiments, subsequent to cleavage of the target polynucleotide sequences, homology-directed repair occurs. In some embodiments, homology-directed repair is performed using an exogenously introduced DNA repair template. In some embodiments, the exogenously introduced DNA repair template is single-stranded. In some embodiments, the exogenously introduced DNA repair template is double-stranded.

In some embodiments, the cell is a peripheral blood cell. In some embodiments, the cell is a stem cell or a pluripotent cell. In some embodiments, the cell is a hematopoietic stem cell. In some embodiments, the cell is a $CD34^+$ cell. In some embodiments, the cell is a $CD34^+$ mobilized peripheral blood cell. In some embodiments, the cell is a $CD34^+$ cord blood cell. In some embodiments, the cell is a $CD34^+$ bone marrow cell. In some embodiments, the cell is a $CD34^+$ $CD38$-Lineage-$CD90^+CD45RA^-$ cell.

In some embodiments, the target polynucleotide sequence is ADA. In some embodiments, at least one of the one to two ribonucleic acids comprises a sequence selected from the group consisting of the ribonucleic acid sequences of FIG. 1 or at least a 12 nucleotide fragment thereof. In some embodiments, at least one of the one to two ribonucleic acids comprises a sequence with a single nucleotide mismatch to a sequence selected from the group consisting of the ribonucleic acid sequences of FIG. 1 or at least a 12 nucleotide fragment thereof.

In some embodiments, the target polynucleotide sequence is AK2. In some embodiments, at least one of the one to two ribonucleic acids comprises a sequence selected from the group consisting of the ribonucleic acid sequences of FIG.

2 or at least a 12 nucleotide fragment thereof. In some embodiments, at least one of the one to two ribonucleic acids comprises a sequence with a single nucleotide mismatch to a sequence selected from the group consisting of the ribonucleic acid sequences of FIG. 2 or at least a 12 nucleotide fragment thereof.

In some embodiments, the target polynucleotide sequence is CD3D. In some embodiments, at least one of the one to two ribonucleic acids comprises a sequence selected from the group consisting of the ribonucleic acid sequences of FIG. 3 or at least a 12 nucleotide fragment thereof. In some embodiments, at least one of the one to two ribonucleic acids comprises a sequence with a single nucleotide mismatch to a sequence selected from the group consisting of the ribonucleic acid sequences of FIG. 3 or at least a 12 nucleotide fragment thereof.

In some embodiments, the target polynucleotide sequence is DCLRE1C. In some embodiments, at least one of the one to two ribonucleic acids comprises a sequence selected from the group consisting of the ribonucleic acid sequences of FIG. 4 or at least a 12 nucleotide fragment thereof. In some embodiments, at least one of the one to two ribonucleic acids comprises a sequence with a single nucleotide mismatch to a sequence selected from the group consisting of the ribonucleic acid sequences of FIG. 4 or at least a 12 nucleotide fragment thereof.

In some embodiments, the target polynucleotide sequence is IL2RG. In some embodiments, at least one of the one to two ribonucleic acids comprises a sequence selected from the group consisting of the ribonucleic acid sequences of FIG. 6 or at least a 12 nucleotide fragment thereof. In some embodiments, at least one of the one to two ribonucleic acids comprises a sequence with a single nucleotide mismatch to a sequence selected from the group consisting of the ribonucleic acid sequences of FIG. 6 or at least a 12 nucleotide fragment thereof.

In some embodiments, the target polynucleotide sequence is IL7R. In some embodiments, at least one of the one to two ribonucleic acids comprises a sequence selected from the group consisting of the ribonucleic acid sequences of FIG. 7 or at least a 12 nucleotide fragment thereof. In some embodiments, at least one of the one to two ribonucleic acids comprises a sequence with a single nucleotide mismatch to a sequence selected from the group consisting of the ribonucleic acid sequences of FIG. 7 or at least a 12 nucleotide fragment thereof.

In some embodiments, the target polynucleotide sequence is JAK3. In some embodiments, at least one of the one to two ribonucleic acids comprises a sequence selected from the group consisting of the ribonucleic acid sequences of FIG. 8 or at least a 12 nucleotide fragment thereof. In some embodiments, at least one of the one to two ribonucleic acids comprises a sequence with a single nucleotide mismatch to a sequence selected from the group consisting of the ribonucleic acid sequences of FIG. 8 or at least a 12 nucleotide fragment thereof.

In some embodiments, the target polynucleotide sequence is LIG4. In some embodiments, at least one of the one to two ribonucleic acids comprises a sequence selected from the group consisting of the ribonucleic acid sequences of FIG. 9 or at least a 12 nucleotide fragment thereof. In some embodiments, at least one of the one to two ribonucleic acids comprises a sequence with a single nucleotide mismatch to a sequence selected from the group consisting of the ribonucleic acid sequences of FIG. 9 or at least a 12 nucleotide fragment thereof.

In some embodiments, the target polynucleotide sequence is NHEJ1. In some embodiments, at least one of the one to two ribonucleic acids comprises a sequence selected from the group consisting of the ribonucleic acid sequences of FIG. 10 or at least a 12 nucleotide fragment thereof. In some embodiments, at least one of the one to two ribonucleic acids comprises a sequence with a single nucleotide mismatch to a sequence selected from the group consisting of the ribonucleic acid sequences of FIG. 10 or at least a 12 nucleotide fragment thereof.

In some embodiments, the target polynucleotide sequence is PNP. In some embodiments, at least one of the one to two ribonucleic acids comprises a sequence selected from the group consisting of the ribonucleic acid sequences of FIG. 11 or at least a 12 nucleotide fragment thereof. In some embodiments, at least one of the one to two ribonucleic acids comprises a sequence with a single nucleotide mismatch to a sequence selected from the group consisting of the ribonucleic acid sequences of FIG. 11 or at least a 12 nucleotide fragment thereof.

In some embodiments, the target polynucleotide sequence is PRKDC. In some embodiments, at least one of the one to two ribonucleic acids comprises a sequence selected from the group consisting of the ribonucleic acid sequences of FIG. 12 or at least a 12 nucleotide fragment thereof. In some embodiments, at least one of the one to two ribonucleic acids comprises a sequence with a single nucleotide mismatch to a sequence selected from the group consisting of the ribonucleic acid sequences of FIG. 12 or at least a 12 nucleotide fragment thereof.

In some embodiments, the target polynucleotide sequence is RAG1. In some embodiments, at least one of the one to two ribonucleic acids comprises a sequence selected from the group consisting of the ribonucleic acid sequences of FIG. 13 or at least a 12 nucleotide fragment thereof. In some embodiments, at least one of the one to two ribonucleic acids comprises a sequence with a single nucleotide mismatch to a sequence selected from the group consisting of the ribonucleic acid sequences of FIG. 13 or at least a 12 nucleotide fragment thereof.

In some embodiments, the target polynucleotide sequence is RAG2. In some embodiments, at least one of the one to two ribonucleic acids comprises a sequence selected from the group consisting of the ribonucleic acid sequences of FIG. 14 or at least a 12 nucleotide fragment thereof. In some embodiments, at least one of the one to two ribonucleic acids comprises a sequence with a single nucleotide mismatch to a sequence selected from the group consisting of the ribonucleic acid sequences of FIG. 14 or at least a 12 nucleotide fragment thereof.

In some embodiments, the target polynucleotide sequence is ZAP70. In some embodiments, at least one of the one to two ribonucleic acids comprises a sequence selected from the group consisting of the ribonucleic acid sequences of FIG. 15 or at least a 12 nucleotide fragment thereof. In some embodiments, at least one of the one to two ribonucleic acids comprises a sequence with a single nucleotide mismatch to a sequence selected from the group consisting of the ribonucleic acid sequences of FIG. 15 or at least a 12 nucleotide fragment thereof.

In some embodiments, the target polynucleotide sequence is HBB. In some embodiments, at least one of the one to two ribonucleic acids comprises a sequence selected from the group consisting of the ribonucleic acid sequences of FIG. 5 or at least a 12 nucleotide fragment thereof. In some embodiments, at least one of the one to two ribonucleic acids comprises a sequence with a single nucleotide mismatch to a sequence selected from the group consisting of the ribonucleic acid sequences of FIG. 5 or at least a 12 nucleotide fragment thereof. In some embodiments, at least one of the one to two ribonucleic acids comprises a sequence of GTAACGGCAGACTTCTCCACAGG (SEQ ID NO: 5321) or at least a 12 nucleotide fragment thereof. In some embodiments, at least one of the one to two ribonucleic acids comprises a sequence with a single nucleotide mismatch to ribonucleic acid sequence GTAACGGCAGACTTCTCCACAGG (SEQ ID NO: 5321) or at least a 12 nucleotide fragment thereof.

In some embodiments, the target polynucleotide sequences comprise multiple different portions of ADA. In some embodiments, each of the multiple ribonucleic acids comprises a different sequence selected from the group consisting of the ribonucleic acid sequences of FIG. 1 or at least 12 nucleotide fragments thereof. In some embodiments, each of the multiple ribonucleic acids comprises a sequence with a single nucleotide mismatch to a different sequence selected from the group consisting of the ribonucleic acid sequences of FIG. 1 or at least 12 nucleotide fragments thereof.

In some embodiments, the target polynucleotide sequences comprise multiple different portions of AK2. In some embodiments, each of the multiple ribonucleic acids comprises a different sequence selected from the group consisting of the ribonucleic acid sequences of FIG. 2 or at least 12 nucleotide fragments thereof. In some embodiments, each of the multiple ribonucleic acids comprises a sequence with a single nucleotide mismatch to a different sequence selected from the group consisting of the ribonucleic acid sequences of FIG. 2 or at least 12 nucleotide fragments thereof.

In some embodiments, the target polynucleotide sequences comprise multiple different portions of CD3D. In some embodiments, each of the multiple ribonucleic acids comprises a different sequence selected from the group consisting of the ribonucleic acid sequences of FIG. 3 or at least 12 nucleotide fragments thereof. In some embodiments, each of the multiple ribonucleic acids comprises a sequence with a single nucleotide mismatch to a different sequence selected from the group consisting of the ribonucleic acid sequences of FIG. 3 or at least 12 nucleotide fragments thereof.

In some embodiments, the target polynucleotide sequences comprise multiple different portions of DCLRE1C. In some embodiments, each of the multiple ribonucleic acids comprises a different sequence selected from the group consisting of the ribonucleic acid sequences of FIG. 4 or at least 12 nucleotide fragments thereof. In some embodiments, each of the multiple ribonucleic acids comprises a sequence with a single nucleotide mismatch to a different sequence selected from the group consisting of the ribonucleic acid sequences of FIG. 4 or at least 12 nucleotide fragments thereof.

In some embodiments, the target polynucleotide sequences comprise multiple different portions of IL2RG. In some embodiments, each of the multiple ribonucleic acids comprises a different sequence selected from the group consisting of the ribonucleic acid sequences of FIG. 6 or at least 12 nucleotide fragments thereof. In some embodiments, each of the multiple ribonucleic acids comprises a sequence with a single nucleotide mismatch to a different sequence selected from the group consisting of the ribonucleic acid sequences of FIG. 6 or at least 12 nucleotide fragments thereof.

In some embodiments, the target polynucleotide sequences comprise multiple different portions of IL7R. In some embodiments, each of the multiple ribonucleic acids comprises a different sequence selected from the group consisting of the ribonucleic acid sequences of FIG. 7 or at least 12 nucleotide fragments thereof. In some embodiments, each of the multiple ribonucleic acids comprises a sequence with a single nucleotide mismatch to a different sequence selected from the group consisting of the ribonucleic acid sequences of FIG. 7 or at least 12 nucleotide fragments thereof.

In some embodiments, the target polynucleotide sequences comprise multiple different portions of JAK3. In some embodiments, each of the multiple ribonucleic acids comprises a different sequence selected from the group consisting of the ribonucleic acid sequences of FIG. 8 or at least 12 nucleotide fragments thereof. In some embodiments, each of the multiple ribonucleic acids comprises a sequence with a single nucleotide mismatch to a different sequence selected from the group consisting of the ribonucleic acid sequences of FIG. 8 or at least 12 nucleotide fragments thereof.

In some embodiments, the target polynucleotide sequences comprise multiple different portions of LIG4. In some embodiments, each of the multiple ribonucleic acids comprises a different sequence selected from the group consisting of the ribonucleic acid sequences of FIG. 9 or at least 12 nucleotide fragments thereof. In some embodiments, each of the multiple ribonucleic acids comprises a sequence with a single nucleotide mismatch to a different sequence selected from the group consisting of the ribonucleic acid sequences of FIG. 9 or at least 12 nucleotide fragments thereof.

In some embodiments, the target polynucleotide sequences comprise multiple different portions of NHEJ1. In some embodiments, each of the multiple ribonucleic acids comprises a different sequence selected from the group consisting of the ribonucleic acid sequences of FIG. 10 or at least 12 nucleotide fragments thereof. In some embodiments, each of the multiple ribonucleic acids comprises a sequence with a single nucleotide mismatch to a different sequence selected from the group consisting of the ribonucleic acid sequences of FIG. 10 or at least 12 nucleotide fragments thereof.

In some embodiments, the target polynucleotide sequences comprise multiple different portions of PNP. In some embodiments, each of the multiple ribonucleic acids comprises a different sequence selected from the group consisting of the ribonucleic acid sequences of FIG. 11 or at least 12 nucleotide fragments thereof. In some embodiments, each of the multiple ribonucleic acids comprises a sequence with a single nucleotide mismatch to a different sequence selected from the group consisting of the ribonucleic acid sequences of FIG. 11 or at least 12 nucleotide fragments thereof.

In some embodiments, the target polynucleotide sequences comprise multiple different portions of PRKDC. In some embodiments, each of the multiple ribonucleic acids comprises a different sequence selected from the group consisting of the ribonucleic acid sequences of FIG. 12 or at least 12 nucleotide fragments thereof. In some embodiments, each of the multiple ribonucleic acids comprises a sequence with a single nucleotide mismatch to a different sequence selected from the group consisting of the ribonucleic acid sequences of FIG. 12 or at least 12 nucleotide fragments thereof.

In some embodiments, the target polynucleotide sequences comprise multiple different portions of RAG1. In some embodiments, each of the multiple ribonucleic acids comprises a different sequence selected from the group consisting of the ribonucleic acid sequences of FIG. 13 or at least 12 nucleotide fragments thereof. In some embodiments, each of the multiple ribonucleic acids comprises a sequence with a single nucleotide mismatch to a different sequence selected from the group consisting of the ribonucleic acid sequences of FIG. 13 or at least 12 nucleotide fragments thereof.

In some embodiments, the target polynucleotide sequences comprise multiple different portions of RAG2. In some embodiments, each of the multiple ribonucleic acids comprises a different sequence selected from the group consisting of the ribonucleic acid sequences of FIG. 14 or at least 12 nucleotide fragments thereof. In some embodiments, each of the multiple ribonucleic acids comprises a sequence with a single nucleotide mismatch to a different sequence selected from the group consisting of the ribonucleic acid sequences of FIG. 14 or at least 12 nucleotide fragments thereof.

In some embodiments, the target polynucleotide sequences comprise multiple different portions of ZAP70. In some embodiments, each of the multiple ribonucleic acids comprises a different sequence selected from the group consisting of the ribonucleic acid sequences of FIG. 15 or at least 12 nucleotide fragments thereof. In some embodiments, each of the multiple ribonucleic acids comprises a sequence with a single nucleotide mismatch to a different sequence selected from the group consisting of the ribonucleic acid sequences of FIG. 15 or at least 12 nucleotide fragments thereof.

In some embodiments, the target polynucleotide sequences comprise multiple different portions of HBB. In some embodiments, each of the multiple ribonucleic acids comprises a different sequence selected from the group consisting of the ribonucleic acid sequences of FIG. 5 or at least 12 nucleotide fragments thereof. In some embodiments, each of the multiple ribonucleic acids comprises a sequence with a single nucleotide mismatch to a different sequence selected from the group consisting of the ribonucleic acid sequences of FIG. 5 or at least 12 nucleotide fragments thereof.

In some embodiments, the target polynucleotide sequences comprise at least a portion of any combination of target polynucleotide sequences selected from the group consisting of ADA, AK2, CD3D, DCLRE1C, IL2RG, IL7R, JAK3, LIG4, NHEJ1, PNP, PRKDC, RAG1, RAG2, and ZAP70. In some embodiments, each of the multiple ribonucleic acids comprises a different sequence selected from the group consisting of the ribonucleic acid sequences of FIGS. 1-15 or at least a 12 nucleotide fragment thereof. In some embodiments, each of the multiple ribonucleic acids comprises a sequence with a single nucleotide mismatch to a different sequence selected from the group consisting of the ribonucleic acid sequences of FIGS. 1-15 or at least a 12 nucleotide fragment thereof.

In some embodiments, the disorder is SCID. In some embodiments, the disorder is sickle cell disease. In some embodiments, the disorder is beta thalassemia.

In some embodiments, the one to two ribonucleic acids are designed to hybridize to a target motif immediately adjacent to a deoxyribonucleic acid motif recognized by the Cas protein. In some embodiments, each of the one to two ribonucleic acids are designed to hybridize to target motifs immediately adjacent to deoxyribonucleic acid motifs recognized by the Cas protein which flank a mutant allele located between the target motifs. In some embodiments, the multiple ribonucleic acids are designed to hybridize to target motifs immediately adjacent to deoxyribonucleic acid motifs recognized by the Cas protein. In some embodiments, the multiple ribonucleic acids are designed to hybridize to target motifs immediately adjacent to deoxyribonucleic acid motifs recognized by the Cas protein which flank mutant alleles located between the target motifs. In some embodiments, the one to two ribonucleic acids are selected to minimize hybridization with nucleic acid sequences other than the target polynucleotide sequence. In some embodiments, the multiple ribonucleic acids are selected to minimize hybridization with nucleic acid sequences other than the target polynucleotide sequence. In some embodiments, the target motif is selected such that it contains at least two mismatches when compared with all other genomic nucleotide sequences in the cell. In some embodiments, each target motif is selected such that it contains at least two mismatches when compared with all other genomic nucleotide sequences in the cell. In some embodiments, the target motif is selected such that it contains at least one mismatch when compared with all other genomic nucleotide sequences in the cell. In some embodiments, the target motif is selected such that it contains at least one mismatch when compared with all other genomic nucleotide sequences in the cell. In some embodiments, the one to two ribonucleic acids hybridize to a target motif that it contains at least two mismatches when compared with all other genomic nucleotide sequences in the cell. In some embodiments, each of the multiple ribonucleic acids hybridize to target motifs that contain at least two mismatches when compared with all other genomic nucleotide sequences in the cell. In some embodiments, the one to two ribonucleic acids hybridize to a target motif that contains at least one mismatch when compared with all other genomic nucleotide sequences in the cell. In some embodiments, each of the multiple ribonucleic acids hybridize to target motifs that contain at least one mismatch when compared with all other genomic nucleotide sequences in the cell.

In some embodiments, the Cas protein and the one to two ribonucleic acids are contained in a nanoparticle. In some embodiments, the Cas protein and the one to two ribonucleic acids are contained in a lipid nanoparticle. In some embodiments, the lipid nanoparticle comprises at least one of a cationic lipid, a neutral lipid, an amino lipid, a sterol, and a PEG or PEG-modified lipid. In some embodiments, the cationic lipid is selected from the group consisting of ALNY-100, C12-200, DODAC, DDAB, DOTAP, DOTMA, DODMA, DLinDMA, DLenDMA, DLin-C-DAP, DLin-DAC, DLin-MA, DLinDAP, DLin-S-DMA, DLin-2-DMAP, DLin-TMA.Cl, DLin-TAP.Cl, DLin-MPZ, DLinAP, DOAP, DLin-EG-DMA, DLinDMA, DLin-K-DMA, DLin-KC2-DMA, DLin-M-C3-DMA, KC2, MC3, DOTAP.Cl, DOSPA, DOGS, DOPE, DODAP, DMRIE, XTC, and mixtures thereof. In some embodiments, the neutral lipid is selected from the group consisting of DPSC, DPPC, POPC, DOPE, SM, and mixtures thereof. In some embodiments, the PEG-modified lipid is selected from the group consisting of PEG-DMG, PEG-CerC14, PEG-CerC20, and mixtures thereof. In some embodiments, the Cas protein and the multiple ribonucleic acids are contained in nanoparticles. In some embodiments, the Cas protein and the multiple ribonucleic acids are contained in lipid nanoparticles. In some embodiments, the lipid nanoparticles comprise at least one of a cationic lipid, a neutral lipid, an amino lipid, a sterol, and a PEG or PEG-modified lipid. In some embodiments, the cationic lipid is selected from the group consisting of ALNY-100, C12-200, DODAC, DDAB, DOTAP, DOTMA, DODMA, DLinDMA, DLenDMA, DLin-C-DAP, DLin-DAC, DLin-MA, DLinDAP, DLin-S-DMA, DLin-2-DMAP, DLin-TMA.Cl, DLin-TAP.Cl, DLin-MPZ, DLinAP, DOAP, DLin-EG-DMA, DLinDMA, DLin-K-DMA, DLin-KC2-DMA, DLin-M-C3-DMA, KC2, MC3, DOTAP.Cl, DOSPA, DOGS, DOPE, DODAP, DMRIE, XTC, and mixtures thereof. In some embodiments, the neutral lipid is selected from the group consisting of DPSC, DPPC, POPC, DOPE, SM, and mixtures thereof. In some embodiments, the PEG-modified lipid is selected from the group consisting of PEG-DMG, PEG-CerC14, PEG-CerC20, and mixtures thereof.

In some embodiments, the efficiency of alteration at each loci is from about 50% to about 80%. In some embodiments, the efficiency of alteration is at least about 5%. In some embodiments, the efficiency of alteration is at least about 10%. In some embodiments, the efficiency of alteration is from about 50% to about 80%.

In some embodiments, the Cas protein is encoded by a modified nucleic acid. In some embodiments, the modified nucleic acid comprises a ribonucleic acid containing at least one modified nucleotide selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate. In some embodiments, at least one of the ribonucleic acids is a modified ribonucleic acid comprising one to two modified nucleotides selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate.

In some embodiments, any of the Cas protein or the ribonucleic acids are expressed from a plasmid. In some embodiments, any of the Cas protein or the ribonucleic acids are expressed using a promoter optimized for increased expression in stem cells. In some embodiments, the promoter is selected from the group consisting of a Cytomegalovirus (CMV) early enhancer element and a chicken beta-actin promoter, a chicken beta-actin promoter, an elongation factor-1 alpha promoter, and a ubiquitin promoter.

In some embodiments, the method further comprises selecting cells that express the Cas protein. In some embodiments, selecting cells comprises FACS. In some embodiments, FACs is used to select cells which co-express Cas and a fluorescent protein selected from the group consisting of green fluorescent protein and red fluorescent protein.

In some aspects, disclosed herein is a method for altering a target SCID-associated polynucleotide sequence in a cell comprising contacting the SCID-associated polynucleotide sequence in a cell selected from the group consisting of a human pluripotent cell, a primary human cell, and a non-transformed human cell, with a clustered regularly interspaced short palindromic repeats-associated (Cas) protein and from one to two ribonucleic acids, wherein the ribonucleic acids direct Cas protein to and hybridize to a target motif of the target SCID-associated polynucleotide sequence, wherein the target SCID-associated polynucleotide sequence is cleaved, and wherein the efficiency of alteration of cells that express Cas protein is from about 8% to about 80%.

In some aspects, disclosed herein is a method for altering a target SCD-associated polynucleotide sequence in a cell comprising contacting the SCD-associated polynucleotide sequence in a cell selected from the group consisting of a human pluripotent cell, a primary human cell, and a non-transformed human cell, with a clustered regularly interspaced short palindromic repeats-associated (Cas) protein and from one to two ribonucleic acids, wherein the ribonucleic acids direct Cas protein to and hybridize to a target motif of the target SCD-associated polynucleotide sequence, wherein the target SCD-associated polynucleotide sequence is cleaved, and wherein the efficiency of alteration of cells that express Cas protein is from about 8% to about 80%.

In some aspects, disclosed herein is a method for altering a target beta thalassemia-associated polynucleotide sequence in a cell comprising contacting the beta thalassemia-associated polynucleotide sequence in a cell selected from the group consisting of a human pluripotent cell, a primary human cell, and a non-transformed human cell, with a clustered regularly interspaced short palindromic repeats-associated (Cas) protein and from one to two ribonucleic acids, wherein the ribonucleic acids direct Cas protein to and hybridize to a target motif of the target beta thalassemia-associated polynucleotide sequence, wherein the target beta thalassemia-associated polynucleotide sequence is cleaved, and wherein the efficiency of alteration of cells that express Cas protein is from about 8% to about 80%.

In some aspects, disclosed herein is a method for treating or preventing a disorder associated with expression of a SCID-associated polynucleotide sequence in a subject, the method comprising (a) altering a target SCID-associated polynucleotide sequence in a cell ex vivo by contacting the SCID-associated polynucleotide sequence in a cell selected from the group consisting of a human pluripotent cell, a primary human cell, and a non-transformed human cell, with a clustered regularly interspaced short palindromic repeats-associated (Cas) protein and from one to two ribonucleic acids, wherein the ribonucleic acids direct Cas protein to and hybridize to a target motif of the target SCID-associated polynucleotide sequence, wherein the target SCID-associated polynucleotide sequence is cleaved, and wherein the efficiency of alteration is from about 8% to about 80%, and (b) introducing the cell into the subject, thereby treating or preventing a disorder associated with expression of the SCID-associated polynucleotide sequence.

In some aspects, disclosed herein is a method for treating or preventing a disorder associated with expression of a SCD-associated polynucleotide sequence in a subject, the method comprising (a) altering a target SCD-associated polynucleotide sequence in a cell ex vivo by contacting the SCD-associated polynucleotide sequence in a cell selected from the group consisting of a human pluripotent cell, a primary human cell, and a non-transformed human cell, with a clustered regularly interspaced short palindromic repeats-associated (Cas) protein and from one to two ribonucleic acids, wherein the ribonucleic acids direct Cas protein to and hybridize to a target motif of the target SCD-associated polynucleotide sequence, wherein the target SCD-associated polynucleotide sequence is cleaved, and wherein the efficiency of alteration is from about 8% to about 80%, and (b) introducing the cell into the subject, thereby treating or preventing a disorder associated with expression of the SCD-associated polynucleotide sequence.

In some aspects, disclosed herein is a method for treating or preventing a disorder associated with expression of a beta thalassemia-associated polynucleotide sequence in a subject, the method comprising (a) altering a target beta thalassemia-associated polynucleotide sequence in a cell ex vivo by contacting the beta thalassemia-associated polynucleotide sequence in a cell selected from the group consisting of a human pluripotent cell, a primary human cell, and a non-transformed human cell, with a clustered regularly interspaced short palindromic repeats-associated (Cas) protein and from one to two ribonucleic acids, wherein the ribonucleic acids direct Cas protein to and hybridize to a target motif of the target beta thalassemia-associated polynucleotide sequence, wherein the target beta thalassemia-associated polynucleotide sequence is cleaved, and wherein the efficiency of alteration is from about 8% to about 80%, and (b) introducing the cell into the subject, thereby treating or preventing a disorder associated with expression of the beta thalassemia-associated polynucleotide sequence.

In some aspects, disclosed herein is a method for simultaneously altering multiple target SCID-associated polynucleotide sequences in a cell comprising contacting the SCID-associated polynucleotide sequences in a cell selected from the group consisting of a human pluripotent cell, a primary human cell, and a non-transformed human cell, with a clustered regularly interspaced short palindromic repeats-associated (Cas) protein and multiple ribonucleic acids, wherein the ribonucleic acids direct Cas protein to and hybridize to target motifs of the target SCID-associated polynucleotide sequences, wherein the target SCID-associated polynucleotide sequences are cleaved, and wherein the efficiency of alteration of cells that express Cas protein is from about 8% to about 80%.

In some aspects, disclosed herein is a method for simultaneously altering multiple target SCD-associated polynucleotide sequences in a cell comprising contacting the SCD-associated polynucleotide sequences in a cell selected from the group consisting of a human pluripotent cell, a primary human cell, and a non-transformed human cell, with a clustered regularly interspaced short palindromic repeats-associated (Cas) protein and multiple ribonucleic acids, wherein the ribonucleic acids direct Cas protein to and hybridize to target motifs of the target SCD-associated polynucleotide sequences, wherein the target SCD-associated polynucleotide sequences are cleaved, and wherein the efficiency of alteration of cells that express Cas protein is from about 8% to about 80%.

In some aspects, disclosed herein is a method for simultaneously altering multiple target beta thalassemia-associated polynucleotide sequences in a cell comprising contacting the beta thalassemia-associated polynucleotide sequences in a cell selected from the group consisting of a human pluripotent cell, a primary human cell, and a non-transformed human cell, with a clustered regularly interspaced short palindromic repeats-associated (Cas) protein and multiple ribonucleic acids, wherein the ribonucleic acids direct Cas protein to and hybridize to target motifs of the target beta thalassemia-associated polynucleotide sequences, wherein the target beta thalassemia-associated polynucleotide sequences are cleaved, and wherein the efficiency of alteration of cells that express Cas protein is from about 8% to about 80%.

In some aspects, disclosed herein is a method for treating or preventing a disorder associated with expression of SCID-associated polynucleotide sequences in a subject, the method comprising (a) altering target SCID-associated polynucleotide sequences in a cell ex vivo by contacting the SCID-associated polynucleotide sequences in a cell selected from the group consisting of a human pluripotent cell, a primary human cell, and a non-transformed human cell, with a clustered regularly interspaced short palindromic repeats-associated (Cas) protein and multiple ribonucleic acids, wherein the ribonucleic acids direct Cas protein to and hybridize to target motifs of the target SCID-associated polynucleotide sequences, wherein the target SCID-associated polynucleotide sequences are cleaved, and wherein the efficiency of alteration of cells that express Cas protein is from about 8% to about 80%, and (b) introducing the cell into the subject, thereby treating or preventing a disorder associated with expression of the SCID-associated polynucleotide sequences.

In some aspects, disclosed herein is a method for treating or preventing a disorder associated with expression of SCD-associated polynucleotide sequences in a subject, the method comprising (a) altering target SCD-associated polynucleotide sequences in a cell ex vivo by contacting the SCD-associated polynucleotide sequences in a cell selected from the group consisting of a human pluripotent cell, a primary human cell, and a non-transformed human cell, with a clustered regularly interspaced short palindromic repeats-associated (Cas) protein and multiple ribonucleic acids, wherein the ribonucleic acids direct Cas protein to and hybridize to target motifs of the target SCD-associated polynucleotide sequences, wherein the target SCD-associated polynucleotide sequences are cleaved, and wherein the efficiency of alteration of cells that express Cas protein is from about 8% to about 80%, and (b) introducing the cell into the subject, thereby treating or preventing a disorder associated with expression of the SCD-associated polynucleotide sequences.

In some aspects, disclosed herein is a method for treating or preventing a disorder associated with expression of beta thalassemia-associated polynucleotide sequences in a subject, the method comprising (a) altering target beta thalassemia-associated polynucleotide sequences in a cell ex vivo by contacting the beta thalassemia-associated polynucleotide sequences in a cell selected from the group consisting of a human pluripotent cell, a primary human cell, and a non-transformed human cell, with a clustered regularly interspaced short palindromic repeats-associated (Cas) protein and multiple ribonucleic acids, wherein the ribonucleic acids direct Cas protein to and hybridize to target motifs of the target SCID-associated polynucleotide sequences, wherein the target beta thalassemia-associated polynucleotide sequences are cleaved, and wherein the efficiency of alteration of cells that express Cas protein is from about 8% to about 80%, and (b) introducing the cell into the subject, thereby treating or preventing a disorder associated with expression of the beta thalassemia-associated polynucleotide sequences.

In some aspects, disclosed herein is a composition, comprising at least one ribonucleic acid having a sequence selected from the group consisting of the ribonucleic acid sequences of FIGS. 1-15 or at least a 12 nucleotide fragment thereof.

In some aspects, disclosed herein is a composition, comprising at least one ribonucleic acid comprising a sequence with a single nucleotide mismatch to a sequence selected from the group consisting of the ribonucleic acid sequences of FIGS. 1-15 or at least a 12 nucleotide fragment thereof.

In some embodiments, the at least one ribonucleic acid is contained in a nanoparticle. In some embodiments, the at least one ribonucleic acid is contained in a lipid nanoparticle. In some embodiments, the lipid nanoparticle comprises at least one of a cationic lipid, a neutral lipid, an amino lipid, a sterol, and a PEG or PEG-modified lipid. In some embodiments, the cationic lipid is selected from the group consisting of ALNY-100, C12-200, DODAC, DDAB, DOTAP, DOTMA, DODMA, DLinDMA, DLenDMA, DLin-C-DAP, DLin-DAC, DLin-MA, DLinDAP, DLin-S-DMA, DLin-2-DMAP, DLin-TMA.Cl, DLin-TAP.Cl, DLin-MPZ, DLinAP, DOAP, DLin-EG-DMA, DLinDMA, DLin-K-DMA, DLin- KC2-DMA, DLin-M-C3-DMA, KC2, MC3, DOTAP.Cl, DOSPA, DOGS, DOPE, DODAP, DMRIE, XTC, and mixtures thereof. In some embodiments, the neutral lipid is selected from the group consisting of DPSC, DPPC, POPC, DOPE, SM, and mixtures thereof. In some embodiments, the PEG-modified lipid is selected from the group consisting of PEG-DMG, PEG-CerC14, PEG-CerC20, and mixtures thereof. In some embodiments, at least one of the ribonucleic acids is a modified ribonucleic acid comprising one to two modified nucleotides selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate.

In some embodiments, a composition further comprises a nucleic acid sequence encoding a Cas protein.

In some embodiments, a composition further comprises a nucleic acid sequence encoding a Cas9 protein or a functional portion thereof. In some embodiments, the nucleic acid comprises a modified ribonucleic acid comprising at least one modified nucleotide selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate.

In some aspects, disclosed herein is a composition, comprising a chimeric nucleic acid comprising a ribonucleic acid encoding a Cas protein and at least one additional ribonucleic acid having a sequence selected from the group consisting of the ribonucleic acid sequences of FIGS. 1-15 or at least a 12 nucleotide fragment thereof.

In some aspects, disclosed herein is a composition, comprising a chimeric nucleic acid comprising a ribonucleic acid encoding a Cas protein and at least one additional ribonucleic acid sequence comprising a sequence with a single nucleotide mismatch to a sequence selected from the group consisting of the ribonucleic acid sequences of FIGS. 1-15 or at least a 12 nucleotide fragment thereof.

In some embodiments, the composition further comprises a nucleic acid sequence encoding a fluorescent protein selected from the group consisting of green fluorescent protein and red fluorescent protein. In some embodiments, the composition further comprises a promoter operably linked to the chimeric nucleic acid. In some embodiments, the promoter is optimized for increased expression in human stem cells. In some embodiments, the promoter is selected from the group consisting of a Cytomegalovirus (CMV) early enhancer element and a chicken beta-actin promoter, a chicken beta-actin promoter, an elongation factor-1 alpha promoter, and a ubiquitin promoter.

In some embodiments, the chimeric nucleic acid is contained in a nanoparticle. In some embodiments, the chimeric nucleic acid is contained in a lipid nanoparticle. In some embodiments, the lipid nanoparticle comprises at least one of a cationic lipid, a neutral lipid, an amino lipid, a sterol, and a PEG or PEG-modified lipid. In some embodiments, the cationic lipid is selected from the group consisting of ALNY-100, C12-200, DODAC, DDAB, DOTAP, DOTMA, DODMA, DLinDMA, DLenDMA, DLin-C-DAP, DLin-DAC, DLin-MA, DLinDAP, DLin-S-DMA, DLin-2-DMAP, DLin-TMA.Cl, DLin-TAP.Cl, DLin-MPZ, DLinAP, DOAP, DLin-EG-DMA, DLinDMA, DLin-K-DMA, DLin-KC2-DMA, DLin-M-C3-DMA, KC2, MC3, DOTAP.Cl, DOSPA, DOGS, DOPE, DODAP, DMRIE, XTC, and mixtures thereof. In some embodiments, the neutral lipid is selected from the group consisting of DPSC, DPPC, POPC, DOPE, SM, and mixtures thereof. In some embodiments, the PEG-modified lipid is selected from the group consisting of PEG-DMG, PEG-CerC14, PEG-CerC20, and mixtures thereof. In some embodiments, the chimeric nucleic acid comprises at least one modified nucleotide selected from the group consisting of pseudouridine, 5-methylcytodine, 2-thiouridine, 5-methyluridine-5'-triphosphate, 4-thiouridine-5'-triphosphate, 5,6-dihydrouridine-5'-triphosphate, and 5-azauridine-5'-triphosphate.

In some embodiments, the Cas protein comprises a Cas9 protein or a functional portion thereof.

In some aspects, disclosed herein is a kit for altering a target polynucleotide sequence in a cell comprising a Cas9 protein or a nucleic acid encoding the Cas9 protein, and at least one ribonucleic acid sequence selected from the group consisting of the ribonucleic acid sequences of FIGS. 1-15, a sequence with a single nucleotide mismatch to a ribonucleic acid sequence of FIGS. 1-15 or at least a 12 nucleotide fragment thereof.

In some embodiments, the kit further comprises one or more cell lines, cultures, or populations selected from the group consisting of human pluripotent cells, primary human cells, and non-transformed cells. In some embodiments, the kit further comprises a DNA repair template selected from the group consisting of an ADA DNA repair template, a AK2 DNA repair template, a CD3D DNA repair template, a DCLRE1C DNA repair template, a IL2RG DNA repair template, IL7R DNA repair template, a JAK3 DNA repair template, a LIG4 DNA repair template, a NHEJ1 DNA repair templates PNP DNA repair template, a PRKDC DNA repair template, a RAG1 DNA repair template, a RAG2 DNA repair template, a ZAP70 DNA repair template, and a HBB DNA repair template.

In some aspects, the disclosure provides a composition comprising at least one ribonucleic acid having a ribonucleic acid sequence of GTAACGGCAGACTTCTCCACAGG (SEQ ID NO: 5321) or at least a 12 nucleotide fragment thereof. In some aspects, the disclosure provides a composition comprising at least one ribonucleic acid comprising a sequence with a single nucleotide mismatch to a ribonucleic acid sequence of GTAACGGCAGACTTCTCCACAGG (SEQ ID NO: 5321) or at least a 12 nucleotide fragment thereof. In some embodiments, the at least one ribonucleic acid is contained in a nanoparticle. In some embodiments, the at least one ribonucleic acid is contained in a lipid nanoparticle. In some embodiments, the lipid nanoparticle comprises at least one of a cationic lipid, a neutral lipid, an amino lipid, a sterol, and a PEG or PEG-modified lipid. In some embodiments, the cationic lipid is selected from the group consisting of ALNY-100, C12-200, DODAC, DDAB, DOTAP, DOTMA, DODMA, DLinDMA, DLenDMA, DLin-C-DAP, DLin-DAC, DLin-MA, DLinDAP, DLin-S-DMA, DLin-2-DMAP, DLin-TMA.Cl, DLin-TAP.Cl, DLin-MPZ, DLinAP, DOAP, DLin-EG-DMA, DLinDMA, DLin-K-DMA, DLin-KC2-DMA, DLin-M-C3-DMA, KC2, MC3, DOTAP.Cl, DOSPA, DOGS, DOPE, DODAP, DMRIE, XTC, and mixtures thereof. In some embodiments, the neutral lipid is selected from the group consisting of DPSC, DPPC, POPC, DOPE, SM, and mixtures thereof. In some embodiments, the PEG-modified lipid is selected from the group consisting of PEG-DMG, PEG-CerC14, PEG-CerC20, and mixtures thereof. In some embodiments, at least one of the ribonucleic acids is a modified ribonucleic acid comprising one to two modified nucleotides selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate. In some embodiments, the composition includes a nucleic acid sequence encoding a Cas protein. In some embodiments, the composition includes a nucleic acid sequence encoding a Cas9 protein or a functional portion thereof. In some embodiments, the nucleic acid comprises a modified ribonucleic acid comprising at least one modified nucleotide selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate.

In some aspects, the disclosure provides a composition comprising a chimeric nucleic acid comprising a ribonucleic acid encoding a Cas protein and at least one additional ribonucleic acid having a ribonucleic acid sequences of GTAACGGCAGACTTCTCCACAGG (SEQ ID NO: 5321) or at least a 12 nucleotide fragment thereof. In some aspects, the disclosure provides a composition comprising a chimeric nucleic acid comprising a ribonucleic acid encoding a Cas protein and at least one additional ribonucleic acid sequence comprising a sequence with a single nucleotide mismatch to a ribonucleic acid sequence of GTAACGGCAGACTTCTCCACAGG (SEQ ID NO: 5321) or at least a 12 nucleotide fragment thereof. In some embodiments, the composition includes a nucleic acid sequence encoding a fluorescent protein selected from the group consisting of green fluorescent protein and red fluorescent protein. In some embodiments, the composition includes a promoter operably linked to the chimeric nucleic acid. In some embodiments, the promoter is optimized for increased expression in human stem cells. In some embodiments, the promoter is selected from the group consisting of a Cytomegalovirus (CMV) early enhancer element and a chicken beta-actin promoter, a chicken beta-actin promoter, an elongation factor-1 alpha promoter, and a ubiquitin promoter. In some embodiments, the chimeric nucleic acid is contained in a nanoparticle. In some embodiments, the chimeric nucleic acid is contained in a lipid nanoparticle. In some embodiments, the lipid nanoparticle comprises at least one of a cationic lipid, a neutral lipid, an amino lipid, a sterol, and a PEG or PEG-modified lipid. In some embodiments, the cationic lipid is selected from the group consisting of ALNY-100, C12-200, DODAC, DDAB, DOTAP, DOTMA, DODMA, DLinDMA, DLenDMA, DLin-C-DAP, DLin-DAC, DLin-MA, DLin-DAP, DLin-S-DMA, DLin-2-DMAP, DLin-TMA.Cl, DLin-TAP.Cl, DLin-MPZ, DLinAP, DOAP, DLin-EG-DMA, DLinDMA, DLin-K-DMA, DLin-KC2-DMA, DLin-M-C3-DMA, KC2, MC3, DOTAP.Cl, DOSPA, DOGS, DOPE, DODAP, DMRIE, XTC, and mixtures thereof. In some embodiments, the neutral lipid is selected from the group consisting of DPSC, DPPC, POPC, DOPE, SM, and mixtures thereof. In some embodiments, the PEG-modified lipid is selected from the group consisting of PEG-DMG, PEG-CerC14, PEG-CerC20, and mixtures thereof. In some embodiments, the chimeric nucleic acid comprises at least one modified nucleotide selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate. In some embodiments, the Cas protein comprises a Cas9 protein or a functional portion thereof.

In some aspects, the disclosure provides a kit for altering a target polynucleotide sequence in a cell comprising a Cas9 protein or a nucleic acid encoding the Cas9 protein, and at least one ribonucleic acid sequence selected from the group consisting of the ribonucleic acid sequences of GTAACGGCAGACTTCTCCACAGG (SEQ ID NO: 5321), a sequence with a single nucleotide mismatch to a ribonucleic acid sequence of GTAACGGCAGACTTCTCCACAGG (SEQ ID NO: 5321) or at least a 12 nucleotide fragment thereof. In some embodiments, the kit includes one or more cell lines, cultures, or populations selected from the group consisting of human pluripotent cells, primary human cells, and non-transformed cells. In some embodiments, the kit includes a HBB DNA repair template.

BRIEF DESCRIPTION OF THE DRAWINGS

FIG. 1 shows exemplary guide RNA sequences useful when the target polynucleotide sequence is human ADA.

FIG. 2 shows exemplary guide RNA sequences useful when the target polynucleotide sequence is human AK2.

FIG. 3 shows exemplary guide RNA sequences useful when the target polynucleotide sequence is human CD3D.

FIG. 4 shows exemplary guide RNA sequences useful when the target polynucleotide sequence is human DCLRE1C.

FIG. 5 shows exemplary guide RNA sequences useful when the target polynucleotide sequence is human HBB.

FIG. 6 shows exemplary guide RNA sequences useful when the target polynucleotide sequence is human IL2RG.

FIG. 7 shows exemplary guide RNA sequences useful when the target polynucleotide sequence is human IL7R.

FIG. 8 shows exemplary guide RNA sequences useful when the target polynucleotide sequence is human JAK3.

FIG. 9 shows exemplary guide RNA sequences useful when the target polynucleotide sequence is human LIG4.

FIG. 10 shows exemplary guide RNA sequences useful when the target polynucleotide sequence is human NHEJ1.

FIG. 11 shows exemplary guide RNA sequences useful when the target polynucleotide sequence is human PNP.

FIG. 12 shows exemplary guide RNA sequences useful when the target polynucleotide sequence is human PRKDC.

FIG. 13 shows exemplary guide RNA sequences useful when the target polynucleotide sequence is human RAG1.

FIG. 14 shows exemplary guide RNA sequences useful when the target polynucleotide sequence is human RAG2.

FIG. 15 shows exemplary guide RNA sequences useful when the target polynucleotide sequence is human ZAP70.

FIG. 16 shows an exemplary amino acid sequence of a Cas protein. Yellow highlights indicate Ruv-C-like domain. Underlining indicates HNH nuclease domain.

FIGS. 17A, 17B, 17C and 17D demonstrate targeted capture and extremely deep sequencing of on-target and predicted off-target sites in CD34+HPSCs. FIG. 17A is a schematic overview of targeted capture and deep sequencing of on-target and predicted off-target sites (red bar). A 500 bp flanking cutting site (in yellow) were included in sequence analysis for detection of structural rearrangements, including translocations. Probe sets are indicated in blue. FIG. 17B features plots showing consistent sequencing depth coverage at both on-target (left panel) and off-target (right panel) sites, achieving a coverage exceeding 3,000× for all on-target sites. Decrease in sequencing depth at the on-target sites in dual-gRNA libraries is marked by arrow, supporting predicted deletions (bottom left; i=35 bp, ii=205 bp, iii=205 bp). FIG. 17C is a Table depicting the precise estimation of on-target mutation allele frequencies by capture sequencing. Notably, the observed rate of effective null mutation exceeds previous estimates by PCR validation of predictable deletions, as smaller InDels and inversions also occur at appreciable frequencies. FIG. 17D is a Table depicting the estimation of mutation frequencies at predicted off-target sites (*One off-target site was statistically different from controls following correction for multiple comparisons; $p \leq 7.6 \times 10^-$ 11). N-fold enrichment is determined based on the ratio of non-reference reads in treated libraries compared to untreated library. Each value represents the average of all off-target sites for a given single gRNA or dual-gRNA experiment. Enrichment of 1 is equivalent to baseline (untreated control). **For reference to on-target enrichments, on-target combined represents the proportion of non-reference reads (including single and dual-gRNA treatments using a given gRNA) to total reads at on-target sites in treatment compared to control.

FIGS. 18A and 18B demonstrate potential off-target sites identified in CCR5 homologue CCR2 and analysis of events detected at the single off-target site in which mutagenesis was significantly detected above background. FIG. 18A depicts a sequence alignment of CCR5 gRNAs utilized in this study in relation to the closest homologous sequence in CCR2 showing mismatched nucleotides in bold. Noteworthy is the fact that guide crCCR5_B, which yielded the sole significantly detected off-target mutagenesis in CCR2 (detailed in panel B), has 3 nucleotide mismatches, which are distal to the PAM (underlined) and seed (grey box) sequences. FIG. 18B is a Table depicting in-depth analyses of all sequence reads at the single off-target site in which mutagenesis was significantly detected above background in both capture libraries treated with the associated gRNA (B; libraries treated with single gRNA crCCR5_B & dual-gRNA crCCR5_A+B), as well as the library treated with gRNA crCCR5_A as a comparison. Total off-target mutation frequency at this site was 0.6% in the single gRNA treatment (crCCR5_B) and notably decreased to 0.24% in the dual gRNA treatment (crCCR5_A+B) in which gRNA plasmid concentration of each gRNA was half of that utilized in single gRNA treatments.

FIG. 19A is a schematic illustrating the steps employed to generate Fgm knockout mice using the CRISPR/Cas system employing the Cas9 modified RNA. FIG. 19B shows part of a gel picture depicting results from PCR screening of surviving pups for genetic mutations resulting from genomic editing using the CRISPR/Cas system and the modified Cas9 mRNA.

FIG. 20 shows predicted gRNA mapping in Ensembl GRCh37v71.

FIG. 21 shows guide pair crCCR5_A+B on-target alleles.

FIG. 22 shows guide pair crCCR5_C+D on-target alleles.

FIG. 23 shows guide pair crCCR5 D+Q on-target alleles.

FIG. 24 shows off-target sites with statistically significant mutational burden.

FIG. 25 shows a comparison of on- and off-target mutational burdens.

DETAILED DESCRIPTION OF THE INVENTION

Figure 19A:
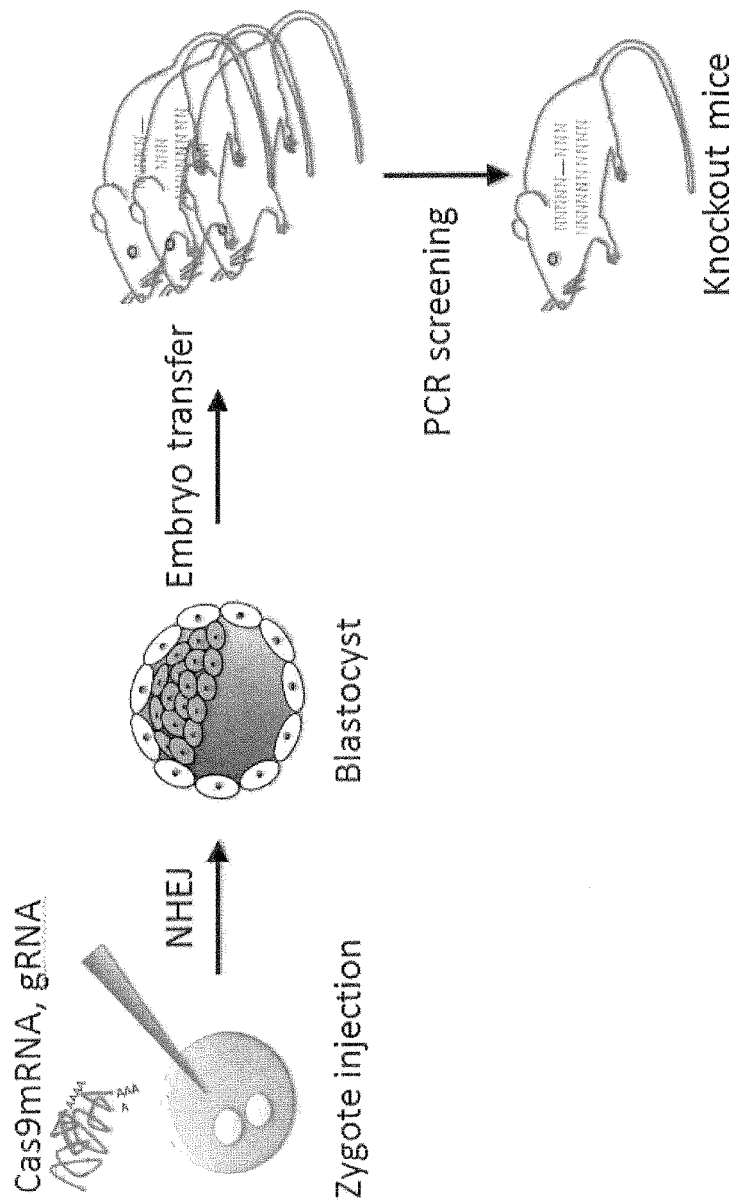
FIGS. 19A and 19B demonstrate the generation of Fgm knockout mice by a CRISPR/Cas system employing a modified Cas9 mRNA.

Work described herein demonstrates methods of allele targeting using CRISPR/Cas systems resulting in mutant cells with efficiencies of up to 80%. These vastly improved methods permit CRISPR/Cas systems to be utilized effectively for the first time for therapeutic purposes. Methods of delivery of CRISPR/Cas systems to human stem cells are provided. In addition, methods of specifically identifying useful RNA guide sequences are provided, along with particular guide sequences useful in targeting specific genes (e.g., ADA, AK2, CD3D, DCLRE1C, HBB, IL2RG, IL7R, JAK3, LIG4, NHEJ1, PNP, PRKDC, RAG1, RAG2, and ZAP70). Moreover, methods of treatment (e.g., methods of treating severe combined immunodeficiency, sickle cell disease, and beta thalassemia) utilizing the compositions and methods disclosed herein are provided.

In one aspect, the present invention provides methods for altering target polynucleotide sequences in a cell.

In certain embodiments, the target polynucleotide sequence is a severe combined immunodeficiency (SCID)-associated polynucleotide sequence. In such embodiments, a method for altering a target polynucleotide sequence in a cell comprises a method for altering a target SCID-associated polynucleotide sequence. As used herein, "severe combined immunodeficiency-associated polynucleotide sequence" and "SCID-associated polynucleotide sequence" are used interchangeably to refer to a polynucleotide sequence of a gene displaying one or more mutations associated with SCID. As used herein "severe combined immunodeficiency" and "SCID" refer to a genetic disorder characterized by dysfunctional T-lymphocytes causing a defective antibody response due to either a direct involvement with B lymphocytes or aberrant B lymphocyte activation resulting from non-functional T-helper cells. SCID encompasses dysfunctional B and T cell responses of the adaptive immune system due to mutations in one or more genes, including, but not limited to, ADA, AK2, CD3D, DCLRE1C, IL2RG, IL7R, JAK3, LIG4, NHEJ1, PNP, PRKDC, RAG1, RAG2, and ZAP70. As such, a "SCID-associated polynucleotide sequence" encompasses nucleotide sequences of any of these genes along with variant or mutant forms thereof.

An exemplary method for altering a target severe combined immunodeficiency (SCID)-associated polynucleotide sequence in a cell comprises contacting the SCID-associated polynucleotide sequence with a clustered regularly interspaced short palindromic repeats-associated (Cas) protein and from one to two ribonucleic acids, wherein the ribonucleic acids direct Cas protein to and hybridize to a target motif of the target SCID-associated polynucleotide sequence, wherein the target SCID associated polynucleotide sequence is cleaved. In some embodiments, the efficiency of alteration of cells that express Cas protein is from about 50% to about 80%.

In some embodiments, the SCID-associated polynucleotide sequence is adenosine deaminase (ADA) or a variant thereof. An exemplary ADA sequence is a human ADA sequence (NCBI Gene ID: 100). Those skilled in the art will appreciate that the guide sequences shown in FIG. 1 can be used with the CRISPR/Cas systems of the present invention to alter target polynucleotide sequences of human ADA.

It should also be appreciated that altering a target polynucleotide sequence of ADA can be used to treat any abnormal phenotype associated with an altered ADA polynucleotide sequence. Table 1 below shows gene phenotype relationships identified by the Online Mendelian Inheritance in Man® (OMIM®) database. Further information regarding a phenotype listed in Table 1 is publicly accessible by querying OMIM for the search term "ADA" and then clicking on a hyperlink in the "Phenotype MIM number" column corresponding to the phenotype listed.

TABLE 1

ADA Gene Phenotype Relationships

| Location | Phenotype | Phenotype MIM number |
| --- | --- | --- |
| 20q13.12 | Adenosine deaminase deficiency, partial | 102700 |
|  | Severe combined immunodeficiency due to ADA deficiency | 102700 |

In some embodiments, the SCID-associated polynucleotide sequence is adenylate kinase 2 (AK2) or a variant thereof. An exemplary AK2 sequence is a human AK2 sequence (NCBI Gene ID: 204, also known as ADK2 and AK 2). In some embodiments, the human AK2 sequence comprises all or a portion of AK2 coding sequence 1. In some embodiments, the human AK2 sequence comprises all or a portion of AK2 coding sequence 2. In some embodiments, the human AK2 sequence comprises all or a portion of AK2 coding sequence 3. Those skilled in the art will appreciate that the guide sequences shown in FIGS. 2, 3 and 4 can be used with the CRISPR/Cas systems of the present invention to alter target polynucleotide sequences of human AK2, and in particular human AK2 coding sequences 1, 2 and 3, respectively.

It should also be appreciated that altering a target polynucleotide sequence of AK2 can be used to treat any abnormal phenotype associated with an altered AK2 polynucleotide sequence. Table 2 below shows gene phenotype relationships identified by the OMIM® database. Further information regarding a phenotype listed in Table 2 is publicly accessible by querying OMIM for the search term "AK2" and then clicking on a hyperlink in the "Phenotype MIM number" column corresponding to the phenotype listed.

TABLE 2

AK2 Gene Phenotype Relationships

| Location | Phenotype | Phenotype MIM number |
|---|---|---|
| 1p35.1 | Reticular dysgenesis | 267500 |

In some embodiments, the SCID-associated polynucleotide sequence is CD3 antigen, delta subunit (CD3D) or a variant thereof. An exemplary CD3D sequence is a human CD3D sequence (NCBI Gene ID: 915, also known as T3D and CD3-DELTA). In some embodiments, the human CD3D sequence comprises all or a portion of CD3D coding sequence 1. In some embodiments, the human CD3D sequence comprises all or a portion of CD3D coding sequence 2. Those skilled in the art will appreciate that the guide sequences shown in FIGS. 5 and 6 can be used with the CRISPR/Cas systems of the present invention to alter target polynucleotide sequences of human CD3D, and in particular human CD3D coding sequences 1 and 2, respectively.

It should also be appreciated that altering a target polynucleotide sequence of CD3D can be used to treat any abnormal phenotype associated with an altered CD3D polynucleotide sequence. Table 3 below shows gene phenotype relationships identified by the OMIM® database. Further information regarding a phenotype listed in Table 3 is publicly accessible by querying OMIM for the search term "CD3D" and then clicking on a hyperlink in the "Phenotype MIM number" column corresponding to the phenotype listed.

TABLE 3

CD3D Gene Phenotype Relationships

| Location | Phenotype | Phenotype MIM number |
|---|---|---|
| 11q23.3 | Severe combined immunodeficiency, T cell-negative, B-cell/natural killer-cell positive | 608971 |

In some embodiments, the SCID-associated polynucleotide sequence is DNA cross-link repair protein 1C (DCLRE1C) or a variant thereof. An exemplary DCLRE1C sequence is a human DCLREIC sequence (NCBI Gene ID: 64421, also known as SCIDA, SNMIC, A-SCID, hSNM1C, RS-SCID, DCLREIC). In some embodiments, the human DCLREIC sequence comprises all or a portion of DCLRE1C coding sequence 1. In some embodiments, the human DCLREIC sequence comprises all or a portion of DCLREIC coding sequence 2. In some embodiments, the human DCLREIC sequence comprises all or a portion of DCLREIC coding sequence 3. In some embodiments, the human DCLREIC sequence comprises all or a portion of DCLREIC coding sequence 4. Those skilled in the art will appreciate that the guide sequences shown in FIGS. 7, 8, 9, and 10 can be used with the CRISPR/Cas systems of the present invention to alter target polynucleotide sequences of human DCLRE1C, and in particular human DCLRE1C coding sequences 1, 2, 3, and 4, respectively.

It should also be appreciated that altering a target polynucleotide sequence of DCLREIC can be used to treat any abnormal phenotype associated with an altered DCLREIC polynucleotide sequence. Table 4 below shows gene phenotype relationships identified by the OMIM® database. Further information regarding a phenotype listed in Table 4 is publicly accessible by querying OMIM for the search term "DCLREIC" and then clicking on a hyperlink in the "Phenotype MIM number" column corresponding to the phenotype listed.

TABLE 4

DCLRE1C Gene Phenotype Relationships

| Location | Phenotype | Phenotype MIM number |
|---|---|---|
| 10p13 | Omenn syndrome | 603554 |
|  | Severe combined immunodeficiency, Athabascan type | 602450 |

In some embodiments, the SCID-associated polynucleotide sequence is interleukin 2 receptor, gamma (IL2RG) or a variant thereof. An exemplary IL2RG sequence is a human IL2RG sequence (NCBI Gene ID: 3561, also known as P64; CIDX; IMD4; CD132; SCIDX; IL-2RG; and SCIDX1). Those skilled in the art will appreciate that the guide sequences shown in FIG. 12 can be used with the CRISPR/Cas systems of the present invention to alter target polynucleotide sequences of human IL2RG.

It should also be appreciated that altering a target polynucleotide sequence of IL2RG can be used to treat any abnormal phenotype associated with an altered IL2RG polynucleotide sequence. Table 5 below shows gene phenotype relationships identified by the OMIM® database. Further information regarding a phenotype listed in Table 5 is publicly accessible by querying OMIM for the search term "IL2RG" and then clicking on a hyperlink in the "Phenotype MIM number" column corresponding to the phenotype listed.

TABLE 5

IL2RG Gene Phenotype Relationships

| Location | Phenotype | Phenotype MIM number |
|---|---|---|
| Xq13.1 | Combined immunodeficiency, X-linked, moderate | 312863 |
|  | Severe combined immunodeficiency, X-linked | 300400 |

In some embodiments, the SCID-associated polynucleotide sequence is interleukin 7 receptor (IL7R) or a variant thereof. An exemplary IL7R sequence is a human IL7R sequence (NCBI Gene ID: 3575, also known as ILRA, CD127, IL7RA, CDW127, IL-7R-alpha). Those skilled in the art will appreciate that the guide sequences shown in FIG. 13 can be used with the CRISPR/Cas systems of the present invention to alter target polynucleotide sequences of human IL7R.

It should also be appreciated that altering a target polynucleotide sequence of IL7R can be used to treat any abnormal phenotype associated with an altered IL7R polynucleotide sequence. Table 6 below shows gene phenotype relationships identified by the OMIM® database. Further information regarding a phenotype listed in Table 6 is publicly accessible by querying OMIM for the search term "IL7R" and then clicking on a hyperlink in the "Phenotype MIM number" column corresponding to the phenotype listed.

TABLE 6

IL7R Gene Phenotype Relationships

| Location | Phenotype | Phenotype MIM number |
|---|---|---|
| 5p13.2 | Severe combined immunodeficiency, T-cell negative, B-cell/natural killer cell-positive type | 608971 |

In some embodiments, the SCID-associated polynucleotide sequence is Janus kinase 3(JAK3) or a variant thereof. An exemplary JAK3 sequence is a human JAK3 sequence (NCBI Gene ID: 3718, also known as JAKL; LJAK; JAK-3; L-JAK; JAK3_HUMAN). Those skilled in the art will appreciate that the guide sequences shown in FIG. 14 can be used with the CRISPR/Cas systems of the present invention to alter target polynucleotide sequences of human JAK3.

It should also be appreciated that altering a target polynucleotide sequence of JAK3 can be used to treat any abnormal phenotype associated with an altered JAK3 polynucleotide sequence. Table 7 below shows gene phenotype relationships identified by the OMIM® database. Further information regarding a phenotype listed in Table 7 is publicly available by querying OMIM for the search term "JAK3" and then clicking on a hyperlink in the "Phenotype MIM number" column corresponding to the phenotype listed.

TABLE 7

JAK3 Gene Phenotype Relationships

| Location | Phenotype | Phenotype MIM number |
|---|---|---|
| 19p13.11 | SCID, autosomal recessive, T-negative/B-positive type | 600802 |

In some embodiments, the SCID-associated polynucleotide sequence is ligase IV, DNA, ATP-dependent (LIG4) or a variant thereof. An exemplary LIG4 sequence is a human LIG4 sequence (NCBI Gene ID: 3981). In some embodiments, the human LIG4 sequence comprises all or a portion of LIG4 coding sequence 1. In some embodiments, the human LIG4 sequence comprises all or a portion of LIG4 coding sequence 2. In some embodiments, the human LIG4 sequence comprises all or a portion of LIG4 coding sequence 3. Those skilled in the art will appreciate that the guide sequences shown in FIGS. 15, 16, and 17 can be used with the CRISPR/Cas systems of the present invention to alter target polynucleotide sequences of human LIG4, and in particular human LIG4 coding sequences 1, 2, and 3, respectively.

It should also be appreciated that altering a target polynucleotide sequence of LIG4 can be used to treat any abnormal phenotype associated with an altered LIG4 polynucleotide sequence. Table 8 below shows gene phenotype relationships identified by the OMIM® database. Further information regarding a phenotype listed in Table 8 is publicly accessible by querying OMIM for the search term "LIG4" and then clicking on a hyperlink in the "Phenotype MIM number" column corresponding to the phenotype listed.

TABLE 8

LIG4 Gene Phenotype Relationships

| Location | Phenotype | Phenotype MIM number |
|---|---|---|
| 13q33.3 | LIG4 syndrome | 606593 |
| | Severe combined immunodeficiency with sensitivity to ionizing radiation | 602450 |
| | {Multiple myeloma, resistance to} | 254500 |

In some embodiments, the SCID-associated polynucleotide sequence is nonhomologous end-joining factor 1 (NHEJ1) or a variant thereof. An exemplary NHEJ1 sequence is the human NHEJ1 sequence (NCBI Gene ID: 79840, also known as XLF). Those skilled in the art will appreciate that the guide sequences shown in FIG. 18 can be used with the CRISPR/Cas systems of the present invention to alter target polynucleotide sequences of human NHEJ1.

It should also be appreciated that altering a target polynucleotide sequence of NHEJ1 can be used to treat any abnormal phenotype associated with an altered NHEJ1 polynucleotide sequence. Table 9 below shows gene phenotype relationships identified by the OMIM® database. Further information regarding a phenotype listed in Table 9 is publicly accessible by querying OMIM for the search term "NHEJ1" and then clicking on a hyperlink in the "Phenotype MIM number" column corresponding to the phenotype listed.)

TABLE 9

NHEJ1 Gene Phenotype Relationships

| Location | Phenotype | Phenotype MIM number |
|---|---|---|
| 2q35 | Severe combined immunodeficiency with microcephaly, growth retardation, and sensitivity to ionizing radiation | 611291 |

In some embodiments, the SCID-associated polynucleotide sequence is a purine nucleoside phosphorylase sequence (PNP) or a variant thereof. An exemplary PNP sequence is human PNP (NCBI Gene ID: 4860, also known as NP, PUNP, and PRO1837). Those skilled in the art will appreciate that the guide sequences shown in FIG. 19 can be used with the CRISPR/Cas systems of the present invention to alter target polynucleotide sequences of human PNP.

It should also be appreciated that altering a target polynucleotide sequence of PNP can be used to treat any abnormal phenotype associated with an altered PNP polynucleotide sequence. Table 10 below shows gene phenotype relationships identified by the OMIM® database. Further information regarding a phenotype listed in Table 10 is publicly accessible by querying OMIM for the search term "PNP" and then clicking on a hyperlink in the "Phenotype MIM number" column corresponding to the phenotype listed.

TABLE 10

PNP Gene Phenotype Relationships

| Location | Phenotype | Phenotype MIM number |
|---|---|---|
| 14q11.2 | Immunodeficiency due to purine nucleoside phosphorylase deficiency | 613179 |

In some embodiments, the SCID-associated polynucleotide sequence is a protein kinase, DNA activated, catalytic polypeptide sequence (PRKDC) or a variant thereof. An exemplary PRKDC sequence is human PRKDC (NCBI Gene ID: 5591, also known as HYRC; p350; DNAPK; DNPK1; HYRC1; XRCC7; and DNA-PKcs). In some embodiments, the human PRKDC sequence comprises all or a portion of PRKDC coding sequence 1. In some embodiments, the human PRKDC sequence comprises all or a portion of PRKDC coding sequence 2. Those skilled in the art will appreciate that the guide sequences shown in FIGS. 20 and 21 can be used with the CRISPR/Cas systems of the present invention to alter target polynucleotide sequences of human PRKDC, and in particular human PRKDC coding sequences 1 and 2, respectively.

It should also be appreciated that altering a target polynucleotide sequence of PRKDC can be used to treat any abnormal phenotype associated with an altered PRKDC polynucleotide sequence. In some embodiments, the phenotype associated with an altered PRKDC polynucleotide sequence is SCID. In some embodiments, the phenotype associated with an altered PRKDC polynucleotide sequence is radiosensitivity in xeroderma pigmentosum (Abbaszadeh et al., A novel splice variant of the DNA-PKcs gene is associated with clinical and cellular radiosensitivity in a patient with xeroderma pigmentosum. J Med Genet. 2010; 47(3):176-81).

In some embodiments, the SCID-associated polynucleotide sequence is a recombination activating gene 1 sequence (RAG1) or a variant thereof. An exemplary RAG1 sequence is human RAG1 (NCBI Gene ID: 5896, also known as RAG-1 and RNF74). Those skilled in the art will appreciate that the guide sequences shown in FIG. 22 can be used with the CRISPR/Cas systems of the present invention to alter target polynucleotide sequences of human RAG1.

It should also be appreciated that altering a target polynucleotide sequence of RAG1 can be used to treat any abnormal phenotype associated with an altered RAG1 polynucleotide sequence. Table 11 below shows gene phenotype relationships identified by the OMIM® database. Further information regarding a phenotype listed in Table 11 is publicly accessible by querying OMIM for the search term "RAG1" and then clicking on a hyperlink in the "Phenotype MIM number" column corresponding to the phenotype listed.

TABLE 11

RAG1 Gene Phenotype Relationships

| Location | Phenotype | Phenotype MIM number |
|---|---|---|
| 11p12 | Alpha/beta T-cell lymphopenia with gamma/delta T-cell expansion, severe cytomegalovirus infection, and autoimmunity | 609889 |
| | Combined cellular and humoral immune defects with granulomas | 233650 |
| | Omenn syndrome | 603554 |
| | Severe combined immunodeficiency, B cell-negative | 601457 |

In some embodiments, the SCID-associated polynucleotide sequence is a recombination activating gene 2 sequence (RAG2) or a variant thereof. An exemplary RAG2 sequence is human RAG2 (NCBI Gene ID: 5897, also known as RAG-2). In some embodiments, the human RAG2 sequence comprises all or a portion of human RAG2 coding sequence 1. In some embodiments, the human RAG2 sequence comprises all or a portion of human RAG2 coding sequence 2. In some embodiments, the human RAG2 sequence comprises all or a portion of human RAG2 coding sequence 3. Those skilled in the art will appreciate that the guide sequences shown in FIGS. 23, 24 and 25 can be used with the CRISPR/Cas systems of the present invention to alter target polynucleotide sequences of human RAG2, and in particular human RAG2 coding sequences 1, 2 and 3, respectively.

It should also be appreciated that altering a target polynucleotide sequence of RAG2 can be used to treat any abnormal phenotype associated with an altered RAG2 polynucleotide sequence. Table 12 below shows gene phenotype relationships identified by the OMIM® database. Further information regarding a phenotype listed in Table 12 is publicly accessible by querying OMIM for the search term "RAG2" and then clicking on a hyperlink in the "Phenotype MIM number" column corresponding to the phenotype listed.

TABLE 12

RAG2 Gene Phenotype Relationships

| Location | Phenotype | Phenotype MIM number |
|---|---|---|
| 11p12 | Combined cellular and humoral immune defects with granulomas | 233650 |
| | Omenn syndrome | 603554 |
| | Severe combined immunodeficiency, B cell-negative | 601457 |

In some embodiments, the SCID-associated polynucleotide sequence is a zeta-chain-associated protein kinase sequence (ZAP70) or a variant thereof. An exemplary ZAP70 sequence is human ZAP70 (NCBI Gene ID: 7535, also known as SRK; STD; TZK; STCD; and ZAP-70). In some embodiments, the human ZAP70 sequence comprises all or a portion of human ZAP70 coding sequence 1. In some embodiments, the human ZAP70 sequence comprises all or a portion of human ZAP70 coding sequence 2. Those skilled in the art will appreciate that the guide sequences shown in FIGS. 26 and 27 can be used with the CRISPR/Cas systems of the present invention to alter target polynucleotide sequences of human ZAP70, and in particular human ZAP70 coding sequences 1 and 2, respectively.

It should also be appreciated that altering a target polynucleotide sequence of ZAP70 can be used to treat any abnormal phenotype associated with an altered ZAP70 polynucleotide sequence. Table 13 below shows gene phenotype relationships identified by the OMIM® database. Further information regarding a phenotype listed in Table 13 is publicly accessible by querying OMIM for the search term "ZAP70" and then clicking on a hyperlink in the "Phenotype MIM number" column corresponding to the phenotype listed.

TABLE 13

ZAP 70 Gene Phenotype Relationships

| Location | Phenotype | Phenotype MM number |
|---|---|---|
| 2q11.2 | Selective T-cell defect | 269840 |

In some embodiments, the target polynucleotide sequence is hemoglobin beta ("HBB") (e.g., human hemoglobin beta, NCBI Gene ID: 3043) or a variant thereof. Those skilled in the art will appreciate that the guide sequences shown in FIG. 11 can be used with the CRISPR/Cas systems of the present invention to alter target polynucleotide sequences of human HBB.

It should also be appreciated that altering a target polynucleotide sequence of HBB can be used to treat any abnormal phenotype associated with an altered HBB polynucleotide sequence. Table 14 below shows gene phenotype relationships as identified by the OMIM® database. Further information regarding a phenotype listed in Table 14 is publicly accessible by querying OMIM for the search term "HBB" and then clicking on a hyperlink in the "Phenotype MIM number" column corresponding to the phenotype listed.

TABLE 14

HBB Gene Phenotype Relationships

| Location | Phenotype | Phenotype MIM number |
|---|---|---|
| 11p15.4 | Delta-beta thalassemia | 141749 |
| | Erythremias, beta- | |
| | Heinz body anemias, beta- | 140700 |
| | Hereditary persistence of fetal hemoglobin | 141749 |
| | Methemoglobinemias, beta- | |
| | Sickle cell anemia | 603903 |
| | Thalassemia-beta, dominant inclusion-body | 603902 |
| | Thalassemias, beta- | 613985 |
| | {Malaria, resistance to} | 611162 |

Normal adult hemoglobin is a tetramer that consists of two alpha chains and two beta chains. HBB determines the structure of the beta chains of hemoglobin. HBB mutations are associated with sickle cell diseases and/or beta thalassemia. For example, sickle cell anemia is caused by mutant beta globin. The absence of the beta chain results in beta-zero thalassemia. Diminished amounts of detectable beta globin results in beta-plus-thalassemia. Exemplary mutant forms of HBB involved in sickle cell disease are Hemoglobin S (Glu6Val), Hemoglobin C (Glu6Lys), Hemoglobin D and Hemoglobin O (Glu121Lys).

Insertion of an L1 retrotransposable fragment within the IVS-II of the beta-globin gene results in beta°-thal. This represents a form of beta thalassemia in which the beta globin gene expresses full length beta-globin transcripts at levels equal to about 15% of the total beta-globin mRNA.

In some embodiments, a method for altering a target polynucleotide sequence in a cell comprises a method for altering a target sickle cell disease (SCD)-associated polynucleotide sequence. As used herein, "sickle cell disease-associated polynucleotide sequence" or "SCD-associated polynucleotide sequence" are used interchangeably to refer to a polynucleotide sequence of the HBB gene displaying one or more HBB mutations associated with SCD. As used herein, "sickle cell disease" refers to a group of symptomatic disorders involving mutations in HBB and defined by the presence of hemoglobin S (Hb S). Normal hemoglobin is a heterotetramer consisting of two alpha-hemoglobin and two beta-hemoglobin chains. Point mutations in HBB cause hemoglobin S to result, for example a point mutation changing the sixth amino acid in the beta-hemoglobin chain from glutamic acid to valine (Glu6Val). Sickle cell anemia (homogzygous HbSS) is an example of a sickle cell disease which makes up between 60-70% of reported sickle cell disease in the United States. Examples of other forms of sickle cell disease are due to coinhereitance of Hb S with various mutant beta-globin chain variants, including sickle-hemoglobin C disease (Hb SC), and two different types of sickle beta thalassemia (Hb Sβ$^+$. thalassemia and Hb S β°. thalassemia).

An exemplary method for altering a target sickle cell disease (SCD)-associated polynucleotide sequence in a cell comprises contacting the SCD-associated polynucleotide sequence with a clustered regularly interspaced short palindromic repeats-associated (Cas) protein and from one to two ribonucleic acids, wherein the ribonucleic acids direct Cas protein to and hybridize to a target motif of the target SCD-associated polynucleotide sequence, wherein the target SCD-associated polynucleotide sequence is cleaved. In some embodiments of this and other aspects, the efficiency of alteration of cells that express Cas protein is from about 50% to about 80%.

In some embodiments, a method for altering a target polynucleotide sequence in a cell comprises a method for altering a target beta thalassemia-associated polynucleotide sequence. As used herein, "beta thalassemia-associated polynucleotide sequence" refers to a polynucleotide sequence of the HBB gene displaying one or more HBB mutations associated with beta thalassemia. As used herein, "beta thalassemia" refers to inherited autosomal recessive diseases characterized by decreased production of the hemoglobin subunit beta (e.g., hemoglobin beta chain) that are caused by over 200 different HBB mutations. As will be appreciated by the skilled artisan, HBB mutations resulting in beta thalassemia include non-deletional HBB mutants, deletional HBB mutants, and HBB mutants resulting from transposable elements. Table 15 below illustrates exemplary non-deletional HBB mutations.

TABLE 15

Non-deletional HBB mutations associated with beta thalassemia

−101 (C−>T)
−92 (C−>T)
−90 (C−>T)
−88 (C−>A)
−88 (C−>T)
−87 (C−>A)
−87 (C−>G)
−87 (C−>T)
−86 (C−>A)

TABLE 15-continued

Non-deletional HBB mutations associated with beta thalassemia

−86 (C−>G)
−32 (C−>A)
−31 (A−>C)
−31 (A−>G)
−30 (T−>A)
−30 (T−>C)
−29 (A−>G)
−28 (A−>C)
−28 (A−>G)
CAP +1 (A−>C)
5′UTR; +10 (−T)
5′UTR; +22 (G−>A)
5′UTR; +33 (C−>G)
5′UTR; +43 to +40 (−AAAC)
Initiation codon A*T*G−>*G*TG
Initiation codon A*T*G−>A*C*G
Initiation codon A*T*G−>A*G*G
Initiation codon AT*G*−>AT*A*
Initiation codon AT*G*−>AT*C*
Initiation codon AT*G*−>AT*T*
Codon 1 (−G); GTG(Val)−>-TG
Codons 2/3/4 (−9 bp; +31 bp); (see below)
Codon 5 (−CT); CCT(Pro)−>C--
Codon 6 (−A); GAG(Glu)−>G-G
Codon 8 (−AA); AAG(Lys)−>--G
Codons 8/9 (+G); AAG•TCT(Lys;Ser)−>AAG•G•TCT
Codons 9/10 (+T); TCT•GCC(Ser;Ala)−>TCT•T•GCC
Codon 10 (C−>A); GCC(Ala)−>GCA(Ala)
Codon 11 (−T); GTT(Val)−>GT-
Codons 14/15 (+G);
Codon 15 (G−>A); TGG(Trp)−>TAG(stop codon)
Codon 15 (G−>A); TGG(Trp)−>TGA(stop codon)
Codon 15 (−T); TGG(Trp)−>-GG
Codon 16 (−C); GGC(Gly)−>GG-
Codon 17 (A−>T); AAG(Lys)−>TAG(stop codon)
Codon 19 (A−>G); AAC(Asn)−>AGC(Ser)
Codon 22 (A−>C); G*A*A(Glu)−>GCA(Ala) (not listed in Table I; this mutation is likely not associated with thalassemia)
Codon 22 (G−>T); GAA(Glu)−>TAA(stop codon)
Codons 22/23/24 (GAA•GTT•GGT; Glu•Val•Gly); deletion of −AAGTTGG
Codon 24; GGT(Gly); (−G; +CAC)
Codon 24 (T−>A); GGT(Gly)−>GGA(Gly)
Codons 24/25 (−GGT); GGT•GGT(Gly-Gly)−>---•GGT(Gly)
Codons 25/26 (+T); GGT•GAG(Gly-Glu)−>GGT•T•GAG(Gly-Term)
Codon 26 (*G*AG−>*A*AG)
Codon 26 (G−>T); GAG(Glu)−>TAG(stop codon)
Codon 26 (+T); GAG(Glu)−>GTAG
Codon 27 (G−>T); GCC(Ala)−>TCC(Ser)
Codons 27/28 (+C); GCC•CTG(Ala•Ser)−>GCC•C•CTG
Codon 28 (−C); CTG(Leu)−>-TG
Codon 28 (T−>G); CTG(Leu)−>CGG(Arg)
Codons 28/29 (−G); CTG•GGC(Leu•Gly)−>CTG•-GC
IVS-I (−3) or codon 29 (C−>T); GGC(Gly)−>GGT(Gly)
IVS-I (−2) or codon 30 (A−>G); *AG*ˆGTTGGT−>*GG*ˆGTTGGT
IVS-I (−1) or codon 30 (G−>A); *AG*ˆGTTGGT−>*AA*ˆGTTGGT
IVS-I (−1) or codon 30 (G−>C); *AG*ˆGTTGGT−>*AC*ˆGTTGGT
IVS-I-1 (G−>A); AGˆ*G*TTGGT−>AGˆ*A*TTGGT
IVS-I-1 (G−>T); AGˆ*G*TTGGT−>AGˆ*T*TTGGT
IVS-I-2 (T−>A); AGˆG*T*TGGT−>AGGˆ*A*TGGT
IVS-I-2 (T−>C); AGˆG*T*TGGT−>AGA*C*TGGT
IVS-I-2 (T−>G); AGˆG*T*TGGT−>AGG*G*TGGT
IVS-I-5 (G−>A)
IVS-I-5 (G−>A) plus the 7,201 bp deletion involving part of the delta gene; the Corfu deletion (deltabeta-thal)
IVS-I-5 (G−>C)
IVS-I-5 (G−>T)
IVS-I-6 (T−>C); the Portuguese type
IVS-I-110 (G−>A)
IVS-I-116 (T−>G)
IVS-I-128 (T−>G); TTAGˆGCTG−>TGAGˆGCTG
IVS-I-130 (G−>A); TTAGˆGCTG−>TTAA GCTG
IVS-I-130 (G−>C); TTAGˆGCTG−>TTAC GCTG
Codon 30 (AG*G*−>AG*C*) [IVS-I-130 (+1)]
IVS-I, 3′ end; −17 bp
Codon 31 (−C); CTG−>-TG
Codons 31/32 (+CGG)
Codon 32 (T−>A) C*T*G−>C*A*G; codon 98 (G−>A) GTG−>*A*TG TABLE 15-continued Non-deletional HBB mutations associated with beta thalassemia Codons 33/34 (−GTG); GTG•GTC(Val-Val)−>GTC•---(Val)
Codon 35 (C−>A); TAC−>TAA (Tyr−>Term codon)
Codon 35 (−C); TAC(Tyr)−>TA-
Codons 36/37 (−T); CCT•TGG(Pro-Trp)−>CCT•-GG
Codon 37 (G−>A); TGG(Trp)−>TGA(stop codon)
Codons 37/38/39 (−7 nts)
Codons 38/39 (−C); ACC•CAG(Thr•Gln)−>ACC•-AG
Codons 38/39 (−CC); ACC•CAG(Thr-Glu)−>A--•CAG
Codon 39 (C−>T); CAG(Gln)−>TAG(stop codon)
Codon 40 (−G); AGG(Arg)−>AG-
Codons 40/41 (+T); AGG•TTC(Arg-Phe)−>AGG•T•TTC
Codon 41 (−C); TTC(Phe)−>TT-
Codons 41/42 (−TTCT); TTC•TTT(Phe-Phe)−>--- -TT
Codons 42/43 (+G); TTT•GAG(Phe•Glu)−>TTT•G•GAG
Codons 42/43 (+T) TTT•GAG(Phe•Glu)−>TTT•TGA•G(Phe;stop codon)
Codon 43 (G−>T); GAG(Glu)−>TAG (stop codon)
Codon 44 (−C); TCC(Ser)−>TC-
Codon 45 (−T); TTT(Phe)−>-TT
Codon 47 (+A); GAT(Asp)−>GAA(Glu)•T
Codons 47/48 (+ATCT); GAT•CTG(Asp-Leu)−>GAT•CT*ATCT*G
Codon 51 (−C); CCT(Pro)−>-CT
53/54 (+G); GCT•GTT(Ala-Val)−>GCT•G•GTT
Codon 54 (−T); GTT(Val)−>GT-
Codons 54/55 (+A); GTT•ATG(Val•Met)−>GTT•A•ATG
Codons 56/57/58/59/60 (GGC•AAC•CCT•AAG•GTG) (SEQ ID NO: 5345); duplication of 14 bp
Codons 57/58 (+C); AAC•CCT(Asn•Pro)−>AAC•C•CCT
Codon 59 (−A); AAG(Lys)−>-AG
Codon 60 (T−>A); GTG(Val)−>GAG(Glu)
Codon 61 (A−>T); AAG(Lys)−>TAG(stop codon)
Codon 64 (−G); GGC(Gly)−>-GC
Codon 67 (−TG); GTG(Val)−>--G
Codons 71/72 (+A); TTT•AGT(Phe•Ser)−>TTT•A•AGT
Codons 71/72 (+T); TTT•AGT(Phe•Ser)−>TTT•T•AGT
Codons 72/73; −AGTGA, +T; AGT•GAT(Ser-Asp)−>--- -TT
Codons 74/75 (−C); GGC•CTG(Gly•Leu)−>GG- •CTG
Codon 76 (−C); GCT(Ala)−>G-T
Codons 82/83 (−G); AAG•GGC(Lys•Gly)−>AAG•-GC
Codons 84/85 (+C); ACC•TTT(Thr•Phe)−>ACC•C•TTT
Codons 84/85/86 (+T); ACC•TTT•GCC(Thr•Phe•Ala)−>ACC•TTT•T•GCC
Codon 88 (+T); CTG(Leu)−>CTTG
Codons 89/90 (−GT); AGT•GAG(Ser•Glu)−>A--•GAG
Codon 90 (G−>T); GAG(Glu)−>TAG(stop codon)
Codon 94 (+TG); GAC(Asp)−>G*TG*AC
Codon 95 (+A); AAG(Lys)−>AAAG
Codon 100; -CTT, +TCTGAGAACTT
IVS-II-1 (G−>A);
IVS-II-1 (G−>C);
IVS-II-2,3 (+11, −2); insertion of 11 bp (5′-ACGTTCT CTGA-3′) (SEQ ID NO: 5346) and deletion of GA (nts 2 and 3 of IVS-II) between positions 1 and 4 of IVS-II
IVS-II-4,5 (−AG);
IVS-II-5 (G−>C)
IVS-II-654 (C−>T); AAGG*C*AATA−>AAGˆ*GT*AATA
IVS-II-705 (T−>G); GA*T*GTAAGA−>GAGˆGTAAGA
IVS-II-745 (C−>G); CAG*C*TACCAT−>CAGˆGTACCAT
IVS-II-837 (T−>G);
IVS-II-843 (T−>G);
IVS-II-844 (C−>G);
IVS-II-848 (C−>A);
IVS-II-848 (C−>G);
IVS-II-849 (A−>C);
IVS-II-849 (A−>G);
IVS-II-850 (−G);
IVS-II-850 (G−>A);
IVS-II-850 (G−>C);
IVS-II-850 (G−>T);
Codons 106/107 (+G); CTG•GGC(Leu•Gly)−>CTG•G•GC
Codons 108/109/110/111/112 (−12 bp);
Codon 109 (−G); GTG(Val)−>TG
Codon 110 (T−>C); CTG(Leu)−>CCG(Pro)
Codon 112 (T−>A); TGT(Cys)−>TGA(stop codon)
Codon 114 (T−>C); CTG(Leu)−>CCG(Pro)
Codon 114 (−CT; +G); CTG(Leu)−>-GG
Codon 115 (C−>A); GCC(Ala)−>GAC(Asp)
Codons 120/121 (+A); AAA•GAA(Lys-Glu)−>AAA•*A*•GAA
Codon 121 (G−>T); GAA(Glu)−>TAA(stop codon)

TABLE 15-continued

Non-deletional HBB mutations associated with beta thalassemia

Codon 123 (–A); ACC(Thr)–>-CC
Codons 123/124/125 (–ACCCCACC);
ACC•CCA•CCA(Thr•Pro•Pro)–>--- --- --A
Codon 124 (–A); CCA(Pro)–>CC-
Codon 125 (–A); CCA(Pro)–>CC-
Codons 124/125/126 (+CCA); CCA•CCA•GTG(Pro•Pro•Val)
(SEQ ID NO: 5347) ->CCA•CCA•CCA•GTG (Pro•Pro•Pro•Val)
(SEQ ID NO: 5348)
Codon 126 (–T); GTG(Val)–>G-G
Codon 126 (T–>G); GTG(Val)–>GGG(Gly)
Codons 126-131 (Val-Gln-Ala-Ala-Thr-Gln (SEQ ID NO: 5349)) (–17
bp); G*TG•CAG•GCT•GCC•TAT•CAG* (SEQ ID NO: 5350) ->G
Codon 127 (A–>C); CAG(Gln)–>CCG(Pro)
Codon 127 (A–>G); CAG(Gln)–>CGG(Arg)
Codon 127 (C–>T); CAG(Gln)–>TAG(stop codon)
Codons 127/128 (–AGG); CAG•GCT(Gln•Ala)–>C-- -CT(Pro)
Codons 128/129 (–4 bp, –GCTG; +5 bp, +CCACA)
Codons 132-135 (–11 bp, –AAAGTGGTGGC) (SEQ ID NO: 5351)
Codons 134/135/136/137 [–(G)TGGCTGGTGT(G) (SEQ ID NO: 5352)
and +(G)GCAG(G)]; GTG•GCT•GGT•GTG (SEQ ID NO: 5353) (Val-
Ala-Gly-Val) (SEQ ID NO: 5354) ->GGC•AGG(Gly-Arg)
+1480 (C–>G); also known as 3' terminating codon +6 (C–>G)
3'UTR (–GCATCTGGATTCT) (SEQ ID NO: 5355) 13 bp deletion
between positions +1565 to +1577 (the numbers are relative to the
Cap site)

Those skilled in the art will also appreciate that a variety of deletional beta thalassemia alleles exist, which tend to be prevalent in certain at-risk populations. Examples of such deletional beta thalassemia alleles include, but are not limited to, a 25 bp deletion, a 44 bp deletion, a 105 bp deletion, a 290 bp deletion, a 532 bp deletion, a 619 bp deletion, a 1,393 bp deletion, a 1,605 bp deletion ("Croatian deletion"), a 3,485 bp deletion ("Thai deletion"), a 4,237 bp deletion ("Czech deletion"), a 7.6 kb deletion ("Turkish deletion"); a 10,329 bp deletion ("Asian Indian deletion"), a 12,023 bp deletion ("Australian deletion"); a 12,620 bp deletion ("Dutch deletion"), a 27 kb deletion ("Southeast Asian deletion"), a 45 kb deletion ("Filipino deletion"), and a 65 kb deletion ("Italian deletion"). Those skilled in the art will be able to retrieve the corresponding nucleic acid and protein sequences corresponding to these deletions from publicly available sources (e.g., A Syllabus of Thalassemia Mutations (1997) by Titus H. J. Huisman, et al, published by The Sickle Cell Anemia Foundation in Augusta, Ga., USA, available online at http://globin.cse.psu.edu/html/huisman/thals/l-b.entries.html).

An exemplary method for altering a target beta thalassemia-associated polynucleotide sequence in a cell comprises contacting the beta thalassemia-associated polynucleotide sequence with a clustered regularly interspaced short palindromic repeats-associated (Cas) protein and from one to two ribonucleic acids, wherein the ribonucleic acids direct Cas protein to and hybridize to a target motif of the target beta thalassemia-associated polynucleotide sequence, wherein the target beta thalassemia associated polynucleotide sequence is cleaved. In some embodiments of this and other aspects, the efficiency of alteration of cells that express Cas protein is from about 50% to about 80%.

As used herein, the term "contacting" (i.e., contacting a polynucleotide sequence with a clustered regularly interspaced short palindromic repeats-associated (Cas) protein and/or ribonucleic acids) is intended to include incubating the Cas protein and/or the ribonucleic acids in the cell together in vitro (e.g., adding the Cas protein or nucleic acid encoding the Cas protein to cells in culture). In some embodiments, the term "contacting" is not intended to include the in vivo exposure of cells to the Cas protein and/or ribonucleic acids as disclosed herein that may occur naturally in a microorganism (i.e., bacteria). The step of contacting a target polynucleotide sequence with a Cas protein and/or ribonucleic acids as disclosed herein can be conducted in any suitable manner. For example, the cells may be treated in adherent culture, or in suspension culture. It is understood that the cells contacted with a Cas protein and/or ribonucleic acids as disclosed herein can also be simultaneously or subsequently contacted with another agent, such as a growth factor or other differentiation agent or environments to stabilize the cells, or to differentiate the cells further.

In another aspect, the present invention provides a method for treating or preventing a disorder associated with expression of a polynucleotide sequence in a subject.

The terms "treat", "treating", "treatment", etc., as applied to an isolated cell, include subjecting the cell to any kind of process or condition or performing any kind of manipulation or procedure on the cell. As applied to a subject, the terms refer to providing medical or surgical attention, care, or management to an individual. The individual is usually ill or injured, or at increased risk of becoming ill relative to an average member of the population and in need of such attention, care, or management.

As used herein, the term "treating" and "treatment" refers to administering to a subject an effective amount of a composition so that the subject has a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Thus, one of skill in the art realizes that a treatment may improve the disease condition, but may not be a complete cure for the disease. As used herein, the term "treatment" includes prophylaxis. Alternatively, treatment is "effective" if the progression of a disease is reduced or halted. "Treatment" can also mean prolonging survival as compared to expected survival if not receiving treatment. Those in need of treatment include those already diagnosed with a disorder associated with expression of a polynucleotide sequence, as well as those likely to develop such a disorder due to genetic susceptibility or other factors.

By "treatment", "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, the symptoms of a disease or disorder are alleviated by at least 5%, at least 10%, at least 20%, at least 30%, at least 40%, or at least 50%.

In some embodiments, a method for treating or preventing a disorder associated with expression of a polynucleotide sequence comprises a method for treating or preventing a disorder associated with expression of a SCID-associated polynucleotide sequence:

An exemplary method for treating or preventing a disorder associated with expression of a SCID-associated polynucleotide sequence in a subject comprises (a) altering a target SCID-associated polynucleotide sequence in a cell ex vivo by contacting the SCID-associated polynucleotide sequence with a clustered regularly interspaced short palindromic repeats-associated (Cas) protein and from one to two ribonucleic acids, wherein the ribonucleic acids direct Cas protein to and hybridize to a target motif of the target SCID-associated polynucleotide sequence, wherein the target SCD-associated polynucleotide sequence is cleaved, and (b) introducing the cell into the subject, thereby treating or preventing a disorder associated with expression of the SCID-associated polynucleotide sequence. In some embodiments of this and other aspects, the efficiency of alteration of cells that express Cas protein is from about 50% to about 80%.

An exemplary method for treating or preventing a disorder associated with expression of a SCID-associated polynucleotide sequence in a subject comprises altering a target SCID-associated polynucleotide sequence in a cell by contacting the SCID-associated polynucleotide sequence with a clustered regularly interspaced short palindromic repeats-associated (Cas) protein and from one to two ribonucleic acids, wherein the ribonucleic acids direct Cas protein to and hybridize to a target motif of the target SCID-associated polynucleotide sequence, and wherein the target SCID-associated polynucleotide sequence is cleaved, thereby treating or preventing a disorder associated with expression of the SCID-associated polynucleotide sequence.

In some embodiments, a method for treating or preventing a disorder associated with expression of a polynucleotide sequence comprises a method for treating or preventing a disorder associated with expression of a SCD-associated polynucleotide sequence.

An exemplary method for treating or preventing a disorder associated with expression of a SCD-associated polynucleotide sequence in a subject comprises (a) altering a target SCD-associated polynucleotide sequence in a cell ex vivo by contacting the SCD-associated polynucleotide sequence with a clustered regularly interspaced short palindromic repeats-associated (Cas) protein and from one to two ribonucleic acids, wherein the ribonucleic acids direct Cas protein to and hybridize to a target motif of the target SCD-associated polynucleotide sequence, wherein the target SCD-associated polynucleotide sequence is cleaved, and (b) introducing the cell into the subject, thereby treating or preventing a disorder associated with expression of the SCD-associated polynucleotide sequence. In some embodiments of this and other aspects, the efficiency of alteration of cells that express Cas protein is from about 50% to about 80%.

An exemplary method for treating or preventing a disorder associated with expression of a SCD-associated polynucleotide sequence in a subject comprises altering a target SCD-associated polynucleotide sequence in a cell by contacting the SCD-associated polynucleotide sequence with a clustered regularly interspaced short palindromic repeats-associated (Cas) protein and from one to two ribonucleic acids, wherein the ribonucleic acids direct Cas protein to and hybridize to a target motif of the target SCD-associated polynucleotide sequence, and wherein the target SCD-associated polynucleotide sequence is cleaved, thereby treating or preventing a disorder associated with expression of the SOD-associated polynucleotide sequence.

In some embodiments, a method for treating or preventing a disorder associated with expression of a polynucleotide sequence comprises a method for treating or preventing a disorder associated with expression of a beta thalassemia-associated polynucleotide sequence.

An exemplary method for treating or preventing a disorder associated with expression of a beta thalassemia-associated polynucleotide sequence in a subject comprises (a) altering a target beta thalassemia-associated polynucleotide sequence in a cell ex vivo by contacting the beta thalassemia-associated polynucleotide sequence with a clustered regularly interspaced short palindromic repeats-associated (Cas) protein and from one to two ribonucleic acids, wherein the ribonucleic acids direct Cas protein to and hybridize to a target motif of the target beta thalassemia-associated polynucleotide sequence, wherein the target beta thalassemia-associated polynucleotide sequence is cleaved, and (b) introducing the cell into the subject, thereby treating or preventing a disorder associated with expression of the beta thalassemia-associated polynucleotide sequence. In some embodiments of this and other aspects, the efficiency of alteration of cells that express Cas protein is from about 50% to about 80%.

An exemplary method for treating or preventing a disorder associated with expression of a beta thalassemia-associated polynucleotide sequence in a subject comprises altering a target beta thalassemia-associated polynucleotide sequence in a cell by contacting the beta thalassemia-associated polynucleotide sequence with a clustered regularly interspaced short palindromic repeats-associated (Cas) protein and from one to two ribonucleic acids, wherein the ribonucleic acids direct Cas protein to and hybridize to a target motif of the target beta thalassemia-associated polynucleotide sequence, and wherein the target beta thalassemia-associated polynucleotide sequence is cleaved, thereby treating or preventing a disorder associated with expression of the beta thalassemia-associated polynucleotide sequence.

The present invention contemplates altering target polynucleotide sequences in any manner which is available to the skilled artisan utilizing a CRISPR/Cas system of the present invention. Any CRISPR/Cas system that is capable of altering a target polynucleotide sequence in a cell can be used. Such CRISPR-Cas systems can employ a variety of Cas proteins (Haft et al. *PLoS Comput Biol.* 2005; 1(6)e60). The molecular machinery of such Cas proteins that allows the CRISPR/Cas system to alter target polynucleotide sequences in cells include RNA binding proteins, endo- and exo-nucleases, helicases, and polymerases. In some embodiments, the CRISPR/Cas system is a CRISPR type I system. In some embodiments, the CRISPR/Cas system is a CRISPR type II system.

The CRISPR/Cas systems of the present invention can be used to alter a target polynucleotide sequence in a cell. The present invention contemplates altering target polynucleotide sequences in a cell for any purpose. In some embodiments, the target polynucleotide sequence in a cell is altered to produce a mutant cell. As used herein, a "mutant cell" refers to a cell with a resulting genotype that differs from its original genotype. In some instances, a "mutant cell" exhibits a mutant phenotype, for example when a normally functioning gene is altered using the CRISPR/Cas systems of the present invention. In other instances, a "mutant cell" exhibits a wild-type phenotype, for example when a CRISPR/Cas system of the present invention is used to correct a mutant genotype. In exemplary embodiments, a mutant cell exhibits a wild-type ADA phenotype. In exemplary embodiments, a mutant cell exhibits a wild-type AK2 phenotype. In exemplary embodiments, a mutant cell exhibits a wild-type CD3D phenotype. In exemplary embodiments, a mutant cell exhibits a wild-type DCLRE1C phenotype. In exemplary embodiments, a mutant cell exhibits a wild-type IL2RG phenotype. In exemplary embodiments, a mutant cell exhibits a wild-type IL7R phenotype. In exemplary embodiments, a mutant cell exhibits a wild-type JAK3 phenotype. In exemplary embodiments, a mutant cell exhibits a wild-type LIG4 phenotype. In exemplary embodiments, a mutant cell exhibits a wild-type NHEJ1 phenotype. In exemplary embodiments, a mutant cell exhibits a wild-type PNP phenotype. In exemplary embodiments, a mutant cell exhibits a wild-type PRKDC phenotype. In exemplary embodiments, a mutant cell exhibits a wild-type RAG1 phenotype. In exemplary embodiments, a mutant cell exhibits a wild-type RAG2 phenotype. In exemplary embodiments, a mutant cell exhibits a wild-type ZAP70 phenotype. In exemplary embodiments, a mutant cell exhibits a wild-type HBB phenotype. In some embodiments, the target polynucleotide sequence in a cell is altered to correct or repair a genetic mutation (e.g., to restore a normal phenotype to the cell). In an exemplary embodiment, a target SCID-associated polynucleotide sequence in a cell is altered to correct or repair one or more ADA mutations involved in SCID. In an exemplary embodiment, a target SCID-associated polynucleotide sequence in a cell is altered to correct or repair one or more AK2 mutations involved in SCID. In an exemplary embodiment, a target SCID-associated polynucleotide sequence in a cell is altered to correct or repair one or more CD3D mutations involved in SCID. In an exemplary embodiment, a target SCID-associated polynucleotide sequence in a cell is altered to correct or repair one or more DCRE1C mutations involved in SCID. In an exemplary embodiment, a target SCID-associated polynucleotide sequence in a cell is altered to correct or repair one or more IL2RG mutations involved in SCID. In an exemplary embodiment, a target SCID-associated polynucleotide sequence in a cell is altered to correct or repair one or more IL7R mutations involved in SCID. In an exemplary embodiment, a target SCID-associated polynucleotide sequence in a cell is altered to correct or repair one or more JAK3 mutations involved in SCID. In an exemplary embodiment, a target SCID-associated polynucleotide sequence in a cell is altered to correct or repair one or more LIG4 mutations involved in SCID. In an exemplary embodiment, a target SCID-associated polynucleotide sequence in a cell is altered to correct or repair one or more NHEJ1 mutations involved in SCID. In an exemplary embodiment, a target SCID-associated polynucleotide sequence in a cell is altered to correct or repair one or more RAG2 mutations involved in SCID. In an exemplary embodiment, a target SCID-associated polynucleotide sequence in a cell is altered to correct or repair one or more PRKDC mutations involved in SCID. In an exemplary embodiment, a target SCID-associated polynucleotide sequence in a cell is altered to correct or repair one or more RAG1 mutations involved in SCID. In an exemplary embodiment, a target SCID-associated polynucleotide sequence in a cell is altered to correct or repair one or more RAG2 mutations involved in SCID. In an exemplary embodiment, a target SCID-associated polynucleotide sequence in a cell is altered to correct or repair one or more ZAP70 mutations involved in SCID. In an exemplary embodiment, a target SCD-associated polynucleotide sequence in a cell is altered to correct or repair one or more HBB mutations involved in SCD. In an exemplary embodiment, a target SCD-associated polynucleotide sequence in a cell is altered to correct or repair one or more HBB mutations involved in SCD. In another exemplary embodiment, a target beta thalassemia-associated polynucleotide sequence in a cell is altered to correct or repair one or more HBB mutations involved in beta thalassemia. In some embodiments, the target polynucleotide sequence in a cell is altered to induce a genetic mutation (e.g., to disrupt the function of a gene or genomic element).

In some embodiments, the alteration is an indel. As used herein, "indel" refers to a mutation resulting from an insertion, deletion, or a combination thereof. As will be appreciated by those skilled in the art, an indel in a coding region of a genomic sequence will result in a frameshift mutation, unless the length of the indel is a multiple of three. In some embodiments, the alteration is a point mutation. As used herein, "point mutation" refers to a substitution that replaces one of the nucleotides. A CRISPR/Cas system of the present invention can be used to induce an indel of any length or a point mutation in a target polynucleotide sequence.

In some embodiments, the alteration results in a knock out of the target polynucleotide sequence or a portion thereof. Knocking out a target polynucleotide sequence or a portion thereof using a CRISPR/Cas system of the present invention can be useful for a variety of applications. For example, knocking out a target polynucleotide sequence in a cell can be performed in vitro for research purposes. For ex vivo or in vivo purposes, knocking out a target polynucleotide sequence in a cell can be useful for treating or preventing a disorder associated with expression of the target polynucleotide sequence.

As used herein, "knock out" includes deleting all or a portion of the target polynucleotide sequence in a way that interferes with the function of the target polynucleotide sequence. For example, a knock out can be achieved by altering a target polynucleotide sequence by inducing an indel in the target polynucleotide sequence in a functional domain of the target polynucleotide sequence (e.g., a DNA binding domain). Those skilled in the art will readily appreciate how to use the CRISPR/Cas systems of the present invention to knock out a target polynucleotide sequence or a portion thereof based upon the details described herein.

In some embodiments, the alteration results in reduced expression of the target polynucleotide sequence. The terms "decrease," "reduced," "reduction," and "decrease" are all used herein generally to mean a decrease by a statistically significant amount. However, for avoidance of doubt, decrease," "reduced," "reduction," "decrease" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

In some embodiments, the alteration results in increased expression of the target polynucleotide sequence. The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

In some embodiments, the alteration is a homozygous alteration. In some embodiments, the alteration is a heterozygous alteration.

In some embodiments, the alteration results in correction of the target polynucleotide sequence from an undesired sequence to a desired sequence. The CRISPR/Cas systems of the present invention can be used to correct any type of mutation or error in a target polynucleotide sequence. For example, the CRISPR/Cas systems of the present invention can be used to insert a nucleotide sequence that is missing from a target polynucleotide sequence due to a deletion. The CRISPR/Cas systems of the present invention can also be used to delete or excise a nucleotide sequence from a target polynucleotide sequence due to an insertion mutation. In some instances, the CRISPR/Cas systems of the present invention can be used to replace an incorrect nucleotide sequence with a correct nucleotide sequence (e.g., to restore function to a target polynucleotide sequence that is impaired due to a loss of function mutation, i.e., a SNP).

In exemplary embodiments, the CRISPR/Cas systems of the present invention can be used to replace mutant ADA polynucleotide sequences with wild-type ADA polynucleotide sequences.

In exemplary embodiments, the CRISPR/Cas systems of the present invention can be used to replace mutant AK2 polynucleotide sequences with wild-type AK2 polynucleotide sequences.

In exemplary embodiments, the CRISPR/Cas systems of the present invention can be used to replace mutant CD3D polynucleotide sequences with wild-type CD3D polynucleotide sequences.

In exemplary embodiments, the CRISPR/Cas systems of the present invention can be used to replace mutant DCLRE1C polynucleotide sequences with wild-type DCLRE1C polynucleotide sequences.

In exemplary embodiments, the CRISPR/Cas systems of the present invention can be used to replace mutant IL2RG polynucleotide sequences with wild-type IL2RG polynucleotide sequences.

In exemplary embodiments, the CRISPR/Cas systems of the present invention can be used to replace mutant IL7R polynucleotide sequences with wild-type IL7R polynucleotide sequences.

In exemplary embodiments, the CRISPR/Cas systems of the present invention can be used to replace mutant JAK3 polynucleotide sequences with wild-type JAK3 polynucleotide sequences.

In exemplary embodiments, the CRISPR/Cas systems of the present invention can be used to replace mutant LIG4 polynucleotide sequences with wild-type LIG4 polynucleotide sequences.

In exemplary embodiments, the CRISPR/Cas systems of the present invention can be used to replace mutant NHEJ1 polynucleotide sequences with wild-type NHEJ1 polynucleotide sequences.

In exemplary embodiments, the CRISPR/Cas systems of the present invention can be used to replace mutant PNP polynucleotide sequences with wild-type PNP polynucleotide sequences.

In exemplary embodiments, the CRISPR/Cas systems of the present invention can be used to replace mutant PRKDC polynucleotide sequences with wild-type PRKDC polynucleotide sequences.

In exemplary embodiments, the CRISPR/Cas systems of the present invention can be used to replace mutant RAG1 polynucleotide sequences with wild-type RAG1 polynucleotide sequences.

In exemplary embodiments, the CRISPR/Cas systems of the present invention can be used to replace mutant RAG2 polynucleotide sequences with wild-type RAG2 polynucleotide sequences.

In exemplary embodiments, the CRISPR/Cas systems of the present invention can be used to replace mutant ZAP70 polynucleotide sequences with wild-type ZAP70 polynucleotide sequences.

In exemplary embodiments, the CRISPR/Cas systems of the present invention can be used to replace mutant HBB polynucleotide sequences with wild-type HBB polynucleotide sequences.

The CRISPR/Cas systems of the present invention can alter target polynucleotides with surprisingly high efficiency as compared to conventional CRISPR/Cas systems. In certain embodiments, the efficiency of alteration is at least about 5%. In certain embodiments, the efficiency of alteration is at least about 10%. In certain embodiments, the efficiency of alteration is from about 10% to about 80%. In certain embodiments, the efficiency of alteration is from about 30% to about 80%. In certain embodiments, the efficiency of alteration is from about 50% to about 80%. In some embodiments, the efficiency of alteration is greater than or equal to about 80%.

The CRISPR/Cas systems of the present invention can be used to alter any target polynucleotide sequence in a cell. Those skilled in the art will readily appreciate that desirable target polynucleotide sequences to be altered in any particular cell may correspond to any genomic sequence for which expression of the genomic sequence is associated with a disorder or otherwise facilitates entry of a pathogen into the cell. For example, a desirable target polynucleotide sequence to alter in a cell may be a polynucleotide sequence corresponding to a genomic sequence which contains a disease associated single polynucleotide polymorphism (e.g., sickle cell disease, e.g., sickle cell anemia). In such example, the CRISPR/Cas systems of the present invention can be used to correct the disease associated SNP by replacing it with a wild-type allele (e.g., replacing a Glu6Val SNP in hemoglobin S to Val6Glu, a Glu6Lys SNP in hemoglobin C to Lys6Glu, a Glu121Gln SNP in hemoglobin D to Gln121Glu, a Glu121Lys SNP in hemoglobin O to Lys121Glu). As another example, a polynucleotide sequence of a target gene which is responsible for entry or proliferation of a pathogen into a cell may be a suitable target for deletion or insertion to disrupt the function of the target gene to prevent the pathogen from entering the cell or proliferating inside the cell.

In some embodiments, the target polynucleotide sequence is a genomic sequence. In some embodiments, the target polynucleotide sequence is a human genomic sequence. In some embodiments, the target polynucleotide sequence is a mammalian genomic sequence. In some embodiments, the target polynucleotide sequence is a vertebrate genomic sequence. In some embodiments, the target sequence is a mutant or variant genomic sequence (e.g., a ADA mutant, a AK2 mutant, a CD3D mutant, a DCLREIC mutant, a IL2RG mutant, a IL7R mutant, a JAK3 mutant, a LIG4 mutant, a NHEJ1 mutant, a PNP mutant, a PRKDC mutant, a RAG1 mutant, a RAG2 mutant, a ZAP70 mutant, a HBB mutant). In some embodiments, the target polynucleotide sequence is a human genomic mutant or variant sequence (e.g., ADA, AK2, CD3D, DCLREIC, IL2RG, IL7R, JAK3, LIG4, NHEJ1, PNP, PRKDC, RAG1, RAG2, ZAP70, HBB). In some embodiments, the target polynucleotide sequence is a mutant or variant mammalian genomic sequence. In some embodiments, the target polynucleotide sequence is a mammalian mutant or variant genomic sequence.

In some embodiments, a target polynucleotide sequence is a pathogenic genomic sequence. Exemplary pathogenic genomic sequences include, but are not limited to a viral genomic sequence, a bacterial genomic sequence, a fungal genomic sequence, a toxin genomic sequence, or a parasitic genomic sequence. In such embodiments, the CRISPR/Cas systems of the present invention can be used to disrupt the function of a pathogen (e.g., to treat or prevent an infection by the pathogen) by cleaving a genomic sequence of the pathogen (e.g., a genomic sequence that is critical for entry into a cell, or responsible for multiplication, growth or survival once the pathogen is inside a cell).

In some embodiments, the target polynucleotide sequence is an SCID-associated polynucleotide sequence.

In some embodiments, the target polynucleotide sequence is ADA or a portion thereof. In some embodiments, the target polynucleotide sequence is a variant of ADA or a portion thereof. In some embodiments, the target polynucleotide sequence is a homolog of ADA or a portion thereof. In some embodiments, the target polynucleotide sequence is an ortholog of ADA or a portion thereof.

In some embodiments, the target polynucleotide sequence is AK2 or a portion thereof. In some embodiments, the target polynucleotide sequence is a variant of AK2 or a portion thereof. In some embodiments, the target polynucleotide sequence is AK2 coding sequence 1 or a portion thereof. In some embodiments, the target polynucleotide sequence is AK2 coding sequence 2 or a portion thereof. In some embodiments, the target polynucleotide sequence is AK2 coding sequence 3 or a portion thereof. In some embodiments, the target polynucleotide sequence is a homolog of AK2 or a portion thereof. In some embodiments, the target polynucleotide sequence is an ortholog of AK2 or a portion thereof.

In some embodiments, the target polynucleotide sequence is CD3D or a portion thereof. In some embodiments, the target polynucleotide sequence is a variant of CD3D or a portion thereof. In some embodiments, the target polynucleotide sequence is CD3D coding sequence 1 or a portion thereof. In some embodiments, the target polynucleotide sequence is CD3D coding sequence 2 or a portion thereof. In some embodiments, the target polynucleotide sequence is a homolog of CD3D or a portion thereof. In some embodiments, the target polynucleotide sequence is an ortholog of CD3D or a portion thereof.

In some embodiments, the target polynucleotide sequence is DCLREIC or a portion thereof. In some embodiments, the target polynucleotide sequence is a variant of DCLRE1C or a portion thereof. In some embodiments, the target polynucleotide sequence is DCLREIC coding sequence 1 or a portion thereof. In some embodiments, the target polynucleotide sequence is DCLREIC coding sequence 1 or a portion thereof. In some embodiments, the target polynucleotide sequence is DCLREIC coding sequence 2 or a portion thereof. In some embodiments, the target polynucleotide sequence is DCLREIC coding sequence 3 or a portion thereof. In some embodiments, the target polynucleotide sequence is DCLREIC coding sequence 4 or a portion thereof. In some embodiments, the target polynucleotide sequence is a homolog of DCLREIC or a portion thereof. In some embodiments, the target polynucleotide sequence is an ortholog of DCLREIC or a portion thereof.

In some embodiments, the target polynucleotide sequence is IL2RG or a portion thereof. In some embodiments, the target polynucleotide sequence is a variant of IL2RG or a portion thereof. In some embodiments, the target polynucleotide sequence is a homolog of IL2RG or a portion thereof. In some embodiments, the target polynucleotide sequence is an ortholog of IL2RG or a portion thereof.

In some embodiments, the target polynucleotide sequence is IL7R or a portion thereof. In some embodiments, the target polynucleotide sequence is a variant of IL7R or a portion thereof. In some embodiments, the target polynucleotide sequence is a homolog of IL7R or a portion thereof. In some embodiments, the target polynucleotide sequence is an ortholog of IL7R or a portion thereof.

In some embodiments, the target polynucleotide sequence is JAK3 or a portion thereof. In some embodiments, the target polynucleotide sequence is a variant of JAK3 or a portion thereof. In some embodiments, the target polynucleotide sequence is a homolog of JAK3 or a portion thereof. In some embodiments, the target polynucleotide sequence is an ortholog of JAK3 or a portion thereof.

In some embodiments, the target polynucleotide sequence is LIG4 or a portion thereof. In some embodiments, the target polynucleotide sequence is a variant of LIG4 or a portion thereof. In some embodiments, the target polynucleotide sequence is LIG4 coding sequence 1 or a portion thereof. In some embodiments, the target polynucleotide sequence is LIG4 coding sequence 2 or a portion thereof. In some embodiments, the target polynucleotide sequence is LIG4 coding sequence 3 or a portion thereof. In some embodiments, the target polynucleotide sequence is a homolog of LIG4 or a portion thereof. In some embodiments, the target polynucleotide sequence is an ortholog of LIG4 or a portion thereof.

In some embodiments, the target polynucleotide sequence is NHEJ1 or a portion thereof. In some embodiments, the target polynucleotide sequence is a variant of PNP or a portion thereof. In some embodiments, the target polynucleotide sequence is a homolog of NHEJ1 or a portion thereof. In some embodiments, the target polynucleotide sequence is an ortholog of NHEJ1 or a portion thereof.

In some embodiments, the target polynucleotide sequence is PNP or a portion thereof. In some embodiments, the target polynucleotide sequence is a variant of PNP or a portion thereof. In some embodiments, the target polynucleotide sequence is a homolog of PNP or a portion thereof. In some embodiments, the target polynucleotide sequence is an ortholog of PNP or a portion thereof.

In some embodiments, the target polynucleotide sequence is PRKDC or a portion thereof. In some embodiments, the target polynucleotide sequence is a variant of PRKDC or a portion thereof. In some embodiments, the target polynucleotide sequence is PRKDC coding sequence 1 or a portion thereof. In some embodiments, the target polynucleotide sequence is PRKDC coding sequence 2 or a portion thereof. In some embodiments, the target polynucleotide sequence is a homolog of PRKDC or a portion thereof. In some embodiments, the target polynucleotide sequence is an ortholog of PRKDC or a portion thereof.

In some embodiments, the target polynucleotide sequence is RAG1 or a portion thereof. In some embodiments, the target polynucleotide sequence is a variant of RAG1 or a portion thereof. In some embodiments, the target polynucleotide sequence is a homolog of RAG1 or a portion thereof. In some embodiments, the target polynucleotide sequence is an ortholog of RAG1 or a portion thereof.

In some embodiments, the target polynucleotide sequence is RAG2 or a portion thereof. In some embodiments, the target polynucleotide sequence is a variant of RAG2 or a portion thereof. In some embodiments, the target polynucleotide sequence is RAG2 coding sequence 1 or a portion thereof. In some embodiments, the target polynucleotide sequence is RAG2 coding sequence 2 or a portion thereof. In some embodiments, the target polynucleotide sequence is RAG2 coding sequence 3 or a portion thereof. In some embodiments, the target polynucleotide sequence is a homolog of RAG2 or a portion thereof. In some embodiments, the target polynucleotide sequence is an ortholog of RAG2 or a portion thereof.

In some embodiments, the target polynucleotide sequence is ZAP70 or a portion thereof. In some embodiments, the target polynucleotide sequence is a variant of ZAP70 or a portion thereof. In some embodiments, the target polynucleotide sequence is ZAP70 coding sequence 1 or a portion thereof. In some embodiments, the target polynucleotide sequence is ZAP70 coding sequence 2 or a portion thereof. In some embodiments, the target polynucleotide sequence is a homolog of ZAP70 or a portion thereof. In some embodiments, the target polynucleotide sequence is an ortholog of ZAP70 or a portion thereof.

In some embodiments, the target polynucleotide sequence is a SCD-associated polynucleotide sequence (e.g., a mutant form of HBB; NCBI Gene ID: 3043) or a portion thereof. In some embodiments, the target polynucleotide sequence is a mutant homolog of a SCD-associated polynucleotide sequence (e.g., a mutated homolog of HBB) or a portion thereof. In some embodiments, the target polynucleotide sequence is a mutant ortholog of a SCD-associated polynucleotide sequence (e.g., a mutated ortholog of HBB) or a portion thereof.

In some embodiments, the target polynucleotide sequence is a beta thalassemia-associated polynucleotide sequence (e.g., a mutant form of HBB).

In some embodiments, the target polynucleotide sequence is a mutant homolog of a beta thalassemia-associated polynucleotide sequence (e.g., a mutated homolog of HBB) or a portion thereof. In some embodiments, the target polynucleotide sequence is a mutant ortholog of a beta thalassemia-associated polynucleotide sequence (e.g., a mutated ortholog of HBB) or a portion thereof. The relevant portions of these target polynucleotide sequences correspond to the guide sequences shown in FIGS. 1, 2-4, 5-6, 7-10, 12, 13, 14, 15-17, 18, 19, 20-21, 22, 23-25, 26-27, and 11, respectively.

It should be appreciated that the CRISPR/Cas systems of the present invention can cleave target polynucleotide sequences in a variety of ways. In some embodiments, the target polynucleotide sequence is cleaved such that a double-strand break results. In some embodiments, the target polynucleotide sequence is cleaved such that a single-strand break results.

The methods of the present invention can be used to alter any target polynucleotide sequence in a cell, as long as the target polynucleotide sequence in the cell contains a suitable target motif that allows at least one ribonucleic acid of the CRISPR/Cas system to direct the Cas protein to and hybridize to the target motif. Those skilled in the art will appreciate that the target motif for targeting a particular polynucleotide depends on the CRISPR/Cas system being used, and the sequence of the polynucleotide to be targeted.

In some embodiments, the target motif is at least 20 bp in length. In some embodiments, the target motif is a 20-nucleotide DNA sequence. In some embodiments, the target motif is a 20-nucleotide DNA sequence beginning with G and immediately precedes an NGG motif recognized by the Cas protein. In some embodiments, the target motif is $G(N)_{19}NGG$. In some embodiments, the target motif is a 20-nucleotide DNA sequence and immediately precedes an NGG motif recognized by the Cas protein. In some embodiments, the target motif is $(N)_{20}NGG$. It is to be understood that the type of target motif for each of the ADA, AK2, CD3D, DCLREIC, HBB, IL2RG, IL7R, JAK3, LIG4, NHEJ1, PNP, PRKDC, RAG1, RAG2, and ZAP70 target polynucleotide sequences can be found in the "site_type" column of FIGS. 1, 2-4, 5-6, 7-10, 11, 12, 13, 14, 15-17, 18, 19, 20-21, 22, 23-25, and 26-27, respectively.

The target motifs of the present invention can be selected to minimize off-target effects of the CRISPR/Cas systems of the present invention. In some embodiments, the target motif is selected such that it contains at least two mismatches when compared with all other genomic nucleotide sequences in the cell. In some embodiments, the target motif is selected such that it contains at least one mismatch when compared with all other genomic nucleotide sequences in the cell. Those skilled in the art will appreciate that a variety of techniques can be used to select suitable target motifs for minimizing off-target effects (e.g., bioinformatics analyses).

In some embodiments, the CRISPR/Cas systems of the present invention utilize homology-directed repair to correct target polynucleotide sequences. In some embodiments, subsequent to cleavage of the target polynucleotide sequence, homology-directed repair occurs. In some embodiments, homology-directed repair is performed using an exogenously introduced DNA repair template. The exogenously introduced DNA repair template can be single-stranded or double-stranded. The DNA repair template can be of any length. Those skilled in the art will appreciate that the length of any particular DNA repair template will depend on the target polynucleotide sequence that is to be corrected. The DNA repair template can be designed to repair or replace any target polynucleotide sequence, particularly target polynucleotide sequences comprising disease associated polymorphisms (e.g., SNPs). For example, homology-directed repair of a mutant allele comprising such SNPs can be achieved with a CRISPR/Cas system by selecting two target motifs which flank the mutant allele, and an designing a DNA repair template to match the wild-type allele.

In an exemplary embodiment, a cleaved target SCID-associated polynucleotide associated sequence is corrected by homology-directed repair utilizing a corresponding normal wild-type gene sequence as a DNA repair template.

In an exemplary embodiment, a cleaved target SCID-associated polynucleotide associated sequence (i.e., mutant ADA) is corrected by homology-directed repair utilizing a normal wild-type ADA sequence or portions thereof as a DNA repair template.

In an exemplary embodiment, a cleaved target SCID-associated polynucleotide associated sequence (i.e., mutant AK2) is corrected by homology-directed repair utilizing a normal wild-type AK2 sequence (e.g., wild-type AK2 coding sequence 1, AK2 coding sequence 2, and AK2 coding sequence 3 or portions thereof) as a DNA repair template.

In an exemplary embodiment, a cleaved target SCID-associated polynucleotide associated sequence (i.e., mutant CD3D) is corrected by homology-directed repair utilizing a normal wild-type CD3D sequence (e.g., wild-type CD3D coding sequence 1, and CD3D coding sequence 2 or portions thereof) as a DNA repair template.

In an exemplary embodiment, a cleaved target SCID-associated polynucleotide associated sequence (i.e., mutant DCLRE1C) is corrected by homology-directed repair utilizing a normal wild-type DCLRE1C sequence (e.g., wild-type DCLRE1C coding sequence 1, DCLRE1C coding sequence 2, DCLRE1C coding sequence 3, and DCLRE1C coding sequence 4 or portions thereof) as a DNA repair template.

In an exemplary embodiment, a cleaved target SCID-associated polynucleotide associated sequence (i.e., mutant IL2RG) is corrected by homology-directed repair utilizing a normal wild-type IL2RG sequence or portions thereof as a DNA repair template.

In an exemplary embodiment, a cleaved target SCID-associated polynucleotide associated sequence (i.e., mutant IL7R) is corrected by homology-directed repair utilizing a normal wild-type IL7R sequence or portions thereof as a DNA repair template.

In an exemplary embodiment, a cleaved target SCID-associated polynucleotide associated sequence (i.e., mutant JAK3) is corrected by homology-directed repair utilizing a normal wild-type JAK3 sequence or portions thereof as a DNA repair template.

In an exemplary embodiment, a cleaved target SCID-associated polynucleotide associated sequence (i.e., mutant LIG4) is corrected by homology-directed repair utilizing a normal wild-type LIG4 sequence (e.g., wild-type LIG4 coding sequence 1, LIG4 coding sequence 2, LIG4 coding sequence 3, or portions thereof) as a DNA repair template.

In an exemplary embodiment, a cleaved target SCID-associated polynucleotide associated sequence (i.e., mutant NHEJ1) is corrected by homology-directed repair utilizing a normal wild-type NHEJ1 sequence or portions thereof as a DNA repair template.

In an exemplary embodiment, a cleaved target SCID-associated polynucleotide associated sequence (i.e., mutant PNP) is corrected by homology-directed repair utilizing a normal wild-type PNP sequence or portions thereof as a DNA repair template.

In an exemplary embodiment, a cleaved target SCID-associated polynucleotide associated sequence (i.e., mutant PRKDC) is corrected by homology-directed repair utilizing a normal wild-type PRKDC sequence (e.g., wild-type PRKDC coding sequence 1, PRKDC coding sequence 2, or portions thereof) as a DNA repair template.

In an exemplary embodiment, a cleaved target SCID-associated polynucleotide associated sequence (i.e., mutant RAG1) is corrected by homology-directed repair utilizing a normal wild-type RAG1 sequence or portions thereof as a DNA repair template.

In an exemplary embodiment, a cleaved target SCID-associated polynucleotide associated sequence (i.e., mutant RAG2) is corrected by homology-directed repair utilizing a normal wild-type RAG2 sequence (e.g., wild-type RAG2 coding sequence 1, RAG2 coding sequence 2, RAG2 coding sequence 3, or portions thereof) as a DNA repair template.

In an exemplary embodiment, a cleaved target SCID-associated polynucleotide associated sequence (i.e., mutant ZAP70) is corrected by homology-directed repair utilizing a normal wild-type ZAP70 sequence (e.g., wild-type ZAP70 coding sequence 1, ZAP70 coding sequence 2, or portions thereof) as a DNA repair template.

In an exemplary embodiment, a cleaved target SCD-associated polynucleotide associated sequence is corrected by homology-directed repair utilizing a normal wild-type HBB sequence or portions thereof as a DNA repair template.

In an exemplary embodiment, a cleaved target beta thalassemia-associated polynucleotide associated sequence is corrected by homology-directed repair utilizing a normal wild-type HBB sequence or portions thereof as a DNA repair template.

In some embodiments, a CRISPR/Cas system of the present invention includes a Cas protein and at least one to two one ribonucleic acids that are capable of directing the Cas protein to and hybridizing to a target motif of a target polynucleotide sequence.

As used herein, "protein" and "polypeptide" are used interchangeably to refer to a series of amino acid residues joined by peptide bonds (i.e., a polymer of amino acids) and include modified amino acids (e.g., phosphorylated, glycated, glycosolated, etc.) and amino acid analogs. Exemplary polypeptides or proteins include gene products, naturally occurring proteins, homologs, paralogs, fragments and other equivalents, variants, and analogs of the above.

In some embodiments, a Cas protein comprises one or more amino acid substitutions or modifications. In some embodiments, the one or more amino acid substitutions comprises a conservative amino acid substitution. In some instances, substitutions and/or modifications can prevent or reduce proteolytic degradation and/or extend the half-life of the polypeptide in a cell. In some embodiments, the Cas protein can comprise a peptide bond replacement (e.g., urea, thiourea, carbamate, sulfonyl urea, etc.). In some embodiments, the Cas protein can comprise a naturally occurring amino acid. In some embodiments, the Cas protein can comprise an alternative amino acid (e.g., D-amino acids, beta-amino acids, homocysteine, phosphoserine, etc.). In some embodiments, a Cas protein can comprise a modification to include a moiety (e.g., PEGylation, glycosylation, lipidation, acetylation, end-capping, etc.).

In some embodiments, a Cas protein comprises a core Cas protein. Exemplary Cas core proteins include, but are not limited to Cas1, Cast, Cas3, Cas4, Cas5, Cas6, Cas7, Cas8 and Cas9. In some embodiments, a Cas protein comprises a Cas protein of an *E. coli* subtype (also known as CASS2). Exemplary Cas proteins of the *E. Coli* subtype include, but are not limited to Cse1, Cse2, Cse3, Cse4, and Cas5e. In some embodiments, a Cas protein comprises a Cas protein of the Ypest subtype (also known as CASS3). Exemplary Cas proteins of the Ypest subtype include, but are not limited to Csy1, Csy2, Csy3, and Csy4. In some embodiments, a Cas protein comprises a Cas protein of the Nmeni subtype (also known as CASS4). Exemplary Cas proteins of the Nmeni subtype include, but are not limited to Csn1 and Csn2. In some embodiments, a Cas protein comprises a Cas protein of the Dvulg subtype (also known as CASS1). Exemplary Cas proteins of the Dvulg subtype include Csd1, Csd2, and Cas5d. In some embodiments, a Cas protein comprises a Cas protein of the Tneap subtype (also known as CASS7). Exemplary Cas proteins of the Tneap subtype include, but are not limited to, Cst1, Cst2, Cas5h. In some embodiments, a Cas protein comprises a Cas protein of the Hmari subtype. Exemplary Cas proteins of the Hmari subtype include, but are not limited to Csh1, Csh2, and Cas5h. In some embodiments, a Cas protein comprises a Cas protein of the Apern subtype (also known as CASS5). Exemplary Cas proteins of the Apern subtype include, but are not limited to Csa1, Csa2, Csa3, Csa4, Csa5, and Cas5a. In some embodiments, a Cas protein comprises a Cas protein of the Mtube subtype (also known as CASS6). Exemplary Cas proteins of the Mtube subtype include, but are not limited to Csm1, Csm2, Csm3, Csm4, and Csm5. In some embodiments, a Cas protein comprises a RAMP module Cas protein. Exemplary RAMP module Cas proteins include, but are not limited to, Cmr1, Cmr2, Cmr3, Cmr4, Cmr5, and Cmr6.

In some embodiments, the Cas protein is a *Streptococcus pyogenes* Cas9 protein or a functional portion thereof. In some embodiments, the Cas protein is Cas9 protein from any bacterial species or functional portion thereof. Cas9 protein is a member of the type II CRISPR systems which typically include a trans-coded small RNA (tracrRNA), endogenous ribonuclease 3 (rnc) and a Cas protein. Cas 9 protein (also known as CRISPR-associated endonuclease Cas9/Csn1) is a polypeptide comprising 1368 amino acids. An exemplary amino acid sequence of a Cas9 protein (SEQ ID NO: 298) is shown in FIG. 28. Cas 9 contains 2 enconuclease domains, including an RuvC-like domain (residues 7-22, 759-766 and 982-989) which cleaves target DNA that is noncomplementary to crRNA, and an HNH nuclease domain (residues 810-872) which cleave target DNA complementary to crRNA. In FIG. 28, the RuvC-like domain is highlighted in yellow and the HNH nuclease domain is underlined.

As used herein, "functional portion" refers to a portion of a peptide which retains its ability to complex with at least one ribonucleic acid (e.g., guide RNA (gRNA)) and cleave a target polynucleotide sequence. In some embodiments, the functional portion comprises a combination of operably linked Cas9 protein functional domains selected from the group consisting of a DNA binding domain, at least one RNA binding domain, a helicase domain, and an endonuclease domain. In some embodiments, the functional domains form a complex.

In some embodiments, a functional portion of the Cas9 protein comprises a functional portion of a RuvC-like domain. In some embodiments, a functional portion of the Cas9 protein comprises a functional portion of the HNH nuclease domain.

It should be appreciated that the present invention contemplates various of ways of contacting a target polynucleotide sequence with a Cas protein (e.g., Cas9). In some embodiments, exogenous Cas protein can be introduced into the cell in polypeptide form. In certain embodiments, Cas proteins can be conjugated to or fused to a cell-penetrating polypeptide or cell-penetrating peptide. As used herein, "cell-penetrating polypeptide" and "cell-penetrating peptide" refers to a polypeptide or peptide, respectively, which facilitates the uptake of molecule into a cell. The cell-penetrating polypeptides can contain a detectable label.

In certain embodiments, Cas proteins can be conjugated to or fused to a charged protein (e.g., that carries a positive, negative or overall neutral electric charge). Such linkage may be covalent. In some embodiments, the Cas protein can be fused to a superpositively charged GFP to significantly increase the ability of the Cas protein to penetrate a cell (Cronican et al. *ACS Chem Biol.* 2010; 5(8):747-52).

In certain embodiments, the Cas protein can be fused to a protein transduction domain (PTD) to facilitate its entry into a cell. Exemplary PTDs include Tat, oligoarginine, and penetratin.

In some embodiments, the Cas9 protein comprises a Cas9 polypeptide fused to a cell-penetrating peptide. In some embodiments, the Cas9 protein comprises a Cas9 polypeptide fused to a PTD. In some embodiments, the Cas9 protein comprises a Cas9 polypeptide fused to a tat domain. In some embodiments, the Cas9 protein comprises a Cas9 polypeptide fused to an oligoarginine domain. In some embodiments, the Cas9 protein comprises a Cas9 polypeptide fused to a penetratin domain. In some embodiments, the Cas9 protein comprises a Cas9 polypeptide fused to a superpositively charged GFP.

In some embodiments, the Cas protein can be introduced into a cell containing the target polynucleotide sequence in the form of a nucleic acid encoding the Cas protein (e.g., Cas9). The process of introducing the nucleic acids into cells can be achieved by any suitable technique. Suitable techniques include calcium phosphate or lipid-mediated transfection, electroporation, and transduction or infection using a viral vector. In some embodiments, the nucleic acid comprises DNA. In some embodiments, the nucleic acid comprises a modified DNA, as described herein. In some embodiments, the nucleic acid comprises mRNA. In some embodiments, the nucleic acid comprises a modified mRNA, as described herein (e.g., a synthetic, modified mRNA).

In some embodiments, the Cas protein is complexed with the one to two ribonucleic acids. In some embodiments, the Cas protein and the one to two ribonucleic acids are contained in a nanoparticle. In some embodiments, the Cas protein and the one to two ribonucleic acids are contained in a lipid nanoparticle, as described herein. In some embodiments, the Cas protein is encoded by a modified nucleic acid, as described herein (e.g., a synthetic, modified mRNA).

The methods of the present invention contemplate the use of any ribonucleic acid that is capable of directing a Cas protein to and hybridizing to a target motif of a target polynucleotide sequence. In some embodiments, at least one of the ribonucleic acids comprises tracrRNA. In some embodiments, at least one of the ribonucleic acids comprises CRISPR RNA (crRNA). In some embodiments, at least one of the ribonucleic acids comprises a guide RNA that directs the Cas protein to and hybridizes to a target motif of the target polynucleotide sequence in a cell.

The ribonucleic acids of the present invention can be selected to hybridize to a variety of different target motifs, depending on the particular CRISPR/Cas system employed, and the sequence of the target polynucleotide, as will be appreciated by those skilled in the art. The one to two ribonucleic acids can also be selected to minimize hybridization with nucleic acid sequences other than the target polynucleotide sequence. In some embodiments, the one to two ribonucleic acids hybridize to a target motif that contains at least two mismatches when compared with all other genomic nucleotide sequences in the cell. In some embodiments, the one to two ribonucleic acids hybridize to a target motif that contains at least one mismatch when compared with all other genomic nucleotide sequences in the cell. In some embodiments, the one to two ribonucleic acids are designed to hybridize to a target motif immediately adjacent to a deoxyribonucleic acid motif recognized by the Cas protein. In some embodiments, each of the one to two ribonucleic acids are designed to hybridize to target motifs immediately adjacent to deoxyribonucleic acid motifs recognized by the Cas protein which flank a mutant allele located between the target motifs.

In some embodiments, at least one of the one to two ribonucleic acids comprises a sequence selected from the group consisting of the ribonucleic acid sequence of GTAACGGCAGACTTCTCCAC (SEQ ID NO: 5322). In some embodiments, at least one of the one to two ribonucleic acids comprises a sequence selected from the group consisting of the ribonucleic acid sequence of GTAACG-GCAGACTTCTCCACAGG (SEQ ID NO: 5321). It should be appreciated that the former sequence is the protospacer sequence in the guide RNA, whereas the latter sequence is the protospacer plus the PAM.

In some embodiments, at least one of the one to two ribonucleic acids comprises a sequence selected from the group consisting of the ribonucleic acid sequences of FIG. 1.

In some embodiments, at least one of the one to two ribonucleic acids comprises a sequence with a single nucleotide mismatch to a sequence selected from the group consisting of the ribonucleic acid sequences of FIG. 1.

In some embodiments, at least one of the one to two ribonucleic acids comprises a sequence selected from the group consisting of the ribonucleic acid sequences of FIG. 2. In some embodiments, at least one of the one to two ribonucleic acids comprises a sequence with a single nucleotide mismatch to a sequence selected from the group consisting of the ribonucleic acid sequences of FIG. 2.

In some embodiments, at least one of the one to two ribonucleic acids comprises a sequence selected from the group consisting of the ribonucleic acid sequences of FIG. 3. In some embodiments, at least one of the one to two ribonucleic acids comprises a sequence with a single nucleotide mismatch to a sequence selected from the group consisting of the ribonucleic acid sequences of FIG. 3.

In some embodiments, at least one of the one to two ribonucleic acids comprises a sequence selected from the group consisting of the ribonucleic acid sequences of FIG. 4. In some embodiments, at least one of the one to two ribonucleic acids comprises a sequence with a single nucleotide mismatch to a sequence selected from the group consisting of the ribonucleic acid sequences of FIG. 4.

In some embodiments, at least one of the one to two ribonucleic acids comprises a sequence selected from the group consisting of the ribonucleic acid sequences of FIG. 5. In some embodiments, at least one of the one to two ribonucleic acids comprises a sequence with a single nucleotide mismatch to a sequence selected from the group consisting of the ribonucleic acid sequences of FIG. 5.

In some embodiments, at least one of the one to two ribonucleic acids comprises a sequence selected from the group consisting of the ribonucleic acid sequences of FIG. 6. In some embodiments, at least one of the one to two ribonucleic acids comprises a sequence with a single nucleotide mismatch to a sequence selected from the group consisting of the ribonucleic acid sequences of FIG. 6.

In some embodiments, at least one of the one to two ribonucleic acids comprises a sequence selected from the group consisting of the ribonucleic acid sequences of FIG. 7. In some embodiments, at least one of the one to two ribonucleic acids comprises a sequence with a single nucleotide mismatch to a sequence selected from the group consisting of the ribonucleic acid sequences of FIG. 7.

In some embodiments, at least one of the one to two ribonucleic acids comprises a sequence selected from the group consisting of the ribonucleic acid sequences of FIG. 8. In some embodiments, at least one of the one to two ribonucleic acids comprises a sequence with a single nucleotide mismatch to a sequence selected from the group consisting of the ribonucleic acid sequences of FIG. 8.

In some embodiments, at least one of the one to two ribonucleic acids comprises a sequence selected from the group consisting of the ribonucleic acid sequences of FIG. 9. In some embodiments, at least one of the one to two ribonucleic acids comprises a sequence with a single nucleotide mismatch to a sequence selected from the group consisting of the ribonucleic acid sequences of FIG. 9.

In some embodiments, at least one of the one to two ribonucleic acids comprises a sequence selected from the group consisting of the ribonucleic acid sequences of FIG. 10. In some embodiments, at least one of the one to two ribonucleic acids comprises a sequence with a single nucleotide mismatch to a sequence selected from the group consisting of the ribonucleic acid sequences of FIG. 10.

In some embodiments, at least one of the one to two ribonucleic acids comprises a sequence selected from the group consisting of the ribonucleic acid sequences of FIG. 11. In some embodiments, at least one of the one to two ribonucleic acids comprises a sequence with a single nucleotide mismatch to a sequence selected from the group consisting of the ribonucleic acid sequences of FIG. 11.

In some embodiments, at least one of the one to two ribonucleic acids comprises a sequence selected from the group consisting of the ribonucleic acid sequences of FIG. 12. In some embodiments, at least one of the one to two ribonucleic acids comprises a sequence with a single nucleotide mismatch to a sequence selected from the group consisting of the ribonucleic acid sequences of FIG. 12.

In some embodiments, at least one of the one to two ribonucleic acids comprises a sequence selected from the group consisting of the ribonucleic acid sequences of FIG. 13. In some embodiments, at least one of the one to two ribonucleic acids comprises a sequence with a single nucleotide mismatch to a sequence selected from the group consisting of the ribonucleic acid sequences of FIG. 13.

In some embodiments, at least one of the one to two ribonucleic acids comprises a sequence selected from the group consisting of the ribonucleic acid sequences of FIG. 14. In some embodiments, at least one of the one to two ribonucleic acids comprises a sequence with a single nucleotide mismatch to a sequence selected from the group consisting of the ribonucleic acid sequences of FIG. 14.

In some embodiments, at least one of the one to two ribonucleic acids comprises a sequence selected from the group consisting of the ribonucleic acid sequences of FIG. 15. In some embodiments, at least one of the one to two ribonucleic acids comprises a sequence with a single nucleotide mismatch to a sequence selected from the group consisting of the ribonucleic acid sequences of FIG. 15.

In some embodiments, the ribonucleic acid sequences of the at least one of the one to two ribonucleic acids described above do not include the 3 nucleotide NGG sequence. For example, if the target site sequence is GATGCTCAGTACAGCCACCTTGG (SEQ ID NO: 5323), the ribonucleic acid sequence of the at least one of the one to two ribonucleic acid sequences is GATGCTCAGTACAGCCACCT (SEQ ID NO: 5324). As another example, if the target sequence is GATGCTCAGTACAGCCACCTTGG (SEQ ID NO: 5325), a ribonucleic acid sequence with a single nucleotide mismatch which does not include the 3 nucleotide NGG sequence is GATGCTGAGTACAGCCACCT (SEQ ID NO: 5326), with the italicized G being the mismatched nucleotide. Those skilled in the art will appreciate, however, that the single nucleotide mismatch can comprise any nucleotide in the ribonucleic acid, e.g., the first nucleotide, the second nucleotide, the third nucleotide, the fourth nucleotide, the fifth nucleotide, the sixth nucleotide, the seventh nucleotide, the eighth nucleotide, the ninth nucleotide, the tenth nucleotide, the eleventh nucleotide, the twelfth nucleotide, the thirteenth nucleotide, the fourteenth nucleotide, the fifteenth nucleotide, the sixteenth nucleotide, the seventeenth nucleotide, the eighteenth nucleotide, the nineteenth nucleotide, or the twentieth nucleotide of the ribonucleic acid.

In some embodiments, the ribonucleic acid sequences of the at least one of the one to two ribonucleic acids described above comprise at least a 12 nucleotide fragment of a ribonucleic acid sequence of any of FIGS. 1-15. In some embodiments, the ribonucleic acid sequences of the at least one of the one to two ribonucleic acids described above comprise at least a 12 nucleotide fragment of a sequence with a single nucleotide mismatch to sequence selected from the group consisting of a ribonucleic acid sequence of any of FIGS. 1-15. In some embodiments, the ribonucleic acid sequences of the at least one of the one to two ribonucleic acids described above comprise at least a 12 nucleotide fragment of a ribonucleic acid sequence of GTAACGGCAGACTTCTCCACAGG (SEQ ID NO: 5321). In some embodiments, the ribonucleic acid sequences of the at least one of the one to two ribonucleic acids described above comprise at least a 12 nucleotide fragment of a sequence with a single nucleotide mismatch to a ribonucleic acid sequence of GTAACGGCAGACTTCTCCACAGG (SEQ ID NO: 5321). For example, if the target sequence is GATGCTCAGTACAGCCACCTTGG (SEQ ID NO: 5323), the ribonucleic acid sequence of the at least one of the one to two ribonucleic acids which comprises at least a 12 nucleotide fragment is GTACAGCCACCT (SEQ ID NO: 5327).

In some embodiments, the ribonucleic acid sequences of the at least one of the one to two ribonucleic acids described above comprise at least a 13 nucleotide fragment of a ribonucleic acid sequence of any of FIGS. 1-15. In some embodiments, the ribonucleic acid sequences of the at least one of the one to two ribonucleic acids described above comprise at least a 13 nucleotide fragment of a sequence with a single nucleotide mismatch to a sequence selected from the group consisting of a ribonucleic acid sequence of any of FIGS. 1-15 In some embodiments, the ribonucleic acid sequences of the at least one of the one to two ribonucleic acids described above comprise at least a 13 nucleotide fragment of a ribonucleic acid sequence of GTAACGGCAGACTTCTCCACAGG (SEQ ID NO: 5321). In some embodiments, the ribonucleic acid sequences of the at least one of the one to two ribonucleic acids described above comprise at least a 13 nucleotide fragment of a sequence with a single nucleotide mismatch to a ribonucleic acid sequence of GTAACGGCAGACTTCTCACAGG (SEQ ID NO: 5321). For example, if the target sequence is GATGCTCAGTACAGCCACCTTGG (SEQ ID NO: 5323), the ribonucleic acid sequence of the at least one of the one to two ribonucleic acids which comprises at least a 13 nucleotide fragment is AGTACAGCCACCT (SEQ ID NO: 5328).

In some embodiments, the ribonucleic acid sequences of the at least one of the one to two ribonucleic acids described above comprise at least a 14 nucleotide fragment of a ribonucleic acid sequence of any of FIGS. 1-15. In some embodiments, the ribonucleic acid sequences of the at least one of the one to two ribonucleic acids described above comprise at least a 14 nucleotide fragment of a sequence with a single nucleotide mismatch to a sequence selected from the group consisting of a ribonucleic acid sequence of any of FIGS. 1-15. In some embodiments, the ribonucleic acid sequences of the at least one of the one to two ribonucleic acids described above comprise at least 14 nucleotide fragment of a ribonucleic acid sequence of GTAACGGCAGACTTCTCCACAGG (SEQ ID NO: 5321). In some embodiments, the ribonucleic acid sequences of the at least one of the one to two ribonucleic acids described above comprise at least a 14 nucleotide fragment of a sequence with a single nucleotide mismatch to a ribonucleic acid sequence of GTAACGGCAGACTTCTCACAGG (SEQ ID NO: 5321). For example, if the target sequence is GATGCTCAGTACAGCCACCTTGG (SEQ ID NO: 5323), the ribonucleic acid sequence of the at least one of the one to two ribonucleic acids which comprises at least a 14 nucleotide fragment is CAGTACAGCCACCT (SEQ ID NO: 5329).

In some embodiments, the ribonucleic acid sequences of the at least one of the one to two ribonucleic acids described above comprise at least a 15 nucleotide fragment of a ribonucleic acid sequence of any of FIGS. 1-15. In some embodiments, the ribonucleic acid sequences of the at least one of the one to two ribonucleic acids described above comprise at least a 15 nucleotide fragment of a sequence with a single nucleotide mismatch to a sequence selected from the group consisting of a ribonucleic acid sequence of any of FIGS. 1-15. In some embodiments, the ribonucleic acid sequences of the at least one of the one to two ribonucleic acids described above comprise at least a 15 nucleotide fragment of a ribonucleic acid sequence of GTAACGGCAGACTTCTCCACAGG (SEQ ID NO: 5321). In some embodiments, the ribonucleic acid sequences of the at least one of the one to two ribonucleic acids described above comprise at least a 15 nucleotide fragment of a sequence with a single nucleotide mismatch to a ribonucleic acid sequence of GTAACGGCAGACTTCTC-CACAGG (SEQ ID NO: 5321). For example, if the target sequence is GATGCTCAGTACAGCCACCTTGG (SEQ ID NO: 5323), the ribonucleic acid sequence of the at least one of the one to two ribonucleic acids which comprises at least a 15 nucleotide fragment is TCAGTACAGCCACCT (SEQ ID NO: 5330).

In some embodiments, the ribonucleic acid sequences of the at least one of the one to two ribonucleic acids described above comprise at least a 16 nucleotide fragment of a ribonucleic acid sequence of any of FIGS. 1-15. In some embodiments, the ribonucleic acid sequences of the at least one of the one to two ribonucleic acids described above comprise at least a 16 nucleotide fragment of a sequence with a single nucleotide mismatch to a sequence selected from the group consisting of a ribonucleic acid sequence of any of FIGS. 1-15. In some embodiments, the ribonucleic acid sequences of the at least one of the one to two ribonucleic acids described above comprise at least a 16 nucleotide fragment of a ribonucleic acid sequence of GTAACGGCAGACTTCTCCACAGG (SEQ ID NO: 5321). In some embodiments, the ribonucleic acid sequences of the at least one of the one to two ribonucleic acids described above comprise at least a 16 nucleotide fragment of a sequence with a single nucleotide mismatch to a ribonucleic acid sequence of GTAACGGCAGACTTCTC-CACAGG (SEQ ID NO: 5321). For example, if the target sequence is GATGCTCAGTACAGCCACCTTGG (SEQ ID NO: 5323), the ribonucleic acid sequence of the at least one of the one to two ribonucleic acids which comprises at least a 16 nucleotide fragment is CTCAGTACAGCCACCT (SEQ ID NO: 5331).

In some embodiments, the ribonucleic acid sequences of the at least one of the one to two ribonucleic acids described above comprise at least a 17 nucleotide fragment of a ribonucleic acid sequence of any of FIGS. 1-15. In some embodiments, the ribonucleic acid sequences of the at least one of the one to two ribonucleic acids described above comprise at least a 17 nucleotide fragment of a sequence with a single nucleotide mismatch to a sequence selected from the group consisting of a ribonucleic acid sequence of any of FIGS. 1-15. In some embodiments, the ribonucleic acid sequences of the at least one of the one to two ribonucleic acids described above comprise at least a 17 nucleotide fragment of a ribonucleic acid sequence of any of GTAACGGCAGACTTCTCCACAGG (SEQ ID NO: 5321). In some embodiments, the ribonucleic acid sequences of the at least one of the one to two ribonucleic acids described above comprise at least a 17 nucleotide fragment of a sequence with a single nucleotide mismatch to a ribonucleic acid sequence of GTAACGGCAGACTTCTCCACAGG (SEQ ID NO: 5321). For example, if the target sequence is GATGCTCAGTACAGCCACCTTGG (SEQ ID NO: 5323), the ribonucleic acid sequence of the at least one of the one to two ribonucleic acids which comprises at least a 17 nucleotide fragment is GCTCAGTACAGCCACCT (SEQ ID NO: 5332).

In some embodiments, the ribonucleic acid sequences of the at least one of the one to two ribonucleic acids described above comprise at least a 18 nucleotide fragment of a ribonucleic acid sequence of any of FIGS. 1-15. In some embodiments, the ribonucleic acid sequences of the at least one of the one to two ribonucleic acids described above comprise at least a 18 nucleotide fragment of a sequence with a single nucleotide mismatch to a sequence selected from the group consisting of a ribonucleic acid sequence of any of FIGS. 1-15. In some embodiments, the ribonucleic acid sequences of the at least one of the one to two ribonucleic acids described above comprise at least a 18 nucleotide fragment of a ribonucleic acid sequence of GTAACGGCAGACTTCTCCACAGG (SEQ ID NO: 5321). In some embodiments, the ribonucleic acid sequences of the at least one of the one to two ribonucleic acids described above comprise at least a 18 nucleotide fragment of a sequence with a single nucleotide mismatch to a ribonucleic acid sequence of GTAACGGCAGACTTCTCCACAGG (SEQ ID NO: 5321). For example, if the target sequence is GATGCTCAGTACAGCCACCTTGG (SEQ ID NO: 5323), the ribonucleic acid sequence of the at least one of the one to two ribonucleic acids which comprises at least a 18 nucleotide fragment is TGCTCAGTACAGCCACCT (SEQ ID NO: 5333).

In some embodiments, the ribonucleic acid sequences of the at least one of the one to two ribonucleic acids described above comprise at least a 19 nucleotide fragment of a ribonucleic acid sequence of any of FIGS. 1-15. In some embodiments, the ribonucleic acid sequences of the at least one of the one to two ribonucleic acids described above comprise at least a 19 nucleotide fragment of a sequence with a single nucleotide mismatch to a sequence selected from the group consisting of a ribonucleic acid sequence of any of FIGS. 1-15. In some embodiments, the ribonucleic acid sequences of the at least one of the one to two ribonucleic acids described above comprise at least a 19 nucleotide fragment of a ribonucleic acid sequence of GTAACGGCAGACTTCTCCACAGG (SEQ ID NO: 5321). In some embodiments, the ribonucleic acid sequences of the at least one of the one to two ribonucleic acids described above comprise at least a 19 nucleotide fragment of a sequence with a single nucleotide mismatch to a ribonucleic acid sequence of GTAACGGCAGACTTCTCCACAGG (SEQ ID NO: 5321). For example, if the target sequence is GATGCTCAGTACAGCCACCTTGG (SEQ ID NO: 5323), the ribonucleic acid sequence of the at least one of the one to two ribonucleic acids which comprises at least a 19 nucleotide fragment is ATGCTCAGTACAGCCACCT (SEQ ID NO: 5334).

In some embodiments, the ribonucleic acid sequences of the at least one of the one to two ribonucleic acids described above comprise at least a 20 nucleotide fragment of a ribonucleic acid sequence of any of FIGS. 1-15. In some embodiments, the ribonucleic acid sequences of the at least one of the one to two ribonucleic acids described above comprise at least a 20 nucleotide fragment of a sequence with a single nucleotide mismatch to a sequence selected from the group consisting of a ribonucleic acid sequence of any of FIGS. 1-15. In some embodiments, the ribonucleic acid sequences of the at least one of the one to two ribonucleic acids described above comprise at least a 20 nucleotide fragment of a ribonucleic acid sequence of GTAACGGCAGACTTCTCCACAGG (SEQ ID NO: 5321). In some embodiments, the ribonucleic acid sequences of the at least one of the one to two ribonucleic acids described above comprise at least a 20 nucleotide fragment of a sequence with a single nucleotide mismatch to a ribonucleic acid sequence of GTAACGGCAGACTTCTCCACAGG (SEQ ID NO: 5321). For example, if the target sequence is GATGCTCAGTACAGCCACCTTGG (SEQ ID NO: 5323), the ribonucleic acid sequence of the at least one of the one to two ribonucleic acids which comprises at least a 20 nucleotide fragment is GATGCTCAGTACAGCCACCT (SEQ ID NO: 5324).

The present invention also contemplates multiplex genomic editing. Those skilled in the art will appreciate that the description above with respect to genomic editing of a single gene is equally applicable to the multiplex genomic editing embodiments described below.

In another aspect, the present invention provides a method for simultaneously altering multiple target polynucleotide sequences in a cell.

In some embodiments, a method for simultaneously altering multiple target polynucleotide sequences in a cell comprises a method for simultaneously altering multiple target SCID-associated polynucleotides in a cell.

An exemplary method for simultaneously altering multiple target SCID-associated polynucleotide sequences in a cell comprises contacting the SCID-associated polynucleotide sequences with a clustered regularly interspaced short palindromic repeats-associated (Cas) protein and multiple ribonucleic acids, wherein the ribonucleic acids direct Cas protein to and hybridize to target motifs of the target SCID-associated polynucleotide sequences, wherein the target SCID-associated polynucleotide sequences are cleaved. In some embodiments, the efficiency of alteration of cells that express Cas protein is from about 50% to about 80%.

In some embodiments, a method for simultaneously altering multiple target polynucleotide sequences in a cell comprises a method for simultaneously altering multiple target SCD-associated polynucleotides in a cell.

An exemplary method for simultaneously altering multiple target SCD-associated polynucleotide sequences in a cell comprises contacting the SCD-associated polynucleotide sequences with a clustered regularly interspaced short palindromic repeats-associated (Cas) protein and multiple ribonucleic acids, wherein the ribonucleic acids direct Cas protein to and hybridize to target motifs of the target SCD-associated polynucleotide sequences, wherein the target SCD-associated polynucleotide sequences are cleaved. In some embodiments, the efficiency of alteration of cells that express Cas protein is from about 50% to about 80%.

In some embodiments, a method for simultaneously altering multiple target polynucleotide sequences in a cell comprises a method for simultaneously altering multiple target beta thalassemia-associated polynucleotides in a cell.

An exemplary method for simultaneously altering multiple target beta thalassemia-associated polynucleotide sequences in a cell comprises contacting the polynucleotide sequences with a clustered regularly interspaced short palindromic repeats-associated (Cas) protein and multiple ribonucleic acids, wherein the ribonucleic acids direct Cas protein to and hybridize to target motifs of the target beta thalassemia-associated polynucleotide sequences, wherein the target beta thalassemia-associated polynucleotide sequences are cleaved. In some embodiments, the efficiency of alteration of cells that express Cas protein is from about 50% to about 80%.

In yet another aspect, the present invention provides a method for treating or preventing a disorder associated with expression of polynucleotide sequences in a subject.

In some embodiments, a method for treating or preventing a disorder associated with expression of polynucleotide sequences in a subject comprises a method for treating or preventing a disorder associated with expression of SCID-associated polynucleotide sequences in a subject.

An exemplary method for treating or preventing a disorder associated with expression of SCID-associated polynucleotide sequences in a subject comprises (a) altering target SCID-associated polynucleotide sequences in a cell ex vivo by contacting the SCID-associated polynucleotide sequences with a clustered regularly interspaced short palindromic repeats-associated (Cas) protein and multiple ribonucleic acids, wherein the ribonucleic acids direct Cas protein to and hybridize to target motifs of the target SCID-associated polynucleotide sequences, wherein the target SCID-associated polynucleotide sequences are cleaved, and (b) introducing the cell into the subject, thereby treating or preventing a disorder associated with expression of the SCID-associated polynucleotide sequences. In some embodiments, the efficiency of alteration of cells that express Cas protein is from about 50% to about 80%. In some embodiments, the method includes the step of contacting, before the step of introducing the cell into the subject, the cleaved SCID-associated polynucleotide sequences with an exogenously introduced DNA repair template comprising a corresponding wild-type or normal polynucleotide sequence, thereby allowing homology-directed repair to replace the cleaved SCID-associated polynucleotide sequence with the wild-type or normal gene sequence.

In embodiments in which the target SCID-associated polynucleotide sequences comprise ADA polynucleotide sequences, the exogenously introduced DNA repair template comprises a corresponding wild-type or normal ADA polynucleotide sequence.

In embodiments in which the target SCID-associated polynucleotide sequences comprise AK2 polynucleotide sequences, the exogenously introduced DNA repair template comprises a corresponding wild-type or normal AK2 polynucleotide sequence.

In embodiments in which the target SCID-associated polynucleotide sequences comprise CD3D polynucleotide sequences, the exogenously introduced DNA repair template comprises a corresponding wild-type or normal CD3D polynucleotide sequence.

In embodiments in which the target SCID-associated polynucleotide sequences comprise DCLRE1C polynucleotide sequences, the exogenously introduced DNA repair template comprises a corresponding wild-type or normal DCLRE1C polynucleotide sequence.

In embodiments in which the target SCID-associated polynucleotide sequences comprise IL2RG polynucleotide sequences, the exogenously introduced DNA repair template comprises a corresponding wild-type or normal IL2RG polynucleotide sequence.

In embodiments in which the target SCID-associated polynucleotide sequences comprise IL7R polynucleotide sequences, the exogenously introduced DNA repair template comprises a corresponding wild-type or normal IL7R polynucleotide sequence.

In embodiments in which the target SCID-associated polynucleotide sequences comprise JAK3 polynucleotide sequences, the exogenously introduced DNA repair template comprises a corresponding wild-type or normal JAK3 polynucleotide sequence.

In embodiments in which the target SCID-associated polynucleotide sequences comprise LIG4 polynucleotide sequences, the exogenously introduced DNA repair template comprises a corresponding wild-type or normal L1G4 polynucleotide sequence.

In embodiments in which the target SCID-associated polynucleotide sequences comprise NHEJ1 polynucleotide sequences, the exogenously introduced DNA repair template comprises a corresponding wild-type or normal NHEJ1 polynucleotide sequence.

In embodiments in which the target SCID-associated polynucleotide sequences comprise PNP polynucleotide sequences, the exogenously introduced DNA repair template comprises a corresponding wild-type or normal PNP polynucleotide sequence.

In embodiments in which the target SCID-associated polynucleotide sequences comprise PRKDC polynucleotide sequences, the exogenously introduced DNA repair template comprises a corresponding wild-type or normal PRKDC polynucleotide sequence.

In embodiments in which the target SCID-associated polynucleotide sequences comprise RAG1 polynucleotide sequences, the exogenously introduced DNA repair template comprises a corresponding wild-type or normal RAG1 polynucleotide sequence.

In embodiments in which the target SCID-associated polynucleotide sequences comprise RAG2 polynucleotide sequences, the exogenously introduced DNA repair template comprises a corresponding wild-type or normal RAG2 polynucleotide sequence.

In embodiments in which the target SCID-associated polynucleotide sequences comprise ZAP70 polynucleotide sequences, the exogenously introduced DNA repair template comprises a corresponding wild-type or normal ZAP70 polynucleotide sequence.

In some embodiments, a method for treating or preventing a disorder associated with expression of polynucleotide sequences in a subject comprises a method for treating or preventing a disorder associated with expression of SCD-associated polynucleotide sequences in a subject.

An exemplary method for treating or preventing a disorder associated with expression of SCD-associated polynucleotide sequences in a subject comprises (a) altering target SCD-associated polynucleotide sequences in a cell ex vivo by contacting the SCD-associated polynucleotide sequences with a clustered regularly interspaced short palindromic repeats-associated (Cas) protein and multiple ribonucleic acids, wherein the ribonucleic acids direct Cas protein to and hybridize to target motifs of the target SCD-associated polynucleotide sequences, wherein the target SCD-associated polynucleotide sequences are cleaved, and (b) introducing the cell into the subject, thereby treating or preventing a disorder associated with expression of the SCD-associated polynucleotide sequences. In some embodiments, the efficiency of alteration of cells that express Cas protein is from about 50% to about 80%. In some embodiments, the method includes the step of contacting, before the step of introducing the cell into the subject, the cleaved SCD-associated polynucleotide sequences with an exogenously introduced DNA repair template comprising a normal HBB sequence, thereby allowing homology-directed repair to replace the cleaved SCD-associated polynucleotide sequence with the normal HBB sequence.

In some embodiments, a method for treating or preventing a disorder associated with expression of polynucleotide sequences in a subject comprises a method for treating or preventing a disorder associated with expression of beta thalassemia-associated polynucleotide sequences in a subject.

An exemplary method for treating or preventing a disorder associated with expression of beta thalassemia-associated polynucleotide sequences in a subject comprises (a) altering target beta thalassemia-associated polynucleotide sequences in a cell ex vivo by contacting the beta thalassemia-associated polynucleotide sequences with a clustered regularly interspaced short palindromic repeats-associated (Cas) protein and multiple ribonucleic acids, wherein the ribonucleic acids direct Cas protein to and hybridize to target motifs of the target beta thalassemia-associated polynucleotide sequences, wherein the target beta thalassemia-associated polynucleotide sequences are cleaved, and (b) introducing the cell into the subject, thereby treating or preventing a disorder associated with expression of the beta thalassemia-associated polynucleotide sequences. In some embodiments, the efficiency of alteration of cells that express Cas protein is from about 50% to about 80%, In some embodiments, the method includes the step of contacting, before the step of introducing the cell into the subject, the cleaved beta thalassemia-associated polynucleotide sequences with an exogenously introduced DNA repair template comprising a normal HBB sequence, thereby allowing homology-directed repair to replace the cleaved beta thalassemia-associated polynucleotide sequence with the normal HBB sequence.

As used herein, the terms "administering," "introducing" and "transplanting" are used interchangeably in the context of the placement of cells, e.g. cells described herein comprising a target polynucleotide sequence altered according to the methods of the invention into a subject, by a method or route which results in at least partial localization of the introduced cells at a desired site. The cells can be implanted directly to the desired site, or alternatively be administered by any appropriate route which results in delivery to a desired location in the subject where at least a portion of the implanted cells or components of the cells remain viable. The period of viability of the cells after administration to a subject can be as short as a few hours, e. g. twenty-four hours, to a few days, to as long as several years. In some instances, the cells can also be administered a location other than the desired site, such as in the liver or subcutaneously, for example, in a capsule to maintain the implanted cells at the implant location and avoid migration of the implanted cells.

For ex vivo methods, cells can include autologous cells, i.e., a cell or cells taken from a subject who is in need of altering a target polynucleotide sequence in the cell or cells (i.e., the donor and recipient are the same individual). Autologous cells have the advantage of avoiding any immunologically-based rejection of the cells. Alternatively, the cells can be heterologous, e.g., taken from a donor. The second subject can be of the same or different species. Typically, when the cells come from a donor, they will be from a donor who is sufficiently immunologically compatible with the recipient, i.e., will not be subject to transplant rejection, to lessen or remove the need for immunosuppression. In some embodiments, the cells are taken from a xenogeneic source, i.e., a non-human mammal that has been genetically engineered to be sufficiently immunologically compatible with the recipient, or the recipient's species. Methods for determining immunological compatibility are known in the art, and include tissue typing to assess donor-recipient compatibility for HLA and ABO determinants. See, e.g., *Transplantation Immunology*, Bach and Auchincloss, Eds. (Wiley, John & Sons, Incorporated 1994).

Any suitable cell culture media can be used for ex vivo methods of the invention.

Another exemplary method for treating or preventing a disorder associated with expression of SCID-associated polynucleotide sequences in a subject comprises altering target SCID-associated polynucleotide sequences in a cell by contacting the SCID-associated polynucleotide sequences with a clustered regularly interspaced short palindromic repeats-associated (Cas) protein and multiple ribonucleic acids, wherein the ribonucleic acids direct Cas protein to and hybridize to target moieties of the target SCID-associated polynucleotide sequences, and wherein the target SCID-associated polynucleotide sequences are cleaved, thereby treating or preventing a disorder associated with expression of the polynucleotide sequences.

In some embodiments, the method includes the step of contacting the cleaved SCID-associated polynucleotide sequences with an exogenously introduced DNA repair template comprising a corresponding wild-type or normal polynucleotide sequence, thereby allowing homology-directed repair to replace the cleaved SCID-associated polynucleotide sequence with the corresponding wild-type or normal polynucleotide sequence.

In embodiments in which the target SCID-associated polynucleotide sequences comprise ADA polynucleotide sequences, the exogenously introduced DNA repair template comprises a corresponding wild-type or normal ADA polynucleotide sequence.

In embodiments in which the target SCID-associated polynucleotide sequences comprise AK2 polynucleotide sequences, the exogenously introduced DNA repair template comprises a corresponding wild-type or normal AK2 polynucleotide sequence.

In embodiments in which the target SCID-associated polynucleotide sequences comprise CD3D polynucleotide sequences, the exogenously introduced DNA repair template comprises a corresponding wild-type or normal CD3D polynucleotide sequence.

In embodiments in which the target SCID-associated polynucleotide sequences comprise DCLRE1C polynucleotide sequences, the exogenously introduced DNA repair template comprises a corresponding wild-type or normal DCLRE1C polynucleotide sequence.

In embodiments in which the target SCID-associated polynucleotide sequences comprise IL2RG polynucleotide sequences, the exogenously introduced DNA repair template comprises a corresponding wild-type or normal IL2RG polynucleotide sequence.

In embodiments in which the target SCID-associated polynucleotide sequences comprise IL7R polynucleotide sequences, the exogenously introduced DNA repair template comprises a corresponding wild-type or normal IL7R polynucleotide sequence.

In embodiments in which the target SCID-associated polynucleotide sequences comprise JAK3 polynucleotide sequences, the exogenously introduced DNA repair template comprises a corresponding wild-type or normal JAK3 polynucleotide sequence.

In embodiments in which the target SCID-associated polynucleotide sequences comprise LIG4 polynucleotide sequences, the exogenously introduced DNA repair template comprises a corresponding wild-type or normal LIG4 polynucleotide sequence.

In embodiments in which the target SCID-associated polynucleotide sequences comprise NHEJ1 polynucleotide sequences, the exogenously introduced DNA repair template comprises a corresponding wild-type or normal NHEJ1 polynucleotide sequence.

In embodiments in which the target SCID-associated polynucleotide sequences comprise PNP polynucleotide sequences, the exogenously introduced DNA repair template comprises a corresponding wild-type or normal PNP polynucleotide sequence.

In embodiments in which the target SCID-associated polynucleotide sequences comprise PRKDC polynucleotide sequences, the exogenously introduced DNA repair template comprises a corresponding wild-type or normal PRKDC polynucleotide sequence.

In embodiments in which the target SCID-associated polynucleotide sequences comprise RAG1 polynucleotide sequences, the exogenously introduced DNA repair template comprises a corresponding wild-type or normal RAG1 polynucleotide sequence.

In embodiments in which the target SCID-associated polynucleotide sequences comprise RAG2 polynucleotide sequences, the exogenously introduced DNA repair template comprises a corresponding wild-type or normal RAG2 polynucleotide sequence.

In embodiments in which the target SCID-associated polynucleotide sequences comprise ZAP70 polynucleotide sequences, the exogenously introduced DNA repair template comprises a corresponding wild-type or normal ZAP70 polynucleotide sequence.

Another exemplary method for treating or preventing a disorder associated with expression of SCD-associated polynucleotide sequences in a subject comprises altering target SCD-associated polynucleotide sequences in a cell by contacting the SCD-associated polynucleotide sequences with a clustered regularly interspaced short palindromic repeats-associated (Cas) protein and multiple ribonucleic acids, wherein the ribonucleic acids direct Cas protein to and hybridize to target moieties of the target SCD-associated polynucleotide sequences, and wherein the target SCD-associated polynucleotide sequences are cleaved, thereby treating or preventing a disorder associated with expression of the polynucleotide sequences.

In some embodiments, the method includes the step of contacting the cleaved SCD-associated polynucleotide sequences with an exogenously introduced DNA repair template comprising a normal HBB sequence, thereby allowing homology-directed repair to replace the cleaved SCD-associated polynucleotide sequence with the normal HBB sequence.

Another exemplary method for treating or preventing a disorder associated with expression of beta thalassemia-associated polynucleotide sequences in a subject comprises altering target beta thalassemia-associated polynucleotide sequences in a cell by contacting the beta thalassemia-associated polynucleotide sequences with a clustered regularly interspaced short palindromic repeats-associated (Cas) protein and multiple ribonucleic acids, wherein the ribonucleic acids direct Cas protein to and hybridize to target moieties of the target beta thalassemia-associated polynucleotide sequences, and wherein the target beta thalassemia-associated polynucleotide sequences are cleaved, thereby treating or preventing a disorder associated with expression of the beta thalassemia-associated polynucleotide sequences.

In some embodiments, the method includes the step of contacting the cleaved beta thalassemia-associated polynucleotide sequences with an exogenously introduced DNA repair template comprising a normal HBB sequence, thereby allowing homology-directed repair to replace the cleaved beta thalassemia-associated polynucleotide sequence with the normal HBB sequence.

The terms "subject" and "individual" are used interchangeably herein, and refer to an animal, for example, a human from whom cells can be obtained and/or to whom treatment, including prophylactic treatment, with the cells as described herein, is provided. For treatment of those infections, conditions or disease states which are specific for a specific animal such as a human subject, the term subject refers to that specific animal. The "non-human animals" and "non-human mammals" as used interchangeably herein, includes mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g. dog, cat, horse, and the like, or production mammal, e.g. cow, sheep, pig, and the like.

In some embodiments, the alteration results in reduced expression of the target polynucleotide sequences. In exemplary embodiments, the alteration results in reduced expression of the target SCID-associated polynucleotide sequences. In exemplary embodiments, the alteration results in reduced expression of the target ADA polynucleotide sequences. In exemplary embodiments, the alteration results in reduced expression of the target AK2 polynucleotide sequences. In exemplary embodiments, the alteration results in reduced expression of the target CD3D polynucleotide sequences. In exemplary embodiments, the alteration results in reduced expression of the target DCLRE1C polynucleotide sequences. In exemplary embodiments, the alteration results in reduced expression of the target IL2RG polynucleotide sequences. In exemplary embodiments, the alteration results in reduced expression of the target IL7R polynucleotide sequences. In exemplary embodiments, the alteration results in reduced expression of the target JAK3 polynucleotide sequences. In exemplary embodiments, the alteration results in reduced expression of the target LIG4 polynucleotide sequences. In exemplary embodiments, the alteration results in reduced expression of the target NHEJ1 polynucleotide sequences. In exemplary embodiments, the alteration results in reduced expression of the target PNP polynucleotide sequences. In exemplary embodiments, the alteration results in reduced expression of the target PRKDC polynucleotide sequences. In exemplary embodiments, the alteration results in reduced expression of the target RAG1 polynucleotide sequences. In exemplary embodiments, the alteration results in reduced expression of the target RAG2 polynucleotide sequences. In exemplary embodiments, the alteration results in reduced expression of the target ZAP70 polynucleotide sequences. In exemplary embodiments, the alteration results in reduced expression of the target SCD-associated polynucleotide sequences. In exemplary embodiments, the alteration results in reduced expression of the target beta thalassemia-associated polynucleotide sequences. In some embodiments, the alteration results in a knock out of the target polynucleotide sequences. In exemplary embodiments, the alteration results in a knock out of the target SCID-associated polynucleotide sequences. In exemplary embodiments, the alteration results in a knock out of the target ADA polynucleotide sequences. In exemplary embodiments, the alteration results in a knock out of the target AK2 polynucleotide sequences. In exemplary embodiments, the alteration results in a knock out of the target CD3D polynucleotide sequences. In exemplary embodiments, the alteration results in a knock out of the target DCLRE1C polynucleotide sequences. In exemplary embodiments, the alteration results in a knock out of the target IL2RG polynucleotide sequences. In exemplary embodiments, the alteration results in a knock out of the target IL7R polynucleotide sequences. In exemplary embodiments, the alteration results in a knock out of the target JAK3 polynucleotide sequences. In exemplary embodiments, the alteration results in a knock out of the target LIG4 polynucleotide sequences. In exemplary embodiments, the alteration results in a knock out of the target NHEJ1 polynucleotide sequences. In exemplary embodiments, the alteration results in a knock out of the target PNP polynucleotide sequences. In exemplary embodiments, the alteration results in a knock out of the target PRKDC polynucleotide sequences. In exemplary embodiments, the alteration results in a knock out of the target RAG1 polynucleotide sequences. In exemplary embodiments, the alteration results in a knock out of the target RAG2 polynucleotide sequences. In exemplary embodiments, the alteration results in a knock out of the target ZAP70 polynucleotide sequences. In exemplary embodiments, the alteration results in a knock out of the target SCD-associated polynucleotide sequences. In exemplary embodiments, the alteration results in a knock out of the target beta thalassemia-associated polynucleotide sequences.

In some embodiments, the alteration results in correction of the target polynucleotide sequences from undesired sequences to desired sequences. In exemplary embodiments, the alteration results in correction of the target SCID-associated polynucleotide sequences to corresponding normal wild-type polynucleotide sequences. In exemplary embodiments, the alteration results in correction of the target SCID-associated polynucleotide sequences to corresponding normal wild-type ADA sequences. In exemplary embodiments, the alteration results in correction of the target SCID-associated polynucleotide sequences to corresponding normal wild-type AK2 sequences. In exemplary embodiments, the alteration results in correction of the target SCID-associated polynucleotide sequences to corresponding normal wild-type CD3D sequences. In exemplary embodiments, the alteration results in correction of the target SCID-associated polynucleotide sequences to corresponding normal wild-type DCLRE1C sequences. In exemplary embodiments, the alteration results in correction of the target SCID-associated polynucleotide sequences to corresponding normal wild-type IL2RG sequences. In exemplary embodiments, the alteration results in correction of the target SCID-associated polynucleotide sequences to corresponding normal wild-type IL7R sequences. In exemplary embodiments, the alteration results in correction of the target SCID-associated polynucleotide sequences to corresponding normal wild-type JAK3 sequences. In exemplary embodiments, the alteration results in correction of the target SCID-associated polynucleotide sequences to corresponding normal wild-type LIG4 sequences. In exemplary embodiments, the alteration results in correction of the target SCID-associated polynucleotide sequences to corresponding normal wild-type NHEJ1 sequences. In exemplary embodiments, the alteration results in correction of the target SCID-associated polynucleotide sequences to corresponding normal wild-type PNP sequences. In exemplary embodiments, the alteration results in correction of the target SCID-associated polynucleotide sequences to corresponding normal wild-type PRKDC sequences. In exemplary embodiments, the alteration results in correction of the target SCID-associated polynucleotide sequences to corresponding normal wild-type RAG1 sequences. In exemplary embodiments, the alteration results in correction of the target SCID-associated polynucleotide sequences to corresponding normal wild-type RAG2 sequences. In exemplary embodiments, the alteration results in correction of the target SCID-associated polynucleotide sequences to corresponding normal wild-type ZAP70 sequences. In exemplary embodiments, the alteration results in correction of the target SCD-associated polynucleotide sequences to normal wild-type HBB sequences. In exemplary embodiments, the alteration results in correction of the target beta thalassemia-associated polynucleotide sequences to normal wild-type HBB sequences. In some embodiments, each alteration is a homozygous alteration. In some embodiments, the efficiency of alteration at each loci is from about 5% to about 80%. In some embodiments, the efficiency of alteration at each loci is from about 10% to about 80%. In some embodiments, the efficiency of alteration at each loci is from about 30% to about 80%. In some embodiments, the efficiency of alteration at each loci is from about 50% to about 80%. In some embodiments, the efficiency of alteration at each loci is from greater than or equal to about 80%.

In some embodiments, each target polynucleotide sequence is cleaved such that a double-strand break results. In some embodiments, each target polynucleotide sequence is cleaved such that a single-strand break results.

In some embodiments, the target polynucleotide sequences comprise multiple different portions of ADA (e.g., one or more mutations in the ADA gene). In some embodiments, the target polynucleotide sequences comprise at least a portion of ADA.

In some embodiments, the target polynucleotide sequences comprise multiple different portions of AK2 (e.g., one or more mutations in the AK2 gene). In some embodiments, the target polynucleotide sequences comprise at least a portion of AK2.

In some embodiments, the target polynucleotide sequences comprise multiple different portions of CD3D (e.g., one or more mutations in the CD3D gene). In some embodiments, the target polynucleotide sequences comprise at least a portion of CD3D.

In some embodiments, the target polynucleotide sequences comprise multiple different portions of DCLRE1C (e.g., one or more mutations in the DCLRE1C gene). In some embodiments, the target polynucleotide sequences comprise at least a portion of DCLRE1C.

In some embodiments, the target polynucleotide sequences comprise multiple different portions of IL2RG (e.g., one or more mutations in the IL2RG gene). In some embodiments, the target polynucleotide sequences comprise at least a portion of IL2RG.

In some embodiments, the target polynucleotide sequences comprise multiple different portions of IL7R (e.g., one or more mutations in the IL7R gene). In some embodiments, the target polynucleotide sequences comprise at least a portion of IL7R.

In some embodiments, the target polynucleotide sequences comprise multiple different portions of JAK3

(e.g., one or more mutations in the JAK3 gene). In some embodiments, the target polynucleotide sequences comprise at least a portion of JAK3.

In some embodiments, the target polynucleotide sequences comprise multiple different portions of LIG4 (e.g., one or more mutations in the LIG4 gene). In some embodiments, the target polynucleotide sequences comprise at least a portion of LIG4.

In some embodiments, the target polynucleotide sequences comprise multiple different portions of NHEJ1 (e.g., one or more mutations in the NHEJ1 gene). In some embodiments, the target polynucleotide sequences comprise at least a portion of NHEJ1.

In some embodiments, the target polynucleotide sequences comprise multiple different portions of PNP (e.g., one or more mutations in the PNP gene). In some embodiments, the target polynucleotide sequences comprise at least a portion of PNP.

In some embodiments, the target polynucleotide sequences comprise multiple different portions of PRKDC (e.g., one or more mutations in the PRKDC gene). In some embodiments, the target polynucleotide sequences comprise at least a portion of PRKDC.

In some embodiments, the target polynucleotide sequences comprise multiple different portions of RAG1 (e.g., one or more mutations in the RAG1 gene). In some embodiments, the target polynucleotide sequences comprise at least a portion of RAG1.

In some embodiments, the target polynucleotide sequences comprise multiple different portions of RAG2 (e.g., one or more mutations in the RAG2 gene). In some embodiments, the target polynucleotide sequences comprise at least a portion of RAG2.

In some embodiments, the target polynucleotide sequences comprise multiple different portions of ZAP70 (e.g., one or more mutations in the ZAP70 gene). In some embodiments, the target polynucleotide sequences comprise at least a portion of ZAP70.

In some embodiments, the target polynucleotide sequences comprise multiple different portions of HBB (e.g., one or more mutations in the HBB gene). In some embodiments, the target polynucleotide sequences comprise at least a portion of HBB.

In some embodiments, each target motif is a 20-nucleotide DNA sequence. In some embodiments, each target motif is a 20-nucleotide DNA sequence beginning with G and immediately precedes an NGG motif recognized by the Cas protein. In some embodiments, each target motif is a 20-nucleotide DNA sequence and immediately precedes an NGG motif recognized by the Cas protein. In some embodiments, each target motif is G(N)19NGG. In some embodiments, each target motif is (N)20NGG. In some embodiments, each target motif is selected such that it contains at least two mismatches when compared with all other genomic nucleotide sequences in the cell. In some embodiments, each target motif is selected such that it contains at least two mismatches when compared with all other genomic nucleotide sequences in the cell.

In some embodiments, subsequent to cleavage of the target polynucleotide sequences, homology-directed repair occurs. In some embodiments, homology-directed repair is performed using an exogenously introduced DNA repair template. In some embodiments, the exogenously introduced DNA repair template is single-stranded. In some embodiments, the exogenously introduced DNA repair template is double-stranded.

In some embodiments, the exogenously introduced DNA repair template is a normal or wild-type ADA sequence. In some embodiments, the exogenously introduced DNA repair template is a normal or wild-type ADA sequence corresponding to the mutant ADA sequence comprising the SCID-associated polynucleotide sequence.)

In some embodiments, the exogenously introduced DNA repair template is a normal or wild-type AK2 sequence. In some embodiments, the exogenously introduced DNA repair template is a normal or wild-type AK2 sequence corresponding to the mutant AK2 sequence comprising the SCID-associated polynucleotide sequence.

In some embodiments, the exogenously introduced DNA repair template is a normal or wild-type CD3D sequence. In some embodiments, the exogenously introduced DNA repair template is a normal or wild-type CD3D sequence corresponding to the mutant CD3D sequence comprising the SCID-associated polynucleotide sequence.

In some embodiments, the exogenously introduced DNA repair template is a normal or wild-type DCLREIC sequence. In some embodiments, the exogenously introduced DNA repair template is a normal or wild-type DCLRE1C sequence corresponding to the mutant DCLREIC sequence comprising the SCID-associated polynucleotide sequence.

In some embodiments, the exogenously introduced DNA repair template is a normal or wild-type IL2RG sequence. In some embodiments, the exogenously introduced DNA repair template is a normal or wild-type IL2RG sequence corresponding to the mutant IL2RG sequence comprising the SCID-associated polynucleotide sequence.

In some embodiments, the exogenously introduced DNA repair template is a normal or wild-type IL7R sequence. In some embodiments, the exogenously introduced DNA repair template is a normal or wild-type IL7R sequence corresponding to the mutant IL7R sequence comprising the SCID-associated polynucleotide sequence.

In some embodiments, the exogenously introduced DNA repair template is a normal or wild-type JAK3 sequence. In some embodiments, the exogenously introduced DNA repair template is a normal or wild-type JAK3 sequence corresponding to the mutant JAK3 sequence comprising the SCID-associated polynucleotide sequence.

In some embodiments, the exogenously introduced DNA repair template is a normal or wild-type LIG4 sequence. In some embodiments, the exogenously introduced DNA repair template is a normal or wild-type LIG4 sequence corresponding to the mutant LIG4 sequence comprising the SCID-associated polynucleotide sequence.

In some embodiments, the exogenously introduced DNA repair template is a normal or wild-type NHEJ1 sequence. In some embodiments, the exogenously introduced DNA repair template is a normal or wild-type NHEJ1 sequence corresponding to the mutant NHEJ1 sequence comprising the SCID-associated polynucleotide sequence.

In some embodiments, the exogenously introduced DNA repair template is a normal or wild-type PNP sequence. In some embodiments, the exogenously introduced DNA repair template is a normal or wild-type PNP sequence corresponding to the mutant PNP sequence comprising the SCID-associated polynucleotide sequence.

In some embodiments, the exogenously introduced DNA repair template is a normal or wild-type PRKDC sequence. In some embodiments, the exogenously introduced DNA repair template is a normal or wild-type PRKDC sequence corresponding to the mutant PRKDC sequence comprising the SCID-associated polynucleotide sequence.

In some embodiments, the exogenously introduced DNA repair template is a normal or wild-type RAG1 sequence. In some embodiments, the exogenously introduced DNA repair template is a normal or wild-type RAG1 sequence corresponding to the mutant RAG1 sequence comprising the SCID-associated polynucleotide sequence.

In some embodiments, the exogenously introduced DNA repair template is a normal or wild-type RAG2 sequence. In some embodiments, the exogenously introduced DNA repair template is a normal or wild-type RAG2 sequence corresponding to the mutant RAG2 sequence comprising the SCID-associated polynucleotide sequence.

In some embodiments, the exogenously introduced DNA repair template is a normal or wild-type ZAP70 sequence. In some embodiments, the exogenously introduced DNA repair template is a normal or wild-type ZAP70 sequence corresponding to the mutant ZAP70 sequence comprising the SCID-associated polynucleotide sequence.

In some embodiments, the exogenously introduced DNA repair template is a normal or wild-type HBB sequence. In some embodiments, the exogenously introduced DNA repair template is a normal or wild-type HBB sequence corresponding to the mutant HBB sequence comprising the SCD-associated polynucleotide sequence. In some embodiments, the exogenously introduced DNA repair template is a normal or wild-type HBB sequence corresponding to the mutant HBB sequence comprising the beta thalassemia-associated polynucleotide sequence.

In some embodiments, the Cas protein (e.g., Cas9) is complexed with the multiple ribonucleic acids. In some embodiments, the Cas protein and the multiple ribonucleic acids are contained in nanoparticles, as described herein. In some embodiments, the Cas protein and the multiple ribonucleic acids are contained in lipid nanoparticles, as described herein. In some embodiments, a nucleic acid encoding a Cas protein and the multiple ribonucleic acids are contained in nanoparticles. In some embodiments, a nucleic acid encoding a Cas protein and the multiple ribonucleic acids are contained in lipid nanoparticles, as described herein. In some embodiments, a modified, synthetic mRNA encoding a Cas protein as described herein, and multiple ribonucleic acids at least one of which comprises a modified, synthetic RNA as described herein, are contained in lipid nanoparticles. In some embodiments, a modified, synthetic mRNA encoding a Cas9 protein as described herein, and multiple ribonucleic acids at least one of which comprises a modified, synthetic RNA as described herein, are contained in lipid nanoparticles.

In some embodiments, the multiple ribonucleic acids are selected to minimize hybridization with nucleic acid sequences other than the target polynucleotide sequence (e.g., multiple alterations of a single target polynucleotide sequence). In some embodiments, the multiple ribonucleic acids are selected to minimize hybridization with nucleic acid sequences other than the target polynucleotide sequences (e.g., one or more alterations of multiple target polynucleotide sequences). In some embodiments, each of the multiple ribonucleic acids hybridize to target motifs that contain at least two mismatches when compared with all other genomic nucleotide sequences in the cell. In some embodiments, each of the multiple ribonucleic acids hybridize to target motifs that contain at least one mismatch when compared with all other genomic nucleotide sequences in the cell. In some embodiments, each of the multiple ribonucleic acids are designed to hybridize to target motifs immediately adjacent to deoxyribonucleic acid motifs recognized by the Cas protein. In some embodiments, each of the multiple ribonucleic acids are designed to hybridize to target motifs immediately adjacent to deoxyribonucleic acid motifs recognized by the Cas protein which flank mutant alleles located between the target motifs.

In some embodiments, each of the multiple ribonucleic acids comprises a different sequence selected from the group consisting of the ribonucleic acid sequences of FIG. 1. In some embodiments, each of the multiple ribonucleic acids comprises a sequence with a single nucleotide mismatch to a different sequence selected from the group consisting of the ribonucleic acid sequences of FIG. 1.

In some embodiments, each of the multiple ribonucleic acids comprises a different sequence selected from the group consisting of the ribonucleic acid sequences of FIG. 2. In some embodiments, each of the multiple ribonucleic acids comprises a sequence with a single nucleotide mismatch to a different sequence selected from the group consisting of the ribonucleic acid sequences of FIG. 2.

In some embodiments, each of the multiple ribonucleic acids comprises a different sequence selected from the group consisting of the ribonucleic acid sequences of FIG. 3. In some embodiments, each of the multiple ribonucleic acids comprises a sequence with a single nucleotide mismatch to a different sequence selected from the group consisting of the ribonucleic acid sequences of FIG. 3.

In some embodiments, each of the multiple ribonucleic acids comprises a different sequence selected from the group consisting of the ribonucleic acid sequences of FIG. 4. In some embodiments, each of the multiple ribonucleic acids comprises a sequence with a single nucleotide mismatch to a different sequence selected from the group consisting of the ribonucleic acid sequences of FIG. 4.

In some embodiments, each of the multiple ribonucleic acids comprises a different sequence selected from the group consisting of the ribonucleic acid sequences of FIG. 5. In some embodiments, each of the multiple ribonucleic acids comprises a sequence with a single nucleotide mismatch to a different sequence selected from the group consisting of the ribonucleic acid sequences of FIG. 5.

In some embodiments, each of the multiple ribonucleic acids comprises a different sequence selected from the group consisting of the ribonucleic acid sequences of FIG. 6. In some embodiments, each of the multiple ribonucleic acids comprises a sequence with a single nucleotide mismatch to a different sequence selected from the group consisting of the ribonucleic acid sequences of FIG. 6.

In some embodiments, each of the multiple ribonucleic acids comprises a different sequence selected from the group consisting of the ribonucleic acid sequences of FIG. 7. In some embodiments, each of the multiple ribonucleic acids comprises a sequence with a single nucleotide mismatch to a different sequence selected from the group consisting of the ribonucleic acid sequences of FIG. 7.

In some embodiments, each of the multiple ribonucleic acids comprises a different sequence selected from the group consisting of the ribonucleic acid sequences of FIG. 8. In some embodiments, each of the multiple ribonucleic acids comprises a sequence with a single nucleotide mismatch to a different sequence selected from the group consisting of the ribonucleic acid sequences of FIG. 8.

In some embodiments, each of the multiple ribonucleic acids comprises a different sequence selected from the group consisting of the ribonucleic acid sequences of FIG. 9. In some embodiments, each of the multiple ribonucleic acids comprises a sequence with a single nucleotide mismatch to a different sequence selected from the group consisting of the ribonucleic acid sequences of FIG. 9.

In some embodiments, each of the multiple ribonucleic acids comprises a different sequence selected from the group consisting of the ribonucleic acid sequences of FIG. 9. In some embodiments, each of the multiple ribonucleic acids comprises a sequence with a single nucleotide mismatch to a different sequence selected from the group consisting of the ribonucleic acid sequences of FIG. 9.

In some embodiments, each of the multiple ribonucleic acids comprises a different sequence selected from the group consisting of the ribonucleic acid sequences of FIG. 10. In some embodiments, each of the multiple ribonucleic acids comprises a sequence with a single nucleotide mismatch to a different sequence selected from the group consisting of the ribonucleic acid sequences of FIG. 10.

In some embodiments, each of the multiple ribonucleic acids comprises a different sequence selected from the group consisting of the ribonucleic acid sequences of FIG. 11. In some embodiments, each of the multiple ribonucleic acids comprises a sequence with a single nucleotide mismatch to a different sequence selected from the group consisting of the ribonucleic acid sequences of FIG. 11.

In some embodiments, each of the multiple ribonucleic acids comprises a different sequence selected from the group consisting of the ribonucleic acid sequences of FIG. 12. In some embodiments, each of the multiple ribonucleic acids comprises a sequence with a single nucleotide mismatch to a different sequence selected from the group consisting of the ribonucleic acid sequences of FIG. 12.

In some embodiments, each of the multiple ribonucleic acids comprises a different sequence selected from the group consisting of the ribonucleic acid sequences of FIG. 13. In some embodiments, each of the multiple ribonucleic acids comprises a sequence with a single nucleotide mismatch to a different sequence selected from the group consisting of the ribonucleic acid sequences of FIG. 13.

In some embodiments, each of the multiple ribonucleic acids comprises a different sequence selected from the group consisting of the ribonucleic acid sequences of FIG. 14. In some embodiments, each of the multiple ribonucleic acids comprises a sequence with a single nucleotide mismatch to a different sequence selected from the group consisting of the ribonucleic acid sequences of FIG. 14.

In some embodiments, each of the multiple ribonucleic acids comprises a different sequence selected from the group consisting of the ribonucleic acid sequences of FIG. 15. In some embodiments, each of the multiple ribonucleic acids comprises a sequence with a single nucleotide mismatch to a different sequence selected from the group consisting of the ribonucleic acid sequences of FIG. 15.

In some embodiments, each of the multiple ribonucleic acids comprises a different sequence selected from the group consisting of the ribonucleic acid sequences of FIGS. 1-15 and combinations thereof. In some embodiments, the different sequences of the multiple ribonucleic acids described above do not include the 3 nucleotide NGG sequence.

For example, if a target site sequence is GATGCTCAGTACAGCCACCTTGG (SEQ ID NO: 5323), a sequence of the multiple ribonucleic acids is GATGCTCAGTACAGCCACCT (SEQ ID NO: 5324). As another example, if the target sequence is GATGCTCAGTACAGCCACCTTGG (SEQ ID NO: 5323), a sequence with a single nucleotide mismatch which does not include the 3 nucleotide NGG sequence is GATGCTGAGTACAGCCACCT (SEQ ID NO: 5326), with the italicized G being the mismatched nucleotide. Those skilled in the art will appreciate, however, that the single nucleotide mismatch can comprise any nucleotide in the ribonucleic acid, e.g., the first nucleotide, the second nucleotide, the third nucleotide, the fourth nucleotide, the fifth nucleotide, the sixth nucleotide, the seventh nucleotide, the eighth nucleotide, the ninth nucleotide, the tenth nucleotide, the eleventh nucleotide, the twelfth nucleotide, the thirteenth nucleotide, the fourteenth nucleotide, the fifteenth nucleotide, the sixteenth nucleotide, the seventeenth nucleotide, the eighteenth nucleotide, the nineteenth nucleotide, or the twentieth nucleotide of the ribonucleic acid.

In some embodiments, the different sequences of the multiple ribonucleic acids described above comprise at least 12 nucleotide fragments of a ribonucleic acid sequence of any of FIGS. 1-15. In some embodiments, the different sequences of the multiple ribonucleic acids described above comprise at least 12 nucleotide fragments sequences with single nucleotide mismatches to a sequence selected from the group consisting of a ribonucleic acid sequence of any of FIGS. 1-15. For example, if a target sequence is GATGCTCAGTACAGCCACCTTGG (SEQ ID NO: 5323), a different sequence of the multiple ribonucleic acids comprising at least a 12 nucleotide fragment with single nucleotide mismatch comprises GTACAGCCACCT (SEQ ID NO: 5327).

In some embodiments, the different sequences of the multiple ribonucleic acids described above comprise at least 13 nucleotide fragments of a ribonucleic acid sequence of any of FIGS. 1-15. In some embodiments, the different sequences of the multiple ribonucleic acids described above comprise at least 13 nucleotide fragments sequences with single nucleotide mismatches to a sequence selected from the group consisting of a ribonucleic acid sequence of any of FIGS. 1-15. For example, if a target sequence is GATGCTCAGTACAGCCACCTTGG (SEQ ID NO: 5323), a different sequence of the multiple ribonucleic acids comprising at least a 13 nucleotide fragment with single nucleotide mismatch comprises AGTACAGCCACCT (SEQ ID NO: 5328).

In some embodiments, the different sequences of the multiple ribonucleic acids described above comprise at least 14 nucleotide fragments of a ribonucleic acid sequence of any of FIGS. 1-15. In some embodiments, the different sequences of the multiple ribonucleic acids described above comprise at least 14 nucleotide fragments sequences with single nucleotide mismatches to a sequence selected from the group consisting of a ribonucleic acid sequence of any of FIGS. 1-15. For example, if a target sequence is GATGCTCAGTACAGCCACCTTGG (SEQ ID NO: 5323), a different sequence of the multiple ribonucleic acids comprising at least a 14 nucleotide fragment with single nucleotide mismatch comprises CAGTACAGCCACCT (SEQ ID NO: 5329).

In some embodiments, the different sequences of the multiple ribonucleic acids described above comprise at least 15 nucleotide fragments of a ribonucleic acid sequence of any of FIGS. 1-15. In some embodiments, the different sequences of the multiple ribonucleic acids described above comprise at least 15 nucleotide fragments sequences with single nucleotide mismatches to a sequence selected from the group consisting of a ribonucleic acid sequence of any of FIGS. 1-15. For example, if a target sequence is GATGCTCAGTACAGCCACCTTGG (SEQ ID NO: 5323), a different sequence of the multiple ribonucleic acids comprising at least a 15 nucleotide fragment with single nucleotide mismatch comprises TCAGTACAGCCACCT (SEQ ID NO: 5330).

In some embodiments, the different sequences of the multiple ribonucleic acids described above comprise at least 16 nucleotide fragments of a ribonucleic acid sequence of any of FIGS. 1-15. In some embodiments, the different sequences of the multiple ribonucleic acids described above comprise at least 16 nucleotide fragments sequences with single nucleotide mismatches to a sequence selected from the group consisting of a ribonucleic acid sequence of any of FIGS. 1-15. For example, if a target sequence is GATGCTCAGTACAGCCACCTTGG (SEQ ID NO: 5323), a different sequence of the multiple ribonucleic acids comprising at least a 16 nucleotide fragment with single nucleotide mismatch comprises CTCAGTACAGCCACCT (SEQ ID NO: 5331).

In some embodiments, the different sequences of the multiple ribonucleic acids described above comprise at least 17 nucleotide fragments of a ribonucleic acid sequence of any of FIGS. 1-15. In some embodiments, the different sequences of the multiple ribonucleic acids described above comprise at least 17 nucleotide fragments sequences with single nucleotide mismatches to a sequence selected from the group consisting of a ribonucleic acid sequence of any of FIGS. 1-15. For example, if a target sequence is GATGCTCAGTACAGCCACCTTGG (SEQ ID NO: 5323), a different sequence of the multiple ribonucleic acids comprising at least a 17 nucleotide fragment with single nucleotide mismatch comprises GCTCAGTACAGCCACCT (SEQ ID NO: 5332).

In some embodiments, the different sequences of the multiple ribonucleic acids described above comprise at least 18 nucleotide fragments of a ribonucleic acid sequence of any of FIGS. 1-15. In some embodiments, the different sequences of the multiple ribonucleic acids described above comprise at least 18 nucleotide fragments sequences with single nucleotide mismatches to a sequence selected from the group consisting of a ribonucleic acid sequence of any of FIGS. 1-15. For example, if a target sequence is GATGCTCAGTACAGCCACCTTGG (SEQ ID NO: 5323), a different sequence of the multiple ribonucleic acids comprising at least a 18 nucleotide fragment with single nucleotide mismatch comprises TGCTCAGTACAGCCACCT (SEQ ID NO: 5333).

In some embodiments, the different sequences of the multiple ribonucleic acids described above comprise at least 19 nucleotide fragments of a ribonucleic acid sequence of any of FIGS. 1-15. In some embodiments, the different sequences of the multiple ribonucleic acids described above comprise at least 19 nucleotide fragments sequences with single nucleotide mismatches to a sequence selected from the group consisting of a ribonucleic acid sequence of any of FIGS. 1-15. For example, if a target sequence is GATGCTCAGTACAGCCACCTTGG (SEQ ID NO: 5323), a different sequence of the multiple ribonucleic acids comprising at least a 19 nucleotide fragment with single nucleotide mismatch comprises ATGCTCAGTACAGCCACCT (SEQ ID NO: 5334).

In some embodiments, the different sequences of the multiple ribonucleic acids described above comprise at least 20 nucleotide fragments of a ribonucleic acid sequence of any of FIGS. 1-15. In some embodiments, the different sequences of the multiple ribonucleic acids described above comprise at least 20 nucleotide fragments sequences with single nucleotide mismatches to a sequence selected from the group consisting of a ribonucleic acid sequence of any of FIGS. 1-15. For example, if a target sequence is GATGCTCAGTACAGCCACCTTGG (SEQ ID NO: 5323), a different sequence of the multiple ribonucleic acids comprising at least a 12 nucleotide fragment with single nucleotide mismatch comprises GATGCTCAGTACAGCCACCT (SEQ ID NO: 5324).

It should be appreciated that any of the Cas protein or the ribonucleic acids can be expressed from a plasmid. In some embodiments, any of the Cas protein or the ribonucleic acids are expressed using a promoter optimized for increased expression in stem cells (e.g., human stem cells). In some embodiments, the promoter is selected from the group consisting of a Cytomegalovirus (CMV) early enhancer element and a chicken beta-actin promoter, a chicken beta-actin promoter, an elongation factor-1 alpha promoter, and a ubiquitin promoter.

In some embodiments, the methods of the present invention further comprise selecting cells that express the Cas protein. The present invention contemplates any suitable method for selecting cells. In some embodiments, selecting cells comprises FACS. In some embodiments, FACs is used to select cells which co-express Cas and a fluorescent protein selected from the group consisting of green fluorescent protein and red fluorescent protein.

The present invention contemplates treating and/or preventing a variety of disorders which are associated with expression of a target polynucleotide sequences. It should be appreciated that the methods and compositions described herein can be used to treat or prevent disorders associated with increased expression of a target polynucleotide sequence, as well as decreased expression of a target polynucleotide sequence in a cell. Increased and decreased expression of a target polynucleotide sequence includes circumstances where the expression levels of the target polynucleotide sequence are increased or decreased, respectively, as well as circumstances in which the function and/or level of activity of an expression product of the target polynucleotide sequence increases or decreases, respectively, compared to normal expression and/or activity levels. Those skilled in the art will appreciate that treating or preventing a disorder associated with increased expression of a target polynucleotide sequence can be assessed by determining whether the levels and/or activity of the target polynucleotide sequence (or an expression product thereof) are decreased in a relevant cell after employing a method or administering a composition described herein. The skilled artisan will also appreciate that treating or preventing a disorder associated with decreased expression of a target polynucleotide sequence can be assessed by determining whether the levels and/or activity of the target polynucleotide sequence (or an expression product thereof) are increased in the relevant cell after employing a method or administering a composition described herein.

In some embodiments, the disorder is a genetic disorder. In some embodiments, the disorder is a monogenic disorder. In some embodiments, the disorder is a multigenic disorder. In some embodiments, the disorder is a disorder associated with one or more SNPs. Exemplary disorders associated with one or more SNPs include a complex disease described in U.S. Pat. No. 7,627,436, Alzheimer's disease as described in PCT International Application Publication No. WO/2009/112882, inflammatory diseases as described in U.S. Patent Application Publication No. 2011/0039918, polycystic ovary syndrome as described in U.S. Patent Application Publication No. 2012/0309642, cardiovascular disease as described in U.S. Pat. No. 7,732,139, Huntington's disease as described in U.S. Patent Application Publication No. 2012/0136039, thromboembolic disease as described in European Patent Application Publication No. EP2535424, neurovascular diseases as described in PCT International Application Publication No. WO/2012/001613, psychosis as described in U.S. Patent Application Publication No. 2010/0292211, multiple sclerosis as described in U.S. Patent Application Publication No. 2011/0319288, schizopherenia, schizoaffective disorder, and bipolar disorder as described in PCT International Application Publication No. WO/2006/023719A2, bipolar disorder and other ailments as described in U.S. Patent Application Publication No. U.S. 2011/0104674, colorectal cancer as described in PCT International Application Publication No. WO/2006/104370A1, a disorder associated with a SNP adjacent to the AKT1 gene locus as described in U.S. Patent Application Publication No. U.S. 2006/0204969, an eating disorder as described in PCT International Application Publication No. WO/2003/012143A1, autoimmune disease as described in U.S. Patent Application Publication No. U.S. 2007/0269827, fibrostenosing disease in patients with Chrohn's disease as described in U.S. Pat. No. 7,790,370, and Parkinson's disease as described in U.S. Pat. No. 8,187,811, each of which is incorporated herein by reference in its entirety. Other disorders associated with one or more SNPs which can be treated or prevented according to the methods of the present invention will be apparent to the skilled artisan.

In some embodiments, the disorder is severe combined immunodeficiency. In some embodiments, the disorder is X-linked moderate combined immunodeficiency. In some embodiments, the disorder is X-linked severe combined immunodeficiency. In some embodiments, the disorder is adenosine deaminase deficiency or SCID associated with adenosine deaminase deficiency. In some embodiments, the disorder is Athabascan type SCID. In some embodiments, the disorder is T cell-negative, B-cell/natural killer cell-positive SCID. In some embodiments, the disorder is T-negative/B-positive type autosomal recessive SCID. In some embodiments, the disorder is SCID with sensitivity to ionizing radiation. In some embodiments, the disorder is SCID with microcephaly, growth retardation, and sensitivity to ionizing radiation. In some embodiments, the disorder is reticular dysgenesis. In some embodiments, the disorder is LIG4 syndrome. In some embodiments, the disorder is alpha/beta T-cell lymphopenia with gamma/delta T-cell expansion, severe cytomegalovirus infection, and autoimmunity. In some embodiments, the disorder is combined cellular and humoral immune defects with granulomas. In some embodiments, the disorder is B cell-negative SCID. In some embodiments, the disorder is a selective T-cell defect or selective T-cell defect associated with SCID. In some embodiments, the disorder is purine nucleoside phosphorylase deficiency or SCID associated with purine nucleoside phosphorylase deficiency. In some embodiments, the disorder is Omenn syndrome. In some embodiments, the disorder is bare lymphocyte syndrome. In some embodiments, the disorder is SCID associated with JAK3 mutation. In some embodiments, the disorder is SCID associated with DCLRE1C mutation. In some embodiments, the disorder is a disorder listed in any one of the Gene Phenotype Relationship tables listed herein. In some embodiments, the disorder is sickle cell anemia. In some embodiments, the disorder is sickle cell disease. In some embodiments, the disorder is sickle cell anemia. In some embodiments, the disorder is sickle beta thalassemia. In some embodiments, the disorder is beta thalassemia.

The methods of the present invention are capable of altering target polynucleotide sequences in a variety of different cells. In some embodiments, the methods of the present invention are used to alter target polynucleotide sequences in cells ex vivo for subsequent introduction into a subject. In some embodiments, the methods of the present invention can be used to alter target polynucleotide sequences in cells in vivo. In some embodiments, the cell is a peripheral blood cell. In some embodiments, the cell is a stem cell or a pluripotent cell. In some embodiments, the cell is a hematopoietic stem cell. In some embodiments, the cell is a CD34+ cell. In some embodiments, the cell is a CD34+ mobilized peripheral blood cell. In some embodiments, the cell is a CD34+ cord blood cell. In some embodiments, the cell is a CD34+ bone marrow cell. In some embodiments, the cell is a CD34+CD38-Lineage-CD90+CD45RA− cell. In some embodiments, the cell is a hepatocyte. In some embodiments, the cell is a human pluripotent cell. In some embodiments, the cell is a primary human cell. In some embodiments, the cell is a non-transformed cell. In some embodiments, the cell is not a cancer cell. In some embodiments, the cell is not a tumor cell. In some embodiments, the cell is not a transformed cell.

In some aspects, the present invention provides a method for altering a target SCID-associated polynucleotide sequence in a cell comprising contacting the SCID-associated polynucleotide sequence in a cell selected from the group consisting of a human pluripotent cell, a primary human cell, and a non-transformed human cell, with a clustered regularly interspaced short palindromic repeats-associated (Cas) protein and from one to two ribonucleic acids, wherein the ribonucleic acids direct Cas protein to and hybridize to a target motif of the target SCID-associated polynucleotide sequence, wherein the target SCID-associated polynucleotide sequence is cleaved, and wherein the efficiency of alteration of cells that express Cas protein is from about 8% to about 80%.

In some aspects, the present invention provides a method for altering a target SCD-associated polynucleotide sequence in a cell comprising contacting the SCD-associated polynucleotide sequence in a cell selected from the group consisting of a human pluripotent cell, a primary human cell, and a non-transformed human cell, with a clustered regularly interspaced short palindromic repeats-associated (Cas) protein and from one to two ribonucleic acids, wherein the ribonucleic acids direct Cas protein to and hybridize to a target motif of the target SCD-associated polynucleotide sequence, wherein the target SCD-associated polynucleotide sequence is cleaved, and wherein the efficiency of alteration of cells that express Cas protein is from about 8% to about 80%.

In some aspects, the present invention provides a method for altering a target beta thalassemia-associated polynucleotide sequence in a cell comprising contacting the beta thalassemia-associated polynucleotide sequence in a cell selected from the group consisting of a human pluripotent cell, a primary human cell, and a non-transformed human cell, with a clustered regularly interspaced short palindromic repeats-associated (Cas) protein and from one to two ribonucleic acids, wherein the ribonucleic acids direct Cas protein to and hybridize to a target motif of the target beta thalassemia-associated polynucleotide sequence, wherein the target beta thalassemia-associated polynucleotide sequence is cleaved, and wherein the efficiency of alteration of cells that express Cas protein is from about 8% to about 80%.

In some aspects, the present invention provides a method for treating or preventing a disorder associated with expression of a SCID-associated polynucleotide sequence in a subject, the method comprising (a) altering a target SCID-associated polynucleotide sequence in a cell ex vivo by contacting the SCID-associated polynucleotide sequence in a cell selected from the group consisting of a human pluripotent cell, a primary human cell, and a non-transformed human cell, with a clustered regularly interspaced short palindromic repeats-associated (Cas) protein and from one to two ribonucleic acids, wherein the ribonucleic acids direct Cas protein to and hybridize to a target motif of the target SCID-associated polynucleotide sequence, wherein the target SCID-associated polynucleotide sequence is cleaved, and wherein the efficiency of alteration is from about 8% to about 80%, and (b) introducing the cell into the subject, thereby treating or preventing a disorder associated with expression of the SCID-associated polynucleotide sequence.

In some embodiments, the method includes the step of contacting, before the step of introducing the cell into the subject, the cleaved SCID-associated polynucleotide sequences with an exogenously introduced DNA repair template comprising a corresponding normal or wild-type polynucleotide sequence, thereby allowing homology-directed repair to replace the cleaved SCID-associated polynucleotide sequence with the corresponding normal or wild type polynucleotide sequence. In embodiments in which the target SCID-associated polynucleotide sequences comprise ADA polynucleotide sequences, the exogenously introduced DNA repair template comprises a corresponding wild-type or normal ADA polynucleotide sequence.

In embodiments in which the target SCID-associated polynucleotide sequences comprise AK2 polynucleotide sequences, the exogenously introduced DNA repair template comprises a corresponding wild-type or normal AK2 polynucleotide sequence.

In embodiments in which the target SCID-associated polynucleotide sequences comprise CD3D polynucleotide sequences, the exogenously introduced DNA repair template comprises a corresponding wild-type or normal CD3D polynucleotide sequence.

In embodiments in which the target SCID-associated-polynucleotide sequences comprise DCLRE1C polynucleotide sequences, the exogenously introduced DNA repair template comprises a corresponding wild-type or normal DCLRE1C polynucleotide sequence.

In embodiments in which the target SCID-associated polynucleotide sequences comprise IL2RG polynucleotide sequences, the exogenously introduced DNA repair template comprises a corresponding wild-type or normal IL2RG polynucleotide sequence.

In embodiments in which the target SCID-associated polynucleotide sequences comprise IL7R polynucleotide sequences, the exogenously introduced DNA repair template comprises a corresponding wild-type or normal IL7R polynucleotide sequence.

In embodiments in which the target SCID-associated polynucleotide sequences comprise JAK3 polynucleotide sequences, the exogenously introduced DNA repair template comprises a corresponding wild-type or normal JAK3 polynucleotide sequence.

In embodiments in which the target SCID-associated polynucleotide sequences comprise LIG4 polynucleotide sequences, the exogenously introduced DNA repair template comprises a corresponding wild-type or normal LIG4 polynucleotide sequence.

In embodiments in which the target SCID-associated polynucleotide sequences comprise NHEJ1 polynucleotide sequences, the exogenously introduced DNA repair template comprises a corresponding wild-type or normal NHEJ1 polynucleotide sequence.

In embodiments in which the target SCID-associated polynucleotide sequences comprise PNP polynucleotide sequences, the exogenously introduced DNA repair template comprises a corresponding wild-type or normal PNP polynucleotide sequence.

In embodiments in which the target SCID-associated polynucleotide sequences comprise PRKDC polynucleotide sequences, the exogenously introduced DNA repair template comprises a corresponding wild-type or normal PRKDC polynucleotide sequence.

In embodiments in which the target SCID-associated polynucleotide sequences comprise RAG1 polynucleotide sequences, the exogenously introduced DNA repair template comprises a corresponding wild-type or normal RAG1 polynucleotide sequence.

In embodiments in which the target SCID-associated polynucleotide sequences comprise RAG2 polynucleotide sequences, the exogenously introduced DNA repair template comprises a corresponding wild-type or normal RAG2 polynucleotide sequence.

In embodiments in which the target SCID-associated polynucleotide sequences comprise ZAP70 polynucleotide sequences, the exogenously introduced DNA repair template comprises a corresponding wild-type or normal ZAP70 polynucleotide sequence.

In some aspects, the present invention provides a method for treating or preventing a disorder associated with expression of a SCD-associated polynucleotide sequence in a subject, the method comprising (a) altering a target SCD-associated polynucleotide sequence in a cell ex vivo by contacting the SCD-associated polynucleotide sequence in a cell selected from the group consisting of a human pluripotent cell, a primary human cell, and a non-transformed human cell, with a clustered regularly interspaced short palindromic repeats-associated (Cas) protein and from one to two ribonucleic acids, wherein the ribonucleic acids direct Cas protein to and hybridize to a target motif of the target SCD-associated polynucleotide sequence, wherein the target SCD-associated polynucleotide sequence is cleaved, and wherein the efficiency of alteration is from about 8% to about 80%, and (b) introducing the cell into the subject, thereby treating or preventing a disorder associated with expression of the SCD-associated polynucleotide sequence.

In some embodiments, the method includes the step of contacting, before the step of introducing the cell into the subject, the cleaved SCD-associated polynucleotide sequences with an exogenously introduced DNA repair template comprising a normal HBB sequence, thereby allowing homology-directed repair to replace the cleaved SCD-associated polynucleotide sequence with the normal HBB sequence.

In some aspects, the present invention provides a method for treating or preventing a disorder associated with expression of a beta thalassemia-associated polynucleotide sequence in a subject, the method comprising (a) altering a target beta thalassemia-associated polynucleotide sequence in a cell ex vivo by contacting the beta thalassemia-associated polynucleotide sequence in a cell selected from the group consisting of a human pluripotent cell, a primary human cell, and a non-transformed human cell, with a clustered regularly interspaced short palindromic repeats-associated (Cas) protein and from one to two ribonucleic acids, wherein the ribonucleic acids direct Cas protein to and hybridize to a target motif of the target beta thalassemia-associated polynucleotide sequence, wherein the target beta thalassemia-associated polynucleotide sequence is cleaved, and wherein the efficiency of alteration is from about 8% to about 80%, and (b) introducing the cell into the subject, thereby treating or preventing a disorder associated with expression of the beta thalassemia-associated polynucleotide sequence.

In some embodiments, the method includes the step of contacting, before the step of introducing the cell into the subject, the cleaved beta thalassemia-associated polynucleotide sequences with an exogenously introduced DNA repair template comprising a normal HBB sequence, thereby allowing homology-directed repair to replace the cleaved beta thalassemia-associated polynucleotide sequence with the normal HBB sequence.

In some aspects, the present invention provides a method for simultaneously altering multiple target SCID-associated polynucleotide sequences in a cell comprising contacting the SCID-associated polynucleotide sequences in a cell selected from the group consisting of a human pluripotent cell, a primary human cell, and a non-transformed human cell, with a clustered regularly interspaced short palindromic repeats-associated (Cas) protein and multiple ribonucleic acids, wherein the ribonucleic acids direct Cas protein to and hybridize to target motifs of the target SCID-associated polynucleotide sequences, wherein the target SCD-associated polynucleotide sequences are cleaved, and wherein the efficiency of alteration of cells that express Cas protein is from about 8% to about 80%.

In some embodiments, the method includes the step of contacting the cleaved target SCID-associated polynucleotide sequences with an exogenously introduced DNA repair template comprising a corresponding normal or wild-type sequence (e.g., of a ADA gene, a AK2 gene, a CD3D gene, a DCLRE1C gene, a IL2RG gene, IL7R gene, a LIG4 gene, a NHEJ1 gene, a PNP gene, a PRKDC gene, a RAG1 gene, a RAG2 gene, a ZAP70 gene), thereby allowing homology-directed repair to replace the mutant portion of the cleaved SCID-associated polynucleotide sequence with the corresponding normal or wild-type sequence (e.g., of the ADA gene, the AK2 gene, the CD3D gene, the DCLRE1C gene, the IL2RG gene, the IL7R gene, the LIG4 gene, the NHEJ1 gene, the PNP gene, the PRKDC gene, the RAG1 gene, the RAG2 gene, the ZAP70 gene).

In some aspects, the present invention provides a method for simultaneously altering multiple target SCD-associated polynucleotide sequences in a cell comprising contacting the SCD-associated polynucleotide sequences in a cell selected from the group consisting of a human pluripotent cell, a primary human cell, and a non-transformed human cell, with a clustered regularly interspaced short palindromic repeats-associated (Cas) protein and multiple ribonucleic acids, wherein the ribonucleic acids direct Cas protein to and hybridize to target motifs of the target SCD-associated polynucleotide sequences, wherein the target SCD-associated polynucleotide sequences are cleaved, and wherein the efficiency of alteration of cells that express Cas protein is from about 8% to about 80%.

In some embodiments, the method includes the step of contacting the cleaved target SCD-associated polynucleotide sequences with an exogenously introduced DNA repair template comprising a normal HBB sequence, thereby allowing homology-directed repair to replace the mutant portion of the cleaved SCD-associated polynucleotide sequence with the normal HBB sequence.

In some aspects, the present invention provides a method for simultaneously altering multiple target beta thalassemia-associated polynucleotide sequences in a cell comprising contacting the beta thalassemia-associated polynucleotide sequences in a cell selected from the group consisting of a human pluripotent cell, a primary human cell, and a non-transformed human cell, with a clustered regularly interspaced short palindromic repeats-associated (Cas) protein and multiple ribonucleic acids, wherein the ribonucleic acids direct Cas protein to and hybridize to target motifs of the target beta thalassemia-associated polynucleotide sequences, wherein the target beta thalassemia-associated polynucleotide sequences are cleaved, and wherein the efficiency of alteration of cells that express Cas protein is from about 8% to about 80%.

In some embodiments, the method includes the step of contacting the cleaved target beta thalassemia-associated polynucleotide sequences with an exogenously introduced DNA repair template comprising a normal HBB sequence, thereby allowing homology-directed repair to replace the mutant portion of the cleaved beta thalassemia-associated polynucleotide sequence with the normal HBB sequence.

In some aspects, the present invention provides a method for treating or preventing a disorder associated with expression of SCID-associated polynucleotide sequences in a subject, the method comprising (a) altering target SCID-associated polynucleotide sequences in a cell ex vivo by contacting the SCD-associated polynucleotide sequences in a cell selected from the group consisting of a human pluripotent cell, a primary human cell, and a non-transformed human cell, with a clustered regularly interspaced short palindromic repeats-associated (Cas) protein and) multiple ribonucleic acids, wherein the ribonucleic acids direct Cas protein to and hybridize to target motifs of the target SCID-associated polynucleotide sequences, wherein the target SCID-associated polynucleotide sequences are cleaved, and wherein the efficiency of alteration of cells that express Cas protein is from about 8% to about 80%, and (b) introducing the cell into the subject, thereby treating or preventing a disorder associated with expression of the SCID-associated polynucleotide sequences.

In some embodiments, the method includes the step of contacting, before the step of introducing the cell into the subject, the cleaved SCID-associated polynucleotide sequences with an exogenously introduced DNA repair template comprising a corresponding normal or wild-type sequence (e.g., of a ADA gene, a AK2 gene, a CD3D gene, a DCLRE1C gene, a IL2RG gene, a IL7R gene, a LIG4 gene, a NHEJ1 gene, a PNP gene, a PRKDC gene, a RAG1 gene, a RAG2 gene, a ZAP70 gene), thereby allowing homology-directed repair to replace the cleaved SCD-associated polynucleotide sequence with the normal or wild-type sequence (e.g., of the ADA gene, the AK2 gene, the CD3D gene, the DCLRE1C gene, the IL2RG gene, the IL7R gene, the LIG4 gene, the NHEJ1 gene, the PNP gene, the PRKDC gene, the RAG1 gene, the RAG2 gene, the ZAP70 gene).

In some aspects, the present invention provides a method for treating or preventing a disorder associated with expression of SCD-associated polynucleotide sequences in a subject, the method comprising (a) altering target SCD-associated polynucleotide sequences in a cell ex vivo by contacting the SCD-associated polynucleotide sequences in a cell selected from the group consisting of a human pluripotent cell, a primary human cell, and a non-transformed human cell, with a clustered regularly interspaced short palindromic repeats-associated (Cas) protein and multiple ribonucleic acids, wherein the ribonucleic acids direct Cas protein to and hybridize to target motifs of the target SCD-associated polynucleotide sequences, wherein, the target SCD-associated polynucleotide sequences are cleaved, and wherein the efficiency of alteration of cells that express Cas protein is from about 8% to about 80%, and (b) introducing the cell into the subject, thereby treating or preventing a disorder associated with expression of the SCD-associated polynucleotide sequences.

In some embodiments, the method includes the step of contacting, before the step of introducing the cell into the subject, the cleaved SCD-associated polynucleotide sequences with an exogenously introduced DNA repair template comprising a normal HBB sequence, thereby allowing homology-directed repair to replace the cleaved SCD-associated polynucleotide sequence with the normal HBB sequence.

In some aspects, the present invention provides a method for treating or preventing a disorder associated with expression of beta thalassemia-associated polynucleotide sequences in a subject, the method comprising (a) altering target beta thalassemia-associated polynucleotide sequences in a cell ex vivo by contacting the beta thalassemia-associated polynucleotide sequences in a cell selected from the group consisting of a human pluripotent cell, a primary human cell, and a non-transformed human cell, with a clustered regularly interspaced short palindromic repeats-associated (Cas) protein and multiple ribonucleic acids, wherein the ribonucleic acids direct Cas protein to and hybridize to target motifs of the target beta thalassemia-associated polynucleotide sequences, wherein the target beta thalassemia-associated polynucleotide sequences are cleaved, and wherein the efficiency of alteration of cells that express Cas protein is from about 8% to about 80%, and (b) introducing the cell into the subject, thereby treating or preventing a disorder associated with expression of the beta thalassemia-associated polynucleotide sequences.

In some embodiments, the method includes the step of contacting, before the step of introducing the cell into the subject, the cleaved beta thalassemia-associated polynucleotide sequences with an exogenously introduced DNA repair template comprising a normal HBB sequence, thereby allowing homology-directed repair to replace the cleaved beta thalassemia-associated polynucleotide sequence with the normal HBB sequence.

The present invention also provides compositions comprising Cas proteins of the present invention or functional portions thereof, nucleic acids encoding the Cas proteins or functional portions thereof and ribonucleic acid sequences which direct Cas proteins to and hybridize to target motifs of target polynucleotides in a cell.

For administration to a subject, a composition as disclosed herein can be administered to a subject, for example in pharmaceutically acceptable compositions. Pharmaceutically acceptable compositions comprise a therapeutically-effective amount of a Cas protein of the present invention or functional portion thereof, nucleic acids encoding the Cas proteins (e.g., modified, synthetic mRNA), and ribonucleic acid sequences which direct Cas proteins to and hybridize, formulated together with one or more pharmaceutically acceptable carriers (additives) and/or diluents.

As described in detail below, the pharmaceutical compositions of the present invention can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. Nos. 3,773,919; and 35 3,270,960.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The phrase "therapeutically-effective amount" as used herein in respect to a Cas protein and/or ribonucleic acids described herein means that amount of relevant protein and/or ribonucleic acid, or composition comprising the same which is effective for producing some desired therapeutic effect in at least a sub-population of cells in an animal at a reasonable benefit/risk ratio applicable to any medical treatment. For example, an amount administered to a subject that is sufficient to produce a statistically significant, measurable change in at least one symptom of sickle cell anemia (e.g., reduced red blood cell count.). Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

In some aspects, the present invention provides a composition comprising at least one ribonucleic acid having a sequence selected from the group consisting of the ribonucleic acid sequences of FIG. 1.

In some aspects, the present invention provides a composition comprising at least one ribonucleic acid comprising a sequence with a single nucleotide mismatch to a sequence selected from the group consisting of the ribonucleic acid sequences of FIG. 1.

In some aspects, the present invention provides a composition comprising at least one ribonucleic acid having a sequence selected from the group consisting of the ribonucleic acid sequences of FIG. 2.

In some aspects, the present invention provides a composition comprising at least one ribonucleic acid comprising a sequence with a single nucleotide mismatch to a sequence selected from the group consisting of the ribonucleic acid sequences of FIG. 2.

In some aspects, the present invention provides a composition comprising at least one ribonucleic acid having a sequence selected from the group consisting of the ribonucleic acid sequences of FIG. 3. In some aspects, the present invention provides a composition comprising at least one ribonucleic acid comprising a sequence with a single nucleotide mismatch to a sequence selected from the group consisting of the ribonucleic acid sequences of FIG. 3.

In some aspects, the present invention provides a composition comprising at least one ribonucleic acid having a sequence selected from the group consisting of the ribonucleic acid sequences of FIG. 4. In some aspects, the present invention provides a composition comprising at least one ribonucleic acid comprising a sequence with a single nucleotide mismatch to a sequence selected from the group consisting of the ribonucleic acid sequences of FIG. 4.

In some aspects, the present invention provides a composition comprising at least one ribonucleic acid having a sequence selected from the group consisting of the ribonucleic acid sequences of FIG. 5. In some aspects, the present invention provides a composition comprising at least one ribonucleic acid comprising a sequence with a single nucleotide mismatch to a sequence selected from the group consisting of the ribonucleic acid sequences of FIG. 5.

In some aspects, the present invention provides a composition comprising at least one ribonucleic acid having a sequence selected from the group consisting of the ribonucleic acid sequences of FIG. 6. In some aspects, the present invention provides a composition comprising at least one ribonucleic acid comprising a sequence with a single nucleotide mismatch to a sequence selected from the group consisting of the ribonucleic acid sequences of FIG. 6.

In some aspects, the present invention provides a composition comprising at least one ribonucleic acid having a sequence selected from the group consisting of the ribonucleic acid sequences of FIG. 7. In some aspects, the present invention provides a composition comprising at least one ribonucleic acid comprising a sequence with a single nucleotide mismatch to a sequence selected from the group consisting of the ribonucleic acid sequences of FIG. 7.

In some aspects, the present invention provides a composition comprising at least one ribonucleic acid having a sequence selected from the group consisting of the ribonucleic acid sequences of FIG. 8. In some aspects, the present invention provides a composition comprising at least one ribonucleic acid comprising a sequence with a single nucleotide mismatch to a sequence selected from the group consisting of the ribonucleic acid sequences of FIG. 8.

In some aspects, the present invention provides a composition comprising at least one ribonucleic acid having a sequence selected from the group consisting of the ribonucleic acid sequences of FIG. 9. In some aspects, the present invention provides a composition comprising at least one ribonucleic acid comprising a sequence with a single nucleotide mismatch to a sequence selected from the group consisting of the ribonucleic acid sequences of FIG. 9.

In some aspects, the present invention provides a composition comprising at least one ribonucleic acid having a sequence selected from the group consisting of the ribonucleic acid sequences of FIG. 10. In some aspects, the present invention provides a composition comprising at least one ribonucleic acid comprising a sequence with a single nucleotide mismatch to a sequence selected from the group consisting of the ribonucleic acid sequences of FIG. 10.

In some aspects, the present invention provides a composition comprising at least one ribonucleic acid having a sequence selected from the group consisting of the ribonucleic acid sequences of FIG. 11. In some aspects, the present invention provides a composition comprising at least one ribonucleic acid comprising a sequence with a single nucleotide mismatch to a sequence selected from the group consisting of the ribonucleic acid sequences of FIG. 11.

In some aspects, the present invention provides a composition comprising at least one ribonucleic acid having a sequence selected from the group consisting of the ribonucleic acid sequences of FIG. 12. In some aspects, the present invention provides a composition comprising at least one ribonucleic acid comprising a sequence with a single nucleotide mismatch to a sequence selected from the group consisting of the ribonucleic acid sequences of FIG. 12.

In some aspects, the present invention provides a composition comprising at least one ribonucleic acid having a sequence selected from the group consisting of the ribonucleic acid sequences of FIG. 13. In some aspects, the present invention provides a composition comprising at least one ribonucleic acid comprising a sequence with a single nucleotide mismatch to a sequence selected from the group consisting of the ribonucleic acid sequences of FIG. 13.

In some aspects, the present invention provides a composition comprising at least one ribonucleic acid having a sequence selected from the group consisting of the ribonucleic acid sequences of FIG. 14. In some aspects, the present invention provides a composition comprising at least one ribonucleic acid comprising a sequence with a single nucleotide mismatch to a sequence selected from the group consisting of the ribonucleic acid sequences of FIG. 14.

In some aspects, the present invention provides a composition comprising at least one ribonucleic acid having a sequence selected from the group consisting of the ribonucleic acid sequences of FIG. 15. In some aspects, the present invention provides a composition comprising at least one ribonucleic acid comprising a sequence with a single nucleotide mismatch to a sequence selected from the group consisting of the ribonucleic acid sequences of FIG. 15.

In some aspects, the present invention provides a composition comprising at least one ribonucleic acid having a ribonucleic acid sequences of GTAACGGCAGACTTCTC-CACAGG (SEQ ID NO: 5321). In some aspects, the present invention provides a composition comprising at least one ribonucleic acid comprising a sequence with a single nucleotide mismatch to ribonucleic acid sequences of GTAACG-GCAGACTTCTCCACAGG (SEQ ID NO: 5321). In some embodiments, the at least one ribonucleic acid sequences described above do not include the 3 nucleotide NGG sequence.

For example, if the target site sequence is GATGCTCA-GTACAGCCACCTTGG (SEQ ID NO: 5323), the ribonucleic acid sequence of the at least one ribonucleic acid sequence is GATGCTCAGTACAGCCACCT (SEQ ID NO: 5324). As another example, if the target sequence is GAT-GCTCAGTACAGCCACCTTGG (SEQ ID NO: 5323), a ribonucleic acid sequence with a single nucleotide mismatch which does not include the 3 nucleotide NGG sequence is GATGCTGAGTACAGCCACCT (SEQ ID NO: 5326), with the italicized G being the mismatched nucleotide. Those skilled in the art will appreciate, however, that the single nucleotide mismatch can comprise any nucleotide in the ribonucleic acid, e.g., the first nucleotide, the second nucleotide, the third nucleotide, the fourth nucleotide, the fifth nucleotide, the sixth nucleotide, the seventh nucleotide, the eighth nucleotide, the ninth nucleotide, the tenth nucleotide, the eleventh nucleotide, the twelfth nucleotide, the thirteenth nucleotide, the fourteenth nucleotide, the fifteenth nucleotide, the sixteenth nucleotide, the seventeenth nucleotide, the eighteenth nucleotide, the nineteenth nucleotide, or the twentieth nucleotide of the ribonucleic acid.

In some embodiments, the at least one ribonucleic acid described above comprises at least a 12 nucleotide fragment of a ribonucleic acid sequence of any of FIGS. 1-15. In some embodiments, the at least one ribonucleic acid described above comprises at least a 12 nucleotide fragment of a sequence with a single nucleotide mismatch to a sequence selected from the group consisting of a ribonucleic acid sequence of any of FIGS. 1-15. In some embodiments, the at least one ribonucleic acid described above comprises at least a 12 nucleotide fragment of a ribonucleic acid sequence of GTAACGGCAGACTTCTCCACAGG (SEQ ID NO: 5321). In some embodiments, the at least one ribonucleic acid described above comprises at least a 12 nucleotide fragment of a sequence with a single nucleotide mismatch to a ribonucleic acid sequence of any of GTAACGGCAGACT-TCTCCACAGG (SEQ ID NO: 5321). For example, if the target sequence is GATGCTCAGTACAGCCACCTTGG (SEQ ID NO: 5323), the ribonucleic acid sequence of the at least one ribonucleic acid which comprises at least a 12 nucleotide fragment is GTACAGCCACCT (SEQ ID NO: 5327).

In some embodiments, the ribonucleic acid sequence of the at least one ribonucleic acid described above comprises at least a 13 nucleotide fragment of a ribonucleic acid sequence of any of FIGS. 1-15. In some embodiments, the ribonucleic acid sequence of the at least one ribonucleic acid described above comprises at least a 13 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprises at least a 13 nucleotide fragment of a ribonucleic acid sequence of GTAACGGCA-GACTTCTCCACAGG (SEQ ID NO: 5321). In some embodiments, the ribonucleic acid sequence of the at least one ribonucleic acid described above comprises at least a 13 nucleotide fragment of a sequence with a single nucleotide mismatch to a ribonucleic acid sequence of GTAACGGCA-GACTTCTCCACAGG (SEQ ID NO: 5321). For example, if the target sequence is GATGCTCAGTACAGCCACCT-TGG (SEQ ID NO: 5323), the ribonucleic acid sequence of the at least one ribonucleic acid which comprises at least a 13 nucleotide fragment is AGTACAGCCACCT (SEQ ID NO: 5328).

In some embodiments, the ribonucleic acid sequence of the at least one ribonucleic acid described above comprises at least a 14 nucleotide fragment of a ribonucleic acid sequence of any of FIGS. 1-15. In some embodiments, the ribonucleic acid sequence of the at least one ribonucleic acid described above comprises at least a 14 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprises at least a 14 nucleotide fragment of a ribonucleic acid sequence of GTAACGGCA-GACTTCTCCACAGG (SEQ ID NO: 5321). In some embodiments, the ribonucleic acid sequence of the at least one ribonucleic acid described above comprises at least a 14 nucleotide fragment of a sequence with a single nucleotide mismatch to a ribonucleic acid sequence of GTAACGGCA-GACTTCTCCACAGG (SEQ ID NO: 5321). For example, if the target sequence is GATGCTCAGTACAGCCACCT-TGG (SEQ ID NO: 5323), the ribonucleic acid sequence of the at least one ribonucleic acid which comprises at least a 14 nucleotide fragment is CAGTACAGCCACCT (SEQ ID NO: 5329).

In some embodiments, the ribonucleic acid sequence of the at least one ribonucleic acid described above comprises at least a 15 nucleotide fragment of a ribonucleic acid sequence of any of FIGS. 1-15. In some embodiments, the ribonucleic acid sequence of the at least one ribonucleic acid described above comprises at least a 15 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprises at least a 15 nucleotide fragment of a ribonucleic acid sequence of GTAACGGCA-GACTTCTCCACAGG (SEQ ID NO: 5321). In some embodiments, the ribonucleic acid sequence of the at least one ribonucleic acid described above comprises at least a 15 nucleotide fragment of a sequence with a single nucleotide mismatch to a ribonucleic acid sequence of GTAACGGCA-GACTTCTCCACAGG (SEQ ID NO: 5321). For example, if the target sequence is GATGCTCAGTACAGCCACCT-TGG (SEQ ID NO: 5323), the ribonucleic acid sequence of the at least one ribonucleic acid which comprises at least a 15 nucleotide fragment is TCAGTACAGCCACCT (SEQ ID NO: 5330).

In some embodiments, the ribonucleic acid sequence of the at least one ribonucleic acid described above comprise at least a 16 nucleotide fragment of a ribonucleic acid sequence of any of FIGS. 1-15. In some embodiments, the ribonucleic acid sequence of the at least one ribonucleic acid described above comprises at least a 16 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprise at least a 16 nucleotide fragment of a ribonucleic acid sequence of GTAACGGCAGACT-TCTCCACAGG (SEQ ID NO: 5321). In some embodiments, the ribonucleic acid sequence of the at least one ribonucleic acid described above comprises at least a 16 nucleotide fragment of a sequence with a single nucleotide mismatch to a ribonucleic acid sequence of GTAACGGCA-GACTTCTCCACAGG (SEQ ID NO: 5321). For example, if the target sequence is GATGCTCAGTACAGCCACCT-TGG (SEQ ID NO: 5323), the ribonucleic acid sequence of the at least one ribonucleic acid which comprises at least a 16 nucleotide fragment is CTCAGTACAGCCACCT (SEQ ID NO: 5331).

In some embodiments, the ribonucleic acid sequence of the at least one ribonucleic acid described above comprises at least a 17 nucleotide fragment of a ribonucleic acid sequence of any of FIGS. 1-15. In some embodiments, the ribonucleic acid sequence of the at least one ribonucleic acid described above comprises at least a 17 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprises at least a 17 nucleotide fragment of a ribonucleic acid sequence of GTAACGGCA-GACTTCTCCACAGG (SEQ ID NO: 5321). In some embodiments, the ribonucleic acid sequence of the at least one ribonucleic acid described above comprises at least a 17 nucleotide fragment of a sequence with a single nucleotide mismatch to a ribonucleic acid sequence of GTAACGGCA-GACTTCTCCACAGG (SEQ ID NO: 5321). For example, if the target sequence is GATGCTCAGTACAGCCACCT-TGG (SEQ ID NO: 5323), the ribonucleic acid sequence of the at least one ribonucleic acid which comprises at least a 17 nucleotide fragment is GCTCAGTACAGCCACCT (SEQ ID NO: 5332).

In some embodiments, the ribonucleic acid sequence of the at least one ribonucleic acid described above comprises at least a 18 nucleotide fragment of a ribonucleic acid sequence of any of FIGS. 1-15. In some embodiments, the ribonucleic acid sequence of the at least one ribonucleic acid described above comprises at least a 18 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprises at least a 18 nucleotide fragment of a ribonucleic acid sequence of GTAACGGCA-GACTTCTCCACAGG (SEQ ID NO: 5321). In some embodiments, the ribonucleic acid sequence of the at least one ribonucleic acid described above comprises at least a 18 nucleotide fragment of a sequence with a single nucleotide mismatch to a ribonucleic acid sequence of GTAACGGCA-GACTTCTCCACAGG (SEQ ID NO: 5321). For example, if the target sequence is GATGCTCAGTACAGCCACCT-TGG (SEQ ID NO: 5323), the ribonucleic acid sequence of the at least one ribonucleic acid which comprises at least a 18 nucleotide fragment is TGCTCAGTACAGCCACCT (SEQ ID NO: 5333).

In some embodiments, the ribonucleic acid sequence of the at least one ribonucleic acid described above comprise at least a 19 nucleotide fragment of a ribonucleic acid sequence of any of FIGS. 1-15. In some embodiments, the ribonucleic acid sequence of the at least one ribonucleic acid described above comprises at least a 19 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprise at least a 19 nucleotide fragment of a ribonucleic acid sequence of GTAACGGCAGACT-TCTCCACAGG (SEQ ID NO: 5321). In some embodiments, the ribonucleic acid sequence of the at least one ribonucleic acid described above comprises at least a 19 nucleotide fragment of a sequence with a single nucleotide mismatch to a ribonucleic acid sequence of GTAACGGCA-GACTTCTCCACAGG (SEQ ID NO: 5321). For example, if the target sequence is GATGCTCAGTACAGCCACCT-TGG (SEQ ID NO: 5323), the ribonucleic acid sequence of the at least one ribonucleic acid which comprises at least a 19 nucleotide fragment is ATGCTCAGTACAGCCACCT (SEQ ID NO: 5334).

In some embodiments, the ribonucleic acid sequence of the at least one ribonucleic acid described above comprises at least a 20 nucleotide fragment of a ribonucleic acid sequence of any of FIGS. 1-15. In some embodiments, the ribonucleic acid sequence of the at least one ribonucleic acid described above comprises at least a 20 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprises at least a 20 nucleotide fragment of a ribonucleic acid sequence of GTAACGGCA-GACTTCTCCACAGG (SEQ ID NO: 5321). In some embodiments, the ribonucleic acid sequence of the at least one ribonucleic acid described above comprises at least a 20 nucleotide fragment of a sequence with a single nucleotide mismatch to a ribonucleic acid sequence of GTAACGGCA-GACTTCTCCACAGG (SEQ ID NO: 5321). For example, if the target sequence is GATGCTCAGTACAGCCACCT-TGG (SEQ ID NO: 5323), the ribonucleic acid sequence of the at least one ribonucleic acid which comprises at least a 20 nucleotide fragment is GATGCTCAGTACAGCCACCT (SEQ ID NO: 5324).

In some embodiments, the at least one ribonucleic acid in the composition is contained in a nanoparticle. In some embodiments, the at least one ribonucleic acid is contained in a lipid nanoparticle. In some embodiments, the lipid nanoparticle comprises at least one of a cationic lipid, a neutral lipid, an amino lipid, a sterol, and a PEG or PEG-modified lipid.

In some embodiments, at least one of the ribonucleic acids in the composition is a modified ribonucleic acid as described herein (e.g., a synthetic, modified ribonucleic acid, e.g., comprising one to two modified nucleotides selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate, or any other modified nucleotides or modifications described herein).

In some embodiments, a composition of the present invention comprises a nucleic acid sequence encoding a Cas protein. In some embodiments, a composition of the present invention comprises nucleic acid sequence encoding Cas9 protein or a functional portion thereof.

In some embodiments, the nucleic acid encoding the Cas protein (e.g., Cas9) comprises a modified ribonucleic acid as described herein (e.g., a synthetic, modified mRNA described herein, e.g., comprising at least one modified nucleotide selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate or any other modified nucleotides or modifications described herein).

In some aspects, the present invention provides a composition comprising a chimeric nucleic acid comprising a ribonucleic acid encoding a Cas protein and at least one additional ribonucleic acid having a sequence selected from the group consisting of the ribonucleic acid sequences of FIG. 1.

In some aspects, the present invention provides a composition comprising a chimeric nucleic acid comprising a ribonucleic acid encoding a Cas protein and at least one additional ribonucleic acid having a sequence selected from the group consisting of the ribonucleic acid sequences of FIG. 2.

In some aspects, the present invention provides a composition comprising a chimeric nucleic acid comprising a ribonucleic acid encoding a Cas protein and at least one additional ribonucleic acid having a sequence selected from the group consisting of the ribonucleic acid sequences of FIG. 3.

In some aspects, the present invention provides a composition comprising a chimeric nucleic acid comprising a ribonucleic acid encoding a Cas protein and at least one additional ribonucleic acid having a sequence selected from the group consisting of the ribonucleic acid sequences of FIG. 4.

In some aspects, the present invention provides a composition comprising a chimeric nucleic acid comprising a ribonucleic acid encoding a Cas protein and at least one additional ribonucleic acid having a sequence selected from the group consisting of the ribonucleic acid sequences of FIG. 5.

In some aspects, the present invention provides a composition comprising a chimeric nucleic acid comprising a ribonucleic acid encoding a Cas protein and at least one additional ribonucleic acid having a sequence selected from the group consisting of the ribonucleic acid sequences of FIG. 6.

In some aspects, the present invention provides a composition comprising a chimeric nucleic acid comprising a ribonucleic acid encoding a Cas protein and at least one additional ribonucleic acid having a sequence selected from the group consisting of the ribonucleic acid sequences of FIG. 7.

In some aspects, the present invention provides a composition comprising a chimeric nucleic acid comprising a ribonucleic acid encoding a Cas protein and at least one additional ribonucleic acid having a sequence selected from the group consisting of the ribonucleic acid sequences of FIG. 8.

In some aspects, the present invention provides a composition comprising a chimeric nucleic acid comprising a ribonucleic acid encoding a Cas protein and at least one additional ribonucleic acid having a sequence selected from the group consisting of the ribonucleic acid sequences of FIG. 9.

In some aspects, the present invention provides a composition comprising a chimeric nucleic acid comprising a ribonucleic acid encoding a Cas protein and at least one additional ribonucleic acid having a sequence selected from the group consisting of the ribonucleic acid sequences of FIG. 10.

In some aspects, the present invention provides a composition comprising a chimeric nucleic acid comprising a ribonucleic acid encoding a Cas protein and at least one additional ribonucleic acid having a sequence selected from the group consisting of the ribonucleic acid sequences of FIG. 11.

In some aspects, the present invention provides a composition comprising a chimeric nucleic acid comprising a ribonucleic acid encoding a Cas protein and at least one additional ribonucleic acid having a sequence selected from the group consisting of the ribonucleic acid sequences of FIG. 12.

In some aspects, the present invention provides a composition comprising a chimeric nucleic acid comprising a ribonucleic acid encoding a Cas protein and at least one additional ribonucleic acid having a sequence selected from the group consisting of the ribonucleic acid sequences of FIG. 13.

In some aspects, the present invention provides a composition comprising a chimeric nucleic acid comprising a ribonucleic acid encoding a Cas protein and at least one additional ribonucleic acid having a sequence selected from the group consisting of the ribonucleic acid sequences of FIG. 14.

In some aspects, the present invention provides a composition comprising a chimeric nucleic acid comprising a ribonucleic acid encoding a Cas protein and at least one additional ribonucleic acid having a sequence selected from the group consisting of the ribonucleic acid sequences of FIG. 15.

In some aspects, the present invention provides a composition comprising a chimeric nucleic acid comprising a ribonucleic acid encoding a Cas protein and at least one additional ribonucleic acid having a ribonucleic acid sequence of GTAACGGCAGACTTCTCCACAGG (SEQ ID NO: 5321).

In some embodiments, the at least one additional ribonucleic acid sequences described above do not include the 3 nucleotide NGG sequence.

For example, if the target site sequence is GATGCTCAGTACAGCCACCTTGG (SEQ ID NO: 5323), the ribonucleic acid sequence of the at least one additional ribonucleic acid is GATGCTCAGTACAGCCACCT (SEQ ID NO: 5324). As another example, if the target sequence is GATGCTCAGTACAGCCACCTTGG (SEQ ID NO: 5323), a ribonucleic acid sequence with a single nucleotide mismatch which does not include the 3 nucleotide NGG sequence is GATGCTGAGTACAGCCACCT (SEQ ID NO: 5326), with the italicized G being the mismatched nucleotide. Those skilled in the art will appreciate, however, that the single nucleotide mismatch can comprise any nucleotide in the ribonucleic acid, e.g., the first nucleotide, the second nucleotide, the third nucleotide, the fourth nucleotide, the fifth nucleotide, the sixth nucleotide, the seventh nucleotide, the eighth nucleotide, the ninth nucleotide, the tenth nucleotide, the eleventh nucleotide, the twelfth nucleotide, the thirteenth nucleotide, the fourteenth nucleotide, the fifteenth nucleotide, the sixteenth nucleotide, the seventeenth nucleotide, the eighteenth nucleotide, the nineteenth nucleotide, or the twentieth nucleotide of the ribonucleic acid.

In some embodiments, the at least one additional ribonucleic acid described above comprises at least a 12 nucleotide fragment of a ribonucleic acid sequence of any of FIGS. 1-15. In some embodiments, the at least one additional ribonucleic acid described above comprises at least a 12 nucleotide fragment of a sequence with a single nucleotide mismatch to a sequence selected from the group consisting of a ribonucleic acid sequence of any of FIGS. 1-15. In some embodiments, the at least one additional ribonucleic acid described above comprises at least a 12 nucleotide fragment of a ribonucleic acid sequence of any of GTAACGGCAGACTTCTCCACAGG (SEQ ID NO: 5321). In some embodiments, the at least one additional ribonucleic acid described above comprises at least a 12 nucleotide fragment of a sequence with a single nucleotide mismatch to a ribonucleic acid sequence of GTAACGGCAGACTTCTCCACAGG (SEQ ID NO: 5321). For example, if the target sequence is GATGCTCAGTACAGCCACCTTGG (SEQ ID NO: 5323), the ribonucleic acid sequence of the at least one additional ribonucleic acid which comprises at least a 12 nucleotide fragment is GTACAGCCACCT (SEQ ID NO: 5327).

In some embodiments, the ribonucleic acid sequence of the at least one additional ribonucleic acid described above comprises at least a 13 nucleotide fragment of a ribonucleic acid sequence of any of FIGS. 1-15. In some embodiments, the ribonucleic acid sequence of the at least one additional ribonucleic acid described above comprises at least a 13 nucleotide fragment of a sequence with a single nucleotide mismatch to a sequence selected from the group consisting of a ribonucleic acid sequence of any of FIGS. 1-15. In some embodiments, the ribonucleic acid sequence of the at least one additional ribonucleic acid described above comprises at least a 13 nucleotide fragment of a ribonucleic acid sequence of GTAACGGCAGACTTCTCCACAGG (SEQ ID NO: 5321). In some embodiments, the ribonucleic acid sequence of the at least one additional ribonucleic acid described above comprises at least a 13 nucleotide fragment of a sequence with a single nucleotide mismatch to a ribonucleic acid sequence of GTAACGGCAGACTTCTCCACAGG (SEQ ID NO: 5321). For example, if the target sequence is GATGCTCAGTACAGCCACCTTGG (SEQ ID NO: 5323), the ribonucleic acid sequence of the at least one additional ribonucleic acid which comprises at least a 13 nucleotide fragment is AGTACAGCCACCT (SEQ ID NO: 5328).

In some embodiments, the ribonucleic acid sequence of the at least one additional ribonucleic acid described above comprises at least a 14 nucleotide fragment of a ribonucleic acid sequence of any of FIGS. 1-15. In some embodiments, the ribonucleic acid sequence of the at least one additional ribonucleic acid described above comprises at least a 14 nucleotide fragment of a sequence with a single nucleotide mismatch to a sequence selected from the group consisting of a ribonucleic acid sequence of any of FIGS. 1-15. In some embodiments, the ribonucleic acid sequence of the at least one additional ribonucleic acid described above comprises at least a 14 nucleotide fragment of a ribonucleic acid sequence of GTAACGGCAGACTTCTCCACAGG (SEQ ID NO: 5321). In some embodiments, the ribonucleic acid sequence of the at least one additional ribonucleic acid described above comprises at least a 14 nucleotide fragment of a sequence with a single nucleotide mismatch to a ribonucleic acid sequence of GTAACGGCAGACTTCTCCACAGG (SEQ ID NO: 5321). For example, if the target sequence is GATGCTCAGTACAGCCACCTTGG (SEQ ID NO: 5323), the ribonucleic acid sequence of the at least one additional ribonucleic acid which comprises at least a 14 nucleotide fragment is CAGTACAGCCACCT (SEQ ID NO: 5329).

In some embodiments, the ribonucleic acid sequence of the at least one additional ribonucleic acid described above comprises at least a 15 nucleotide fragment of a ribonucleic acid sequence of any of FIGS. 1-15. In some embodiments, the ribonucleic acid sequence of the at least one additional ribonucleic acid described above comprises at least a 15 nucleotide fragment of a sequence with a single nucleotide mismatch to a sequence selected from the group consisting of a ribonucleic acid sequence of any of FIGS. 1-15. In some embodiments, the ribonucleic acid sequence of the at least one additional ribonucleic acid described above comprises at least a 15 nucleotide fragment of a ribonucleic acid sequence of GTAACGGCAGACTTCTCCACAGG (SEQ ID NO: 5321). In some embodiments, the ribonucleic acid sequence of the at least one additional ribonucleic acid described above comprises at least a 15 nucleotide fragment of a sequence with a single nucleotide mismatch to a ribonucleic acid sequence of GTAACGGCAGACTTCTCCACAGG (SEQ ID NO: 5321). For example, if the target sequence is GATGCTCAGTACAGCCACCTTGG (SEQ ID NO: 5323), the ribonucleic acid sequence of the at least one additional ribonucleic acid which comprises at least a 15 nucleotide fragment is TCAGTACAGCCACCT (SEQ ID NO: 5330).

In some embodiments, the ribonucleic acid sequence of the at least one additional ribonucleic acid described above comprise at least a 16 nucleotide fragment of a ribonucleic acid sequence of any of FIGS. 1-15. In some embodiments, the ribonucleic acid sequence of the at least one additional ribonucleic acid described above comprises at least a 16 nucleotide fragment of a sequence with a single nucleotide mismatch to a sequence selected from the group consisting of a ribonucleic acid sequence of any of FIGS. 1-15. In some embodiments, the ribonucleic acid sequence of the at least one additional ribonucleic acid described above comprise at least a 16 nucleotide fragment of a ribonucleic acid sequence of GTAACGGCAGACTTCTCCACAGG (SEQ ID NO: 5321). In some embodiments, the ribonucleic acid sequence of the at least one additional ribonucleic acid described above comprises at least a 16 nucleotide fragment of a sequence with a single nucleotide mismatch to a ribonucleic acid sequence of GTAACGGCAGACTTCTCCACAGG (SEQ ID NO: 5321). For example, if the target sequence is GATGCTCAGTACAGCCACCTTGG (SEQ ID NO: 5323), the ribonucleic acid sequence of the at least one additional ribonucleic acid which comprises at least a 16 nucleotide fragment is CTCAGTACAGCCACCT (SEQ ID NO: 5331).

In some embodiments, the ribonucleic acid sequence of the at least one ribonucleic acid described above comprises at least a 17 nucleotide fragment of a ribonucleic acid sequence of any of FIGS. 1-15. In some embodiments, the ribonucleic acid sequence of the at least one additional ribonucleic acid described above comprises at least a 17 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprises at least a 17 nucleotide fragment of a ribonucleic acid sequence of GTAACGGCAGACTTCTCCACAGG (SEQ ID NO: 5321). In some embodiments, the ribonucleic acid sequence of the at least one additional ribonucleic acid described above comprises at least a 17 nucleotide fragment of a sequence with a single nucleotide mismatch to a ribonucleic acid sequence of GTAACGGCAGACTTCTCCACAGG (SEQ ID NO: 5321). For example, if the target sequence is GATGCTCAGTACAGCCACCTTGG (SEQ ID NO: 5323), the ribonucleic acid sequence of the at least one additional ribonucleic acid which comprises at least a 17 nucleotide fragment is GCTCAGTACAGCCACCT (SEQ ID NO: 5332).

In some embodiments, the ribonucleic acid sequence of the at least one additional ribonucleic acid described above comprises at least a 18 nucleotide fragment of a ribonucleic acid sequence of any of FIGS. 1-15. In some embodiments, the ribonucleic acid sequence of the at least one additional ribonucleic acid described above comprises at least a 18 nucleotide fragment of a sequence with a single nucleotide mismatch to a sequence selected from the group consisting of a ribonucleic acid sequence of any of FIGS. 1-15. In some embodiments, the ribonucleic acid sequence of the at least one additional ribonucleic acid described above comprises at least a 18 nucleotide fragment of a ribonucleic acid sequence of GTAACGGCAGACTTCTCCACAGG (SEQ ID NO: 5321). In some embodiments, the ribonucleic acid sequence of the at least one additional ribonucleic acid described above comprises at least a 18nucleotide fragment of a sequence with a single nucleotide mismatch to a ribonucleic acid sequence of GTAACGGCAGACTTCTCCACAGG (SEQ ID NO: 5321). For example, if the target sequence is GATGCTCAGTACAGCCACCTTGG (SEQ ID NO: 5323), the ribonucleic acid sequence of the at least one additional ribonucleic acid which comprises at least a 18nucleotide fragment is TGCTCAGTACAGCCACCT (SEQ ID NO: 5333).

In some embodiments, the ribonucleic acid sequence of the at least one additional ribonucleic acid described above comprise at least a 19 nucleotide fragment of a ribonucleic acid sequence of any of FIGS. 1-15. In some embodiments, the ribonucleic acid sequence of the at least one additional ribonucleic acid described above comprises at least a 19 nucleotide fragment of a sequence with a single nucleotide mismatch to a sequence selected from the group consisting of a ribonucleic acid sequence of any of FIGS. 1-15. In some embodiments, the ribonucleic acid sequence of the at least one additional ribonucleic acid described above comprise at least a 19 nucleotide fragment of a ribonucleic acid sequence of GTAACGGCAGACTTCTCCACAGG (SEQ ID NO: 5321). In some embodiments, the ribonucleic acid sequence of the at least one additional ribonucleic acid described above comprises at least a 19 nucleotide fragment of a sequence with a single nucleotide mismatch to a ribonucleic acid sequence of GTAACGGCAGACTTCTCCACAGG (SEQ ID NO: 5321). For example, if the target sequence is GATGCTCAGTACAGCCACCTTGG (SEQ ID NO: 5323), the ribonucleic acid sequence of the at least one additional ribonucleic acid which comprises at least a 19 nucleotide fragment is ATGCTCAGTACAGCCACCT (SEQ ID NO: 5334).

In some embodiments, the ribonucleic acid sequence of the at least one additional ribonucleic acid described above comprises at least a 20 nucleotide fragment of a ribonucleic acid sequence of any of FIGS. 1-15. In some embodiments, the ribonucleic acid sequence of the at least one additional ribonucleic acid described above comprises at least a 20 nucleotide fragment of a sequence with a single nucleotide mismatch to a sequence selected from the group consisting of a ribonucleic acid sequence of any of FIGS. 1-15. In some embodiments, the ribonucleic acid sequence of the at least one additional ribonucleic acid described above comprises at least a 20 nucleotide fragment of a ribonucleic acid sequence of GTAACGGCAGACTTCTCCACAGG (SEQ ID NO: 5321). In some embodiments, the ribonucleic acid sequence of the at least one additional ribonucleic acid described above comprises at least a 20 nucleotide fragment of a sequence with a single nucleotide mismatch to a ribonucleic acid sequence of GTAACGGCAGACTTCTCCACAGG (SEQ ID NO: 5321). For example, if the target sequence is GATGCTCAGTACAGCCACCTTGG (SEQ ID NO: 5323), the ribonucleic acid sequence of the at least one additional ribonucleic acid which comprises at least a 20 nucleotide fragment is GATGCTCAGTACAGCCACCT (SEQ ID NO: 5324).

In some aspects, the present invention provides a composition comprising a chimeric nucleic acid comprising a ribonucleic acid encoding a Cas protein and at least one additional ribonucleic acid sequence comprising a sequence with a single nucleotide mismatch to a sequence selected from the group consisting of the ribonucleic acid sequences of FIG. 1.

In some aspects, the present invention provides a composition comprising a chimeric nucleic acid comprising a ribonucleic acid encoding a Cas protein and at least one additional ribonucleic acid sequence comprising a sequence with a single nucleotide mismatch to a sequence selected from the group consisting of the ribonucleic acid sequences of FIG. 2.

In some aspects, the present invention provides a composition comprising a chimeric nucleic acid comprising a ribonucleic acid encoding a Cas protein and at least one additional ribonucleic acid sequence comprising a sequence with a single nucleotide mismatch to a sequence selected from the group consisting of the ribonucleic acid sequences of FIG. 3.

In some aspects, the present invention provides a composition comprising a chimeric nucleic acid comprising a ribonucleic acid encoding a Cas protein and at least one additional ribonucleic acid sequence comprising a sequence with a single nucleotide mismatch to a sequence selected from the group consisting of the ribonucleic acid sequences of FIG. 4.

In some aspects, the present invention provides a composition comprising a chimeric nucleic acid comprising a ribonucleic acid encoding a Cas protein and at least one additional ribonucleic acid sequence comprising a sequence with a single nucleotide mismatch to a sequence selected from the group consisting of the ribonucleic acid sequences of FIG. 5.

In some aspects, the present invention provides a composition comprising a chimeric nucleic acid comprising a ribonucleic acid encoding a Cas protein and at least one additional ribonucleic acid sequence comprising a sequence with a single nucleotide mismatch to a sequence selected from the group consisting of the ribonucleic acid sequences of FIG. 6.

In some aspects, the present invention provides a composition comprising a chimeric nucleic acid comprising a ribonucleic acid encoding a Cas protein and at least one additional ribonucleic acid sequence comprising a sequence with a single nucleotide mismatch to a sequence selected from the group consisting of the ribonucleic acid sequences of FIG. 7.

In some aspects, the present invention provides a composition comprising a chimeric nucleic acid comprising a ribonucleic acid encoding a Cas protein and at least one additional ribonucleic acid sequence comprising a sequence with a single nucleotide mismatch to a sequence selected from the group consisting of the ribonucleic acid sequences of FIG. 8.

In some aspects, the present invention provides a composition comprising a chimeric nucleic acid comprising a ribonucleic acid encoding a Cas protein and at least one additional ribonucleic acid sequence comprising a sequence with a single nucleotide mismatch to a sequence selected from the group consisting of the ribonucleic acid sequences of FIG. 9.

In some aspects, the present invention provides a composition comprising a chimeric nucleic acid comprising a ribonucleic acid encoding a Cas protein and at least one additional ribonucleic acid sequence comprising a sequence with a single nucleotide mismatch to a sequence selected from the group consisting of the ribonucleic acid sequences of FIG. 10.

In some aspects, the present invention provides a composition comprising a chimeric nucleic acid comprising a ribonucleic acid encoding a Cas protein and at least one additional ribonucleic acid sequence comprising a sequence with a single nucleotide mismatch to a sequence selected from the group consisting of the ribonucleic acid sequences of FIG. 11.

In some aspects, the present invention provides a composition comprising a chimeric nucleic acid comprising a ribonucleic acid encoding a Cas protein and at least one additional ribonucleic acid sequence comprising a sequence with a single nucleotide mismatch to a sequence selected from the group consisting of the ribonucleic acid sequences of FIG. 12.

In some aspects, the present invention provides a composition comprising a chimeric nucleic acid comprising a ribonucleic acid encoding a Cas protein and at least one additional ribonucleic acid sequence comprising a sequence with a single nucleotide mismatch to a sequence selected from the group consisting of the ribonucleic acid sequences of FIG. 13.

In some aspects, the present invention provides a composition comprising a chimeric nucleic acid comprising a ribonucleic acid encoding a Cas protein and at least one additional ribonucleic acid sequence comprising a sequence with a single nucleotide mismatch to a sequence selected from the group consisting of the ribonucleic acid sequences of FIG. 14.

In some aspects, the present invention provides a composition comprising a chimeric nucleic acid comprising a ribonucleic acid encoding a Cas protein and at least one additional ribonucleic acid sequence comprising a sequence with a single nucleotide mismatch to a sequence selected from the group consisting of the ribonucleic acid sequences of FIG. 15.

In some aspects, the present invention provides a composition comprising a chimeric nucleic acid comprising a ribonucleic acid encoding a Cas protein and at least one additional ribonucleic acid sequence comprising a sequence with a single nucleotide mismatch to a ribonucleic acid sequence of GTAACGGCAGACTTCTCCACAGG (SEQ ID NO: 5321).

In some embodiments, the at least one additional ribonucleic acid sequences described above do not include the 3 nucleotide NGG sequence. For example, if the target site sequence is GATGCTCAGTACAGCCACCTTGG (SEQ ID NO: 5323), the ribonucleic acid sequence of the at least one additional ribonucleic acid is GATGCTCAGTACAGCCACCT (SEQ ID NO: 5324). As another example, if the target sequence is GATGCTCAGTACAGCCACCTTGG (SEQ ID NO: 5323), a ribonucleic acid sequence with a single nucleotide mismatch which does not include the 3 nucleotide NGG sequence is GATGCTGAGTACAGCCACCT (SEQ ID NO: 5326), with the italicized G being the mismatched nucleotide. Those skilled in the art will appreciate, however, that the single nucleotide mismatch can comprise any nucleotide in the ribonucleic acid, e.g., the first nucleotide, the second nucleotide, the third nucleotide, the fourth nucleotide, the fifth nucleotide, the sixth nucleotide, the seventh nucleotide, the eighth nucleotide, the ninth nucleotide, the tenth nucleotide, the eleventh nucleotide, the twelfth nucleotide, the thirteenth nucleotide, the fourteenth nucleotide, the fifteenth nucleotide, the sixteenth nucleotide, the seventeenth nucleotide, the eighteenth nucleotide, the nineteenth nucleotide, or the twentieth nucleotide of the ribonucleic acid.

In some embodiments, the at least one additional ribonucleic acid described above comprises at least a 12 nucleotide fragment of a ribonucleic acid sequence of any of FIGS. 1-15. In some embodiments, the at least one additional ribonucleic acid described above comprises at least a 12 nucleotide fragment of a sequence with a single nucleotide mismatch to a sequence selected from the group consisting of a ribonucleic acid sequence of any of FIGS. 1-15. In some embodiments, the at least one additional ribonucleic acid described above comprises at least a 12 nucleotide fragment of a ribonucleic acid sequence of GTAACGGCAGACTTCTCCACAGG (SEQ ID NO: 5321). In some embodiments, the at least one additional ribonucleic acid described above comprises at least a 12 nucleotide fragment of a sequence with a single nucleotide mismatch to a sequence selected from the group consisting of a ribonucleic acid sequence of GTAACGGCAGACTTCTCCACAGG (SEQ ID NO: 5321). For example, if the target sequence is GATGCTCAGTACAGCCACCTTGG (SEQ ID NO: 5323), the ribonucleic acid sequence of the at least one additional ribonucleic acid which comprises at least a 12 nucleotide fragment is GTACAGCCACCT (SEQ ID NO: 5327).

In some embodiments, the ribonucleic acid sequence of the at least one additional ribonucleic acid described above comprises at least a 13 nucleotide fragment of a ribonucleic acid sequence of any of FIGS. 1-15. In some embodiments, the ribonucleic acid sequence of the at least one additional ribonucleic acid described above comprises at least a 13 nucleotide fragment of a sequence with a single nucleotide mismatch to a sequence selected from the group consisting of a ribonucleic acid sequence of any of FIGS. 1-15. In some embodiments, the ribonucleic acid sequence of the at least one additional ribonucleic acid described above comprises at least a 13 nucleotide fragment of a ribonucleic acid sequence of GTAACGGCAGACTTCTCCACAGG (SEQ ID NO: 5321). In some embodiments, the ribonucleic acid sequence of the at least one additional ribonucleic acid described above comprises at least a 13 nucleotide fragment of a sequence with a single nucleotide mismatch to a ribonucleic acid sequence of GTAACGGCAGACTTCTCCACAGG (SEQ ID NO: 5321). For example, if the target sequence is GATGCTCAGTACAGCCACCTTGG (SEQ ID NO: 5323), the ribonucleic acid sequence of the at least one additional ribonucleic acid which comprises at least a 13 nucleotide fragment is AGTACAGCCACCT (SEQ ID NO: 5328).

In some embodiments, the ribonucleic acid sequence of the at least one additional ribonucleic acid described above comprises at least a 14 nucleotide fragment of a ribonucleic acid sequence of any of FIGS. 1-15. In some embodiments, the ribonucleic acid sequence of the at least one additional ribonucleic acid described above comprises at least a 14 nucleotide fragment of a sequence with a single nucleotide mismatch to a sequence selected from the group consisting of a ribonucleic acid sequence of any of FIGS. 1-15. In some embodiments, the ribonucleic acid sequence of the at least one additional ribonucleic acid described above comprises at least a 14 nucleotide fragment of a ribonucleic acid sequence of GTAACGGCAGACTTCTCCACAGG (SEQ ID NO: 5321). In some embodiments, the ribonucleic acid sequence of the at least one additional ribonucleic acid described above comprises at least a 14 nucleotide fragment of a sequence with a single nucleotide mismatch to a ribonucleic acid sequence of GTAACGGCAGACTTCTC-CACAGG (SEQ ID NO: 5321). For example, if the target sequence is GATGCTCAGTACAGCCACCTTGG (SEQ ID NO: 5323), the ribonucleic acid sequence of the at least one additional ribonucleic acid which comprises at least a 14 nucleotide fragment is CAGTACAGCCACCT (SEQ ID NO: 5329).

In some embodiments, the ribonucleic acid sequence of the at least one additional ribonucleic acid described above comprises at least a 15 nucleotide fragment of a ribonucleic acid sequence of any of FIGS. 1-15. In some embodiments, the ribonucleic acid sequence of the at least one additional ribonucleic acid described above comprises at least a 15 nucleotide fragment of a sequence with a single nucleotide mismatch to a sequence selected from the group consisting of a ribonucleic acid sequence of any of FIGS. 1-15. In some embodiments, the ribonucleic acid sequence of the at least one additional ribonucleic acid described above comprises at least a 15 nucleotide fragment of a ribonucleic acid sequence of GTAACGGCAGACTTCTCCACAGG (SEQ ID NO: 5321). In some embodiments, the ribonucleic acid sequence of the at least one additional ribonucleic acid described above comprises at least a 15 nucleotide fragment of a sequence with a single nucleotide mismatch to a ribonucleic acid sequence of GTAACGGCAGACTTCTCCACAGG (SEQ ID NO: 5321). For example, if the target sequence is GATGCTCAGTACAGCCACCTTGG (SEQ ID NO: 5323), the ribonucleic acid sequence of the at least one additional ribonucleic acid which comprises at least a 15 nucleotide fragment is TCAGTACAGCCACCT (SEQ ID NO: 5330).

In some embodiments, the ribonucleic acid sequence of the at least one additional ribonucleic acid described above comprise at least a 16 nucleotide fragment of a ribonucleic acid sequence of any of FIGS. 1-15. In some embodiments, the ribonucleic acid sequence of the at least one additional ribonucleic acid described above comprises at least a 16 nucleotide fragment of a sequence with a single nucleotide mismatch to a sequence selected from the group consisting of a ribonucleic acid sequence of any of FIGS. 1-15. In some embodiments, the ribonucleic acid sequence of the at least one additional ribonucleic acid described above comprise at least a 16 nucleotide fragment of a ribonucleic acid sequence of GTAACGGCAGACTTCTCCACAGG (SEQ ID NO: 5321). In some embodiments, the ribonucleic acid sequence of the at least one additional ribonucleic acid described above comprises at least a 16 nucleotide fragment of a sequence with a single nucleotide mismatch to a ribonucleic acid sequence of GTAACGGCAGACTTCTCCACAGG (SEQ ID NO: 5321). For example, if the target sequence is GATGCTCAGTACAGCCACCTTGG (SEQ ID NO: 5323), the ribonucleic acid sequence of the at least one additional ribonucleic acid which comprises at least a 16 nucleotide fragment is CTCAGTACAGCCACCT (SEQ ID NO: 5331).

In some embodiments, the ribonucleic acid sequence of the at least one ribonucleic acid described above comprises at least a 17 nucleotide fragment of a ribonucleic acid sequence of any of FIGS. 1-15. In some embodiments, the ribonucleic acid sequence of the at least one additional ribonucleic acid described above comprises at least a 17 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprises at least a 17 nucleotide fragment of a ribonucleic acid sequence of GTAACGGCAGACTTCTCCACAGG (SEQ ID NO: 5321). In some embodiments, the ribonucleic acid sequence of the at least one additional ribonucleic acid described above comprises at least a 17 nucleotide fragment of a sequence with a single nucleotide mismatch to a ribonucleic acid sequence of GTAACGGCAGACTTCTCCACAGG (SEQ ID NO: 5321). For example, if the target sequence is GATGCTCAGTACAGCCACCTTGG (SEQ ID NO: 5323), the ribonucleic acid sequence of the at least one additional ribonucleic acid which comprises at least a 17 nucleotide fragment is GCTCAGTACAGCCACCT (SEQ ID NO: 5332).

In some embodiments, the ribonucleic acid sequence of the at least one additional ribonucleic acid described above comprises at least a 18 nucleotide fragment of a ribonucleic acid sequence of any of FIGS. 1-15. In some embodiments, the ribonucleic acid sequence of the at least one additional ribonucleic acid described above comprises at least a 18 nucleotide fragment of a sequence with a single nucleotide mismatch to a sequence selected from the group consisting of a ribonucleic acid sequence of any of FIGS. 1-15. In some embodiments, the ribonucleic acid sequence of the at least one additional ribonucleic acid described above comprises at least a 18 nucleotide fragment of a ribonucleic acid sequence of GTAACGGCAGACTTCTCCACAGG (SEQ ID NO: 5321). In some embodiments, the ribonucleic acid sequence of the at least one additional ribonucleic acid described above comprises at least a 18 nucleotide fragment of a sequence with a single nucleotide mismatch to a ribonucleic acid sequence of GTAACGGCAGACTTCTCCACAGG (SEQ ID NO: 5321). For example, if the target sequence is GATGCTCAGTACAGCCACCTTGG (SEQ ID NO: 5323), the ribonucleic acid sequence of the at least one additional ribonucleic acid which comprises at least a 18 nucleotide fragment is TGCTCAGTACAGCCACCT (SEQ ID NO: 5333).

In some embodiments, the ribonucleic acid sequence of the at least one additional ribonucleic acid described above comprise at least a 19 nucleotide fragment of a ribonucleic acid sequence of any of FIGS. 1-15. In some embodiments, the ribonucleic acid sequence of the at least one additional ribonucleic acid described above comprises at least a 19 nucleotide fragment of a sequence with a single nucleotide mismatch to a sequence selected from the group consisting of a ribonucleic acid sequence of any of FIGS. 1-15. In some embodiments, the ribonucleic acid sequence of the at least one additional ribonucleic acid described above comprise at least a 19 nucleotide fragment of a ribonucleic acid sequence of GTAACGGCAGACTTCTCCACAGG (SEQ ID NO: 5321). In some embodiments, the ribonucleic acid sequence of the at least one additional ribonucleic acid described above comprises at least a 19 nucleotide fragment of a sequence with a single nucleotide mismatch to a ribonucleic acid sequence of GTAACGGCAGACTTCTC-CACAGG (SEQ ID NO: 5321). For example, if the target sequence is GATGCTCAGTACAGCCACCTTGG (SEQ ID NO: 5323), the ribonucleic acid sequence of the at least one additional ribonucleic acid which comprises at least a 19 nucleotide fragment is ATGCTCAGTACAGCCACCT (SEQ ID NO: 5334).

In some embodiments, the ribonucleic acid sequence of the at least one additional ribonucleic acid described above comprises at least a 20 nucleotide fragment of a ribonucleic acid sequence of any of FIGS. 1-15. In some embodiments, the ribonucleic acid sequence of the at least one additional ribonucleic acid described above comprises at least a 20 nucleotide fragment of a sequence with a single nucleotide mismatch to a sequence selected from the group consisting of a ribonucleic acid sequence of any of FIGS. 1-15. In some embodiments, the ribonucleic acid sequence of the at least one additional ribonucleic acid described above comprises at least a 20 nucleotide fragment of a ribonucleic acid sequence of GTAACGGCAGACTTCTCCACAGG (SEQ ID NO: 5321). In some embodiments, the ribonucleic acid sequence of the at least one additional ribonucleic acid described above comprises at least a 20 nucleotide fragment of a sequence with a single nucleotide mismatch to a ribonucleic acid sequence of GTAACGGCAGACTTCTCCACAGG (SEQ ID NO: 5321). For example, if the target sequence is GATGCTCAGTACAGCCACCTTGG (SEQ ID NO: 5323), the ribonucleic acid sequence of the at least one additional ribonucleic acid which comprises at least a 20 nucleotide fragment is GATGCTCAGTACAGCCACCT (SEQ ID NO: 5324).

In some embodiments, a composition of the present invention comprises a nucleic acid sequence encoding a fluorescent protein selected from the group consisting of green fluorescent protein and red fluorescent protein. In some embodiments, a composition of the present invention comprises a promoter operably linked to the chimeric nucleic acid. In some embodiments, the promoter is optimized for increased expression in human stem cells. In some embodiments, the promoter is selected from the group consisting of a Cytomegalovirus (CMV) early enhancer element and a chicken beta-actin promoter, a chicken beta-actin promoter, an elongation factor-1 alpha promoter, and a ubiquitin promoter.

In some embodiments, the chimeric nucleic acid is contained in a nanoparticle. In some embodiments, the chimeric nucleic acid is contained in a lipid nanoparticle as described herein. In some embodiments, the chimeric nucleic acid comprises at least one modified nucleotide described herein. In some embodiments, the Cas protein comprises a Cas9 protein or a functional portion thereof.

For in vivo methods, a therapeutically effective amount of a composition described herein can be administered to a subject. Methods of administering compositions to a subject are known in the art and easily available to one of skill in the art.

In some embodiments, a composition described herein includes one or more additional pharmaceutically active agents for treating or preventing the disorder associated with expression of the target polynucleotide sequence.

The present invention also provides kits for practicing any of the methods of the present invention, as well as kits comprising the compositions of the present invention, and instructions for using the kits for altering target polynucleotide sequences in a cell.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of the ribonucleic acid sequences of FIG. 1.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of the ribonucleic acid sequences of FIG. 2.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of the ribonucleic acid sequences of FIG. 3.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of the ribonucleic acid sequences of FIG. 4.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of the ribonucleic acid sequences of FIG. 5.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of the ribonucleic acid sequences of FIG. 6.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of the ribonucleic acid sequences of FIG. 7.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of the ribonucleic acid sequences of FIG. 8.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of the ribonucleic acid sequences of FIG. 9.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of the ribonucleic acid sequences of FIG. 10.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of the ribonucleic acid sequences of FIG. 11.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of the ribonucleic acid sequences of FIG. 12.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of the ribonucleic acid sequences of FIG. 13.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of the ribonucleic acid sequences of FIG. 14.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of the ribonucleic acid sequences of FIG. 15.

In some aspects, the present invention comprises a kit for altering a target polynucleotide sequence in a cell comprising a Cas9 protein or a nucleic acid encoding the Cas9 protein, and at least one ribonucleic acid sequence having a ribonucleic acid sequence of GTAACGGCAGACTTCTCCACAGG (SEQ ID NO: 5321).

In some embodiments, the at least one ribonucleic acid sequences described above do not include the 3 nucleotide NGG sequence. For example, if the target site sequence is GATGCTCAGTACAGCCACCTTGG (SEQ ID NO: 5323), the ribonucleic acid sequence of the at least one ribonucleic acid sequence is GATGCTCAGTACAGCCACCT (SEQ ID NO: 5324). As another example, if the target sequence is GATGCTCAGTACAGCCACCTTGG (SEQ ID NO: 5323), a ribonucleic acid sequence with a single nucleotide mismatch which does not include the 3 nucleotide NGG sequence is GATGCTGAGTACAGCCACCT (SEQ ID NO: 5326), with the italicized G being the mismatched nucleotide. Those skilled in the art will appreciate, however, that the single nucleotide mismatch can comprise any nucleotide in the ribonucleic acid, e.g., the first nucleotide, the second nucleotide, the third nucleotide, the fourth nucleotide, the fifth nucleotide, the sixth nucleotide, the seventh nucleotide, the eighth nucleotide, the ninth nucleotide, the tenth nucleotide, the eleventh nucleotide, the twelfth nucleotide, the thirteenth nucleotide, the fourteenth nucleotide, the fifteenth nucleotide, the sixteenth nucleotide, the seventeenth nucleotide, the eighteenth nucleotide, the nineteenth nucleotide, or the twentieth nucleotide of the ribonucleic acid.

In some embodiments, the at least one ribonucleic acid described above comprises at least a 12 nucleotide fragment of a ribonucleic acid sequence of any of FIGS. 1-15. In some embodiments, the at least one ribonucleic acid described above comprises at least a 12 nucleotide fragment of a sequence with a single nucleotide mismatch to a sequence selected from the group consisting of a ribonucleic acid sequence of any of FIGS. 1-15. In some embodiments, the at least one ribonucleic acid described above comprises at least a 12 nucleotide fragment of a ribonucleic acid sequence of GTAACGGCAGACTTCTCCACAGG (SEQ ID NO: 5321). In some embodiments, the at least one ribonucleic acid described above comprises at least a 12 nucleotide fragment of a sequence with a single nucleotide mismatch to a ribonucleic acid sequence of GTAACGGCAGACTTCTCCACAGG (SEQ ID NO: 5321). For example, if the target sequence is GATGCTCAGTACAGCCACCTTGG (SEQ ID NO: 5323), the ribonucleic acid sequence of the at least one ribonucleic acid which comprises at least a 12 nucleotide fragment is GTACAGCCACCT (SEQ ID NO: 5327).

In some embodiments, the ribonucleic acid sequence of the at least one ribonucleic acid described above comprises at least a 13 nucleotide fragment of a ribonucleic acid sequence of any of FIGS. 1-15. In some embodiments, the ribonucleic acid sequence of the at least one ribonucleic acid described above comprises at least a 13 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprises at least a 13nucleotide fragment of a ribonucleic acid sequence of GTAACGGCAGACTTCTCCACAGG (SEQ ID NO: 5321). In some embodiments, the ribonucleic acid sequence of the at least one ribonucleic acid described above comprises at least a 13 nucleotide fragment of a sequence with a single nucleotide mismatch to f a ribonucleic acid sequence of GTAACGGCAGACTTCTCCACAGG (SEQ ID NO: 5321). For example, if the target sequence is GATGCTCAGTACAGCCACCTTGG (SEQ ID NO: 5323), the ribonucleic acid sequence of the at least one ribonucleic acid which comprises at least a 13 nucleotide fragment is AGTACAGCCACCT (SEQ ID NO: 5328).

In some embodiments, the ribonucleic acid sequence of the at least one ribonucleic acid described above comprises at least a 14 nucleotide fragment of a ribonucleic acid sequence of any of FIGS. 1-15 In some embodiments, the ribonucleic acid sequence of the at least one ribonucleic acid described above comprises at least a 14 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprises at least a 14 nucleotide fragment of a ribonucleic acid sequence of GTAACGGCAGACTTCTCCACAGG (SEQ ID NO: 5321). In some embodiments, the ribonucleic acid sequence of the at least one ribonucleic acid described above comprises at least a 14 nucleotide fragment of a sequence with a single nucleotide mismatch to a ribonucleic acid sequence of GTAACGGCAGACTTCTCTCCACAGG (SEQ ID NO: 5321). For example, if the target sequence is GATGCTCAGTACAGCCACCTTGG (SEQ ID NO: 5323), the ribonucleic acid sequence of the at least one ribonucleic acid which comprises at least a 14 nucleotide fragment is CAGTACAGCCACCT (SEQ ID NO: 5329).

In some embodiments, the ribonucleic acid sequence of the at least one ribonucleic acid described above comprises at least a 15 nucleotide fragment of a ribonucleic acid sequence of any of FIGS. 1-15. In some embodiments, the ribonucleic acid sequence of the at least one ribonucleic acid described above comprises at least a 15 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprises at least a 15 nucleotide fragment of a ribonucleic acid sequence of GTAACGGCAGACTTCTCCACAGG (SEQ ID NO: 5321). In some embodiments, the ribonucleic acid sequence of the at least one ribonucleic acid described above comprises at least a 15 nucleotide fragment of a sequence with a single nucleotide mismatch to a ribonucleic acid sequence of GTAACGGCAGACTTCTCCACAGG (SEQ ID NO: 5321). For example, if the target sequence is GATGCTCAGTACAGCCACCTTGG (SEQ ID NO: 5323), the ribonucleic acid sequence of the at least one ribonucleic acid which comprises at least a 15 nucleotide fragment is TCAGTACAGCCACCT (SEQ ID NO: 5330).

In some embodiments, the ribonucleic acid sequence of the at least one ribonucleic acid described above comprise at least a 16 nucleotide fragment of a ribonucleic acid sequence of any of FIGS. 1-15. In some embodiments, the ribonucleic acid sequence of the at least one ribonucleic acid described above comprises at least a 16 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprise at least a 16 nucleotide fragment of a ribonucleic acid sequence of GTAACGGCAGACT-TCTCCACAGG (SEQ ID NO: 5321). In some embodiments, the ribonucleic acid sequence of the at least one ribonucleic acid described above comprises at least a 16 nucleotide fragment of a sequence with a single nucleotide mismatch to a ribonucleic acid sequence of GTAACGGCA-GACTTCTCCACAGG (SEQ ID NO: 5321). For example, if the target sequence is GATGCTCAGTACAGCCACCT-TGG (SEQ ID NO: 5323), the ribonucleic acid sequence Jr the at least one ribonucleic acid which comprises at least a 16 nucleotide fragment is CTCAGTACAGCCACCT (SEQ ID NO: 5331).

In some embodiments, the ribonucleic acid sequence of the at least one ribonucleic acid described above comprises at least a 17 nucleotide fragment of a ribonucleic acid sequence of any of FIGS. 1-15. In some embodiments, the ribonucleic acid sequence of the at least one ribonucleic acid described above comprises at least a 17 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprises at least a 17 nucleotide fragment of a ribonucleic acid sequence of GTAACGGCA-GACTTCTCCACAGG (SEQ ID NO: 5321). In some embodiments, the ribonucleic acid sequence of the at least one ribonucleic acid described above comprises at least a 17 nucleotide fragment of a sequence with a single nucleotide mismatch to a ribonucleic acid sequence of GTAACGGCA-GACTTCTCCACAGG (SEQ ID NO: 5321). For example, if the target sequence is GATGCTCAGTACAGCCACCT-TGG (SEQ ID NO: 5323), the ribonucleic acid sequence of the at least one ribonucleic acid which comprises at least a 17 nucleotide fragment is GCTCAGTACAGCCACCT (SEQ ID NO: 5332).

In some embodiments, the ribonucleic acid sequence of the at least one ribonucleic acid described above comprises at least a 18 nucleotide fragment of a ribonucleic acid sequence of any of FIGS. 1-15. In some embodiments, the ribonucleic acid sequence of the at least one ribonucleic acid described above comprises at least a 18 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprises at least a 18 nucleotide fragment of a ribonucleic acid sequence of GTAACGGCA-GACTTCTCCACAGG (SEQ ID NO: 5321). In some embodiments, the ribonucleic acid sequence of the at least one ribonucleic acid described above comprises at least a 18 nucleotide fragment of a sequence with a single nucleotide mismatch to a ribonucleic acid sequence of GTAACGGCA-GACTTCTCCACAGG (SEQ ID NO: 5321). For example, if the target sequence is GATGCTCAGTACAGCCACCT-TGG (SEQ ID NO: 5323), the ribonucleic acid sequence of the at least one ribonucleic acid which comprises at least a 18 nucleotide fragment is TGCTCAGTACAGCCACCT (SEQ ID NO: 5333).

In some embodiments, the ribonucleic acid sequence of the at least one ribonucleic acid described above comprise at least a 19 nucleotide fragment of a ribonucleic acid sequence of any of FIGS. 1-15. In some embodiments, the ribonucleic acid sequence of the at least one ribonucleic acid described above comprises at least a 19 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprise at least a 19 nucleotide fragment of a ribonucleic acid sequence of GTAACGGCAGACT-TCTCCACAGG (SEQ ID NO: 5321). In some embodiments, the ribonucleic acid sequence of the at least one ribonucleic acid described above comprises at least a 19 nucleotide fragment of a sequence with a single nucleotide mismatch to a ribonucleic acid sequence of GTAACGGCA-GACTTCTCCACAGG CSEQ ID NO: 5321). For example, if the target sequence is GATGCTCAGTACAGCCACCT-TGG (SEQ ID NO: 5323), the ribonucleic acid sequence of the at least one ribonucleic acid which comprises at least a 19 nucleotide fragment is ATGCTCAGTACAGCCACCT (SEQ ID NO: 5334).

In some embodiments, the ribonucleic acid sequence of the at least one ribonucleic acid described above comprises at least a 20 nucleotide fragment of a ribonucleic acid sequence of any of FIGS. 1-15. In some embodiments, the ribonucleic acid sequence of the at least one ribonucleic acid described above comprises at least a 20 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprises at least a 20 nucleotide fragment of a ribonucleic acid sequence of GTAACGGCA-GACTTCTCCACAGG (SEQ ID NO: 5321). In some embodiments, the ribonucleic acid sequence of the at least one ribonucleic acid described above comprises at least a 20 nucleotide fragment of a sequence with a single nucleotide mismatch to a ribonucleic acid sequence of GTAACGGCA-GACTTCTCCACAGG (SEQ ID NO: 5321). For example, if the target sequence is GATGCTCAGTACAGCCACCT-TGG (SEQ ID NO: 5323), the ribonucleic acid sequence of the at least one ribonucleic acid which comprises at least a 20 nucleotide fragment is GATGCTCAGTACAGCCACCT (SEQ ID NO: 5324).

In some aspects, the present invention comprises a kit for altering a target polynucleotide sequence in a cell comprising a Cas9 protein or a nucleic acid encoding the Cas9 protein, and at least one ribonucleic acid sequence with a single nucleotide mismatch to a ribonucleic acid sequence selected from the group consisting of the ribonucleic acid sequences of FIG. 1, and any combination thereof.

In some aspects, the present invention comprises a kit for altering a target polynucleotide sequence in a cell comprising a Cas9 protein or a nucleic acid encoding the Cas9 protein, and at least one ribonucleic acid sequence with a single nucleotide mismatch to a ribonucleic acid sequence selected from the group consisting of the ribonucleic acid sequences of FIG. 2, and any combination thereof.

In some aspects, the present invention comprises a kit for altering a target polynucleotide sequence in a cell comprising a Cas9 protein or a nucleic acid encoding the Cas9 protein, and at least one ribonucleic acid sequence with a single nucleotide mismatch to a ribonucleic acid sequence selected from the group consisting of the ribonucleic acid sequences of FIG. 3, and any combination thereof.

In some aspects, the present invention comprises a kit for altering a target polynucleotide sequence in a cell comprising a Cas9 protein or a nucleic acid encoding the Cas9 protein, and at least one ribonucleic acid sequence with a single nucleotide mismatch to a ribonucleic acid sequence selected from the group consisting of the ribonucleic acid sequences of FIG. 4, and any combination thereof.

In some aspects, the present invention comprises a kit for altering a target polynucleotide sequence in a cell comprising a Cas9 protein or a nucleic acid encoding the Cas9 protein, and at least one ribonucleic acid sequence with a single nucleotide mismatch to a ribonucleic acid sequence selected from the group consisting of the ribonucleic acid sequences of FIG. 5, and any combination thereof.

In some aspects, the present invention comprises a kit for altering a target polynucleotide sequence in a cell comprising a Cas9 protein or a nucleic acid encoding the Cas9 protein, and at least one ribonucleic acid sequence with a single nucleotide mismatch to a ribonucleic acid sequence selected from the group consisting of the ribonucleic acid sequences of FIG. 6, and any combination thereof.

In some aspects, the present invention comprises a kit for altering a target polynucleotide sequence in a cell comprising a Cas9 protein or a nucleic acid encoding the Cas9 protein, and at least one ribonucleic acid sequence with a single nucleotide mismatch to a ribonucleic acid sequence selected from the group consisting of the ribonucleic acid sequences of FIG. 7, and any combination thereof.

In some aspects, the present invention comprises a kit for altering a target polynucleotide sequence in a cell comprising a Cas9 protein or a nucleic acid encoding the Cas9 protein, and at least one ribonucleic acid sequence with a single nucleotide mismatch to a ribonucleic acid sequence selected from the group consisting of the ribonucleic acid sequences of FIG. 8, and any combination thereof.

In some aspects, the present invention comprises a kit for altering a target polynucleotide sequence in a cell comprising a Cas9 protein or a nucleic acid encoding the Cas9 protein, and at least one ribonucleic acid sequence with a single nucleotide mismatch to a ribonucleic acid sequence selected from the group consisting of the ribonucleic acid sequences of FIG. 9, and any combination thereof.

In some aspects, the present invention comprises a kit for altering a target polynucleotide sequence in a cell comprising a Cas9 protein or a nucleic acid encoding the Cas9 protein, and at least one ribonucleic acid sequence with a single nucleotide mismatch to a ribonucleic acid sequence selected from the group consisting of the ribonucleic acid sequences of FIG. 10, and any combination thereof.

In some aspects, the present invention comprises a kit for altering a target polynucleotide sequence in a cell comprising a Cas9 protein or a nucleic acid encoding the Cas9 protein, and at least one ribonucleic acid sequence with a single nucleotide mismatch to a ribonucleic acid sequence selected from the group consisting of the ribonucleic acid sequences of FIG. 11, and any combination thereof.

In some aspects, the present invention comprises a kit for altering a target polynucleotide sequence in a cell comprising a Cas9 protein or a nucleic acid encoding the Cas9 protein, and at least one ribonucleic acid sequence with a single nucleotide mismatch to a ribonucleic acid sequence selected from the group consisting of the ribonucleic acid sequences of FIG. 12, and any combination thereof.

In some aspects, the present invention comprises a kit for altering a target polynucleotide sequence in a cell comprising a Cas9 protein or a nucleic acid encoding the Cas9 protein, and at least one ribonucleic acid sequence with a single nucleotide mismatch to a ribonucleic acid sequence selected from the group consisting of the ribonucleic acid sequences of FIG. 13, and any combination thereof.

In some aspects, the present invention comprises a kit for altering a target polynucleotide sequence in a cell comprising a Cas9 protein or a nucleic acid encoding the Cas9 protein, and at least one ribonucleic acid sequence with a single nucleotide mismatch to a ribonucleic acid sequence selected from the group consisting of the ribonucleic acid sequences of FIG. 14, and any combination thereof.

In some aspects, the present invention comprises a kit for altering a target polynucleotide sequence in a cell comprising a Cas9 protein or a nucleic acid encoding the Cas9 protein, and at least one ribonucleic acid sequence with a single nucleotide mismatch to a ribonucleic acid sequence selected from the group consisting of the ribonucleic acid sequences of FIG. 15, and any combination thereof.

In some aspects, the present invention comprises a kit for altering a target polynucleotide sequence in a cell comprising a Cas9 protein or a nucleic acid encoding the Cas9 protein, and at least one ribonucleic acid sequence with a single nucleotide mismatch to a ribonucleic acid sequence of GTAACGGCAGACTTCTCCACAGG (SEQ ID NO: 5321).

In some embodiments, the at least one ribonucleic acid sequences with the single nucleotide mismatches described above do not include the 3 nucleotide NGG sequence. For example, if the target site sequence is GATGCTCAGTACAGCCACCTTGG (SEQ ID NO: 5323), the ribonucleic acid sequence of the at least one ribonucleic acid sequence is GATGCTCAGTACAGCCACCT (SEQ ID NO: 5324). As another example, if the target sequence is GATGCTCAGTACAGCCACCTTGG (SEQ ID NO: 5323), a ribonucleic acid sequence with a single nucleotide mismatch which does not include the 3 nucleotide NGG sequence is GATGCTGAGTACAGCCACCT (SEQ ID NO: 5326), with the italicized G being the mismatched nucleotide. Those skilled in the art will appreciate, however, that the single nucleotide mismatch can comprise any nucleotide in the ribonucleic acid, e.g., the first nucleotide, the second nucleotide, the third nucleotide, the fourth nucleotide, the fifth nucleotide, the sixth nucleotide, the seventh nucleotide, the eighth nucleotide, the ninth nucleotide, the tenth nucleotide, the eleventh nucleotide, the twelfth nucleotide, the thirteenth nucleotide, the fourteenth nucleotide, the fifteenth nucleotide, the sixteenth nucleotide, the seventeenth nucleotide, the eighteenth nucleotide, the nineteenth nucleotide, or the twentieth nucleotide of the ribonucleic acid.

In some embodiments, the at least one ribonucleic acid described above comprises at least a 12 nucleotide fragment of a ribonucleic acid sequence of any of FIGS. 1-15. In some embodiments, the at least one ribonucleic acid described above comprises at least a 12 nucleotide fragment of a sequence with a single nucleotide mismatch to a sequence selected from the group consisting of a ribonucleic acid sequence of any of FIGS. 1-15. In some embodiments, the at least one ribonucleic acid described above comprises at least a 12 nucleotide fragment of a ribonucleic acid sequence of GTAACGGCAGACTTCTCCACAGG (SEQ ID NO: 5321). In some embodiments, the at least one ribonucleic acid described above comprises at least a 12 nucleotide fragment of a sequence with a single nucleotide mismatch to a ribonucleic acid sequence of GTAACGGCAGACTTCTC-CACAGG (SEQ ID NO: 5321). For example, if the target sequence is GATGCTCAGTACAGCCACCTTGG (SEQ ID NO: 5323), the ribonucleic acid sequence of the at least one ribonucleic acid which comprises at least a 12 nucleotide fragment is GTACAGCCACCT (SEQ ID NO: 5327).

In some embodiments, the ribonucleic acid sequence of the at least one ribonucleic acid described above comprises at least a 13 nucleotide fragment of a ribonucleic acid sequence of any of FIGS. 1-15. In some embodiments, the ribonucleic acid sequence of the at least one ribonucleic acid described above comprises at least a 13 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprises at least a 13 nucleotide fragment of a ribonucleic acid sequence of GTAACGGCA-GACTTCTCCACAGG (SEQ ID NO: 5321). In some embodiments, the ribonucleic acid sequence of the at least one ribonucleic acid described above comprises at least a 13 nucleotide fragment of a sequence with a single nucleotide mismatch to a ribonucleic acid sequence of GTAACGGCA-GACTTCTCCACAGG (SEQ ID NO: 5321). For example, if the target sequence is GATGCTCAGTACAGCCACCT-TGG (SEQ ID NO: 5323), the ribonucleic acid sequence of the at least one ribonucleic acid which comprises at least a 13 nucleotide fragment is AGTACAGCCACCT (SEQ ID NO: 5328).

In some embodiments, the ribonucleic acid sequence of the at least one ribonucleic acid described above comprises at least a 14 nucleotide fragment of a ribonucleic acid sequence of any of FIGS. 1-15. In some embodiments, the ribonucleic acid sequence of the at least one ribonucleic acid described above comprises at least a 14 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprises at least a 14 nucleotide fragment of a ribonucleic acid sequence of GTAACGGCA-GACTTCTCCACAGG (SEQ ID NO: 5321). In some embodiments, the ribonucleic acid sequence of the at least one ribonucleic acid described above comprises at least a 14 nucleotide fragment of a sequence with a single nucleotide mismatch to a ribonucleic acid sequence of GTAACGGCA-GACTTCTCCACAGG (SEQ ID NO: 5321). For example, if the target sequence is GATGCTCAGTACAGCCACCT-TGG (SEQ ID NO: 5323), the ribonucleic acid sequence of the at least one ribonucleic acid which comprises at least a 14 nucleotide fragment is CAGTACAGCCACCT (SEQ ID NO: 5329).

In some embodiments, the ribonucleic acid sequence of the at least one ribonucleic acid described above comprises at least a 15 nucleotide fragment of a ribonucleic acid sequence of any of FIGS. 1-15. In some embodiments, the ribonucleic acid sequence of the at least one ribonucleic acid described above comprises at least a 15 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprises at least a 15 nucleotide fragment of a ribonucleic acid sequence of GTAACGGCA-GACTTCTCCACAGG (SEQ ID NO: 5321). In some embodiments, the ribonucleic acid sequence of the at least one ribonucleic acid described above comprises at least a 15 nucleotide fragment of a sequence with a single nucleotide mismatch to a ribonucleic acid sequence of GTAACGGCA-GACTTCTCCACAGG (SEQ ID NO: 5321). For example, if the target sequence is GATGCTCAGTACAGCCACCT-TGG (SEQ ID NO: 5323), the ribonucleic acid sequence of the at least one ribonucleic acid which comprises at least a 15 nucleotide fragment is TCAGTACAGCCACCT (SEQ ID NO: 5330).

In some embodiments, the ribonucleic acid sequence of the at least one ribonucleic acid described above comprise at least a 16 nucleotide fragment of a ribonucleic acid sequence of any of FIGS. 1-15. In some embodiments, the ribonucleic acid sequence of the at least one ribonucleic acid described above comprises at least a 16 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprise at least a 16 nucleotide fragment of a ribonucleic acid sequence of GTAACGGCAGACT-TCTCCACAGG (SEQ ID NO: 5321). In some embodiments, the ribonucleic acid sequence of the at least one ribonucleic acid described above comprises at least a 16 nucleotide fragment of a sequence with a single nucleotide mismatch to a ribonucleic acid sequence of GTAACGGCA-GACTTCTCCACAGG (SEQ ID NO: 5321). For example, if the target sequence is GATGCTCAGTACAGCCACCT-TGG (SEQ ID NO: 5323), the ribonucleic acid sequence of the at least one ribonucleic acid which comprises at least a 16 nucleotide fragment is CTCAGTACAGCCACCT (SEQ ID NO: 5331).

In some embodiments, the ribonucleic acid sequence of the at least one ribonucleic acid described above comprises at least a 17 nucleotide fragment of a ribonucleic acid sequence of any of FIGS. 1-15. In some embodiments, the ribonucleic acid sequence of the at least one ribonucleic acid described above comprises at least a 17 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprises at least a 17 nucleotide fragment of a ribonucleic acid sequence of GTAACGGCA-GACTTCTCCACAGG (SEQ ID NO: 5321). In some embodiments, the ribonucleic acid sequence of the at least one ribonucleic acid described above comprises at least a 17 nucleotide fragment of a sequence with a single nucleotide mismatch to a ribonucleic acid sequence of GTAACGGCA-GACTTCTCCACAGG (SEQ ID NO: 5321). For example, if the target sequence is GATGCTCAGTACAGCCACCT-TGG (SEQ ID NO: 5323), the ribonucleic acid sequence of the at least one ribonucleic acid which comprises at least a 17 nucleotide fragment is GCTCAGTACAGCCACCT (SEQ ID NO: 5332).

In some embodiments, the ribonucleic acid sequence of the at least one ribonucleic acid described above comprises at least a 18 nucleotide fragment of a ribonucleic acid sequence of any of FIGS. 1-15. In some embodiments, the ribonucleic acid sequence of the at least one ribonucleic acid described above comprises at least a 18 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprises at least a 18 nucleotide fragment of a ribonucleic acid sequence of GTAACGGCA- GACTTCTCCACAGG (SEQ ID NO: 5321). In some embodiments, the ribonucleic acid sequence of the at least one ribonucleic acid described above comprises at least a 18 nucleotide fragment of a sequence with a single nucleotide mismatch to a ribonucleic acid sequence of GTAACGGCA-GACTTCTCCACAGG (SEQ ID NO: 5321). For example, if the target sequence is GATGCTCAGTACAGCCACCT-TGG (SEQ ID NO: 5323), the ribonucleic acid sequence of the at least one ribonucleic acid which comprises at least a 18 nucleotide fragment is TGCTCAGTACAGCCACCT (SEQ ID NO: 5333).

In some embodiments, the ribonucleic acid sequence of the at least one ribonucleic acid described above comprise at least a 19 nucleotide fragment of a ribonucleic acid sequence of any of FIGS. 1-15. In some embodiments, the ribonucleic acid sequence of the at least one ribonucleic acid described above comprises at least a 19 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprise at least a 19 nucleotide fragment of a ribonucleic acid sequence of GTAACGGCAGACT-TCTCCACAGG (SEQ ID NO: 5321). In some embodiments, the ribonucleic acid sequence of the at least one ribonucleic acid described above comprises at least a 19 nucleotide fragment of a sequence with a single nucleotide mismatch to a ribonucleic acid sequence of GTAACGGCA-GACTTCTCCACAGG (SEQ ID NO: 5321). For example, if the target sequence is GATGCTCAGTACAGCCACCT-TGG (SEQ ID NO: 5323), the ribonucleic acid sequence of the at least one ribonucleic acid which comprises at least a 19 nucleotide fragment is ATGCTCAGTACAGCCACCT (SEQ ID NO: 5334).

In some embodiments, the ribonucleic acid sequence of the at least one ribonucleic acid described above comprises at least a 20 nucleotide fragment of a ribonucleic acid sequence of any of FIGS. 1-15. In some embodiments, the ribonucleic acid sequence of the at least one ribonucleic acid described above comprises at least a 20 nucleotide fragment of a sequence with a single nucleotide mismatch to a sequence selected from the group consisting of a ribonucleic acid sequence of any of FIGS. 1-15. In some embodiments, the ribonucleic acid sequence of the at least one ribonucleic acid described above comprises at least a 20 nucleotide fragment of a ribonucleic acid sequence of GTAACGGCA-GACTTCTCCACAGG (SEQ ID NO: 5321). In some embodiments, the ribonucleic acid sequence of the at least one ribonucleic acid described above comprises at least a 20 nucleotide fragment of a sequence with a single nucleotide mismatch to a ribonucleic acid sequence of GTAACGGCA-GACTTCTCCACAGG (SEQ ID NO: 5321). For example, if the target sequence is GATGCTCAGTACAGCCACCT-TGG (SEQ ID NO: 5323), the ribonucleic acid sequence of the at least one ribonucleic acid which comprises at least a 20 nucleotide fragment is GATGCTCAGTACAGCCACCT (SEQ ID NO: 5324).

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of at least one ribonucleic acid sequence of FIG. 1 and at least one ribonucleic acid sequence with a single nucleotide mismatch to a ribonucleic acid sequence of FIG. 1, and combinations thereof.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of at least one ribonucleic acid sequence of FIG. 2 and at least one ribonucleic acid sequence with a single nucleotide mismatch to a ribonucleic acid sequence of FIG. 2, and combinations thereof.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of at least one ribonucleic acid sequence of FIG. 3 and at least one ribonucleic acid sequence with a single nucleotide mismatch to a ribonucleic acid sequence of FIG. 3, and combinations thereof.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of at least one ribonucleic acid sequence of FIG. 4 and at least one ribonucleic acid sequence with a single nucleotide mismatch to a ribonucleic acid sequence of FIG. 4, and combinations thereof.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of at least one ribonucleic acid sequence of FIG. 5 and at least one ribonucleic acid sequence with a single nucleotide mismatch to a ribonucleic acid sequence of FIG. 5, and combinations thereof.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of at least one ribonucleic acid sequence of FIG. 6 and at least one ribonucleic acid sequence with a single nucleotide mismatch to a ribonucleic acid sequence of FIG. 6, and combinations thereof.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of at least one ribonucleic acid sequence of FIG. 7 and at least one ribonucleic acid sequence with a single nucleotide mismatch to a ribonucleic acid sequence of FIG. 7, and combinations thereof.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of at least one ribonucleic acid sequence of FIG. 8 and at least one ribonucleic acid sequence with a single nucleotide mismatch to a ribonucleic acid sequence of FIG. 8, and combinations thereof.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of at least one ribonucleic acid sequence of FIG. 9 and at least one ribonucleic acid sequence with a single nucleotide mismatch to a ribonucleic acid sequence of FIG. 9, and combinations thereof.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of at least one ribonucleic acid sequence of FIG. 10 and at least one ribonucleic acid sequence with a single nucleotide mismatch to a ribonucleic acid sequence of FIG. 10, and combinations thereof.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of at least one ribonucleic acid sequence of FIG. 11 and at least one ribonucleic acid sequence with a single nucleotide mismatch to a ribonucleic acid sequence of FIG. 11, and combinations thereof.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of at least one ribonucleic acid sequence of FIG. 12 and at least one ribonucleic acid sequence with a single nucleotide mismatch to a ribonucleic acid sequence of FIG. 12, and combinations thereof.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of at least one ribonucleic acid sequence of FIG. 13 and at least one ribonucleic acid sequence with a single nucleotide mismatch to a ribonucleic acid sequence of FIG. 13, and combinations thereof.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of at least one ribonucleic acid sequence of FIG. 14 and at least one ribonucleic acid sequence with a single nucleotide mismatch to a ribonucleic acid sequence of FIG. 14, and combinations thereof.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of at least one ribonucleic acid sequence of FIG. 15 and at least one ribonucleic acid sequence with a single nucleotide mismatch to a ribonucleic acid sequence of FIG. 15, and combinations thereof.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of at least one ribonucleic acid sequence of GTAACGGCAGACTTCTCCACAGG (SEQ ID NO: 5321) and at least one ribonucleic acid sequence with a single nucleotide mismatch to a ribonucleic acid sequence of GTAACGGCAGACTTCTCCACAGG (SEQ ID NO: 5321).

In some embodiments, the at least one ribonucleic acid sequences described above do not include the 3 nucleotide NGG sequence. For example, if the target site sequence is GATGCTCAGTACAGCCACCTTGG (SEQ ID NO: 5323), the ribonucleic acid sequence of the at least one ribonucleic acid sequence is GATGCTCAGTACAGCCACCT (SEQ ID NO: 5324). As another example, if the target sequence is GATGCTCAGTACAGCCACCTTGG (SEQ ID NO: 5323), a ribonucleic acid sequence with a single nucleotide mismatch which does not include the 3 nucleotide NGG sequence is GATGCTGAGTACAGCCACCT (SEQ ID NO: 5326), with the italicized G being the mismatched nucleotide. Those skilled in the art will appreciate, however, that the single nucleotide mismatch can comprise any nucleotide in the ribonucleic acid, e.g., the first nucleotide, the second nucleotide, the third nucleotide, the fourth nucleotide, the fifth nucleotide, the sixth nucleotide, the seventh nucleotide, the eighth nucleotide, the ninth nucleotide, the tenth nucleotide, the eleventh nucleotide, the twelfth nucleotide, the thirteenth nucleotide, the fourteenth nucleotide, the fifteenth nucleotide, the sixteenth nucleotide, the seventeenth nucleotide, the eighteenth nucleotide, the nineteenth nucleotide, or the twentieth nucleotide of the ribonucleic acid.

In some embodiments, the at least one ribonucleic acid described above comprises at least a 12 nucleotide fragment of a ribonucleic acid sequence of any of FIGS. 1-15. In some embodiments, the at least one ribonucleic acid described above comprises at least a 12 nucleotide fragment of a sequence with a single nucleotide mismatch to a sequence selected from the group consisting of a ribonucleic acid sequence of any of FIGS. 1-15. For example, if the target sequence is GATGCTCAGTACAGCCACCTTGG (SEQ ID NO: 5323), the ribonucleic acid sequence of the at least one ribonucleic acid which comprises at least a 12 nucleotide fragment is GTACAGCCACCT (SEQ ID NO: 5327).

In some embodiments, the ribonucleic acid sequence of the at least one ribonucleic acid described above comprises at least a 13 nucleotide fragment of a ribonucleic acid sequence of any of FIGS. 1-15. In some embodiments, the ribonucleic acid sequence of the at least one ribonucleic acid described above comprises at least a 13 nucleotide fragment of a sequence with a single nucleotide mismatch to a sequence selected from the group consisting of a ribonucleic acid sequence of any of FIGS. 1-15. For example, if the target sequence is GATGCTCAGTACAGCCACCTTGG (SEQ ID NO: 5323), the ribonucleic acid sequence of the at least one ribonucleic acid which comprises at least a 13 nucleotide fragment is AGTACAGCCACCT (SEQ ID NO: 5328).

In some embodiments, the ribonucleic acid sequence of the at least one ribonucleic acid described above comprises at least a 14 nucleotide fragment of a ribonucleic acid sequence of any of FIGS. 1-15. In some embodiments, the ribonucleic acid sequence of the at least one ribonucleic acid described above comprises at least a 14 nucleotide fragment of a sequence with a single nucleotide mismatch to a sequence selected from the group consisting of a ribonucleic acid sequence of any of FIGS. 1-15. For example, if the target sequence is GATGCTCAGTACAGCCACCTTGG (SEQ ID NO: 5323), the ribonucleic acid sequence of the at least one ribonucleic acid which comprises at least a 14 nucleotide fragment is CAGTACAGCCACCT (SEQ ID NO: 5329).

In some embodiments, the ribonucleic acid sequence of the at least one ribonucleic acid described above comprises at least a 15 nucleotide fragment of a ribonucleic acid sequence of any of FIGS. 1-15. In some embodiments, the ribonucleic acid sequence of the at least one ribonucleic acid described above comprises at least a 15 nucleotide fragment of a sequence with a single nucleotide mismatch to a sequence selected from the group consisting of a ribonucleic acid sequence of any of FIGS. 1-15. For example, if the target sequence is GATGCTCAGTACAGCCACCTTGG (SEQ ID NO: 5323), the ribonucleic acid sequence of the at least one ribonucleic acid which comprises at least a 15 nucleotide ragment is TCAGTACAGCCACCT (SEQ ID NO: 5330).

In some embodiments, the ribonucleic acid sequence of the at least one ribonucleic acid described above comprise at least a 16 nucleotide fragment of a ribonucleic acid sequence of any of FIGS. 1-15. In some embodiments, the ribonucleic acid sequence of the at least one ribonucleic acid described above comprises at least a 16 nucleotide fragment of a sequence with a single nucleotide mismatch to a sequence selected from the group consisting of a ribonucleic acid sequence of any of FIGS. 1-15. For example, if the target sequence is GATGCTCAGTACAGCCACCTTGG (SEQ ID NO: 5323), the ribonucleic acid sequence of the at least one ribonucleic acid which comprises at least a 16 nucleotide fragment is CTCAGTACAGCCACCT (SEQ ID NO: 5331).

In some embodiments, the ribonucleic acid sequence of the at least one ribonucleic acid described above comprises at least a 17 nucleotide fragment of a ribonucleic acid sequence of any of FIGS. 1-15. In some embodiments, the ribonucleic acid sequence of the at least one ribonucleic acid described above comprises at least a 17 nucleotide fragment of a sequence with a single nucleotide mismatch to a sequence selected from the group consisting of a ribonucleic acid sequence of any of FIGS. 1-15. For example, if the target sequence is GATGCTCAGTACAGCCACCTTGG (SEQ ID NO: 5323), the ribonucleic acid sequence of the at least one ribonucleic acid which comprises at least a 17 nucleotide fragment is GCTCAGTACAGCCACCT (SEQ ID NO: 5332).

In some embodiments, the ribonucleic acid sequence of the at least one ribonucleic acid described above comprises at least a 18 nucleotide fragment of a ribonucleic acid sequence of any of FIGS. 1-15. In some embodiments, the ribonucleic acid sequence of the at least one ribonucleic acid described above comprises at least a 18 nucleotide fragment of a sequence with a single nucleotide mismatch to a sequence selected from the group consisting of a ribonucleic acid sequence of any of FIGS. 1-15. For example, if the target sequence is GATGCTCAGTACAGCCACCTTGG (SEQ ID NO: 5323), the ribonucleic acid sequence of the at least one ribonucleic acid which comprises at least a 18 nucleotide fragment is TGCTCAGTACAGCCACCT (SEQ ID NO: 5333).

In some embodiments, the ribonucleic acid sequence of the at least one ribonucleic acid described above comprise at least a 19 nucleotide fragment of a ribonucleic acid sequence of any of FIGS. 1-15. In some embodiments, the ribonucleic acid sequence of the at least one ribonucleic acid described above comprises at least a 19 nucleotide fragment of a sequence with a single nucleotide mismatch to a sequence selected from the group consisting of a ribonucleic acid sequence of any of FIGS. 1-15. For example, if the target sequence is GATGCTCAGTACAGCCACCTTGG (SEQ ID NO: 5323), the ribonucleic acid sequence of the at least one ribonucleic acid which comprises at least a 19 nucleotide fragment is ATGCTCAGTACAGCCACCT (SEQ ID NO: 5334).

In some embodiments, the ribonucleic acid sequence of the at least one ribonucleic acid described above comprises at least a 20 nucleotide fragment of a ribonucleic acid sequence of any of FIGS. 1-15. In some embodiments, the ribonucleic acid sequence of the at least one ribonucleic acid described above comprises at least a 20 nucleotide fragment of a sequence with a single nucleotide mismatch to a sequence selected from the group consisting of a ribonucleic acid sequence of any of FIGS. 1-15. For example, if the target sequence is GATGCTCAGTACAGCCACCTTGG (SEQ ID NO: 5323), the ribonucleic acid sequence of the at least one ribonucleic acid which comprises at least a 20 nucleotide fragment is GATGCTCAGTACAGCCACCT (SEQ ID NO: 5324).

In some embodiments, the at least one ribonucleic acid described above comprises at least a 12 nucleotide fragment, at least a 13 nucleotide fragment, at least a 14 nucleotide fragment, at least a 15 nucleotide fragment, at least a 16 nucleotide fragment, at least a 17 nucleotide fragment, at least an 18 nucleotide fragment, at least a 19 nucleotide fragment, or at least a 20 nucleotide sequence of a ribonucleic acid sequence of GTAACGGCAGACTTCTCCACAGG (SEQ ID NO: 5321). In some embodiments, the at least one ribonucleic acid described above comprises at least a 12, at least a 13, at least a 14, at least a 15, at least a 16, at least a 17, at least an 18, at least a 19, or at least a 20 nucleotide fragment of a sequence with a single nucleotide mismatch to a ribonucleic acid sequence of GTAACGGCAGACTTCTCCACAGG (SEQ ID NO: 5321).

In some embodiments, the kit comprises one or more cell lines, cultures, or populations selected from the group consisting of human pluripotent cells, primary human cells, and non-transformed cells. In some embodiments, the kit comprises a DNA repair template.

In some embodiments, the DNA repair template comprises one or more normal or wild-type ADA gene sequences. In some embodiments, the DNA repair template comprises one or more normal or wild-type DNA sequences that correspond to mutant ADA sequences to be cleaved from target SCID-associated polynucleotide sequences.

In some embodiments, the DNA repair template comprises one or more normal or wild-type AK2 gene sequences. In some embodiments, the DNA repair template comprises one or more normal or wild-type DNA sequences that correspond to mutant AK2 sequences to be cleaved from target SCID-associated polynucleotide sequences.

In some embodiments, the DNA repair template comprises one or more normal or wild-type CD3D gene sequences. In some embodiments, the DNA repair template comprises one or more normal or wild-type DNA sequences that correspond to mutant CD3D sequences to be cleaved from target SCID-associated polynucleotide sequences.

In some embodiments, the DNA repair template comprises one or more normal or wild-type DCLRE1C gene sequences. In some embodiments, the DNA repair template comprises one or more normal or wild-type DNA sequences that correspond to mutant DCLRE1C sequences to be cleaved from target SCID-associated polynucleotide sequences.

In some embodiments, the DNA repair template comprises one or more normal or wild-type IL2RG gene sequences. In some embodiments, the DNA repair template comprises one or more normal or wild-type DNA sequences that correspond to mutant IL2RG sequences to be cleaved from target SCID-associated polynucleotide sequences.

In some embodiments, the DNA repair template comprises one or more normal or wild-type IL7R gene sequences. In some embodiments, the DNA repair template comprises one or more normal or wild-type DNA sequences that correspond to mutant IL7R sequences to be cleaved from target SCID-associated polynucleotide sequences.

In some embodiments, the DNA repair template comprises one or more normal or wild-type JAK3 gene sequences. In some embodiments, the DNA repair template comprises one or more normal or wild-type DNA sequences that correspond to mutant JAK3 sequences to be cleaved from target SCID-associated polynucleotide sequences.

In some embodiments, the DNA repair template comprises one or more normal or wild-type NHEJ1 gene sequences. In some embodiments, the DNA repair template comprises one or more normal or wild-type DNA sequences that correspond to mutant NHEJ1 sequences to be cleaved from target SCID-associated polynucleotide sequences.

In some embodiments, the DNA repair template comprises one or more normal or wild-type PNP gene sequences. In some embodiments, the DNA repair template comprises one or more normal or wild-type DNA sequences that correspond to mutant PNP sequences to be cleaved from target SCID-associated polynucleotide sequences.

In some embodiments, the DNA repair template comprises one or more normal or wild-type PRKDC gene sequences. In some embodiments, the DNA repair template comprises one or more normal or wild-type DNA sequences that correspond to mutant PRKDC sequences to be cleaved from target SCID-associated polynucleotide sequences.

In some embodiments, the DNA repair template comprises one or more normal or wild-type RAG1 gene sequences. In some embodiments, the DNA repair template comprises one or more normal or wild-type DNA sequences that correspond to mutant RAG1 sequences to be cleaved from target SCID-associated polynucleotide sequences.

In some embodiments, the DNA repair template comprises one or more normal or wild-type RAG2 gene sequences. In some embodiments, the DNA repair template comprises one or more normal or wild-type DNA sequences that correspond to mutant RAG2 sequences to be cleaved from target SCID-associated polynucleotide sequences.

In some embodiments, the DNA repair template comprises one or more normal or wild-type ZAP70 gene sequences. In some embodiments, the DNA repair template comprises one or more normal or wild-type DNA sequences that correspond to mutant ZAP70 sequences to be cleaved from target SCID-associated polynucleotide sequences.

In some embodiments, the DNA repair template comprises one or more normal or wild-type HBB gene sequences. In some embodiments, the DNA repair template comprises one or more normal or wild-type DNA sequences that correspond to mutant HBB sequences to be cleaved from target SCD-associated polynucleotide sequences.

In some embodiments, the DNA repair template comprises one or more normal or wild-type DNA sequences that correspond to mutant HBB sequences to be cleaved from target beta thalassemia-associated polynucleotide sequences.

It should be appreciated that the methods, compositions, and kits of the present invention may employ nanoparticles or lipid nanoparticles as a vehicle for delivering, or introducing a Cas protein and/or a ribonucleic acid of the present invention into a cell.

In some embodiments, the lipid nanoparticle comprises at least one of a cationic lipid, a neutral lipid, an amino lipid, a sterol, and a PEG or PEG-modified lipid.

The cationic lipid may be, for example, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxyl)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino) acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAR.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLin-K-DMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl) tetrahydro-3 aH-cyclopenta[d][1,3]dioxol-5-amine (ALNY-100), (6Z,9Z,28Z,31Z)-heptatriaconta-6,9,28,31-tetraen-19-yl 4-(dimethylamino)butanoate (MC3), or a mixture thereof.

Other cationic lipids, which carry a net positive charge at about physiological pH, in addition to those specifically described above, may also be included in lipid particles of the invention. Such cationic lipids include, but are not limited to, N,N-dioleyl-N,N-dimethylammonium chloride ("DODAC"); N-(2,3-dioleyloxyl)propyl-N,N-N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 1,2-Dioleyloxy-3-trimethylaminopropane chloride salt ("DOTAP.Cl"); 3.beta.-(N-(N',N'-dimethylaminoethane)-carbamoyl)cholesterol ("DC-Chol"), N-(1-(2,3-dioleyloxyl)propyl)-N-2-(sperminecarboxamido)ethyl)-N,N-dimethylammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DOTAP"), N,N-dimethyl-2,3-dioleyloxy)propylamine ("DODMA"), and N-(1,2-dimyristyloxyprop-3-yl)-N,N-dimethyl-N-hydroxyethyl ammonium bromide ("DMRIE"), and mixtures thereof. Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL). In particular embodiments, a cationic lipid is an amino lipid.

As used herein, the term "amino lipid" is meant to include those lipids having one or two fatty acid or fatty alkyl chains and an amino head group (including an alkylamino or dialkylamino group) that may be protonated to form a cationic lipid at physiological pH.

Other amino lipids would include those having alternative fatty acid groups and other dialkylamino groups, including those in which the alkyl substituents are different (e.g., N-ethyl-N-methylamino-, N-propyl-N-ethylamino- and the like). For those embodiments in which $R^{11}$ and $R^{12}$ are both long chain alkyl or acyl groups, they can be the same or different. In general, amino lipids having less saturated acyl chains are more easily sized, particularly when the complexes must be sized below about 0.3 microns, for purposes of filter sterilization. Amino lipids containing unsaturated fatty acids with carbon chain lengths in the range of $C_{14}$ to $C_{22}$ are preferred. Other scaffolds can also be used to separate the amino group and the fatty acid or fatty alkyl portion of the amino lipid. Suitable scaffolds are known to those of skill in the art.

Specific examples of PEG-modified lipids (or lipid-polyoxyethylene conjugates) that are useful in the present invention can have a variety of "anchoring" lipid portions to secure the PEG portion to the surface of the lipid vesicle. Examples of suitable PEG-modified lipids include PEG-modified phosphatidylethanolamine and phosphatidic acid, PEG-ceramide conjugates (e.g., PEG-CerC14 or PEG-CerC20) which are described in U.S. Pat. No. 5,820,873, incorporated herein by reference, PEG-modified dialkylamines and PEG-modified 1,2-diacyloxypropan-3-amines. Particularly preferred are PEG-modified diacylglycerols and dialkylglycerols.

Examples of suitable neutral lipid include DPSC, DPPC, POPC, DOPE, SM, and mixtures thereof.

As used herein "nucleic acid," in its broadest sense, includes any compound and/or substance that comprise a polymer of nucleotides linked via a phosphodiester bond. Exemplary nucleic acids include ribonucleic acids (RNAs), deoxyribonucleic acids (DNAs), threose nucleic acids (TNAs), glycol nucleic acids (GNAs), peptide nucleic acids (PNAs), locked nucleic acids (LNAs) or hybrids thereof. They may also include RNAi-inducing agents, RNAi agents, siRNAs, shRNAs, miRNAs, antisense RNAs, ribozymes, catalytic DNA, tRNA, RNAs that induce triple helix formation, aptamers, vectors, etc. In some embodiments, the nucleic acid encoding the Cas protein is an mRNA. In some embodiments, the Cas protein is encoded by a modified nucleic acid (e.g., a synthetic, modified mRNA described herein).

The present invention contemplates the use of any nucleic acid modification available to the skilled artisan. The nucleic acids of the present invention can include any number of modifications. In some embodiments, the nucleic acid comprises one or more modifications selected from the group consisting of pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl)adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine, and combinations thereof.

Preparation of modified nucleosides and nucleotides used in the manufacture or synthesis of modified RNAs of the present invention can involve the protection and deprotection of various chemical groups. The need for protection and deprotection, and the selection of appropriate protecting groups can be readily determined by one skilled in the art.

The chemistry of protecting groups can be found, for example, in Greene, et al., Protective Groups in Organic Synthesis, 2d. Ed., Wiley & Sons, 1991, which is incorporated herein by reference in its entirety.

Modified nucleosides and nucleotides can be prepared according to the synthetic methods described in Ogata et al. Journal of Organic Chemistry 74:2585-2588, 2009; Purmal et al. Nucleic Acids Research 22(1): 72-78, 1994; Fukuhara et al. Biochemistry 1(4): 563-568, 1962; and Xu et al. Tetrahedron 48(9): 1729-1740, 1992, each of which are incorporated by reference in their entirety.

Modified nucleic acids (e.g., ribonucleic acids) need not be uniformly modified along the entire length of the molecule. Different nucleotide modifications and/or backbone structures may exist at various positions in the nucleic acid. One of ordinary skill in the art will appreciate that the nucleotide analogs or other modification(s) may be located at any position(s) of a nucleic acid such that the function of the nucleic acid is not substantially decreased. A modification may also be a 5' or 3' terminal modification. The nucleic acids may contain at a minimum one and at maximum 100% modified nucleotides, or any intervening percentage, such as at least 50% modified nucleotides, at least 80% modified nucleotides, or at least 90% modified nucleotides.

In some embodiments, at least one of the one to two ribonucleic acids is a modified ribonucleic acid. In some embodiments, each of the one to two ribonucleic acids is a modified ribonucleic acid. In some embodiments, at least one of the multiple ribonucleic acids is a modified ribonucleic acid. In some embodiments, a plurality of the multiple ribonucleic acids are modified. In some embodiments, each of the multiple ribonucleic acids are modified. Those skilled in the art will appreciate that the modified ribonucleic acids can include one or more of the nucleic acid modification described herein.

In some aspects, provided herein are synthetic, modified RNA molecules encoding polypeptides, where the synthetic, modified RNA molecules comprise one or more modifications, such that introducing the synthetic, modified RNA molecules to a cell results in a reduced innate immune response relative to a cell contacted with synthetic RNA molecules encoding the polypeptides not comprising the one or more modifications. In some embodiments, the Cas protein comprises a synthetic, modified RNA molecule encoding a Cas protein. In some embodiments, the Cas protein comprises a synthetic, modified RNA molecule encoding a Cas9 protein.

The synthetic, modified RNAs described herein include modifications to prevent rapid degradation by endo- and exo-nucleases and to avoid or reduce the cell's innate immune or interferon response to the RNA. Modifications include, but are not limited to, for example, (a) end modifications, e.g., 5' end modifications (phosphorylation dephosphorylation, conjugation, inverted linkages, etc.), 3' end modifications (conjugation, DNA nucleotides, inverted linkages, etc.), (b) base modifications, e.g., replacement with modified bases, stabilizing bases, destabilizing bases, or bases that base pair with an expanded repertoire of partners, or conjugated bases, (c) sugar modifications (e.g., at the 2' position or 4' position) or replacement of the sugar, as well as (d) internucleoside linkage modifications, including modification or replacement of the phosphodiester linkages. To the extent that such modifications interfere with translation (i.e., results in a reduction of 50% or more in translation relative to the lack of the modification—e.g., in a rabbit reticulocyte in vitro translation assay), the modification is not suitable for the methods and compositions described herein. Specific examples of synthetic, modified RNA compositions useful with the methods described herein include, but are not limited to, RNA molecules containing modified or non-natural internucleoside linkages. Synthetic, modified RNAs having modified internucleoside linkages include, among others, those that do not have a phosphorus atom in the internucleoside linkage. In other embodiments, the synthetic, modified RNA has a phosphorus atom in its internucleoside linkage(s).

Non-limiting examples of modified internucleoside linkages include phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and RE39464, each of which is herein incorporated by reference in its entirety.

Modified internucleoside linkages that do not include a phosphorus atom therein have internucleoside linkages that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of modified oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and 5,677,439, each, of which is herein incorporated by reference in its entirety.

Some embodiments of the synthetic, modified RNAs described herein include nucleic acids with phosphorothioate internucleoside linkages and oligonucleosides with heteroatom internucleoside linkage, and in particular $CH_2$-NH—$CH_2$-, —$CH_2$-N($CH_3$)-O—$CH_2$-[known as a methylene (methylimino) or MMI], —$CH_2$-O—N($CH_3$)-$CH_2$-, —$CH_2$-N($CH_3$)-N($CH_3$)-$CH_2$- and —N($CH_3$)-$CH_2$-$CH_2$-[wherein the native phosphodiester internucleoside linkage is represented as —O—P—O—$CH_2$-] of the above-referenced U.S. Pat. No. 5,489,677, and the amide backbones of the above-referenced U.S. Pat. No. 5,602,240, both of which are herein incorporated by reference in their entirety. In some embodiments, the nucleic acid sequences featured herein have morpholino backbone structures of the above-referenced U.S. Pat. No. 5,034,506, herein incorporated by reference in its entirety.

Synthetic, modified RNAs described herein can also contain one or more substituted sugar moieties. The nucleic acids featured herein can include one of the following at the 2' position: H (deoxyribose); OH (ribose); F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted C1 to C10 alkyl or C2 to C10 alkenyl and alkynyl. Exemplary modifications include O[($CH_2$)nO]m$CH_3$, O($CH_2$).nO$CH_3$, O($CH_2$)n$NH_2$, O($CH_2$)n$CH_3$, O($CH_2$)nO$NH_2$, and O($CH_2$)nON[($CH_2$)n$CH_3$)]2, where n and m are from 1 to about 10. In some embodiments, synthetic, modified RNAs include one of the following at the 2' position: C1 to C10 lower alkyl, substituted lower alkyl, alkaryl, aralkyl, O-alkaryl or O-aralkyl, SH, S$CH_3$, OCN, Cl, Br, CN, $CF_3$, O$CF_3$, SO$CH_3$, SO$_2$$CH_3$, ONO$_2$, NO$_2$, N$_3$, NH$_2$, heterocycloalkyl, heterocycloalkaryl, aminoalkylamino, polyalkylamino, substituted silyl, a reporter group, an intercalator, a group for improving the pharmacokinetic properties of an RNA, or a group for improving the pharmacodynamic properties of a synthetic, modified RNA, and other substituents having similar properties. In some embodiments, the modification includes a 2' methoxyethoxy (2'-O—$CH_2$$CH_2$O$CH_3$, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O($CH_2$)2ON($CH_3$)2 group, also known as 2'-DMAOE, and 2'-dimethylaminoethoxyethoxy (also known in the art as 2'-O-dimethylaminoethoxyethyl or 2'-DMAEOE), i.e., 2'-O—$CH_2$-O—$CH_2$-N($CH_2$)2.

Other modifications include 2'-methoxy (2'-O$CH_3$), 2'-aminopropoxy (2'-O$CH_2$$CH_2$$CH_2$$NH_2$) and 2'-fluoro (2'-F). Similar modifications can also be made at other positions on the nucleic acid sequence, particularly the 3' position of the sugar on the 3' terminal nucleotide or in 2'-5' linked nucleotides and the 5' position of 5' terminal nucleotide. A synthetic, modified RNA can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

As non-limiting examples, synthetic, modified RNAs described herein can include at least one modified nucleoside including a 2'-O-methyl modified nucleoside, a nucleoside comprising a 5' phosphorothioate group, a 2'-amino-modified nucleoside, 2'-alkyl-modified nucleoside, morpholino nucleoside, a phosphoramidate or a non-natural base comprising nucleoside, or any combination thereof.

In some embodiments of this aspect and all other such aspects described herein, the at least one modified nucleoside is selected from the group consisting of 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Urn), 2' deoxyuridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m2,7G), N2,N2,7-trimethylguanosine (m2,2,7G), and inosine (I).

Alternatively, a synthetic, modified RNA can comprise at least two modified nucleosides, at least 3, at least 4, at least 5, at least 6, at least 7, at least 8, at least 9, at least 10, at least 15, at least 20 or more, up to the entire length of the nucleotide. At a minimum, a synthetic, modified RNA molecule comprising at least one modified nucleoside comprises a single nucleoside with a modification as described herein. It is not necessary for all positions in a given synthetic, modified RNA to be uniformly modified, and in fact more than one of the aforementioned modifications can be incorporated in a single synthetic, modified RNA or even at a single nucleoside within a synthetic, modified RNA. However, it is preferred, but not absolutely necessary, that each occurrence of a given nucleoside in a molecule is modified (e.g., each cytosine is a modified cytosine e.g., 5mC). However, it is also contemplated that different occurrences of the same nucleoside can be modified in a different way in a given synthetic, modified RNA molecule (e.g., some cytosines modified as 5mC, others modified as 2'-O-methylcytidine or other cytosine analog). The modifications need not be the same for each of a plurality of modified nucleosides in a synthetic, modified RNA. Furthermore, in some embodiments of the aspects described herein, a synthetic, modified RNA comprises at least two different modified nucleosides. In some such preferred embodiments of the aspects described herein, the at least two different modified nucleosides are 5-methylcytidine and pseudouridine. A synthetic, modified RNA can also contain a mixture of both modified and unmodified nucleosides.

As used herein, "unmodified" or "natural" nucleosides or nucleobases include the purine bases adenine (A) and guanine (G), and the pyrimidine bases thymine (T), cytosine (C) and uracil (U). In some embodiments, a synthetic, modified RNA comprises at least one nucleoside ("base") modification or substitution. Modified nucleosides include other synthetic and natural nucleobases such as inosine, xanthine, hypoxanthine, nebularine, isoguanisine, tubercidine, 2-(halo)adenine, 2-(alkyl)adenine, 2-(propyl)adenine, 2 (amino)adenine, 2-(aminoalkyl)adenine, 2 (aminopropyl) adenine, 2 (methylthio) N6 (isopentenyl)adenine, 6 (alkyl) adenine, 6 (methyl)adenine, 7 (deaza)adenine, 8 (alkenyl) adenine, 8-(alkyl)adenine, 8 (alkynyl)adenine, 8 (amino) adenine, 8-(halo)adenine, 8-(hydroxyl)adenine, 8 (thioalkyl) adenine, 8-(thiol)adenine, N6-(isopentyl)adenine, N6 (methyl)adenine, N6, N6 (dimethyl)adenine, 2-(alkyl)guanine, 2 (propyl)guanine, 6-(alkyl)guanine, 6 (methyl)guanine, 7 (alkyl)guanine, 7 (methyl)guanine, 7 (deaza)guanine, 8 (alkyl)guanine, 8-(alkenyl)guanine, 8 (alkynyl)guanine, 8-(amino)guanine, 8 (halo)guanine, 8-(hydroxyl)guanine, 8 (thioalkyl)guanine, 8-(thiol)guanine, N (methyl)guanine, 2-(thio)cytosine, 3 (deaza) 5 (azo)cytosine, 3-(alkyl)cytosine, 3 (methyl)cytosine, 5-(alkyl)cytosine, 5-(alkynyl)cytosine, 5 (halo)cytosine, 5 (methyl)cytosine, 5 (propynyl) cytosine, 5 (propynyl)cytosine, 5 (trifluoromethyl)cytosine, 6-(azo)cytosine, N4 (acetyl)cytosine, 3 (3 amino-3 carboxypropyl)uracil, 2-(thio)uracil, 5 (methyl) 2 (thio)uracil, 5 (methylaminomethyl)-2 (thio)uracil, 4-(thio)uracil, 5 (methyl) 4 (thio)uracil, 5 (methylaminomethyl)-4 (thio)uracil, 5 (methyl) 2,4 (dithio)uracil, (methylaminomethyl)-2,4 (dithio)uracil, 5 (2-aminopropyl)uracil, 5-(alkyl)uracil, 5-(alkynyl)uracil, 5-(allylamino)uracil, 5 (aminoallyl)uracil, 5 (aminoalkyl)uracil, 5 (guanidiniumalkyl)uracil, 5 (1,3-diazole-1-alkyl)uracil, 5-(cyanoalkyl)uracil, 5-(dialkylaminoalkyl)uracil, 5 (dimethylaminoalkyl)uracil, 5-(halo)uracil, 5-(methoxy)uracil, uracil-5 oxyacetic acid, 5 (methoxycarbonylmethyl)-2-(thio)uracil, 5 (methoxycarbonyl-methyl)uracil, 5 (propynyl)uracil, 5 (propynyl)uracil, 5 (trifluoromethyl)uracil, 6 (azo)uracil, dihydrouracil, N3 (methyl)uracil, 5-uracil (i.e., pseudouracil), 2 (thio)pseudouracil, 4 (thio)pseudouracil, 2,4-(dithio)psuedouracil, 5-(alkyl)pseudouracil, 5-(methyl)pseudouracil, 5-(alkyl)-2-(thio)pseudouracil, 5-(methyl)-2-(thio)pseudouracil, 5-(alkyl)-4 (thio)pseudouracil, 5-(methyl)-4 (thio)pseudouracil, 5-(alkyl)-2,4 (dithio)pseudouracil, 5-(methyl)-2,4 (dithio)pseudouracil, 1 substituted pseudouracil, 1 substituted 2(thio)-pseudouracil, 1 substituted 4 (thio)pseudouracil, 1 substituted 2,4-(dithio)pseudouracil, 1 (aminocarbonylethylenyl)-pseudouracil, 1 (aminocarbonylethylenyl)-2(thio)-pseudouracil, 1 (aminocarbonylethylenyl)-4 (thio)pseudouracil, 1 (aminocarbonylethylenyl)-2,4-(dithio)pseudouracil, 1 (aminoalkylaminocarbonylethylenyl)-pseudouracil, 1 (aminoalkylaminocarbonylethylenyl)-2(thio)-pseudouracil, 1 (aminoalkylaminocarbonylethylenyl)-4 (thio)pseudouracil, 1 (aminoalkylaminocarbonylethylenyl)-2,4-(dithio) pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkylhydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynypisocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenzyl, tetracenyl, pentacenyl, difluorotolyl, 4-(fluoro)-6-(methyl)benzimidazole, 4-(methyl)benzimidazole, 6-(azo) thymine, 2-pyridinone, 5 nitroindole, 3 nitropyrrole, 6-(aza)

pyrimidine, 2 (amino)purine, 2,6-(diamino)purine, 5 substituted pyrimidines, N2-substituted purines, N6-substituted purines, 06-substituted purines, substituted 1,2,4-triazoles, pyrrolo-pyrimidin-2-on-3-yl, 6-phenyl-pyrrolo-pyrimidin-2-on-3-yl, para-substituted-6-phenyl-pyrrolo-pyrimidin-2-on-3-yl, ortho-substituted-6-phenyl-pyrrolo-pyrimidin-2-on-3-yl, bis-ortho-substituted-6-phenyl-pyrrolo-pyrimidin-2-on-3-yl, para-(aminoalkylhydroxy)-6-phenyl-pyrrolo-pyrimidin-2-on-3-yl, ortho-(aminoalkylhydroxy)-6-phenyl-pyrrolo-pyrimidin-2-on-3-yl, bis-ortho-(aminoalkylhydroxy)-6-phenyl-pyrrolo-pyrimidin-2-on-3-yl, pyridopyrimidin-3-yl, 2-oxo-7-amino-pyridopyrimidin-3-yl, 2-oxo-pyridopyrimidine-3-yl, or any O-alkylated or N-alkylated derivatives thereof. Modified nucleosides also include natural bases that comprise conjugated moieties, e.g. a ligand. As discussed herein above, the RNA containing the modified nucleosides must be translatable in a host cell (i.e., does not prevent translation of the polypeptide encoded by the modified RNA). For example, transcripts containing s2U and m6A are translated poorly in rabbit reticulocyte lysates, while pseudouridine, m5U, and m5C are compatible with efficient translation. In addition, it is known in the art that 2'-fluoro-modified bases useful for increasing nuclease resistance of a transcript, leads to very inefficient translation. Translation can be assayed by one of ordinary skill in the art using e.g., a rabbit reticulocyte lysate translation assay.

Further modified nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in Int. Appl. No. PCT/US09/038,425, filed Mar. 26, 2009; those disclosed in The Concise Encyclopedia Of Polymer Science And Engineering, pages 858-859, Kroschwitz, J. L, ed. John Wiley & Sons, 1990, and those disclosed by Englisch et al., Angewandte Chemie, International Edition, 1991, 30, 613.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,457,191; 5,459,255; 5,484,908; 5,502,177; 5,525,711; 5,552,540; 5,587,469; 5,594,121, 5,596,091; 5,614,617; 5,681,941; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference in its entirety, and U.S. Pat. No. 5,750,692, also herein incorporated by reference in its entirety.

Another modification for use with the synthetic, modified RNAs described herein involves chemically linking to the RNA one or more ligands, moieties or conjugates that enhance the activity, cellular distribution or cellular uptake of the RNA. Ligands can be particularly useful where, for example, a synthetic, modified RNA is administered in vivo. Such moieties include but are not limited to lipid moieties such as a cholesterol moiety (Letsinger et al., Proc. Natl. Acid. Sci. USA, 1989, 86: 6553-6556, herein incorporated by reference in its entirety), cholic acid (Manoharan et al., Biorg. Med. Chem. Let., 1994, 4:1053-1060, herein incorporated by reference in its entirety), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770, each of which is herein incorporated by reference in its entirety), a thiocholesterol (Oberhauser et al., Nucl. Acids Res., 1992, 20:533-538, herein incorporated by reference in its entirety), an aliphatic chain, e.g., dodecan-diol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54, each of which is herein incorporated by reference in its entirety), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783, each of which is herein incorporated by reference in its entirety), a polyamine or a polyethylene glycol chain (Manoharan et al., Nucleosides & Nucleotides, 1995, 14:969-973, herein incorporated by reference in its entirety), or adamantane acetic acid (Manoharan et al., Tetrahedron Lett., 1995, 36:3651-3654, herein incorporated by reference in its entirety), a palmityl moiety (Mishra et al., Biochim. Biophys. Acta, 1995, 1264:229-237, herein incorporated by reference in its entirety), or an octadecylamine or hexylamino-carbonyloxycholesterol moiety (Crooke et al., J. Pharmacol. Exp. Ther., 1996, 277:923-937, herein incorporated by reference in its entirety).

The synthetic, modified RNAs described herein can further comprise a 5' cap. In some embodiments of the aspects described herein, the synthetic, modified RNAs comprise a 5' cap comprising a modified guanine nucleotide that is linked to the 5' end of an RNA molecule using a 5'-5' triphosphate linkage. As used herein, the term "5' cap" is also intended to encompass other 5' cap analogs including, e.g., 5' diguanosine cap, tetraphosphate cap analogs having a methylene-bis(phosphonate) moiety (see e.g., Rydzik, A M et al., (2009) Org Biomol Chem 7(22):4763-76), dinucleotide cap analogs having a phosphorothioate modification (see e.g., Kowalska, J. et al., (2008) RNA 14(6):1119-1131), cap analogs having a sulfur substitution for a non-bridging oxygen (see e.g., Grudzien-Nogalska, E. et al., (2007) RNA 13(10): 1745-1755), N7-benzylated dinucleoside tetraphosphate analogs (see e.g., Grudzien, E. et al., (2004) RNA 10(9):1479-1487), or anti-reverse cap analogs (see e.g., Jemielity, J. et al., (2003) RNA 9(9): 1108-1122 and Stepinski, J. et al., (2001) RNA 7(10):1486-1495). In one such embodiment, the 5' cap analog is a 5' diguanosine cap. In some embodiments, the synthetic, modified RNA does not comprise a 5' triphosphate.

The 5' cap is important for recognition and attachment of an mRNA to a ribosome to initiate translation. The 5' cap also protects the synthetic, modified RNA from 5' exonuclease mediated degradation. It is not an absolute requirement that a synthetic, modified RNA comprise a 5' cap, and thus in other embodiments the synthetic, modified RNAs lack a 5' cap. However, due to the longer half-life of synthetic, modified RNAs comprising a 5' cap and the increased efficiency of translation, synthetic, modified RNAs comprising a 5' cap are preferred herein.

The synthetic, modified RNAs described herein can further comprise a 5' and/or 3' untranslated region (UTR). Untranslated regions are regions of the RNA before the start codon (5') and after the stop codon (3'), and are therefore not translated by the translation machinery. Modification of an RNA molecule with one or more untranslated regions can improve the stability of an mRNA, since the untranslated regions can interfere with ribonucleases and other proteins involved in RNA degradation. In addition, modification of an RNA with a 5' and/or 3' untranslated region can enhance translational efficiency by binding proteins that alter ribosome binding to an mRNA. Modification of an RNA with a 3' UTR can be used to maintain a cytoplasmic localization of the RNA, permitting translation to occur in the cytoplasm of the cell. In one embodiment, the synthetic, modified RNAs described herein do not comprise a 5' or 3' UTR. In another embodiment, the synthetic, modified RNAs comprise either a 5' or 3' UTR. In another embodiment, the synthetic, modified RNAs described herein comprise both a 5' and a 3' UTR. In one embodiment, the 5' and/or 3' UTR is selected from an mRNA known to have high stability in the cell (e.g., a murine alpha-globin 3' UTR). In some embodiments, the 5' UTR, the 3' UTR, or both comprise one or more modified nucleosides.

In some embodiments, the synthetic, modified RNAs described herein further comprise a Kozak sequence. The "Kozak sequence" refers to a sequence on eukaryotic mRNA having the consensus (gcc)gccRccAUGG SEQ ID NO: 1481, where R is a purine (adenine or guanine) three bases upstream of the start codon (AUG), which is followed by another 'G'. The Kozak consensus sequence is recognized by the ribosome to initiate translation of a polypeptide. Typically, initiation occurs at the first AUG codon encountered by the translation machinery that is proximal to the 5' end of the transcript. However, in some cases, this AUG codon can be bypassed in a process called leaky scanning. The presence of a Kozak sequence near the AUG codon will strengthen that codon as the initiating site of translation, such that translation of the correct polypeptide occurs. Furthermore, addition of a Kozak sequence to a synthetic, modified RNA will promote more efficient translation, even if there is no ambiguity regarding the start codon. Thus, in some embodiments, the synthetic, modified RNAs described herein further comprise a Kozak consensus sequence at the desired site for initiation of translation to produce the correct length polypeptide. In some such embodiments, the Kozak sequence comprises one or more modified nucleosides.

In some embodiments, the synthetic, modified RNAs described herein further comprise a "poly (A) tail", which refers to a 3' homopolymeric tail of adenine nucleotides, which can vary in length (e.g., at least 5 adenine nucleotides) and can be up to several hundred adenine nucleotides). The inclusion of a 3' poly(A) tail can protect the synthetic, modified RNA from degradation in the cell, and also facilitates extra-nuclear localization to enhance translation efficiency. In some embodiments, the poly(A) tail comprises between 1 and 500 adenine nucleotides; in other embodiments the poly(A) tail comprises at least 5, at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 225, at least 250, at least 275, at least 300, at least 325, at least 350, at least 375, at least 400, at least 425, at least 450, at least 475, at least 500 adenine nucleotides or more. In one embodiment, the poly(A) tail comprises between 1 and 150 adenine nucleotides. In another embodiment, the poly(A) tail comprises between 90 and 120 adenine nucleotides. In some such embodiments, the poly(A) tail comprises one or more modified nucleosides.

It is contemplated that one or more modifications to the synthetic, modified RNAs described herein permit greater stability of the synthetic, modified RNA in a cell. To the extent that such modifications permit translation and either reduce or do not exacerbate a cell's innate immune or interferon response to the synthetic, modified RNA with the modification, such modifications are specifically contemplated for use herein. Generally, the greater the stability of a synthetic, modified RNA, the more protein can be produced from that synthetic, modified RNA. Typically, the presence of AU-rich regions in mammalian mRNAs tend to destabilize transcripts, as cellular proteins are recruited to AU-rich regions to stimulate removal of the poly(A) tail of the transcript. Loss of a poly(A) tail of a synthetic, modified RNA can result in increased RNA degradation. Thus, in one embodiment, a synthetic, modified RNA as described herein does not comprise an AU-rich region. In particular, it is preferred that the 3' UTR substantially lacks AUUUA sequence elements.

In one embodiment, a ligand alters the cellular uptake, intracellular targeting or half-life of a synthetic, modified RNA into which it is incorporated. In some embodiments a ligand provides an enhanced affinity for a selected target, e.g., molecule, cell or cell type, intracellular compartment, e.g., mitochondria, cytoplasm, peroxisome, lysosome, as, e.g., compared to a composition absent such a ligand. Preferred ligands do not interfere with expression of a polypeptide from the synthetic, modified RNA.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin or hyaluronic acid); or a lipid. The ligand can also be a recombinant or synthetic molecule, such as a synthetic polymer, e.g., a synthetic polyamino acid. Examples of polyamino acids include polylysine (PLL), poly L aspartic acid, poly L-glutamic acid, styrene-maleic acid anhydride copolymer, poly(L-lactide-co-glycolied) copolymer, divinyl ether-maleic anhydride copolymer, N-(2-hydroxypropyl) methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell targeting agent, (e.g., a lectin, glycoprotein, lipid or protein), or an antibody, that binds to a specified cell type such as a fibroblast cell. A targeting group can be, for example, a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or ROD peptide mimetic, among others.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, amino, mercapto, PEG (e.g., PEG-40K), MPEG, [MPEG]2, polyamino, alkyl, substituted alkyl, radiolabeled markers, enzymes, haptens (e.g. biotin), and transport/absorption facilitators (e.g., aspirin, vitamin E, folic acid).

Ligands can be proteins, e.g., glycoproteins, or peptides, e.g., molecules having a specific affinity for a co-ligand, or antibodies e.g., an antibody, that binds to a specified cell type such as a fibroblast cell, or other cell useful in the production of polypeptides. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose.

The ligand can be a substance, e.g., a drug, which can increase the uptake of the synthetic, modified RNA or a composition thereof into the cell, for example, by disrupting the cell's cytoskeleton, e.g., by disrupting the cell's microtubules, microfilaments, and/or intermediate filaments. The drug can be, for example, taxol, vincristine, vinblastine, cytochalasin, nocodazole, japlakinolide, latrunculin A, phalloidin, swinholide A, indanocine, or myoservin.

One exemplary ligand is a lipid or lipid-based molecule. A lipid or lipid-based ligand can (a) increase resistance to degradation, and/or (b) increase targeting or transport into a target cell or cell membrane. A lipid based ligand can be used to modulate, e.g., binding of the modified RNA composition to a target cell.

In another aspect, the ligand is a moiety, e.g., a vitamin, which is taken up by a host cell. Exemplary vitamins include vitamin A, E, and K. Other exemplary vitamins include B vitamin, e.g., folic acid, B12, riboflavin, biotin, pyridoxal or other vitamins or nutrients taken up, for example, by cancer cells. Also included are HSA and low density lipoprotein (LDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, nonpeptide or pseudo-peptide linkages, and use of D-amino acids. The helical agent is preferably an alpha-helical agent, which preferably has a lipophilic and a lipophobic phase.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

The synthetic, modified RNAs described herein can be synthesized and/or modified by methods well established in the art, such as those described in "Current Protocols in Nucleic Acid Chemistry," Beaucage, S. L. et al. (Edrs.), John Wiley & Sons, Inc., New York, N.Y., USA, which is hereby incorporated herein by reference in its entirety. Transcription methods are described further herein in the Examples.

In one embodiment of the aspects described herein, a template for a synthetic, modified RNA is synthesized using "splint-mediated ligation," which allows for the rapid synthesis of DNA constructs by controlled concatenation of long oligos and/or dsDNA PCR products and without the need to introduce restriction sites at the joining regions. It can be used to add generic untranslated regions (UTRs) to the coding sequences of genes during T7 template generation. Splint mediated ligation can also be used to add nuclear localization sequences to an open reading frame, and to make dominant-negative constructs with point mutations starting from a wild-type open reading frame. Briefly, single-stranded and/or denatured dsDNA components are annealed to splint oligos which bring the desired ends into conjunction, the ends are ligated by a thermostable DNA ligase and the desired constructs amplified by PCR. A synthetic, modified RNA is then synthesized from the template using an RNA polymerase in vitro. After synthesis of a synthetic, modified RNA is complete, the DNA template is removed from the transcription reaction prior to use with the methods described herein.

In some embodiments of these aspects, the synthetic, modified RNAs are further treated with an alkaline phosphatase.)

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more active agents, additives, ingredients, optional agents, types of organism, disorders, subjects, or combinations thereof, can be excluded.

Where the claims or description relate to a composition of matter, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately".

"Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

\*\*\*

EXAMPLES

Example 1

Transcription activator-like effector nucleases (TALENs) bind as a pair around a genomic site, in which a double-strand break (DSB) is introduced by a dimer of FokI nuclease domains. The use of a TALEN genome-editing system to rapidly and efficiently generate mutant alleles of 15 different genes in human pluripotent stem cells (hPSCs) as a means of performing rigorous disease modeling was recently reported (Ding et al., Cell Stem Cell 12:238-251 (2013)); the proportions of clones bearing at least one mutant allele ranged from 2%-34%.

As described below, the relative efficacies of CRISPRs and TALENs targeting the same genomic sites in the same hPSC lines was assessed with the use of the same delivery platform described previously (Ding et al., Cell Stem Cell 12:238-251 (2013)). In the TALEN genome-editing system, the CAG promoter was used to co-translate (via a viral 2A peptide) each TALEN with green fluorescent protein (GFP) or red fluorescent protein (RFP). For CRISPRs, a human codon-optimized Cas9 gene was subcloned with a C-terminal nuclear localization signal (Mali et al., Science 339:823-826 (2013)) into the same CAG expression plasmid with GFP, and the guide RNA (gRNA) was separately expressed from a plasmid with the human U6 polymerase III promoter (Mali et al., Science 339:823-826 (2013)). The 20-nucleotide protospacer sequence for each gRNA was introduced using polymerase chain reaction (PCR)-based methods. Whether using TALENs or CRISPRs, equal amounts of the two plasmids were co-electroporated into hPSCs (either 25 µg of each plasmid, or 12.5 µg of each plasmid along with 25 µg of a DNA repair template if attempting knock-in) followed by fluorescence-activated cell sorting (FACS) after 24-48 hours, clonal expansion of single cells, and screening for mutations at the genomic target site via PCR.

gRNAs were designed matching G(N)19NGG sequences in seven loci in six genes (AKT2, CELSR2, CIITA, GLUT4, LINC00116, and SORT1) previously successfully targeted with TALENs (Ding et al., Cell Stem Cell 12:238-251 (2013)) and one additional locus in LDLR. In this system, CRISPRs consistently and substantially outperformed TALENs across loci and hPSC lines (see Table S1). The TALENs yielded clones with at least one mutant allele at efficiencies of 0%-34%, but matched CRISPRs yielded mutant clones at efficiencies of 51%-79% (Table SI). Just as with TALENs, CRISPRs produced a variety of indels of sizes ranging from one nucleotide to several dozen nucleotides in size, centered on the predicted cleavage sites, suggesting that non-homologous end-joining mutagenesis occurs in the same way regardless of whether CRISPRs or TALENs are used. Moreover, CRISPRs readily generated homozygous mutant clones (7%-25% of all clones; Table S1) as discerned by sequencing.

Knock-in of E17K mutations into AKT2 was also attempted using a 67-nucleotide single-stranded DNA oligonucleotide as previously described (Ding et al., Cell Stem Cell 12:238-251 (2013)). Although the predicted CRISPR cleavage site lay 11 and 13 nucleotides from the point mutations, respectively, the CRISPR yielded knock-in clones at a rate of 11%, whereas TALENs yielded only 1.6% (Table SI).

TABLE S1

Targeting Efficiency of CRISPRs Versus TALENs in Human Pluripotent Stem Cells

| Gene | Chromosome:Position (Start of Target Sequence) | Target Sequence[a] | Cell Line[b] | TALENs Efficiency (Mutants/Clones Screened)[c] | CRISPRs Efficiency (Mutants/Clones Screened)[c] | CRISPRs Efficiency of Homozygous Mutants |
|---|---|---|---|---|---|---|
| AKT2 | chr19:40762982 | TCCCTTCCTGCCTCATTTCAGGTGAATACATCAAGACCTGGAGGCCA | HUES 9 | 8.9% (17/192) | (SEQ ID NO: 335) | |
| AKT2 | chr19:40762982 | TCCCTTCCTGCCTCATTTCAGGTGAATACATCAAGACCTGGAGGCCA | HUES 9 | (SEQ ID NO: 336) | 60.6% (86/142) | 12.7% (18/142) |
| CELSR2 | chr1:109817568 | TGCTGGCTCGGCTCCCTGAGGTTGCTCTCAATCAAGCACAGGTTTCAA | HUES 1 | 3.5% (18/506) | (SEQ ID NO: 337) | |
| CELSR2 | chr1:109817568 | TGCTGGCTCGGCTCCCTGAGGTTGCTCAATCAAGICACAGGTTTCAA | HUES 1 | (SEQ ID NO: 338) | 66.2% (45/68) | 7.4% (5/68) |
| CIITA | chr16:10989200 | TAACAGCGATGCTGACCCCCTGTGCCTCTACCACTTCTATGACCAGA | BJ-RiPS | 12.7% (37/292) | (SEQ ID NO: 339) | |
| CIITA | chr16:10989206 | CGATGCTGACCCCCTGTGCCTCTACCACTTTCTATGACCAGATGACC | BJ-RiPS | (SEQ ID NO: 340) | 78.7% (96/122) | 11.5% (14/122) |
| GLUT4 | chr17:7186601 | TGGTCCTTGCTGTGTCTCTGCGGTGCTTGGCTCCCTGCAGTTTGGGTA | HUES 9 | 33.5% (52/155) | (SEQ ID NO: 341) | |
| GLUT4 | chr17:7186601 | TGGTCCTTGCTGTGTTCTTCTGCGGTGCTTGGCTCCCTGCAGTTTGGGTA | HUES 9 | (SEQ ID NO: 342) | 66.5% (123/185) | 24.9% (46/185) |
| LDLR | chr19:11210899 | TGGGCGACAGATGCGAAAGAAACAGAGTTCCAGTGCCAAGACGGAAA | HUES 9 | 0% (0/568) | (SEQ ID NO: 343) | |
| LDLR | chr19:11210917 | GAAACGAGTTCCAGTGCCAAGACGGAAAATGCATCTCCTACIAAGTGG | HUES 9 | (SEQ ID NO: 344) | 51.1% (90/176) | 8.0% (14/176) |
| LINC00116 | chr2:110970090 | TCAGAGAGGACACTGCAGTTGTCCGTGCTAGTAGCCTTCGCTTCTGA | HUES 9 | 29.5% (26/88) | (SEQ ID NO: 345) | |
| LINC00116 | chr2:110970090 | TCAGAGAGGACACTGCAGTTGTCCGTGCTAGTAGCCTTCGCITTCTGGA | HUES 9 | (SEQ ID NO: 346) | 57.4% (93/162) | 8.6% (14/162) |
| SORT1 exon 2 | chr1:109912203 | TGATGATCTCAGAGGCTCAGTATCCTTGTCCTGGGTTGGAGATAGCA | HUES 1 | 22.2% (128/576) | (SEQ ID NO: 347) | |
| SORT1 exon 2 | chr1:109912203 | TGATGATCTCAGAGGCTCAGTATCCTTGTTCCTGGGTTGGAGATAGCA | HUES 1 | (SEQ ID NO: 348) | 68.5% (100/146) | 13.0% (19/145) |
| SORT1 exon 3 | chr1:109910069 | TGGTAATTATGACTTTTGGACAGTCCAAGCTATATCGAAGGTGAGATCA | HUES 9 | 10.9% (21/192) | (SEQ ID NO: 349) | |
| SORT1 exon 3 | chr1:109910069 | TGGTAATTATGACTTTTGGACAGTCCAAGCTATATTCGAAGGTGAGATCA | HUES 9 | (SEQ ID NO: 350) | 75.9% (148/195) | 10.3% (20/195) |
| AKT2 E17K | chr19:40762982 | TCCCTTCCTGCCTCATTTCAGGTGAATACATCAAGACCTGGAGGCCA | HUES 9 | 1.6% (3/192)[c] | (SEQ ID NO: 351) | |
| ALT2 E17K | chr19:40762982 | TCCCTTCCTCCTTCATTTCAGGTGAATACATCAAGACCTGGAGGCCA | HUES 9 | (SEQ ID NO: 352) | 10.6% (10/94)[c] | 1.1% (1/94)[d] |
| AKT2 off-target | chr5:22683972 | CTATGCCCTCCTTCATTTCAGTTCAGTGAAGA*T*GAAATCCCTGGAGCTTGG | HUES 9 | (SEQ ID NO: 353) | 0% (0/142) | 0% (0/142) |

[a]For TALENs, the binding sites are indicated with underlines, with the cleavage site predicted to be midway between the binding sites; for CRISPRs, the protospacer is underlined, the NGG motif is in bold (maybe on the antisense strand), and the predicted cleavage site is indicated with 'I'; for the ALT2 E17K target sequence, the sites of the knock-in mutations are indicated in bold/italics; for the AKT2 off-target site, the two mismatches in the protospacer are indicated in bold/italics
[b]HUES 1 and HUES 9 are human embryonic stem cell lines; BJ-RiPS is an induced pluripotent stem cell line
[c]Mutants include single heterozygotes, compound heterozygotes, and homozygous mutants; TALEN data is from Table 1 of Ding et al. (2013), with the exception of LDLR
[d]Successfully inserted E17K knock-in mutations into an AKT2 allele(s) using single-stranded DNA oligonucleotide (refer to FIG. 3 of Ding et al. 2013)

It is worth noting that the requirement for a G(N)19NGG target sequence somewhat limits site selection. Because either DNA strand can be targeted, a target sequence occurs on average every 32 basepairs. This is no barrier for gene knockout, where any coding sequence can be targeted, but it may present difficulties when trying to knock in or correct a mutation at a specific location. However, the requirement for a G at the start of the protospacer is dictated by the use of the U6 promoter to express the gRNA, and alternative CRISPR/Cas systems can relieve this requirement (Cong et al., Science 339:819-823 (2013)). This allows for the use of (N)20NGG target sequences, which are found on average every 8 basepairs.

In addition, the extent of CRISPR off-target effects remains to be defined and is highly sequence-dependent. Previous analyses have suggested that one-nucleotide mismatches in the first half of the protospacer are better tolerated than mismatches in second half (Jinek et al., Science 337:816-821 (2012); Cong et al., Science 339:819-823 (2013)). For the AKT2 sequence, there is a two-mismatch sequence differing at nucleotides 1 and 3, in the more "tolerant" half of the protospacer. Zero clones were obtained with mutations at this potential off-target site, as compared to 61% at the on-target site (Table S 1). For one of the SORT' sequences, use of a different human pluripotent stem cell line in which a single nucleotide polymorphism results in a one-nucleotide mismatch at the target site yielded mutant clones at an efficiency of 42%, compared to 66% in the original cell line. Thus, judicious selection of target sites is necessary to minimize systematic off-target effects; target sites with perfect-match or single-nucleotide-mismatch sequences elsewhere in the genome should be avoided.

From a practical standpoint, CRISPRs are easier to implement than TALENs. Each TALEN pair must be constructed do novo, whereas for CRISPRs the Cas9 component is fixed and the gRNA requires only swapping of the 20-nucleotide protospacer. Given this consideration and the demonstration herein of substantially increased efficiency as a result of replacing TALENs with CRISPRs in an otherwise identical system, CRISPRs appear to be a very powerful and broadly applicable tool for genome editing, particularly in a therapeutic context.

Example 2

Modified Cas9 mRNA Functions to Efficiently Introduce On-Target Mutations

Figure 19B:
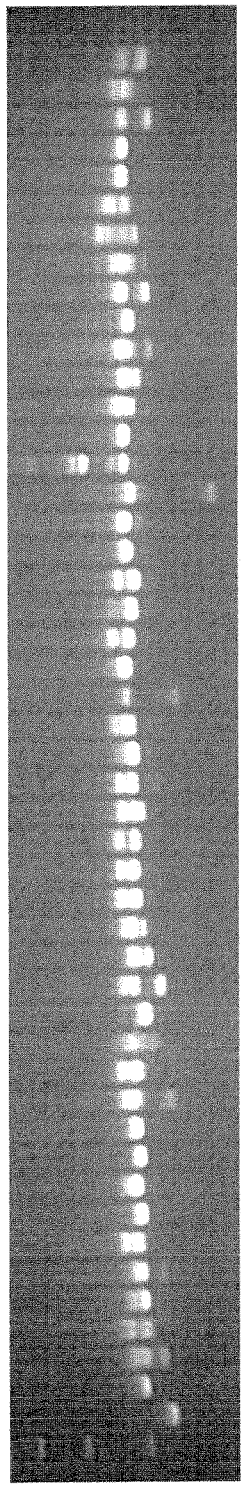

The inventors generated Figment (Fgm) knockout mice by CRIPSR/Cas9 gene editing utilizing a modified Cas9 mRNA. Fgm is a coding gene within the long non-coding RNA Lnc-Rap-5 (referred to herein as Fgm (Lnc-Rap-5; see Sun et al., "Long noncoding RNAs regulate adipogenesis," PNAS; 2013; 110(9):3387-3392, incorporated herein by reference in its entirety). The guide RNA (gRNA) sequence employed in this example was; 5' gaggcgaaagccactagcac 3'. The modified Cas9 mRNA used in this example was made using an in vitro transcription reaction in which pseudouridine and 5-methyl-cytosine were reacted with unmodified nucleotides and randomly integrated into the resulting modified Cas9 mRNA. An exemplary protocol for generating Fgm knockout mice using CRISPR/Cas9 gene editing utilizing a modified Cas9mRNA is shown in FIG. 19A. As shown in FIG. 19A, 100 ng/µl of the resulting modified Cas9 mRNA and 50 ng/µl of the guide RNA noted above targeting Fgm (Lnc-Rap-5) were injected into 250 C57BL/6 mouse zygotes that were subsequently transferred to pseudo-pregnant mice and after weening screened for mutations by PCR. As shown in the gel pictured in FIG. 19B, PCR screening revealed 63 mutant animals out of 65. These results indicate that modified Cas9 mRNA functions in vivo to efficiently (i.e., 97% efficiency) introduce on target mutations in mammals.

Example 3

Mutational Analysis of Genome Edited Hematopoietic Stem-Progenitor Cells (HSPCs) by Target Capture Deep Sequencing CRISPR/Cas9 has previously been shown to generate off-target mutations to varying degrees depending upon experimental setting and cell type (Cho et al., 2014; Cradick et al., 2013; Fu et al., 2013; Fu et al., 2014; Hruscha et al., 2013; Lin et al., 2014). To examine this in primary $CD34^+$ HSPCs we performed target capture sequencing, of $CD34^+$ HSPCs-mPB subjected to CRISPR/Cas9 CCR5-editing. Experimental design included capture of each gRNA target site (n=6) and predicted off-target sites (n=172) with expanded capture intervals of 500 base pairs flanking each site to ensure accurate detection of any genetic lesion occurring at or near the selected sites (FIGS. 17A and 20). We have previously shown that this approach can also capture structural variation breakpoints, such as translocations and inversions, in proximity to the capture site (Talkowski et al., 2011) (See supplemental text and methods for detailed description). Sorted $CD34^+$ HSPCs treated with Cas9 alone or in combination with multiple single gRNA (crCCR5_A, crCCR5_B, or crCCR5_C) or dual gRNA combinations (crCCR5_A+B, crCCR5_C+D, or crCCR5_D+Q) were sequenced to a mean target coverage of 3,390× across each 23 bp gRNA sequence and PAM (range 379.6×-7,969.5×)(FIG. 17B). Analysis of the resulting data revealed highly efficacious on-target mutagenesis with a diverse array of mutated sequence variants observed in both single-gRNA and dual-gRNA treatments (FIG. 17C). As expected we detected small InDels of up to 10 bp in addition to varying single nucleotide substitutions at the predicted target sites in the single-gRNA libraries. Strikingly, in each dual-gRNA library, no fewer than 15 alternate mutant alleles were observed at either one of the gRNA sites (FIGS. 21-23). Notably, the extreme sequencing depth of our analysis permitted estimation of mutation frequency for each particular variant, including mutations that were observed in only a few hundredths of a percent of the sample sequenced (FIG. 24). Predicted deletions (i.e. deletions spanning between the two gRNA target sites) were the most common mutations observed (crCCR5_A+B: 19.95%; crCCR5_C+D: 20.45%; crCCR5_D+Q: 42.13%), while small InDels (crCCR5_A+B: 3.06%; crCCR5_C+D: 0.50%; crCCR5_D+Q: 2.95%) were also frequent (FIG. 17C). Interestingly, for two dual gRNA combinations (crCCR5_A+B and crCCR5_D+Q) we also observed inversions between the two predicted Cas9 cleavage sites (crCCR5_A+B: 3.06%; crCCR5_D+Q: 2.48%). The most efficacious dual gRNA combination crCCR5_D+Q led to mutations in approximately 48% of the captured sequence reads (FIG. 17C).

We next examined the capture sequence reads at predicted off-target sites in the genome (FIG. 20). An N-fold enrichment analysis was performed, wherein we compared the total number of non-reference sequencing reads at each predicted off-target site in gRNA treated and control (Cas9 only) samples. This analysis generated a ratio where 1.0 indicates an equivalent number of non-reference sequence reads in both treated and control samples, values less than 1.0 indicate fewer non-reference reads in treated samples, and values greater than 1.0 indicate a greater number of non-reference reads in treated samples (see supplementary materials for additional details) (FIG. 17D). Strikingly, this analysis showed that the mean enrichment of mutations at off-target sites in all the gRNA-treated samples compared to control closely conformed to the null hypothesis (i.e., 0.99-fold enrichment compared to controls) indicating that off-target mutation events were extremely rare. Indeed, statistical evaluation of all captured off-target sites yielded a single site (1/172; 0.6%) in the sample treated with gRNA crCCR5_B alone that passed multiple test correction for a statistically significant enrichment for off-target InDels in the gRNA crCCR5 B treated libraries versus control ($p \leq 7.6 \times 10^{-11}$) (FIGS. 24-25). When we scrutinized the sequencing reads from the only statistically significant off-target site, which was located in the highly homologous CCR2 gene (FIG. 18A), we found that all sequence variants (36 out of 5,963 total reads) were one or two base InDels, (FIG. 18B). Of note, the other sample in which gRNA crCCR5_B was used (in combination with gRNA crCCR5_A) only 13 out of 5,339 reads supported mutation, however these events did not meet statistical significance above control or samples treated with other gRNAs (FIG. 18B, FIG. 24). Thus, off-target mutagenesis was exceedingly rare and moreover, the use of two gRNAs in combination did not increase the very low incidence of off-target mutagenesis. We also performed targeted analyses for structural variation at all sites and though we could easily detect on-target inversions in dual gRNA combination crCCR5_A+B and crCCR5_D+Q, there was no evidence for inversion or translocation at any off-target sites in any of the treatments. These data indicate that on-target mutagenesis efficiency was very high, and further that off-target mutagenesis was extremely infrequent for both single- and dual gRNA treatments.

Discussion

Our mutational analysis revealed highly efficacious mutagenesis of on-target sites in CD34 HSPCs. Single gRNAs generated a range of mutations with the vast majority comprised of small InDels. In contrast, dual gRNA combinations largely led to predicted deletions through a diverse array of mutations including InDels and even inversions were detected. Importantly, we only identified one statistically significant off-target site in the highly homologous CCR2 gene, which occurred in one out of 6 experimental settings (gRNA crCCR5_B alone). Sequence analysis of gRNA crCCR5_B in comparison to the identified off-target site in CCR2 indicated that it perfectly matched in the seed region and contained 3 sequence mismatches at the 5' end of the gRNA sequence (positions 1, 4 and 6). This data is consistent with previous studies showing that mismatches in the 5' proximal end of the gRNA are well tolerated by Cas9 (Lin et al., 2014; Wu et al., 2014). Our data therefore supports the idea that judicious guide design is critical for minimizing off-target mutations. Of note, our very deep sequencing analysis enabled detection of the sole off-target event we describe, whereas sequence analysis performed at lower sequencing depth—such as 50× coverage that has been used in previous off-target analyses (Smith et al., 2014; Suzuki et al., 2014; Veres et al., 2014)—would have been unable to detect this event. Overall, our analysis of CRISPR/Cas9 mutational activity in CD34+ HSPCs revealed very high on-target mutation rates and extremely low incidence of off-target mutagenesis.

Off-Target Prediction and Capture Sequencing

Degenerate gRNA off-target sequences were predicted for each gRNA targeting CCR5 using the CRISPR Design off-target prediction tool (Hsu et al., 2013). Off-target sequences were further supplemented by alignment of each gRNA to the human genome using BOWTIE of which all results up to and including 3 mismatches were added to the total off-target list (Langmead et al., 2009). All instances of each predicted off-target sequence existent in the human genome reference build GRCh37v71 were recorded (FIG. 20). Each guide RNA target site (n=6) and predicted off-target site (n=172) was selected for capture sequencing using the Agilent SureSelectXT Target Enrichment System. Capture intervals were expanded by approximately 500 bp in both the 5' and 3' directions to ensure exhaustive capture of the targeted region and detection of any genetic lesion occurring at or near a predicted gRNA on- or off-target site, as we have previously shown accurate capability to detect translocations and inversions using targeted capture of probes in proximity to a rearrangement breakpoint using a CapBP procedure as described (Talkowski et al., 2011). Probes were tiled with 60-fold greater density over each predicted 23 bp on- or off-target gRNA binding site than the flanking kilobase of sequence. Isogenic CD34+ HSPCs-mPB were transfected with CRISPR/Cas9 plasmids (one Cas9 only-treated control group, three treatment groups transfected with a single gRNA, and three treatment groups transfected with dual gRNAs). Sorted CD34+ genome edited HSPCs were cultured for two weeks prior to DNA isolation. Capture libraries were prepared from DNA extracted from seven treatment groups. Capture libraries were sequenced as 101 bp paired-end reads on an Illumina HiSeq2000 platform.

NGS Data Processing and Computational Analysis

Read pairs were aligned to GRCh37v71 with Bwa-MEM v0.7.10-r789 (Li, arXiv 2013). Alignments were processed using PicardTools and SAMBLASTER (Faust and Hall, 2014). The Genome Analysis Toolkit (GATK) v3.1-1-g07a4bf8 was applied for base quality score recalibration, insertion/deletion (InDel) realignment, duplicate removal, and single nucleotide variant (SNV) and InDel discovery and genotyping per published best-practice protocols (McKenna et al, Genome Res 2010; DePristo et al, Nat Genet 2011; Van der Auwera et al, 2013). SNVs and InDels were annotated using ANNOVAR (Wang et al., 2010). Structural variants (SVs) were detected with LUMPY v0.2.5 considering both anomalous pair and split read evidence at a minimum call weight threshold of 7 and an evidence set score ≤0.05 (Layer et al., 2014). Candidate copy number variants (CNVs) were further statistically assessed by Student's t-test for a concomitant change in depth of coverage across the putative CNV. As a final exhaustive measure, each on- and off-target site was manually scrutinized in each capture library for evidence supporting predictable mutagenesis that is not detectable by the computational algorithms due to low levels of mosaicism in the sequenced population.

Evaluation of Off-Target Mutation Frequency

A statistical framework was developed to assess off-target mutational burden for each gRNA. For each off-target site (n=172), all reads with at least one nucleotide of overlap with that 23 bp off-target site were collected and their CIGAR information was tabulated into categories as follows: reads representing small InDels (CIGAR contains at least one "I" or "D"), reads potentially representative of other rearrangements (CIGAR contains at least one "S" or "H"), and reads reflecting reference sequence (CIGAR did not match either of the two former categories). Such counts were gathered at all 172 sites in all seven libraries and were further pooled to form comparison groups of "treatment" libraries (transfected gRNA matches corresponding off-target site gRNA) and "control" libraries (transfected gRNA does not match corresponding off-target site gRNA). Next, at each off-target site, relative n-fold enrichment of each read classification between treatment and control libraries was evaluated. Finally, a one-tailed Fisher's Exact Test was performed to assess the statistical significance of enrichment of variant reads in treatments versus controls at each off-target site, followed by Bonferroni correction to retain an experiment-wide significance threshold of $\alpha=0.05$.

REFERENCES

1. Cong, L., et al., 2013. Multiplex genome engineering using CRISPR/Cas systems. Science. 339, 819-23.
2. Ding, Q., et al., 2013. Enhanced efficiency of human pluripotent stem cell genome editing through replacing TALENs with CRISPRs. Cell Stem Cell. 12, 393-4.
3. Jinek, M., et al., 2013. RNA-programmed genome editing in human cells. Elife. 2, e00471.
4. Li, D., et al., 2013. Heritable gene targeting in the mouse and rat using a CRISPR-Cas system. Nat Biotechnol. 31, 681-3.
5. Mali, P., et al., 2013. RNA-guided human genome engineering via Cas9. Science. 339, 823-6.
6. Niu, Y., et al., 2014. Generation of Gene-Modified Cynomolgus Monkey via Cas9/RNA-Mediated Gene Targeting in One-Cell Embryos. Cell. 156, 836-43.
7. Ran, F. A., et al., 2013. Double nicking by RNA-guided CRISPR Cas9 for enhanced genome editing specificity. Cell. 154, 1380-9.
8. Wang, H., et al., 2013. One-step generation of mice carrying mutations in multiple genes by CRISPR/Cas-mediated genome engineering. Cell. 153, 910-8.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10208319B2). An electronic copy of the "Sequence Listing" will also be available from the USPTO upon request and payment of the fee set forth in 37 CFR 1.19(b)(3).

What is claimed is:

1. A method for altering a target sickle cell disease (SCD)-associated polynucleotide sequence in a cell comprising contacting the SCD-associated polynucleotide sequence with a clustered regularly interspaced short palindromic repeats-associated (Cas) protein and from one to two ribonucleic acids, wherein the ribonucleic acids direct Cas protein to and hybridize to a target motif of the target SCD-associated polynucleotide sequence comprising nucleotides located between position 5246806 and position 5248263 of human chromosome 11, wherein the target SCD-associated polynucleotide sequence is cleaved, and wherein the efficiency of alteration is from about 50% to about 80%.

2. A method according to claim 1, wherein the Cas protein is *Streptococcus pyogenes* Cas9 protein or a functional portion thereof selected from the group consisting of a DNA binding domain, at least one RNA binding domain, a helicase domain, and an endonuclease domain.

3. A method according to claim 1, wherein the Cas protein is Cas9 protein from any bacterial species or functional portion thereof selected from the group consisting of a DNA binding domain, at least one RNA binding domain, a helicase domain, and an endonuclease domain.

4. A method according to claim 1, wherein the Cas protein is complexed with the one to two ribonucleic acids.

5. A method according to claim 1, wherein the target motif is $G(N)_{19}NGG$ or $(N)_{20}NGG$.

6. A method according to claim 1, wherein the alteration results in reduced expression of the target polynucleotide sequence, a knock out of the target polynucleotide sequence, or correction of the target polynucleotide sequence from an undesired sequence to a desired sequence.

7. A method according to claim 1, wherein the cell is selected from the group consisting of a peripheral blood cell, a stem cell, a pluripotent cell, a hematopoietic stem cell, a CD34+cell, a CD34+ mobilized peripheral blood cell, a CD34+ cord blood cell, a CD34+ bone marrow cell, a $CD34^+CD38\text{-Lineage-}CD90^+CD45RA^-$ cell, a primary human cell, a non-transformed human cell, and combinations thereof.

8. A method according to claim 1, wherein one or two ribonucleic acids hybridize to a target motif that contains at least one mismatch when compared with all other genomic nucleotide sequences in the cell.

9. A method according to claim 1, wherein the Cas protein is encoded by a modified nucleic acid selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate.

10. A method according to claim 1, wherein at least one of the ribonucleic acids is a modified ribonucleic acid comprising one to two modified nucleotides selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate.

11. A method according to claim 1, wherein the cell was selected for Cas protein expression.

* * * * *